(12) United States Patent
Bauer et al.

(10) Patent No.: US 10,533,001 B2
(45) Date of Patent: *Jan. 14, 2020

(54) INHIBITORS OF PROTEIN KINASES

(71) Applicant: PORTOLA PHARMACEUTICALS, INC., South San Francisco, CA (US)

(72) Inventors: Shawn M. Bauer, Pacifica, CA (US); Zhaozhong J. Jia, San Mateo, CA (US); Mukund Mehrotra, South San Francisco, CA (US); Yonghong Song, Foster City, CA (US); Qing Xu, Foster City, CA (US); Wolin Huang, Foster City, CA (US); Chandrasekar Venkataramani, Redwood City, CA (US); Jack W. Rose, San Mateo, CA (US); Anjali Pandey, Fremont, CA (US)

(73) Assignee: PORTOLA PHARMACEUTICALS, INC., South San Francisco, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 15/828,154

(22) Filed: Nov. 30, 2017

(65) Prior Publication Data

US 2018/0186783 A1 Jul. 5, 2018

Related U.S. Application Data

(63) Continuation of application No. 14/561,821, filed on Dec. 5, 2014, now Pat. No. 9,868,729, which is a
(Continued)

(51) Int. Cl.
*C07D 239/28* (2006.01)
*C07D 403/02* (2006.01)
(Continued)

(52) U.S. Cl.
CPC ........ *C07D 417/12* (2013.01); *A61K 31/4985* (2013.01); *A61K 31/505* (2013.01);
(Continued)

(58) Field of Classification Search
CPC .. C07D 239/28; C07D 403/02; C07D 413/02; C07D 279/12
See application file for complete search history.

(56) References Cited

U.S. PATENT DOCUMENTS 5,691,364 A 11/1997 Buckman et al.
5,728,536 A 3/1998 Ihle et al.
(Continued)

FOREIGN PATENT DOCUMENTS

EP 1 054 004 A1 11/2000
EP 1 184 376 A1 3/2002
(Continued)

OTHER PUBLICATIONS

Berge, S.M. et al., "Pharmaceutical Salts," Journal of Pharmaceutical Science, 66:1-19, 1977.
(Continued)

*Primary Examiner* — Marcos L Sznaidman
*Assistant Examiner* — Rayna Rodriguez
(74) *Attorney, Agent, or Firm* — Mintz Levin Cohn Ferris Glovsky and Popeo, P.C.

(57) ABSTRACT

The present invention is directed to topical pharmaceutical compositions of Formula (If)
(Continued)

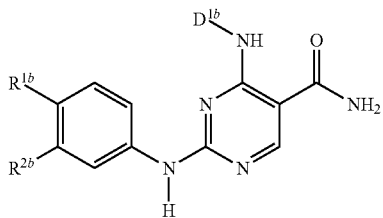

(If)

or pharmaceutically acceptable salt thereof, which act as inhibitors of syk and/or JAK kinase activity. The described topical pharmaceutical compositions are useful in preventing or treating a number of conditions mediated at least in part by syk and/or JAK kinase activity.

13 Claims, 121 Drawing Sheets

Related U.S. Application Data continuation of application No. 13/916,926, filed on Jun. 13, 2013, now Pat. No. 8,937,070, which is a continuation of application No. 13/360,862, filed on Jan. 30, 2012, now Pat. No. 8,501,944, which is a continuation of application No. 12/386,509, filed on Apr. 16, 2009, now Pat. No. 8,138,339.

(60) Provisional application No. 61/120,348, filed on Dec. 5, 2008, provisional application No. 61/120,346, filed on Dec. 5, 2008, provisional application No. 61/120,344, filed on Dec. 5, 2008, provisional application No. 61/120,341, filed on Dec. 5, 2008, provisional application No. 61/045,499, filed on Apr. 16, 2008, provisional application No. 61/045,417, filed on Apr. 16, 2008, provisional application No. 61/045,406, filed on Apr. 16, 2008, provisional application No. 61/045,399, filed on Apr. 16, 2008.

(51) Int. Cl.
*C07D 413/02* (2006.01)
*C07D 279/12* (2006.01)
*A61K 31/506* (2006.01)
*A61K 31/501* (2006.01)
*A61K 31/5377* (2006.01)
*A61K 31/551* (2006.01)
*A61K 31/541* (2006.01)
*C07D 417/12* (2006.01)
*A61K 31/4985* (2006.01)
*A61K 31/505* (2006.01)
*A61K 31/5355* (2006.01)
*C07D 239/48* (2006.01)
*C07D 401/14* (2006.01)
*C07D 403/12* (2006.01)
*C07D 403/14* (2006.01)
*C07D 413/12* (2006.01)
*C07D 413/14* (2006.01)
*C07D 401/12* (2006.01)
*C07D 405/12* (2006.01)

(52) U.S. Cl.
CPC ........ *A61K 31/506* (2013.01); *A61K 31/5355* (2013.01); *A61K 31/5377* (2013.01); *A61K 31/551* (2013.01); *C07D 239/48* (2013.01); *C07D 401/12* (2013.01); *C07D 401/14* (2013.01); *C07D 403/12* (2013.01); *C07D 403/14* (2013.01); *C07D 405/12* (2013.01); *C07D 413/12* (2013.01); *C07D 413/14* (2013.01)

(56) References Cited

U.S. PATENT DOCUMENTS

| | | |
|---|---|---|
| 5,811,428 A | 9/1998 | Suto et al. |
| 5,877,181 A | 3/1999 | Buckman et al. |
| 5,883,100 A | 3/1999 | Buckman et al. |
| 5,889,005 A | 3/1999 | Buckman et al. |
| 6,004,981 A | 12/1999 | Buckman et al. |
| 6,004,985 A | 12/1999 | Kochanny et al. |
| 6,008,234 A | 12/1999 | Kochanny et al. |
| 6,034,084 A | 3/2000 | Kochanny et al. |
| 6,034,103 A | 3/2000 | Buckman et al. |
| 6,080,747 A | 6/2000 | Uckun et al. |
| 6,080,748 A | 6/2000 | Uckun et al. |
| 6,127,376 A | 10/2000 | Davey et al. |
| 6,133,305 A | 10/2000 | Tang et al. |
| 6,150,382 A | 11/2000 | Kochanny et al. |
| 6,162,807 A | 12/2000 | Kochanny et al. |
| 6,166,014 A | 12/2000 | Kochanny et al. |
| 6,177,433 B1 | 1/2001 | Uckun et al. |
| 6,177,473 B1 | 1/2001 | Kochanny et al. |
| 6,210,654 B1 | 4/2001 | Ihle et al. |
| 6,221,886 B1 | 4/2001 | Kochanny et al. |
| 6,232,325 B1 | 5/2001 | Kochanny et al. |
| 6,262,088 B1 | 7/2001 | Phillips |
| 6,265,404 B1 | 7/2001 | Kochanny et al. |
| 6,306,884 B1 | 10/2001 | Buckman et al. |
| 6,313,130 B1 | 11/2001 | Uckun et al. |
| 6,316,635 B1 | 11/2001 | Tang et al. |
| 6,350,746 B1 | 2/2002 | Buckman et al. |
| 6,372,751 B1 | 4/2002 | Davey et al. |
| 6,432,963 B1 | 8/2002 | Hisamichi et al. |
| 6,433,018 B1 | 8/2002 | Siddiqui et al. |
| 6,465,459 B2 | 10/2002 | Buckman et al. |
| 6,479,485 B2 | 11/2002 | Buckman et al. |
| 6,486,185 B1 | 11/2002 | McMahon et al. |
| 6,492,376 B2 | 12/2002 | Phillips |
| 6,495,574 B2 | 12/2002 | Phillips |
| 6,495,684 B2 | 12/2002 | Phillips |
| 6,506,763 B2 | 1/2003 | Tang et al. |
| 6,525,051 B2 | 2/2003 | Davey et al. |
| 6,528,509 B1 | 3/2003 | Hale et al. |
| 6,552,030 B2 | 4/2003 | Phillips |
| 6,559,147 B2 | 5/2003 | Phillips |
| 6,593,357 B1 | 7/2003 | Green et al. |
| 6,608,048 B2 | 8/2003 | Tsou et al. |
| 6,610,688 B2 | 8/2003 | Liang et al. |
| 6,635,651 B2 | 10/2003 | Uckun et al. |
| 6,677,368 B2 | 1/2004 | Cui et al. |
| 6,683,082 B2 | 1/2004 | Tang et al. |
| 6,686,364 B2 | 2/2004 | Buckman et al. |
| 6,686,367 B2 | 2/2004 | Phillips |
| 6,696,448 B2 | 2/2004 | Tang et al. |
| 6,699,865 B2 | 3/2004 | Hale et al. |
| 6,716,831 B1 | 4/2004 | Breault et al. |
| 6,740,655 B2 | 5/2004 | Magee et al. |
| 6,777,417 B2 | 8/2004 | Liang et al. |
| 6,784,195 B2 | 8/2004 | Hale et al. |
| 6,797,706 B1 | 9/2004 | Hisamichi et al. |
| 6,815,439 B2 | 11/2004 | Harris et al. |
| 6,825,190 B2 | 11/2004 | Moon et al. |
| 6,908,920 B2 | 6/2005 | Thomas et al. |
| 6,949,580 B2 | 9/2005 | Hale et al. |
| 6,969,760 B2 | 11/2005 | Ihle et al. |
| 6,998,391 B2 | 2/2006 | Lyons et al. |
| 7,056,944 B2 | 6/2006 | Hale et al. |
| 7,060,827 B2 | 6/2006 | Singh et al. |
| 7,074,793 B2 | 7/2006 | Hukdins et al. |
| 7,105,529 B2 | 9/2006 | Davis et al. |
| 7,122,542 B2 | 10/2006 | Singh et al. |
| 7,189,729 B2 | 3/2007 | Chopiuk et al. |
| 7,276,510 B2 | 10/2007 | Kukla et al. |

(56) References Cited

U.S. PATENT DOCUMENTS

| | | |
|---|---|---|
| 7,329,671 B2 | 2/2008 | Singh et al. |
| 7,329,672 B2 | 2/2008 | Singh et al. |
| 7,332,484 B2 | 2/2008 | Singh et al. |
| 7,435,814 B2 | 10/2008 | Singh et al. |
| 7,449,456 B2 | 11/2008 | Nagashima et al. |
| 7,449,458 B2 | 11/2008 | Singh et al. |
| 7,485,724 B2 | 2/2009 | Singh et al. |
| 7,498,435 B2 | 3/2009 | Singh et al. |
| 7,514,446 B2 | 4/2009 | Davis-Ward et al. |
| 7,517,886 B2 | 4/2009 | Singh et al. |
| 7,550,460 B2 | 6/2009 | Singh et al. |
| 7,557,207 B2 | 7/2009 | Cooper |
| 7,557,210 B2 | 7/2009 | Singh et al. |
| 7,563,892 B1 | 7/2009 | Singh |
| 7,589,200 B2 | 9/2009 | Singh et al. |
| 7,642,351 B2 | 1/2010 | Singh et al. |
| 7,820,819 B2 | 10/2010 | Singh et al. |
| 7,851,480 B2 | 12/2010 | Cooper |
| 7,943,628 B2 | 5/2011 | Bell et al. |
| 8,063,058 B2 | 11/2011 | Jia |
| 8,138,339 B2 | 3/2012 | Bauer |
| 8,148,525 B2 | 4/2012 | Singh et al. |
| 8,158,621 B2 | 4/2012 | Singh et al. |
| 8,178,671 B2 | 5/2012 | Singh et al. |
| 8,258,129 B2 | 9/2012 | Engelhardt et al. |
| 8,318,755 B2 | 11/2012 | Jia |
| 8,349,860 B2 | 1/2013 | Jia |
| 8,501,944 B2 | 8/2013 | Bauer |
| 8,785,437 B2 | 7/2014 | Singh |
| 8,877,760 B2 | 11/2014 | Song |
| 8,937,070 B2 | 1/2015 | Bauer |
| 8,952,027 B2 | 2/2015 | Jia |
| 9,868,729 B2 | 1/2018 | Bauer et al. |
| 2001/0007033 A1 | 7/2001 | Tang et al. |
| 2002/0115173 A1 | 8/2002 | Ben-Sasson et al. |
| 2002/0137141 A1 | 9/2002 | Ben-Sasson |
| 2002/0155173 A1 | 10/2002 | Chopp et al. |
| 2003/0149064 A1 | 8/2003 | Pease |
| 2003/0236244 A1 | 12/2003 | Ledford |
| 2004/0029902 A1 | 2/2004 | Singh et al. |
| 2004/0102455 A1 | 5/2004 | Burns |
| 2004/0142404 A1 | 7/2004 | Wilks |
| 2004/0147507 A1 | 7/2004 | Ledeboer |
| 2004/0214817 A1 | 10/2004 | Pierce |
| 2004/0224966 A1 | 11/2004 | Brumby et al. |
| 2005/0234049 A1 | 10/2005 | Singh et al. |
| 2005/0272753 A1 | 12/2005 | Nagashima et al. |
| 2006/0040934 A1 | 2/2006 | Cottam |
| 2006/0247241 A1 | 11/2006 | Garcia-Echeverria et al. |
| 2006/0270694 A1 | 11/2006 | Wong |
| 2007/0060603 A1 | 3/2007 | Singh et al. |
| 2007/0142402 A1 | 6/2007 | Ding et al. |
| 2007/0293522 A1 | 12/2007 | Singh et al. |
| 2007/0293523 A1 | 12/2007 | Singh et al. |
| 2008/0027034 A1 | 1/2008 | Shah et al. |
| 2008/0139531 A1 | 6/2008 | Yanni et al. |
| 2009/0082567 A1 | 3/2009 | Singh et al. |
| 2009/0171086 A1 | 7/2009 | Singh et al. |
| 2009/0196973 A1 | 8/2009 | Piatko |
| 2009/0270418 A1 | 10/2009 | Sloss et al. |
| 2009/0318407 A1 | 12/2009 | Bauer et al. |
| 2010/0010025 A1 | 1/2010 | Duthaler et al. |
| 2010/0048567 A1 | 2/2010 | Jia et al. |
| 2010/0190980 A1 | 7/2010 | Umemiya et al. |
| 2011/0166161 A1 | 7/2011 | Terasawa et al. |
| 2011/0230467 A1 | 9/2011 | Shirakami et al. |
| 2011/0237590 A1 | 9/2011 | Kitamura et al. |
| 2012/0045454 A1 | 2/2012 | Singh et al. |
| 2012/0108566 A1 | 5/2012 | Bauer |
| 2012/0129867 A1 | 5/2012 | Bauer |
| 2012/0230984 A1 | 9/2012 | Singh et al. |
| 2013/0029944 A1 | 1/2013 | Song |
| 2013/0131040 A1 | 5/2013 | Song |
| 2013/0165431 A1 | 6/2013 | Jia |
| 2014/0031361 A1 | 1/2014 | Bauer |
| 2014/0309209 A1 | 10/2014 | Song |
| 2014/0323418 A1 | 10/2014 | Jia et al. |
| 2015/0094298 A1 | 4/2015 | Bauer et al. |
| 2015/0297595 A1 | 10/2015 | Jia et al. |

FOREIGN PATENT DOCUMENTS

| | | |
|---|---|---|
| EP | 1 518 855 A1 | 3/2005 |
| EP | 2 157 090 A1 | 2/2010 |
| JP | 2005-508953 | 4/2005 |
| WO | 1995/03701 A1 | 2/1995 |
| WO | 1996/28427 A1 | 9/1996 |
| WO | 1997/09315 A1 | 3/1997 |
| WO | 1998/11094 A1 | 3/1998 |
| WO | 1998/15547 A1 | 4/1998 |
| WO | 1999/15500 A1 | 4/1999 |
| WO | 1999/031073 | 6/1999 |
| WO | 2000/00202 A1 | 1/2000 |
| WO | 2000/10981 A1 | 3/2000 |
| WO | 2000/31068 A1 | 6/2000 |
| WO | 2000/33844 A1 | 6/2000 |
| WO | 2000/39101 | 7/2000 |
| WO | 2000/47583 A1 | 8/2000 |
| WO | 2000/51587 A2 | 9/2000 |
| WO | 2000/55159 A2 | 9/2000 |
| WO | 2000/075113 A1 | 12/2000 |
| WO | 2000/076980 | 12/2000 |
| WO | 2001/09134 A1 | 2/2001 |
| WO | 2001/42246 A2 | 6/2001 |
| WO | 2001/45641 A2 | 6/2001 |
| WO | 2001/52892 A2 | 7/2001 |
| WO | 2001/56993 A2 | 8/2001 |
| WO | 2001/57022 A2 | 8/2001 |
| WO | 2001/57025 A1 | 8/2001 |
| WO | 2001/72744 A1 | 10/2001 |
| WO | 2001/72758 A1 | 10/2001 |
| WO | 2001/85700 A2 | 11/2001 |
| WO | 2002/000661 A1 | 1/2002 |
| WO | 2002/043735 A1 | 6/2002 |
| WO | 2002/048336 A2 | 6/2002 |
| WO | 2002/051843 A1 | 7/2002 |
| WO | 2002/059110 | 8/2002 |
| WO | 2002/060492 A1 | 8/2002 |
| WO | 2002/060927 A1 | 8/2002 |
| WO | 2002/092571 | 11/2002 |
| WO | 2002/096909 A1 | 12/2002 |
| WO | 2002/102800 A1 | 12/2002 |
| WO | 2003/002542 | 1/2003 |
| WO | 2003/020698 A2 | 3/2003 |
| WO | 2003/030909 | 4/2003 |
| WO | 2003/048162 A1 | 6/2003 |
| WO | 2003/031438 | 7/2003 |
| WO | 2003/063794 A2 | 8/2003 |
| WO | 2003/066601 | 8/2003 |
| WO | 2003/074515 | 9/2003 |
| WO | 2003/078404 | 9/2003 |
| WO | 2003/101989 A1 | 12/2003 |
| WO | 2003/106416 | 12/2003 |
| WO | 2004/014382 A1 | 2/2004 |
| WO | 2004/016597 A2 | 2/2004 |
| WO | 2004/041789 A1 | 5/2004 |
| WO | 2004/041810 A1 | 5/2004 |
| WO | 2004/041814 A1 | 5/2004 |
| WO | 2004/046112 A2 | 6/2004 |
| WO | 2004/046118 | 6/2004 |
| WO | 2004/046120 A2 | 6/2004 |
| WO | 2004/047843 A1 | 6/2004 |
| WO | 2004/058749 A1 | 7/2004 |
| WO | 2004/058753 A1 | 7/2004 |
| WO | 2004/002964 A1 | 8/2004 |
| WO | 2004/074244 A2 | 9/2004 |
| WO | 2004/080980 A1 | 9/2004 |
| WO | 2004/085388 A2 | 10/2004 |
| WO | 2004/092154 A2 | 10/2004 |
| WO | 2005/009443 A1 | 2/2005 |
| WO | 2005/009957 A1 | 2/2005 |
| WO | 2005/012294 A1 | 2/2005 |
| WO | 2005/016344 A1 | 2/2005 |
| WO | 2005/016893 | 2/2005 |

(56) References Cited

FOREIGN PATENT DOCUMENTS

| | | |
|---|---|---|
| WO | 2005/016894 | 2/2005 |
| WO | 2005/026158 | 3/2005 |
| WO | 2005/028475 A2 | 3/2005 |
| WO | 2005/033086 A1 | 4/2005 |
| WO | 2005/033107 A1 | 4/2005 |
| WO | 2005/037800 | 4/2005 |
| WO | 2005/066156 | 7/2005 |
| WO | 2005/095400 | 10/2005 |
| WO | 2005/097135 A2 | 10/2005 |
| WO | 2005/122294 A1 | 12/2005 |
| WO | 2006/027377 A1 | 3/2006 |
| WO | 2006/027378 A1 | 3/2006 |
| WO | 2007/042298 A1 | 4/2007 |
| WO | 2007/046112 A1 | 4/2007 |
| WO | 2007/071393 A2 | 6/2007 |
| WO | 2007/113254 A1 | 10/2007 |
| WO | 2008/009458 A1 | 1/2008 |
| WO | 2008/024963 A1 | 2/2008 |
| WO | 2008/051547 A1 | 5/2008 |
| WO | 2008/080965 A2 | 7/2008 |
| WO | 2008/119792 A1 | 10/2008 |
| WO | 2008/135786 | 11/2008 |
| WO | 2009/032668 A2 | 3/2009 |
| WO | 2009/046840 A1 | 4/2009 |
| WO | 2009/089042 | 7/2009 |
| WO | 2009/136995 A2 | 11/2009 |
| WO | 2009/145856 A1 | 12/2009 |
| WO | 2010/032875 A2 | 3/2010 |
| WO | 2010/058846 A1 | 5/2010 |
| WO | 2010/061971 A1 | 6/2010 |
| WO | 2010/097248 A1 | 9/2010 |
| WO | 2010/129802 A1 | 11/2010 |
| WO | 2012/044936 A1 | 4/2012 |
| WO | 2012/045010 A1 | 4/2012 |
| WO | 2012/053606 | 4/2012 |
| WO | 2012/061415 A1 | 5/2012 |
| WO | 2010/128659 | 11/2012 |

OTHER PUBLICATIONS

Blaire et al., "Lack of Expression of Thy-1 (CD90) on Acute Myeloid Leukemia Cells With Long-Term Proliferative Ability In Vitro and In Vivo," 1997, Blood 89:3104-3112.
Braselmann et al., "R406, an Orally Available Spleen Tyrosine Kinase Inhibitor Blocks Fc Receptor Signaling and Reduces Immune Complex-Mediated Inflammation," J Pharmacol Exp Ther 319(3): 998-1008 (2006).
Brown et al., "Journal of Medicinal Chemistry," American Chemical Society, 1992, vol. 35, pp. 3613-3624.
Burnett and Knapper, "Targeting Treatment in AML," Hematology Am Soc Hematol Educ Program 2007: 429-34 (2007).
Catlett-Falcone et al., "Constitutive Activation of Stat3 Signaling Confers Resistance to Apoptosis in Human U266 Myeloma Cells," (1999), Immunity 10:105-115.
Changelian et al., "Prevention of Organ Allograft Rejection by a Specific Janus Kinase 3 Inhibitor," (2003) Science 302:875-878.
Chen, L., et.al, "Protein tyrosine phosphatase receptor-type O truncated (PTPROt) regulates SYK phosphorylation, proximal B-cell-receptor signaling, and cellular proliferation," Blood, 2006; 108:3428-3433.
Chen, Monti et al., "Syk-dependent tonic B-cell receptor signaling is a rational treatment target in diffuse large B-cell lymphoma," Blood 111(4): 2230-7 (2008).
Chen, R. et al., "MicroRNA regulation in mantle cell lymphoma," Journal of Clinical Oncology, 2007 ASCO Annual Meeting Proceedings (Post-Meeting Edition).vol. 25, No. 18S (Jun. 20 Supplement), 2007: 8056.
Cheng, Rowley et al., "SYK tyrosine kinase required formouse viability and B-cell development," 1995; Turner, Mee et al. Nature 378(6554): 303-6 (1995).
Couture, C. et al., "Activation of p56lck by p72,k through Physical Association and N-Terminal Tyrosine Phosphorylationt," Mol. Cell. Biol., 14:5249-5258, 1994.
Couture, C. et al., "p56lck-independent activation and tyrosine phosphorylation of p72sYk by T-cell antigen receptor/CD3 stimulation," Proc. Natl. Acad. Sci. USA, 91:5301-5305, 1994.
Crow, A.R. et al., "Inhibition of Immune Thrombocytopenic Purpura (ITP) by an Orally Bioavailabl Inhibitor of Syk Kinase Activity," Blood, 106:abstract 2165, 2005.
Crowley, M.T. et al., "A Critical Role for Syk in Signal Transduction and Phagocytosis Mediated by Fc g Receptors on Macrophages," J. Exp. Med., 186:1027-1039, 1997.
Demoulin et al., "A Single Tyrosine of the Interleukin-9 (IL-9) Receptor Is Required for STAT Activation, Antiapoptotic Activity, and Growth Regulation by IL-9," (1996), Mol. Cell. Biol. 16:4710-6.
Frank, "STAT Signaling in the Pathogenesis and Treatment of Cancer," (1999), Mol. Med. 5:432:456.
Friedberg, JW et al, "Inhibition of Syk with fostamatinib disodium has significant clinical activity in non-Hodgkin lymphoma and chronic lymphocytic leukemia," Blood 2010; 115(13), 2578-2585.
Garcia-Bustos et al., "PIK1, an essential phosphatidylinositol 4-kinase associated with the yeast nucleus," (1994), EMBO J. 13:2352-2361.
Gobessi, Stefania et al., "Constitutive activation of the protein tyrosine kinase Syk in Chronic Lymphocytic Leukemia B-cells," Blood, 2007, 110, Abstract 1123.
Gururajan et al., "Cutting Edge: Constitutive B Cell Receptor Signaling Is Critical for Basal Growth of B Lymphoma," 2006, 176:5715-5719.
Gururajan et al., "Spleen Tyrosine Kinase (Syk), a Novel Target of Curcumin, Is Required for B Lymphoma Growth," J Immunol 178(1): 111-21 (2007).
Hahn, Cynthia K. et al., "Syk is a new target for AML differentiation," Blood, 2007, 110, Abstract 209.
Hanks & Hunter, "The eukaryotic protein kinase superfamily: kinase (catalytic) domain structure and classification," (1995), FASEB J. 9:576-596.
Haura et al, "Mechanisms of Disease: insights into the emerging role of signal transducers and activators of transcription in cancer," Oncology, 2005, 2(6), 315-324.
Heinrich, Griffith et al., "Inhibition of c-kit receptor tyrosine kinase activity by STI 571, a selective tyrosine kinase inhibitor," Blood 96(3): 925-32 (2000).
Hiles et al., "Phosphatidylinositol 3-Kinase: Structure and Expression of the 110 kd Catalytic Subunit," (1992), Cell 70:419-429.
Hirabayashi, A. et al., "A novel Syk family kinase inhibitor: Design, synthesis, and structure-activity relationship of 1,2,4-triazolo [4,3-c]pyrimidine and 1,2,4-triazolo[1,5-c]pyrimidine derivatives," *Bioorganic & Medicinal Chemistry*, 2008, vol. 16, pp. 7347-7357.
Hisamichi, H. et al., "Synthetic studies on novel Syk inhibitors. Part 1: Synthesis and structure-activity relationships of pyrimidine-5-carboxamide derivatives," *Bioorganic Medicinal Chemistry*, 2005, vol. 13, pp. 4936-4951.
Hisamichi, H. et al., Corrigendum to "Synthetic studies on novel Syk inhibitors. Part 1: Synthesis and structure-activity relationships of pyrimidine-5-carboxamide derivatives," *Bioorganic Medicinal Chemistry*, 2005, vol. 13, pp. 4936-4951. Bioorganic Medicinal Chemistry, Elsevier Science Ltd, GB, vol. 13, No. 22, Nov. 15, 2005, pp. 6277-6279.
Hutchcroft, J E. et al., "Association of the 72-kDa Protein-tyrosine Kinase PTK72 with the B Cell Antigen Receptor," J. Biol. Chem., 267:8613-8619, 1992.
Irish, Czerwinski et al., "Altered B-cell receptor signaling kinetics distinguish human follicular lymphoma B cells from tumor-infiltrating nonmalignant B cells," J Immunol 176(10): 5715-9 (2006).
Jørgensen, A. et al., "Phosphorus Pentoxide in Organic Synthesis, XXVI. Synthesis of 7H-pyrrolo[2,3-d]pyrimidin-2,4-diones 7-deazaisoguanines from 7H-pyrrolo[2,3-d]pyrimidin-2,4-diones," *Chemica Scripta*, 1998, vol. 28, pp. 201-204.
Jumaa, Hendriks et al., "B cell signaling and tumorigenesis," Annu Rev Immunol 23: 415-45 (2005).

(56) References Cited

OTHER PUBLICATIONS

Jurlander et al., "Characterization of Interleukin-10 Receptor Expression on B-Cell Chronic Lymphocytic Leukemia Cells," (1997), Blood. 89:4146-52.
Kaneko et al., "Characterization of Interleukin-10 Receptor Expression on B-Cell Chronic Lymphocytic Leukemia Cells," (1997), Clin. Exp. Immun. 109:185-193.
Khar, Ashok et al., :Induction of stress response renders human tumor cell lines resistant to curcumin-mediated apoptosis: role of reactive oxygen intermediates, Cell Stress & Chaperones, 2001, 6(4):368-376.
Kirken, "Targeting JAK3 for Immune Suppression and Allograft Acceptance," (2001), Transpl. Proc. 33:3268-3270.
Knighton et al., "Crystal structure of the catalytic subunit of cyclic adenosine monophosphate-dependent protein kinase," (1991), Science 253:407-414.
Kraus et al., "Survival of Resting Mature B Lymphocytes Depends on BCR Signaling via the Igα/β Heterodimer," Cell 117(6): 787-800 (2004).
Kudlacz et al., "The Novel JAK-3 Inhibitor CP-690550 Is a Potent Immunosuppressive Agent in Various Murine Models," (2004) Am. J. Transplant 4:51-57.
Kuno, Y. et.al., "Constitutive kinase activation of the TEL-Syk fusion gene in myelodysplastic syndrome with t(9;12)(q22;p12)," Blood, 2001; 97:1050-1055.
Kunz et al., "Target of Rapamycin in Yeast, TOR2, Is an Essential Phosphatidylinositol Kinase Homolog Required for G1 Progression," (1993), Cell 73:585-596.
Kuppers, R., "Mechanisms of B-Cell Lymphoma Pathogenesis," Nat Rev Cancer, 2005; 5:251-262.
Lam, Kuhn et al., "In Vivo Ablation of Surface Immunoglobulin on Mature B Cells by Inducible Gene Targeting Results in Rapid Cell Death," Cell 90(6): 1073-83 (1997).
Latour, S. et. al., "Regulation of T-Cell Antigen Receptor Signalling by Syk Tyrosine Protein Kinase," Mol Cell Biol., 17:4434-4441, 1997.
Law, D.A. et al., "Genetic and Pharmacological Analyses of Syk Function in allbb3 Signaling in Platelets," Blood, 93:2645-2652, 1999.
Leonard et al., "Molecular mechanisms in allergy and clinical immunology." (2000), J. Allergy Clin. Immunol. 105:877-888.
Leseux, L. et. al., "Syk-dependent mTOR activation in follicular lymphoma cells," Blood, 2006; 108:4156-4162.
Liddle et al., "Discovery of GSK143, a highly potent, selective and orally efficacious spleen tyrosine kinase inhibitor," Bioorg. Med. Chem. Lett,, 21(20):6188-6194 (Oct. 15, 2011).
Malaviya et al., "Genetic and Biochemical Evidence for a Critical Role of Janus Kinase (JAK)-3 in Mast Cell-Mediated Type I Hypersensitivity Reactions," (1999), Biochem. Biophys. Res. Commun. 257:807-813.
Mocsai et al., "Syk Is Required for Integrin Signaling in Neutrophils," (2002), Immunity 16:547-558.
Muller-Ladner et al., "Activation of the IL-4 STAT Pathway in Rheumatoid Synovium," (2000), J. Immunol. 164:3894-3901.
Nagashima, S. et al., "Synthesis and evaluation of 2-{[2-4(hydroxyphenyl)-ethyl]amino}pyrimidine-5-carboxamide derivatives as novel STAT6 inhibitors," *Bioorganic & Medicinal Chemistry*, 2006, vol. 15, pp. 1044-1055.
Nakamura et al., "An Epidermal Growth Factor Receptor/Jak2 Tyrosine Kinase Domain Chimera Induces Tyrosine Phosphorylation of Stat5 and Transduces a Growth Signal in Hematopoietic Cells," (1996), J. Biol. Chem. 271: 19483-8.
Nielsen et al., "Constitutive activation of a slowly migrating isoform of Stat3 in mycosis fungoides: Tyrphostin AG490 inhibits Stat3 activation and growth of mycosis fungoides tumor cell lines," (1997), Prac. Natl. Acad. Sci. USA 94:6764-6769.
Papp, E. et al., "Steady State Kinetics of Spleen Tyrosine Kinase Investigated by a Real Time Fluorescence Assay," *Biochemistry*, 2007, vol. 46, pp. 15103-15114.
Passegue et al., "Normal and leukemic hematopoiesis: Are leukemias a stem cell disorder or a reacquisition of stem cell characteristics?," Proc. Natl. Acad. Sci. USA, 2003, 100:11842-9.
Poole, A. et al., "The Fc receptor g-chain and the tyrosine kinase Syk are essential for activation of mouse platelets by collagen," EMBO J., 16:2333-2341, 1997.
Protest Under 37 C.F.R. § 1.291(a) of U.S. Appl. No. 12/386,848, filed Apr. 22, 2009, for Yonghong Song et al., 14 pages.
Reilly, M.P., "Heparin-induced thrombocytopenia/thrombosis in a transgenic mouse model requires human platelet factor 4 and platelet activation through FcgRIIA," Blood, 98:2442-2447, 2001.
Rinaldi, A. et.al, "Genomic and expression profiling identifies the B-cell associated tyrosine kinase Syk as a possible therapeutic target in mantle cell lymphoma," Br. J. Haematol., 2006; 132:303-316.
Rolli, Gallwitz et al. "Amplification of B Cell Antigen Receptor Signaling by a Syk/ITAM Positive Feedback Loop," Mol Cell 10(5): 1057-69 (2002).
Rossi, A.B. et al., "Identification of the Syk kinase inhibitor R112 by a human mast cell screen," J Allergy Clin Immunol., 118:749-755, 2006.
Seidel et al., "Pharmaceutical intervention in the JAK/STAT signaling pathway," (2000), Oncogene 19:2645-2656.
Seow et al., "Piceatannol, a Syk-selective tyrosine kinase inhibitor, attenuated antigen challenge of guinea pig airways in vitro," European Journal of Pharmacology (2002) 443, 189-196.
Sudbeck et al., « Structure-based Design of Specific Inhibitors of Janus Kinase 3 as Apoptosis-inducing Antileukemic Agents, (1999), Clin. Cancer Res. 5:1569-1582.
Takata, M. et al., "Tyrosine kinases Lyn and Syk regulate B cell receptorcoupled Ca2+ mobilization through distinct pathways," EMBO J., 13:1341-1349, 1994.
Tobe et al., "Bioorganic and Medicinal Chemistry", Pergamon, 2003, vol. 11, pp. 3869-3878.
Trieu et al., "A Specific Inhibitor of Janus Kinase-3 Increases Survival in a Transgenic Mouse Model of Amyotrophic Lateral Sclerosis," (2000), Biochem Biophys. Res. Commun. 267:22-25.
Turhan et al., "Highly Purified Primitive Hematopoietic Stem Cells Are PML-RARA Negative and Generate Nonclonal Progenitors in Acute Promyelocytic Leukemia," 1995, Blood 85:2154-2161.
Turner et al., "Tyrosine kinase SYK: essential functions for immunoreceptor signaling," Immunology Today, (2000) 21:148-154.
Underhill, D.M. et al., "The many faces of ITAMs," Trends Immunol., 28(2):66-73, 2007.
Van Gurp et al., "The Effect of the JAK Inhibitor CP-690,550 on Peripheral Immune Parameters in Stable Kidney Allograft Patients," (2009) Transplantation 87:79-86.
Vlahovic, P. et al., "Dietary curcumin does not protect kidney in glycerol-induced acute renal failure," Food and Chemical Toxicology, 2007, 45:1777-1782.
Villaseñor, A.G. et al., "Structural Insights for Design of Potent Spleen Tyrosine Kinase Inhibitors from Crystallographic Analysis of Three Inhibitor Complexes," *Chem Biol Drug Des*, 2009, vol. 73, pp. 466-470.
Wossning, T. et.al., "Deregulated Syk inhibits differentiation and induces growth factor—independent proliferation of pre-B cells," JEM, 2006; 203:2829-2840.
Yousefi, S. et al., "Requirement of Lyn and Syk Tyrosine Kinases for the Prevention of Apoptosis by Cytokinesin Human Eosinophils," J. E. Med., 183:1407-1414, 1996.
Yu et al., "Constitutive Activation of the Janus Kinase STAT Pathway in T Lymphoma Overexpressing the Lck Protein Tyrosine Kinase," (1997), J. Immunol. 159:5206-5210.

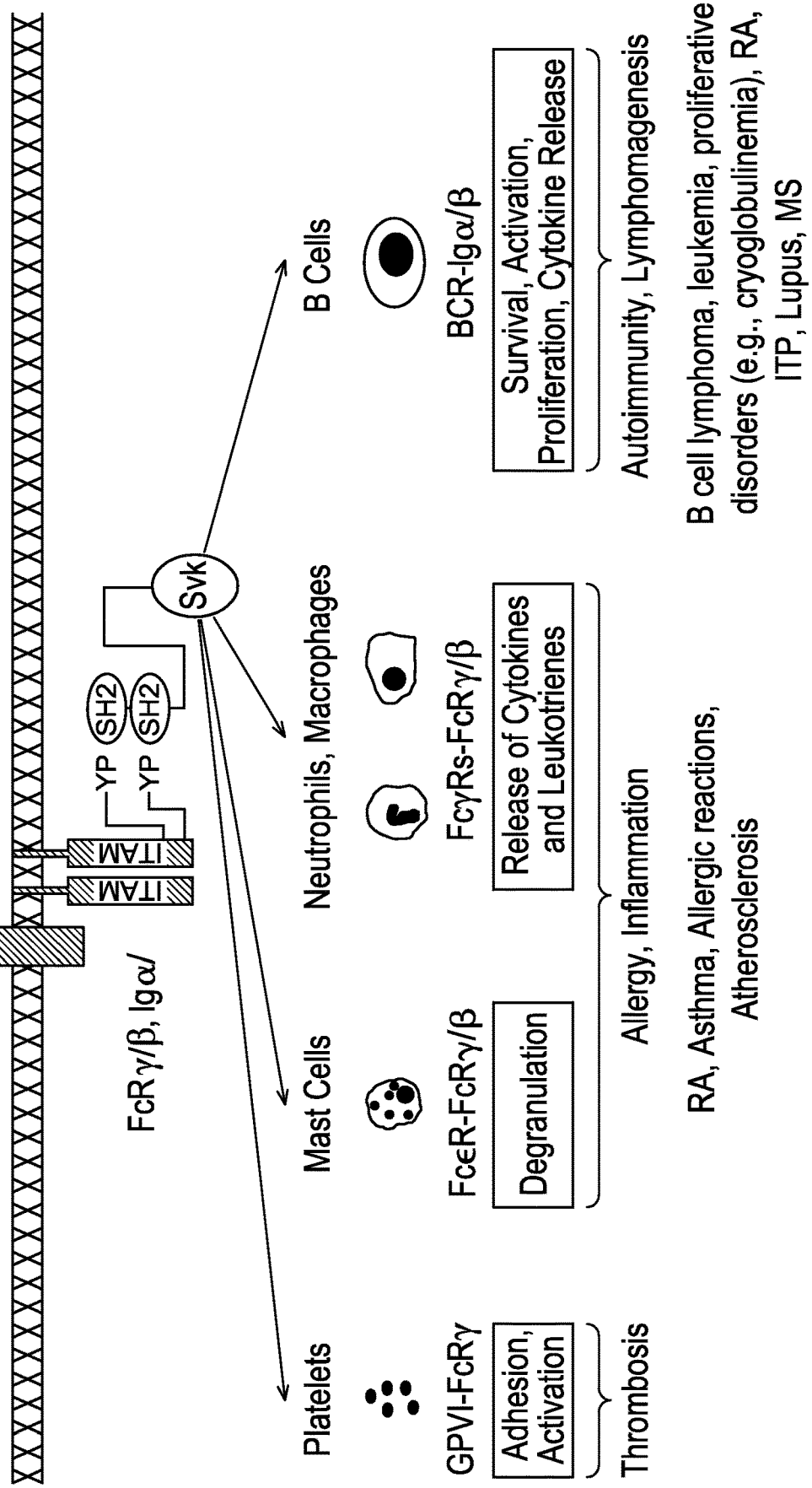

FIG. 4A
| Example No. | Structure | MW | MH+ | Syk IC50 Code |
|---|---|---|---|---|
| 400 | 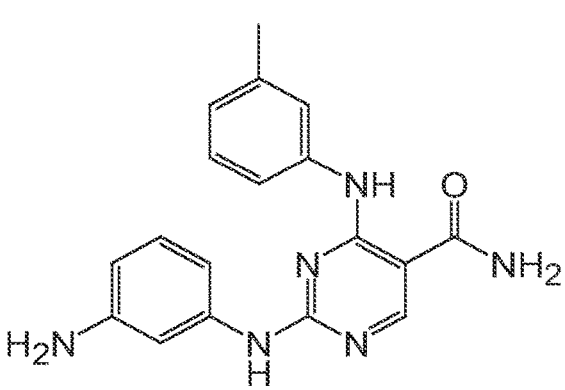 | 334.38 | 335.2 | +++ |
| 401 | 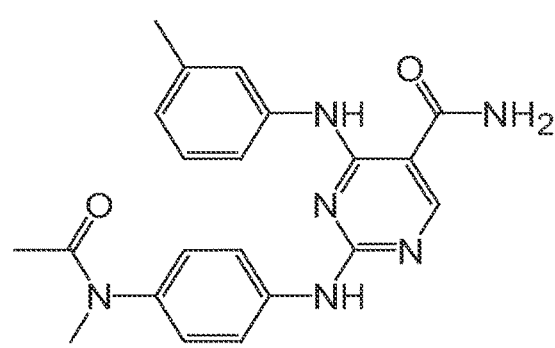 | 390.45 | 390.1 | ++ |
| 402 | 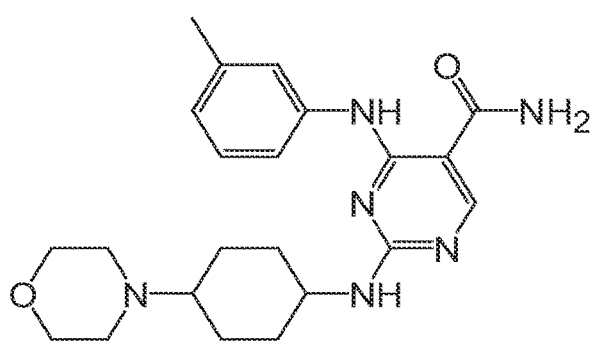 | 404.47 | 404.1 | ++ |

FIG. 4B

| Example No. | Structure | MW | MH+ | Syk IC50 Code |
|---|---|---|---|---|
| 403 | 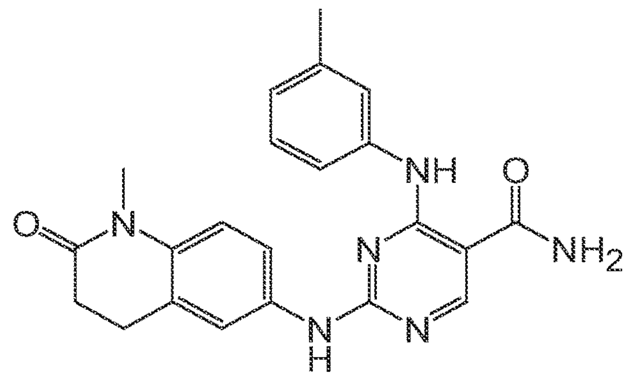 | 402.46 | 403.3 (M+1) | ++ |
| 404 | 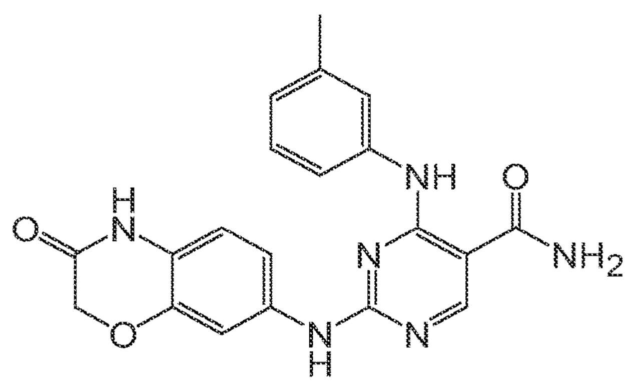 | 390.4 | 391.0 (M+1) | ++ |
| 405 | 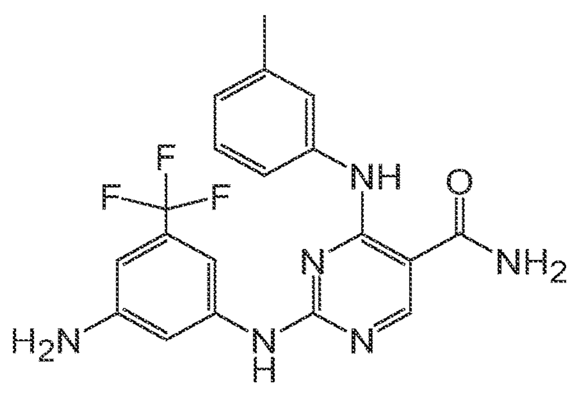 | 402.38 | 403.0 (M+1) | ++ |

FIG. 4C
| Example No. | Structure | MW | MH+ | Syk IC50 Code |
|---|---|---|---|---|
| 406 | 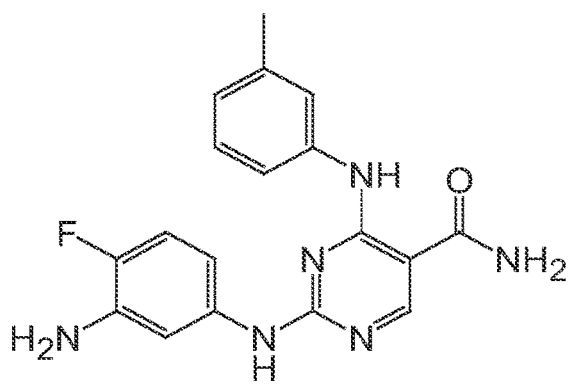 | 352.37 | 353.2 (M+1) | ++ |
| 407 | 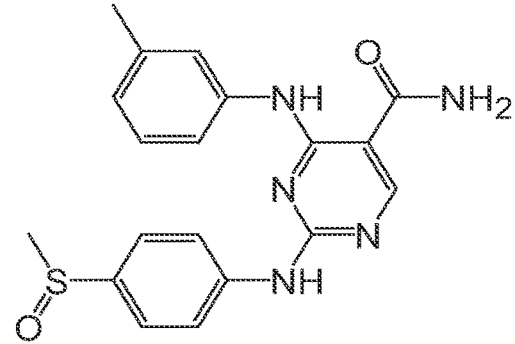 | 381.46 | 382.1 | ++ |
| 408 | 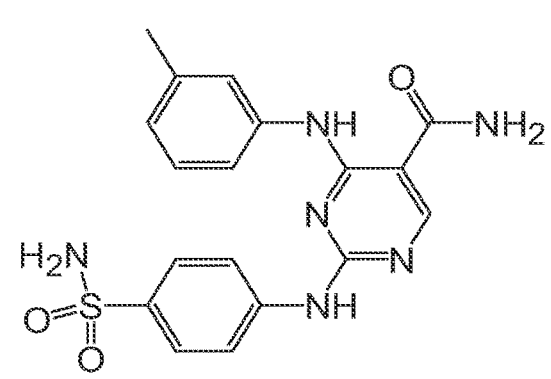 | 398.45 | 399.1 | ++ |

FIG. 4D
| Example No. | Structure | MW | MH+ | Syk IC50 Code |
|---|---|---|---|---|
| 409 | 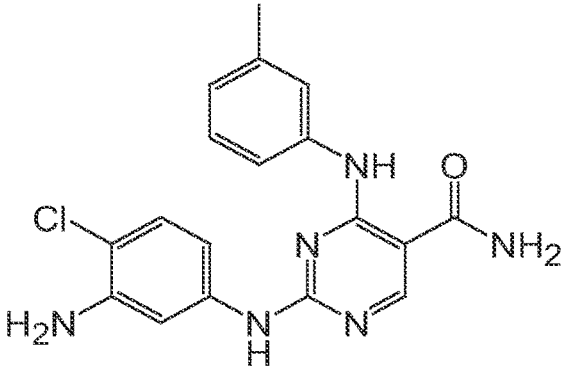 | 368.83 | 369.2 (M+1) | ++ |
| 410 | 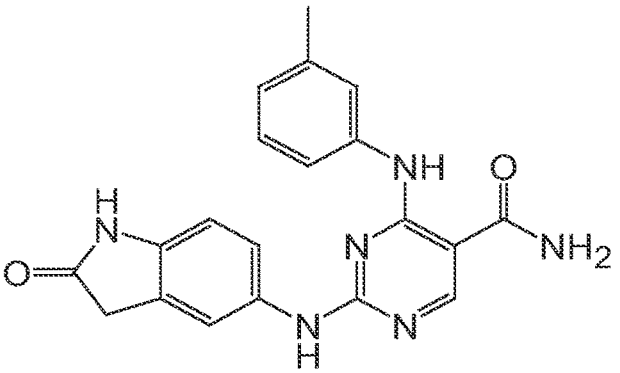 | 374.4 | 375.2 (M+1) | +++ |
| 411 | 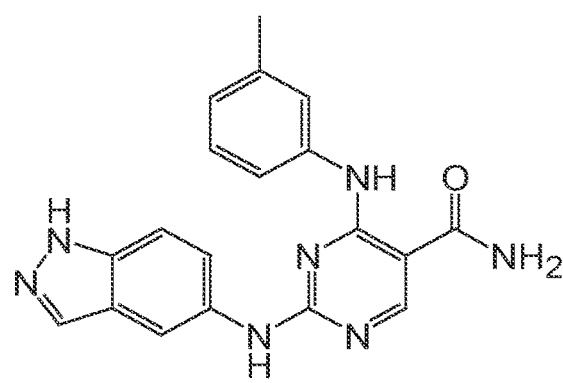 | 359.39 | 360.1 (M+1) | ++ |

FIG. 4E
| Example No. | Structure | MW | MH+ | Syk IC50 Code |
|---|---|---|---|---|
| 412 | 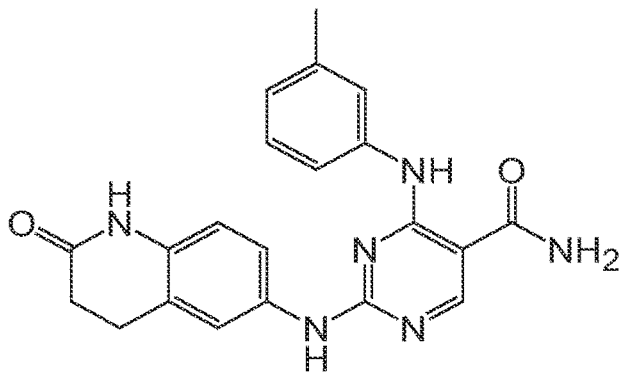 | 388.43 | 389.1 (M+1) | ++ |
| 413 | 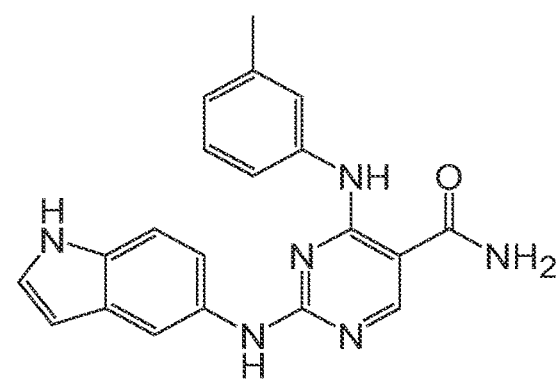 | 358.41 | 359.1 (M+1) | ++ |
| 414 | 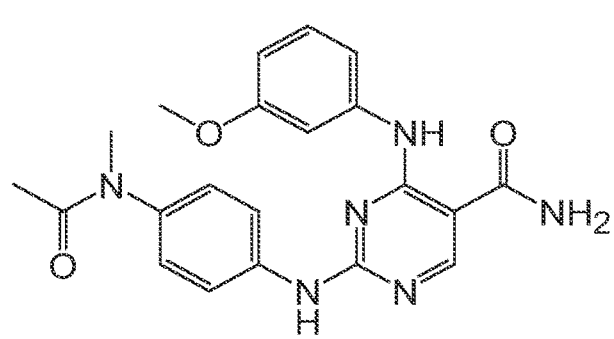 | 406.45 | 407.3 | ++ |

FIG. 4F
| Example No. | Structure | MW | MH+ | Syk IC50 Code |
|---|---|---|---|---|
| 415 | 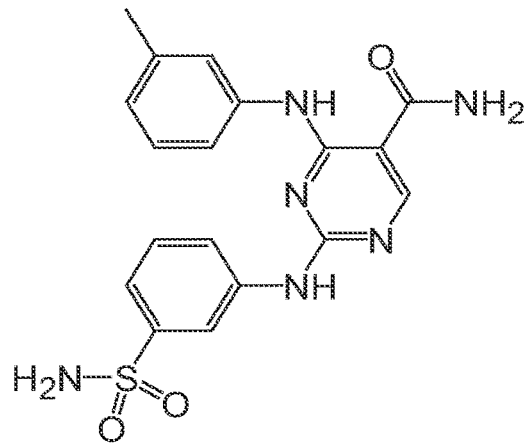 | 398.45 | 399.1 | ++ |
| 416 | 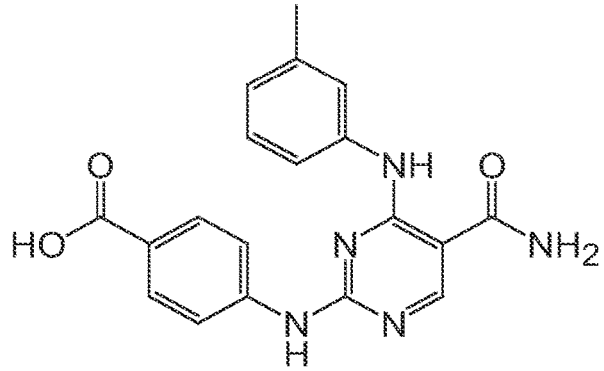 | 363.38 | 364.2 (M+1) | ++ |
| 417 | 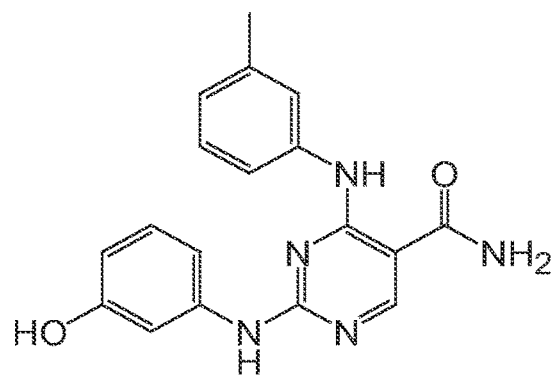 | 335.37 | 334.0 (M-1) | ++ |

FIG. 4G
| Example No. | Structure | MW | MH+ | Syk IC50 Code |
|---|---|---|---|---|
| 418 | 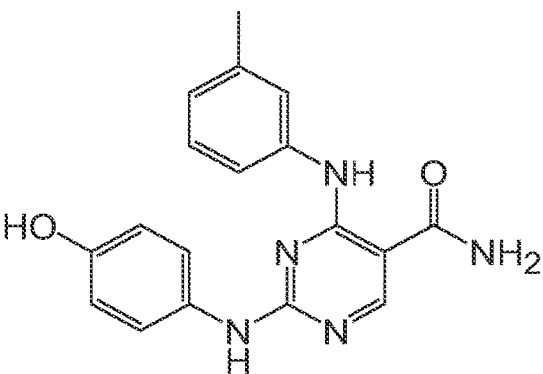 | 335.37 | 336.0 (M+1) | ++ |
| 419 | 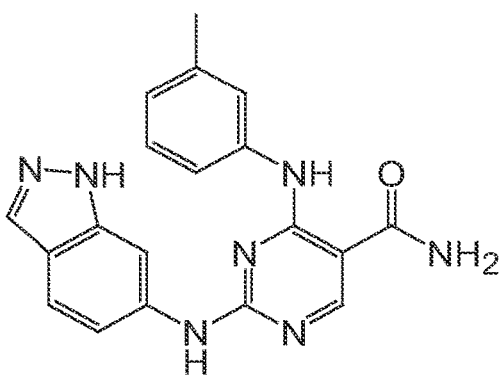 | 359.39 | 360.0 (M+1) | ++ |
| 420 | 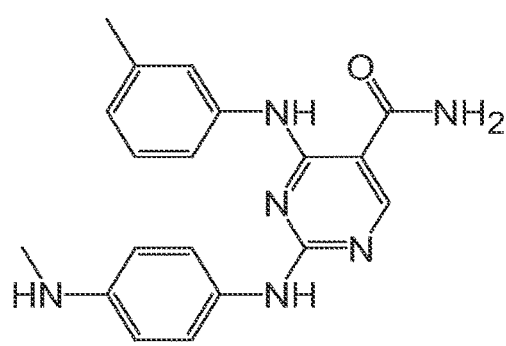 | 348.41 | 349 | ++ |

FIG. 4H
| Example No. | Structure | MW | MH+ | Syk IC50 Code |
|---|---|---|---|---|
| 421 | 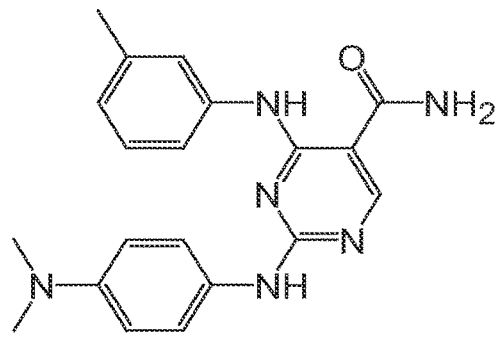 | 362.44 | 363 | ++ |
| 422 | 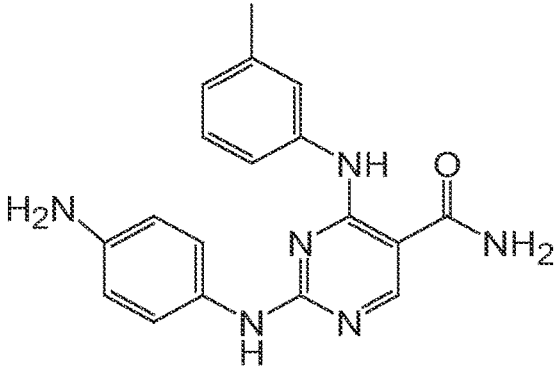 | 334.38 | 335.0 (M+1) | ++ |
| 423 | 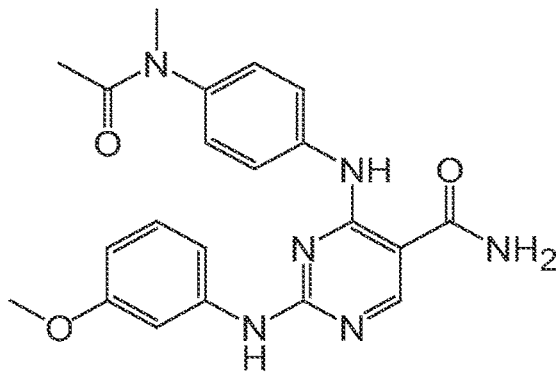 | 406.45 | 407 | ++ |

FIG. 4I

| Example No. | Structure | MW | MH+ | Syk IC50 Code |
|---|---|---|---|---|
| 424 | 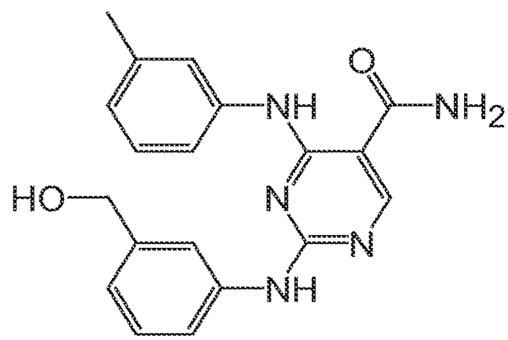 | 349.39 | 350 | ++ |
| 425 | 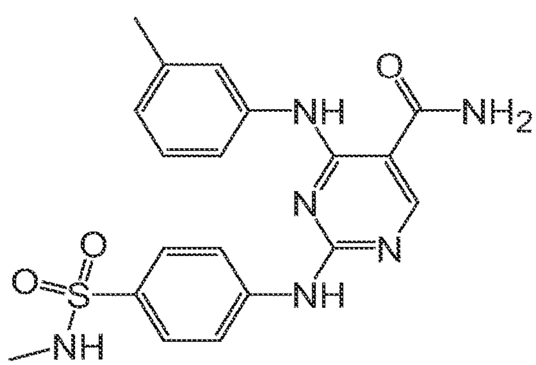 | 412.47 | 413 | ++ |
| 426 | 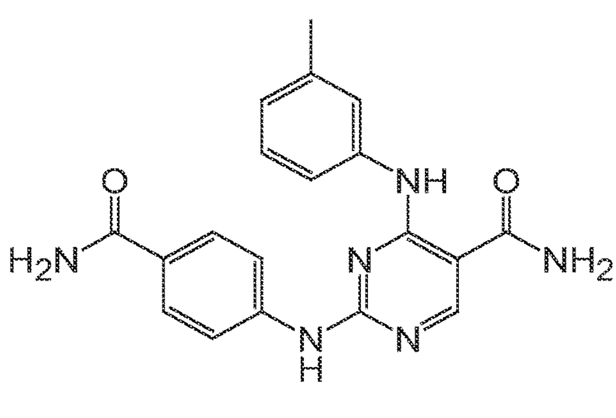 | 362.39 | 363.0 (M+1) | ++ |

FIG. 4J

| Example No. | Structure | MW | MH+ | Syk IC50 Code |
|---|---|---|---|---|
| 427 | 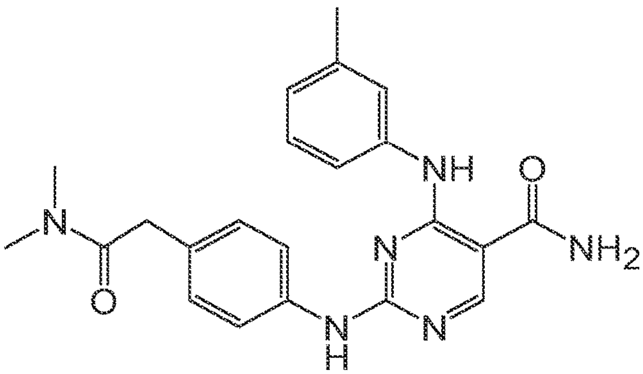 | 404.47 | 405.0 (M+1) | ++ |
| 428 | 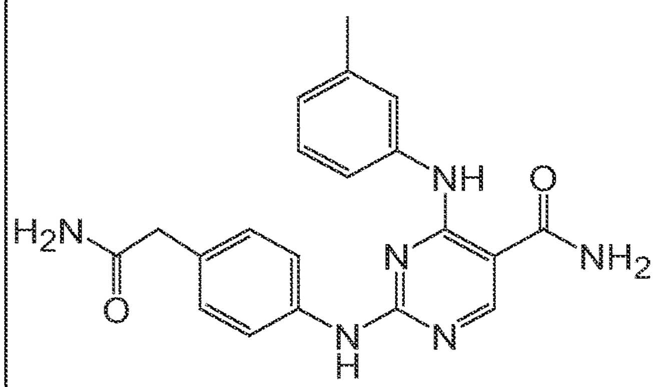 | 376.42 | 377.0 (M+1) | ++ |
| 429 | 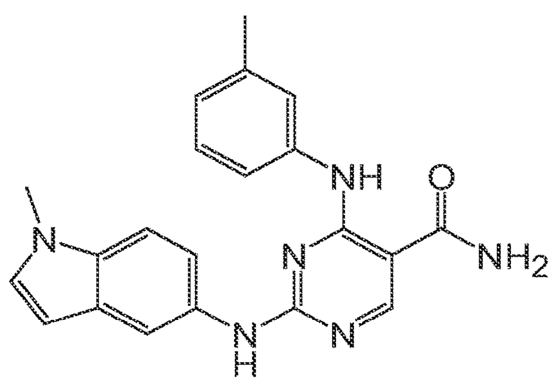 | 372.4 | 373.0 (M+1) | ++ |

FIG. 4K

| Example No. | Structure | MW | MH+ | Syk IC50 Code |
|---|---|---|---|---|
| 430 | 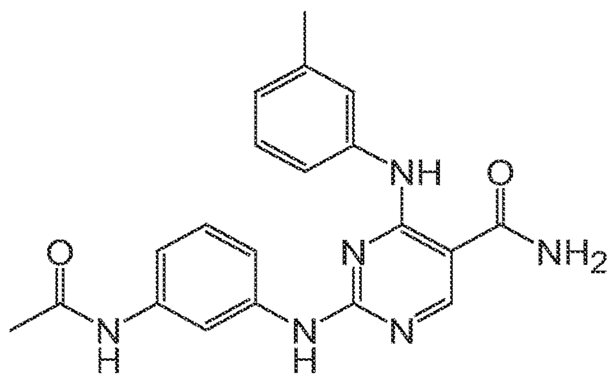 | 376.42 | 377.0 (M+1) | ++ |
| 431 | 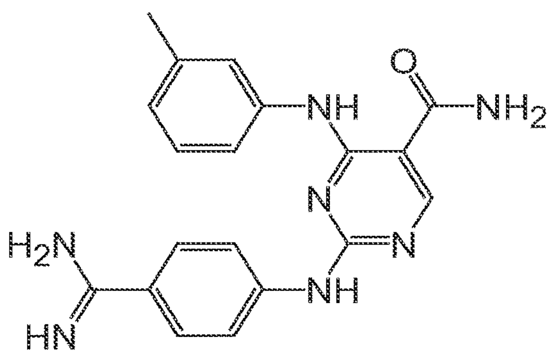 | 361.41 | 362 | ++ |
| 432 | 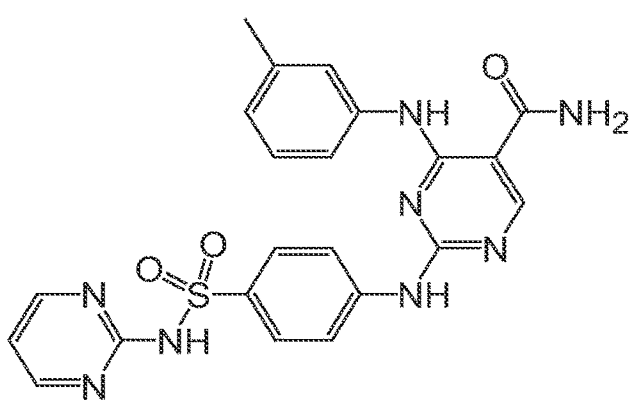 | 476.52 | 477 | ++ |

FIG. 4L

| Example No. | Structure | MW | MH+ | Syk IC50 Code |
|---|---|---|---|---|
| 433 | 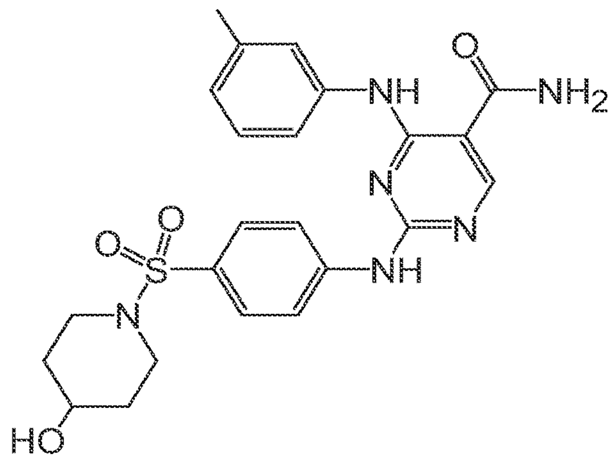 | 482.56 | 483 | ++ |
| 434 | 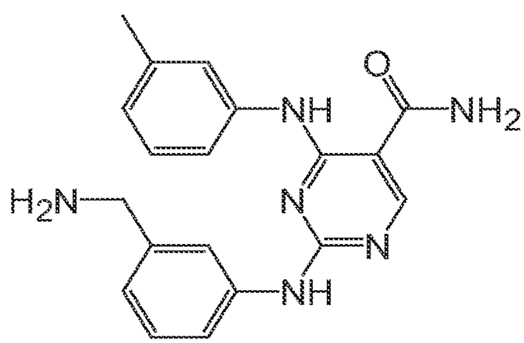 | 348.41 | 349 | ++ |
| 435 | 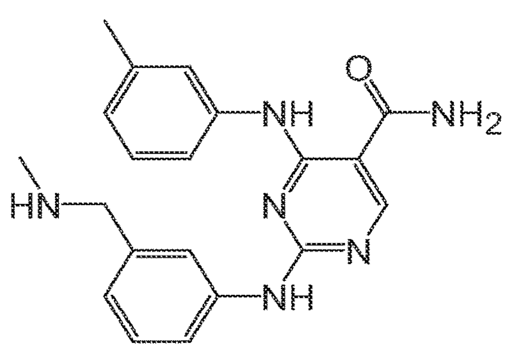 | 362.44 | 363 | ++ |

FIG. 4M

| Example No. | Structure | MW | MH+ | Syk IC50 Code |
|---|---|---|---|---|
| 436 | 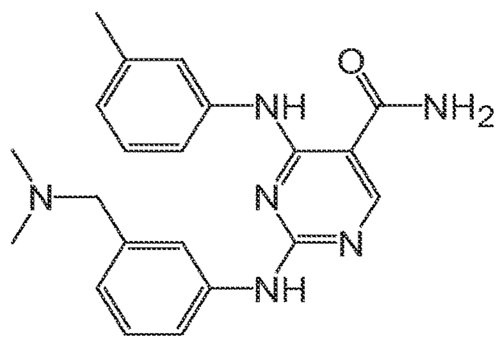 | 376.46 | 377 | ++ |
| 437 | 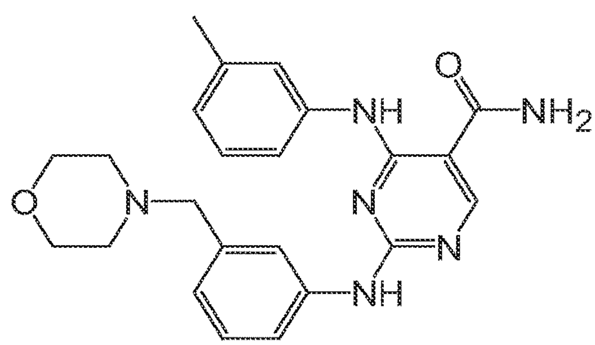 | 418.5 | 419 | ++ |
| 438 | 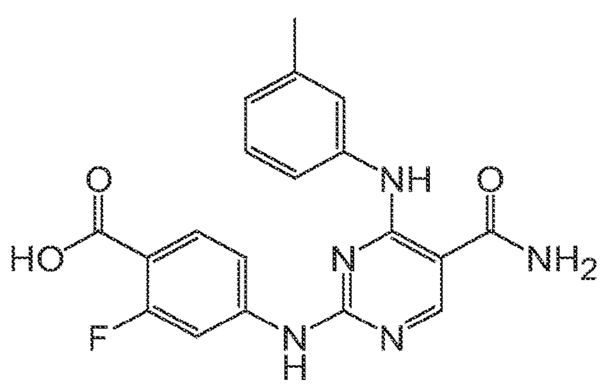 | 381.37 | 382.1 (M+1) | ++ |

FIG. 4N

| Example No. | Structure | MW | MH+ | Syk IC50 Code |
|---|---|---|---|---|
| 439 | 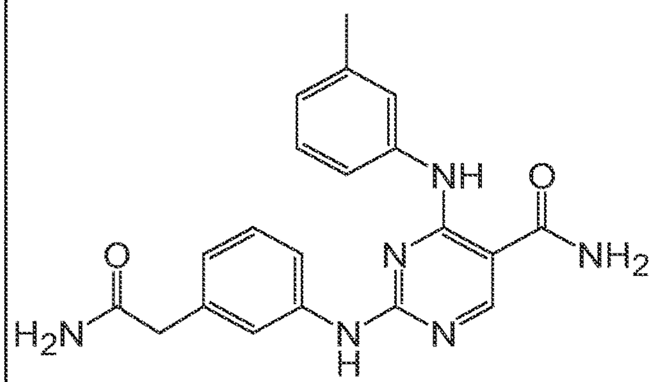 | 376.42 | 377.1 (M+1) | ++ |
| 440 | 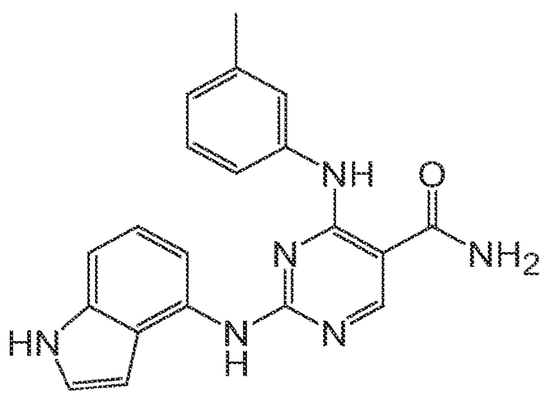 | 358.41 | 359.0 (M+1) | ++ |
| 441 | 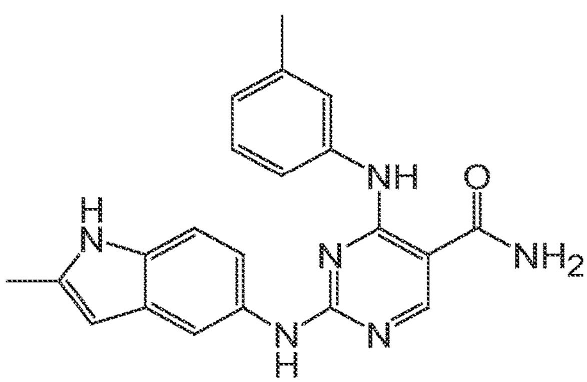 | 372.43 | 373.0 (M+1) | ++ |

FIG. 4O
| Example No. | Structure | MW | MH+ | Syk IC50 Code |
|---|---|---|---|---|
| 442 | 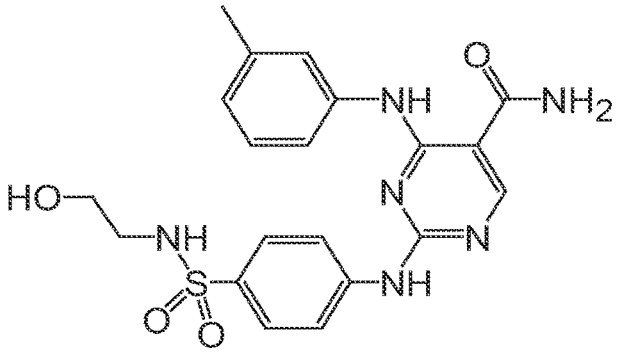 | 442.5 | 443 | ++ |
| 443 | 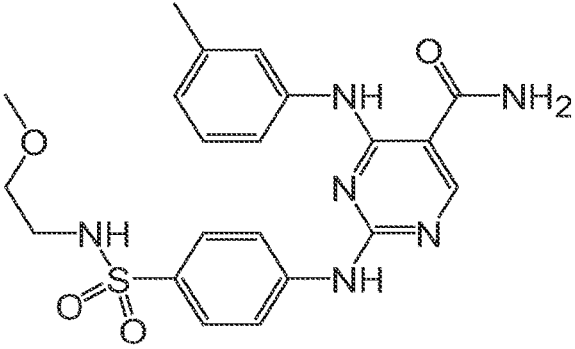 | 456.53 | 457 | ++ |
| 444 | 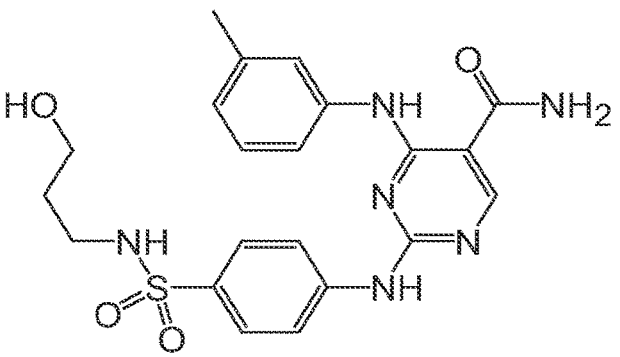 | 456.53 | 457 | ++ |

FIG. 4P
| Example No. | Structure | MW | MH+ | Syk IC50 Code |
|---|---|---|---|---|
| 445 | 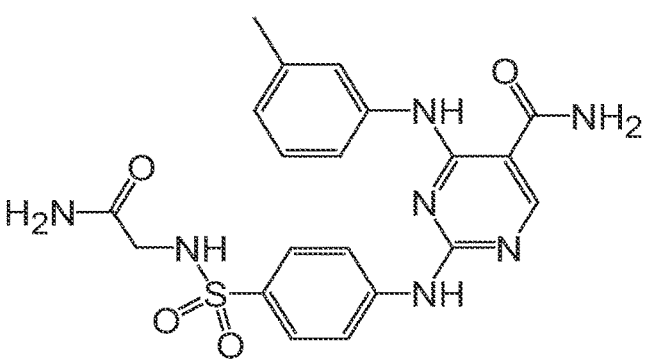 | 455.5 | 456 | ++ |
| 446 | 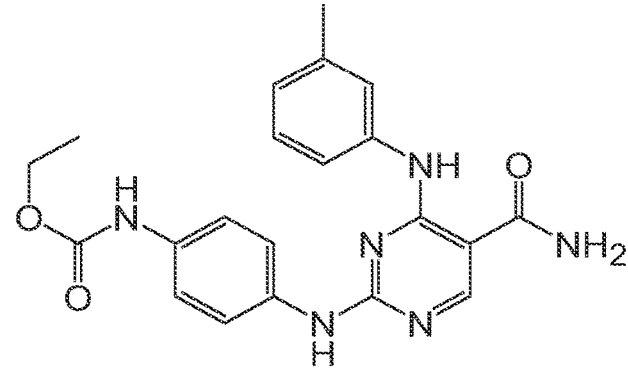 | 422.45 | 423.0 (M+1) | ++ |
| 447 | 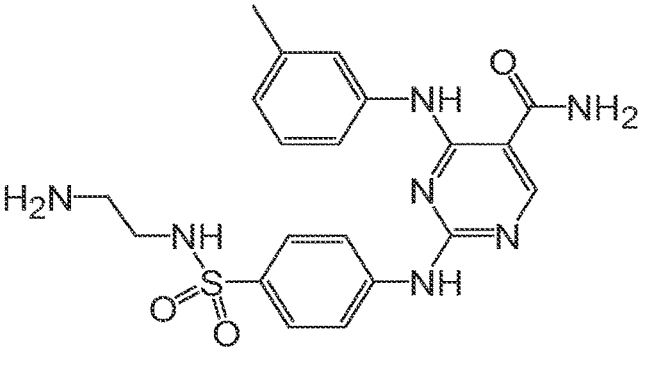 | 441.51 | 442.1 | ++ |

FIG. 4Q
| Example No. | Structure | MW | MH+ | Syk IC50 Code |
|---|---|---|---|---|
| 448 | 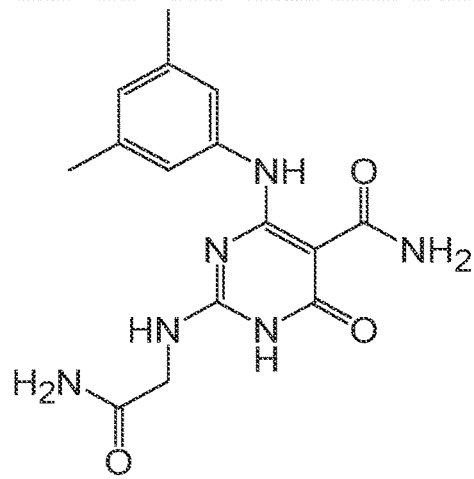 | | | +++ |
| 449 | 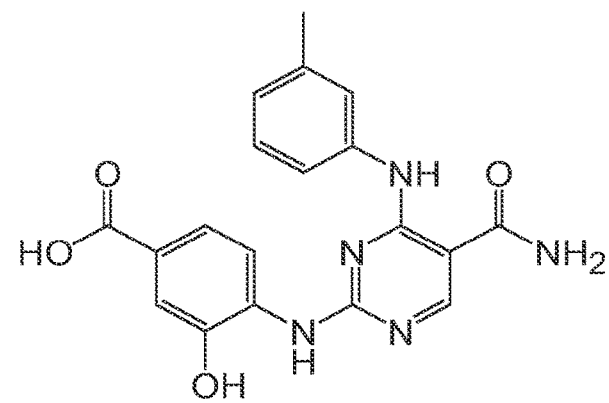 | 379.38 | 380.0 (M+1) | ++ |
| 450 | 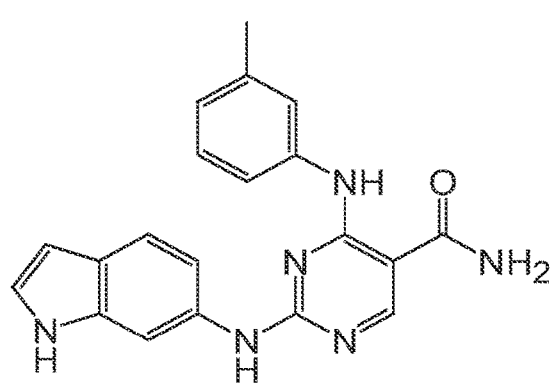 | 358.41 | 359.0 (M+1) | ++ |

FIG. 4R

| Example No. | Structure | MW | MH+ | Syk IC50 Code |
|---|---|---|---|---|
| 451 | 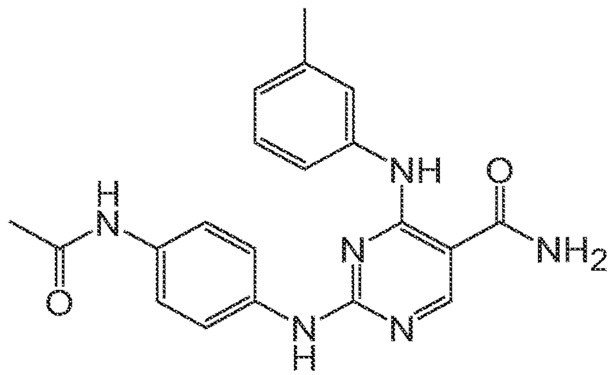 | 376.42 | 377.0 (M+1) | ++ |
| 452 | 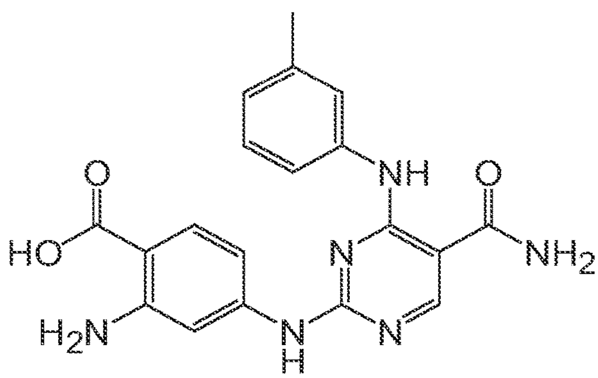 | 378.39 | 379.0 (M+1) | +++ |
| 453 | 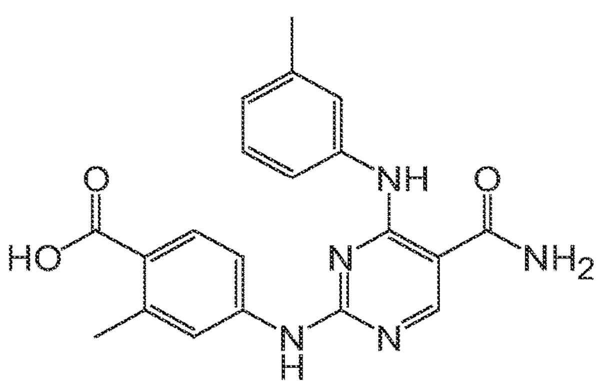 | 377.4 | 378.2 (M+1) | ++ |

FIG. 4S
| Example No. | Structure | MW | MH+ | Syk IC50 Code |
|---|---|---|---|---|
| 454 | 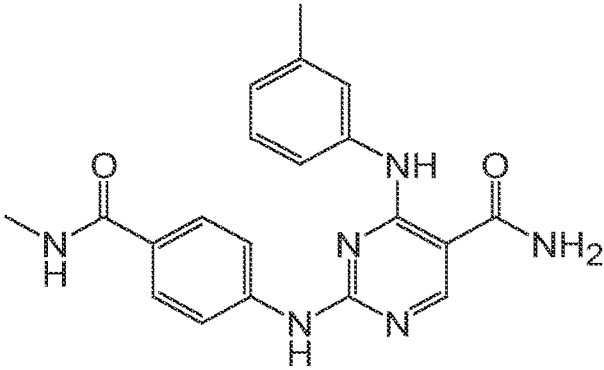 | 376.42 | 377.0 (M+1) | ++ |
| 455 | 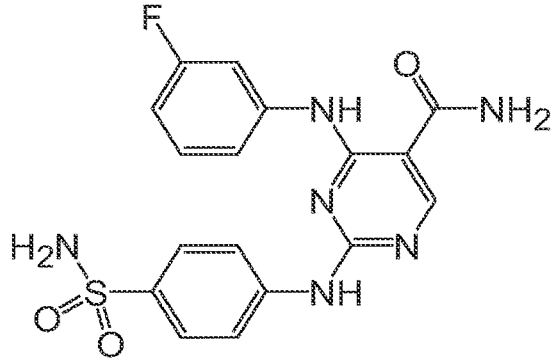 | 402.41 | 403 | ++ |
| 456 | 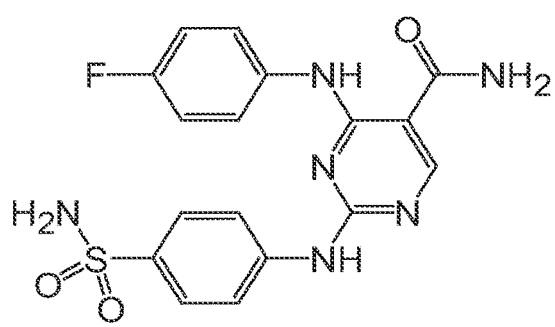 | 402.4 | 403 | ++ |

FIG. 4T

| Example No. | Structure | MW | MH+ | Syk IC50 Code |
|---|---|---|---|---|
| 457 | 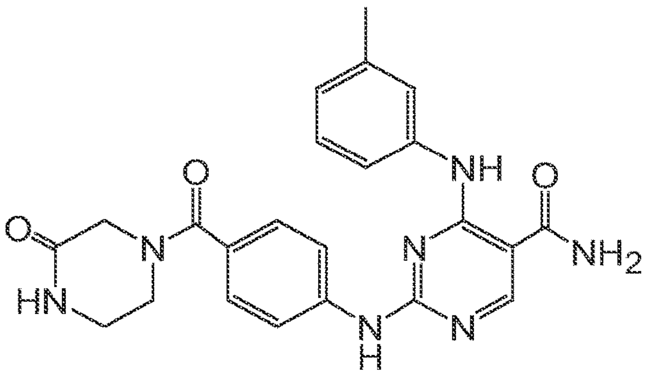 | 445.48 | 446.4 (M+1) | ++ |
| 458 | 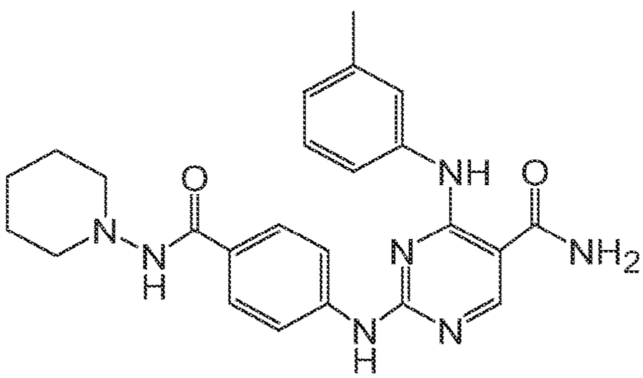 | 445.53 | 446.5 (M+1) | ++ |
| 459 | 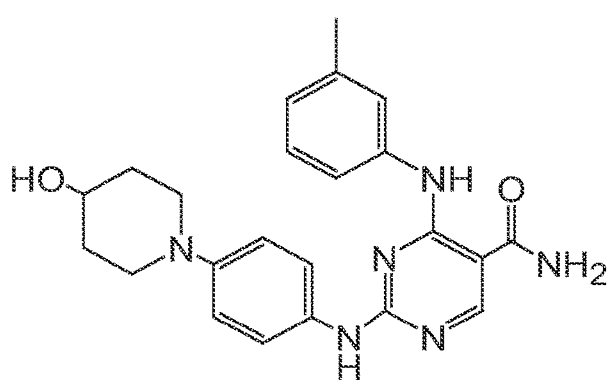 | 418.5 | 419.4 (M+1) | ++ |

FIG. 4U
| Example No. | Structure | MW | MH+ | Syk IC50 Code |
|---|---|---|---|---|
| 460 | 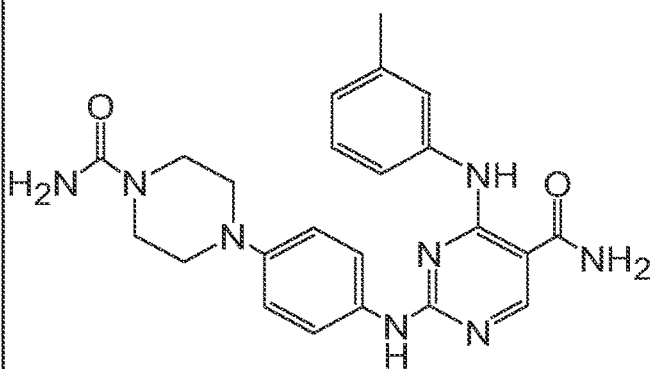 | 446.52 | 447.3 (M+1) | ++ |
| 461 | 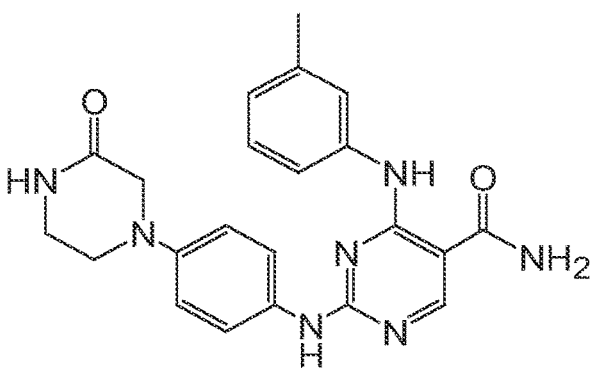 | 417.47 | 418.0 (M+1) | ++ |
| 462 | 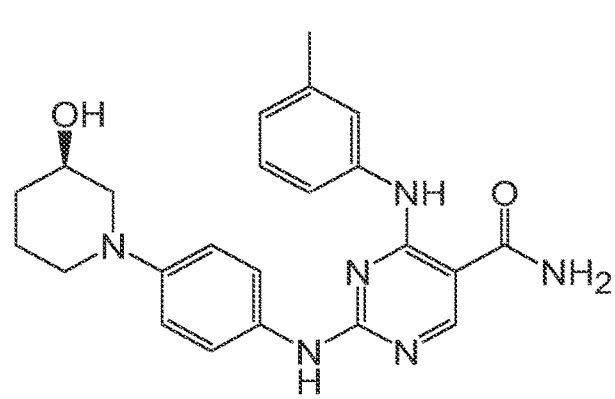 | 418.5 | 419.2 (M+1) | ++ |

FIG. 4V
| Example No. | Structure | MW | MH+ | Syk IC50 Code |
|---|---|---|---|---|
| 463 | 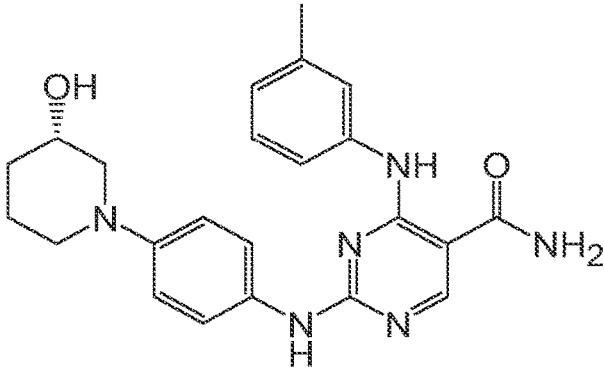 | 418.5 | 419.2 (M+1) | ++ |
| 464 | 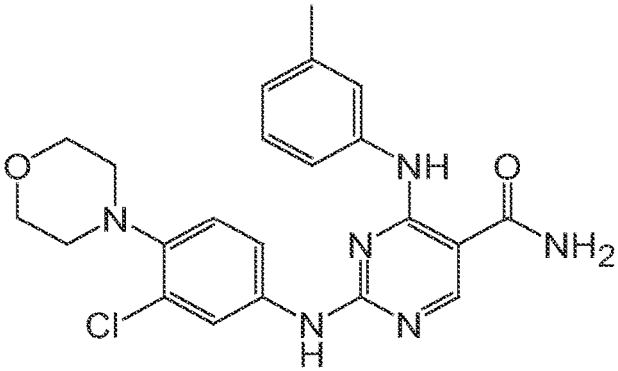 | 438.92 | 439.2 (M+1) | ++ |
| 465 | 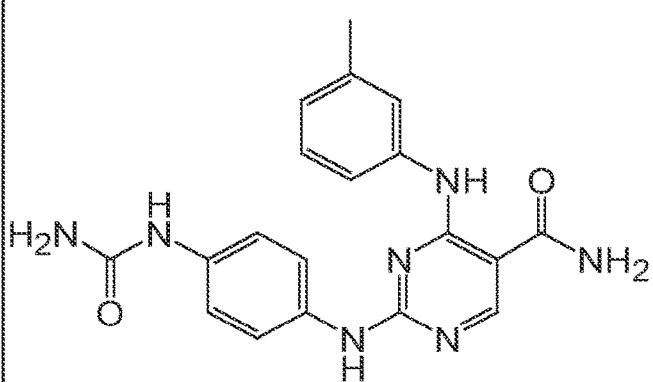 | 377.41 | 378.2 (M+1) | ++ |

FIG. 4W

| Example No. | Structure | MW | MH+ | Syk IC50 Code |
|---|---|---|---|---|
| 466 | 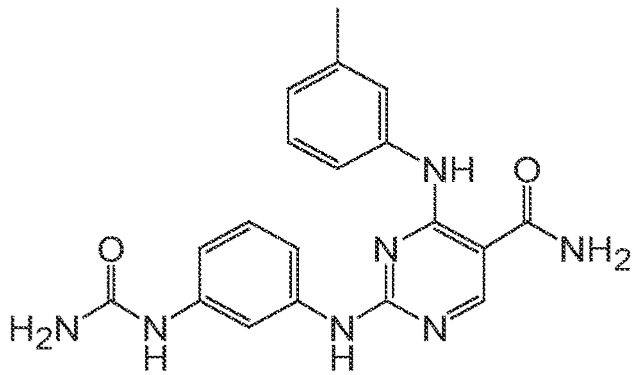 | 377.41 | 378.2 (M+1) | ++ |
| 467 | 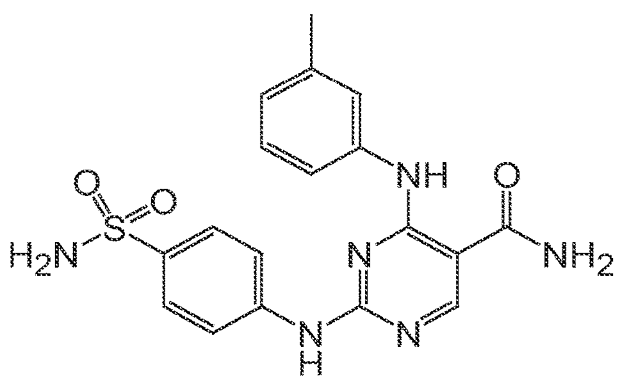 | 414.44 | MS+ 415 | ++ |
| 468 | 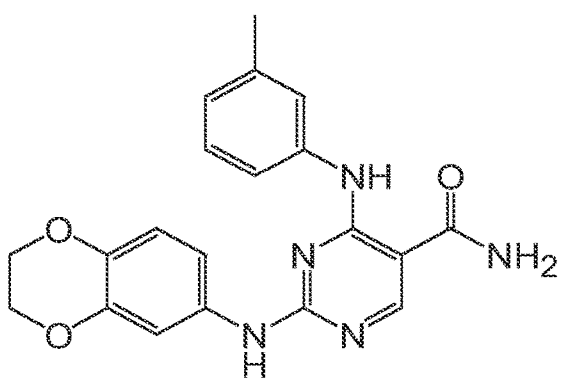 | 377.4 | 378.2 379.2 | ++ |

FIG. 4X

| Example No. | Structure | MW | MH+ | Syk IC50 Code |
|---|---|---|---|---|
| 469 | 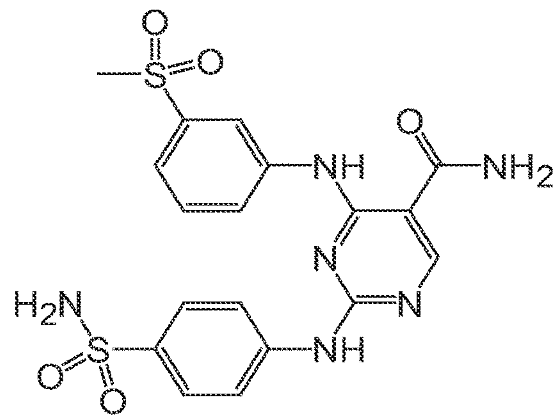 | 462.51 | 463.2 | ++ |
| 470 | 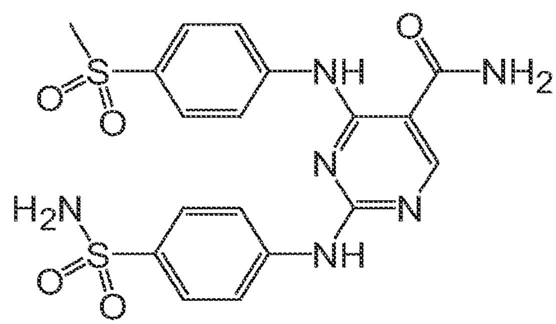 | 462.51 | 463.2 | +++ |
| | | | | |

FIG. 5A
| Example No. | Structure | MW | MH+ | Syk IC50 Code |
|---|---|---|---|---|
| 471 | 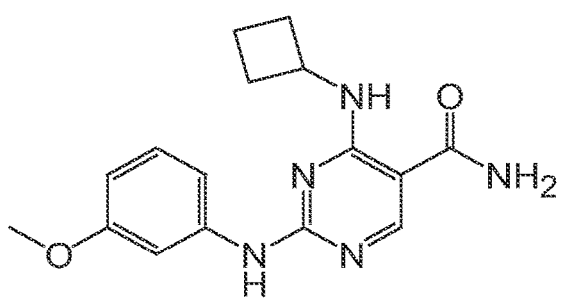 | 313.36 | 314.3 | ++ |
| 472 | 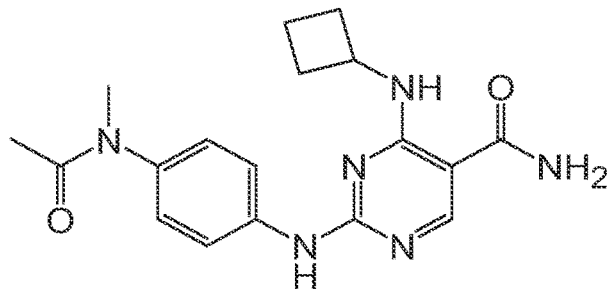 | 354.41 | 355.2 | +++ |
| 473 | 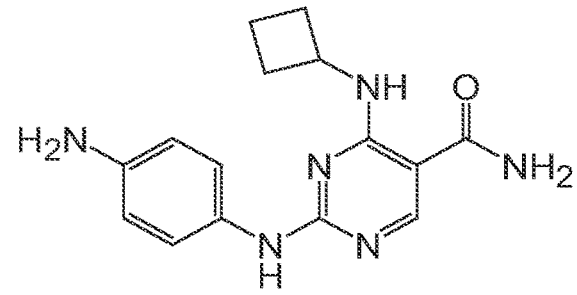 | 298.35 | 299.3 | ++ |

FIG. 5B

| Example No. | Structure | MW | MH+ | Syk IC50 Code |
|---|---|---|---|---|
| 474 | 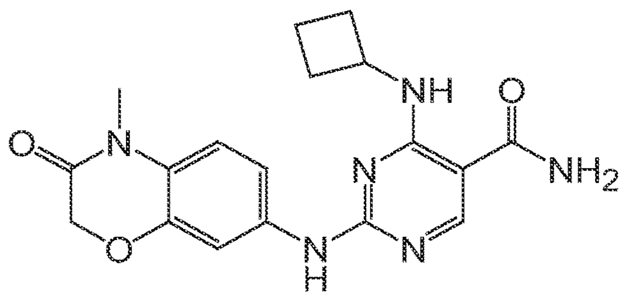 | 368.4 | 369 | ++ |
| 475 | 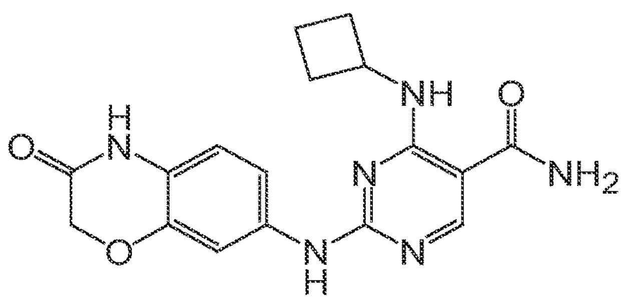 | 352.4 | 353 | +++ |
| 476 | 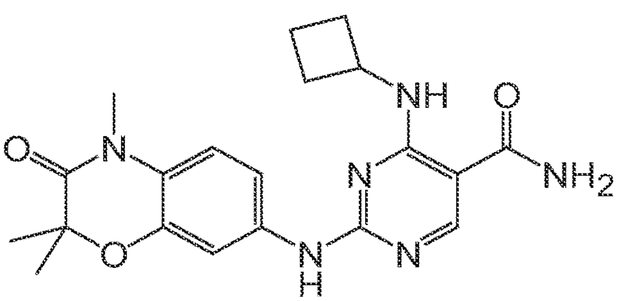 | 396.45 | 397 | ++ |

FIG. 5C

| Example No. | Structure | MW | MH+ | Syk IC50 Code |
|---|---|---|---|---|
| 477 | 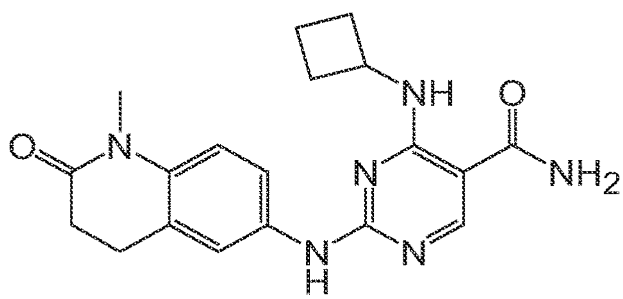 | 366.43 | 367 | +++ |
| 478 | 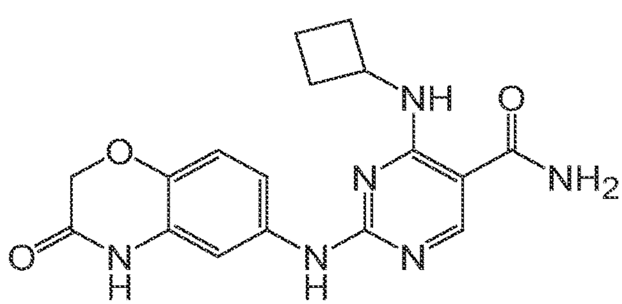 | 354.37 | 355 | +++ |
| 479 | 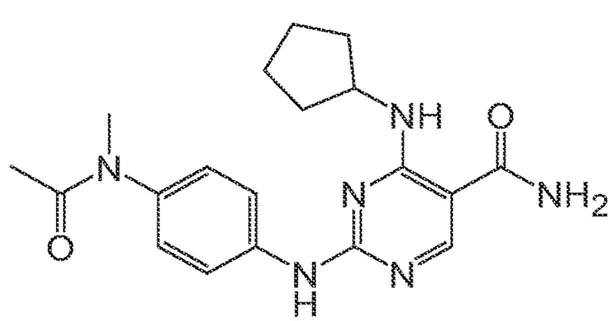 | 368.44 | 369 | ++ |

FIG. 5D

| Example No. | Structure | MW | MH+ | Syk IC50 Code |
|---|---|---|---|---|
| 480 | 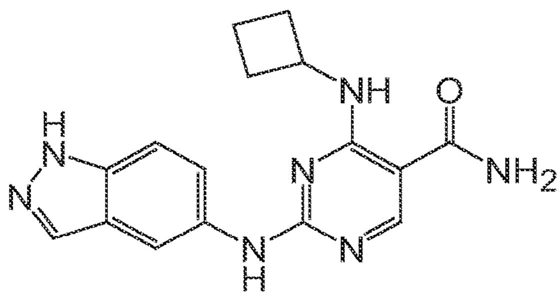 | 323.36 | 324 | +++ |
| 481 | 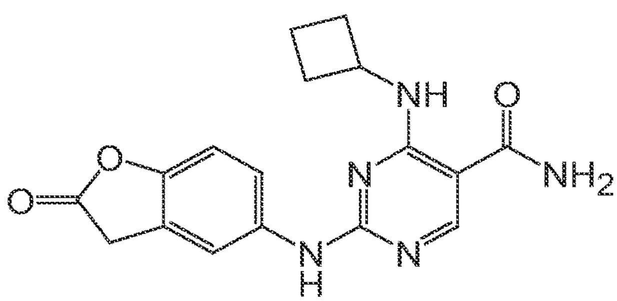 | 339.36 | 340 | ++ |
| 482 | 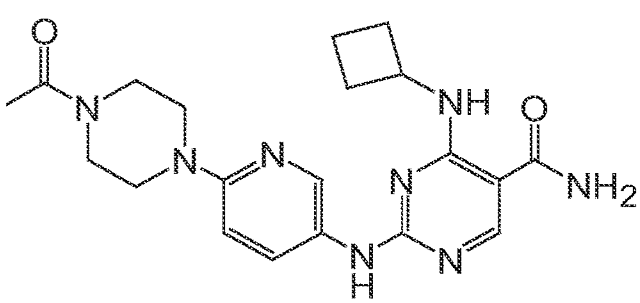 | 410.48 | 411 | ++ |

FIG. 5E

| Example No. | Structure | MW | MH+ | Syk IC50 Code |
|---|---|---|---|---|
| 483 | 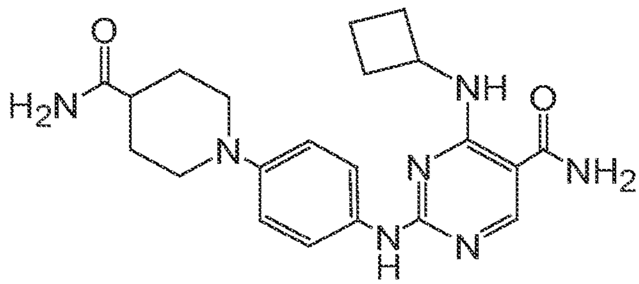 | 409.49 | 410.2 | +++ |
| 484 | 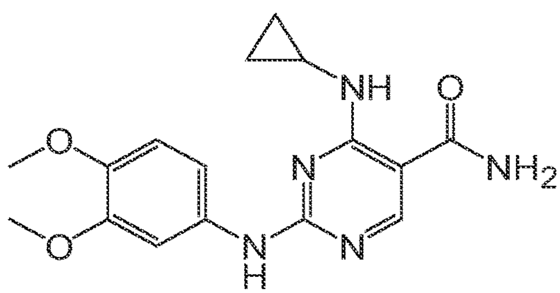 | 329.36 | 330.1 (M+1) | ++ |
| 485 | 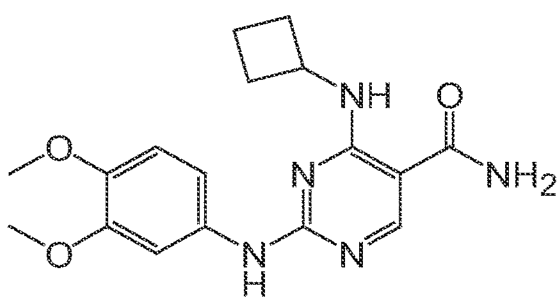 | 343.39 | 344.1 (M+1) | ++ |

FIG. 5F

| Example No. | Structure | MW | MH+ | Syk IC50 Code |
|---|---|---|---|---|
| 486 | 4-(cyclopropylamino)-2-((3-(methylsulfinyl)phenyl)amino)pyrimidine-5-carboxamide | 331.4 | 332.1 | ++ |
| 487 | 4-(cyclopropylamino)-2-((3-(methylsulfonyl)phenyl)amino)pyrimidine-5-carboxamide | 347.4 | 348.1 | ++ |
| 488 | 2-(benzo[d]thiazol-6-ylamino)-4-(cyclopropylamino)pyrimidine-5-carboxamide | 326.38 | 327.1 | +++ |

FIG. 5G
| Example No. | Structure | MW | MH+ | Syk IC50 Code |
|---|---|---|---|---|
| 489 | 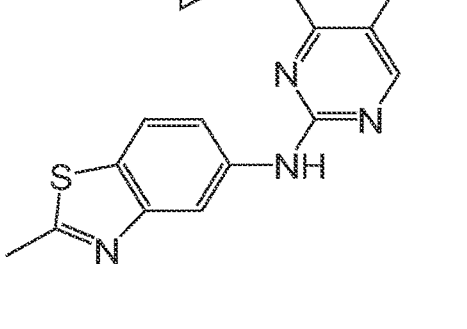 | 340.41 | 341 | ++ |
| 490 | 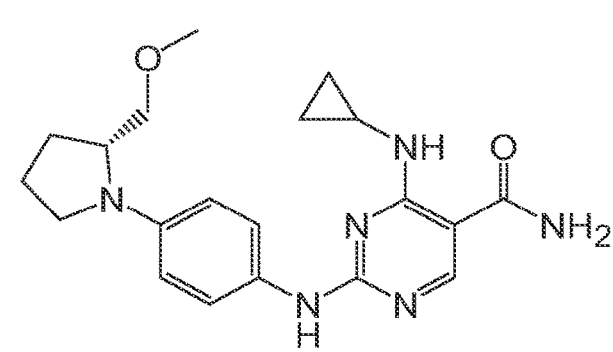 | 382.47 | 383.3 | +++ |
| 491 | 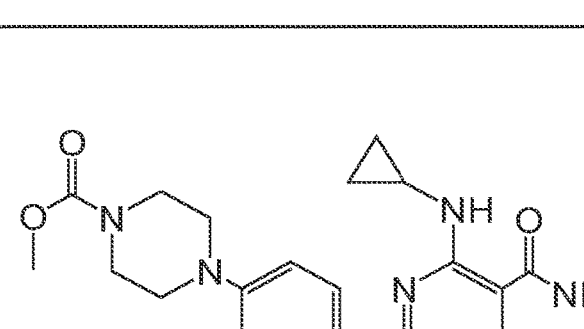 | 411.47 | 412.3 | +++ |

FIG. 5H

| Example No. | Structure | MW | MH+ | Syk IC50 Code |
|---|---|---|---|---|
| 492 | 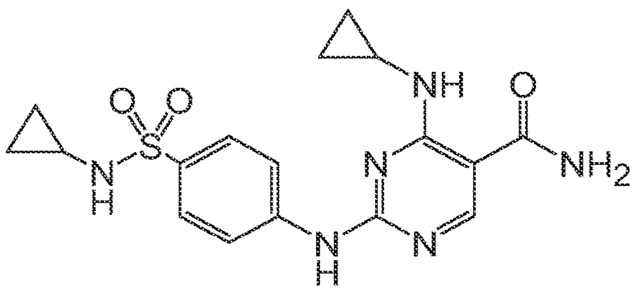 | 388.45 | M+1= 389 | +++ |
| 493 | 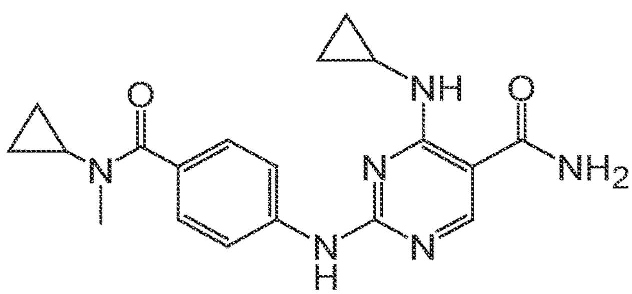 | 366.43 | M+1= 367 | ++ |
| 494 | 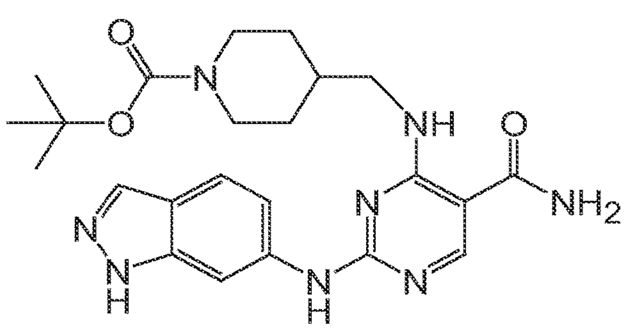 | 466.55 | 467.38 | +++ |

FIG. 5I

| Example No. | Structure | MW | MH+ | Syk IC50 Code |
|---|---|---|---|---|
| 495 | 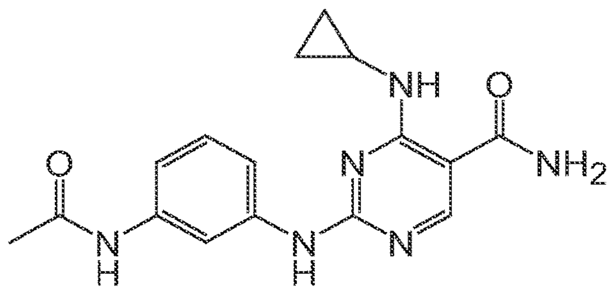 | 326.36 | 327.3 327.4 | +++ |
| 496 | 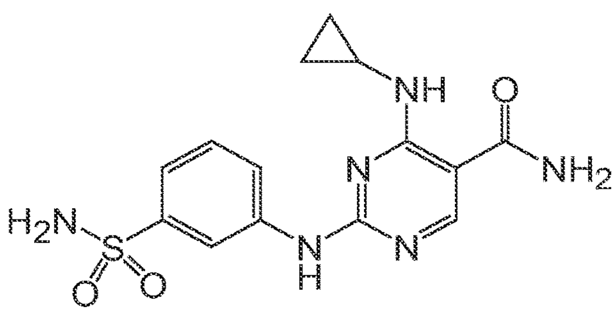 | 348.39 | 349.4 | ++ |
| 497 | 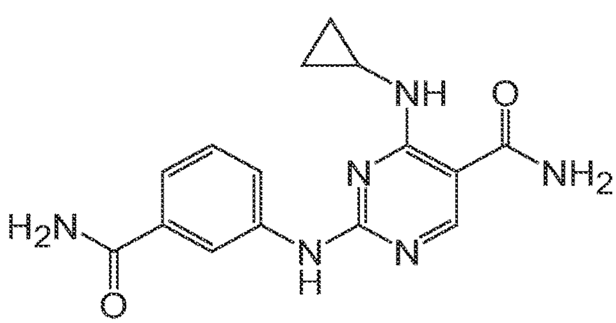 | 312.33 | 313.4 | +++ |

FIG. 5J
| Example No. | Structure | MW | MH+ | Syk IC50 Code |
|---|---|---|---|---|
| 498 | 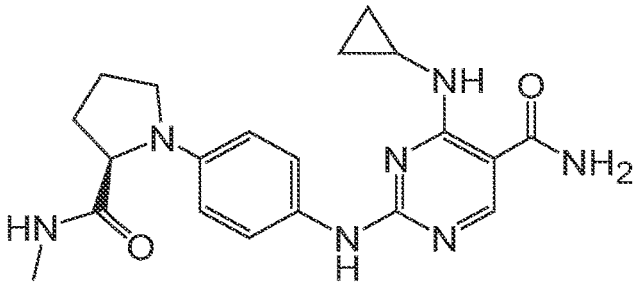 | 395.47 | ES(+) MS [M+1]= 396 | ++ |
| 499 | 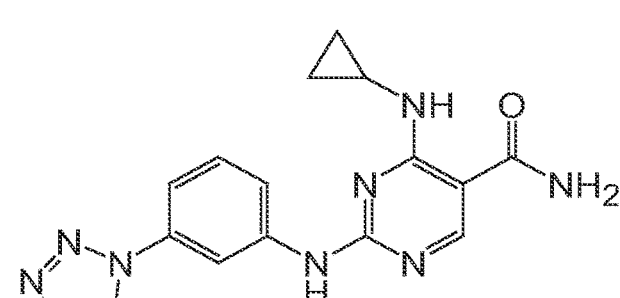 | 337.35 | MS: 338.4 (M+H) | +++ |
| 500 | 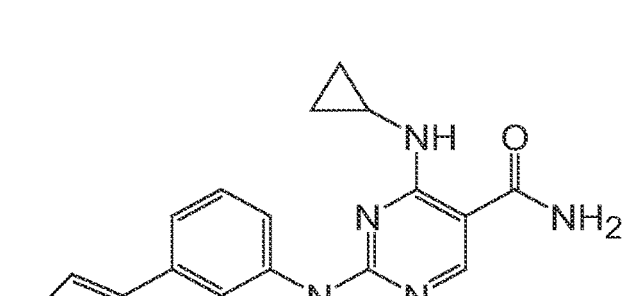 | 336.36 | MS: 337.4 (M+H) | +++ |

FIG. 5K
| Example No. | Structure | MW | MH+ | Syk IC50 Code |
|---|---|---|---|---|
| 501 | 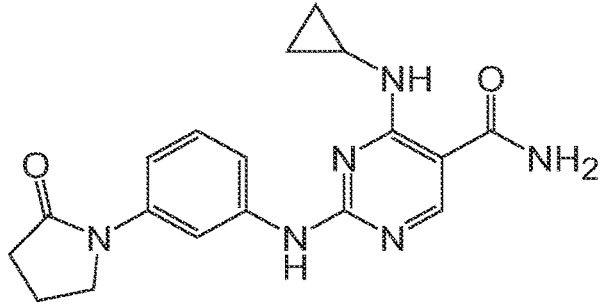 | 352.4 | MS: 353.5 (M+H) | ++ |
| 502 | 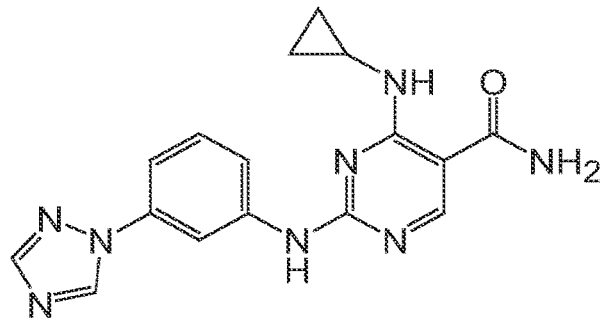 | 336.36 | MS: 337.4 (M+H) | +++ |
| 503 | 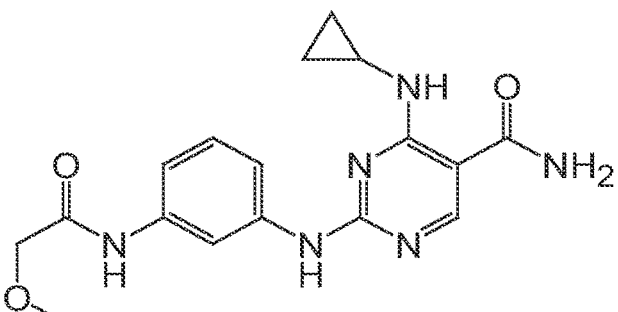 | 356.39 | 357.5 | ++ |

FIG. 5L

| Example No. | Structure | MW | MH+ | Syk IC50 Code |
|---|---|---|---|---|
| 504 | (structure) | 342.36 | 343.4 | +++ |
| 505 | (structure) | 440.5 | 441.4 | + |
| 506 | (structure) | 340.39 | 341.4 | ++ |

FIG. 5M

| Example No. | Structure | MW | MH+ | Syk IC50 Code |
|---|---|---|---|---|
| 507 | 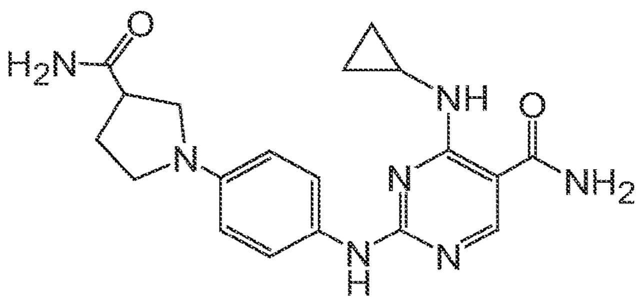 | 381.44 | 382.5 | ++ |
| 508 | 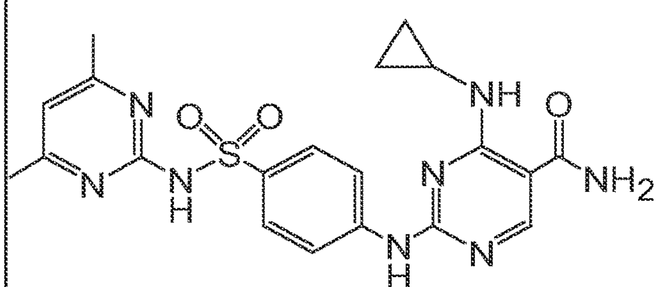 | 454.51 | 455.5 | ++ |
| 509 | 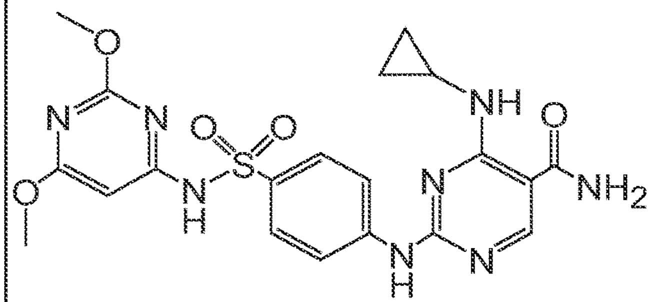 | 486.51 | 487.4 | +++ |

FIG. 5N
| Example No. | Structure | MW | MH+ | Syk IC50 Code |
|---|---|---|---|---|
| 510 | 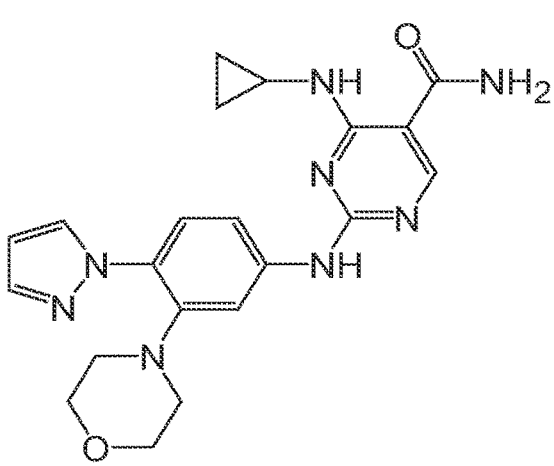 | 420.48 | 421.4 | ++ |
| 511 | 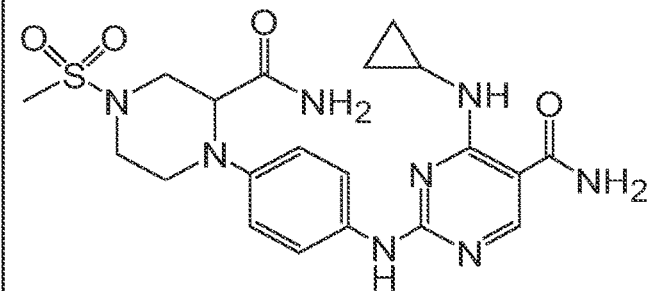 | 474.54 | 475.3 | +++ |
| 512 | 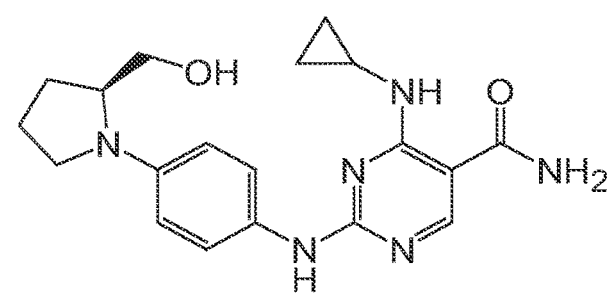 | 368.44 | 369.4 | ++ |

FIG. 5O

| Example No. | Structure | MW | MH+ | Syk IC50 Code |
|---|---|---|---|---|
| 513 | 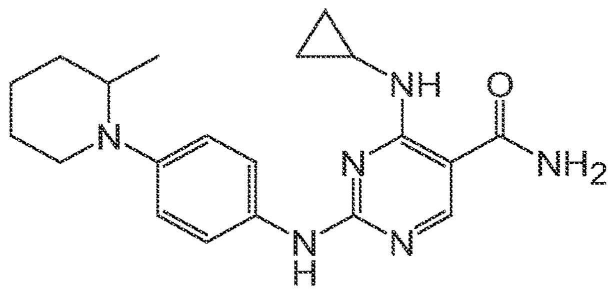 | 366.47 | 367.4 | ++ |
| 514 | 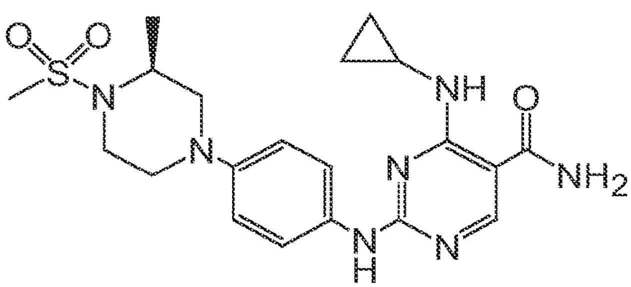 | 445.55 | 446.3 | +++ |
| 515 | 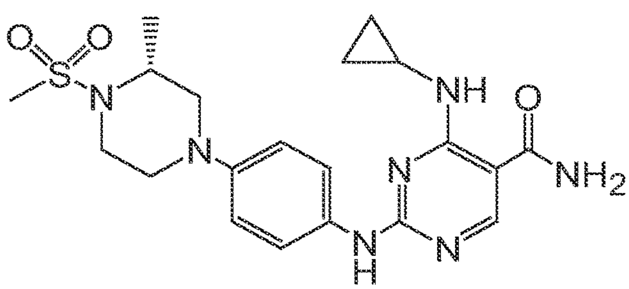 | 445.55 | 446.3 | +++ |

FIG. 5P
| Example No. | Structure | MW | MH+ | Syk IC50 Code |
|---|---|---|---|---|
| 516 | 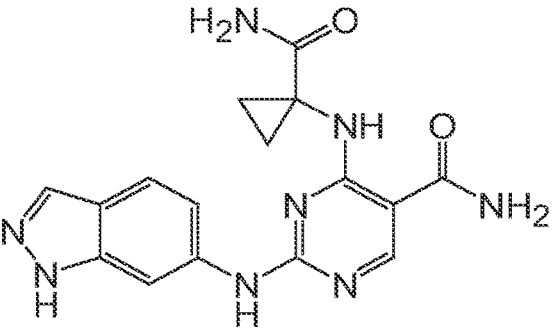 | 352.36 | 353.3 | ++ |
| 517 | 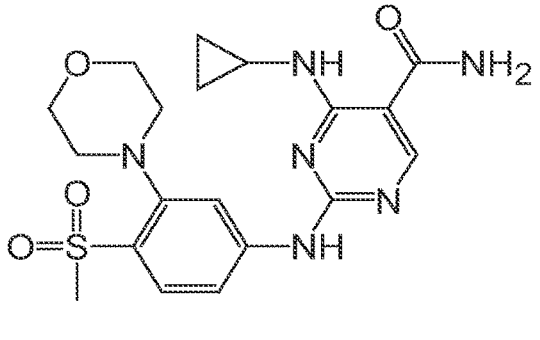 | 432.5 | 433.3 | ++ |
| 518 | 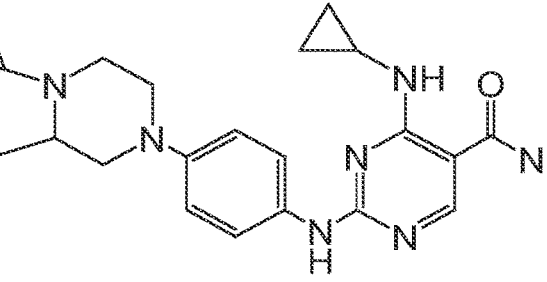 | 407.48 | MS+ 408 | +++ |

FIG. 5Q
| Example No. | Structure | MW | MH+ | Syk IC50 Code |
|---|---|---|---|---|
| 519 | 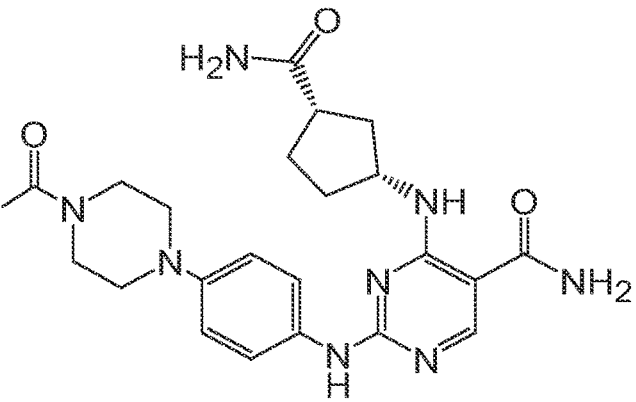 | 466.55 | 467.4 | +++ |
| 520 | 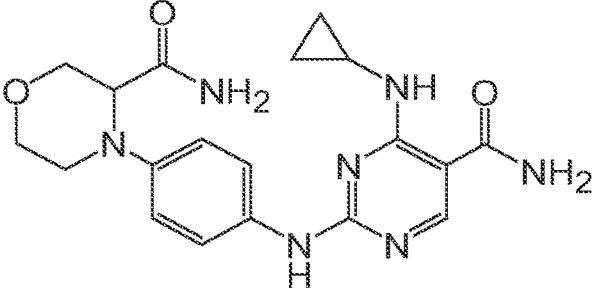 | 397.44 | 398.3 | +++ |
| 521 | 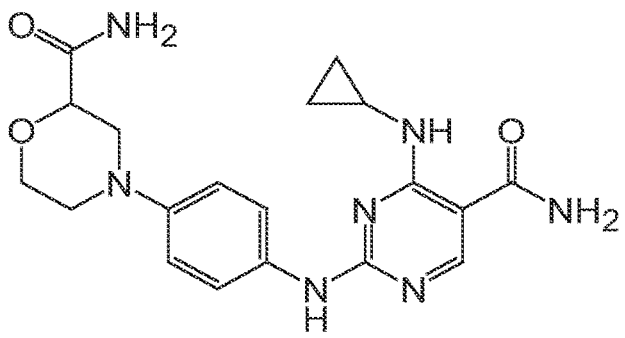 | 397.44 | 398.4 | +++ |

FIG. 5R
| Example No. | Structure | MW | MH+ | Syk IC50 Code |
|---|---|---|---|---|
| 522 | 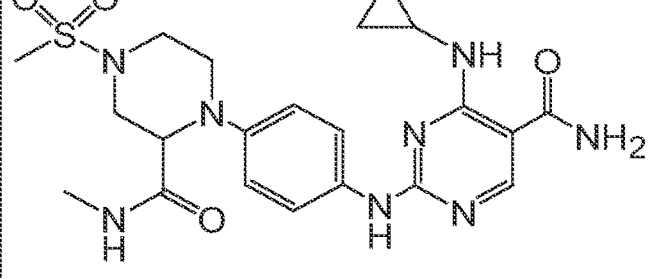 | 488.57 | 489.3 | ++ |
| 523 | 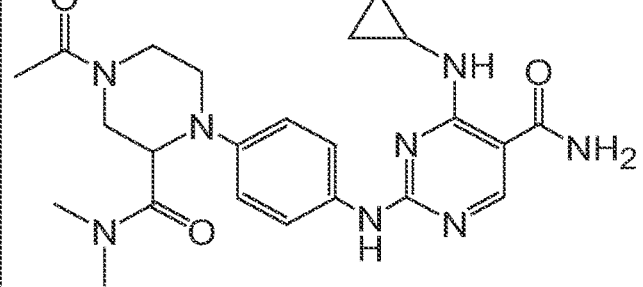 | 466.55 | 467.2 | ++ |
| 524 | 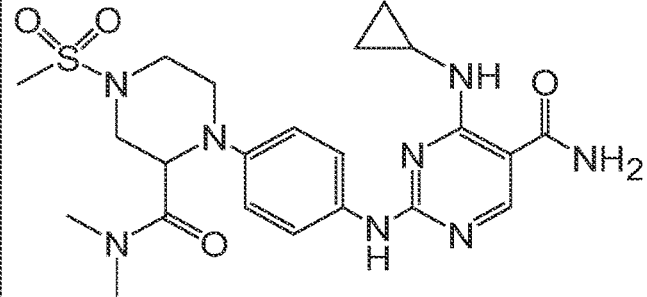 | 502.6 | 503.3 | ++ |

FIG. 5S
| Example No. | Structure | MW | MH+ | Syk IC50 Code |
|---|---|---|---|---|
| 525 | 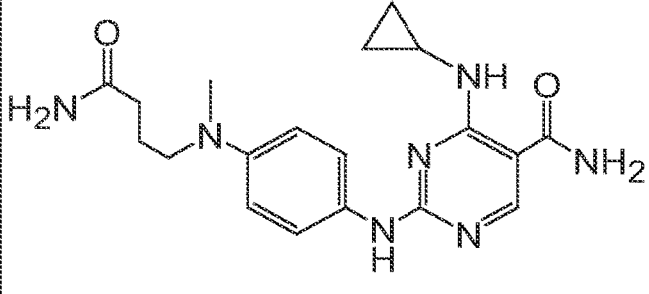 | 383.46 | ES(+) MS [M+1]= 384 | +++ |
| 526 | 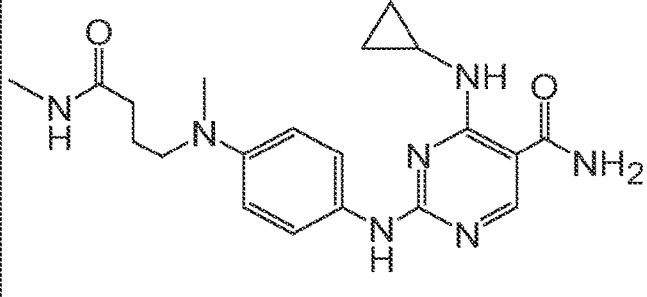 | 397.48 | ES(+) MS [M+1]= 398 | +++ |
| 527 | 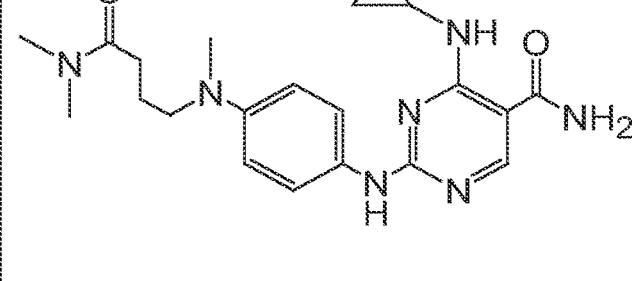 | 411.51 | ES(+) MS [M+1]= 412 | ++ |

FIG. 5T
| Example No. | Structure | MW | MH+ | Syk IC50 Code |
|---|---|---|---|---|
| 528 | 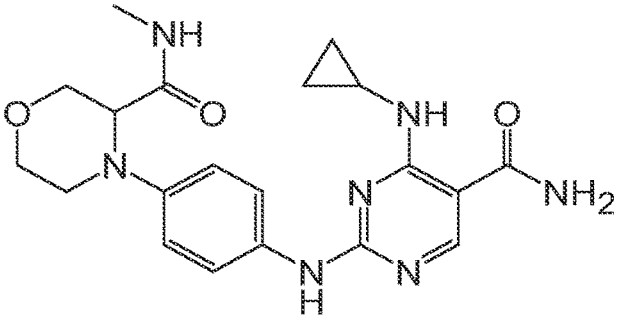 | 411.47 | 412.3 412.4 | ++ |
| 529 | 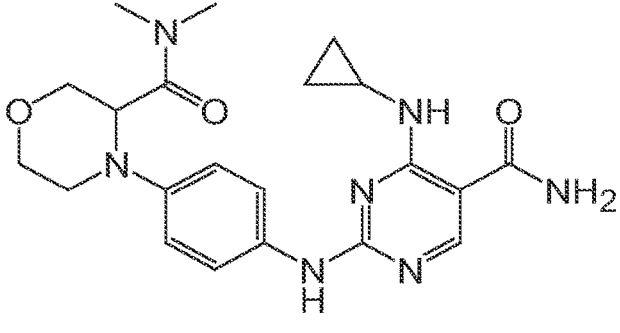 | 425.49 | 426.3 | ++ |
| 530 | 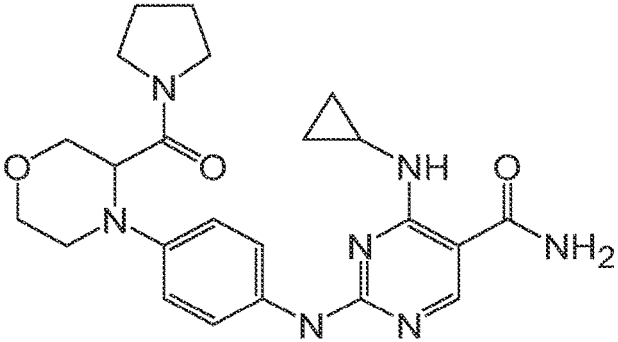 | 451.53 | 452.4 | ++ |

FIG. 5U

| Example No. | Structure | MW | MH+ | Syk IC50 Code |
|---|---|---|---|---|
| 531 | 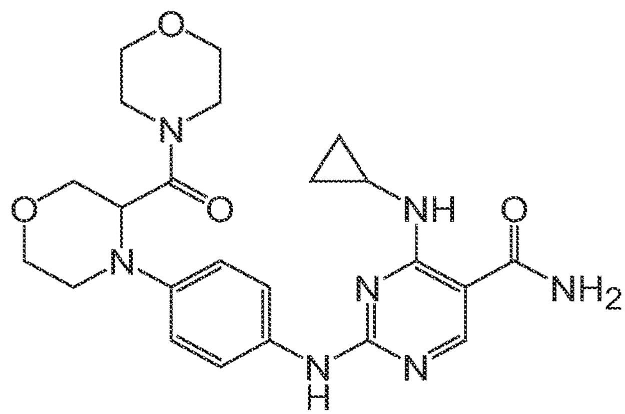 | 467.53 | 468.3 | ++ |
| 532 | 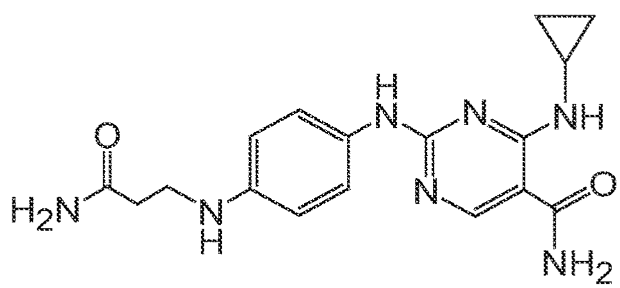 | 355.4 | ES(+) MS [M+1]= 356 | ++ |
| 533 | 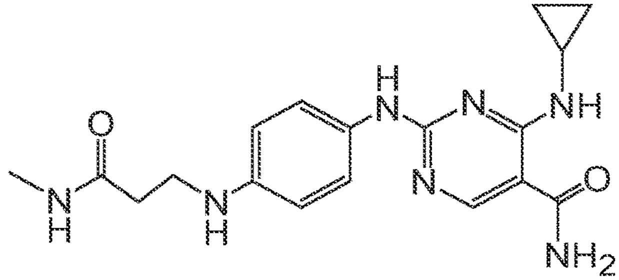 | 369.43 | ES(+) MS [M+1]= 370 | ++ |

FIG. 5V
| Example No. | Structure | MW | MH+ | Syk IC50 Code |
|---|---|---|---|---|
| 534 | 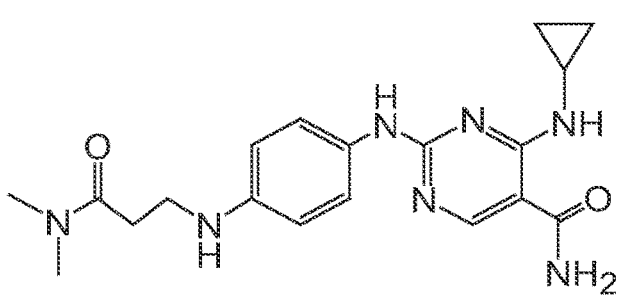 | 383.46 | ES(+) MS [M+1]= 267 | ++ |
| 535 | 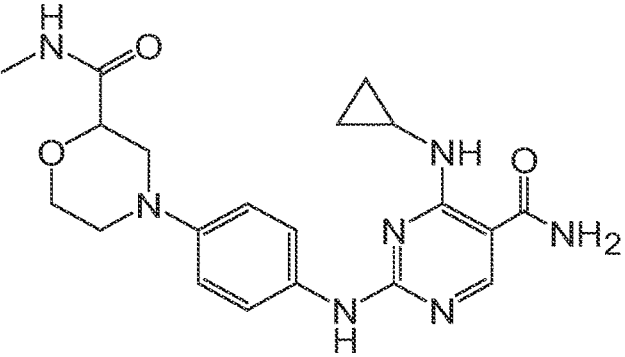 | 411.47 | 412.3 | +++ |
| 536 | 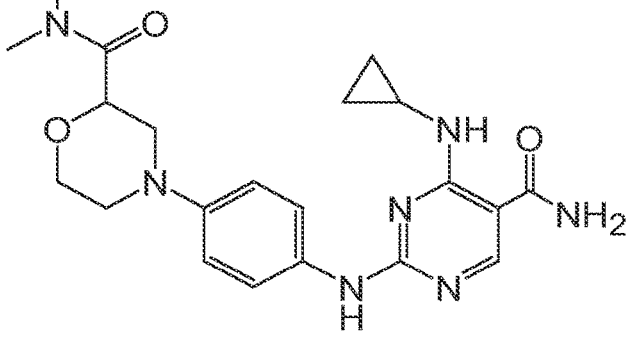 | 425.49 | 426.3 | +++ |

FIG. 5W
| Example No. | Structure | MW | MH+ | Syk IC50 Code |
|---|---|---|---|---|
| 537 | 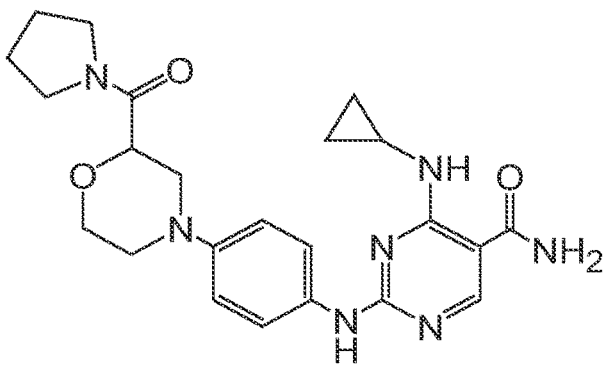 | 451.53 | 452.3 452.5 | +++ |
| 538 | 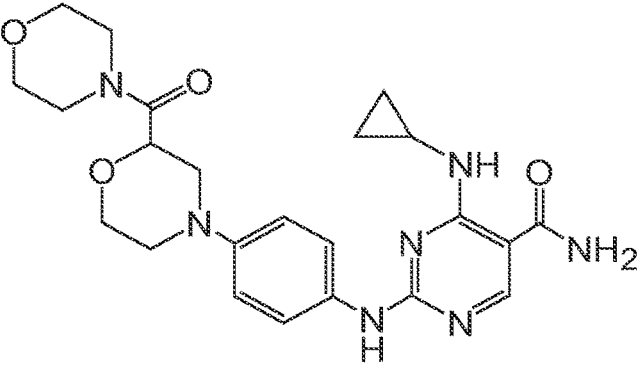 | 467.53 | 468.4 | +++ |
| 539 | 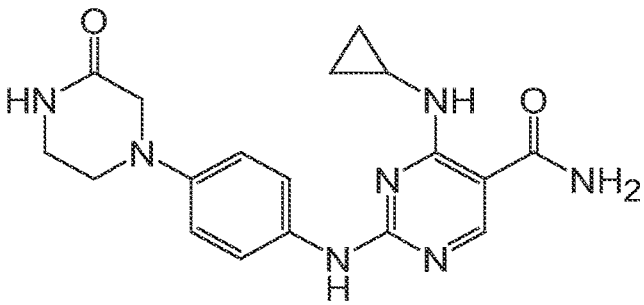 | 367.41 | 368.2 | ++ |

FIG. 5X

| Example No. | Structure | MW | MH+ | Syk IC50 Code |
|---|---|---|---|---|
| 540 | 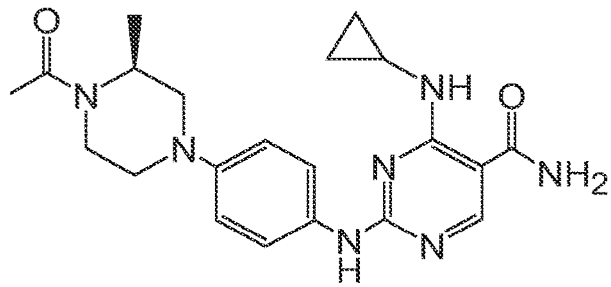 | 409.49 | 410.4 | +++ |
| 541 | 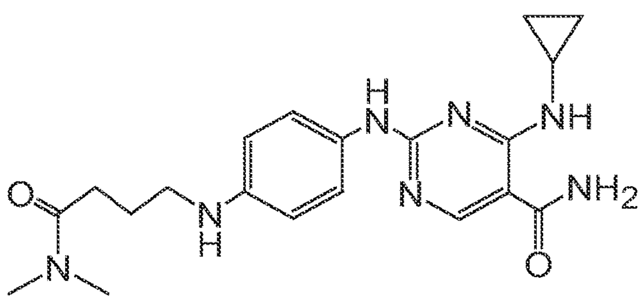 | 397.48 | ES(+) MS [M+1]=398 | ++ |
| 542 | 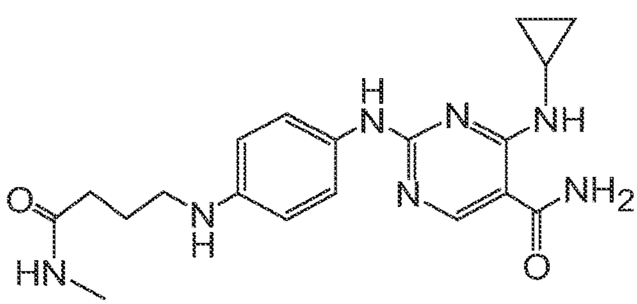 | 383.46 | ES(+) MS [M+1]=384 | ++ |

FIG. 5Y
| Example No. | Structure | MW | MH+ | Syk IC50 Code |
|---|---|---|---|---|
| 543 | 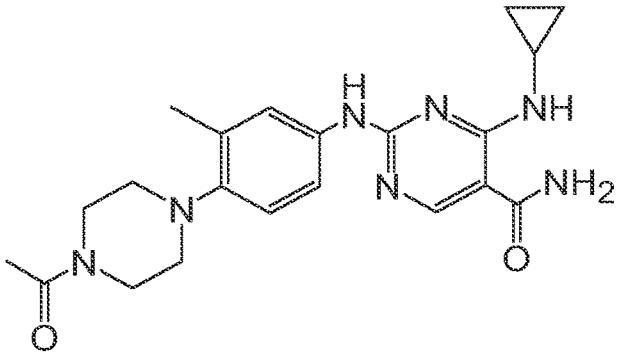 | 409.49 | ES(+) MS [M+1]= 410 | +++ |
| 544 | 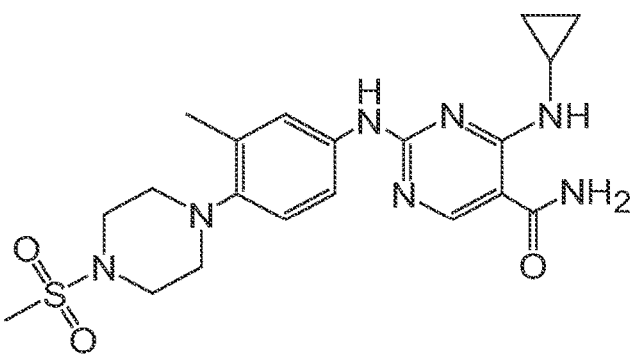 | 445.55 | ES(+) MS [M+1]= 446 | +++ |
| 545 | 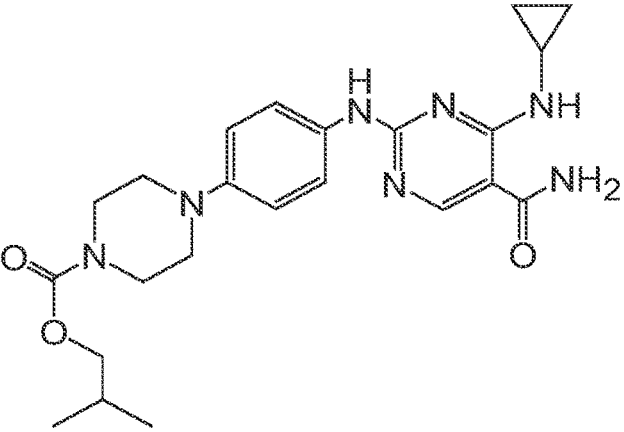 | 453.55 | ES(+) MS [M+1]= 454 | ++ |

FIG. 5Z

| Example No. | Structure | MW | MH+ | Syk IC50 Code |
|---|---|---|---|---|
| 546 | 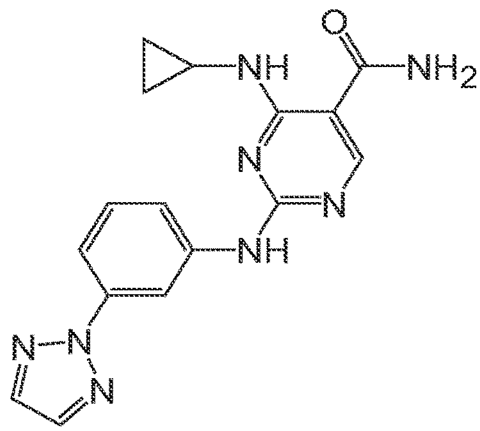 | 336.36 | 337.3 | ++ |
| 547 | 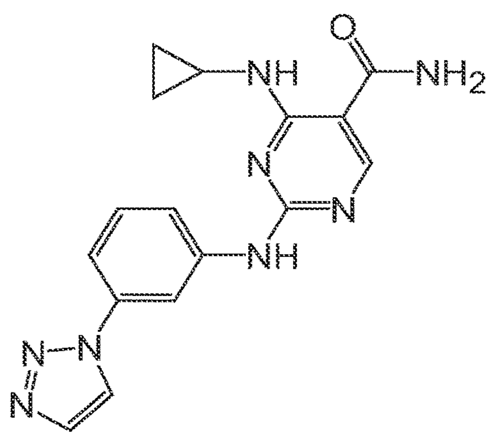 | 336.36 | 337.3 | ++ |
| 548 | 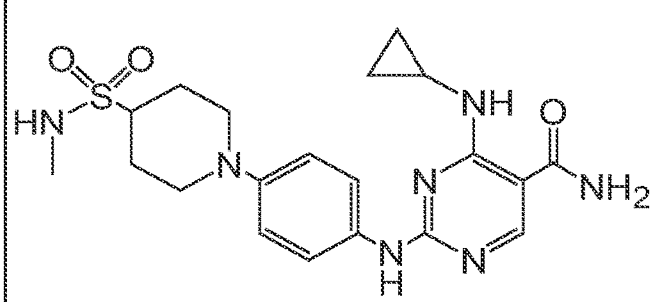 | 445.55 | 446.4 | +++ |

FIG. 5AA

| Example No. | Structure | MW | MH+ | Syk IC50 Code |
|---|---|---|---|---|
| 549 | 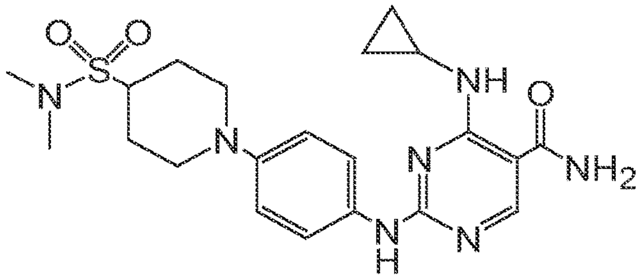 | 459.57 | 460.4 | +++ |
| 550 | 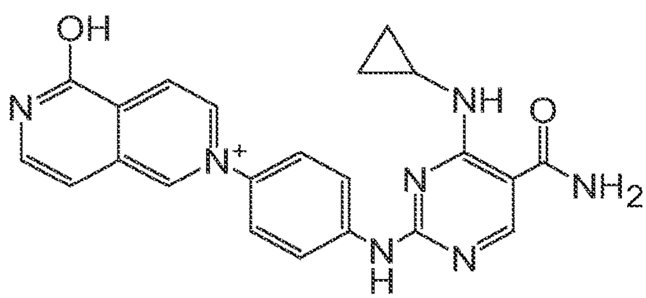 | 414.45 | MS+ 414 | ++ |
| 551 | 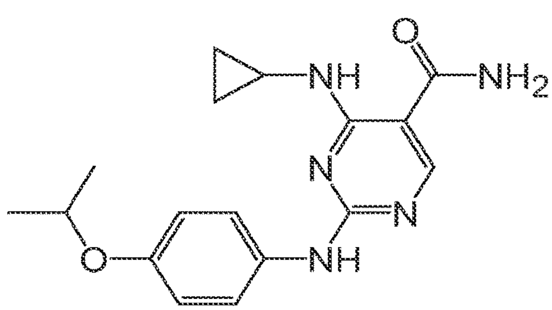 | 327.39 | 328.3 | +++ |

FIG. 5AB
| Example No. | Structure | MW | MH+ | Syk IC50 Code |
|---|---|---|---|---|
| 552 | 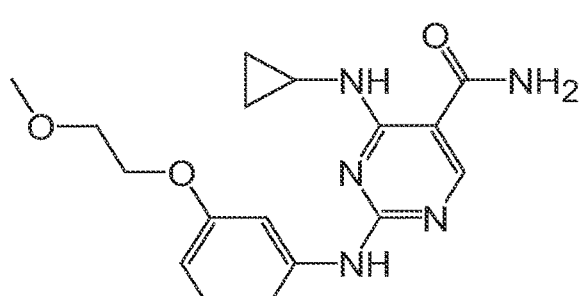 | 343.39 | 344.3 | ++ |
| 553 | 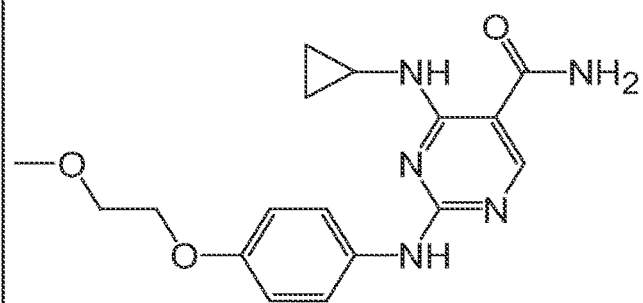 | 343.39 | 344.3 | ++ |
| 554 | 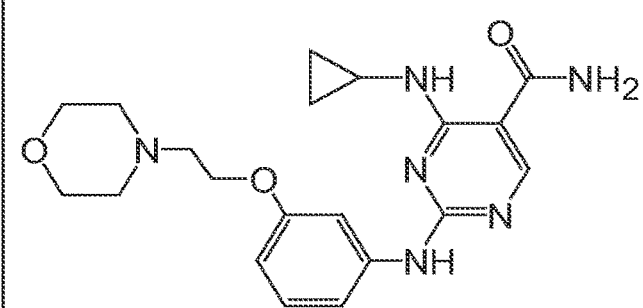 | 398.47 | 399.3 | ++ |

FIG. 5AC
| Example No. | Structure | MW | MH+ | Syk IC50 Code |
|---|---|---|---|---|
| 555 | 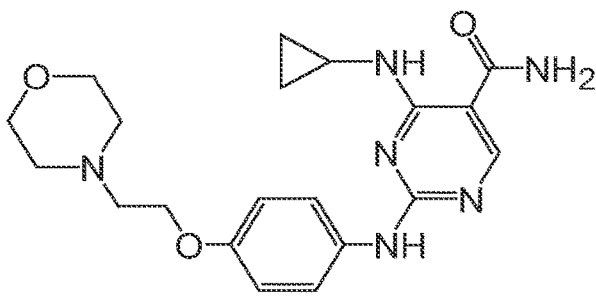 | 398.47 | 399.3 | ++ |
| 556 | 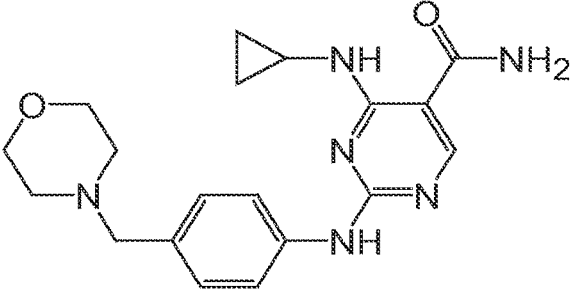 | 368.44 | 369.3 | ++ |
| 557 | 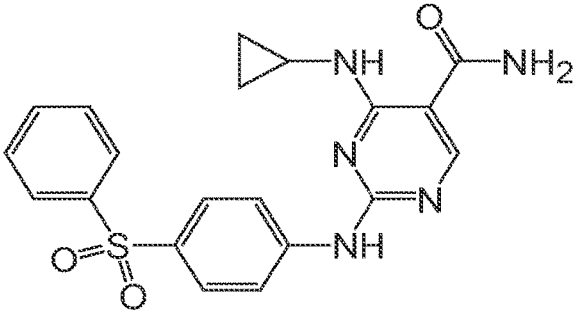 | 409.47 | 410.3 | +++ |

FIG. 5AD
| Example No. | Structure | MW | MH+ | Syk IC50 Code |
|---|---|---|---|---|
| 558 | 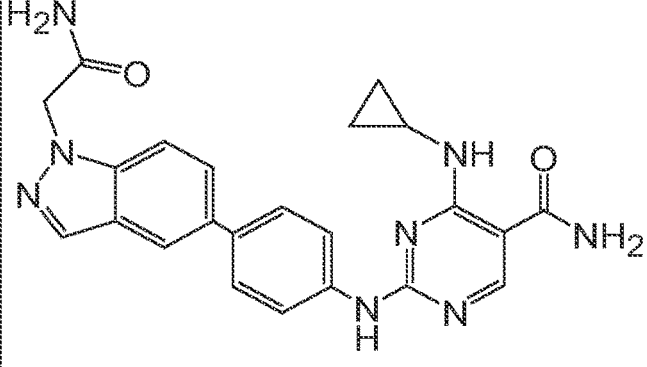 | 366.39 | 367.3 | +++ |
| 559 | 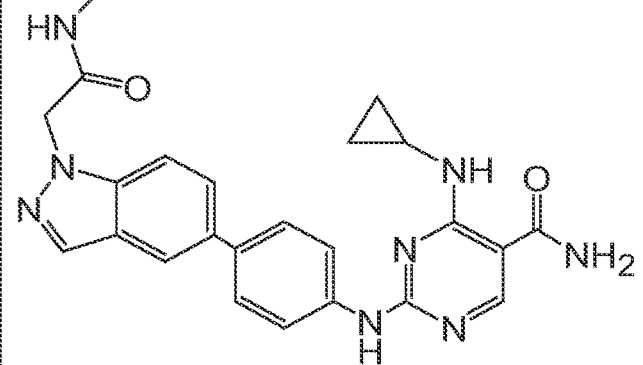 | 380.41 | 381.3 | +++ |
| 560 | 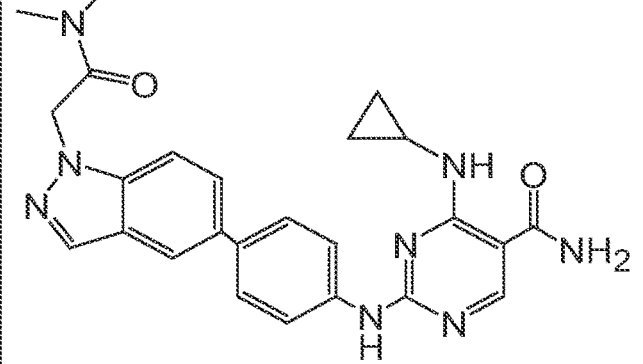 | 394.44 | 395.3 | +++ |

FIG. 5AE
| Example No. | Structure | MW | MH+ | Syk IC50 Code |
|---|---|---|---|---|
| 561 | 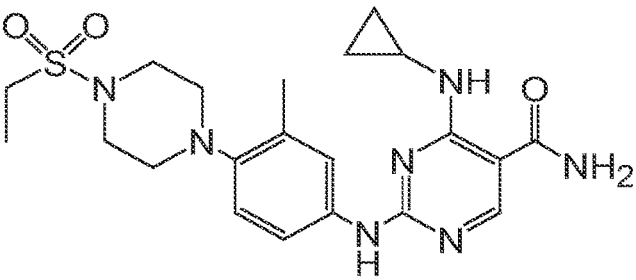 | 459.57 | 460.3 | +++ |
| 562 | 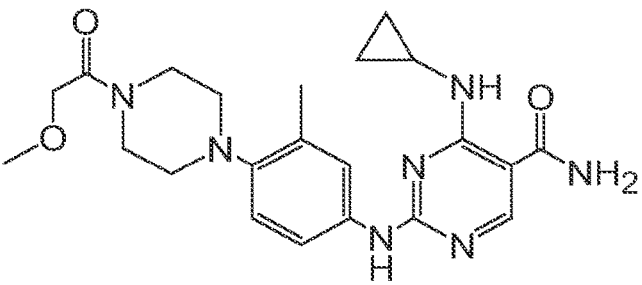 | 439.52 | 440.3 | +++ |
| 563 | 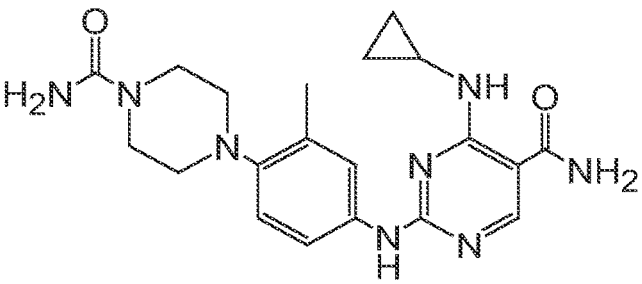 | 410.48 | 411.3 | +++ |

FIG. 5AF
| Example No. | Structure | MW | MH+ | Syk IC50 Code |
|---|---|---|---|---|
| 564 | 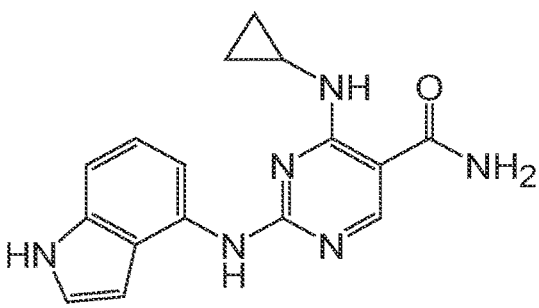 | 308.35 | 309.3 | ++ |
| 565 | 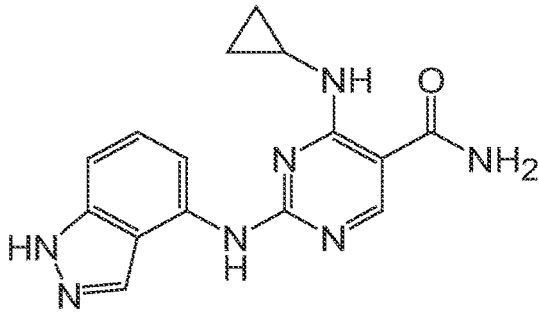 | 309.33 | 310.2 | ++ |
| 566 | 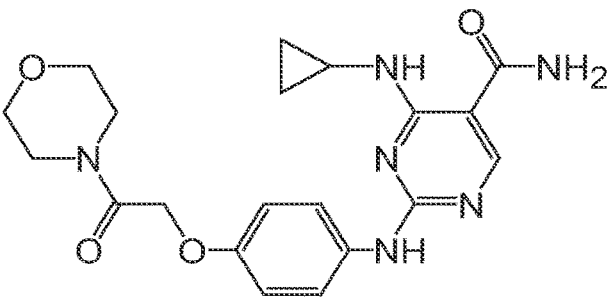 | 412.45 | 413.3 | ++ |

FIG. 5AG

| Example No. | Structure | MW | MH+ | Syk IC50 Code |
|---|---|---|---|---|
| 567 | 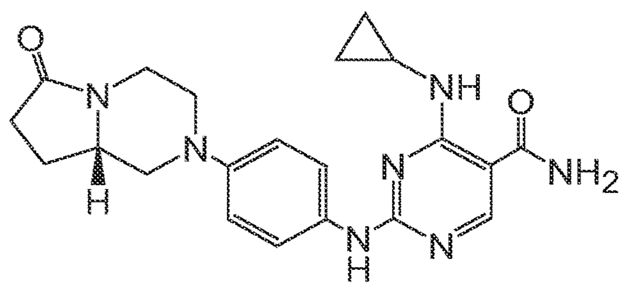 | 407.48 | 408 MS+ 408 | +++ |
| 568 | 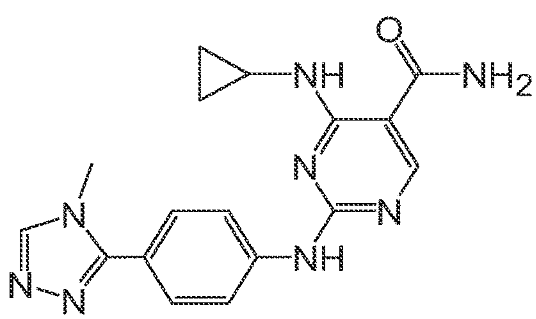 | 350.39 | 351.3 | ++ |
| 569 | 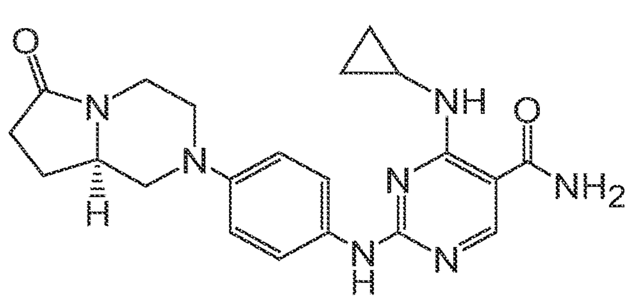 | 407.48 | MS+ 408 | +++ |

FIG. 5AH

| Example No. | Structure | MW | MH+ | Syk IC50 Code |
|---|---|---|---|---|
| 570 | 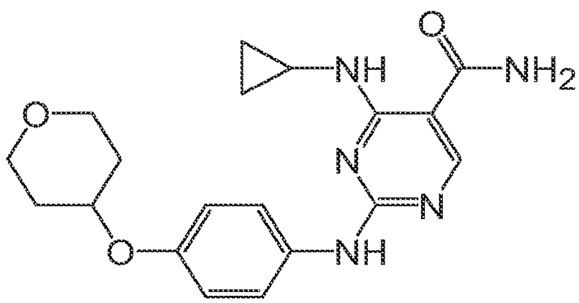 | 369.43 | 370.3 | ++ |
| 571 | 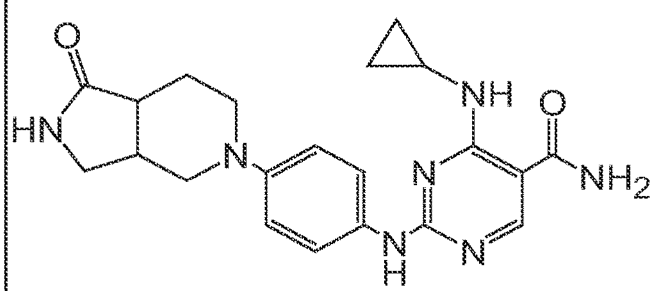 | 407.48 | MS+ 408 | ++ |
| 572 | 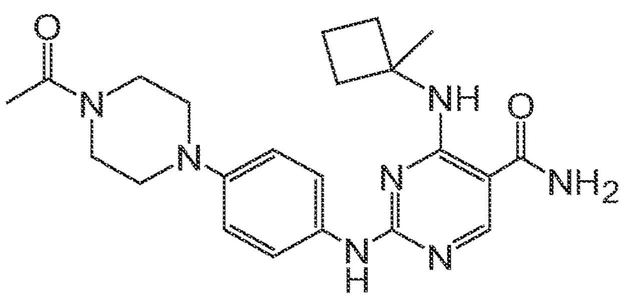 | 423.52 | 424.3 | ++ |

FIG. 5AI
| Example No. | Structure | MW | MH+ | Syk IC50 Code |
|---|---|---|---|---|
| 573 | 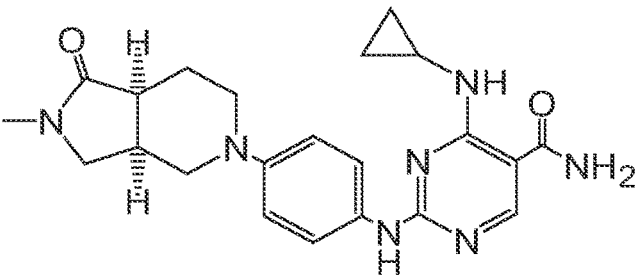 | 421.51 | MS+ 422 | + |
| 574 | 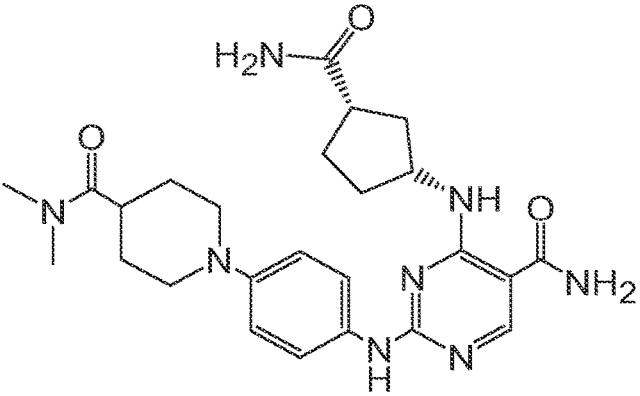 | 494.6 | 495.3 | ++ |
| 575 | 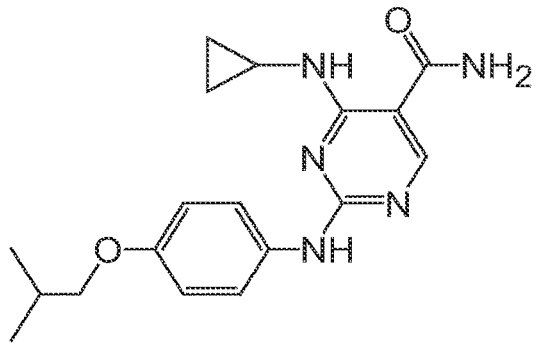 | 341.42 | MW= 341.41 M+1= 342.2 | ++ |

FIG. 5AJ
| Example No. | Structure | MW | MH+ | Syk IC50 Code |
|---|---|---|---|---|
| 576 | 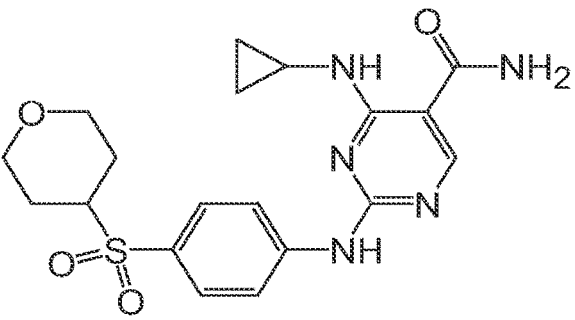 | 417.49 | 418.2 | +++ |
| 577 | 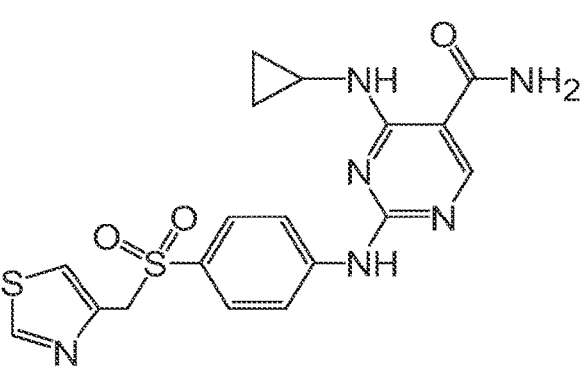 | 430.51 | MW= 430.5 M+1= 431.4 | ++ |
| 578 | 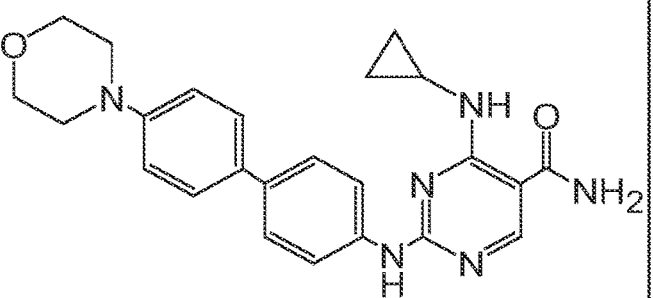 | 430.51 | 431.3 | ++ |

FIG. 5AK
| Example No. | Structure | MW | MH+ | Syk IC50 Code |
|---|---|---|---|---|
| 579 | 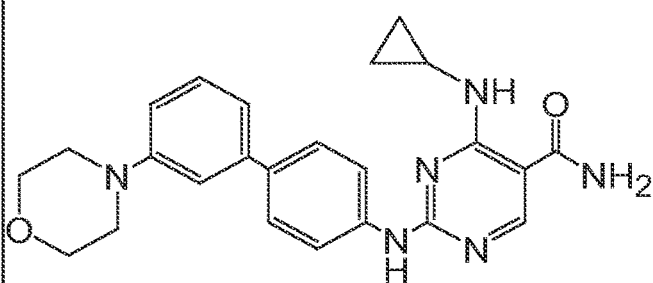 | 430.51 | 431.3 | ++ |
| 580 | 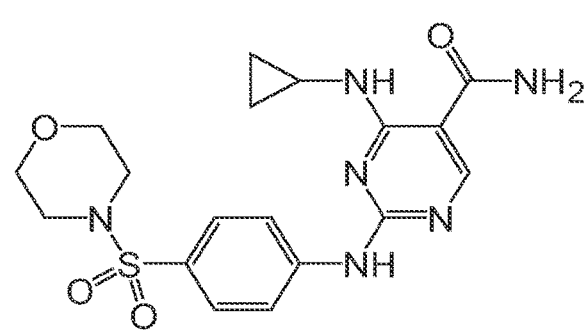 | 418.48 | 419.3 | +++ |
| 581 | 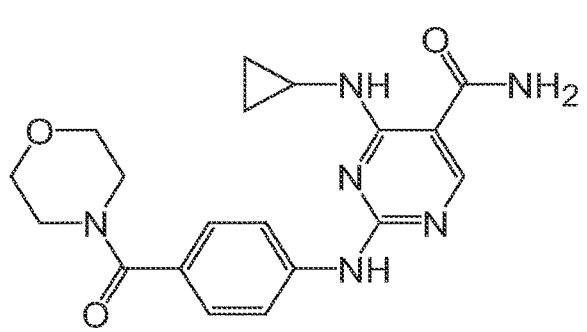 | 382.42 | 383.3 | + |

FIG. 5AL

| Example No. | Structure | MW | MH+ | Syk IC50 Code |
|---|---|---|---|---|
| 582 | (structure) | 355.4 | ES(+) MS [M+1]=356 | +++ |
| 583 | (structure) | 369.43 | ES(+) MS [M+1]=370 | ++ |
| 584 | (structure) | 383.46 | ES(+) MS [M+1]=384 | ++ |

FIG. 5AM

| Example No. | Structure | MW | MH+ | Syk IC50 Code |
|---|---|---|---|---|
| 585 | (structure) | 341.38 | ES(+) MS [M+1]=342 | ++ |
| 586 | (structure) | 355.4 | ES(+) MS [M+1]=356 | ++ |
| 587 | (structure) | 369.43 | ES(+) MS [M+1]=370 | ++ |

FIG. 5AN

| Example No. | Structure | MW | MH+ | Syk IC50 Code |
|---|---|---|---|---|
| 588 | (structure) | 369.43 | ES(+) MS [M+1]=370 | ++ |
| 589 | (structure) | 383.46 | ES(+) MS [M+1]=384 | ++ |
| 590 | (structure) | 397.48 | ES(+) MS [M+1]=398 | ++ |

FIG. 5AO
| Example No. | Structure | MW | MH+ | Syk IC50 Code |
|---|---|---|---|---|
| 591 | 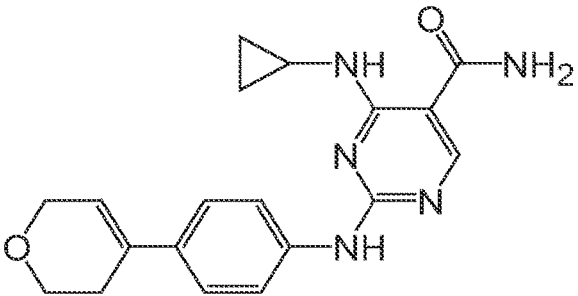 | 351.41 | 352.3 | ++ |
| 592 | 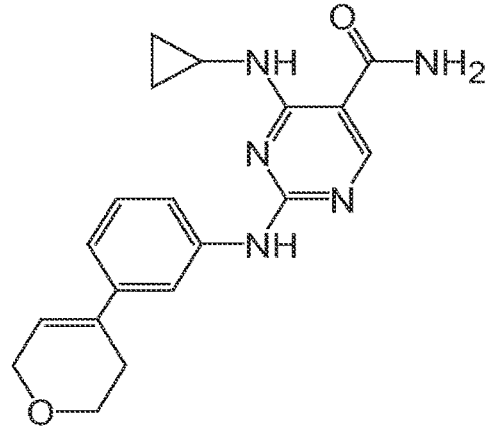 | 351.41 | 352.3 | ++ |
| 593 | 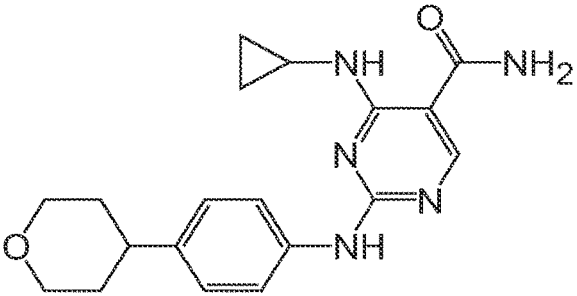 | 353.43 | 354.3 | +++ |

FIG. 5AP
| Example No. | Structure | MW | MH+ | Syk IC50 Code |
|---|---|---|---|---|
| 594 | 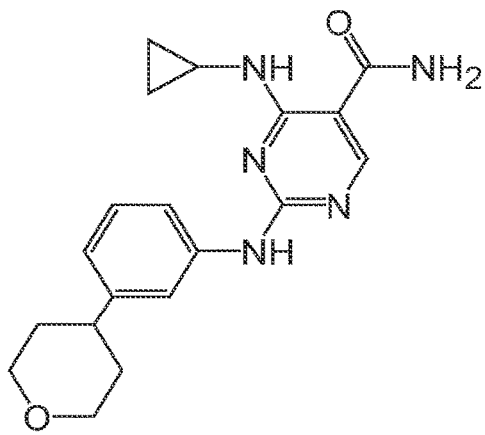 | 353.43 | 354.3 | ++ |
| 595 | 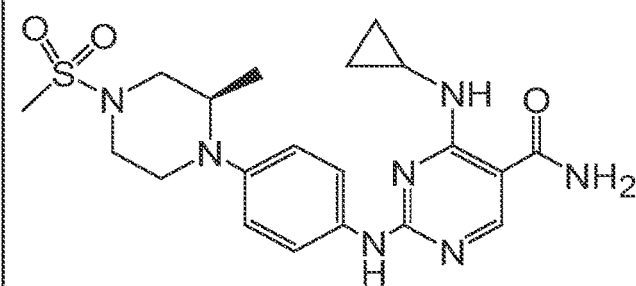 | 445.55 | 446.4 | ++ |
| 596 | 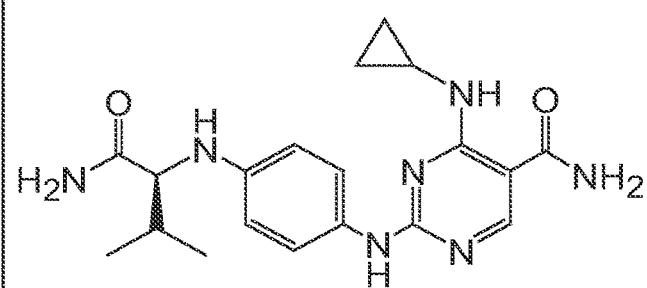 | 383.46 | 384.4 | +++ |

FIG. 5AQ
| Example No. | Structure | MW | MH+ | Syk IC50 Code |
|---|---|---|---|---|
| 597 | 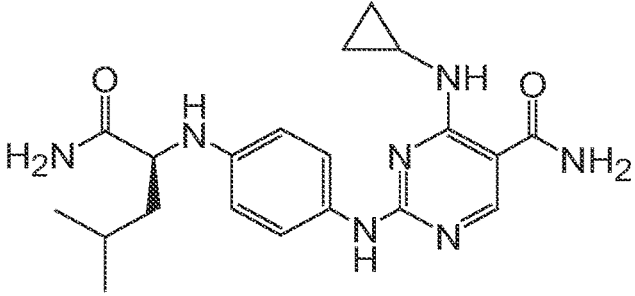 | 397.48 | 398.4 | ++ |
| 598 | 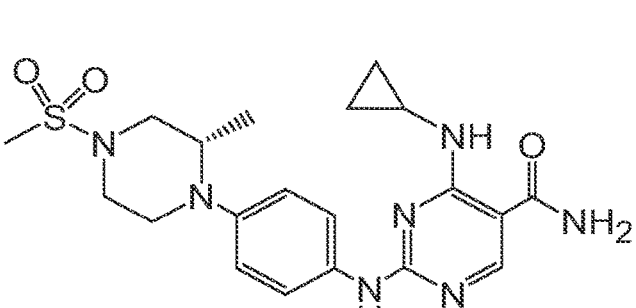 | 445.55 | 446.4 | +++ |
| 599 | 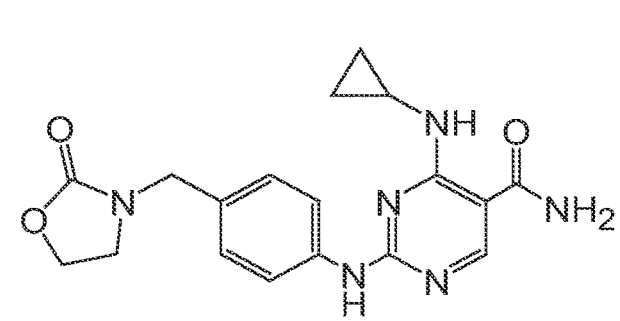 | 368.4 | 369.3 | +++ |

FIG. 5AR

| Example No. | Structure | MW | MH+ | Syk IC50 Code |
|---|---|---|---|---|
| 600 | 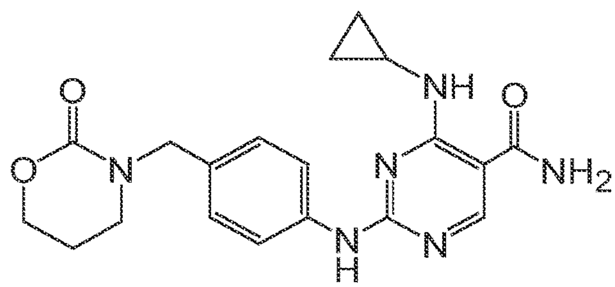 | 382.42 | 383.3 | +++ |
| 601 | 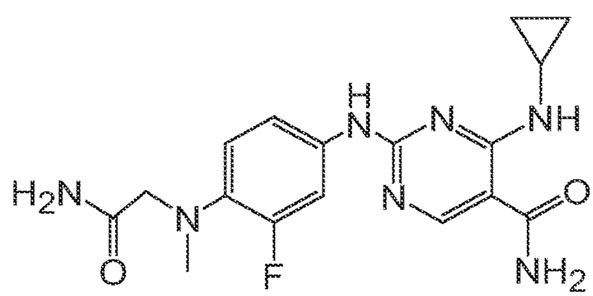 | 373.39 | 374 | +++ |
| 602 | 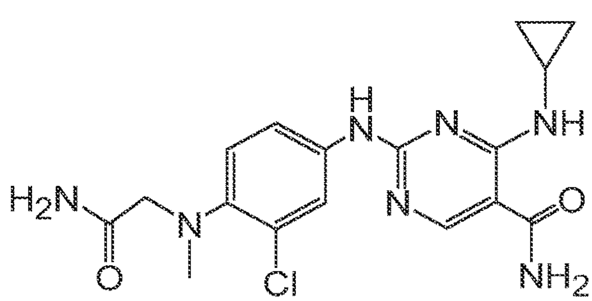 | 389.85 | 390 392 | +++ |

FIG. 5AS

| Example No. | Structure | MW | MH+ | Syk IC50 Code |
|---|---|---|---|---|
| 603 | 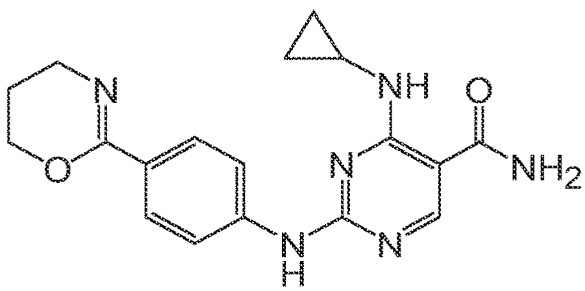 | 352.4 | 353.3 | ++ |
| 604 | 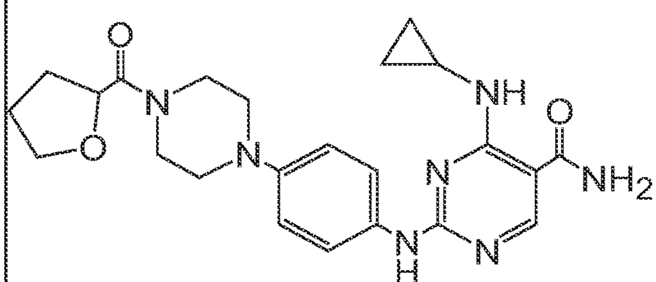 | 451.53 | 452.4 | +++ |
| 605 | 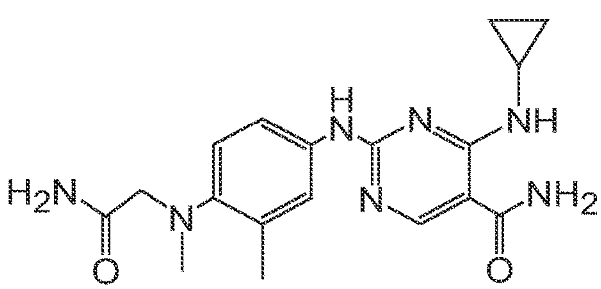 | 369.43 | 370 | +++ |

FIG. 5AT

| Example No. | Structure | MW | MH+ | Syk IC50 Code |
|---|---|---|---|---|
| 606 | 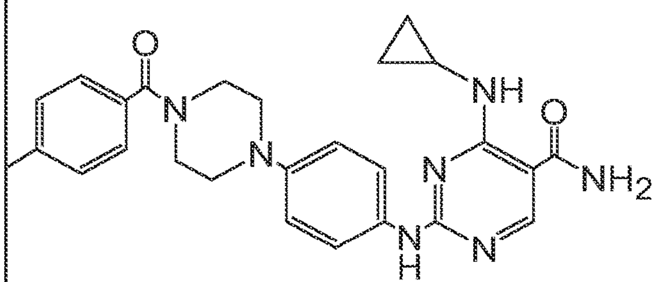 | 471.57 | 472.4 | ++ |
| 607 | 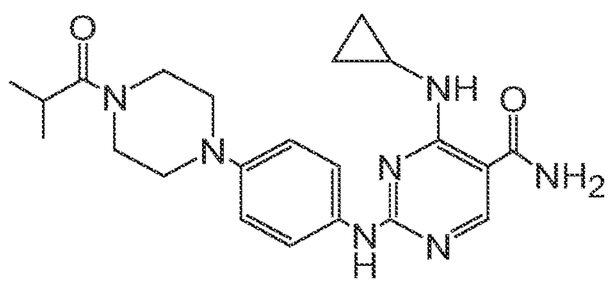 | 423.52 | 424 | ++ |
| 608 | 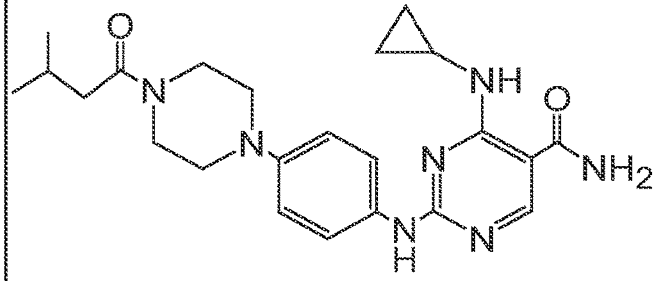 | 437.55 | 438 | ++ |

FIG. 5AU
| Example No. | Structure | MW | MH+ | Syk IC50 Code |
|---|---|---|---|---|
| 609 | 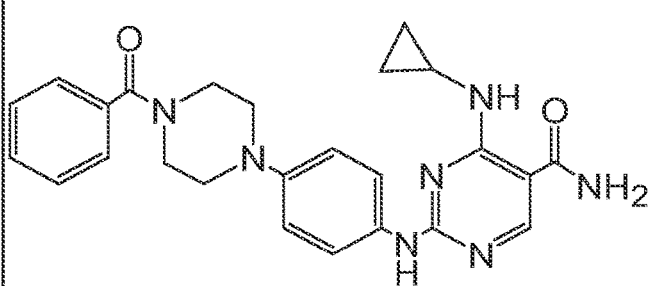 | 457.54 | 458 | ++ |
| 610 | 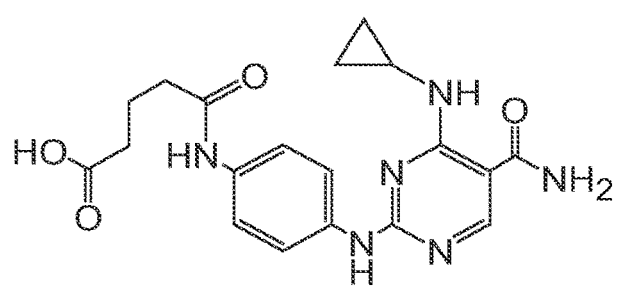 | 398.42 | 399 | ++ |
| 611 | 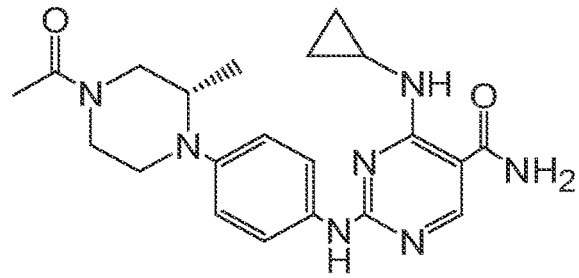 | 409.49 | 410.4 | +++ |

FIG. 5AV
| Example No. | Structure | MW | MH+ | Syk IC50 Code |
|---|---|---|---|---|
| 612 | 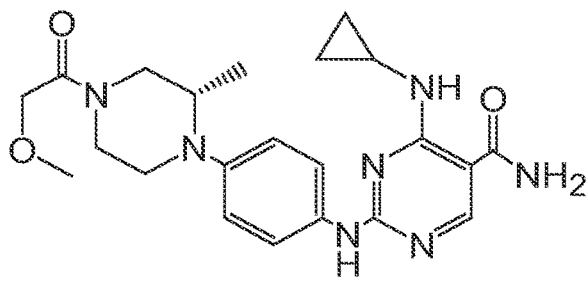 | 439.52 | 440.5 | +++ |
| 613 | 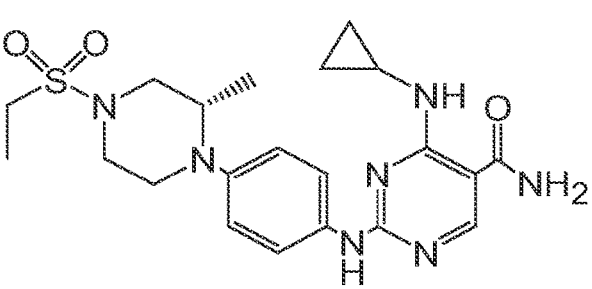 | 459.57 | 460.4 | +++ |
| 614 | 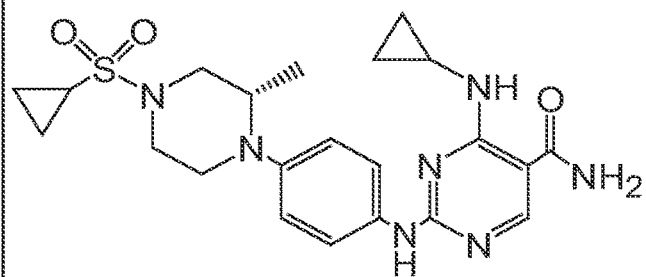 | 471.58 | 472.4 | +++ |

FIG. 5AW
| Example No. | Structure | MW | MH+ | Syk IC50 Code |
|---|---|---|---|---|
| 615 | 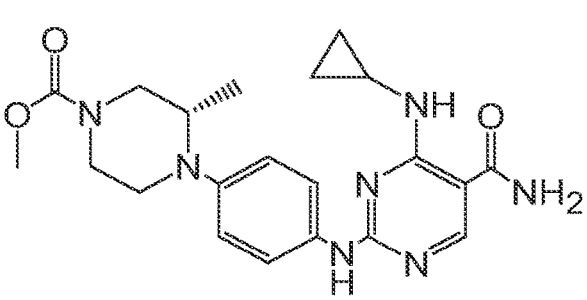 | 425.49 | 426.4 | ++ |
| 616 | 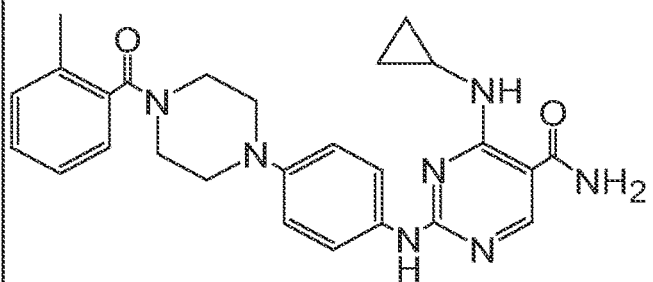 | 471.57 | 472.4 | ++ |
| 617 | 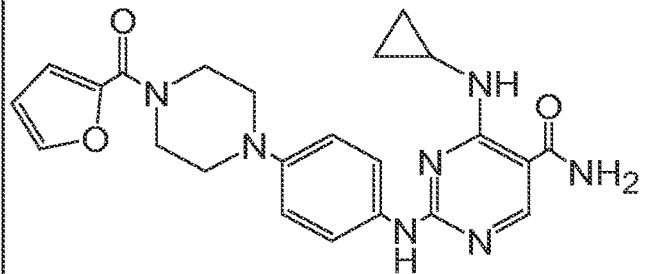 | 447.5 | 448.3 | ++ |

FIG. 5AX

| Example No. | Structure | MW | MH+ | Syk IC50 Code |
|---|---|---|---|---|
| 618 | 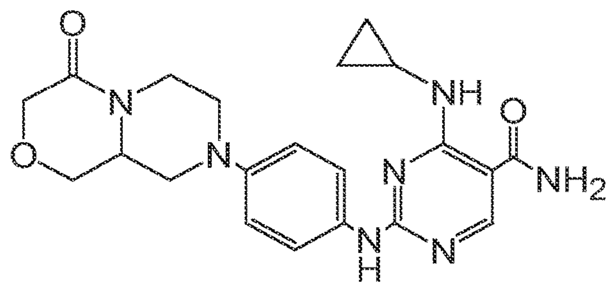 | 423.48 | 424 | +++ |
| 619 | 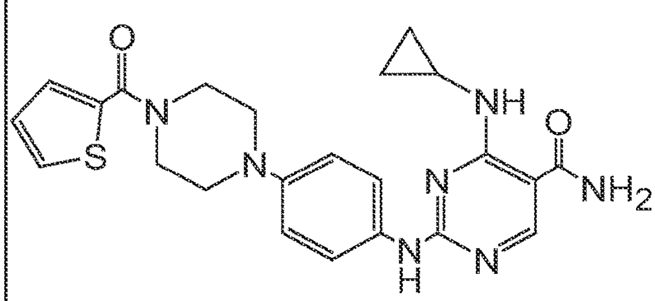 | 463.56 | 464 | ++ |
| 620 | 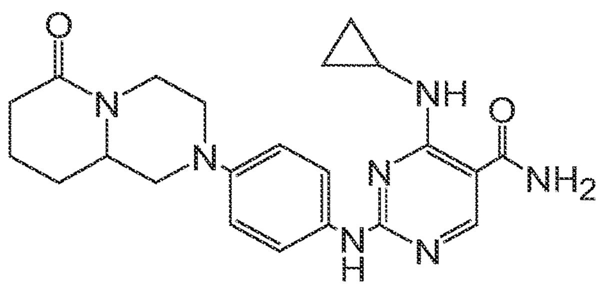 | 421.51 | 422.5 | +++ |

FIG. 5AY
| Example No. | Structure | MW | MH+ | Syk IC50 Code |
|---|---|---|---|---|
| 621 | 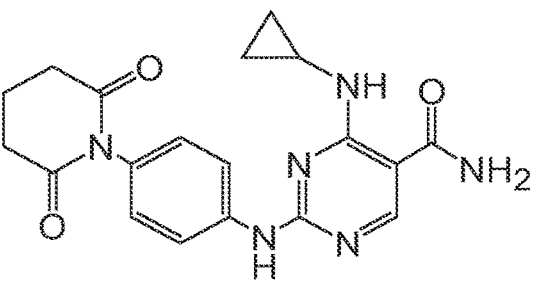 | 380.41 | 381 | ++ |
| 622 | 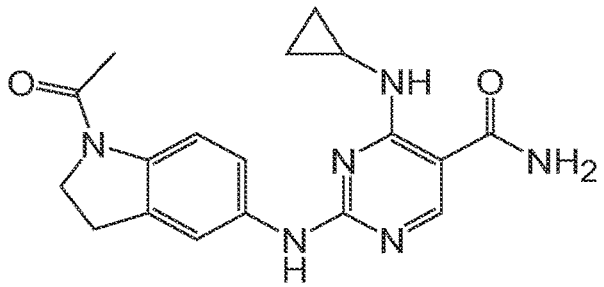 | 352.4 | 353 | ++ |
| 623 | 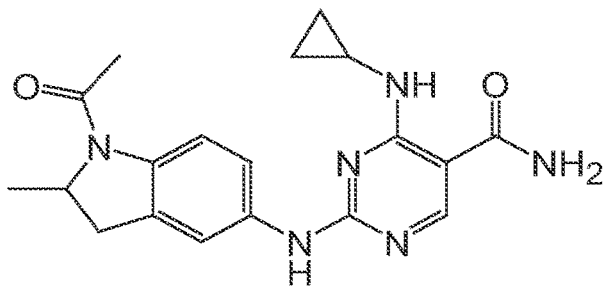 | 366.43 | 367 | +++ |

FIG. 5AZ

| Example No. | Structure | MW | MH+ | Syk IC50 Code |
|---|---|---|---|---|
| 624 | (structure) | 338.37 | 339 | ++ |
| 625 | (structure) | 352.4 | 353 | +++ |
| 626 | (structure) | 366.43 | 367 | +++ |

FIG. 5BA

| Example No. | Structure | MW | MH+ | Syk IC50 Code |
|---|---|---|---|---|
| 627 | 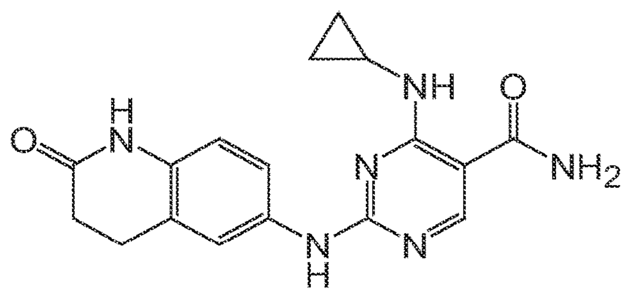 | 338.37 | 339 | +++ |
| 628 | 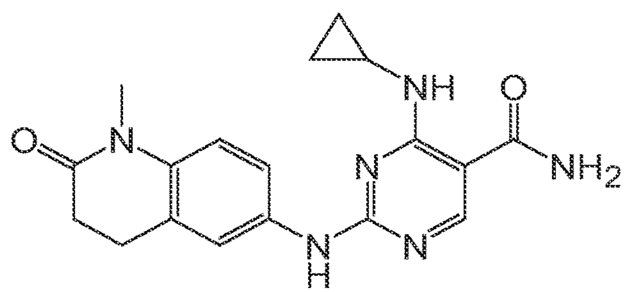 | 352.4 | 353 | +++ |
| 629 | 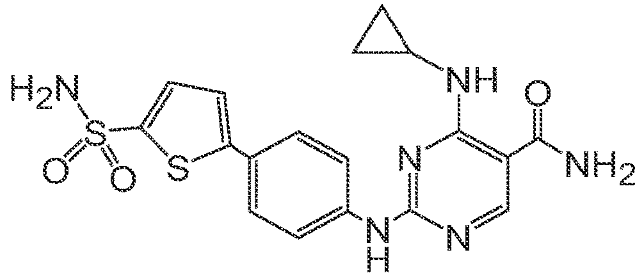 | 430.51 | 431.3 | ++ |

FIG. 5BB

| Example No. | Structure | MW | MH+ | Syk IC50 Code |
|---|---|---|---|---|
| 630 | 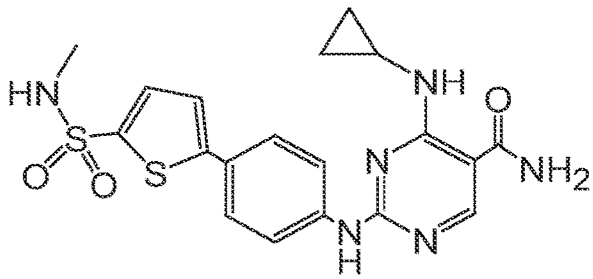 | 444.54 | 445.2 | ++ |
| 631 | 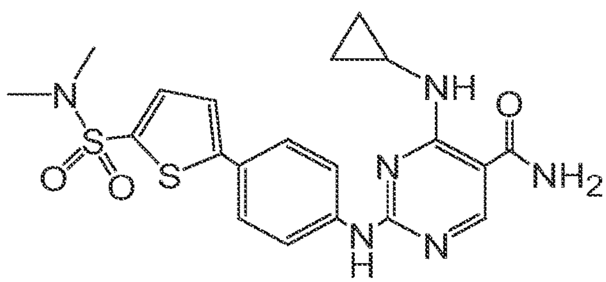 | 458.56 | 459.2 | ++ |
| | | | | |

FIG. 6A

| Example No. | Structure | MW | MH+ | Syk IC50 Code |
|---|---|---|---|---|
| 632 | 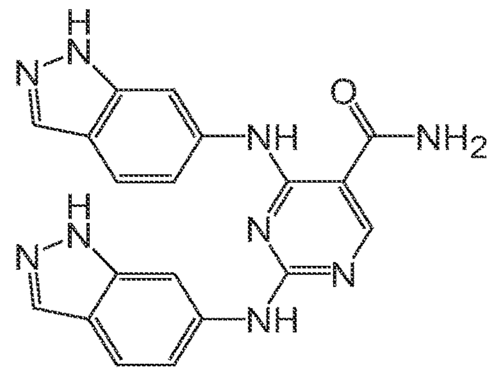 | 385.39 | 386.1 | +++ |
| 633 | 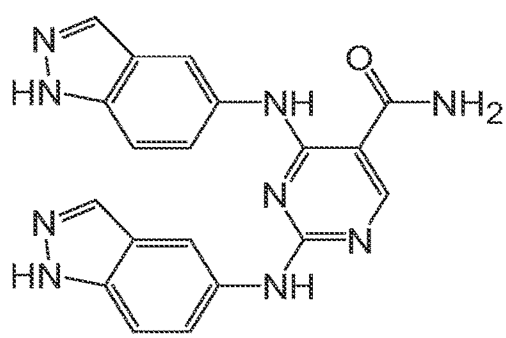 | 385.39 | 386.1 | +++ |
| 634 | 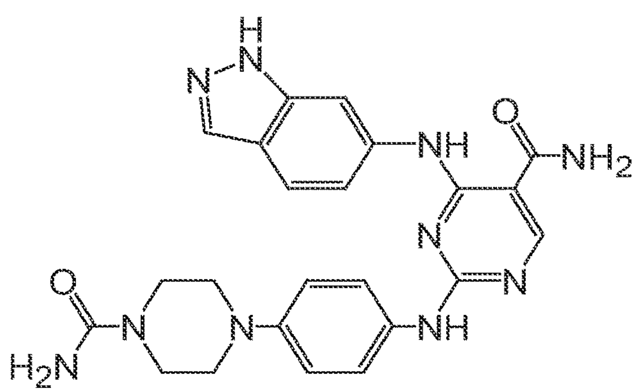 | 472.51 | 473.2 | +++ |

FIG. 6B
| Example No. | Structure | MW | MH+ | Syk IC50 Code |
|---|---|---|---|---|
| 635 | 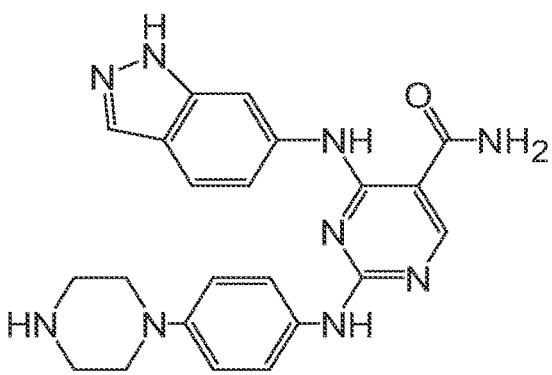 | 429.49 | 430.2 | ++ |
| 636 | 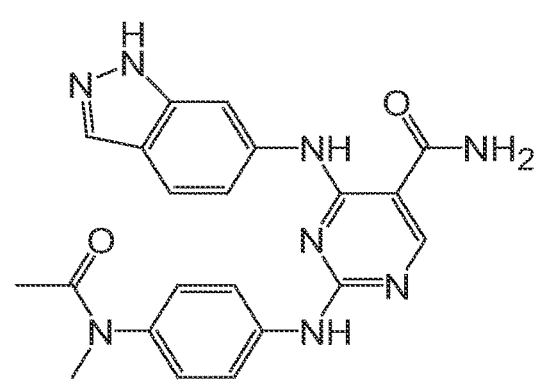 | 416.45 | 417.2 | ++ |
| 637 | 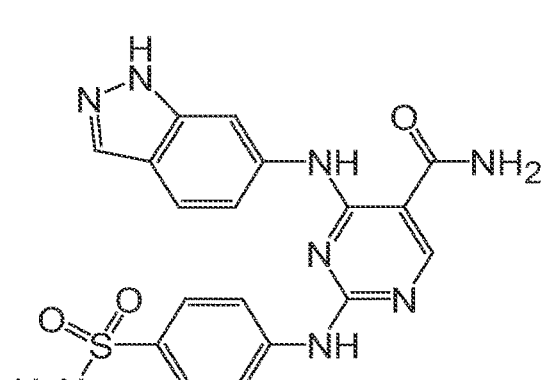 | 424.44 | 425.1 | +++ |

FIG. 6C
| Example No. | Structure | MW | MH+ | Syk IC50 Code |
|---|---|---|---|---|
| 638 | 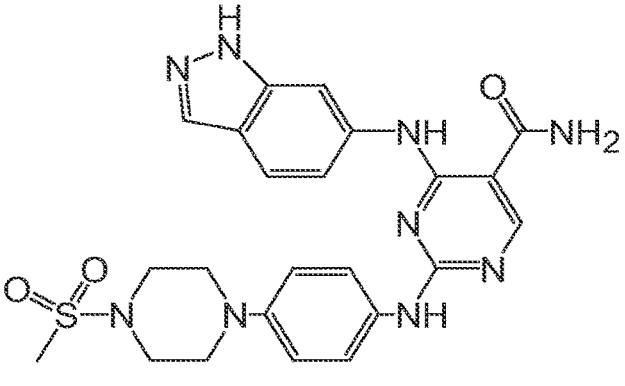 | 507.58 | 508.2 | ++ |
| 639 | 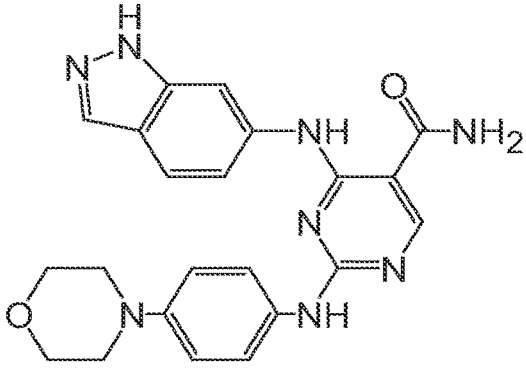 | 430.47 | 431.2 | ++ |
| 640 | 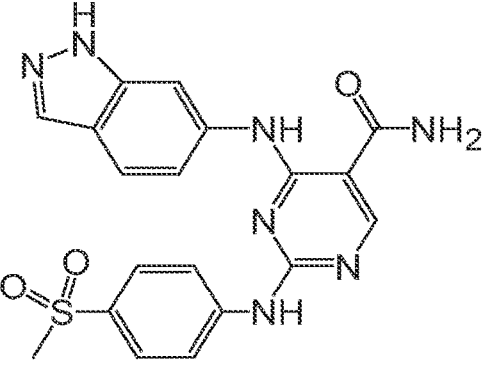 | 423.46 | 424.1 | ++ |

FIG. 6D

| Example No. | Structure | MW | MH+ | Syk IC50 Code |
|---|---|---|---|---|
| 641 | 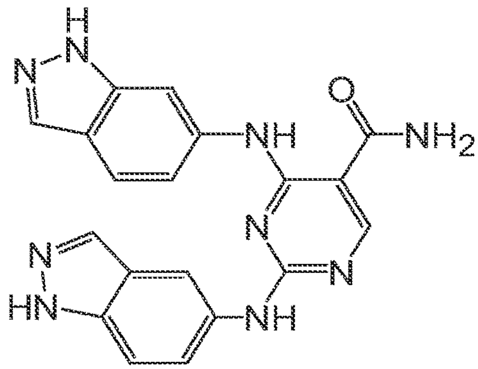 | 385.39 | 386.1 | +++ |
| 642 | 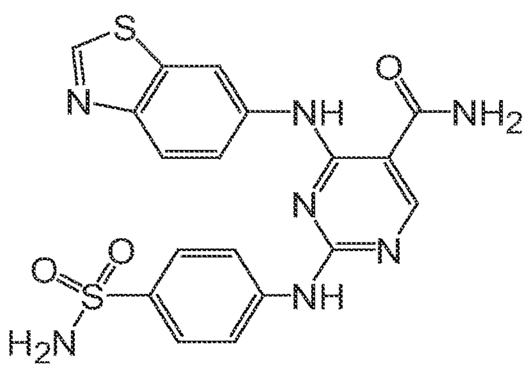 | 441.49 | 442.1 | ++ |
| 643 | 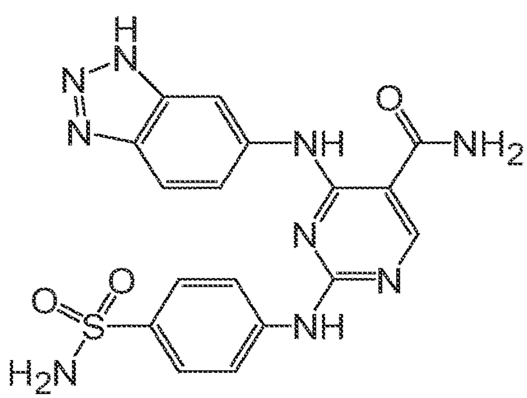 | 425.43 | 426.1 | ++ |

*FIG. 6E*

| Example No. | Structure | MW | MH+ | Syk IC50 Code |
|---|---|---|---|---|
| 644 | (indazol-5-yl-NH)(indazol-6-yl-NH)pyrimidine-5-carboxamide | 385.39 | 386.2 | +++ |
| 645 | (indazol-5-yl-NH)(4-sulfamoylphenyl-NH)pyrimidine-5-carboxamide | 424.44 | 425.2 | ++ |
| 646 | (benzothiazol-6-yl-NH)(indazol-5-yl-NH)pyrimidine-5-carboxamide | 402.44 | 403.2 | ++ |

FIG. 7A
| Example No. | Structure | MW | MH+ | SyK IC50 Code |
|---|---|---|---|---|
| 647 | 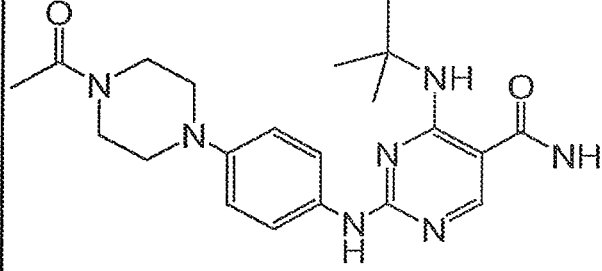 | | | ++ |
| 648 | 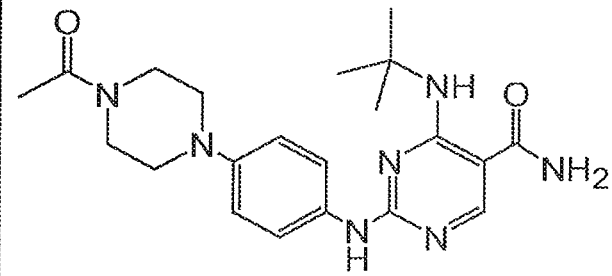 | | | ++ |
| 649 | 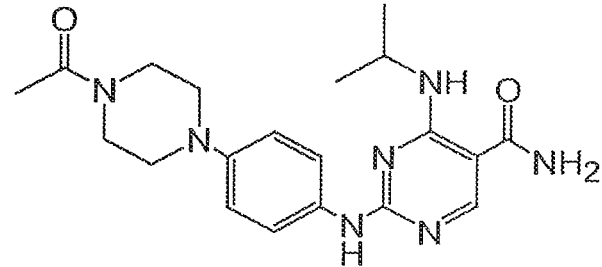 | | | ++ |

FIG. 7B
| Example No. | Structure | MW | MH+ | SyK IC50 Code |
|---|---|---|---|---|
| 650 | 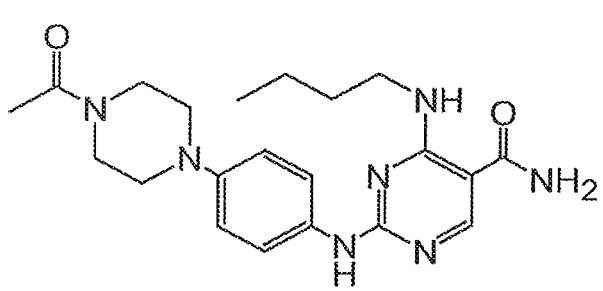 | | | ++ |
| 651 | 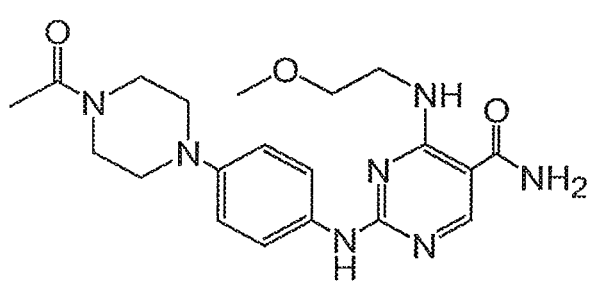 | | | ++ |
| 652 | 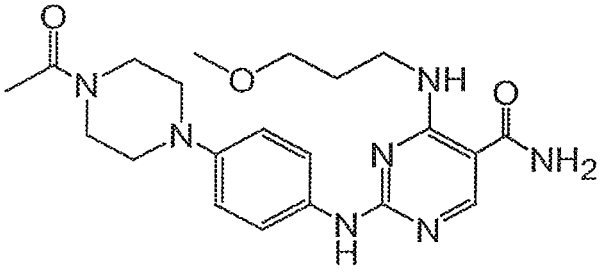 | | | ++ |

FIG. 7C

| Example No. | Structure | MW | MH+ | SyK IC50 Code |
|---|---|---|---|---|
| 653 | 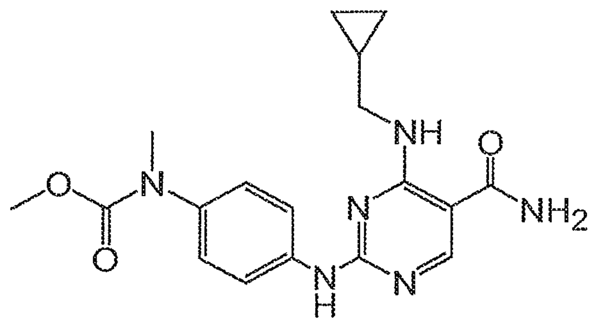 | | | 0.517 |
| 654 | 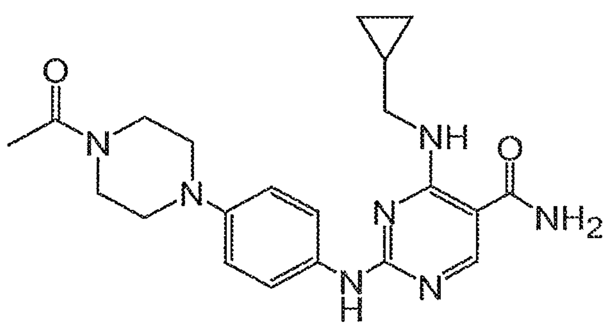 | | | ++ |
| 655 | 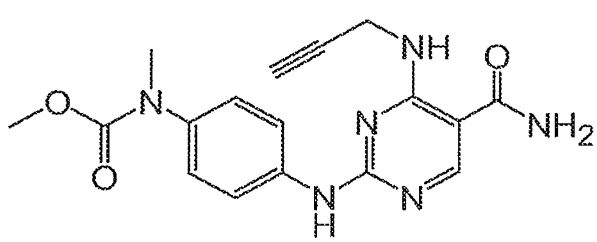 | | | ++ |

FIG. 7D
| Example No. | Structure | MW | MH+ | SyK IC50 Code |
|---|---|---|---|---|
| 656 | 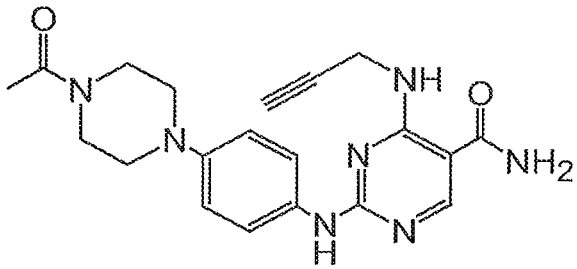 | | | ++ |
| 657 | 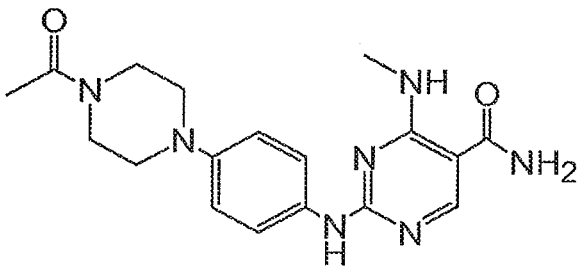 | | | ++ |
| 658 | 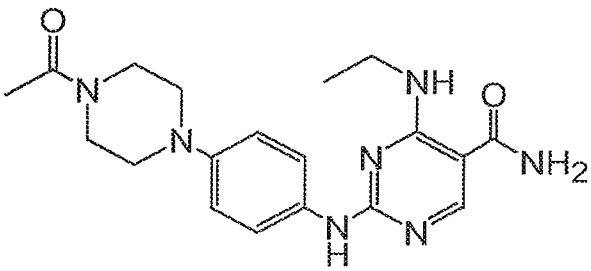 | | | ++ |

FIG. 7E

| Example No. | Structure | MW | MH+ | SyK IC50 Code |
|---|---|---|---|---|
| 659 | (acetyl-piperazinyl-phenyl)-NH-pyrimidine-4-(NH-CH2CF3)-5-carboxamide | | | ++ |
| 660 | (acetyl-piperazinyl-phenyl)-NH-pyrimidine-4-(NH-CH2-(1-acetylpiperidin-4-yl))-5-carboxamide | | | + |
| 661 | (acetyl-piperazinyl-phenyl)-NH-pyrimidine-4-(NH-CH2-(1-methanesulfonylpiperidin-4-yl))-5-carboxamide | | | + |

FIG. 7F
| Example No. | Structure | MW | MH+ | SyK IC50 Code |
|---|---|---|---|---|
| 662 | 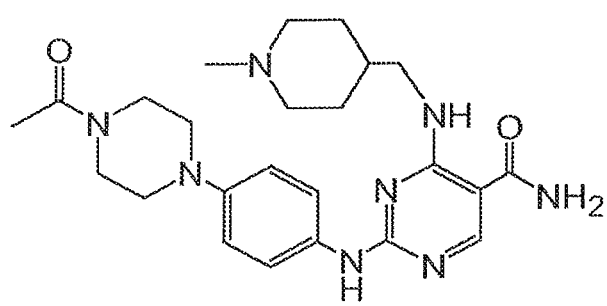 | | | ++ |
| 663 | 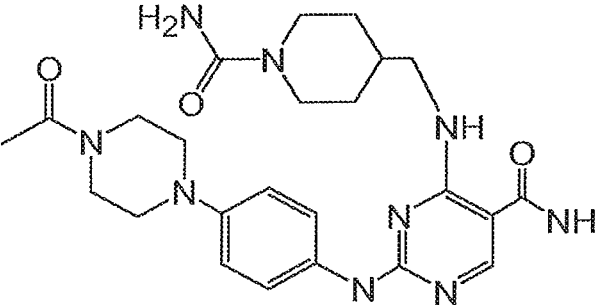 | | | ++ |
| 664 | 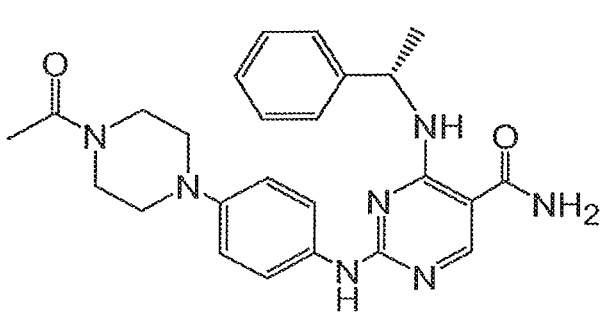 | | | ++ |

FIG. 7G
| Example No. | Structure | MW | MH+ | SyK IC50 Code |
|---|---|---|---|---|
| 665 | 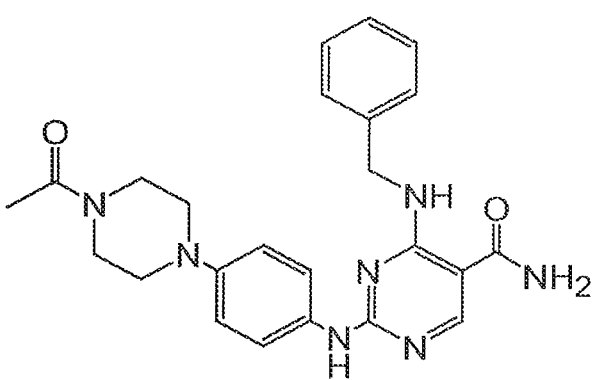 | | | ++ |
| 666 | 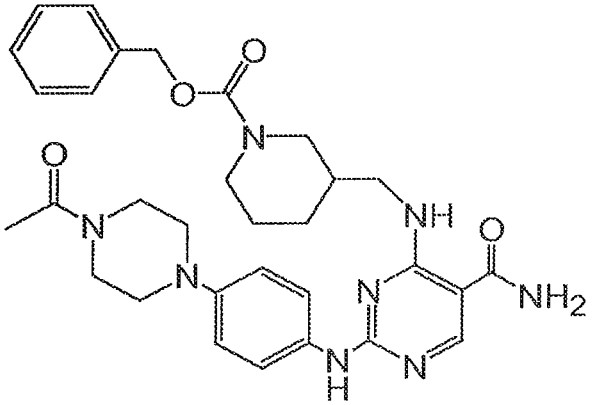 | | | + |
| 667 | 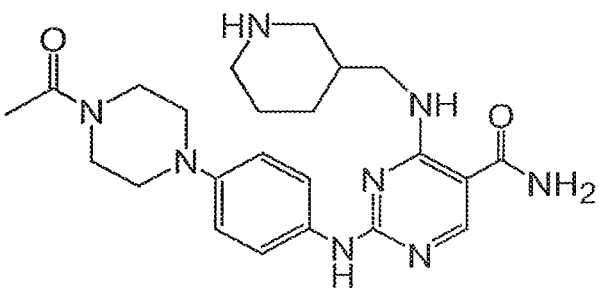 | | | +++ |

FIG. 7H
| Example No. | Structure | MW | MH+ | SyK IC50 Code |
|---|---|---|---|---|
| 668 | 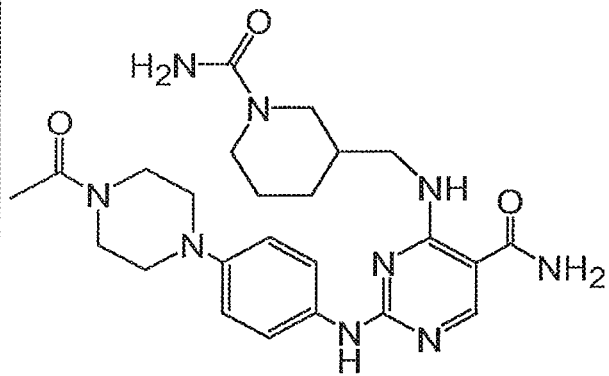 | | | ++ |
| 669 | 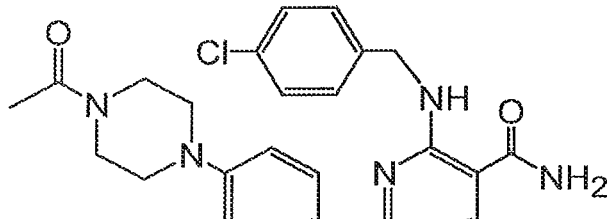 | | | + |
| 670 | 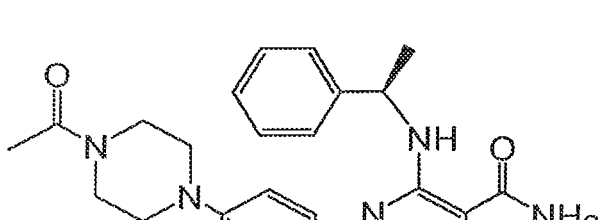 | | | + |

FIG. 7I

| Example No. | Structure | MW | MH+ | SyK IC50 Code |
|---|---|---|---|---|
| 671 | 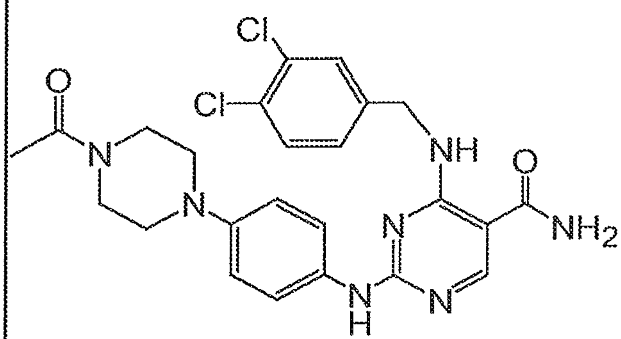 | | | + |
| 672 | 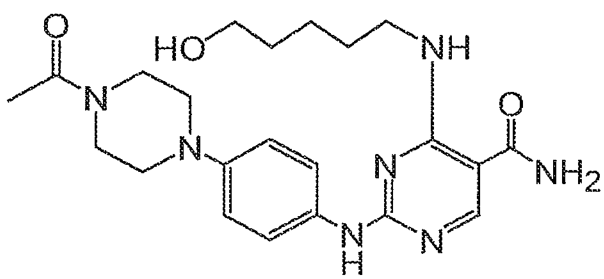 | | | ++ |
| 673 | 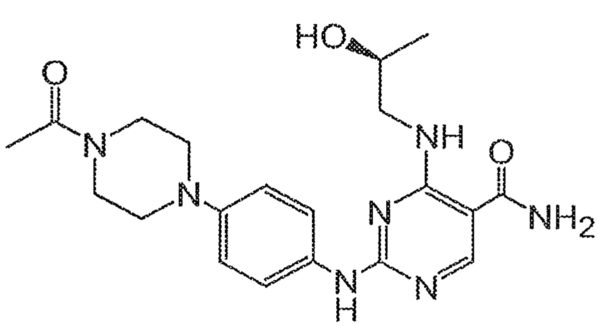 | | | ++ |

FIG. 7J

| Example No. | Structure | MW | MH+ | SyK IC50 Code |
|---|---|---|---|---|
| 674 | 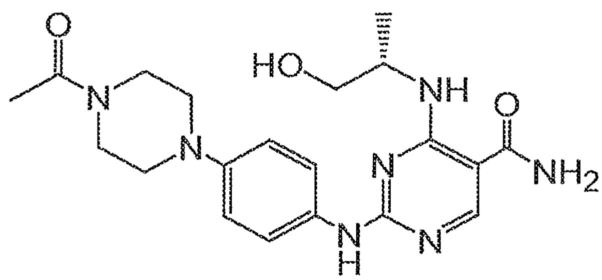 | | | ++ |
| 675 | 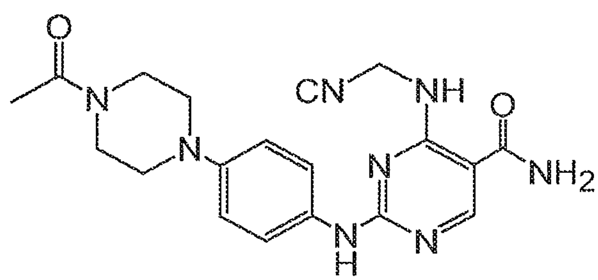 | | | ++ |
| 676 | 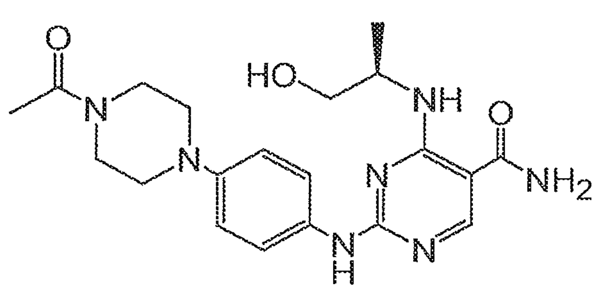 | | | ++ |

FIG. 7K

| Example No. | Structure | MW | MH+ | SyK IC50 Code |
|---|---|---|---|---|
| 677 | (structure) | | | + |
| 678 | (structure) | | | ++ |
| 679 | (structure) | | | ++ |

FIG. 7L
| Example No. | Structure | MW | MH+ | SyK IC50 Code |
|---|---|---|---|---|
| 680 | 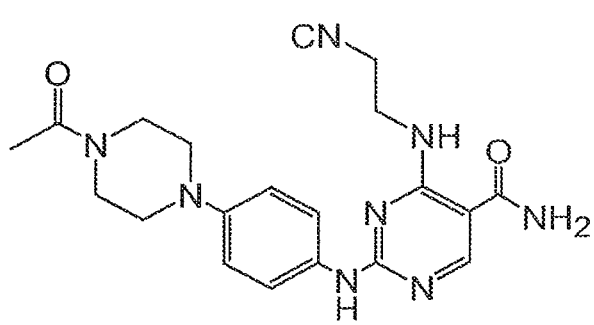 | | | ++ |
| 681 | 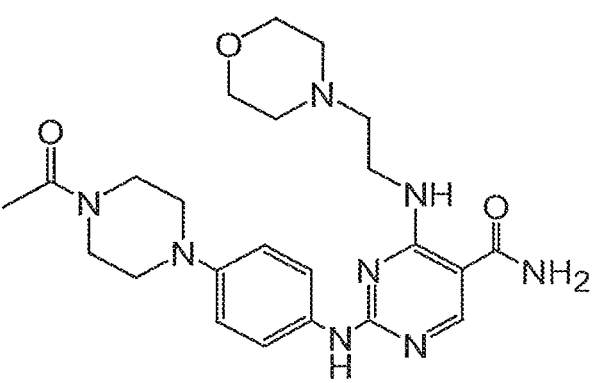 | | | + |
| 682 | 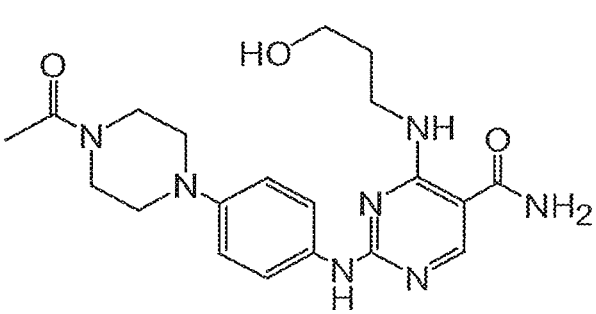 | | | ++ |

FIG. 7M
| Example No. | Structure | MW | MH+ | SyK IC50 Code |
|---|---|---|---|---|
| 683 | 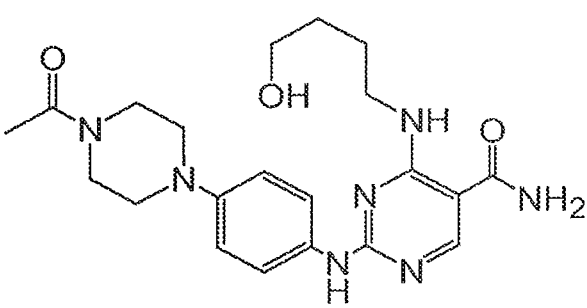 | | | ++ |
| 684 | 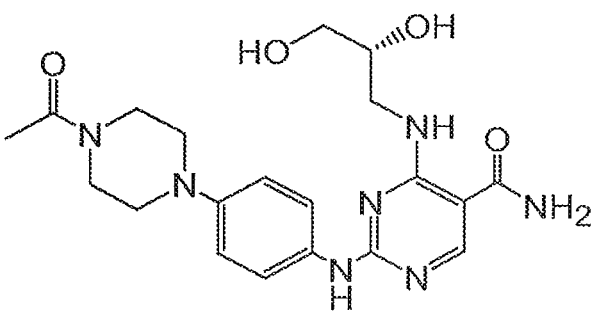 | | | ++ |
| 685 | 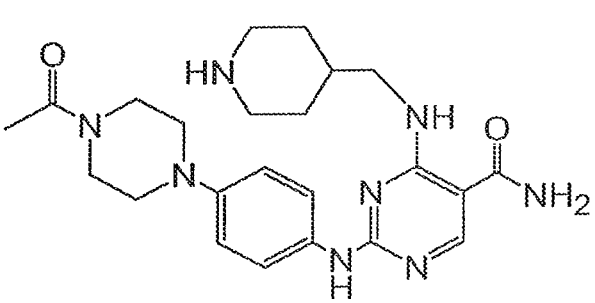 | | | +++ |

FIG. 7N

| Example No. | Structure | MW | MH+ | SyK IC50 Code |
|---|---|---|---|---|
| 686 | 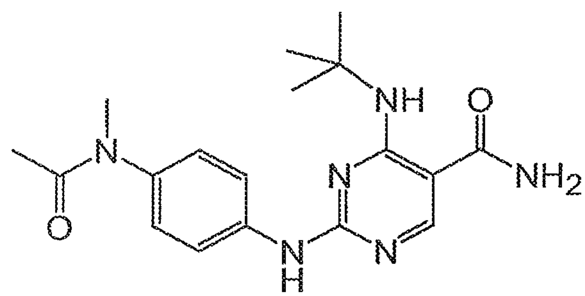 | 356.43 | 357.2 | ++ |
| 687 | 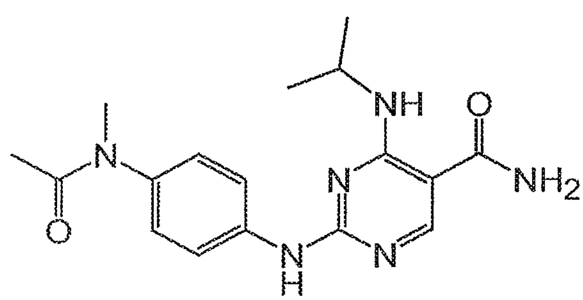 | 342.403 | 343 | ++ |
| 688 | 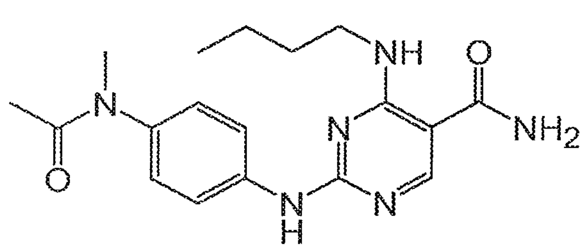 | 356.43 | 357.2 | ++ |

FIG. 7O

| Example No. | Structure | MW | MH+ | SyK IC50 Code |
|---|---|---|---|---|
| 689 | 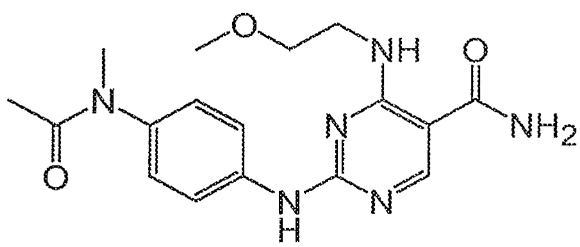 | 358.402 | 359 | ++ |
| 690 | 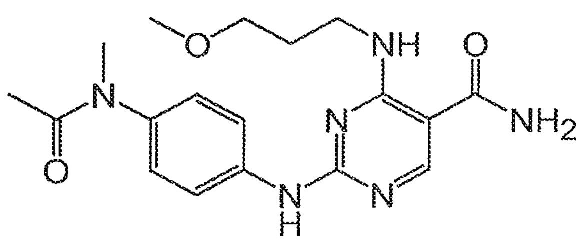 | 372.429 | 373 | ++ |
| 691 | 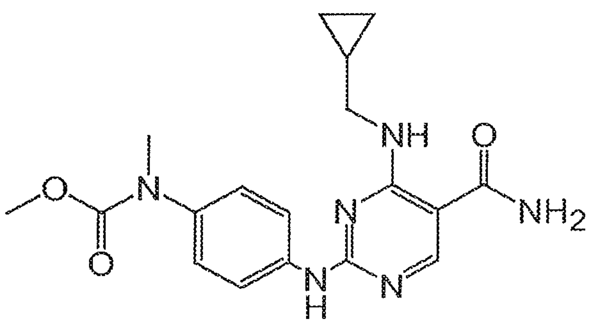 | 370.413 | 371.2 | ++ |

FIG. 7P

| Example No. | Structure | MW | MH+ | SyK IC50 Code |
|---|---|---|---|---|
| 692 | 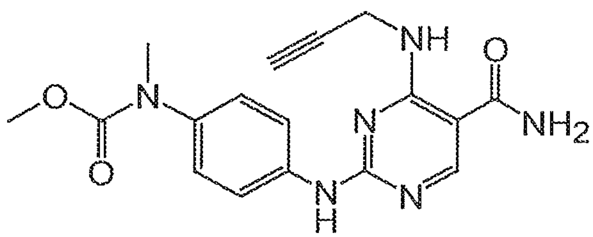 | 354.37 | 355.2 | ++ |
| 693 | 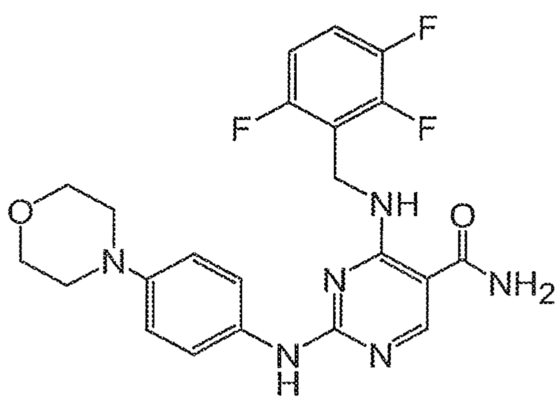 | 458.444 | 459 | ++ |
| 694 | 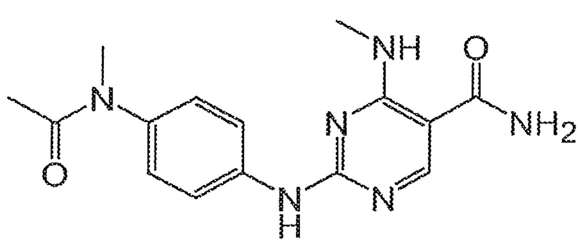 | 314.349 | 315.2 | ++ |

FIG. 7Q

| Example No. | Structure | MW | MH+ | SyK IC50 Code |
|---|---|---|---|---|
| 695 | 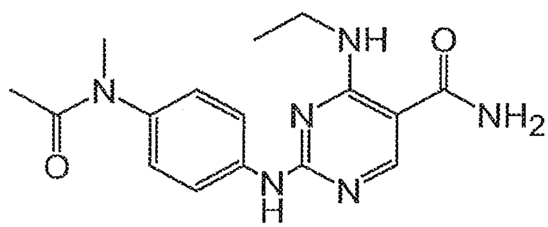 | 328.376 | 329.2 | ++ |
| 696 | 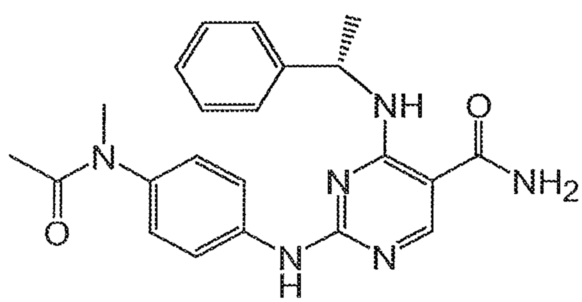 | 404.474 | M+1=405 | ++ |
| 697 | 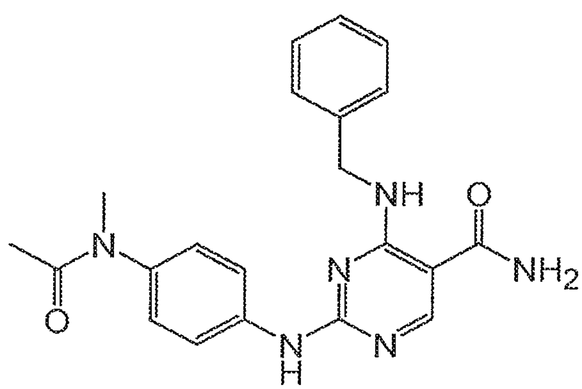 | 390.447 | 391 | ++ |

FIG. 7R
| Example No. | Structure | MW | MH+ | SyK IC50 Code |
|---|---|---|---|---|
| 698 | 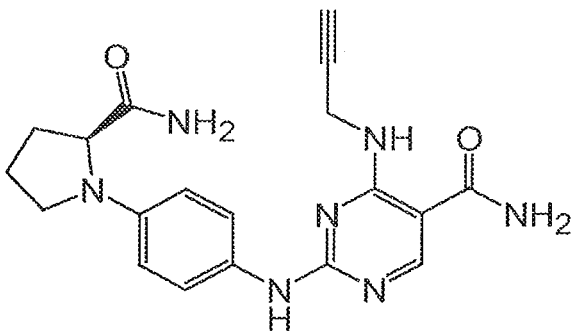 | 379.424 | 380 | ++ |
| 699 | 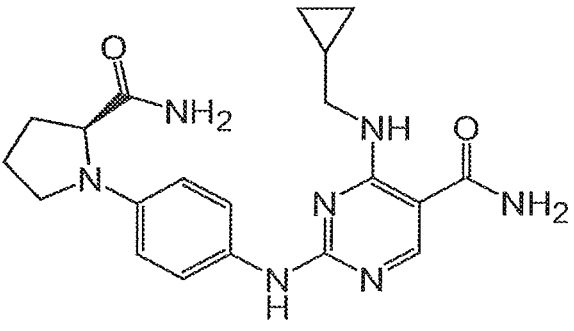 | 395.467 | 396 | ++ |
| 700 | 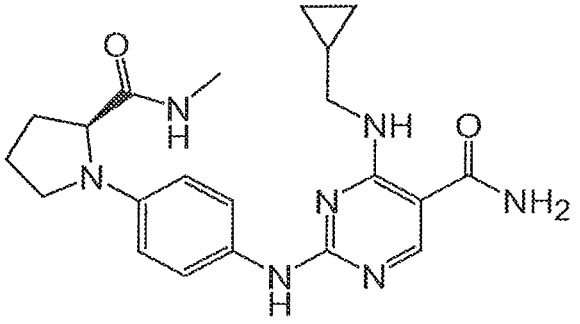 | 409.494 | 411 | ++ |

FIG. 7S
| Example No. | Structure | MW | MH+ | SyK IC50 Code |
|---|---|---|---|---|
| 701 | 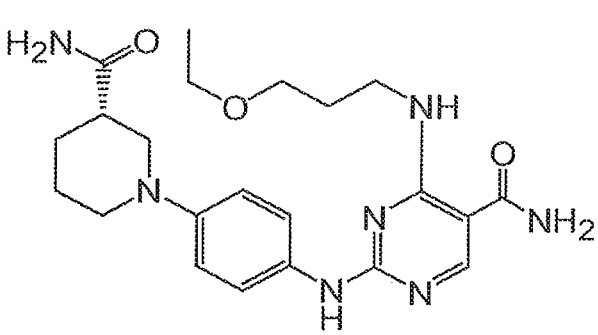 | 441.536 | 442.6 | ++ |
| 702 | 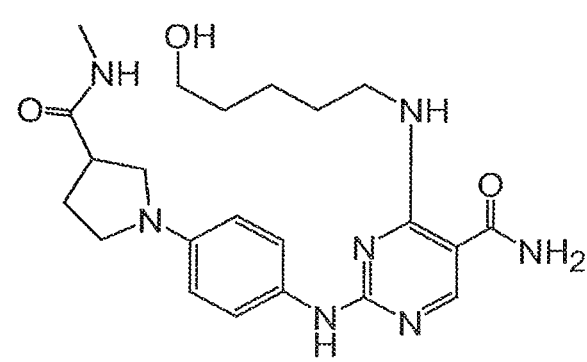 | 441.536 | ES(+) MS [M+1]= 442 | ++ |
| 703 | 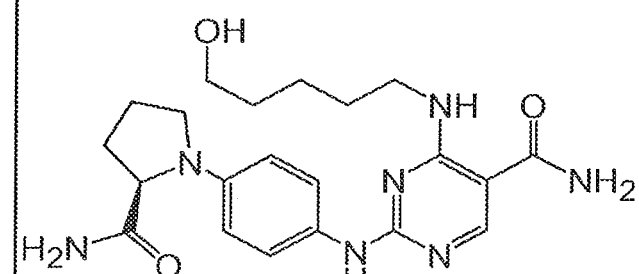 | 427.509 | ES(+) MS [M+1]= 428 | ++ |

FIG. 7T
| Example No. | Structure | MW | MH+ | SyK IC50 Code |
|---|---|---|---|---|
| 704 | 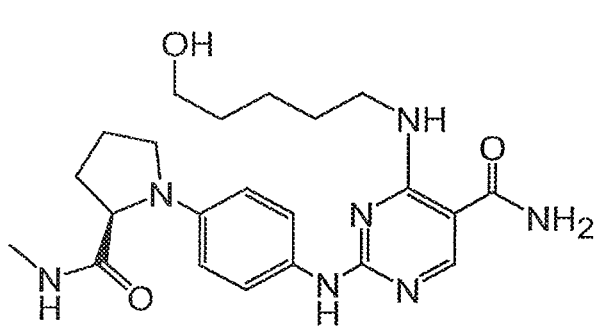 | 441.536 | ES(+) MS [M+1]= 442 | ++ |
| 705 | 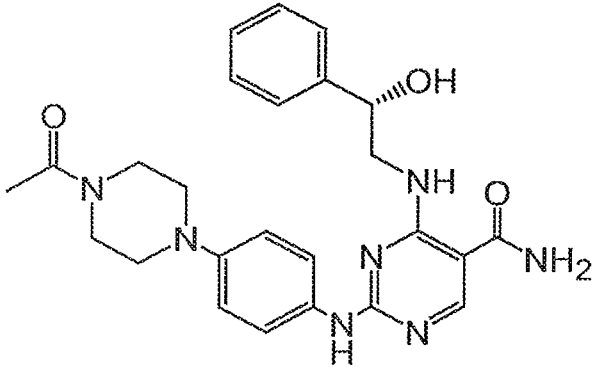 | 475.553 | 476.4 | ++ |
| 706 | 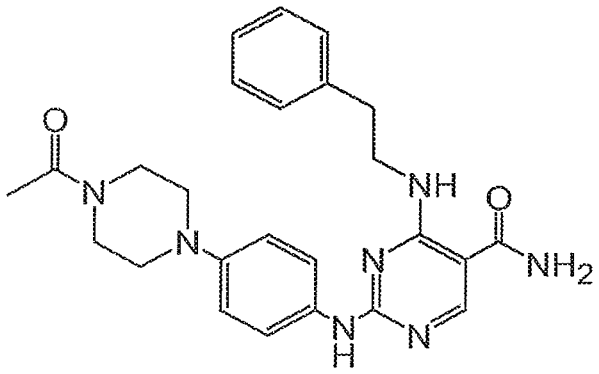 | 459.554 | 460.4 | ++ |

| Example No. | Structure | MW | MH+ | SyK IC50 Code |
|---|---|---|---|---|
| 707 | 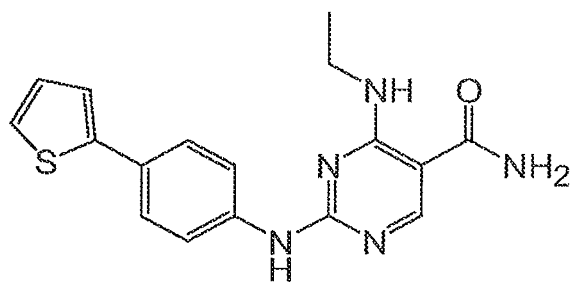 | 339.421 | 340.3 | ++ |
|  |  |  |  |  |
|  |  |  |  |  |

FIG. 7V
| Example No. | Structure | SyK IC50 |
|---|---|---|
| 708 | 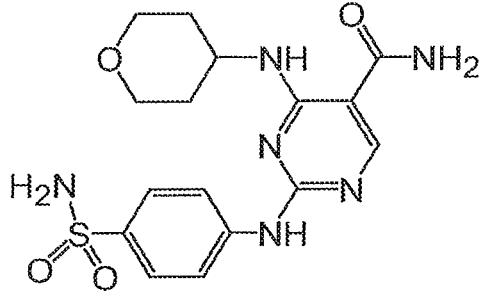 | + |
| 709 | 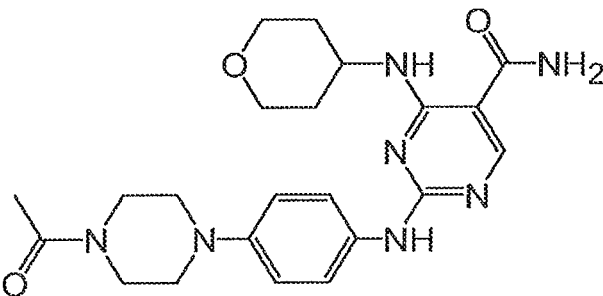 | + |
| 710 | 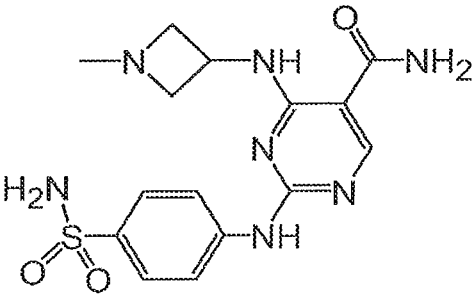 | + |

FIG. 7W
| Example No. | Structure | SyK IC50 |
|---|---|---|
| 711 | 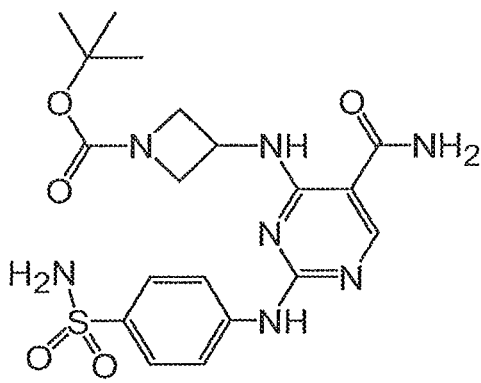 | + |
| 712 | 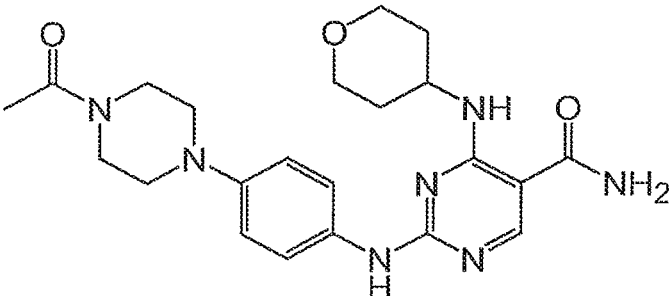 | + |
| 713 | 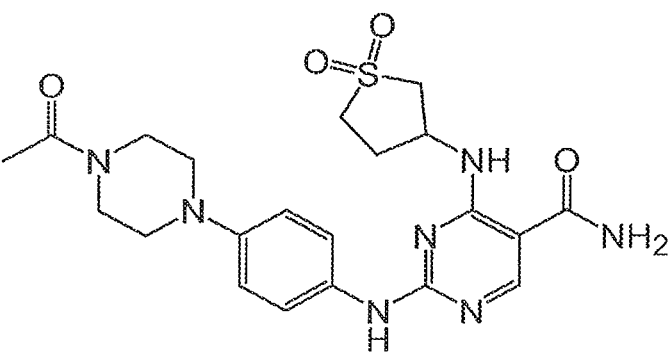 | + |

FIG. 8B

A AMPK(r)
B ARK5(h)
C CHK1(h)
D cKit(D816H)(h)
E cKit(V560G)(h)
F cKit(V654A)(h)
G FGFR1(V561M)(h)
H Flt3(D835Y)(h)
I Flt3(h)
J Flt4(h)
K Fms(h)
L GCK(h)

M Itk(h)
N IAK2(h)
O IAK3(h)
P INK3(h)
Q MARK1(h)
R MELK(h)
S MLK1(h)
T MST1(h)
U MST2(h)
V PAKS
W PAR

X PGDF
Y PDGFRa(V561D)(h)
Z Ret(h)
AA Ret(V804L)(h)
AB Ret(V804M)(h)
AC Rsk2(h)
AD Rsk4(h)
AE Src(T341M)(h)
AF Syk(h)
AG TBK1(h)
AH TSSK1(h)

| | A | B | C | D | E | F | G | H | I | J | K | L | M | N | O | P | Q | R | S | T | U | V | W | X | Y | Z | AA | AB | AC | AD | AE | AF | AG | AH |
|---|---|---|---|---|---|---|---|---|---|---|---|---|---|---|---|---|---|---|---|---|---|---|---|---|---|---|---|---|---|---|---|---|---|---|
| P459-72 | 0 | 17 | 4 | 28 | 11 | 39 | 0 | 46 | 56 | 2 | 5 | 44 | 0 | 0 | 2 | 0 | 0 | 0 | 8 | 0 | 2 | 2 | 51 | 0 | 4 | 14 | 20 | 4 | 28 | 0 | 0 | 13 | 87 | 0 | 26 |
| P505-15 | 14 | 0 | 11 | 45 | 25 | 46 | 9 | 66 | 62 | 12 | 16 | 22 | 0 | 12 | 4 | 3 | 5 | 8 | 39 | 2 | 10 | 61 | 5 | 36 | 16 | 28 | 12 | 34 | 33 | 0 | 34 | 98 | 4 | 18 |
| P420-89 | 91 | 97 | 83 | 95 | 95 | 97 | 98 | 97 | 83 | 93 | 91 | 81 | 89 | 98 | 98 | 93 | 85 | 92 | 92 | 98 | 98 | 95 | 96 | 79 | 90 | 88 | 94 | 98 | 95 | 95 | 98 | 83 | 85 | 93 | 88 | 94 | 38 |

① Ex. 596 Syk IC50 = 43 nM  % Inhib. at 300 nM
② Ex. 587 Syk IC50 = 46 nM  % Inhib. at 50 nM
③ P-420-89 Syk IC50 = 31 nM  % Inhib. at 300 nM FIG. 9A
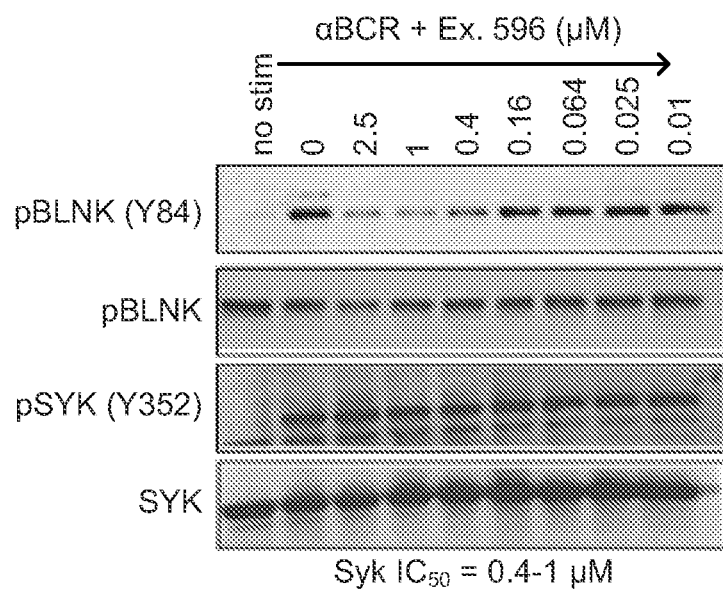
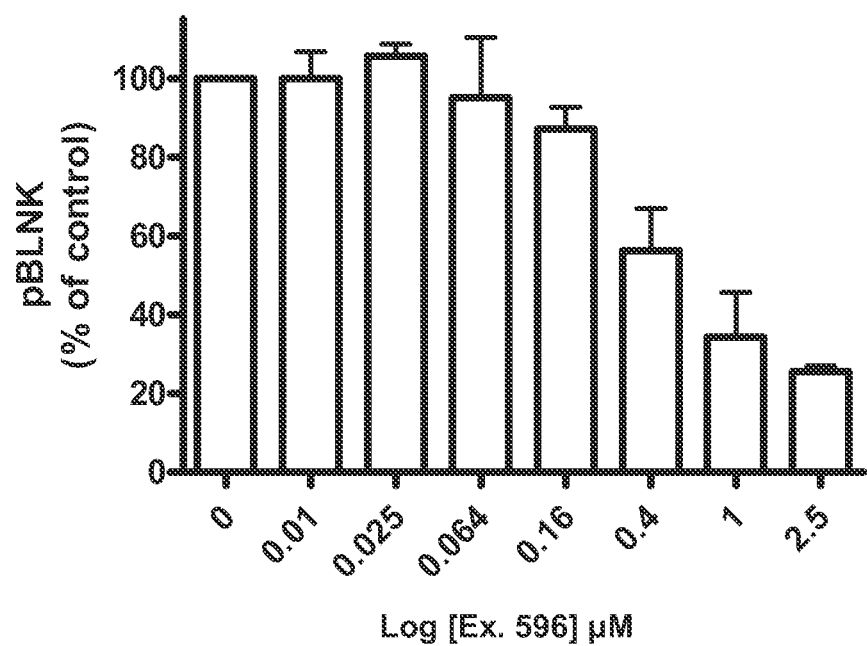

FIG. 9B
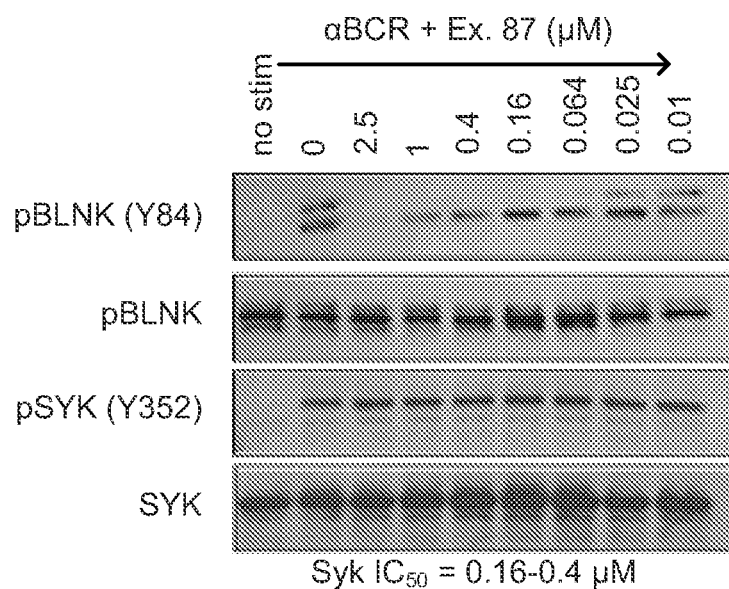
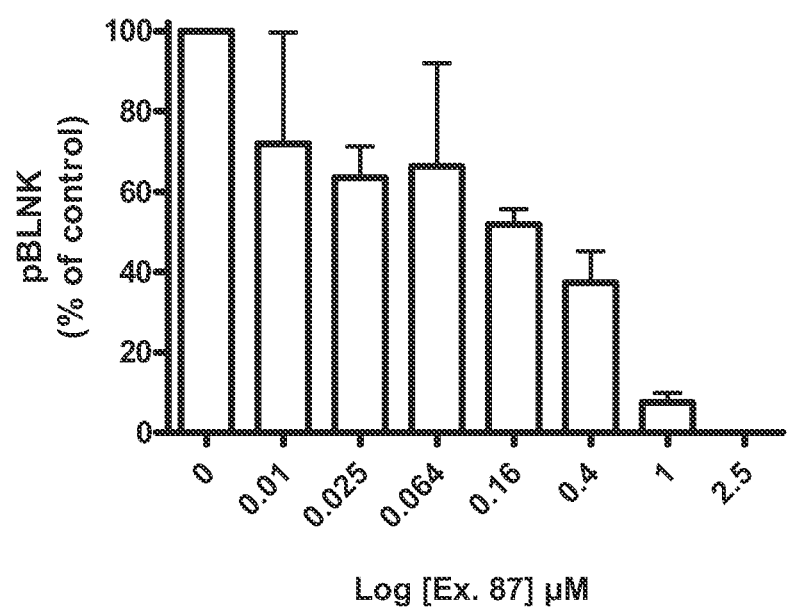

FIG. 9C
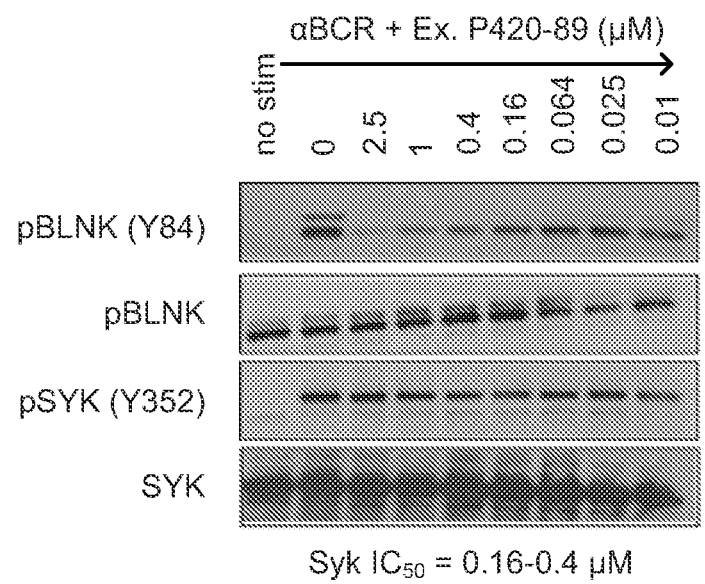
Syk IC$_{50}$ = 0.16-0.4 µM
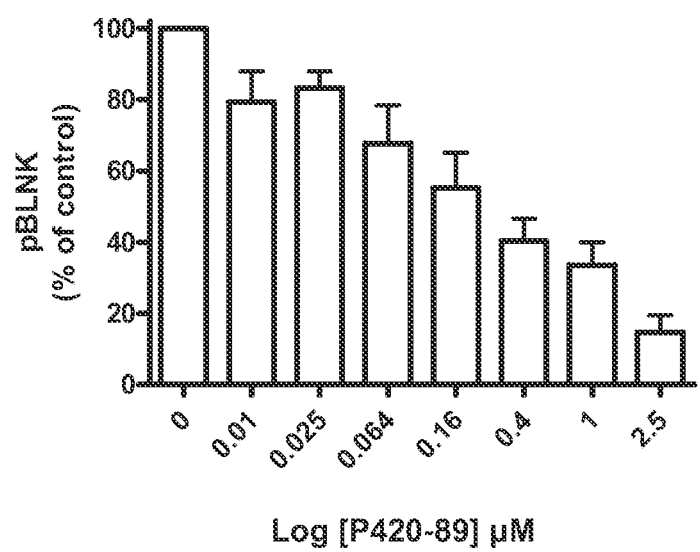

FIG. 11C

| Compound | IC50 (μM) mean ± SD | | |
|---|---|---|---|
| | SUDHL-4 | SUDHL-6 | Toledo |
| Example 596(Syk) | 5.4 ± 1.8 | 2.6 ± 1.4 | 38 ± 19 |
| Example 87(Syk) | 1.8 ± 0.7 | 1.1 ± 0.4 | 9.3 ± 4.0 |
| Example x (Syk/JAK) | 1.8 ± 0.6 | 0.9 ± 0.3 | 9.3 ± 5.4 |

INHIBITORS OF PROTEIN KINASES

CROSS REFERENCES TO RELATED APPLICATIONS

This application is continuation of U.S. application Ser. No. 14/561,821 filed Dec. 5, 2014, which is continuation of U.S. application Ser. No. 13/916,926 filed Jun. 13, 2013 20-1-4, which is continuation of U.S. application Ser. No. 13/360,862 filed Jan. 30, 2012, which is continuation of U.S. application Ser. No. 12/386,509 filed Apr. 16, 2009, which claims the benefit of U.S. Provisional Patent Application No. 61/120,348, filed Dec. 5, 2008, U.S. Provisional Patent Application No. 61/120,346, filed Dec. 5, 2008, U.S. Provisional Patent Application No. 61/120,344, filed Dec. 5, 2008, U.S. Provisional Patent Application No. 61/120,341, filed Dec. 5, 2008, U.S. Provisional Patent Application No. 61/045,499, filed Apr. 16, 2008, U.S. Provisional Patent Application No. 61/045,417, filed Apr. 16, 2008, U.S. Provisional Patent Application No. 61/045,406, filed Apr. 16, 2008, and U.S. Provisional Patent Application No. 61/045,399, filed Apr. 16, 2008, the entire disclosures of which are incorporated herein by reference.

BACKGROUND OF THE INVENTION

Field of the Invention

This invention is directed to pyrimidine-5-carboxamide compounds which act as inhibitors of Spleen tyrosine kinase (syk) and/or JAK kinases. This invention is also directed to pharmaceutical compositions containing the pyrimidine-5-carboxamide compounds and methods of using the compounds or compositions to treat a condition characterized by undesired thrombosis. The invention is also directed to methods of making the compounds described herein.

State of the Art

Protein kinases constitute a large family of structurally related enzymes that are responsible for the control of a variety of signal transduction processes within cells (see, e.g., Hardie and Hanks, The Protein Kinase Facts Book, I and II, Academic Press, San Diego, Calif., 1995). Protein kinases are thought to have evolved from a common ancestral gene due to the conservation of their structure and catalytic function. Almost all kinases contain a similar 250-300 amino acid catalytic domain. The kinases can be categorized into families by the substrates they phosphorylate (e.g., protein-tyrosine, protein-serine/threonine, lipids, etc.). Sequence motifs have been identified that generally correspond to each of these families (see, e.g., Hanks & Hunter, (1995), FASEB J. 9:576-596; Knighton et al., (1991), Science 253:407-414; Hiles et al., (1992), Cell 70:419-429; Kunz et al., (1993), Cell 73:585-596; Garcia-Bustos et al., (1994), EMBO J. 13:2352-2361).

Many diseases are associated with abnormal cellular responses triggered by protein kinase-mediated events. These diseases include autoimmune diseases, inflammatory diseases, bone diseases, metabolic diseases, neurological and neurodegenerative diseases, cancer, cardiovascular diseases, allergies, asthma, alzheimer's disease and hormone-related diseases. As a consequence, there has been substantial efforts in medicinal chemistry to find inhibitors of protein kinases for use as therapeutic agents.

Immunoreceptor tyrosine activation motif (ITAM)-mediated signaling has emerged as a primary event in signaling pathways responsible for human pathologies. ITAM-mediated signaling is responsible for relaying activation signals initiated at classical immune receptors such as T-cell receptors, B-cell receptors, Fc receptors in immune cells and at GPVI and FcγRIIa in platelets to downstream intracellular molecules such as syk and ZAP-70 (Underhill, D. M and Goodridge, H. S., *Trends Immunol.*, 28:66-73, 2007).

The binding of a ligand to an ITAM-containing receptor triggers signaling events which allows for the recruitment of proteins from a family of nonreceptor tyrosine kinases called the Src family. These kinases phosphorylate tyrosine residues within the ITAM sequence, a region with which the tandem SH2 domains on either syk or ZAP-70 interact.

Syk, along with Zap-70, is a member of the syk family of protein tyrosine kinases. The interaction of syk or ZAP-70 with diphosphorylated ITAM sequences induces a conformation change in the kinases that allows for tyrosine phosphorylation of the kinase itself. Phosphorylated Syk family members activate a multitude of downstream signaling pathway proteins which include Src homology 2 (SH2) domain containing leukocyte-specific phosphoprotein of 76 kDa (SLP-76), Linker of Activation of T-cells (LAT) and PLC (phospholipase C)γ2.

Human pathologies attributed to dysfunctional ITAM-mediated signaling include autoimmune diseases such as rheumatoid arthritis, systemic lupus, multiple sclerosis, hemolytic anemia, immune-thrombocytopenia purpura, and heparin-induced thrombocytopenia and arteriosclerosis. Interestingly, many of the above mentioned diseases are thought to occur through crosslinking of Fc receptors by antibodies which, via syk, activate a signaling cascade in mast, basophil and other immune cells that result in the release of cell mediators responsible for inflammatory reactions. The release of mediators and the production of cytokines in IgE stimulation-dependent allergic and inflammatory reactions from mast cells and basophiles can be controlled by inhibiting the tyrosine kinase activity of syk (Rossi, A. B. et al., *J Allergy Clin Immunol.*, 118:749-755, 2006). In immune-thrombocytopenia, antibody bound platelets are cleared by the spleen by an Fc receptor/ITAM/syk-mediated process (Crow, A. R. et al., *Blood*, 106: abstract 2165, 2005). Drug-induced thrombocytopenia, caused by heparin-platelet factor 4 immune complexes that activate platelet FcγRIIa, also involve syk signaling downstream of receptor engagement (Reilly, M. P., *Blood*, 98:2442-2447, 2001).

Platelet agonists induce inside-out integrin signaling resulting in fibrinogen binding and platelet aggregation. This initiates outside-in signaling which produces further stimulation of platelets. syk is activated during both phases of integrin signaling, and inhibition of syk is shown to inhibit platelet adhesion to immobilized proteins (Law, D. A. et al., *Blood*, 93:2645-2652, 1999). Release of arachidonic acid and serotonin and platelet aggregation induced by collagen are markedly inhibited in platelets derived from syk deficient mouse (Poole, A. et al., *EMBO J.*, 16:2333-2341, 1997). Thus syk inhibitors may also possess anticoagulation action.

Because of the role syk plays in Ig-induced platelet activations, it is likely to be important in arteriosclerosis and restenosis. Arteriosclerosis is a class of diseases characterized by the thickening and hardening of the arterial walls of blood vessels. Although all blood vessels are susceptible to this serious degenerative condition, the aorta and the coronary arteries serving the heart are most often affected. Arteriosclerosis is of profound clinical importance since it can increase the risk of heart attacks, myocardial infarctions, strokes, and aneurysms.

The traditional treatment for arteriosclerosis includes vascular recanalization procedures for less-serious blockages and coronary bypass surgery for major blockages. A serious shortcoming of intravascular procedures is that, in a significant number of treated individuals, some or all of the treated vessels restenose (i.e., re-narrow). For example, restenosis of an atherosclerotic coronary artery after PTCA occurs in 10-50% of patients undergoing this procedure and subsequently requires either further angioplasty or a coronary artery bypass graft. Furthermore, restenosis of an atherosclerotic coronary artery after stenting occurs in 10-20% of patients undergoing this procedure and subsequently requires repeat treatments to maintain adequate blood flow through the affected artery. Restenosis generally occurs in a relatively brief time period, e.g., roughly less than six months, after treatment.

While the exact hormonal and cellular processes promoting restenosis have not been determined, restenosis is thought to be due in part to mechanical injury to the walls of the blood vessels caused by the balloon catheter or other intravascular device. For example, the process of PTCA, in addition to opening the obstructed artery, also injures resident coronary arterial smooth muscle cells (SMCs). In response to this injury, adhering platelets, infiltrating macrophages, leukocytes, or the smooth muscle cells themselves release cell-derived growth factors such as platelet-derived growth factor (PDGF), with subsequent proliferation and migration of medial SMCs through the internal elastic lamina to the area of the vessel intima. Further proliferation and hyperplasia of intimal SMCs and, most significantly, production of large amounts of extracellular matrix over a period of three to six months results in the filling in and narrowing of the vascular space sufficient to significantly obstruct blood flow.

In addition to the role syk plays in Ig-induced platelet activations, syk plays a very important role in collagen-mediated signaling. The primary adhesive protein responsible for platelet adhesion and activation is collagen. Collagen is a filamentous protein contained within the fibrotic caps of atheromas which becomes exposed to blood during plaque rupture. Collagen functions initially by binding von Willebrand factor which tethers platelets through binding platelet membrane GPIb. Collagen functions secondarily by engaging the two collagen receptors on platelets, GPVI and integrin α2β1.

GPVI exists in platelet membranes as a complex with FcRγ, an interaction required for the expression of GPVI. Activation of FcγRIIa on platelets results in platelet shape change, secretion and thrombosis. Signaling by the GPVI/FcRγ complex is initiated by tyrosine phosphorylation of the ITAM domain of FCRγ followed by the recruitment of syk. Activation of GPVI leads to induction of multiple platelet functions including: activation of integrins α2β1 to achieve firm platelet adhesion, and GP IIb-IIIa which mediates platelet aggregation and thrombosis growth; platelet secretion, allowing for the delivery of inflammatory proteins such as CD40L, RANTES and TGFβ to the vessel wall; and the expression of P-selectin which allows for the recruitment of leukocytes. Therefore, it is believed that syk inhibitors can inhibit thrombotic events mediated by platelet adhesion, activation and aggregation.

It has been reported that the tyrosine phosphorylation of intracellular protein (activation) induced by stimulation of a receptor for IgG antibody, FcγR, and the phagocytosis mediated by FcγR are considerably inhibited in macrophages derived from syk deficient mouse (Crowley, M. T. et al., *J. Exp. Med.*, 186:1027-1039, 1997). This suggests that syk has a markedly important role in the FcγR-mediated phagocytosis of macrophages.

It has also been reported that an antisense oligonucleotide of syk suppresses the apoptosis inhibition of eosinophils induced by GM-CSF (Yousefi, S. et al., *J E. Med.*, 183: 1407-1414, 1996), showing that syk is essential for the life extending signal of eosinophils caused by GM-CSF and the like. Since life extension of eosinophils is closely related to the transition of diseases into a chronic state in allergic disorders, such as asthma, syk inhibitors can also serve as therapeutic agents for chronic eosinophilic inflammation.

Syk is important for the activation of B-cells via a B-cell antigen receptor and is involved in the phosphatidylinositol metabolism and increase in the intracellular calcium concentration caused by the antigen receptor stimulation (Hutchcroft, J E. et al., *J. Biol. Chem.*, 267:8613-8619, 1992; and Takata, M. et al., *EMBO J.*, 13:1341-1349, 1994). Thus, syk inhibitors may be used to control the function of B-cells and are, therefore, expected to serve as therapeutic agents for antibody-related diseases.

Syk binds to a T-cell antigen receptor, quickly undergoes tyrosine phosphorylation through crosslinking of the receptor and synergistically acts upon intracellular signals mediated by Src tyrosine kinases such as Lck (Couture, C. et al., *Proc. Natl. Acad. Sci. USA*, 91:5301-5305, 1994; and Couture, C. et al., *Mol. Cell. Biol.*, 14:5249-5258, 1994). syk is present in mature T-cell populations, such as intraepithelial γδ T-cells and naïve αβ T-cells, and has been reported to be capable of phosphorylation of multiple components of the TCR signaling cascade (Latour, S. et. al., *Mol Cell Biol.*, 17:4434-4441, 1997). As a consequence, syk inhibitors may serve as agents for inhibiting cellular immunity mediated by T-cell antigen receptor.

Recent comparative genomic hybridization studies have identied syk as another gene important in the pathogenesis of Mantle Cell Lymphoma (MCL) (Chen, R. et al. *Journal of Clinical Oncology*, 2007 ASCO Annual Meeting Proceedings (Post-Meeting Edition). Vol 25, No 18S (June 20 Supplement), 2007: 8056). MCL represents 5-10% of all non-Hodgkins lymphomas and it is a difficult form of lymphoma to treat. It has the worst prognosis among the B cell lymphomas with median survival of three years. It has been reported that Syk is overexpressed in MCL (Rinaldi, A, et. al, *Br. J. Haematol.*, 2006; 132:303-316) and that Syk mediates mTOR (mammalian target of Rapamycin) survival signals in follicular, mantel cell, Burkitt's, and diffuse large B-cell non-Hodgkin's lymphomas (Leseux, L., et. al, *Blood*, 2006; 108:4156-4162).

Several lines of evidence suggest that many B-cell lymphomas depend upon B-cell receptor (BCR)-mediated survival signals. BCR signaling induces receptor oligomerization and phosphorylation of Igα and β immunoreceptor tyrosine-based activated motifs by SRC family kinases. ITAM phosphorylation results in the recruitment and activation of syk that initiates downstream events and amplifies the original BCR signal. Given the role of tonic BCR signaling in normal B cell and syk-dependent survival of non-Hodgkins lymphoma cell lines in vitro (Chen, L., et. al, *Blood*, 2006; 108:3428-3433), syk inhibition is a promising rational treatment target for certain B-cell lymphomas and chronic lymphocytic leukemia (CLL) (Stefania Gobessi, Luca Laurenti, Pablo Longo, Laura Carsetti, Giuseppe Leone, Dimitar G. Efremov, Constitutive activation of the protein tyrosine kinase Syk in Chronic Lymphocytic Leukemia B-cells, Blood, 2007, 110, Abstract 1123). Recent data shows that administration of a multikinase inhibitor which inhibits syk, may have significant clinical activity in CLL patients (Friedberg J W et al, Blood 2008; 112(11), Abstract 3).

The oncogenic potential of the spleen tyrosine kinase (Syk) has been described in a number of different settings. Clinically, Syk over-expression is reported in Mantle Cell Lymphoma (Rinaldi, A, et. al, *Br. J. Haematol.,* 2006; 132:303-316) and the TEL-Syk fusion protein (Translocated ETS Leukemia) generated by a chromosomal translocation (t(9;12)(q22;p12)) leads to increased Syk activity and is associated with myelodysplastic syndrome (Kuno, Y., et. al, *Blood,* 2001; 97:1050-1055). Leukemia is induced in mice by adoptively transferring bone marrow cells that express human TEL-Syk (Wossning, T., JEM, 2006; 203:2829-2840). Further, in mouse primary bone marrow cells, over-expression of Syk results in IL-7 independent growth in culture (Wossning, T., et. al, JEM, 2006; 203:2829-2840).

Interestingly, Syk signaling appears to be required for B-cell development and survival in humans and mouse. Inducible loss of the B-cell receptor (Lam, K., et. al, Cell, 1997; 90:1073-1083) or Igα (Kraus, M., et. al, Cell, 2004; 117:787-800) results in loss of peripheral B-cells in mice. Over-expression of the protein tyrosine phosphatase PTP-RO, which is known to negatively regulate Syk activity, inhibits proliferation and induces apoptosis in cell lines derived from non-Hodgkin's lymphomas (Chen, L., et. al, *Blood,* 2006; 108:3428-3433). Finally, B-cell lymphomas rarely exhibit loss of BCR expression, and anti-idiotype therapy rarely leads to resistance (Kuppers, R. *Nat Rev Cancer,* 2005; 5:251-262).

Engagement of the antigen-specific B cell receptor (BCR) activates multiple signaling pathways that ultimately regulate the cells activation status, promoting survival and clonal expansion. Signaling through the BCR is made possible by its association with two other members of the immunoglobulin super-family; Igα and Igβ, each bearing an immunotyrosine based activation motif (ITAM) (Jumaa, Hendriks et al. Annu Rev Immunol 23: 415-45 (2005). The ITAM domain is directly phosphorylated by Src family kinases in response to BCR engagement. The spleen tyrosine kinase (Syk) docks with and phosphorylates the ITAM, a process that enhances its kinase activity, resulting in Syk autophosphorylation and tyrosine phosphorylation of multiple downstream substrates (Rolli, Gallwitz et al. Mol Cell 10(5): 1057-69 (2002). This signaling pathway is active in B cells beginning at the transition from pro- to pre-B cell stage of development, when the newly formed pre-BCR is expressed. In fact, B cell development arrests at the pro-B cell stage in Syk knockout mice (Cheng, Rowley et al. 1995; Turner, Mee et al. Nature 378(6554): 303-6 (1995). Inducible loss of the B cell receptor (Lam, Kuhn et al. Cell 90(6): 1073-83 (1997) or Igα (Kraus, Alimzhanov et al. Cell 117(6): 787-800 (2004) results in loss of peripheral B cells in mice. Human B cells also appear to require Syk for proliferation and survival. Over-expression of the protein tyrosine phosphatase PTP-RO, a negative regulator of Syk activity, inhibits proliferation and induces apoptosis in cell lines derived from non-Hodgkin's lymphomas (NHL) (Chen, Juszczynski et al. Blood 108(10): 3428-33 (2006). Knock down of Syk by siRNA in the NHL line SUDHL-4 led to a block in the G1/S transition of the cell cycle (Gururajan, Dasu et al. J Immunol 178(1): 111-21 (2007). Together, these data suggest that Syk signaling is required for the development, proliferation, and even survival of human and mouse B cells.

Conversely, the oncogenic potential of Syk has been described in a number of different settings. Clinically, Syk over-expression is reported in Mantle Cell Lymphoma (Rinaldi, Kwee et al. Br J Haematol 132(3): 303-16 (2006) and the TEL-Syk fusion protein (Translocated ETS Leukemia) generated by a chromosomal translocation (t(9;12) (q22;p12)) leads to increased Syk activity and is associated with myelodysplastic syndrome (Kuno, Abe et al. Blood 97(4): 1050-5 (2001). Leukemia is induced in mice by the adoptive transfer of bone marrow cells that express human TEL-Syk (Wossning, Herzog et al. J Exp Med 203(13): 2829-40 (2006). Further, in mouse primary bone marrow cells, over-expression of Syk results in IL-7 independent growth in culture (Wossning, Herzog et al. 2006). Consistently, Syk was reported to mediate mTOR (mammalian target of Rapamycin) survival signals in follicular, mantle cell, Burkitt's, and diffuse large B-cell NHL (Leseux, Hamdi et al. Blood 108(13): 4156-62 (2006). Additional recent studies also suggest that Syk-dependant survival signals may play a role in B-cell malignancies, including DLBCL, mantle cell lymphoma and follicular lymphoma (Gururajan, Jennings et al. 2006; Irish, Czerwinski et al. J Immunol 176(10): 5715-9 (2006). Given the role of tonic BCR signaling in normal B cells and Syk-dependent survival of NHL cell lines in vitro, the specific inhibition of Syk may prove promising for the treatment of certain B-cell lymphomas.

Recently, R406 (Rigel Pharmaceuticals) was reported to inhibit ITAM signaling in response to various stimuli, including FcεR1 and BCR induced Syk activation (Braselmann, Taylor et al. J Pharmacol Exp Ther 319(3): 998-1008 (2006). Interestingly, this ATP-competitive inhibitor of Syk was also active against Flt3, cKit, and JAK kinases, but not against Src kinase (Braselmann, Taylor et al. 2006). Activating mutations to Flt3 are associated with AML and inhibition of this kinase is currently under clinical development (Burnett and Knapper Hematology Am Soc Hematol Educ Program 2007: 429-34 (2007). Over-activation of the tyrosine kinase cKit is also associated with hematologic malignancies, and a target for cancer therapy (Heinrich, Griffith et al. Blood 96(3): 925-32 (2000). Similarly, JAK3 signaling is implicated in leukemias and lymphomas, and is currently exploited as a potential therapeutic target (Heinrich, Griffith et al. 2000). Importantly, the multi-kinase inhibitory activity of R406 attenuates BCR signaling in lymphoma cell lines and primary human lymphoma samples, resulting in apoptosis of the former (Chen, Monti et al. Blood 111(4): 2230-7 (2008). Further, a phase II clinical trial reported favorable results by this compound in refractory NHL and chronic lymphocytic leukemia (Friedberg J W et al, Blood 2008; 112(11), Abstract 3). Although the precise mechanism of action is unclear for R406, the data suggest that inhibition of kinases that mediate survival signaling in lymphocytes is clinically beneficial.

Additional recent studies also suggest that syk-dependant survival signals may play a role in B-cell malignancies, including DLBCL, mantle cell lymphoma and follicular lymphoma (see e.g., S. Linfengshen et al. *Blood*, February 2008; 111: 2230-2237; J. M. Irish et al. *Blood,* 2006; 108: 3135-3142; A. Renaldi et al. *Brit J. Haematology,* 2006; 132: 303-316; M. Guruoajan et al. *J. Immunol,* 2006; 176: 5715-5719; L. Laseux et al. *Blood,* 2006; 108: 4156-4162.

JAK kinases (Janus Kinases) are a family of cytoplasmic protein tyrosine kinases including JAK1, JAK2, JAK3 and TYK2. The JAKs play a crucial role in cytokine signaling. Each of the JAK kinases is selective for the receptors of certain cytokines, though multiple JAK kinases can be affected by particular cytokine or signaling pathways. Studies suggest that JAK3 associates with the common cytokine receptor gamma chain (Fcγ or γc) of the various cytokine receptors. JAK3 in particular selectively binds to receptors and is part of the cytokine signaling pathway for and activated by IL-2, IL-4, IL-7, IL-9, IL-15 and IL-21. JAK1 interacts with, among others, the receptors for cytokines IL-2, IL-4, IL-7, IL-9 and IL-21, while JAK2 interacts with, among others, the receptors for IL-9 and TNF-α. Upon the binding of certain cytokines to their receptors (e.g., IL-2, IL-4, IL-7, IL-9, IL-15 and IL-21), receptor oligomerization occurs, resulting in the cytoplasmic tails of associated JAK kinases being brought into proximity and facilitating the trans-phosphorylation of tyrosine residues on the JAK kinase. This trans-phosphorylation results in the activation of the JAK kinase.

The downstream substrates of JAK family kinases include the signal tranducer activator of transcription (STAT) proteins. Phosphorylated JAK kinases bind various STAT (Signal Transducer and Activator of Transcription) proteins. STAT proteins, which are DNA binding proteins activated by phosphorylation of tyrosine residues, function both as signaling molecules and transcription factors and ultimately bind to specific DNA sequences present in the promoters of cytokine-responsive genes (Leonard et al., (2000), J. Allergy Clin. Immunol. 105:877-888).

JAK/STAT signaling has been implicated in the mediation of many abnormal immune responses such as allergies, asthma, autoimmune diseases such as transplant (allograft) rejection, rheumatoid arthritis, amyotrophic lateral sclerosis and multiple sclerosis, as well as in solid and hematologic malignancies such as leukemia and lymphomas. For a review of the pharmaceutical intervention of the JAK/STAT pathway see Frank, (1999), Mol. Med. 5:432:456 and Seidel et al., (2000), Oncogene 19:2645-2656.

JAK3 in particular has been implicated in a variety of biological processes. For example, the proliferation and survival of murine mast cells induced by IL-4 and IL-9 have been shown to be dependent on JAK3- and gamma chain-signaling (Suzuki et al., (2000), Blood 96:2172-2180). JAK3 also plays a crucial role in IgE receptor-mediated mast cell degranulation responses (Malaviya et al., (1999), Biochem. Biophys. Res. Commun. 257:807-813), and inhibition of JAK3 kinase has been shown to prevent type I hypersensitivity reactions, including anaphylaxis (Malaviya et al., (1999), J. Biol. Chem. 274:27028-27038). JAK3 inhibition has also been shown to result in immune suppression for allograft rejection (Kirken, (2001), Transpl. Proc. 33:3268-3270). JAK3 kinases have also been implicated in the mechanism involved in early and late stages of rheumatoid arthritis (Muller-Ladner et al., (2000), J. Immunal. 164: 3894-3901); familial amyotrophic lateral sclerosis (Trieu et al., (2000), Biochem Biophys. Res. Commun. 267:22-25); leukemia (Sudbeck et al., (1999), Clin. Cancer Res. 5:1569-1582); mycosis fungoides, a form of T-cell lymphoma (Nielsen et al., (1997), Prac. Natl. Acad. Sci. USA 94:6764-6769); and abnormal cell growth (Yu et al., (1997), J. Immunol. 159:5206-5210; Catlett-Falcone et al., (1999), Immunity 10:105-115).

JAK1, JAK2, and TYK2 are expressed ubiquitously, whereas JAK3 is expressed predominantly in hematopoietic cells. The JAK kinases, including JAK3, are abundantly expressed in primary leukemic cells from children with acute lymphoblastic leukemia, the most common form of childhood cancer, and studies have correlated STAT activation in certain cells with signals regulating apoptosis (Demoulin et al., (1996), Mol. Cell. Biol. 16:4710-6; Jurlander et al., (1997), Blood. 89:4146-52; Kaneko et al., (1997), Clin. Exp. Immun. 109:185-193; and Nakamura et al., (1996), J. Biol. Chem. 271: 19483-8). They are also known to be important for lymphocyte differentiation, function and survival. JAK-3 in particular plays an essential role in the function of lymphocytes, macrophages, and mast cells. Given the importance of this JAK kinase, compounds which modulate the JAK pathway, including those selective for JAK3, can be useful for treating diseases or conditions where the function of lymphocytes, macrophages, or mast cells is involved (Kudlacz et al., (2004) Am. J. Transplant 4:51-57; Changelian (2003) Science 302:875-878). Conditions in which targeting of the JAK pathway or modulation of the JAK kinases, particularly JAK3, are contemplated to be therapeutically useful include, leukemia, lymphoma, transplant rejection (e.g., pancreas islet transplant rejection, bone marrow transplant applications (e.g., graft-versus-host disease), autoimmune diseases (e.g., diabetes, rheumatoid arthritis, lupus, psoriasis), and inflammation (e.g., asthma, allergic reactions). Conditions which can benefit from JAK3 inhibition are discussed in greater detail below. Recent data on JAK inhibition has been reported in kidney allograft patients treated with CP-690,550 and showed that markers of allogeneic response (interferon gamma) can be reduced (Van Gurp E A et al (2009) Transplanatation 87:79-86).

In view of the numerous conditions that are contemplated to benefit by treatment involving modulation of the JAK pathway it is immediately apparent that new compounds that modulate JAK pathways and methods of using these compounds should provide substantial therapeutic benefits to a wide variety of patients. Provided herein are novel 2,4-pyrimidinediamine compounds for use in the treatment of conditions in which targeting of the JAK pathway or inhibition of JAK kinases, particularly JAK3, are therapeutically useful.

Patents and patent applications related to modulation of the JAK pathway include: U.S. Pat. Nos. 5,728,536; 6,080,747; 6,080,748; 6,133,305; 6,177,433; 6,210,654; 6,313,130; 6,316,635; 6,433,018; 6,486,185; 6,506,763; 6,528,509; 6,593,357; 6,608,048; 6,610,688; 6,635,651; 6,677,368; 6,683,082; 6,696,448; 6,699,865; 6,777,417; 6,784,195; 6,825,190; 6,506,763; 6,784,195; 6,528,509; 6,608,048; 7,105,529; 6,699,865; 6,825,190; 6,815,439; 6,949,580; 7,056,944; 6,998,391; 7,074,793; 6,969,760; U.S. Pat. App. Pub. No. 2001/0007033 A1; 2002/0115173 A1; 2002/0137141 A1; 2003/0236244 A1; 2004/0102455 A1; 2004/0142404 A1; 2004/0147507 A1; and 2004/0214817 A1; and International patent applications WO 95/03701A1; WO 99/15500A1; WO 00/00202A1; WO 00/10981A1; WO 00/47583A1; WO 00/51587A2; WO 00/55159A2; WO 01/42246A2; WO 01/45641A2; WO 01/52892A2; WO 01/56993A2; WO 01/57022A2; WO 01/72758A1; WO 02/00661A1; WO 02/43735A1; WO 02/48336A2; WO 02/060492A1; WO 02/060927A1; WO 02/096909A1; WO 02/102800A1; WO 03/020698A2; WO 03/048162A1; WO 03/101989A1; WO 2004/016597A2; WO 2004/041789A1; WO 2004/041810A1; WO 2004/041814A1; WO 2004/046112A2; WO 2004/046120A2; WO 2004/047843A1; WO 2004/058749A1; WO 2004/058753A1; WO 2004/085388A2; WO 2004/092154A1; WO 2005/009957A1; WO 2005/016344A1; WO 2005/028475A2; and WO 2005/033107A1.

Patents and patent applications describing substituted pyrimidinediamine compounds include: U.S. application Ser. No. 10/355,543 filed Jan. 31, 2003 (US2004/0029902A1), international application Serial No. PCT/US03/03022 filed Jan. 31, 2003 (WO 03/063794), U.S. application Ser. No. 10/631,029 filed Jul. 29, 2003, international application Serial No. PCT/US03/24087 (WO 04/014382), U.S. application Ser. No. 10/903,263 filed Jul.

30, 2004, and international application Serial No. PCT/US2004/24716 (WO 05/016893), the disclosures of which are incorporated herein by reference. Substituted pyrimidinediamine compounds are also described in international patent application publication numbers: WO 02/059110, WO 03/074515, WO 03/106416, WO 03/066601, WO 03/063794, WO 04/046118, WO 05/016894, WO 05/122294, WO 05/066156, WO 03/002542, WO 03/030909, WO 00/39101, WO 05/037800 and U.S. Pat. Pub. No. 2003/0149064.

While progress has been made in this field, there remains a need in the art for compounds that inhibit syk and/or JAK kinase, as well as for methods for treating conditions in a patient, such as restenosis, thrombosis, and/or inflammation that can benefit from such inhibition. Moreover, the availability of compounds that selectively inhibit one of these kinases as compared to other kinases would also be desirable. The present invention satisfies this and other needs.

BRIEF SUMMARY OF THE INVENTION

The present invention provides novel compounds having activity as inhibitors of syk activity (also referred to herein as "syk inhibitors") and/or JAK kinase activity (also referred to herein as "JAK inhibitors"), as well as to methods for their preparation and use, and to pharmaceutical compositions containing the same. Such compounds have the following structure (I):

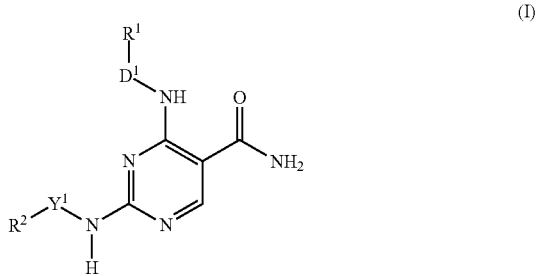

(I)

or a pharmaceutically acceptable tautomer, salt, or stereoisomer thereof, wherein $D^1$, $R^1$, $Y^1$ and $R^2$ are as defined below.

The present invention also provides a pharmaceutical composition comprising a therapeutically effective amount of a compound of formula I, or a pharmaceutical acceptable salt thereof, and a pharmaceutically acceptable carrier and/or diluent.

The compounds of the present invention have utility over a wide range of therapeutic applications, and may be used to treat a variety of conditions, mediated at least in part by syk activity, in both men and women, as well as a mammal in general (also referred to herein as a "subject"). For example, such conditions include, but are not limited to, those associated with cardiovascular disease, inflammatory disease or autoimmune disease. More specifically, the compounds of the present invention have utility for treating conditions or disorders including, but not limited to: restenosis, thrombosis, inflammation, heparin induced thrombocytopenia, dilated cardiomyopathy, sickle cell disease, atherosclerosis, myocardial infarction, vascular inflammation, unstable angina, acute coronary syndromes, allergy, asthma, rheumatoid arthritis, B-cell mediated diseases such as Non Hodgkin's lymphoma, anti-phospholipid syndrome, lupus, psoriasis, multiple sclerosis, end stage renal disease, hemolytic anemia, immune thrombocytopenic purpura, and chronic lymphocytic leukemia. Thus, in one embodiment, methods are disclosed which include the administration of an effective amount of a compound of formula (I), typically in the form of a pharmaceutical composition, to a subject in need thereof.

The conditions associated with cardiovascular disease is selected from the group consisting of acute coronary syndrome, myocardial infarction, unstable angina, refractory angina, occlusive coronary thrombosis occurring post-thrombolytic therapy or post-coronary angioplasty, a thrombotically mediated cerebrovascular syndrome, embolic stroke, thrombotic stroke, transient ischemic attacks, venous thrombosis, deep venous thrombosis, pulmonary embolism, coagulopathy, disseminated intravascular coagulation, thrombotic thrombocytopenic purpura, thromboangiitis obliterans, thrombotic disease associated with heparin-induced thrombocytopenia, thrombotic complications associated with extracorporeal circulation, thrombotic complications associated with instrumentation such as cardiac or other intravascular catheterization, intra-aortic balloon pump, coronary stent or cardiac valve, and conditions requiring the fitting of prosthetic devices.

The present invention also provides a method for inhibiting the syk activity of a blood sample comprising contacting said sample with a compound of the present invention.

The present invention further provides compounds in purified forms, as well as chemical intermediates.

These and other aspects, objects, features and advantages of the invention will be apparent upon reference to the following detailed description and figures. To this end, various references are set forth herein which describe in more detail certain background information, procedures, compounds and/or compositions, and are each hereby incorporated by reference in their entirety.

BRIEF DESCRIPTION OF THE DRAWINGS

FIG. 1 shows how Syk serves as a key mediator of Fc receptor mediated signaling in cellular biology and multiple diseases.

FIGS. 4A-4X provide table 1 illustrating compounds of the present invention and syk $IC_{50}$s.

FIGS. 5A-5BB provide table 2 illustrating compounds of the present invention and syk $IC_{50}$s.

FIGS. 6A-6E provide table 3 illustrating compounds of the present invention and syk $IC_{50}$s.

FIGS. 8A-8C show a series of compounds that were indentied to selectively inhibit Syk in purified kinase assays. (FIG. 8A) Compounds from the Syk-specific series (P459-72 and P505-15) and multi-kinase series (example 100b) were screened at 300 nM against the Millipore purified kinase panel (270 kinases tested with 10 μM ATP) to determine potency and selectivity for Syk. Data are represented as a heat-map, defined at the bottom. (FIG. 8B) Subset of the purified kinases that had >80% inhibition by any of the three compounds. P459-72 only inhibited Syk and MLK1. P505-15 at 50 nM (~10× greater than its Syk IC50) only inhibited Syk. Example 100b inhibited multiple kinases, including Syk, JAK2 and JAK3. The IC50 of Syk inhibition is reported for each compound on the left of the heat map. (FIG. 8C) Percent kinase inhibition is given in each panel within the heat-map.

FIGS. 9A-9C show the selective inhibition of Syk in non-Hodgkin's Lymphoma cell lines. B cells were stimulated with anti-BCR antibody in the presence of the indicated concentrations of Syk specific inhibitors P459-72 and P505-15 (FIG. 9A and FIG. 9B) or the dual Syk/JAK inhibitor example 100b (FIG. 9C). Western blot analyses of whole cell lysates were then performed to evaluate Syk kinase activity (pBLNK Y84 and total BLNK; top two gels) and Src kinase activity (pSyk Y352 and total Syk; bottom two gels). Experiments were performed 2-3 times each, bar graphs represent mean±S.D. of pBLNK Y84. The calculated IC50s of Syk kinase inhibition are presented above the graphs.

(FIG. 10A) bar graphs (mean±S.D., n=3) representing Src activity (pSyk Y352 MFI) and Syk activity (pERK Y204 MFI) following BCR stimulation under the various treatment conditions. (FIG. 10B) Bar graphs depicting pSTAT-6 Y641 MFI (mean±S.D., n=3) following stimulation with IL-4 in the presence of various concentrations of each inhibitor, as indicated.

FIGS. 11A-11C show how Syk-specific inhibitors disrupt proliferation and survival of and induces apoptosis in NHL cell lines. The Syk-dependent "BCR type" and Syk-independent "non-BCR type" NHL cell lines were previously described (Polo, Juszczynski et al. Proc Natl Acad Sci USA 104(9): 3207-12 (2007). (FIG. 11B) Cells were treated for 72 h with 1 and 3 µM of the Syk-specific inhibitor P505-15. Apoptosis was determined by FACS analysis of active caspase 3; data is represented as histograms. (FIG. 11C) Additional cell lines were tested for sensitivity to Syk specific (P459-72 and P505-15) versus dual Syk/JAK (example 100b) inhibition. Bar graphs represent mean±S.D. (n=3) of the percent of caspase 3 positive cells following each condition.

DETAILED DESCRIPTION OF THE INVENTION

Figure 2A:
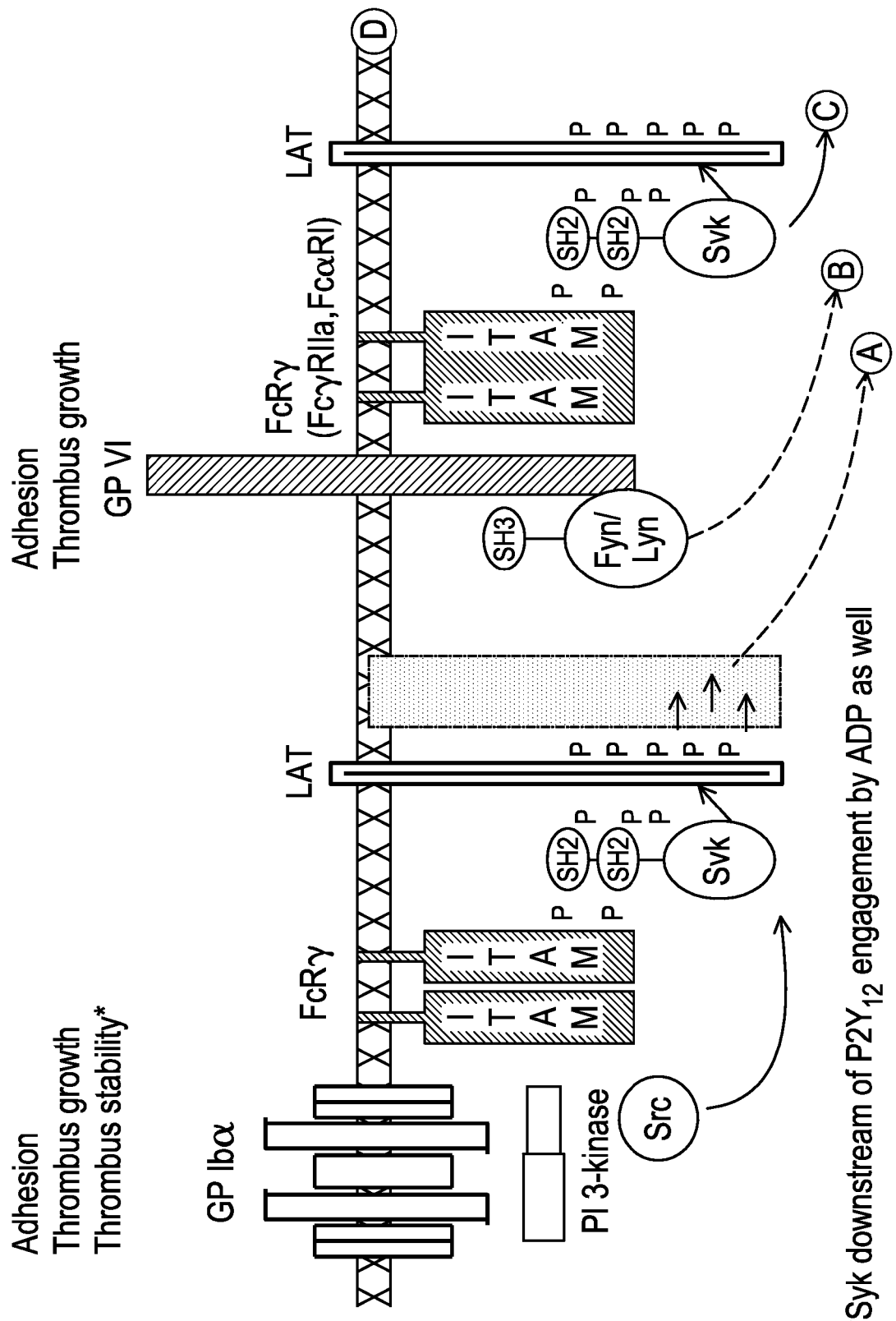
FIGS. 2A-2B show how gene targeting of Syk indicated that Syk serves as a key mediator in arterial platelet biology and a selective target for treating arterial thrombosis.
Figure 2B:
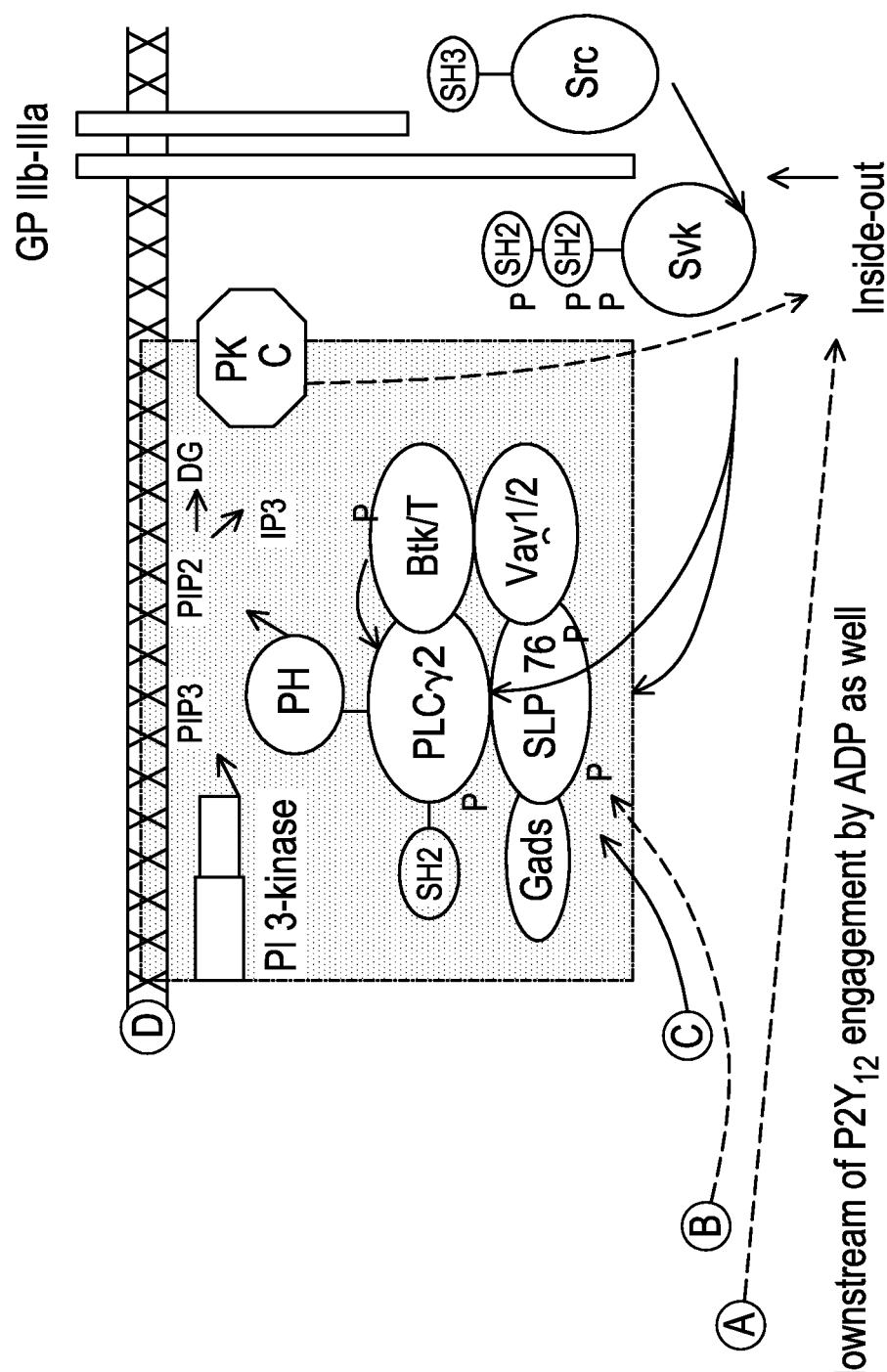

As used herein, the below terms have the following meanings unless specified otherwise:

1. Abbreviations and Definitions

The abbreviations used herein are conventional, unless otherwise defined. The following abbreviations are used: AcOH=acetic acid, AIBN=azobisisobutyronitrile (also azobisisobutylonitrile), aq.=aqueous, Boc=t-butylcarboxy, Bz —benzyl, BOP=benzotriazol-1-yloxytris(dimethylamino)-phosphonium hexafluorophosphate, BPO=benzoyl peroxide, nBuOH=n-butanol, CBr$_4$=tetrabromomethane, mCPBA=m-chloroperoxybenzoic acid, CH$_2$Cl$_2$ or DCM=dichloromethane, Cs$_2$CO$_3$=cesium carbonate, CuCl$_2$=copper chloride; DIBAL=diisobutylaluminum hydride, DIEA=Hunig's base or diisopropyl ethylamine, DME=dimethyl ether, DMF=dimethyl formamide, DMSO=dimethyl sulfoxide, DPPA=diphenyl phosphoryl azide, Et$_3$N=triethylamine, EtOAc=ethyl acetate, g=gram, HATU=2-(1H 7-Azabenzotriazol-1-yl)-1,1,3,3-tetramethyl uronium hexafluorophosphate, H$_2$=hydrogen; H$_2$O=water; HBr=hydrogen bromide; HCl=hydrogen chloride, HIV=human immunodeficiency virus, HPLC=high pressure liquid chromatography, h=hour, IgE=immunoglobulin E, IC$_{50}$=The concentration of an inhibitor that is required for 50% inhibition of an enzyme in vitro, IPA=isopropyl alcohol, kg=kilogram, KCN=potassium cyanide, KOH=potassium hydroxide, K$_2$PO$_4$=potassium phosphate, LDA=lithium diisopropylamine, LiAlH$_4$=lithium aluminum hydride=LiOH: lithium hydroxide; MeCN=acetonitrile; MS=Mass Spec, m/z=mass to charge ratio, MHz=Mega Hertz, MeOH=methanol, µM= micromolar, µL=microliter, mg=milligram, mm=millimeter, mM=millimolar, mmol=millimole, mL=milliliter, mOD/min=millioptical density units per minute, min=minute, M=molar, Na$_2$CO$_3$=sodium carbonate, ng=nanogram, NaHCO$_3$=sodium bicarbonate; NaNO$_2$=sodium nitrite; NaOH=sodium hydroxide; Na$_2$S$_2$O$_3$=sodium bisulfate; Na$_2$SO$_4$=sodium sulfate; NBS=N-bromosuccinamide; NH$_4$Cl=ammonium chloride; NH$_4$OAc=ammonium acetate; NaSMe=sodium methylthiolate, NBS=N-bromosuccinamide, n-BuLi=n-butyl lithium, nm=nanometer, nM= nanomolar, N=Normal, NMP=N-methylpyrrolidine, NMR= nuclear magnetic resonance, Pd/C=palladium on carbon, Pd(PPh$_3$)$_4$=Tetrakis-(triphenyl-phosphine)-palladium, pM= picomolar, Pin=pinacolato, PEG=polyethylene glycol, PPh$_3$ or Ph$_3$P=triphenyl phosphine, RLV=Raucher leukemia virus, Ra-Ni=Rainey Nickel, SOCl$_2$=thionyl chloride, RT= room temperature, TEA=triethylamine, THF=tetra- hydrofuran, TFA=trifluoroacetic acid, TLC=thin layer chromatography, TMS=trimethylsilyl, Tf=trifluoromethylsulfonyl and TSC=trisodium citrate.

It is noted here that as used in this specification and the appended claims, the singular forms "a," "an," and "the" include plural reference unless the context clearly dictates otherwise.

"Alkyl," by itself or as part of another substituent, means, unless otherwise stated, a straight or branched chain, fully saturated aliphatic hydrocarbon radical having the number of carbon atoms designated. For example, "C$_{1-8}$alkyl" refers to a hydrocarbon radical straight or branched, containing from 1 to 8 carbon atoms that is derived by the removal of one hydrogen atom from a single carbon atom of a parent alkane. The phrase "unsubstituted alkyl" refers to alkyl groups that do not contain groups other than fully saturated aliphatic hydrocarbon radicals. Thus the phrase includes straight chain alkyl groups such as methyl, ethyl, propyl, butyl, pentyl, hexyl, heptyl, octyl, nonyl, decyl, undecyl, dodecyl and the like. The phrase also includes branched chain isomers of straight chain alkyl groups such as isopropyl, t-butyl, isobutyl, sec-butyl, and the like. Representative alkyl groups include straight and branched chain alkyl groups having 1, 2, 3, 4, 5, 6, 7, 8, 9, 10, 11 or 12 carbon atoms. Further representative alkyl groups include straight and branched chain alkyl groups having 1, 2, 3, 4, 5, 6, 7 or 8 carbon atoms.

"Alkenyl" by itself or as part of another substituent refers to a straight or branched chain, which may be mono- or polyunsaturated, having the number of carbon atoms designated. For example, "C$_2$-C$_8$ alkenyl" means an alkenyl radical having from 2, 3, 4, 5, 6, 7 or 8 atoms that is derived by the removal of one hydrogen atom from a single carbon atom of a parent alkane. Examples include, but are not limited to vinyl, 2-propenyl i.e. —CH═C(H)(CH$_3$), —CH═C(CH$_3$)$_2$, —C(CH$_3$)═C(H)$_2$, —C(CH$_3$)═C(H) (CH$_3$), —C(CH$_2$CH$_3$)═CH$_2$, butadienyl e.g. 2-(butadienyl), pentadienyl e.g. 2,4-pentadienyl and 3-(1,4-pentadienyl), and hexadienyl, among others, and higher homologs and stereoisomers thereof. A "substituted" alkenyl group includes alkenyl groups in which a non-carbon or non-hydrogen atom is bonded to a carbon double bonded to another carbon and those in which one of the non-carbon or non-hydrogen atoms is bonded to a carbon not involved in a double bond to another carbon. Each site of unsaturation may be either cis or trans configuration about the double bond(s).

The term "alkynyl", by itself or as part of another substituent, means a straight or branched chain hydrocarbon radical, which may be mono- or polyunsaturated, having the number of carbon atoms designated. For example, "$C_2$-$C_5$ alkynyl" means an alkynyl radical having from 2 to 8 carbon atoms that is derived by the removal of one hydrogen atom from a single carbon atom of a parent alkane. "Unsubstituted alkynyl" refers to straight and branched chain groups such as those described with respect to unsubstituted alkyl groups as defined above, except that at least one triple bond exists between two carbon atoms. Examples include, but are not limited to ethynyl e.g. —C≡C(H), 1-propynyl e.g. —C≡C (CH$_3$), —C≡C(CH$_2$CH$_3$), —C(H$_2$)C≡C(H), —C(H)$_2$C≡C (CH$_3$), and —C(H)$_2$C≡C(CH$_2$CH$_3$) among others, and higher homologs and isomers thereof. A "substituted" alkynyl group includes alkynyl groups in which a non-carbon or non-hydrogen atom is bonded to a carbon triple bonded to another carbon and those in which a non-carbon or non-hydrogen atom is bonded to a carbon not involved in a triple bond to another carbon.

"Alkylene" by itself or as part of another substituent means a divalent radical derived from an alkane, as exemplified by —CH$_2$CH$_2$CH$_2$CH$_2$—. Typically, an alkylene group will have from 1, 2, 3, 4, 5, 6, 7 or 8 carbon atoms that is derived by the removal of one hydrogen atom from a single carbon atom of a parent alkyl.

"Cycloalkyl" or "carbocycle", by themselves or in combination with other terms, represent, unless otherwise stated, cyclic versions of "alkyl", "alkenyl" and "alkynyl" in which all ring atoms are carbon. "Cycloalkyl" or "carbocycle" refers to a mono- or polycyclic group. When used in connection with cycloalkyl substituents, the term "polycyclic" refers herein to fused and non-fused alkyl cyclic structures. "Cycloalkyl" or "carbocycle" may form a bridged ring or a spiro ring. The cycloalkyl group may have one or more double or triple bond(s). The term "cycloalkenyl" refers to a cycloalkyl group that has at least one site of alkenyl unsaturation between the ring vertices. The term "cycloalkynyl" refers to a cycloalkyl group that has at least one site of alkynyl unsaturation between the ring vertices. When "cycloalkyl" is used in combination with "alkyl", as in $C_{3-8}$cycloalkyl$C_{3-8}$alkylene-, the cycloalkyl portion is meant to have the stated number of carbon atoms (e.g., from three to eight carbon atoms), while the alkylene portion has from one to eight carbon atoms. Typical cycloalkyl substituents have from 3 to 8 ring atoms. Examples of cycloalkyl include cyclopentyl, cyclohexyl, 1-cyclohexenyl, 3-cyclohexenyl, cycloheptyl, and the like.

"Aryl" by itself or as part of another substituent refers to a polyunsaturated, aromatic, hydrocarbon group containing from 6 to 14 carbon atoms, which can be a single ring or multiple rings (up to three rings) which are fused together or linked covalently. Thus the phrase includes, but is not limited to, groups such as phenyl, biphenyl, anthracenyl, naphthyl by way of example. Non-limiting examples of unsubstituted aryl groups include phenyl, 1-naphthyl, 2-naphthyl and 4-biphenyl. "Substituted aryl group" includes, for example, —CH$_2$OH (one carbon atom and one heteroatom replacing a carbon atom) and —CH$_2$SH. The term "heteroalkylene" by itself or as part of another substituent means a divalent radical derived from heteroalkyl, as exemplified by —CH$_2$—CH$_2$—S—CH$_2$CH$_2$— and —CH$_2$—S—CH$_2$—CH$_2$NH—CH$_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied.

The terms "heterocycle", "heterocyclyl" or "heterocyclic" refer to a saturated or unsaturated non-aromatic cyclic group containing at least one heteroatom. As used herein, the term "heteroatom" is meant to include oxygen (O), nitrogen (N), sulfur (S) and silicon (Si). Each heterocycle can be attached at any available ring carbon or heteroatom. Each heterocycle may have one or more rings. When multiple rings are present, they can be fused together or linked covalently. Each heterocycle typically contains 1, 2, 3, 4 or 5, independently selected heteroatoms. Preferably, these groups contain 1, 2, 3, 4, 5, 6, 7, 8, 9 or 10 carbon atoms, 0, 1, 2, 3, 4 or 5 nitrogen atoms, 0, 1 or 2 sulfur atoms and 0, 1 or 2 oxygen atoms. More preferably, these groups contain 1, 2 or 3 nitrogen atoms, 0-1 sulfur atoms and 0-1 oxygen atoms. Non-limiting examples of heterocycle groups include morpholin-3-one, piperazine-2-one, piperazin-1-oxide, pyridine-2-one, piperidine, morpholine, piperazine, isoxazoline, pyrazoline, imidazoline, pyrazol-5-one, pyrrolidine-2,5-dione, imidazolidine-2,4-dione, pyrrolidine, tetrahydroquinolinyl, decahydroquinolinyl, tetrahydrobenzooxazepinyl dihydrodibenzooxepin and the like.

"Heteroaryl" refers to a cyclic or polycyclic aromatic radical that contain from one to five heteroatoms selected from N, O, and S, wherein the nitrogen and sulfur atoms are optionally oxidized, and the nitrogen atom(s) are optionally quaternized. A heteroaryl group can be attached to the remainder of the molecule through a heteroatom or through a carbon atom and can contain 5 to 10 carbon atoms. Non-limiting examples of heteroaryl groups include 1-pyrrolyl, 2-pyrrolyl, 3-pyrrolyl, 1-pyrazolyl, 3-pyrazolyl, 2-imidazolyl, 4-imidazolyl, pyrazinyl, 2-oxazolyl, 4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl and 4-pyrimidyl. If not specifically stated, substituents for each of the above noted aryl and heteroaryl ring systems are selected from the group of acceptable substituents described herein. "Substituted heteroaryl" refers to a unsubstituted heteroaryl group as defined above in which one or more of the ring members is bonded to a non-hydrogen atom such as described above with respect to substituted alkyl groups and substituted aryl groups. Representative substituents include straight and branched chain alkyl groups —CH$_3$, —C$_2$H$_5$, —CH$_2$OH, —OH, —OCH$_3$, —OC$_2$H$_5$, —OCF$_3$, —OC (=O)CH$_3$, —OC(=O)NH$_2$, —OC(=O)N(CH$_3$)$_2$, —CN, —NO$_2$, —C(=O)CH$_3$, —CO$_2$H, —CO$_2$CH$_3$, —CONH$_2$, —NH$_2$, —N(CH$_3$)$_2$, —NHSO$_2$CH$_3$, —NHCOCH$_3$, —NHC (=O)OCH$_3$, —NHSO$_2$CH$_3$, —SO$_2$CH$_3$, —SO$_2$NH$_2$ and halo.

"Bicyclic heteroaryl" refers to bicyclic aromatic radical that contain from one to five heteroatoms selected from N, O, and S, wherein the nitrogen and sulfur atoms are optionally oxidized, and the nitrogen atom(s) are optionally quaternized. A bicyclic heteroaryl group can be attached to the remainder of the molecule through a heteroatom or through a carbon atom and can contain 5 to 10 carbon atoms. Non-limiting examples of bicyclic heteroaryl groups include 5-benzothiazolyl, purinyl, 2-benzimidazolyl, benzopyrazolyl, 5-indolyl, azaindole, 1-isoquinolyl, 5-isoquinolyl, 2-quinoxalinyl, 5-quinoxalinyl, 3-quinolyl and 6-quinolyl. If not specifically stated, substituents for each of the above noted aryl and heteroaryl ring systems are selected from the group of acceptable substituents described herein.

In each of the above embodiments designating a number of atoms e.g. "$C_{1-8}$" is meant to include all possible embodiments that have one fewer atom. Non-limiting examples include $C_{1-7}$, $C_{2-8}$, $C_{2-7}$, $C_{3-8}$, $C_{3-7}$ and the like.

Each of the terms herein (e.g., "alkyl," "heteroalkyl," "aryl" and "heteroaryl") is meant to include both "unsubstituted" and optionally "substituted" forms of the indicated radical, unless otherwise indicated. Typically each radical is substituted with 0, 1, 2 3 4 or 5 substituents, unless otherwise indicated. Examples of substituents for each type of radical are provided below.

"Substituted" refers to a group as defined herein in which one or more bonds to a carbon(s) or hydrogen(s) are replaced by a bond to non-hydrogen and non-carbon atom "substituents" such as, but not limited to, a halogen atom such as F, Cl, Br, and I; an oxygen atom in groups such as hydroxyl groups, alkoxy groups, aryloxy, and acyloxy groups; a sulfur atom in groups such as thiol groups, alkyl and aryl sulfide groups, sulfone groups, sulfonyl groups, and sulfoxide groups; a nitrogen atom in groups such as amino, alkylamines, dialkylamines, arylamines, alkylarylamines, diarylamines, alkoxyamino, hydroxyamino, acylamino, sulfonylamino, N-oxides, imides, and enamines; and other heteroatoms in various other groups. "Substituents" also include groups in which one or more bonds to a carbon(s) or hydrogen(s) atom is replaced by a higher-order bond (e.g., a double- or triple-bond) to a heteroatom such as oxygen in oxo, acyl, amido, alkoxycarbonyl, aminocarbonyl, carboxyl, and ester groups; nitrogen in groups such as imines, oximes, hydrazones, and nitriles. "Substituents" further include groups in which one or more bonds to a carbon(s) or hydrogen(s) atoms is replaced by a bond to a cycloalkyl, heterocyclyl, aryl, and heteroaryl groups. Representative "substituents" include, among others, groups in which one or more bonds to a carbon or hydrogen atom is/are replaced by one or more bonds to fluoro, chloro, or bromo group. Another representative "substituent" is the trifluoromethyl group and other groups that contain the trifluoromethyl group. Other representative "substituents" include those in which one or more bonds to a carbon or hydrogen atom is replaced by a bond to an oxygen atom such that the substituted alkyl group contains a hydroxyl, alkoxy, or aryloxy group. Other representative "substituents" include alkyl groups that have an amine, or a substituted or unsubstituted alkylamine, dialkylamine, arylamine, (alkyl)(aryl)amine, diarylamine, heterocyclylamine, diheterocyclylamine, (alkyl)(heterocyclyl)amine, or (aryl)(heterocyclyl)amine group. Still other representative "substituents" include those in which one or more bonds to a carbon(s) or hydrogen(s) atoms is replaced by a bond to an alkyl, cycloalkyl, aryl, heteroaryl, or heterocyclyl group.

The herein-defined groups may include prefixes and/or suffixes that are commonly used in the art to create additional well-recognized substituent groups. As examples, "alkylamino" refers to a group of the formula —$NR^aR^b$. Unless stated otherwise, for the following groups containing $R^a$, $R^b$, $R^c$, $R^d$ and $R^e$: $R^a$, and $R^b$ are each independently selected from H, alkyl, alkoxy, thioalkoxy, cycloalkyl, aryl, heteroaryl, or heterocyclyl or are optionally joined together with the atom(s) to which they are attached to form a cyclic group. When $R^a$ and $R^b$ are attached to the same nitrogen atom, they can be combined with the nitrogen atom to form a 5-, 6- or 7-membered ring. For example, —$NR^aR^b$ is meant to include 1-pyrrolidinyl and 4-morpholinyl.

$R^c$, $R^d$, $R^e$ and $R^f$ are each independently selected from alkyl, alkenyl, alkynyl, cycloalkyl, cycloalkenyl, aryl, heteroaryl, heterocyclyl or alkylenearyl as defined herein.

Typically, a particular radical will have 0, 1, 2 or 3 substituents, with those groups having two or fewer substituents being preferred in the present invention. More preferably, a radical will be unsubstituted or monosubstituted. Most preferably, a radical will be unsubstituted.

"Substituents" for the alkyl and heteroalkyl radicals (as well as those groups referred to as alkylene, alkenyl, heteroalkylene, heteroalkenyl, alkynyl, cycloalkyl, heterocyclyl) can be a variety of groups selected from: —$OR^a$, =O, =$NR^a$, =N—$OR^a$, —$NR^aR^b$, —$SR^a$, halogen, —$SiR^aR^bR^c$, —$OC(O)R^a$, —$C(O)R^a$, —$CO_2R^a$, —$CONR^aR^b$, —$OC(O)NR^aR^b$, —$NR^bC(O)R^a$, —$NR^a$—$C(O)NR^bR^c$, —$NR^a$—$SO_2NR^bR^c$, —$NR^bCO_2R^a$, —NH—$C(NH_2)$=NH, —$NR^aC(NH_2)$=NH, —NH—$C(NH_2)$=$NR^a$, —S(O) $R^a$, —$SO_2R^a$, —$SO_2NR^aR^b$, —$NR^bSO_2R$, —CN and —$NO_2$, in a number ranging from zero to three, with those groups having zero, one or two substituents being particularly preferred.

In some embodiments, "substituents" for the alkyl and heteroalkyl radicals are selected from: —$OR^a$, =O, —$NR^aR^b$, —$SR^a$, halogen, —$SiR^aR^bR^c$, —$OC(O)R^a$, —$C(O)R^a$, —$CO_2R^a$, —$CONR^aR^b$, —$OC(O)NR^aR^b$, —$NR^bC(O)R^a$, —$NR^bCO_2R^a$, —$NR^a$—$SO_2NR^bR^c$, —S(O) $R^a$, —$SO_2R^a$, —$SO_2NR^aR^b$, —$NR^cSO_2R$, —CN and —$NO_2$, where $R^a$ and $R^b$ are as defined above. In some embodiments, substituents are selected from: —$OR^a$, =O, —$NR^aR^b$, halogen, —OC(O) $R^a$, —$CO_2R^a$, —$CONR^aR^b$, —$OC(O)NR^aR^b$, —$NR^bC(O)R^a$, —$NR^bCO_2R^a$, —$NR^a$—$SO_2NR^bR^c$, —$SO_2R^a$, —$SO_2NR^aR^b$, —$NR''SO_2R$, —CN and —$NO_2$.

Examples of substituted alkyl are: —$(CH_2)_3NH_2$, —$(CH_2)_3NH(CH_3)$, —$(CH_2)_3NH(CH_3)_2$, —$CH_2C(=CH_2)CH_2NH_2$, —$CH_2C(=O)CH_2NH_2$, —$CH_2S(=O)_2CH_3$, —$CH_2OCH_2NH_2$, —$CO_2H$. Examples of substituents of substituted alkyl are: $CH_2OH$, —OH, —$OCH_3$, —$OC_2H_5$, —$OCF_3$, —OC(=O)$CH_3$, —OC(=O)$NH_2$, —OC(=O)N$(CH_3)_2$, —CN, —$NO_2$, —C(=O)$CH_3$, —$CO_2H$, —$CO_2CH_3$, —$CONH_2$, —$NH_2$, —N$(CH_3)_2$, —$NHSO_2CH_3$, —$NHCOCH_3$, —NHC(=O)$OCH_3$, —$NHSO_2CH_3$, —$SO_2CH_3$, —$SO_2NH_2$, and halo.

Similarly, "substituents" for the aryl and heteroaryl groups are varied and are selected from: -halogen, —$OR^a$, —OC(O) $R^a$, —$NR^aR^b$, —$SR^a$, —$R^a$, —CN, —$NO_2$, —$CO_2R^a$, —$CONR^aR^b$, —C(O) $R^a$, —$OC(O)NR^aR^b$, —$NR^bC(O)$ $R^a$, —$NR^bC(O)_2R^a$, —$NR^a$—$C(O)NR^bR^c$, —NH—$C(NH_2)$=NH, —$NR^aC(NH_2)$=NH, —NH—C$(NH_2)$=$NR^a$, —S(O) $R^a$, —$S(O)_2R^a$, —$S(O)_2NR^aR^b$, —$N_3$, —$CH(Ph)_2$, perfluoro$C_{1-8}$alkoxy, and perfluoro $C_{1-8}$alkyl, in a number ranging from zero to the total number of open valences on the aromatic ring system; and where $R^a$, $R^b$ and $R^c$ are independently selected from hydrogen, $C_{1-6}$alkyl and heteroalkyl, unsubstituted aryl and heteroaryl, (unsubstituted aryl)-$C_{1-8}$alkyl, and (unsubstituted aryl)oxy-$C_{1-8}$alkyl.

Two of the "substituents" on adjacent atoms of the aryl or heteroaryl ring may optionally be replaced with a substituent of the formula -T-C(O)—$(CH_2)q$-U—, wherein T and U are independently —NH—, —O—, —$CH_2$— or a single bond, and q is 0, 1 or 2. Alternatively, two of the substituents on adjacent atoms of the aryl or heteroaryl ring may optionally be replaced with a substituent of the formula -A-$(CH_2)_r$—

B—, wherein A and B are independently —CH$_2$—, —O—, —NH—, —S—, —S(O)—, —S(O)$_2$—, —S(O)$_2$NR$^a$— or a single bond, and r is 1, 2 or 3. One of the single bonds of the new ring so formed may optionally be replaced with a double bond. Alternatively, two of the substituents on adjacent atoms of the aryl or heteroaryl ring may optionally be replaced with a substituent of the formula —(CH$_2$)$_s$—X—(CH$_2$)$_t$—, where s and t are independently integers of from 0 to 3, and X is —O—, —NR$^a$—, —S—, —S(O)—, —S(O)$_2$—, or —S(O)$_2$NR$^a$—. The substituent R$^a$ in —NR$^a$— and —S(O)$_2$NR$^a$— is selected from hydrogen or unsubstituted C$_{1-6}$alkyl. Otherwise, R' is as defined above.

Unless indicated otherwise, the nomenclature of substituents that are not explicitly defined herein are arrived at by naming the terminal portion of the functionality followed by the adjacent functionality toward the point of attachment. For example, the substituent "arylalkyloxycarbonyl" refers to the group (aryl)-(alkyl)-O—C(O)—.

The term "acyl" refers to the group —C(═O)R$^c$ where R$^c$ is alkyl, alkenyl, alkynyl, cycloalkyl, cycloalkenyl, aryl, heteroaryl or heterocyclyl. Acyl includes the "acetyl" group —C(═O)CH$_3$.

"Acylamino-" refers to the group —NR$^a$C(═O)R$^c$ where R$^c$ is alkyl, alkenyl, alkynyl, cycloalkyl, cycloalkenyl, aryl, heteroaryl or heterocyclyl.

"Acyloxy" refers to —OC(═O)—R$^c$ where R$^c$ is alkyl, alkenyl, alkynyl, cycloalkyl, cycloalkenyl, aryl, heteroaryl or heterocyclyl.

"Alkoxy" refers to —OR$^d$ wherein R$^d$ is alkyl as defined herein. Representative examples of alkoxy groups include methoxy, ethoxy, t-butoxy, trifluoromethoxy, and the like.

"Alkoxyamino" refers to the group —NHOR$^d$ where R$^d$ is alkyl.

"Alkoxycarbonyl" refers to —C(═O)OR$^d$ wherein R$^d$ is alkyl. Representative alkoxycarbonyl groups include, for example, those shown below.

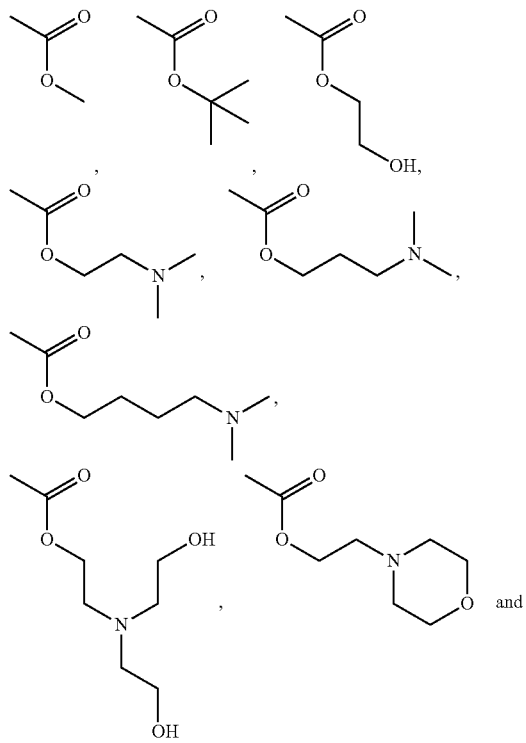

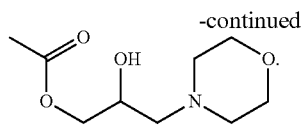

These alkoxycarbonyl groups can be further substituted as will be apparent to those having skill in the organic and medicinal chemistry arts in conjunction with the disclosure herein.

"Alkoxycarbonylamino" refers to to —NR$^a$C(═O)OR$^d$ wherein R$^d$ is alkyl.

"Alkoxysulfonylamino" refers to the group —NR$^a$S(═O)$_2$—OR$^d$ where R$^d$ is alkyl.

"Alkylcarbonyl" refers to the group —C(═O)R$^c$ where R$^c$ is alkyl.

"Alkylcarbonyloxy" refers to —OC(═O)—R$^c$ where R$^c$ is alkyl.

"Alkylcarbonylamino" refers to —NR$^a$C(═O)R$^c$ wherein R is alkyl. Representative alkylcarbonylamino groups include, for example, —NHC(═O)CH$_3$, —NHC(═O)CH$_2$CH$_3$, —NHC(═O)CH$_2$NH(CH$_3$), —NHC(═O)CH$_2$N(CH$_3$)$_2$, or —NHC(═O)(CH$_2$)$_{30}$H.

"Alkylsulfanyl", "alkylthio", or "thioalkoxy" refers to the group S—R$^d$. where R$^d$ is alkyl.

"Alkylsulfonyl" refers to —S(═O)$_2$R$^e$ where R$^e$ is alkyl. Alkylsulfonyl groups employed in compounds of the present invention are typically C$_{1-6}$alkylsulfonyl groups.

"Alkylsulfonylamino" refers to —NR$^a$S(═O)$_2$—R$^e$ wherein R$^e$ is alkyl.

"Alkynyloxy" refers to the group —O-alkynyl, wherein alkynyl is as defined herein. Alkynyloxy includes, by way of example, ethynyloxy, propynyloxy, and the like.

"Amidino" refers to the group —C(═NR$^a$)NR$^b$R$^c$, wherein R$^b$ and R independently are selected from the group consisting of hydrogen, alkyl, substituted alkyl, alkenyl, alkynyl, aryl, cycloalkyl, cycloalkenyl, heteroaryl, heterocyclic, and where R$^b$ and R$^c$ are optionally joined together with the nitrogen bound thereto to form a heterocyclic or substituted heterocyclic group. R$^a$ is selected from the group consisting of hydrogen, alkyl, alkenyl, alkynyl, cycloalkynyl, aryl, cycloalkyl, cycloalkenyl, heteroaryl, heterocyclic, substituted heterocyclic, nitro, nitroso, hydroxy, alkoxy, cyano, —N═N—N-alkyl, —N(alkyl)SO$_2$-alkyl, —N═N═N-alkyl, acyl and —SO$_2$-alkyl.

"Amino" refers to a monovalent radical —NR$^a$R$^b$ or divalent radical —NR$^a$—. The term "alkylamino" refers to the group —NR$^a$R$^b$ where R$^a$ is alkyl and R$^b$ is H or alkyl. The term "arylamino" refers to the group —NR$^a$R$^b$ where at least one R$^a$ or R$^b$ is aryl. The term "(alkyl)(aryl)amino" refers to the group —NR$^a$R$^b$ where R$^a$ is alkyl and R$^b$ is aryl. Additionally, for dialkylamino groups, the alkyl portions can be the same or different and can also be combined to form a 3-7 membered ring with the nitrogen atom to which each is attached. Accordingly, a group represented as —NR$^a$R$^b$ is meant to include piperidinyl, pyrrolidinyl, morpholinyl, azetidinyl and the like.

"Aminocarbonyl" or "aminoacyl" refers to the amide —C(═O)—NR$^a$R$^b$. The term "alkylaminocarbonyl" refers herein to the group —C(═O)—NR$^a$R$^b$ where R$^a$ is alkyl and R$^b$ is H or alkyl. The term "arylaminocarbonyl" refers herein to the group —C(═O)—NR$^a$R$^b$ where R$^a$ or R$^b$ is aryl. Representative aminocarbonyl groups include, for example, those shown below. These aminocarbonyl group can be further substituted as will be apparent to those having skill in the organic and medicinal chemistry arts in conjunction with the disclosure herein.

"Aminocarbonylamino" refers to the group —NR$^a$C(O)NR$^a$R$^b$, wherein R$^a$ is hydrogen or alkyl and R$^a$ and R$^b$ independently are selected from the group consisting of hydrogen, alkyl, alkenyl, alkynyl, aryl, cycloalkyl, cycloalkenyl, heteroaryl, heterocyclic, and where R$^a$ and R$^b$ are optionally joined together with the nitrogen bound thereto to form a heterocyclic or substituted heterocyclic group.

"Aminosulfonyl" refers to —S(O)$_2$NR$^a$R$^b$ where R is independently are selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, substituted heterocyclic and where R$^a$ and R$^b$ are optionally joined together with the nitrogen bound thereto to form a heterocyclic or substituted heterocyclic group and alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic and substituted heterocyclic are as defined herein.

"Aminosulfonyloxy" refers to the group —O—SO$_2$NR$^a$R$^b$, wherein R$^a$ and R$^b$ independently are selected from the group consisting of hydrogen, alkyl, alkenyl, alkynyl, aryl, cycloalkyl, cycloalkenyl, heteroaryl and heterocyclic; R$^a$ and R$^b$ are optionally joined together with the nitrogen bound thereto to form a heterocyclic or substituted heterocyclic group.

"Aminosulfonylamino" refers to the group —NR$^a$—SO$_2$NR$^b$R$^c$, wherein R$^a$ is hydrogen or alkyl and R$^b$ and R$^c$ independently are selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where R$^b$ and R$^c$ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic and substituted heterocyclic are as defined herein.

"Aminothiocarbonyl" refers to the group —C(S)NR$^a$R$^b$, wherein R$^a$ and R$^b$ independently are selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where R$^a$ and R$^b$ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Aminothiocarbonylamino" refers to the group —NR$^a$C(S)NR$^a$R$^b$, wherein R$^a$ is hydrogen or alkyl and R$^b$ and R$^c$ are optionally joined together with the nitrogen bound thereto to form a heterocyclic or substituted heterocyclic group.

"Arylcarbonyl" refers to the group —C(=O)R$^c$ where R$^c$ is aryl.

"Arylcarbonylamino" refers to —NR$^a$C(=O)R$^c$ wherein R$^c$ is aryl.

"Arylcarbonyloxy" refers to —OC(=O)—R$^c$ where R$^c$ is aryl.

"Aryloxy" refers to —OR$^d$ where R$^d$ is aryl. Representative examples of aryloxy groups include phenoxy, naphthoxy, and the like.

"Aryloxycarbonyl" refers to —C(=O)OR$^d$ wherein R$^d$ is aryl.

"Aryloxycarbonylamino" refers to —NR$^a$C(=O)OR$^d$ wherein R$^d$ is aryl.

"Arylsulfanyl", "arylthio", or "thioaryloxy" refers to the group S—R$^d$. where R$^d$ is aryl.

"Arylsulfonyl" refers to —S(=O)$_2$R$^e$ where R$^e$ is is aryl.

"Arylsulfonylamino" refers to —NR$^a$S(=O)$_2$—R$^e$ wherein R$^e$ is aryl.

"Arylthio" refers to the group —S-aryl, wherein aryl is as defined herein. In other embodiments, sulfur may be oxidized to —S(O)— or —SO$_2$— moieties. The sulfoxide may exist as one or more stereoisomers.

"Azido" refers to —N$_3$.

"Bond" when used a element in a Markush group means that the corresponding group does not exist, and the groups of both sides are directly linked.

"Carbonyl" refers to the divalent group —C(=O)—.

"Carboxy" or "carboxyl" refers to the group —CO$_2$H.

"Carboxyl ester" or "carboxy ester" refers to the groups —C(=O)OR$^c$.

"(Carboxyl ester)amino" refers to the groups —NR$^a$—C(O)OR$^c$, where R$^a$ is alkyl or hydrogen.

"(Carboxyl ester)oxy" or "Carbonate ester" refers to the groups —O—C(=O)OR$^c$.

"Cyano" refers to —CN.

"Cycloalkoxy" refers to —OR$^d$ where R$^d$ is cycloalkyl.

"Cycloalkoxycarbonyl" refers to —C(=O)OR$^d$ wherein R$^d$ is cycloalkyl.

"Cycloalkoxycarbonylamino" refers to to —NR$^a$C(=O)OR$^d$ wherein R$^d$ is cycloalkyl.

"Cycloalkylalkylene" refers to a radical —R$^x$R$^y$ wherein R$^x$ is an alkylene group and R$^y$ is a cycloalkyl group as defined herein, e.g., cyclopropylmethyl, cyclohexenylpropyl, 3-cyclohexyl-2-methylpropyl, and the like.

"Cycloalkylcarbonyl" refers to the group —C(=O)R$^c$ where R$^c$ is cycloalkyl.

"Cycloalkylcarbonylamino" refers to —NR$^a$C(=O)R$^c$ wherein R$^c$ is cycloalkyl.

"Cycloalkylcarbonyloxy" refers to —OC(=O)—R$^c$ where R$^c$ is cycloalkyl.

"Cycloalkylsulfonylamino" refers to —NR$^a$S(=O)$_2$—R$^e$ wherein R$^e$ is cycloalkyl.

"Cycloalkylthio" refers to —S-cycloalkyl. In other embodiments, sulfur may be oxidized to —S(O)— or —SO$_2$— moieties. The sulfoxide may exist as one or more stereoisomers.

"Cycloalkenylox" refers to —O-cycloalkenyl.

"Cycloalkenylthio" refers to —S-cycloalkenyl. In other embodiments, sulfur may be oxidized to sulfinyl or sulfonyl moieties. The sulfoxide may exist as one or more stereoisomers.

"Ester" refers to —C(=O)OR$^d$ wherein R$^d$ is alkyl, cycloalkyl, aryl, heteroaryl, or heterocyclyl.

"Guanidino" refers to the group —NHC(=NH)NH$_2$.

"Halo" or "halogen" by themselves or as part of another substituent, mean, unless otherwise stated, a fluorine, chlorine, bromine, or iodine atom. Additionally, terms such as "haloalkyl", are meant to include alkyl in which one or more hydrogen is substituted with halogen atoms which can be the same or different, in a number ranging from one up to the maximum number of halogens permitted e.g. for alkyl, (2m'+1), where m' is the total number of carbon atoms in the alkyl group. For example, the term "haloC$_{1-8}$alkyl" is meant to include trifluoromethyl, 2,2,2-trifluoroethyl, 4-chlorobutyl, 3-bromopropyl, and the like. The term "perhaloalkyl" means, unless otherwise stated, alkyl substituted with (2m'+1) halogen atoms, where m' is the total number of carbon atoms in the alkyl group. For example, the term "perhaloC$_{1-8}$alkyl", is meant to include trifluoromethyl, pentachloroethyl, 1,1,1-trifluoro-2-bromo-2-chloroethyl, and the like. Additionally, term "haloalkoxy" refers to an alkoxy radical substituted with one or more halogen atoms.

"Heteroalkyl" means an alkyl radical as defined herein with one, two or three substituents independently selected from cyano, —OR$^W$, —NR$^x$R$^y$, and —S(O)$_n$R$^z$ (where n is an integer from 0 to 2), with the understanding that the point of attachment of the heteroalkyl radical is through a carbon atom of the heteroalkyl radical. R$^W$ is hydrogen, alkyl, cycloalkyl, cycloalkyl-alkyl, aryl, araalkyl, alkoxycarbonyl, aryloxycarbonyl, carboxamido, or mono- or di-alkylcarbamoyl. R$^x$ is hydrogen, alkyl, cycloalkyl, cycloalkyl-alkyl, aryl or araalkyl. R$^y$ is hydrogen, alkyl, cycloalkyl, cycloalkyl-alkyl, aryl, araalkyl, alkoxycarbonyl, aryloxycarbonyl, carboxamido, mono- or di-alkylcarbamoyl or alkylsulfonyl. R$^z$ is hydrogen (provided that n is 0), alkyl, cycloalkyl, cycloalkyl-alkyl, aryl, araalkyl, amino, mono-alkylamino, di-alkylamino, or hydroxyalkyl. Representative examples include, for example, 2-hydroxyethyl, 2,3-dihydroxypropyl, 2-methoxyethyl, benzyloxymethyl, 2-cyanoethyl, and 2-methylsulfonyl-ethyl. For each of the above, R$^W$, R$^x$, R$^y$, and R$^z$ can be further substituted by amino, fluorine, alkylamino, di-alkylamino, OH or alkoxy. Additionally, the prefix indicating the number of carbon atoms (e.g., C$_1$-C$_{10}$) refers to the total number of carbon atoms in the portion of the heteroalkyl group exclusive of the cyano, —OR$^W$, —NR$^x$R$^y$, or —S(O)$_n$R$^z$ portions.

"Heteroarylcarbonyl" refers to the group —C(=O)R$^c$ where R$^c$ is heteroaryl.

"Heteroarylcarbonylamino" refers to —NR$^a$C(=O)R$^c$ wherein R$^c$ is heteroaryl.

"Heteroarylcarbonyloxy" refers to —OC(=O)—R$^c$ where R$^c$ is heteroaryl.

"Heteroaryloxy" refers to —OR$^d$ where R$^d$ is heteroaryl.

"Heteroaryloxycarbonyl" refers to —C(=O)OR$^d$ wherein R$^d$ is heteroaryl.

"Heteroaryloxycarbonylamino" refers to to —NR$^a$C(=O)OR$^d$ wherein R$^d$ is heteroaryl.

"Heteroarylsulfonyllamino" refers to —NR$^a$S(=O)$_2$—R$^e$ wherein R$^e$ is heteroaryl.

"Heteroarylthio" refers to the group —S-heteroaryl. In other embodiments, sulfur may be oxidized to —S(O)— or —SO$_2$— moieties. The sulfoxide may exist as one or more stereoisomers.

"Heterocyclylalkyl" or "Cycloheteroalkyl-alkyl" means a radical —R$^x$R$^y$ where R$^x$ is an alkylene group and R$^y$ is a heterocyclyl group as defined herein, e.g., tetrahydropyran-2-ylmethyl, 4-(4-substituted-phenyl)piperazin-1-ylmethyl, 3-piperidinylethyl, and the like.

"Heterocycloxycarbonylamino" refers to to —NR$^a$C(=O)OR$^d$ wherein R$^d$ is heterocyclyl.

"Heterocyclylcarbonyl" refers to the —C(=O)R$^c$ where R$^c$ is heterocyclyl.

"Heterocyclylcarbonylamino" refers to —NR$^a$C(=O)R$^c$ wherein R$^c$ is heterocyclyl.

"Heterocyclylcarbonyloxy" refers to —OC(=O)—R$^c$ where R$^c$ s heterocyclyl.

"Heterocyclyloxy" refers to —OR$^d$ where R$^d$ is heterocyclyl.

"Heterocyclyloxycarbonyl" refers to —C(=O)OR$^d$ wherein R$^d$ is heterocyclyl.

"Heterocyclylsulfonyl" refers to —S(=O)$_2$R$^e$ where R$^e$ is heterocyclyl.

"Heterocyclylsulfonyllamino" refers to —NR$^a$S(=O)$_2$—R$^e$ wherein R$^e$ is heterocyclyl.

"Heterocyclylthio" refers to the group —S-heterocycyl. In other embodiments, sulfur may be oxidized to —S(O)— or —SO$_2$— moieties. The sulfoxide may exist as one or more stereoisomers.

"Hydroxy" or "hydroxyl" refers to the group —OH.

"Hydroxyamino" refers to the group —NHOH.

"Nitro" refers to —NO$_2$.

"Nitroso" refers to the group —NO.

The terms "optional" or "optionally" as used throughout the specification means that the subsequently described event or circumstance may but need not occur, and that the description includes instances where the event or circumstance occurs and instances in which it does not. For example, "heterocyclo group optionally mono- or di-substituted with an alkyl group means that the alkyl may but need not be present, and the description includes situations where the heterocyclo group is mono- or disubstituted with an alkyl group and situations where the heterocyclo group is not substituted with the alkyl group.

"Optionally substituted" means a ring which is optionally substituted independently with substituents. A site of a group that is unsubstituted may be substituted with hydrogen.

"Oxo" refers to the divalent group =O.

"Sulfanyl" refers to the group —SR$^f$ where R$^f$ is as defined herein.

"Sulfinyl" refers to the group —S(=O)—R$^e$ where R$^e$ is as defined herein.

"Sulfonic acid" refers to the group —S(O)$_2$—OH.

"Sulfonyl" refers to the group —S(O)$_2$—R$^e$ where R$^e$ is as defined herein.

"Sulfonylamino" refers to —NR$^a$S(=O)$_2$—R$^e$ where R$^a$ is selected from the group consisting of hydrogen, alkyl, alkenyl, alkynyl, aryl, cycloalkyl, cycloalkenyl, heteroaryl and heterocyclyl and R$^e$ is as defined herein.

"Sulfonyloxy" refers to the group —OSO$_2$—R$^c$.

Compounds that have the same molecular formula but differ in the nature or sequence of bonding of their atoms or the arrangement of their atoms in space are termed "isomers". Isomers that differ in the arrangement of their atoms in space are termed "stereoisomers". "Stereoisomer" and "stereoisomers" refer to compounds that exist in different stereoisomeric forms if they possess one or more asymmetric centers or a double bond with asymmetric substitution and, therefore, can be produced as individual stereoisomers or as mixtures. Stereoisomers include enantiomers and diastereomers. Stereoisomers that are not mirror images of one another are termed "diastereomers" and those that are non-superimposable mirror images of each other are termed "enantiomers". When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture". Unless otherwise indicated, the description is intended to include individual stereoisomers as well as mixtures. The methods for the determination of stereochemistry and the separation of stereoisomers are well-known in the art (see discussion in Chapter 4 of ADVANCED ORGANIC CHEMISTRY, 4th edition J. March, John Wiley and Sons, New York, 1992) differ in the chirality of one or more stereocenters.

"Thioacyl" refers to the groups $R^a$—C(S)—.

"Thiol" refers to the group —SH.

"Tautomer" refers to alternate forms of a molecule that differ in the position of a proton, such as enol-keto and imine-enamine tautomers, or the tautomeric forms of heteroaryl groups containing a —N=C(H)—NH— ring atom arrangement, such as pyrazoles, imidazoles, benzimidazoles, triazoles, and tetrazoles. A person of ordinary skill in the art would recognize that other tautomeric ring atom arrangements are possible.

It is understood that in all substituted groups defined above, polymers arrived at by defining substituents with further substituents to themselves (e.g., substituted aryl having a substituted aryl group as a substituent which is itself substituted with a substituted aryl group, which is further substituted by a substituted aryl group, etc.) are not intended for inclusion herein. In such cases, the maximum number of such substitutions is three. For example, serial substitutions of substituted aryl groups are limited to -substituted aryl-(substituted aryl)-substituted aryl.

"Protecting group" refers to a group of atoms that, when attached to a reactive functional group in a molecule, mask, reduce or prevent the reactivity of the functional group. Typically, a protecting group may be selectively removed as desired during the course of a synthesis. Examples of protecting groups can be found in Greene and Wuts, Protective Groups in Organic Chemistry, $3^{rd}$ Ed., 1999, John Wiley & Sons, NY and Harrison et al., Compendium of Synthetic Organic Methods, Vols. 1-8, 1971-1996, John Wiley & Sons, NY. Representative amino protecting groups include, but are not limited to, formyl, acetyl, trifluoroacetyl, benzyl, benzyloxycarbonyl ("CBZ"), tert-butoxycarbonyl ("Boc"), trimethylsilyl ("TMS"), 2-trimethylsilyl-ethanesulfonyl ("TES"), trityl and substituted trityl groups, allyloxycarbonyl, 9-fluorenylmethyloxycarbonyl ("FMOC"), nitroveratryloxycarbonyl ("NVOC") and the like. Representative hydroxy protecting groups include, but are not limited to, those where the hydroxy group is either acylated or alkylated such as benzyl and trityl ethers, as well as alkyl ethers, tetrahydropyranyl ethers, trialkylsilyl ethers (e.g., TMS or TIPPS groups) and allyl ethers.

The term "pharmaceutically acceptable salts" is meant to include salts of the active compounds which are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of salts derived from pharmaceutically-acceptable inorganic bases include aluminum, ammonium, calcium, copper, ferric, ferrous, lithium, magnesium, manganic, manganous, potassium, sodium, zinc and the like. Salts derived from pharmaceutically-acceptable organic bases include salts of primary, secondary and tertiary amines, including substituted amines, cyclic amines, naturally-occurring amines and the like, such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, malonic, benzoic, succinic, suberic, fumaric, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, e.g., Berge, S. M. et al., "Pharmaceutical Salts," Journal of Pharmaceutical Science, 66:1-19, 1977). Certain specific compounds of the present invention contain both basic and acidic functionalities that allow the compounds to be converted into either base or acid addition salts.

The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

In addition to salt forms, the present invention provides compounds which are in a prodrug ester form. "Prodrug"s of the compounds described herein are those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent. Prodrugs are frequently, but not necessarily, pharmacologically inactive until converted into the active drug. Prodrugs are typically obtained by masking a functional group in the drug believed to be in part required for activity with a progroup (defined below) to form a promoiety which undergoes a transformation, such as cleavage, under the specified conditions of use to release the functional group, and hence the active drug. The cleavage of the promoiety may proceed spontaneously, such as by way of a hydrolysis reaction, or it may be catalyzed or induced by another agent, such as by an enzyme, by light, by acid or base, or by a change of or exposure to a physical or environmental parameter, such as a change of temperature. The agent may be endogenous to the conditions of use, such as an enzyme present in the cells to which the prodrug is administered or the acidic conditions of the stomach, or it may be supplied exogenously.

"Progroup" refers to a type of protecting group that, when used to mask a functional group within an active drug to form a promoiety, converts the drug into a prodrug. Progroups are typically attached to the functional group of the drug via bonds that are cleavable under specified conditions of use. Thus, a progroup is that portion of a promoiety that cleaves to release the functional group under the specified conditions of use. As a specific example, an amide promoiety of the formula —NH—C(O)CH$_3$ comprises the progroup —C(O)CH$_3$.

A wide variety of progroups, as well as the resultant promoieties, suitable for masking functional groups in the active syk and/or JAK selective inhibitory compounds to yield prodrugs are well-known in the art. For example, a hydroxyl functional group may be masked as a sulfonate, ester (such as acetate or maleate) or carbonate promoiety, which may be hydrolyzed in vivo to provide the hydroxyl group. An amino functional group may be masked as an amide, carbamate, imine, urea, phosphenyl, phosphoryl or sulfenyl promoiety, which may be hydrolyzed in vivo to provide the amino group. A carboxyl group may be masked as an ester (including methyl, ethyl, pivaloyloxymethyl, silyl esters and thioesters), amide or hydrazide promoiety, which may be hydrolyzed in vivo to provide the carboxyl group. The invention includes those esters and acyl groups known in the art for modifying the solubility or hydrolysis characteristics for use as sustained-release or prodrug formulations. Other specific examples of suitable progroups and their respective promoieties will be apparent to those of skill in the art.

Certain compounds of the present invention can exist in unsolvated forms as well as solvated forms, including hydrated forms. "Solvate" refers to a complex formed by combination of solvent molecules with molecules or ions of the solute. The solvent can be an organic compound, an inorganic compound, or a mixture of both. Some examples of solvents include, but are not limited to, methanol, N,N-dimethylformamide, tetrahydrofuran, dimethylsulfoxide, and water. In general, the solvated forms are equivalent to unsolvated forms and are intended to be encompassed within the scope of the present invention. Certain compounds of the present invention may exist in multiple crystalline or amorphous forms. In general, all physical forms are equivalent for the uses contemplated by the present invention and are intended to be within the scope of the present invention.

Certain compounds of the present invention possess asymmetric carbon atoms (optical centers) or double bonds; the racemates, diastereomers, geometric isomers, regioisomers and individual isomers (e.g., separate enantiomers) are all intended to be encompassed within the scope of the present invention. These isomers can be resolved or asymmetrically synthesized using conventional methods to render the isomers "optically pure", i.e., substantially free of its other isomers. If, for instance, a particular enantiomer of a compound of the present invention is desired, it may be prepared by asymmetric synthesis, or by derivation with a chrial auxilliary, where the resulting diastereomeric mixture is separated and the auxilliary group cleaved to provide the pure desired enantiomers. Alternatively, where the molecule contains a basic functional group, such as amino, or an acidic functional group, such as carboxyl, diastereomeric salts are formed with an appropriate optically-active acid or base, followed by resolution of the diasteromers thus formed by fractional crystallization or chromatagraphic means well known in the art, and subsequent recovery of the pure enantiomers.

The compounds of the present invention may also contain unnatural proportions of atomic isotopes at one or more of the atoms that constitute such compounds. For example, the compounds may be radiolabeled with radioactive isotopes, such as for example tritium ($^3$H), iodine-125 ($^{125}$I) or carbon-14 ($^{14}$C). All isotopic variations of the compounds of the present invention, whether radioactive or not, are intended to be encompassed within the scope of the present invention.

The term "administering" refers to oral administration, administration as a suppository, topical contact, intravenous, intraperitoneal, intramuscular, intralesional, intranasal or subcutaneous administration, or the implantation of a slow-release device e.g., a mini-osmotic pump, to a subject. Administration is by any route, including parenteral and transmucosal (e.g., buccal, sublingual, palatal, gingival, nasal, vaginal, rectal, or transdermal). Parenteral administration includes, e.g., intravenous, intramuscular, intra-arteriole, intradermal, subcutaneous, intraperitoneal, intraventricular, and intracranial. Other modes of delivery include, but are not limited to, the use of liposomal formulations, intravenous infusion, transdermal patches, etc.

An "agonist" or "activator" refers to an agent or molecule that binds to a receptor of the invention, stimulates, increases, opens, activates, facilitates, enhances activation or enzymatic activity, sensitizes or up regulates the activity of a receptor of the invention.

An "antagonist" or "inhibitor" refers to an agent or molecule that inhibits or binds to, partially or totally blocks stimulation or activity, decreases, closes, prevents, delays activation or enzymatic activity, inactivates, desensitizes, or down regulates the activity of a receptor of the invention. As used herein, "antagonist" also includes a reverse or inverse agonist.

As used herein, the term "condition or disorder responsive to modulation of syk and/or JAK" and related terms and phrases refer to a condition or disorder associated with inappropriate, e.g., less than or greater than normal, activity of syk and/or JAK and at least partially responsive to or affected by modulation of syk and/or JAK (e.g., syk and/or JAK antagonist or agonist results in some improvement in patient well-being in at least some patients). Inappropriate functional activity of syk and/or JAK might arise as the result of expression of syk and/or JAK in cells which normally do not express the receptor, greater than normal production of syk and/or JAK, or slower than normal metabolic inactivation or elimination of syk and/or JAK or its active metabolites, increased expression of syk and/or JAK or degree of intracellular activation (leading to, e.g., inflammatory and immune-related disorders and conditions) or decreased expression of syk and/or JAK. A condition or disorder associated with syk and/or JAK may include a "syk and/or JAK-mediated condition or disorder".

As used herein, the phrases "a condition or disorder mediated at least in part by syk or JAK kinase activity", and related phrases and terms refer to a condition or disorder characterized by inappropriate, e.g., greater than normal, syk and/or JAK activity. Inappropriate syk and/or JAK functional activity might arise as the result of syk and/or JAK expression in cells which normally do not express syk and/or JAK or increased syk and/or JAK expression or degree of intracellular activation (leading to, e.g., inflammatory and immune-related disorders and conditions). A condition or disorder mediated at least in part by syk or JAK kinase activity may be completely or partially mediated by inappropriate syk and/or JAK functional activity. However, a condition or disorder mediated at least in part by syk or JAK kinase activity is one in which modulation of syk and/or JAK results in some effect on the underlying condition or disorder (e.g., an syk and/or JAK antagonist results in some improvement in patient well-being in at least some patients).

The term "inflammation" as used herein refers to infiltration of white blood cells (e.g., leukocytes, monocytes, etc.) into the area being treated for restenosis.

The term "intervention" refers to an action that produces an effect or that is intended to alter the course of a disease process. For example, "vascular intervention" refers to the use of an intravascular procedure such as angioplasty or a stent to open an obstructed blood vessel.

The term "intravascular device" refers to a device useful for a vascular recanalization procedure to restore blood flow through an obstructed blood vessel. Examples of intravascular devices include, without limitation, stents, balloon catheters, autologous venous/arterial grafts, prosthetic venous/arterial grafts, vascular catheters, and vascular shunts.

As used herein, the term "JAK" refers to a Janus kinase (RefSeq Accession No. P-43408) or a variant thereof that is capable of mediating gene expression in vitro or in vivo. JAK variants include proteins substantially homologous to native JAK, i.e., proteins having one or more naturally or non-naturally occurring amino acid deletions, insertions or substitutions (e.g., JAK derivatives, homologs and fragments). The amino acid sequence of JAK variant preferably is at least about 80% identical to a native JAK, more preferably at least about 90% identical, and most preferably at least about 95% identical.

The term "leukocyte" refers to any of the various blood cells that have a nucleus and cytoplasm, separate into a thin white layer when whole blood is centrifuged, and help protect the body from infection and disease. Examples of leukocytes include, without limitation, neutrophils, eosinophils, basophils, lymphocytes, and monocytes.

The term "mammal" includes, without limitation, humans, domestic animals (e.g., dogs or cats), farm animals (cows, horses, or pigs), monkeys, rabbits, mice, and laboratory animals.

The terms "modulate", "modulation" and the like refer to the ability of a compound to increase or decrease the function and/or expression of syk and/or JAK, where such function may include transcription regulatory activity and/or protein-binding. Modulation may occur in vitro or in vivo. Modulation, as described herein, includes the inhibition, antagonism, partial antagonism, activation, agonism or partial agonism of a function or characteristic associated with syk and/or JAK, either directly or indirectly, and/or the upregulation or downregulation of the expression of syk and/or JAK, either directly or indirectly. In a preferred embodiment, the modulation is direct. Inhibitors or antagonists are compounds that, e.g., bind to, partially or totally block stimulation, decrease, prevent, inhibit, delay activation, inactivate, desensitize, or downregulate signal transduction. Activators or agonists are compounds that, e.g., bind to, stimulate, increase, open, activate, facilitate, enhance activation, activate, sensitize or upregulate signal transduction. The ability of a compound to inhibit the function of syk and/or JAK can be demonstrated in a biochemical assay, e.g., binding assay, or a cell-based assay, e.g., a transient transfection assay.

"Modulators" of activity are used to refer to "ligands", "antagonists" and "agonists" identified using in vitro and in vivo assays for activity and their homologs and mimetics. Modulators include naturally occurring and synthetic ligands, antagonists, agonists, molecules and the like. Assays to identify antagonists and agonists include, e.g., applying putative modulator compounds to cells, in the presence or absence of a receptor of the invention and then determining the functional effects on a receptor of the invention activity. Samples or assays comprising a receptor of the invention that are treated with a potential activator, inhibitor, or modulator are compared to control samples without the inhibitor, activator, or modulator to examine the extent of effect. Control samples (untreated with modulators) are assigned a relative activity value of 100%. Inhibition is achieved when the activity value of a receptor of the invention relative to the control is about 80%, optionally 50% or 25-1%. Activation is achieved when the activity value of a receptor of the invention relative to the control is 110%, optionally 150%, optionally 200-500%, or 1000-3000% higher.

"Patient" refers to human and non-human animals, especially mammals. Examples of patients include, but are not limited to, humans, cows, dogs, cats, goats, sheep, pigs and rabbits.

Turning next to the compositions of the invention, the term "pharmaceutically acceptable carrier or excipient" means a carrier or excipient that is useful in preparing a pharmaceutical composition that is generally safe, non-toxic and neither biologically nor otherwise undesirable, and includes a carrier or excipient that is acceptable for veterinary use as well as human pharmaceutical use. A "pharmaceutically acceptable carrier or excipient" as used in the specification and claims includes both one and more than one such carrier or excipient.

The terms "pharmaceutically effective amount", "therapeutically effective amount" or "therapeutically effective dose" refers to the amount of the subject compound that will elicit the biological or medical response of a tissue, system, animal or human that is being sought by the researcher, veterinarian, medical doctor or other clinician. The term "therapeutically effective amount" includes that amount of a compound that, when administered, is sufficient to prevent development of, or alleviate to some extent, one or more of the symptoms of the condition or disorder being treated. The therapeutically effective amount will vary depending on the compound, the disorder or condition and its severity and the age, weight, etc., of the mammal to be treated.

The term "platelet" refers to a minute, nonnucleated, disklike cell found in the blood plasma of mammals that functions to promote blood clotting.

The terms "prevent", "preventing", "prevention" and grammatical variations thereof as used herein, refers to a method of partially or completely delaying or precluding the onset or recurrence of a disorder or condition and/or one or more of its attendant symptoms or barring a subject from acquiring or reacquiring a disorder or condition or reducing a subject's risk of acquiring or reacquiring a disorder or condition or one or more of its attendant symptoms.

The term "recanalization" refers to the process of restoring flow to or reuniting an interrupted channel of the body, such as a blood vessel.

The term "restenosis" refers to a re-narrowing or blockage of an artery at the same site where treatment, such as an angioplasty or a stent procedure, has been performed.

The phrase "selectively" or "specifically" when referring to binding to a receptor, refers to a binding reaction that is determinative of the presence of the receptor, often in a heterogeneous population of receptors and other biologics. Thus, under designated conditions, the compounds bind to a particular receptor at least two times the background and more typically more than 10 to 100 times background. Specific binding of a compound under such conditions requires a compound that is selected for its specificity for a particular receptor. For example, small organic molecules can be screened to obtain only those compounds that specifically or selectively bind to a selected receptor and not with other receptors or proteins. A variety of assay formats may be used to select compounds that are selective for a particular receptor. For example, High-throughput screening assays are routinely used to select compounds that are selective for a particular a receptor.

As used herein, the term "Sickle cell anemia" refers to an inherited disorder of the red blood cells in which both hemoglobin alleles encode the sickle hemoglobin (S) protein, i.e., the S/S genotype. The presence of abnormal hemoglobin results in the production of unusually shaped cells, which do not survive the usual length of time in the blood circulation. Thus, anemia results. "Anemia" refers to a decrease in the number of red blood cells and/or hemoglobin in the blood.

The term "Sickle cell disease" refers to an inherited disorder of the red blood cells in which one hemoglobin allele encodes the sickle hemoglobin (S) protein, and the other allele encodes another unusual hemoglobin protein, such as hemoglobin (S), (C), (D), (E), and (βThal). Examples of sickle cell disease genotypes include, without limitation, the S/S, S/C, S/D, S/E, and S/βThal genotypes. The most common types of sickle cell disease include sickle cell anemia, sickle-hemoglobin C disease, sickle beta-plus thalassemia, and sickle beta-zero thalassemia.

The "subject" is defined herein to include animals such as mammals, including, but not limited to, primates (e.g., humans), cows, sheep, goats, horses, dogs, cats, rabbits, rats, mice and the like. In preferred embodiments, the subject is a human.

As used herein, the term "syk" refers to a spleen tyrosine kinase (RefSeq Accession No. P-043405) or a variant thereof that is capable of mediating a cellular response to T-cell receptors in vitro or in vivo. syk variants include proteins substantially homologous to native syk, i.e., proteins having one or more naturally or non-naturally occurring amino acid deletions, insertions or substitutions (e.g., syk derivatives, homologs and fragments). The amino acid sequence of syk variant preferably is at least about 80% identical to a native syk, more preferably at least about 90% identical, and most preferably at least about 95% identical.

The term "syk inhibitor" refers to any agent that inhibits the catalytic activity of spleen tyrosine kinase.

The term "thrombosis" refers to the blockage or clotting of a blood vessel caused by a clumping of cells, resulting in the obstruction of blood flow. The term "thrombosis" refers to the clot that is formed within the blood vessel.

The terms "treat", "treating", "treatment" and grammatical variations thereof as used herein, includes partially or completely delaying, alleviating, mitigating or reducing the intensity of one or more attendant symptoms of a disorder or condition and/or alleviating, mitigating or impeding one or more causes of a disorder or condition. Treatments according to the invention may be applied preventively, prophylactically, palliatively or remedially.

The term "vessel" refers to any channel for carrying a fluid, such as an artery or vein. For example, a "blood vessel" refers to any of the vessels through which blood circulates in the body. The lumen of a blood vessel refers to the inner open space or cavity of the blood vessel.

2. Embodiments of the Invention a. Compounds

The present invention provides in one embodiment, a compound having the formula I:

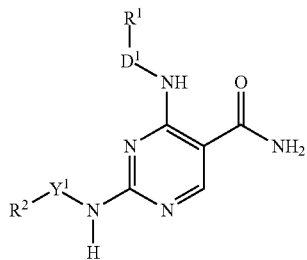

or a pharmaceutically acceptable salt thereof, wherein:
$D^1$ is selected from the group consisting of
(a) $C_{3-8}$cycloalkyl, optionally substituted with from 1 to 4 substituents independently selected from the group consisting of: $C_{1-8}$alkyl, amino, hydroxy, $C_{1-8}$alkylcarbonyl, aminocarbonyl, $C_{1-8}$alkoxycarbonylamino, aryl$C_{1-8}$alkoxycarbonylamino, phenyl and heterocyclyl$C_{1-8}$alkylene;
(b) $C_{1-8}$ alkyl; optionally substituted with from 1 to 4 substituents independently selected from the group consisting of: amino, oxo, $C_{1-8}$alkoxy, $C_{2-8}$alkynyl, cyano, aminocarbonyl, $C_{1-8}$haloalkyl, hydroxy, halogen, $C_{3-8}$cycloalkyl, and phenyl;
(c) $C_{1-8}$ alkyl$C_{3-8}$heterocyclyl; optionally substituted with from 1 to 4 substituents independently selected from the group consisting of: $C_{1-8}$alkyl, $C_{1-8}$alkylcarbonyl; $C_{1-8}$alkylsulfonyl; aminocarbonyl
(d) aryl, which is optionally substituted with from 1 to 4 substituents independently selected from the group consisting of $C_{1-8}$alkyl, $C_{2-8}$alkenyl, $C_{2-8}$alkynyl, $C_{1-8}$haloalkyl, carboxy, acyl, acylamino, cyano, amino, aminocarbonyl, aminosulfonyl, sulfonyl, nitro, hydroxy, $C_{1-8}$alkoxy, aryloxy, halo, sulfonylamino, $C_{3-8}$cycloalkyl, aryl, heterocyclyl $C_{1-8}$alkylsulfonyl, $C_{1-8}$alkylcarbonylheterocyclyl and heteroaryl;
(e) heteroaryl, optionally substituted with from 1 to 4 substituents independently selected from the group consisting of: $C_{1-8}$alkyl, $C_{1-8}$alkylcarbonyl, aminocarbonyl, $C_{1-8}$alkoxycarbonyl, amino, $C_{1-8}$alkoxycarbonylamino, aryl$C_{1-8}$alkoxycarbonylamino, hydroxyl, $C_{1-8}$ alkoxy, $C_{1-8}$alkylsulfonyl, oxo, halo, phenyl and heterocyclyl$C_{1-8}$alkylene;
(f) $C_{3-8}$heterocyclyl, optionally substituted with from 1 to 4 substituents independently selected from the group consisting of: $C_{1-8}$alkyl, $C_{1-8}$alkoxycarbonyl and oxo;
$R^1$ is selected from the group consisting of H, $C_{1-8}$ alkyl, amino, aminocarbonyl, hydroxyl, $C_{1-8}$ alkoxy, $C_{1-8}$ haloalkyl, $C_{2-8}$ alkenyl, $C_{2-8}$ alkynyl, oxo, cyano, $C_{1-8}$ alkoxycarbonyl, $C_{3-8}$ cycloalkyl, aryl and heterocyclyl; and each heterocyclyl is optionally substituted with from 1 to 4 substituents selected from the group consisting of: $C_{1-8}$ alkyl, halo, oxo, amino, $C_{1-8}$alkoxy, $C_{1-8}$alkylcarbonyl, aryl$C_{1-8}$ alkoxycarbonyl, aminocarbonyl, aryl$C_{1-8}$ alkylenecarbonyl and $C_{1-8}$ alkylsulfonyl
$Y^1$ is selected from the group consisting of
(a) aryl; optionally substituted with from 1 to 3 substituents, $R^{4a}$, independently selected from the group consisting of $C_{1-8}$alkyl, $C_{1-8}$alkoxy$C_{1-8}$alkyl, aminocarbonyl-, hydroxyl, oxo, halogen, hydroxy, $C_{1-8}$alkoxy and $C_{1-8}$alkylsulfonyl;
(b) heteroaryl, optionally substituted with from 1 to 3 substituents, $R^{4a}$, independently selected from the group consisting of $C_{1-8}$alkyl, $C_{1-8}$alkoxy$C_{1-8}$alkyl, aminocarbonyl-, hydroxyl, oxo, halogen, hydroxy, $C_{1-8}$alkoxy and $C_{1-8}$alkylsulfonyl;

$R^2$ is selected from the group consisting of heterocyclyl, heterocyclylaminosulfonyl, heterocyclylcarbonyl, heterocyclylcarbonyl$C_{1-8}$alkoxy, heterocyclyl $C_{1-8}$alkoxy, heteroaryl, aminosulfonyl, $C_{1-8}$alkysulfinyl, $C_{1-8}$haloalkoxy, $C_{1-8}$alkoxycarbonylamino, $C_{1-8}$alkoxyaminocarbonyl, aminocarbonyl$C_{1-8}$alkylamino, aminosulfonylheterocyclyl and alkylcarbonylheterocyclyl;

and wherein $R^2$ is further optionally substituted with from 1 to 2 substituents, $R^{4c}$, independently selected from the group consisting of $C_{1-8}$ alkyl, $C_{1-8}$alkoxy, halo, aminocarbonyl, oxo, hydroxyl, amino$C_{1-8}$alkylene, $C_{1-8}$alkoxy$C_{1-8}$alkylene, $C_{1-8}$alkylcarbonyl, $C_{3-8}$cycloalkylcarbonyl, heterocyclylcarbonyl, $C_{1-8}$alkylcarbonylamino, $C_{3-8}$cycloalkylcarbonylamino, heterocyclylcarbonylamino, $C_{1-8}$alkylsulfonyl, $C_{3-8}$cycloalkylsulfonyl, heterocyclylsulfonyl, $C_{3-8}$cycloalkyl, $C_{1-8}$alkylcycloalkylene, heteroaryl.

In one group of embodiments, $Y^1$ is aryl. In another group of embodiments, $Y^1$ is phenyl. In another group of embodiments, $Y^1$ is heteroaryl. In another group of embodiments, $Y^1$ is pyridinyl.

In one group of embodiments, $Y^1$ is aryl. In another group of embodiments, $Y^1$ is phenyl. In another group of embodiments, $Y^1$ is heteroaryl. In another group of embodiments, $Y^1$ is pyridinyl.

In one group of embodiments, $R^2$ is heterocyclyl. In another group of embodiments, $R^2$ is heterocyclylaminosulfonyl. In another group of embodiments, $R^2$ is heterocyclylcarbonyl. In another group of embodiments, $R^2$ is heterocyclylcarbonyl$C_{1-8}$alkoxy. In another group of embodiments, $R^2$ is heterocyclyl$C_{1-8}$alkoxy. In another group of embodiments, $R^2$ is heteroaryl. In another group of embodiments, $R^2$ is aminosulfonyl. In another group of embodiments, $R^2$ is $C_{1-8}$alkysulfinyl. In another group of embodiments, $R^2$ is $C_{1-8}$haloalkoxy. In another group of embodiments, $R^2$ is $C_{1-8}$alkoxycarbonylamino. In another group of embodiments, $R^2$ is $C_{1-8}$alkoxyaminocarbonyl. In another group of embodiments, $R^2$ is aminocarbonyl$C_{1-8}$alkylamino.

In one group of embodiments, if $R^2$ is a heterocyclyl or heteroaryl it is substituted with at least one group, $R^3$, selected from the group consisting of amino$C_{1-8}$alkyl-, $C_{1-8}$alkoxy$C_{1-8}$alkyl-, oxo-, $C_{1-8}$alkylcarbonyl, $C_{3-8}$cycloalkylcarbonyl, heterocyclylcarbonyl, $C_{1-8}$alkylcarbonylamino, $C_{3-8}$cycloalkylcarbonylamino, heterocyclylcarbonylamino, $C_{1-8}$alkylsulfonyl, $C_{3-8}$cycloalkylsulfonyl and heterocyclylsulfonyl.

In another group of embodiments, $D^1$ is $C_{1-8}$ alkyl. In another group of embodiments, $D^1$ is $C_{1-8}$ alkyl$C_{3-8}$heterocyclyl.

In another group of embodiments, $D^1$ is aryl. In another group of embodiments, $D^1$ is phenyl.

In another group of embodiments, $D^1$ is heteroaryl.

The present invention provides in another group of embodiments, a compound wherein a heteroaryl group of the compound of formula I is selected from the group consisting of:

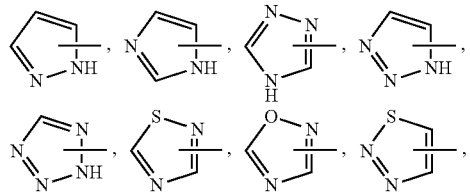

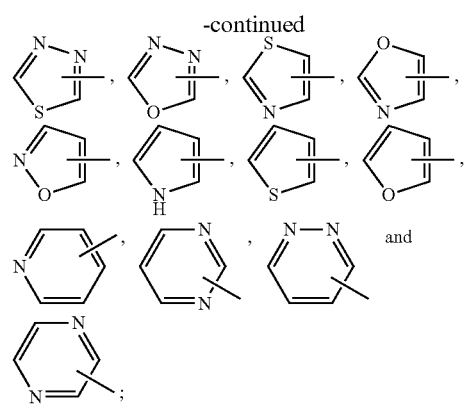

-continued each of which is optionally substituted with from 1 to 2 substituents independently selected from the group consisting of: $C_{1-8}$ alkyl, amino, hydroxyl, oxo, halo, $C_{1-8}$ alkoxy, hydroxy$C_{1-8}$alkyl-, amino$C_{1-8}$alkyl, $C_{1-8}$alkylcarbonyl, halo$C_{1-8}$alkyl, $C_{3-8}$cycloalkyl, $C_{1-8}$aminocycloalkyl, amino$C_{1-8}$alkylenecarbonyl, aminocarbonyl, $C_{1-8}$alkyleneamino$C_{1-8}$alkylenecarbonyl, $C_{1-8}$alkoxy$C_{1-8}$alkylenecarbonyl, hydroxy$C_{1-8}$alkylenecarbonyl, hydroxy$C_{1-8}$alkoxycarbonyl, $C_{1-8}$ alkoxycarbonylamino, aryl, aryl$C_{1-8}$ alkoxycarbonylamino, $C_{1-8}$alkylsulfonyl, amino$C_{1-8}$alkylenesulfonyl, aminosulfonyl, $C_{1-8}$alkyleneamino$C_{1-8}$alkylenesulfonyl, $C_{1-8}$alkoxy$C_{1-8}$alkylenesulfonyl, hydroxy$C_{1-8}$alkylenesulfonyl, hydroxy$C_{1-8}$alkoxysulfonyl, aminosulfonyl, and $C_{1-8}$alkylheterocyclyl.

The present invention provides in another group of embodiments, a compound wherein a heteroaryl group of the compound of formula I is a polycyclic heteroaryl group selected from the group consisting of:

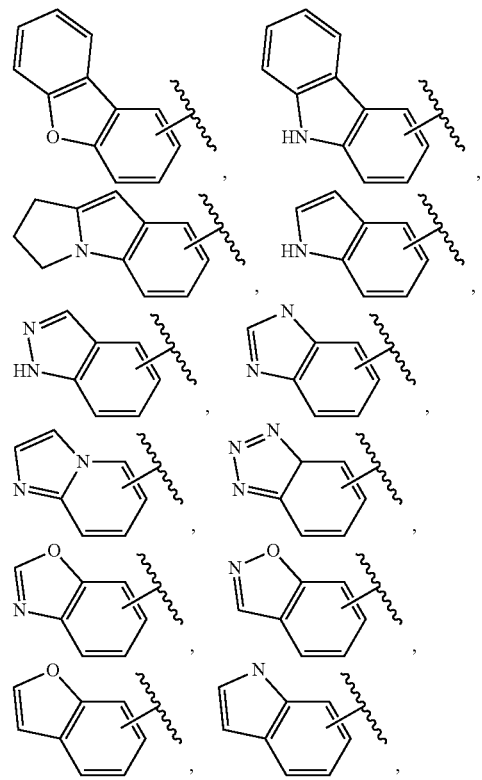

-continued

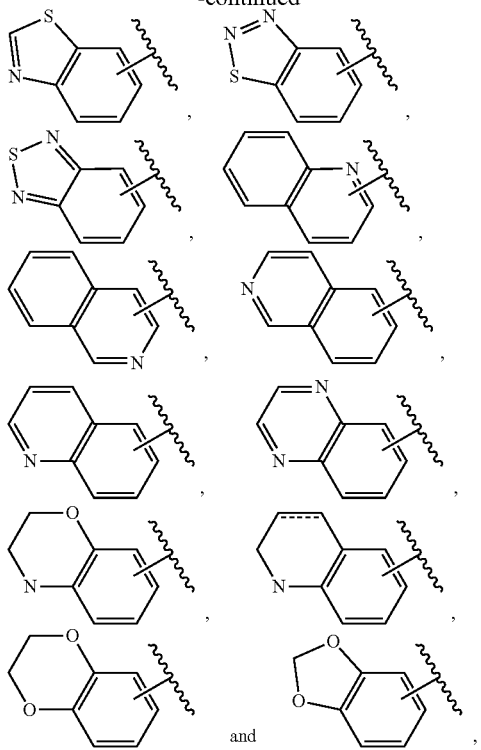

optionally substituted with from 1 to 3 substituents independently selected from the group consisting of: $C_{1-8}$ alkyl, $C_{1-8}$alkylcarbonyl, $C_{1-8}$aminocycloalkyl, amino$C_{1-8}$alkylenecarbonyl, aminocarbonyl, $C_{1-8}$alkyleneamino$C_{1-8}$alkylenecarbonyl, $C_{1-8}$alkoxy$C_{1-8}$alkylenecarbonyl, hydroxy$C_{1-8}$alkylenecarbonyl, hydroxy$C_{1-8}$alkoxycarbonyl, aminocarbonyl, amino, $C_{1-8}$ alkoxycarbonylamino, aryl, aryl$C_{1-8}$ alkoxycarbonylamino, hydroxyl, $C_{1-8}$ alkoxy, $C_{1-8}$alkylsulfonyl, amino$C_{1-8}$alkylenesulfonyl, aminosulfonyl, $C_{1-8}$alkyleneamino$C_{1-8}$alkylenesulfonyl, $C_{1-8}$alkoxy$C_{1-8}$alkylenesulfonyl, hydroxy$C_{1-8}$alkylenesulfonyl, hydroxy$C_{1-8}$alkoxysulfonyl, aminosulfonyl, oxo, halo, phenyl and $C_{1-8}$alkylheterocyclyl; and the wavy line indicates the point of attachment to the rest of the molecule.

The present invention provides in another group of embodiments, a compound wherein: $D^1$ is bicyclic heteroaryl. In another group of embodiments, $D^1$ is selected from the group consisting of:

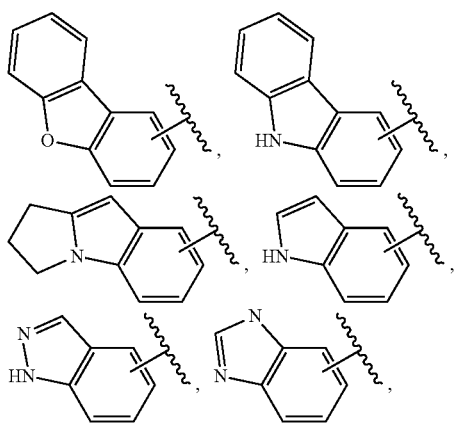

-continued

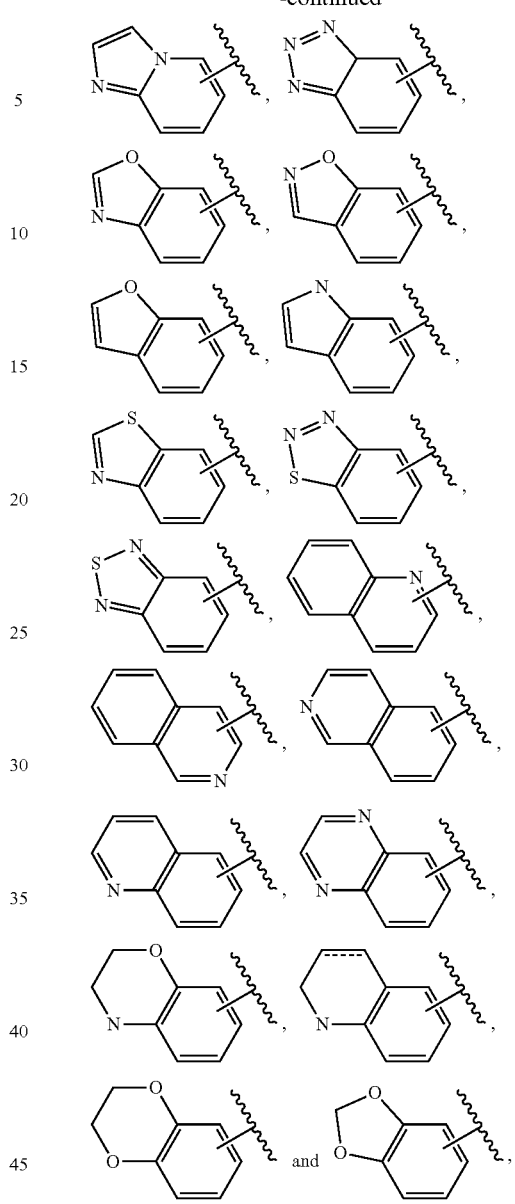

optionally substituted with from 1 to 3 substituents independently selected from the group consisting of: $C_{1-8}$ alkyl, $C_{1-8}$alkylcarbonyl, $C_{1-8}$aminocycloalkyl, amino$C_{1-8}$alkylenecarbonyl, aminocarbonyl, $C_{1-8}$alkyleneamino$C_{1-8}$alkylenecarbonyl, $C_{1-8}$alkoxy$C_{1-8}$alkylenecarbonyl, hydroxy$C_{1-8}$alkylenecarbonyl, hydroxy$C_{1-8}$alkoxycarbonyl, aminocarbonyl, amino, $C_{1-8}$ alkoxycarbonylamino, aryl, aryl$C_{1-8}$ alkoxycarbonylamino, hydroxyl, Cis alkoxy, $C_{1-8}$alkylsulfonyl, amino$C_{1-8}$alkylenesulfonyl, aminosulfonyl, $C_{1-8}$alkyleneamino$C_{1-8}$alkylenesulfonyl, $C_{1-8}$alkoxy$C_{1-8}$alkylenesulfonyl, hydroxy$C_{1-8}$alkylenesulfonyl, hydroxy$C_{1-8}$alkoxysulfonyl, aminosulfonyl, oxo, halo, phenyl and $C_{1-8}$alkylheterocyclyl; and the wavy line indicates the point of attachment to the rest of the molecule.

The present invention provides in another group of embodiments, a compound wherein $D^1$ is $C_{3-8}$heterocyclyl. In one group of embodiments, any of the heterocyclyl groups of formula I is selected from the group consisting of:

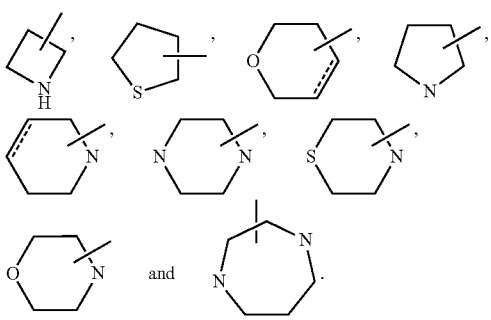

In another group of embodiments, D¹ is selected from the group consisting of:

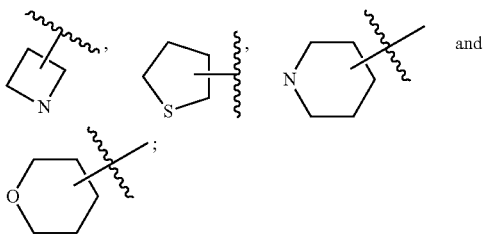

each of which is optionally substituted with from 1 to 3 substituents independently selected from the group consisting of: $C_{1-8}$alkyl, $C_{1-8}$alkoxycarbonyl and oxo; and the wavy line indicates the point of attachment to the rest of the molecule.

The present invention provides in one embodiment, a compound having the formula I:

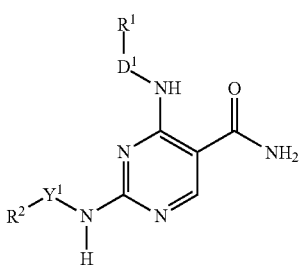

or a pharmaceutically acceptable tautomer, salt, or stereoisomer thereof, wherein:

D¹ is selected from the group consisting of (a) $C_{1-8}$ alkyl; optionally substituted with from 1 to 4 substituents independently selected from the group consisting of: $C_{1-8}$alkoxy, $C_{2-8}$alkynyl, cyano, aminocarbonyl, $C_{1-8}$haloalkyl, hydroxy, $C_{3-8}$cycloalkyl, $C_{3-8}$heterocyclyl and phenyl;

(b) $C_{3-8}$cycloalkyl, optionally substituted with from 1 to 4 substituents independently selected from the group consisting of: $C_{1-8}$ alkyl, amino, hydroxy, $C_{1-8}$alkylcarbonyl, aminocarbonyl, $C_{1-8}$alkoxycarbonylamino, aryl$C_{1-8}$alkoxycarbonylamino, phenyl and heterocyclyl$C_{1-8}$alkylene;

(c) aryl, which is optionally substituted with from 1 to 4 substituents independently selected from the group consisting of $C_{1-8}$alkyl, $C_{2-8}$alkenyl, $C_{2-8}$alkynyl, $C_{1-8}$haloalkyl, carboxy, acyl, acylamino, cyano, amino, aminocarbonyl, aminosulfonyl, sulfonyl, nitro, hydroxy, $C_{1-8}$alkoxy, aryloxy, halo, sulfonylamino, $C_{3-8}$cycloalkyl, aryl, heterocyclyl $C_{1-8}$alkylsulfonyl, $C_{1-8}$alkylcarbonylheterocyclyl and heteroaryl;

(d) heteroaryl, optionally substituted with from 1 to 4 substituents independently selected from the group consisting of: $C_{1-8}$alkyl, $C_{1-8}$alkylcarbonyl, aminocarbonyl, $C_{1-8}$alkoxycarbonyl, amino, $C_{1-8}$ alkoxycarbonylamino, aryl$C_{1-8}$alkoxycarbonylamino, hydroxyl, $C_{1-8}$ alkoxy, $C_{1-8}$alkylsulfonyl, oxo, halo, phenyl and heterocyclyl$C_{1-8}$alkylene;

(e) $C_{3-8}$heterocyclyl, optionally substituted with from 1 to 4 substituents independently selected from the group consisting of: $C_{1-8}$alkyl, $C_{1-8}$alkoxycarbonyl and oxo;

R¹ is selected from the group consisting of H, $C_{1-8}$ alkyl, amino, aminocarbonyl, hydroxyl, $C_{1-8}$ alkoxy, $C_{1-8}$ haloalkyl, $C_{2-8}$ alkenyl, $C_{2-8}$ alkynyl, oxo, cyano, $C_{1-8}$ alkoxycarbonyl, $C_{3-8}$ cycloalkyl, aryl and heterocyclyl; and each heterocyclyl is optionally substituted with from 1 to 4 substituents selected from the group consisting of: $C_{1-8}$ alkyl, halo, oxo, amino, $C_{1-8}$alkoxy, $C_{1-8}$alkylcarbonyl, aryl$C_{1-8}$ alkoxycarbonyl, aminocarbonyl, aryl$C_{1-8}$ alkylenecarbonyl and $C_{1-8}$ alkylsulfonyl Y¹ is selected from the group consisting of (a) aryl; optionally substituted with from 1 to 3 substituents, $R^{4a}$, independently selected from the group consisting of $C_{1-8}$alkyl, $C_{1-8}$alkoxy$C_{1-8}$alkyl, aminocarbonyl-, hydroxyl, oxo, halogen, hydroxy, $C_{1-8}$alkoxy and $C_{1-8}$alkylsulfonyl;

(b) heteroaryl, optionally substituted with from 1 to 3 substituents, $R^{4a}$, independently selected from the group consisting of $C_{1-8}$alkyl, $C_{1-8}$alkoxy$C_{1-8}$alkyl, aminocarbonyl-, hydroxyl, oxo, halogen, hydroxy, $C_{1-8}$alkoxy and $C_{1-8}$alkylsulfonyl;

R² is selected from the group consisting of aminosulfonyl, $C_{1-8}$alkysulfinyl, $C_{1-8}$haloalkoxy, $C_{1-8}$alkoxycarbonylamino and heterocyclyl;

wherein if R² is heterocyclyl it is substituted with at least one group, R³, selected from the group consisting of a min $C_{1-8}$alkyl-, $C_{1-8}$alkoxy$C_{1-8}$alkyl-, oxo-, $C_{1-8}$alkylcarbonyl, $C_{3-8}$cycloalkylcarbonyl, heterocyclylcarbonyl, $C_{1-8}$alkylcarbonylamino, $C_{3-8}$cycloalkylcarbonylamino, heterocyclylcarbonylamino, $C_{1-8}$alkylsulfonyl, $C_{3-8}$cycloalkylsulfonyl, heterocyclylsulfonyl; and wherein R² is further optionally substituted with from 1 to 2 substituents, $R^{4c}$, independently selected from the group consisting of $C_{1-8}$ alkyl, $C_{1-8}$alkoxy, halo, aminocarbonyl, oxo, hydroxyl, amino$C_{1-8}$alkylene, $C_{1-8}$alkoxy$C_{1-8}$alkylene, $C_{1-8}$alkylcarbonyl, $C_{3-8}$cycloalkylcarbonyl, heterocyclylcarbonyl, $C_{1-8}$alkylcarbonylamino, $C_{3-8}$cycloalkylcarbonylamino, heterocyclylcarbonylamino, $C_{1-8}$alkylsulfonyl, $C_{3-8}$cycloalkylsulfonyl, heterocyclylsulfonyl, $C_{3-8}$cycloalkyl and $C_{1-8}$alkylcycloalkylene.

The present invention provides in another embodiment, a compound wherein the moiety —Y¹—R² is selected from the group consisting of:

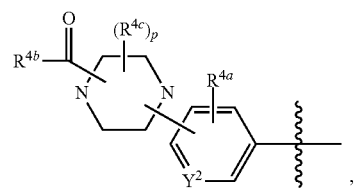

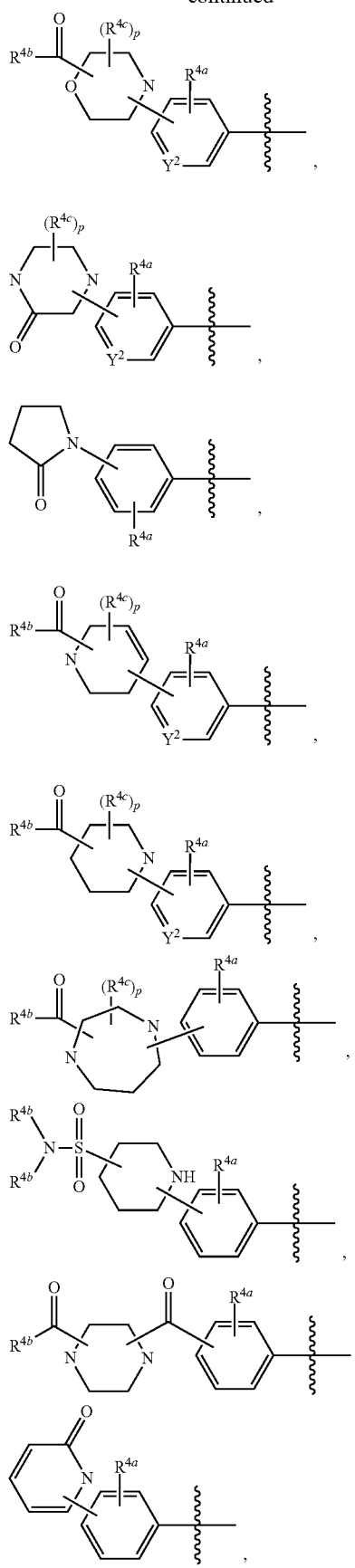
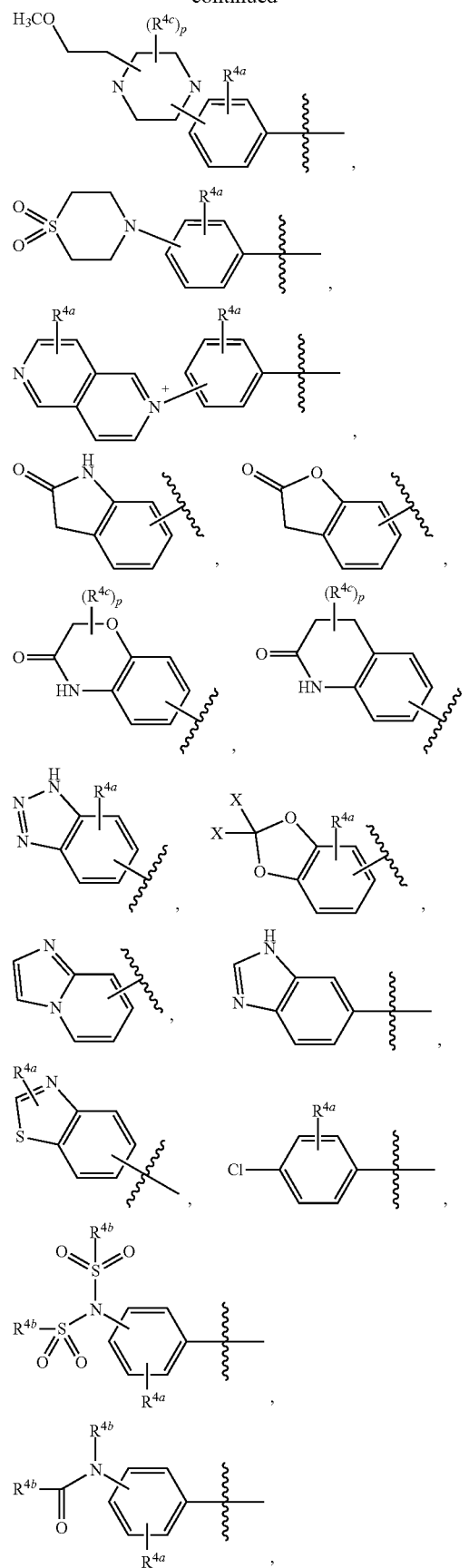

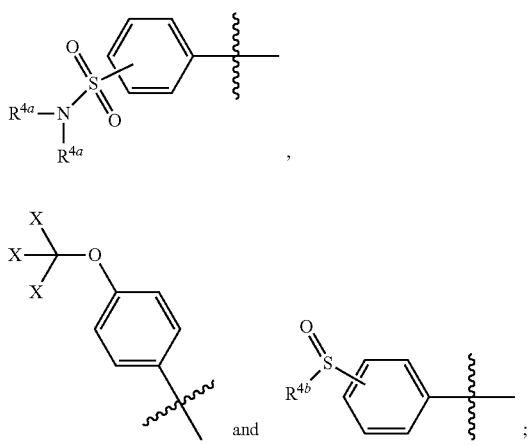

Y² is N, CH or C;

R⁴ᵃ is selected from the group consisting of H and $C_{1-8}$alkyl;

each R⁴ᶜ is independently selected from the group consisting of H, $C_{1-8}$alkyl, $C_{1-8}$alkoxy$C_{1-8}$alkyl, aminocarbonyl-, hydroxyl, oxo, $C_{1-8}$alkoxy and halo;

each R⁴ᵇ is independently selected from the group consisting of H, $C_{1-8}$alkyl, amino, $C_{1-8}$alkoxy and heterocyclyl;

X is halo;

the subscript p is 0, 1, 2 or 3; and the wavy line indicates the point of attachment to the rest of the molecule.

The present invention provides in another embodiment, a compound wherein the moiety —Y¹—R² is selected from the group consisting of:

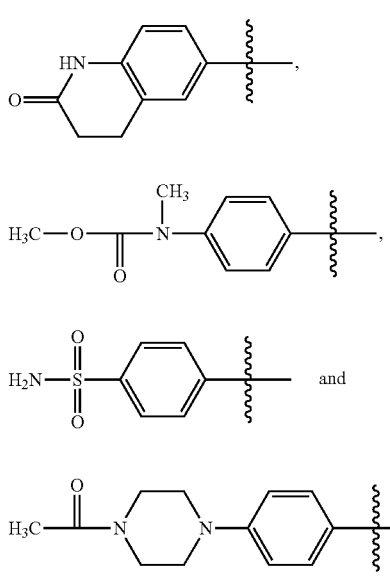

and the wavy line indicates the point of attachment to the rest of the molecule.

The present invention provides in another embodiment, a compound having the formula Ia:

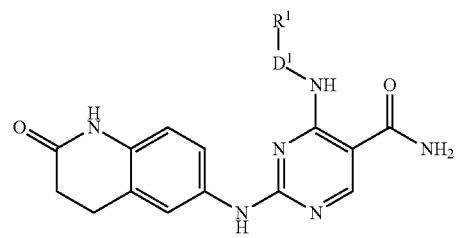

(Ia)

or a pharmaceutically acceptable tautomer, salt, or stereoisomer thereof.

The present invention provides in another embodiment, a compound having the formula Ib:

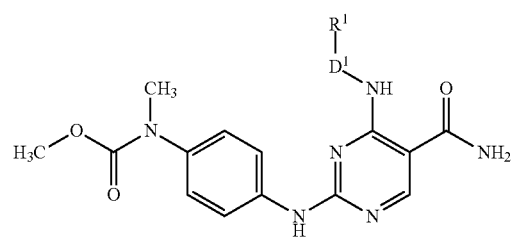

(Ib)

or a pharmaceutically acceptable tautomer, salt, or stereoisomer thereof.

The present invention provides in another embodiment, a compound having the formula Ic:

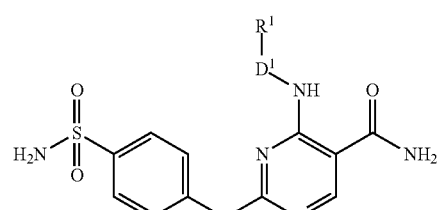

(Ic)

or a pharmaceutically acceptable salt, stereoisomer or prodrug thereof.

The present invention provides in another embodiment, a compound having the formula Id:

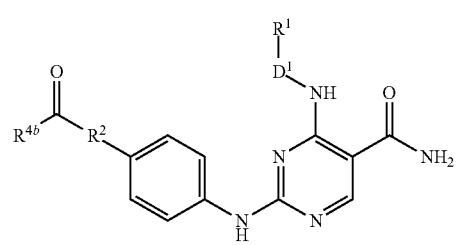

(Id)

or a pharmaceutically acceptable salt, stereoisomer or prodrug thereof.

The present invention provides in another embodiment, a compound having the formula Id1:

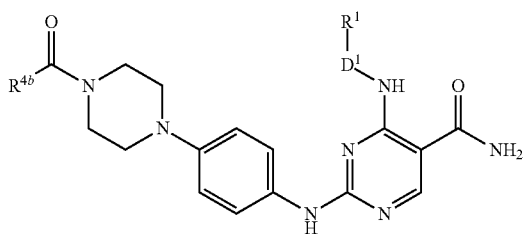

(Id1)

or a pharmaceutically acceptable salt, stereoisomer or prodrug thereof.

The present invention provides in another embodiment, a compound having the formula Id2:

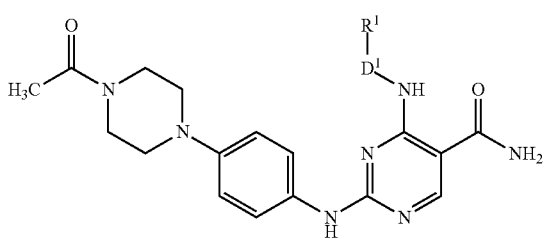

(Id2)

or a pharmaceutically acceptable salt, stereoisomer or prodrug thereof.

The present invention provides in another embodiment, a compound wherein, $D^1$ is $C_{1-8}$ alkyl; optionally substituted with from 1 to 4 substituents independently selected from the group consisting of: $C_{1-8}$alkoxy, $C_{2-8}$alkynyl, CN, aminocarbonyl, $C_{1-8}$haloalkyl, -hydroxyl, —$C_{3-8}$cycloalkyl, —$C_{3-8}$heterocyclyl, and phenyl;

$R^1$ is selected from the group consisting of H, $C_{1-8}$ alkyl, amino, hydroxyl, $C_{1-8}$ alkoxy, $C_{1-8}$ haloalkyl, $C_{2-8}$ alkenyl, $C_{2-8}$ alkynyl, oxo, CN, $C_{1-8}$ alkoxycarbonyl, $C_{3-8}$ cycloalkyl, aryl, heterocyclyl; each heterocyclyl is optionally substituted with from 1 to 4 substituents selected from the group consisting of: alkyl, halo, oxo, amino, alkoxy, $C_{1-8}$ alkylcarbonyl, aryl$C_{1-8}$ alkoxycarbonyl, aminocarbonyl and $C_{1-8}$ alkylsulfonyl.

The present invention provides in another embodiment, a compound wherein: $D^1$ is cycloalkyl, optionally substituted with from 1 to 4 substituents independently selected from the group consisting of: $C_{1-8}$ alkyl, amino, hydroxy, $C_{1-8}$alkylcarbonyl, aminocarbonyl, $C_{1-8}$alkoxycarbonylamino, aryl $C_{1-8}$alkoxycarbonylamino, phenyl and heterocyclyl$C_{1-8}$alkylene.

The present invention provides in another embodiment, a compound wherein: $D^1$ is cyclopropyl.

The present invention provides in another embodiment, a compound wherein: $D^1$ is cyclobutyl.

The present invention provides in another embodiment, a compound wherein: $D^1$ is cyclopentyl.

The present invention provides in another embodiment, a compound wherein: $D^1$ is phenyl, optionally substituted with from 1 to 4 substituents independently selected from the group consisting of: $C_{1-8}$alkyl, $C_{1-8}$alkylsulfonyl, $C_{1-8}$alkylcarbonylheterocyclyl, halo and $C_{1-8}$alkylcarbonylamino- and $C_{1-8}$alkoxy.

The present invention provides in another embodiment, a compound wherein —$Y^1$—$R^2$ is selected from the group consisting of:

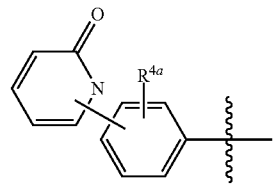

,

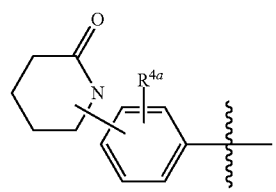

,

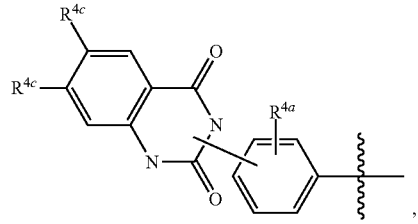

,

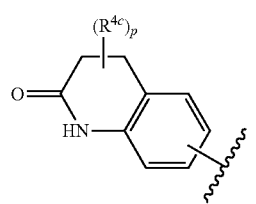

,

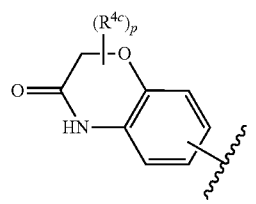

,

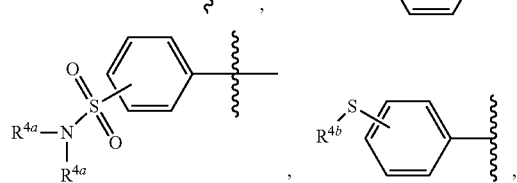

,

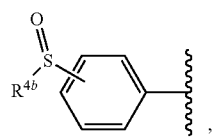

,

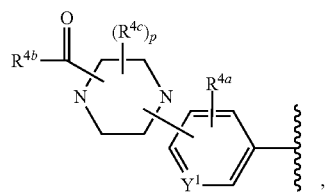

,

-continued

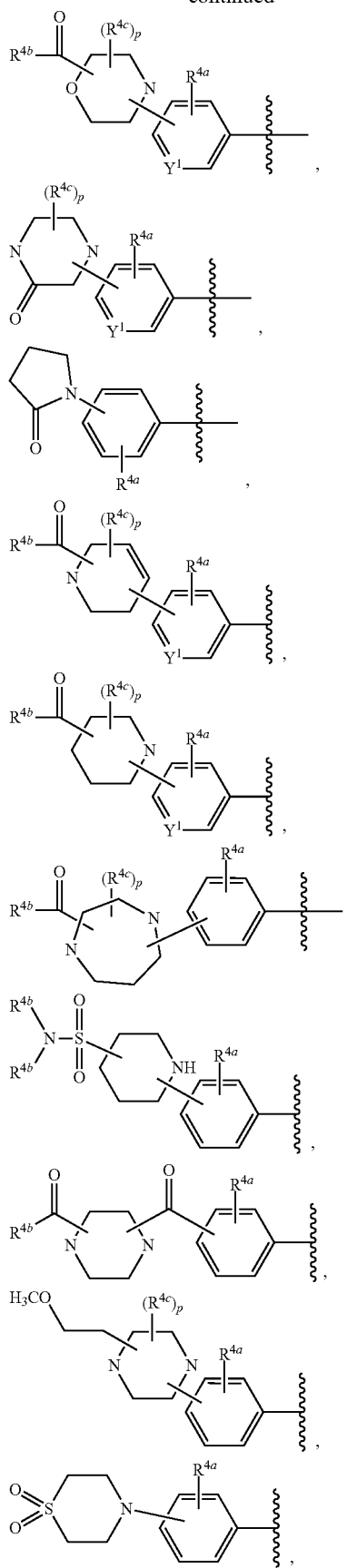

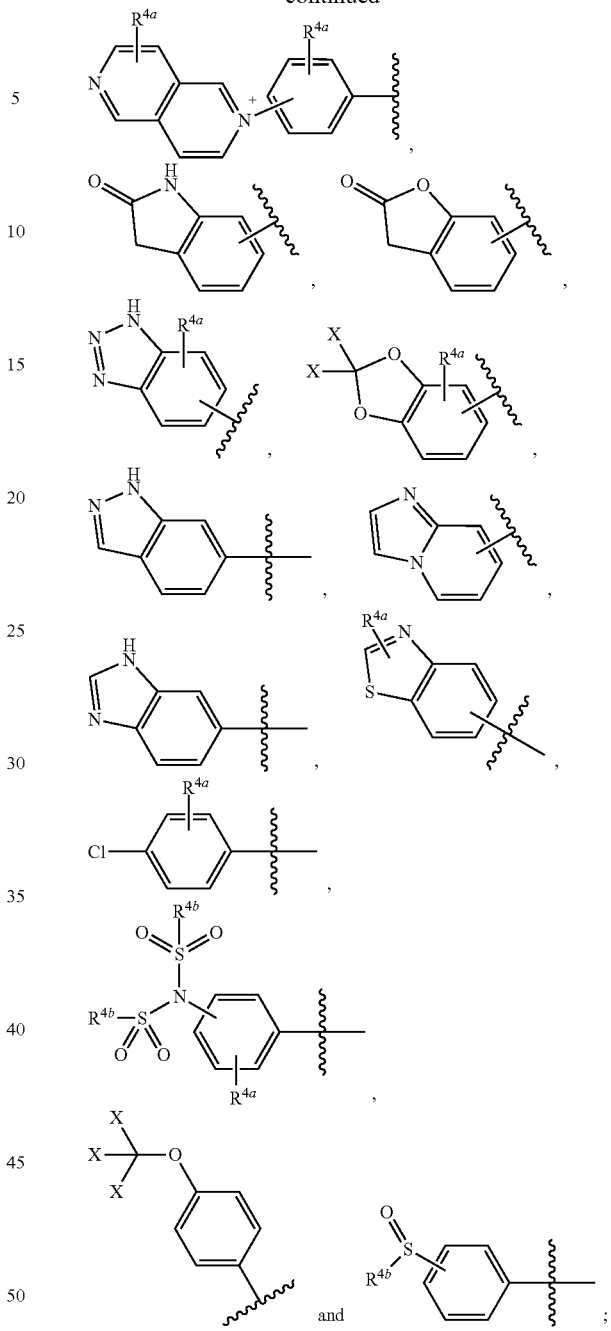

$Y^2$ is N or C;
each $R^{4a}$ is selected from the group consisting of H and halo;
each $R^{4c}$ is independently selected from the group consisting of H and $C_{1-8}$alkyl;
each $R^{4b}$ is independently selected from the group consisting of H and $C_{1-8}$alkyl;
X is halo; and
the subscript p is 0, 1, 2 or 3; and
the wavy line indicates the point of attachment to the rest of the molecule.

The present invention provides in another embodiment, a compound wherein the moiety —$Y^1$—$R^2$ is selected from the group consisting of:

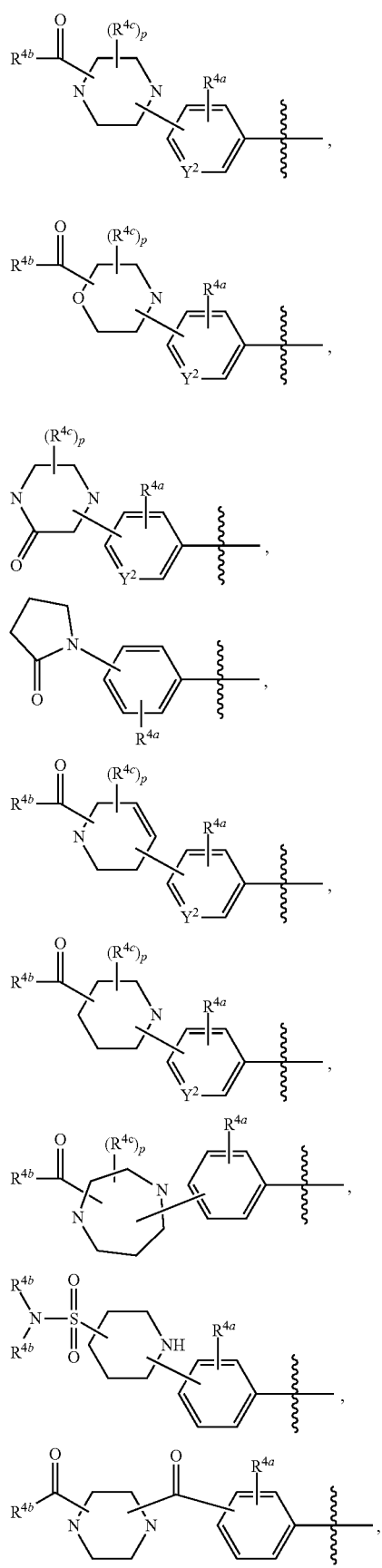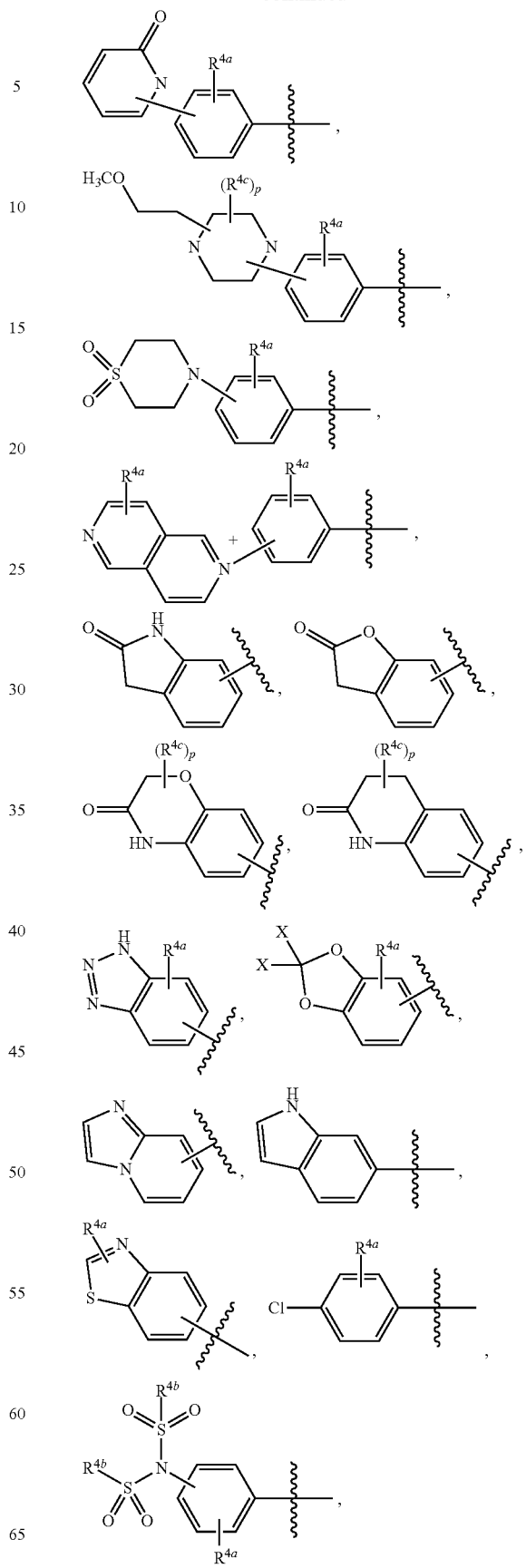

-continued

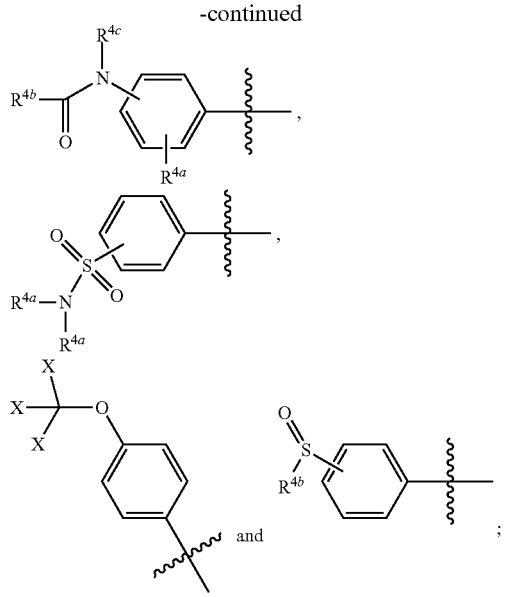

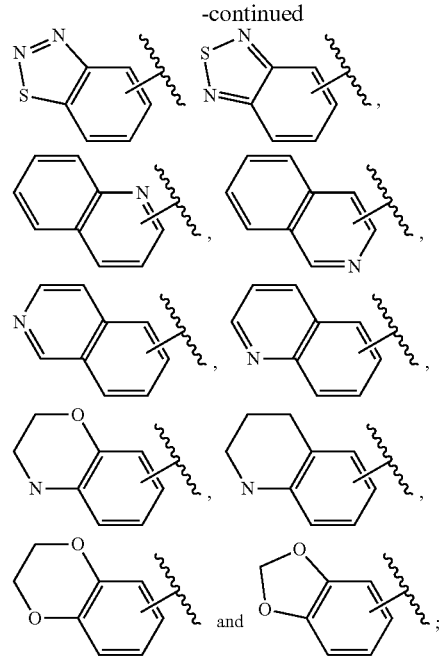

$Y^2$ is N or C;

each $R^{4a}$ is selected from the group consisting of H and $C_{1-8}$alkyl;

each $R^{4c}$ is independently selected from the group consisting of H, $C_{1-8}$alkyl, $C_{1-8}$alkoxy$C_{1-8}$alkyl, aminocarbonyl-, hydroxyl, oxo, $C_{1-8}$alkoxy and halo;

each $R^{4b}$ is independently selected from the group consisting of H, $C_{1-8}$alkyl, amino, $C_{1-8}$alkoxy and heterocyclyl;

X is halo; and the subscript p is 0, 1, 2 or 3; and the wavy line indicates the point of attachment to the rest of the molecule.

The present invention provides in another embodiment, a compound wherein, $D^1$ is heteroaryl; optionally substituted with from 1 to 4 substituents independently selected from the group consisting of: $C_{1-8}$alkyl, $C_{1-8}$alkylcarbonyl, aminocarbonyl, $C_{1-8}$alkoxycarbonyl, amino, $C_{1-8}$ alkoxycarbonylamino, aryl$C_{1-8}$alkoxycarbonylamino, hydroxyl, $C_{1-8}$ alkoxy, $C_{1-8}$alkylsulfonyl, oxo, halo, phenyl and heterocyclyl$C_{1-8}$alkylene.

The present invention provides in another embodiment, a compound wherein $D^1$ is bicyclic heteroaryl; optionally substituted with from 1 to 4 substituents independently selected from the group consisting of: $C_{1-8}$alkyl, $C_{1-8}$alkylcarbonyl, aminocarbonyl, $C_{1-8}$alkoxycarbonyl, amino, $C_{1-8}$ alkoxycarbonylamino, aryl$C_{1-8}$alkoxycarbonylamino, hydroxyl, $C_{1-8}$ alkoxy, $C_{1-8}$alkylsulfonyl, oxo, halo, phenyl and heterocyclyl$C_{1-8}$alkylene.

The present invention provides in another embodiment, a compound wherein $D^1$- is selected from the group consisting of:

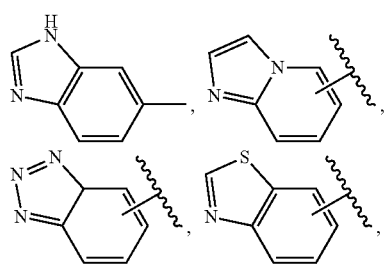

each of which is optionally substituted with from 1 to 4 substituents independently selected from the group consisting of: $C_{1-8}$alkyl, $C_{1-8}$alkylcarbonyl, aminocarbonyl, $C_{1-8}$alkoxycarbonyl, amino, $C_{1-8}$ alkoxycarbonylamino, aryl$C_{1-8}$alkoxycarbonylamino, hydroxyl, $C_{1-8}$ alkoxy, $C_{1-8}$alkylsulfonyl, oxo, halo, phenyl and heterocyclyl$C_{1-8}$alkylene; and the wavy line indicates the point of attachment to the rest of the molecule.

The present invention provides in another embodiment, a compound wherein $D^1$ is selected from the group consisting of

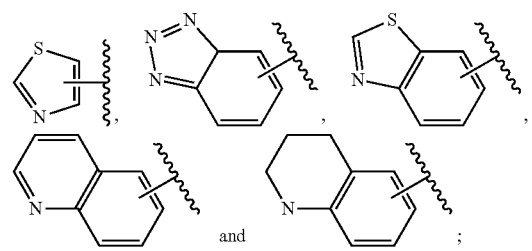

each of which is optionally substituted with $C_{1-8}$alkyl or oxo; and the wavy line indicates the point of attachment to the rest of the molecule.

The present invention provides in another embodiment, a compound wherein $D^1$ is selected from the group consisting of:

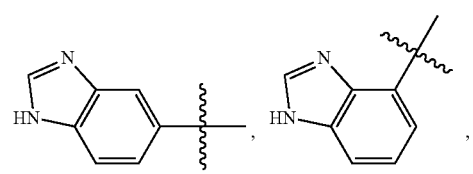

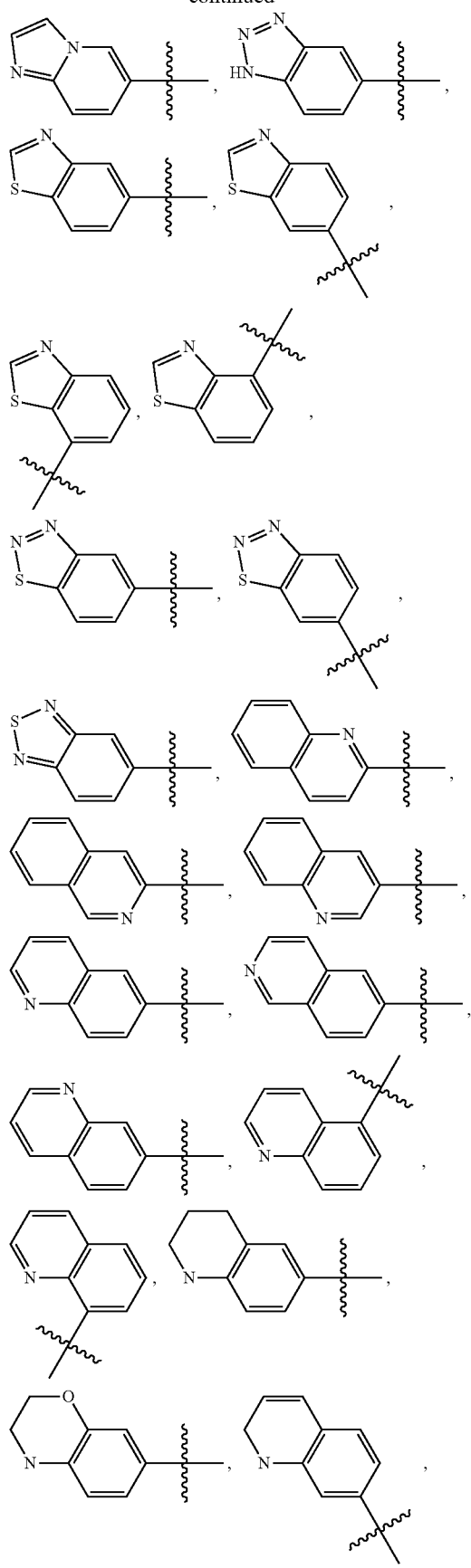
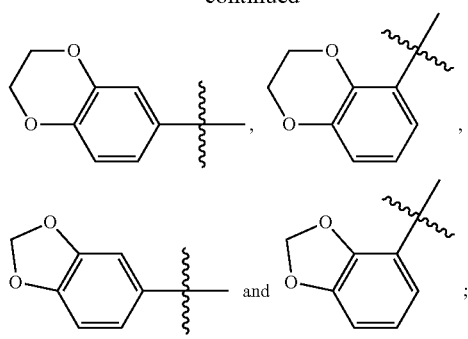

and the wavy line indicates the point of attachment to the rest of the molecule.

The present invention provides in another embodiment, a compound wherein $D^1$- is selected from the group consisting of:

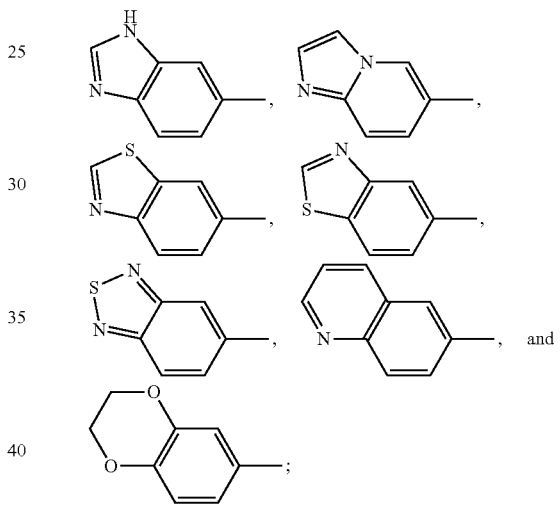

and the wavy line indicates the point of attachment to the rest of the molecule.

The present invention provides in another embodiment, a compound wherein $D^1$- is selected from the group consisting of:

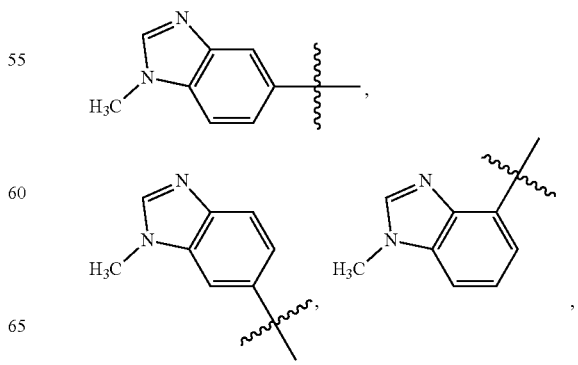

-continued

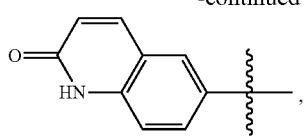

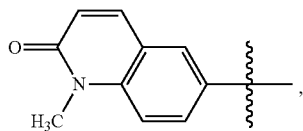

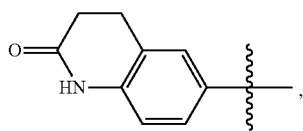

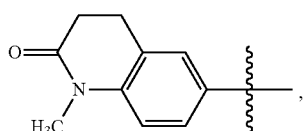

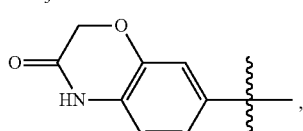

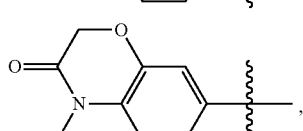

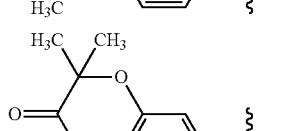

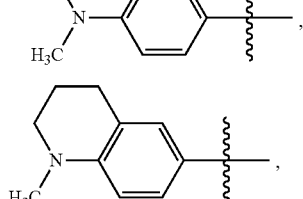

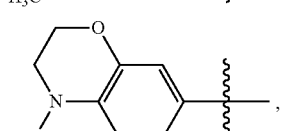

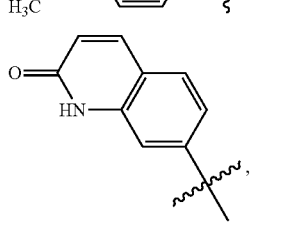

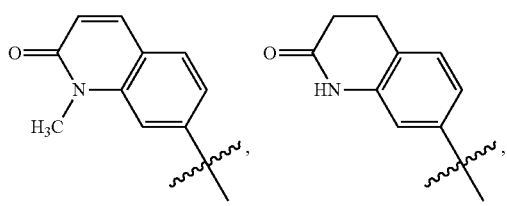

-continued

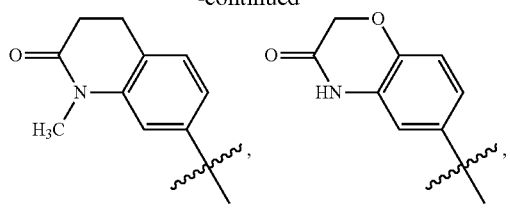

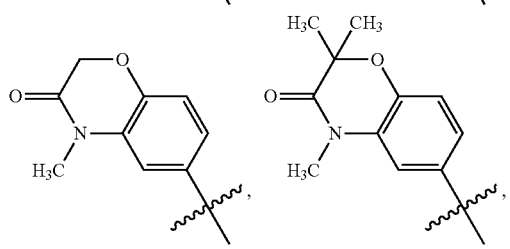

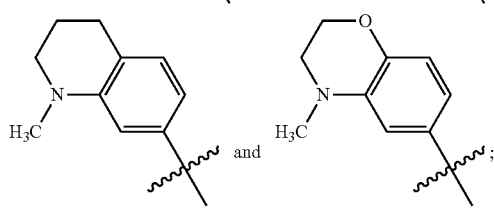

and the wavy line indicates the point of attachment to the rest of the molecule.

The present invention provides in another embodiment, a compound wherein, $D^1$ is heterocyclyl; optionally substituted with from 1 to 4 substituents independently selected from the group consisting of: $C_{1-8}$alkyl, $C_{1-8}$alkoxycarbonyl and oxo;

$R^1$ is selected from the group consisting of H, $C_{1-8}$ alkyl, amino, hydroxyl, $C_{1-8}$ alkoxy, $C_{1-8}$ haloalkyl, $C_{2-8}$ alkenyl, $C_{2-8}$ alkynyl, oxo, CN, $C_{1-8}$ alkoxycarbonyl, $C_{3-8}$ cycloalkyl, aryl and heterocyclyl; wherein heterocyclyl is optionally substituted with from 1 to 4 substituents selected from the group consisting of: alkyl, halo, $C_{1-8}$ alkylcarbonyl, aryl$C_{1-8}$ alkylenecarbonyl, aminocarbonyl and $C_{1-8}$ alkylsufonyl.

The present invention provides in another group of embodiments, a compound wherein $D^1$ is selected from the group consisting of:

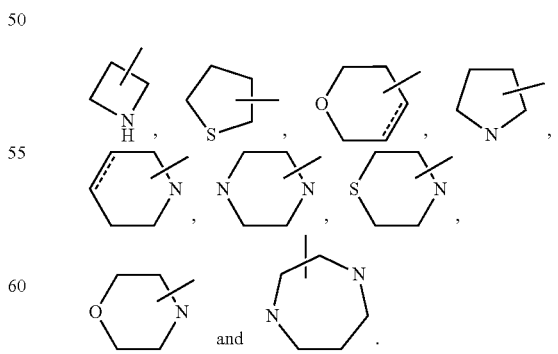

The present invention provides in another embodiment, a compound wherein $D^1$ is selected from the group consisting of

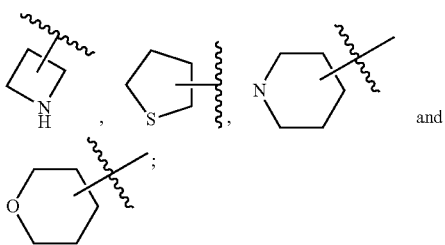

each of which is optionally substituted with from 1 to 3 substituents independently selected from the group consisting of: $C_{1-8}$alkyl, $C_{1-8}$alkoxycarbonyl and oxo; and the wavy line indicates the point of attachment to the rest of the molecule.

The present invention provides in another embodiment, a compound having the formula:

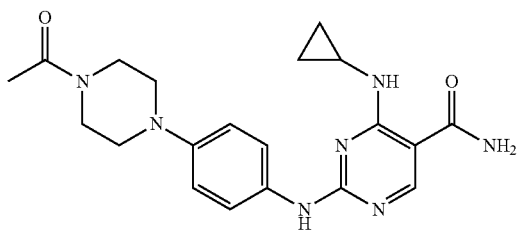 [SMILES: CC(=O)N1CCN(c2ccc(Nc3ncc(C(N)=O)c(NC4CC4)n3)cc2)CC1]

or a pharmaceutically acceptable salt thereof.

The present invention provides in another embodiment, a compound having the formula:

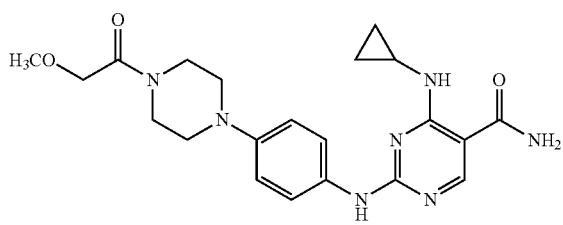 [SMILES: COCC(=O)N1CCN(c2ccc(Nc3ncc(C(N)=O)c(NC4CC4)n3)cc2)CC1]

or a pharmaceutically acceptable salt thereof.

The present invention provides one embodiment, a compound having the formula Ie:

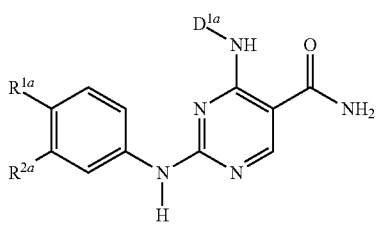

(Ie)

or a pharmaceutically acceptable salt thereof, wherein:

$D^{1a}$ is $C_{3-8}$cycloalkyl;

$R^{1a}$ is selected from the group consisting H, $C_{1-8}$alkyl, $C_{1-8}$alkylaminocarbonyl, $C_{1-8}$alkylcarbonylamino, aminocarbonyl, carbonylamino, $C_{3-8}$cycloalkylcarbonylamino, $C_{3-8}$cycloalkylaminocarbonyl, heteroaryl, heterocyclyl, hydroxy$C_{1-8}$alkyleneaminocarbonyl;

$R^{2a}$ is selected from the group consisting H, hydroxy, halo, $C_{1-8}$alkylsulfonyl and heteroaryl; or is combined with $R^{1a}$ and the atoms to which they are attached to form a heterocyclic moiety selected from the group consisting of *—NH—CH=CH— and *—N=CH—CH=N—, wherein * indicates the attachment of $R^2$; and at least one of $R^{1a}$ and $R^{2a}$ is not H;

each heteraryl or heterocyclyl is independently selected from the group consisting of:

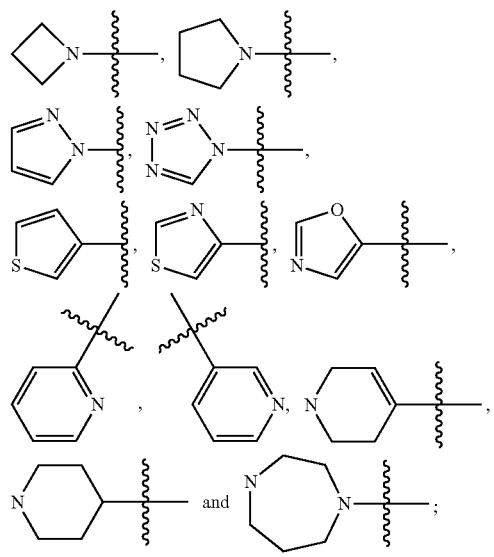

each of which is optionally substituted with from 1 to 2 substituents independently selected from the group consisting of $C_{1-8}$alkyl, hydroxy$C_{1-8}$alkylene, $C_{1-8}$alkoxy$C_{1-8}$alkylene, amino, aminocarbonyl, $C_{1-8}$alkylaminocarbonyl, $C_{1-8}$alkylcarbonyl, carboxy, hydroxy, halo and $C_{1-8}$alkylsulfonyl; and the wavy line indicates the point of attachment to the rest of the molecule.

The present invention provides in another embodiment, a compound having the formula If:

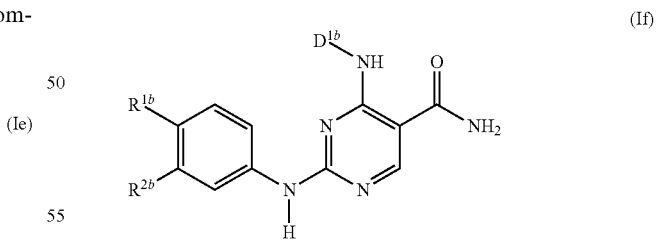

(If)

or a pharmaceutically acceptable salt thereof, wherein:

$D^{1b}$ is $C_{3-8}$cycloalkyl;

$R^{1b}$ is selected from the group consisting of heteroaryl, heterocyclyl, heterocyclylcarbonyl and heterocyclylsulfonyl;

$R^{2b}$ is selected from the group consisting of H or halo;

each heteraryl or heterocyclyl is independently selected from the group consisting of:

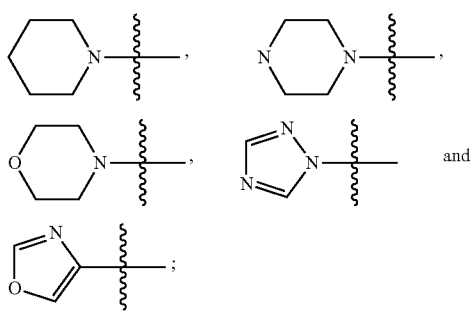

each of which is substituted with from 1 to 2 substituents independently selected from the group consisting of hydroxyl, hydroxyC$_{1-8}$alkylene, C$_{1-8}$alkoxyC$_{1-8}$alkylene, C$_{1-8}$alkylcarbonyl, C$_{1-8}$alkylaminocarbonyl, carboxy and C$_{1-8}$alkylsulfonylamino; and the wavy line indicates the point of attachment to the rest of the molecule.

The present invention provides in another embodiment, a compound having the formula Ig:

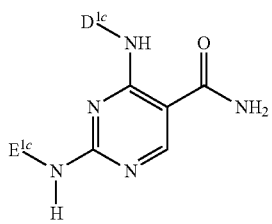

or a pharmaceutically acceptable salt thereof,
wherein:
D$^{1c}$ is C$_{3-8}$cycloalkyl; and
E$^{1c}$ is selected from the group consisting of:

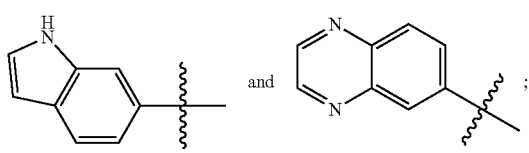 [SMILES: *c1ccc2cc[nH]c2c1 ; *c1ccc2nccnc2c1]

and the wavy line indicates the point of attachment to the rest of the molecule.

The present invention provides in another embodiment, a compound wherein R$^{1b}$ is heterocyclyl, substituted with from 1 to 2 substituents independently selected from the group consisting of aminocarbonyl and C$_{1-8}$alkylsulfonyl.

The present invention provides in another embodiment, a compound wherein D$^{1a}$, D$^{1b}$ or D$^{1c}$ is cyclopropyl or cyclobutyl. The present invention provides in another embodiment, a compound wherein D$^{1a}$, D$^{1b}$ or D$^{1c}$ is cyclopropyl. The present invention provides in another embodiment, a compound wherein D$^{1a}$, D$^{1b}$ or D$^{1c}$ is cyclobutyl.

The present invention provides in another embodiment, a compound having the formula:

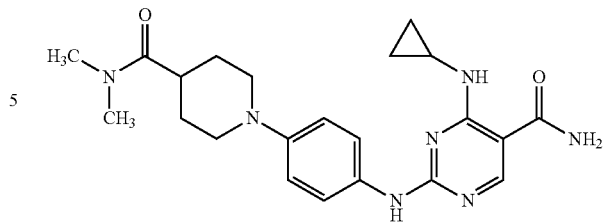

or a pharmaceutically acceptable salt thereof.

The present invention provides in one embodiment, a compound having the formula Ih:

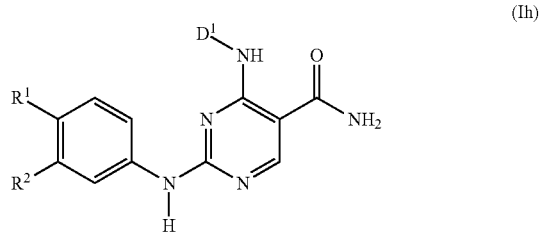

or a pharmaceutically acceptable salt thereof,
wherein:
D$^1$ is C$_{3-8}$cycloalkyl;
R$^1$ is selected from the group consisting H, amino, C$_{1-8}$alkoxycarbonylamino, C$_{1-8}$alkylcarbonylamino, C$_{1-8}$alkoxy, aminocarbonyl, heteroaryl, heterocyclyl, C$_{1-8}$alkylthio, C$_{1-8}$alkylsulfonyl and heterocyclylC$_{1-8}$alkylene; wherein each heteroaryl or heterocyclyl is independently selected from the group consisting of:

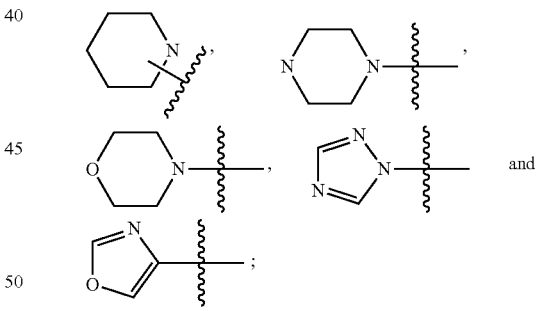

each of which is optionally substituted with from 1 to 2 substituents independently selected from the group consisting of C$_{1-8}$alkyl, —CONH$_2$, hydroxy, halo, C$_{1-8}$alkylsulfonyl and heteroaryl; and R$^2$ is selected from the group consisting H, C$_{1-8}$alkyl, halo, C$_{1-8}$alkoxy and heteroaryl; or is combined with R$^1$ and the atoms to which they are attached to form a heterocyclic moiety selected from the group consisting of —NH—N=CH—*, —CH=N—NH—*, —O—CH$_2$—CH$_2$—O—*; —NH—CH=CH—*, —N=CH—CH=CH—*, wherein * indicates the attachment of R$^2$ and the wavy line indicates the point of attachment to the rest of the molecule.

The present invention provides in another embodiment, a compound having the formula Ii:

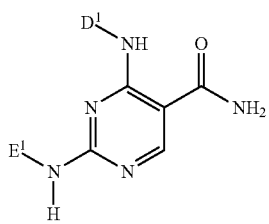 (Ii)

or a pharmaceutically acceptable salt thereof,
wherein:
$D^1$ is $C_{3-8}$cycloalkyl;
$E^1$ is selected from the group consisting of:

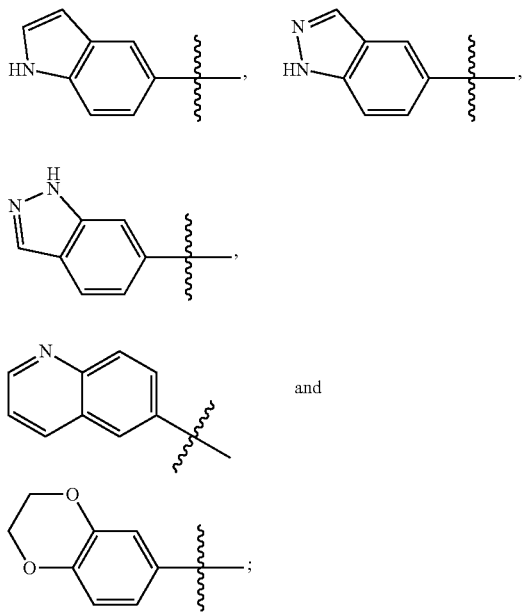

and

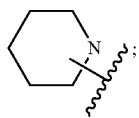

and the wavy line indicates the point of attachment to the rest of the molecule.

The present invention provides in another embodiment a compound wherein $R^1$ is optionally substituted with $CONH_2$ or $C_{1-8}$alkylsulfonyl; and the wavy line indicates the point of attachment to the rest of the molecule.

The present invention provides in another embodiment a compound wherein $R^1$ is $C_{1-8}$alkylsulfonyl.

The present invention provides in another embodiment a compound wherein $R^2$ is H.

The present invention provides in another embodiment a compound having the formula Ij:

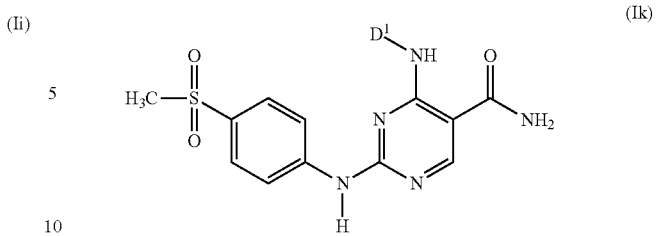 (Ik)

or a pharmaceutically acceptable salt thereof,
wherein: $D^1$ is $C_{3-8}$cycloalkyl.

The present invention provides in another embodiment a compound having the formula:

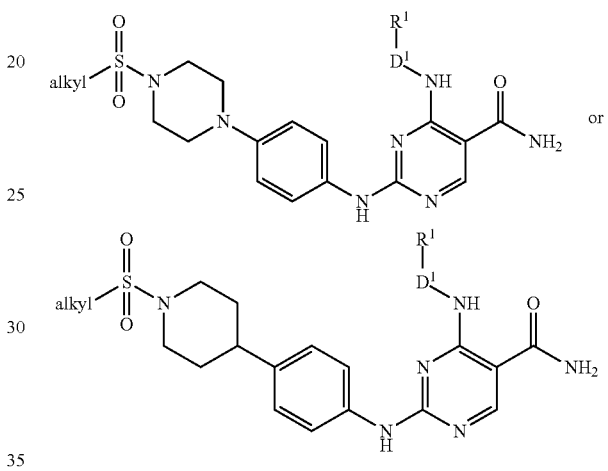

or a pharmaceutically acceptable salt thereof, wherein: $D^1$ is $C_{3-8}$cycloalkyl.

The present invention provides in another embodiment a compound having the formula:

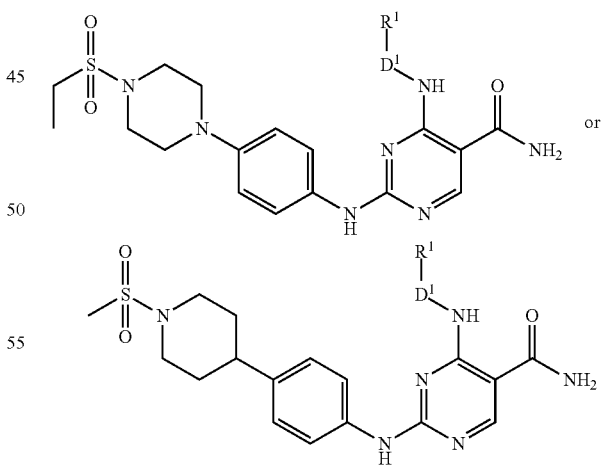

or a pharmaceutically acceptable salt thereof, wherein: $D^1$ is $C_{3-8}$cycloalkyl.

The present invention provides in another embodiment a compound wherein $D^1$ is cyclopropyl or cyclobutyl.

The present invention provides in another embodiment a compound wherein $D^1$ is cyclopropyl.

The present invention provides in another embodiment a compound wherein $D^1$ is cyclobutyl.

The present invention provides in another embodiment a compound selected from the group consisting of:

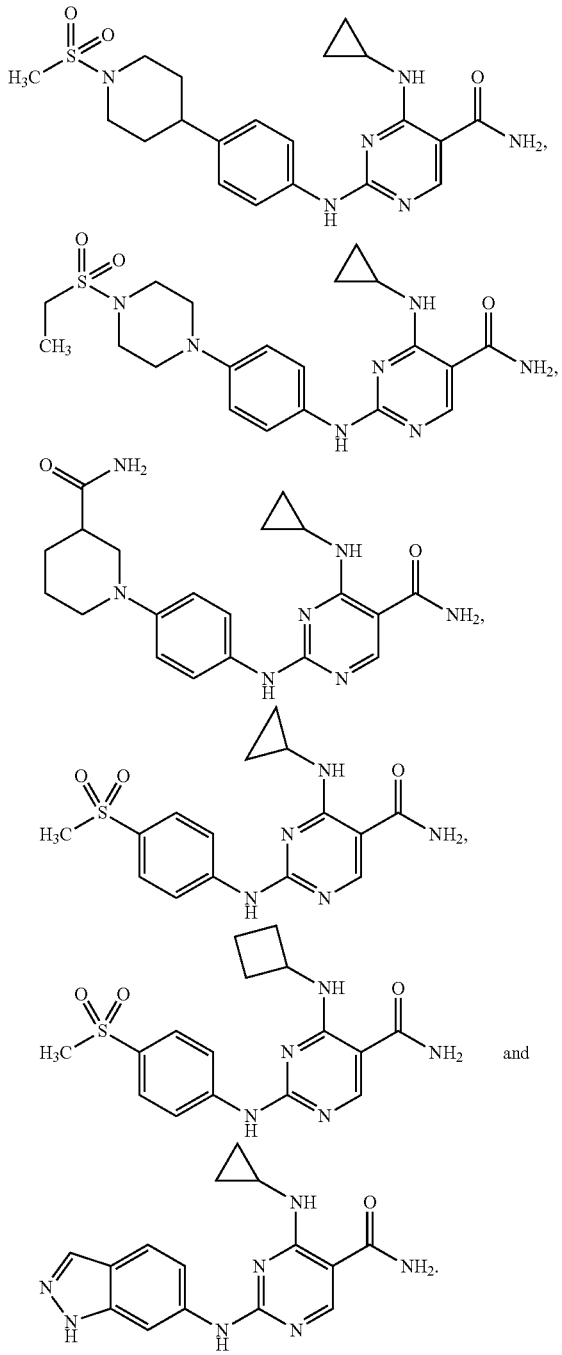

The present invention provides in another embodiment, a compound wherein the compound is found in the Examples.

The present invention provides in another embodiment, a compound having the structure found in the tables.

It is understood that in another group of embodiments, any of the above embodiments may also be combined with other embodiments listed herein, to form other embodiments of the invention.

b. Methods of Synthesis

The compounds of the present invention may be prepared by known organic synthesis techniques, including the methods described in more detail in the Examples. In general, the compounds of structure (I) above may be made by the following FIG. 3, wherein all substituents are as defined above unless indicated otherwise.

Figure 3:
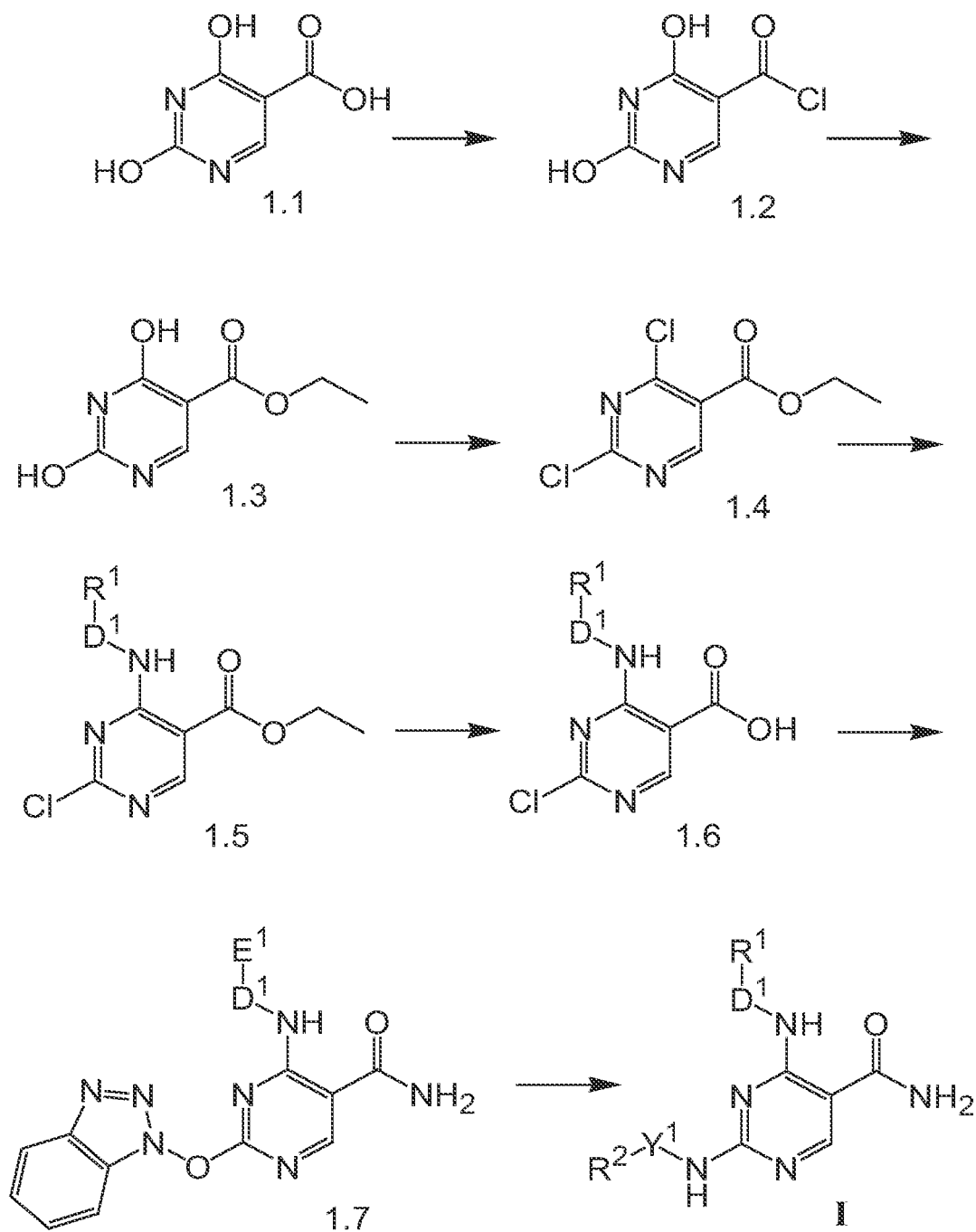
FIG. 3 shows a general synthesis of compounds of the present invention.
Figure 7U:
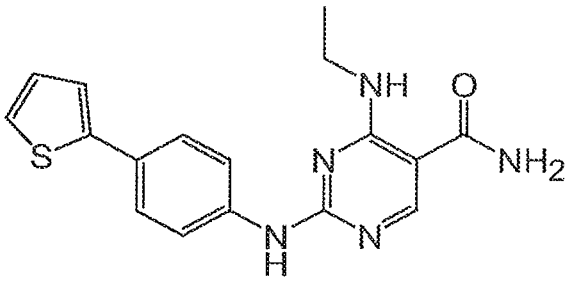
FIGS. 7A-7W provide tables 4A and 4B illustrating compounds of the present invention and syk $IC_{50}$s.

Compounds having formula I may be prepared according to FIG. 3. Carboxylic acid 1.1 is converted to acid chloride 1.2 via a one-step procedure by treatment with a chlorination agent, such as thionyl chloride, and esterification with an alcohol, such as ethanol, to form compound 1.3 using conditions similar to that described below. Ester 1.3 is dichlorinated with a chlorinating agent, such as phosphorous oxychloride. Selective displacement of the 4-chloro group of the 2,4-dichloropyrimidine by an appropriate amine, such as $R^1$-$D^1$-$NH_2$ (available commercially or synthesized using methods known to those skilled in the art), under basic conditions, such as with diisopropylamine (DIA), provides compounds of formula 1.5. Subsequent hydrolysis of the ester, displacement of the second chloro group with EDC and treatment with ammonia gives compound 1.7. Benzotriazolyl ether compound 1.7 may also be prepared through a linear route. Displacement of the benzotriazolyl ether group with an appropriate amine, such as $R^2$—$Y^1$—$NH_2$ (available commercially or synthesized using methods known to those skilled in the art), gives the desired product I, wherein $R^1$ and $R^2$ are as previously defined.

One skilled in the art will recognize that in certain embodiments of structure (I) when $R^1$-$D^1$ or $R^2$—$Y^1$ comprises a terminal heteroatom, it may be advantageous to use a protecting group strategy. The protecting group can be removed using methods known to those skilled in the art to yield compounds of structure (1).

The compounds of the present invention may generally be utilized as the free base. Alternatively, the compounds of this invention may be used in the form of acid addition salts as described below.

c. Inhibition of Syk and JAK Kinases

The activity of a specified compound as an inhibitor of a JAK kinase may be assessed in vitro or in vivo. In some embodiments, the activity of a specified compound can be tested in a cellular assay. Selectivity could also be ascertained in biochemical assays with isolated kinases.

Similar types of assays can be used to assess JAK kinase inhibitory activity and to determine the degree of selectivity of the particular compound as compared to syk kinase. One means of assaying for such inhibition is detection of the effect of the compounds of the present invention on the upregulation of downstream gene products. In the Ramos/IL4 assay, B-cells are stimulated with the cytokine Interleukin-4 (IL-4) leading to the activation of the JAK/Stat pathway through phosphorylation of the JAK family kinases, JAK1 and JAK3, which in turn phosphorylate and activate the transcription factor Stat-6. One of the genes upregulated by activated Stat-6 is the low affinity IgE receptor, CD23. To study the effect of inhibitors (e.g., the 2,4-substituted pyrimidinediamine compounds described herein) on the JAK1 and JAK3 kinases, human Ramos B-cells are stimulated with human IL-4. 10' post-stimulation, cells are subjected to intracellular flow cytometry to measure the extent of STAT-6 phosphorylation. 20 to 24 hours post-stimulation, cells are stained for upregulation of CD23 and analyzed using flow cytometry. A reduction of the amount of phosphorylated STAT-6 and/or cell surface CD23 present compared to control conditions indicates that the test compound actively inhibits the JAK kinase pathway.

Additionally, IL-6 stimulation of Ramos B-cells induces JAKs 1, 2, and Tyk2, leading to Stat-3 and Erk phosphorylation. 10' post-stimulation, cells are subjected to intracellular flow cytometry to measure the ability of compound to inhibit these phosphorylation events. To specifically measure the activity of JAK2, the CellSensor irf1-bla HEL cell line expressing the beta-lactamase reporter gene controlled by StatS will be used (Invitrogen, Carlsbad, Calif.). These cells express a constituitively active JAK2 mutant (JAK2V617F), found naturally in myeloproliferative neoplasms (Constantinescu, S., et. al, *Trends Biochem Sci.*, 2008; 33:122-31). A reduction in the amount of beta-lactamase reporter gene expression is used a measure of the JAK2 inhibitory activity of compounds.

The activity of the compounds of the invention may additionally be characterized by assaying the effect of the compounds of the present invention described herein on A549 lung epithelial cells and U937 cells. A549 lung epithelial cells and U937 cells up-regulate ICAM-1 (CD54) surface expression in response to a variety of different stimuli. Therefore, using ICAM-1 expression as readout, test compound effects on different signaling pathways can be assessed in the same cell type. Stimulation with IL-1β through the IL-1 β receptor activates the TRAF6/NFκB pathway resulting in up-regulation of ICAM-1. IFN.gamma. induces ICAM-1 up-regulation through activation of the JAK1/JAK2 pathway. The up-regulation of ICAM-1 can be quantified by flow cytometry across a compound dose curve and $EC_{50}$ values are calculated.

The activity of the compounds of the invention may additionally be characterized by assaying the effect of the compounds of the present invention described herein on A549 lung epithelial cells and U937 cells. A549 lung epithelial cells and U937 cells up-regulate ICAM-1 (CD54) surface expression in response to a variety of different stimuli. Therefore, using ICAM-1 expression as readout, test compound effects on different signaling pathways can be assessed in the same cell type. Stimulation with IL-1β through the IL-1 β receptor activates the TRAF6/NFκB pathway resulting in up-regulation of ICAM-1. IFN.gamma. induces ICAM-1 up-regulation through activation of the JAK1/JAK2 pathway. The up-regulation of ICAM-1 can be quantified by flow cytometry across a compound dose curve and $EC_{50}$ values are calculated. Exemplary assays of this type are described in greater detail in the Examples.

Active compounds as described herein generally inhibit the JAK kinase pathway with an $IC_{50}$ in the range of about 1 mM or less, as measured in the assays described herein. Of course, skilled artisans will appreciate that compounds which exhibit lower $IC_{50}$s, (on the order, for example, of 100 μM, 75 μM, 50 μM, 40 μM, 30 μM, 20 μM, 15 μM, 10 μM, 5 μM, 1 μM, 500 nM, 100 nM, 10 nM, 1 nM, or even lower) can be particularly useful in therapeutic applications. In instances where activity specific to a particular cell type is desired, the compound can be assayed for activity with the desired cell type and counter-screened for a lack of activity against other cell types. The desired degree of "inactivity" in such counter screens, or the desired ratio of activity vs. inactivity, may vary for different situations and can be selected by the user.

The active compounds also typically inhibit IL-4 stimulated expression of CD23 in B-cells with an $IC_{50}$ in the range of about 20 μM or less, typically in the range of about 10 μM, 1 μM, 500 nM, 100 nM, 10 nM, 1 nM, or even lower. A suitable assay that can be used is the assay described in the Examples, "Assay for Ramos B-cell Line Stimulated with IL-4." In certain embodiments, the active compounds of the present invention have an IC50 of less than or equal to 5 μM, greater than 5 μM but less than 20 μM, greater than 20 μM, or greater than 20 μM but less than 50 μM in the assay described in the Examples.

The active compounds also typically inhibit expression of ICAM1 (CD54) induced by IFN.gamma. exposure in U937 or A549 cells with an $IC_{50}$ in the range of about 20 μM or less, typically in the range of about 10 μM, 1 μM, 500 nM, 100 nM, 10 nM, 1 nM, or even lower. The $IC_{50}$ against expression of ICAM (CD54) in IFN.gamma. stimulated cells can be determined in a functional cellular assay with an isolated A549 or U937 cell line. Suitable assays that can be used are the assays described in the Examples, "A549 Epithelial Line Stimulated with IFNγ" and "U937 IFN.gamma. ICAM1 FACS Assay," respectively. In certain embodiments, the active compounds of the present invention have an $IC_{50}$ of less than or equal to 20 μM, greater than 20 μM, or greater than 20M but less than 50 μM in the assays described in the Examples.

d. Compositions and Methods of Administration

The present invention further provides compositions comprising one or more compounds of formula (I) or a pharmaceutically acceptable salt, ester or prodrug thereof, and a pharmaceutically acceptable carrier or diluent. It will be appreciated that the compounds of formula (I)) in this invention may be derivatized at functional groups to provide prodrug derivatives which are capable of conversion back to the parent compounds in vivo. Examples of such prodrugs include the physiologically acceptable and metabolically labile ester derivatives, such as methoxymethyl esters, methylthiomethyl esters, or pivaloyloxymethyl esters derived from a hydroxyl group of the compound or a carbamoyl moiety derived from an amino group of the compound. Additionally, any physiologically acceptable equivalents of the compounds of formula (I), similar to metabolically labile esters or carbamates, which are capable of producing the parent compounds of formula (I) in vivo, are within the scope of this invention.

As used herein, the term "pharmaceutically acceptable salts" refers to any acid or base addition salt whose counterions are non-toxic to the patient in pharmaceutical doses of the salts. A host of pharmaceutically acceptable salts are well known in the pharmaceutical field. If pharmaceutically acceptable salts of the compounds of this invention are utilized in these compositions, those salts are preferably derived from inorganic or organic acids and bases. Included among such acid salts are the following: acetate, adipate, alginate, aspartate, benzoate, benzene sulfonate, bisulfate, butyrate, citrate, camphorate, camphor sulfonate, cyclopentanepropionate, digluconate, dodecylsulfate, ethanesulfonate, fumarate, lucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, pamoate, pectinate, persulfate, 3-phenyl-propionate, picrate, pivalate, propionate, succinate, tartrate, thiocyanate, tosylate, undecanoate, hydrohalides (e.g., hydrochlorides and hydrobromides), sulphates, phosphates, nitrates, sulphamates, malonates, salicylates, methylene-bis-b-hydroxynaphthoates, gentisates, isethionates, di-p-toluoyltartrates, ethanesulphonates, cyclohexylsulphamates, quinates, and the like. Pharmaceutically acceptable base addition salts include, without limitation, those derived from alkali or alkaline earth metal bases or conventional organic bases, such as triethylamine, pyridine, piperidine, morpholine, N-methylmorpholine, ammonium salts, alkali metal salts, such as sodium and potassium salts, alkaline earth metal salts, such as calcium and magnesium salts, salts with organic bases, such as dicyclohexylamine salts, N-methyl-D-glucamine, and salts with amino acids such as arginine, lysine, and so forth.

Furthermore, the basic nitrogen-containing groups may be quatemized with agents like lower alkyl halides, such as methyl, ethyl, propyl and butyl chlorides, bromides and iodides; dialkyl sulfates, such as dimethyl, diethyl, dibutyl and diamyl sulfates, long chain halides, such as decyl, lauryl, myristyl and stearyl chlorides, bromides and iodides; aralkyl halides, such as benzyl and phenethyl bromides and others. Water or oil-soluble or dispersible products are thereby obtained.

The compounds utilized in the compositions and methods of this invention may also be modified by appending appropriate functionalities to enhance selective biological properties. Such modifications are known in the art and include those which increase biological penetration into a given biological system (e.g., blood, lymphatic system, central nervous system, etc.), increase oral availability, increase solubility to allow administration by injection, alter metabolism and alter rate of excretion.

The pharmaceutical compositions of the invention can be manufactured by methods well known in the art such as conventional granulating, mixing, dissolving, encapsulating, lyophilizing, or emulsifying processes, among others. Compositions may be produced in various forms, including granules, precipitates, or particulates, powders, including freeze dried, rotary dried or spray dried powders, amorphous powders, tablets, capsules, syrup, suppositories, injections, emulsions, elixirs, suspensions or solutions. Formulations may optionally contain stabilizers, pH modifiers, surfactants, bioavailability modifiers and combinations of these.

The term "unit dosage form" refers to physically discrete units suitable as unitary dosages for human subjects and other mammals, each unit containing a predetermined quantity of drug calculated to produce the desired onset, tolerability, and/or therapeutic effects, in association with a suitable pharmaceutical excipient (e.g., an ampoule). In addition, more concentrated compositions may be prepared, from which the more dilute unit dosage compositions may then be produced. The more concentrated compositions thus will contain substantially more than, e.g., at least 1, 2, 3, 4, 5, 6, 7, 8, 9, 10, or more times the amount of one or more syk and/or JAK inhibitors.

Methods for preparing such dosage forms are known to those skilled in the art (see, for example, REMINGTON'S PHARMACEUTICAL SCIENCES, 18TH ED., Mack Publishing Co., Easton, Pa. (1990)). In addition, pharmaceutically acceptable salts of the syk and/or JAK inhibitors of the present invention (e.g., acid addition salts) may be prepared and included in the compositions using standard procedures known to those skilled in the art of synthetic organic chemistry and described, e.g., by J. March, Advanced Organic Chemistry: Reactions, Mechanisms and Structure, 4$^{th}$ Ed. (New York: Wiley-Interscience, 1992).

The compositions typically include a conventional pharmaceutical carrier or excipient and may additionally include other medicinal agents, carriers, adjuvants, diluents, tissue permeation enhancers, solubilizers, and the like. Preferably, the composition will contain about 0.01% to about 90%, preferably about 0.1% to about 75%, more preferably about 0.1% to 50%, still more preferably about 0.1% to 10% by weight of one or more syk and/or JAK inhibitors, with the remainder consisting of suitable pharmaceutical carrier and/or excipients. Appropriate excipients can be tailored to the particular composition and route of administration by methods well known in the art, e.g., REMINGTON'S PHARMACEUTICAL SCIENCES, supra.

Pharmaceutically acceptable carriers that may be used in these compositions include ion exchangers, alumina, aluminum stearate, lecithin, serum proteins, such as human serum albumin, buffer substances, such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

Examples of suitable excipients include, but are not limited to, lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, saline, syrup, methylcellulose, ethylcellulose, hydroxypropylmethylcellulose, and polyacrylic acids such as Carbopols. The compositions can additionally include lubricating agents such as talc, magnesium stearate, and mineral oil; wetting agents; emulsifying agents; suspending agents; preserving agents such as methyl-, ethyl-, and propyl-hydroxy-benzoates; pH adjusting agents such as inorganic and organic acids and bases; sweetening agents; and flavoring agents.

Administration of a composition comprising one or more syk and/or JAK inhibitors with one or more suitable pharmaceutical excipients as advantageous can be carried out via any of the accepted modes of administration. Thus, administration can be, for example, oral, topical, intravenous, subcutaneous, transcutaneous, transdermal, intramuscular, intra-joint, parenteral, intra-arteriole, intradermal, intraventricular, intracranial, intraperitoneal, intralesional, intranasal, rectal, vaginal, by inhalation or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally or intravenously. The formulations of the invention may be designed as short-acting, fast-releasing, or long-acting. Still further, compounds can be administered in a local rather than systemic means, such as administration (e.g., injection) as a sustained release formulation. According to a representative embodiment, the compositions of this invention are formulated for pharmaceutical administration to a mammal, preferably a human being.

The compositions of the present invention containing one or more syk and/or JAK inhibitors can be administered repeatedly, e.g., at least 2, 3, 4, 5, 6, 7, 8, or more times, or the composition may be administered by continuous infusion. Suitable sites of administration include, but are not limited to, skin, bronchial, gastrointestinal, anal, vaginal, eye, and ear. The formulations may take the form of solid, semi-solid, lyophilized powder, or liquid dosage forms, such as, for example, tablets, pills, capsules, powders, solutions, suspensions, emulsions, suppositories, retention enemas, creams, ointments, lotions, gels, aerosols, or the like, preferably in unit dosage forms suitable for simple administration of precise dosages.

The pharmaceutical compositions of this invention may be in any orally acceptable dosage form, including tablets, capsules, cachets, emulsions, suspensions, solutions, syrups, elixirs, sprays, boluses, lozenges, powders, granules, and sustained-release formulations. Suitable excipients for oral administration include pharmaceutical grades of mannitol, lactose, starch, magnesium stearate, sodium saccharine, talcum, cellulose, glucose, gelatin, sucrose, magnesium carbonate, and the like. In the case of tablets for oral use, carriers that are commonly used include lactose and corn starch. Lubricating agents, such as magnesium stearate, are also typically added. For a capsule form, useful diluents include lactose and dried cornstarch. When aqueous suspensions are required for oral use, the active ingredient is combined with emulsifying and suspending agents. If desired, certain sweetening, flavoring or coloring agents may also be added.

In some embodiments, the compositions take the form of a pill, tablet, or capsule, and thus, the composition can contain, along with one or more syk and/or JAK inhibitors, a diluent such as lactose, sucrose, dicalcium phosphate, and the like; a disintegrant such as starch or derivatives thereof; a lubricant such as magnesium stearate and the like; and/or a binder such a starch, gum acacia, polyvinylpyrrolidone, gelatin, cellulose and derivatives thereof. A tablet can be made by any compression or molding process known to those of skill in the art. Compressed tablets may be prepared by compressing in a suitable machine the syk and/or JAK inhibitors in a free-flowing form, e.g., a powder or granules, optionally mixed with accessory ingredients, e.g., binders, lubricants, diluents, disintegrants, or dispersing agents. Molded tablets can be made by molding in a suitable machine a mixture of the powdered syk and/or JAK inhibitors with any suitable carrier.

Alternatively, the pharmaceutical compositions of this invention may be in the form of suppositories for rectal administration. These may be prepared by mixing the agent with a suitable non-irritating excipient which is solid at room temperature but liquid at rectal temperature and therefore will melt in the rectum to release the drug. Such materials include cocoa butter, beeswax, polyethylene glycol (PEG), hard fat, and/or hydrogenated cocoglyceride. Compositions suitable for rectal administration may also comprise a rectal enema unit containing one or more syk and/or JAK inhibitors and pharmaceutically-acceptable vehicles (e.g., 50% aqueous ethanol or an aqueous salt solution) that are physiologically compatible with the rectum and/or colon. The rectal enema unit contains an applicator tip protected by an inert cover, preferably comprised of polyethylene, lubricated with a lubricant such as white petrolatum, and preferably protected by a one-way valve to prevent back-flow of the dispensed formula. The rectal enema unit is also of sufficient length, preferably two inches, to be inserted into the colon via the anus.

Liquid compositions can be prepared by dissolving or dispersing one or more syk and/or JAK inhibitors and optionally one or more pharmaceutically acceptable adjuvants in a carrier such as, for example, aqueous saline, aqueous dextrose, glycerol, ethanol, and the like, to form a solution or suspension, e.g., for oral, topical, or intravenous administration. Pharmaceutical formulations may be prepared as liquid suspensions or solutions using a sterile liquid, such as oil, water, alcohol, and combinations thereof. Pharmaceutically suitable surfactants, suspending agents or emulsifying agents, may be added for oral or parenteral administration. Suspensions may include oils, such as peanut oil, sesame oil, cottonseed oil, corn oil and olive oil. Suspension preparation may also contain esters of fatty acids, such as ethyl oleate, isopropyl myristate, fatty acid glycerides and acetylated fatty acid glycerides. Suspension formulations may include alcohols, such as ethanol, isopropyl alcohol, hexadecyl alcohol, glycerol and propylene glycol. Ethers, such as poly(ethyleneglycol), petroleum hydrocarbons, such as mineral oil and petrolatum, and water may also be used in suspension formulations.

The pharmaceutical compositions of this invention may also be in a topical form, especially when the target of treatment includes areas or organs readily accessible by topical application, including diseases of the eye, the skin, or the lower intestinal tract. Suitable topical formulations are readily prepared for each of these areas or organs. For topical administration, the composition containing one or more syk and/or JAK inhibitors can be in the form of emulsions, lotions, gels, foams, creams, jellies, solutions, suspensions, ointments, and transdermal patches.

Topical application for the lower intestinal tract may be effected in a rectal suppository formulation (see above) or in a suitable enema formulation. Topically-transdermal patches may also be used. For topical applications, the pharmaceutical compositions may be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water. Alternatively, the pharmaceutical compositions may be formulated in a suitable lotion or cream containing the active components suspended or dissolved in one or more pharmaceutically acceptable carriers. Suitable carriers include mineral oil, sorbitan monostearate, polysorbate 60, cetyl esters, wax, cetyl alcohol, 2-octyldodecanol, benzyl alcohol and water.

The pharmaceutical compositions of this invention may also be administered by nasal aerosol or inhalation. For delivery by inhalation, the compositions can be delivered as a dry powder or in liquid form via a nebulizer. Such compositions are prepared according to techniques known in the art of pharmaceutical formulation and may be prepared as solutions in saline, employing benzyl alcohol or other suitable preservatives, absorption promoters to enhance bioavailability, fluorocarbons and/or other conventional solubilizing or dispersing agents.

For ophthalmic use, the pharmaceutical compositions may be formulated as micronized suspensions in isotonic, pH adjusted sterile saline, or, preferably, as solutions in isotonic, pH adjusted sterile saline, either with our without a preservative, such as benzylalkonium chloride. Alternatively, for ophthalmic uses, the pharmaceutical compositions may be formulated in an ointment, such as petrolatum.

For parenteral administration, the compositions can be in the form of sterile injectable solutions and sterile packaged powders. Preferably, injectable solutions are formulated at a pH of about 4.5 to about 7.5.

Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents which are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation. Compounds may be formulated for parenteral administration by injection such as by bolus injection or continuous infusion. A unit dosage form for injection may be in ampoules or in multi-dose containers.

The compositions of the present invention can also be provided in a lyophilized form. Such compositions may include a buffer, e.g., bicarbonate, for reconstitution prior to administration, or the buffer may be included in the lyophilized composition for reconstitution with, e.g., water. The lyophilized composition may further comprise a suitable vasoconstrictor, e.g., epinephrine. The lyophilized composition can be provided in a syringe, optionally packaged in combination with the buffer for reconstitution, such that the reconstituted composition can be immediately administered to a patient.

Any of the above dosage forms containing effective amounts are within the bounds of routine experimentation and within the scope of the invention. A therapeutically effective dose may vary depending upon the route of administration and dosage form. The representative compound or compounds of the invention is a formulation that exhibits a high therapeutic index. The therapeutic index is the dose ratio between toxic and therapeutic effects which can be expressed as the ratio between $LD_{50}$ and $ED_{50}$. The $LD_{50}$ is the dose lethal to 50% of the population and the $ED_{50}$ is the dose therapeutically effective in 50% of the population. The $LD_{50}$ and $ED_{50}$ are determined by standard pharmaceutical procedures in animal cell cultures or experimental animals.

Besides those representative dosage forms described above, pharmaceutically acceptable excipients and carriers and dosage forms are generally known to those skilled in the art and are included in the invention. It should be understood that a specific dosage and treatment regimen for any particular patient will depend upon a variety of factors, including the activity of the specific compound employed, the age, body weight, general health, sex and diet of the patient, and the time of administration, rate of excretion, drug combination, judgment of the treating physician and severity of the particular disease being treated. The amount of active ingredient(s) will also depend upon the particular compound and other therapeutic agent, if present, in the composition.

e. Methods of Use

The invention provides methods of inhibiting or decreasing syk and/or JAK activity as well as treating or ameliorating a syk and/or JAK associated state, symptom, condition, disorder or disease in a patient in need thereof (e.g., human or non-human). In one embodiment, the syk and/or JAK associated state, symptom, condition, disorder or disease is mediated, at least in part by syk and/or JAK kinase activity. In more specific embodiments, the present invention provides a method for treating a condition or disorder mediated at least in part by syk and/or JAK kinase activity is cardiovascular disease, inflammatory disease or autoimmune disease.

In one embodiment, the invention provides methods for preventing or treating a condition in a mammal characterized by undesired thrombosis comprising the step of administering to the mammal a therapeutically effective amount of a compound of the present invention. Such conditions include, but are not limited, to restenosis, acute coronary syndrome, myocardial infarction, unstable angina, refractory angina, occlusive coronary thrombosis occurring post-thrombolytic therapy or post-coronary angioplasty, a thrombotically mediated cerebrovascular syndrome, embolic stroke, thrombotic stroke, transient ischemic attacks, venous thrombosis, deep venous thrombosis, pulmonary embolism, coagulopathy, disseminated intravascular coagulation, thrombotic thrombocytopenic purpura, thromboangiitis obliterans, thrombotic disease associated with heparin-induced thrombocytopenia, thrombotic complications associated with extracorporeal circulation, thrombotic complications associated with instrumentation such as cardiac or other intravascular catheterization, intra-aortic balloon pump, coronary stent or cardiac valve, conditions requiring the fitting of prosthetic devices, and the like.

In a further embodiment, the present invention provides a method for treating thrombosis, immune thrombocytic purura, heparin induced thrombocytopenia, dilated cardiomypathy, sickle cell disease, atherosclerosis, myocardial infarction, vacular inflammation, unstable angina or acute coronary syndromes.

In another embodiment, the present invention also provides a method for treating allergy, asthma, rheumatoid arthritis, B Cell mediated disease such as Non-Hodgkin's Lymphoma, anti phospholipids syndrome, lupus, psoriasis, multiple sclerosis, end stage renal disease or chronic lymphocytic leukemia.

In another embodiment, the present invention provides a method for treating hemolytic anemia or immune thrombocytopenic purpura.

The compounds described herein are also potent and/or selective inhibitors of JAK kinases. As a consequence of this activity, the compounds can be used in a variety of in vitro, in vivo, and ex vivo contexts to regulate or inhibit JAK kinase activity, signaling cascades in which JAK kinases play a role, and the biological responses effected by such signaling cascades. For example, in one embodiment, the compounds can be used to inhibit JAK kinase, either in vitro or in vivo, in virtually any cell type expressing the JAK kinase, such as in hematopoietic cells in which, for example, JAK3 is predominantly expressed. They may also be used to regulate signal transduction cascades in which JAK kinases, particularly JAK3, play a role. Such JAK-dependent signal transduction cascades include, but are not limited to, the signaling cascades of cytokine receptors that involve the common gamma chain, such as, for example, the IL-4, IL-7, IL-5, IL-9, IL-15 and IL-21, or IL-2, IL-4, IL-7, IL-9, IL-15, and IL-21 receptor signaling cascades. The compounds may also be used in vitro or in vivo to regulate, and in particular to inhibit, cellular or biological responses affected by such JAK-dependent signal transduction cascades. Such cellular or biological responses include, but are not limited to, IL-4/ramos CD23 upregulation and IL-2 mediated T-cell proliferation. Importantly, the compounds can be used to inhibit JAK kinases in vivo as a therapeutic approach towards the treatment or prevention of diseases mediated, either wholly or in part, by a JAK kinase activity (referred to herein as "JAK kinase mediated diseases"). Non-limiting examples of JAK kinase mediated diseases that can be treated or prevented with the compounds include, but are not limited to, the following: allergies; asthma; autoimmune diseases such as transplant rejection (e.g., kidney, heart, lung, liver, pancreas, skin, small intestine, large intestine, host versus graft reaction (HVGR), and graft versus host reaction (GVHR)), rheumatoid arthritis, and amyotrophic lateral sclerosis; T-cell mediated autoimmune diseases such as multiple sclerosis, psoraiasis, and Sjogren's syndrome; Type II inflammatory diseases such as vascular inflammation (including vasculitis, arteritis, atherosclerosis, and coronary artery disease); diseases of the central nervous system such as stroke; pulmonary diseases such as bronchitis obliteraus and primary pulmonary hypertension; solid, delayed Type IV hypersensitivity reactions; and hematologic malignancies such as leukemia and lymphomas.

Examples of diseases that are mediated, at least in part, by JAK kinases that can be treated or prevented according to the methods include, but are not limited to, allergies, asthma, autoimmune diseases such as transplant rejection (e.g., kidney, heart, lung, liver, pancreas, skin, host versus graft reaction (HVGR), etc.), rheumatoid arthritis, and amyotrophic lateral sclerosis, multiple sclerosis, psoraiasis and Sjogren's syndrome, Type II inflammatory disease such as vascular inflammation (including vasculitis, ateritis, atherosclerosis and coronary artery disease) or other inflammatory diseases such as osteoarthritis, inflammatory bowel disease, ulcerative colitis, Crohn's disease, idiopathic inflammatory bowel disease, irritable bowel syndrome, spastic colon, low grade scarring (e.g., scleroderma, increased fibrosis, keloids, post-surgical scars, pulmonary fibrosis, vascular spasms, migraine, reperfusion injury and post myocardial infarction), and sicca complex or syndrome, diseases of the central nervous system such as stroke, pulmonary diseases such as bronchitis obliterous and primary and primary pulmonary hypertension, delayed or cell-mediated, Type IV hypersensitivity and solid and hematologic malignancies such as leukemias and lyphomas.

In another embodiment, this invention provides a method of inhibiting an activity of a JAK kinase, comprising contacting the JAK kinase with an amount of a compound effective to inhibit an activity of the JAK kinase, wherein the compound is selected from the compounds of this invention. In certain embodiments of the methods described herein, the method is carried out in vivo.

In another embodiment, this invention provides a method of inhibiting an activity of a JAK kinase, comprising contacting in vitro a JAK3 kinase with an amount of a compound effective to inhibit an activity of the JAK kinase, wherein the compound is selected from the compounds of this invention.

In a specific embodiment, the compounds can be used to treat and/or prevent rejection in organ and/or tissue transplant recipients (i.e., treat and/or prevent allorgraft rejection). Allografts can be rejected through either a cell-mediated or humoral immune reaction of the recipient against transplant (histocompatibility) antigens present on the membranes of the donor's cells. The strongest antigens are governed by a complex of genetic loci termed human leukocyte group A (HLA) antigens. Together with the ABO blood groups antigens, they are the chief transplantation antigens detectable in humans.

Rejection following transplantation can generally be broken into three categories: hyperacute, occurring hours to days following transplantation; acute, occurring days to months following transplantation; and chronic, occurring months to years following transplantation.

Hyperacute rejection is caused mainly by the production of host antibodies that attack the graft tissue. In a hyperacute rejection reaction, antibodies are observed in the transplant vascular very soon after transplantation. Shortly thereafter, vascular clotting occurs, leading to ischemia, eventual necrosis and death. The graft infarction is unresponsive to known immunosuppressive therapies. Because HLA antigens can be identified in vitro, pre-transplant screening is used to significantly reduce hyperacute rejection. As a consequence of this screening, hyperacute rejection is relatively uncommon today.

Acute rejection is thought to be mediated by the accumulation of antigen specific cells in the graft tissue. The T-cell-mediated immune reaction against these antigens (i.e., HVGR or GVHR) is the principle mechanism of acute rejection. Accumulation of these cells leads to damage of the graft tissue. It is believed that both CD4+ helper T-cells and CD8+ cytotoxic T-cells are involved in the process and that the antigen is presented by donor and host dendritic cells. The CD4+ helper T-cells help recruit other effector cells, such as macrophages and eosinophils, to the graft. Accessing T-cell activation signal transduction cascades (for example, CD28, CD40L, and CD2 cascades) are also involved.

The cell-mediated acute rejection can be reversed in many cases by intensifying immunotherapy. After successful reversal, severely damaged elements of the graft heal by fibrosis and the remainder of the graft appears normal. After resolution of acute rejection, dosages of immunosuppressive drugs can be reduced to very low levels.

Chronic rejection, which is a particular problem in renal transplants, often progresses insidiously despite increased immunosuppressive therapy. It is thought to be due, in large part, to cell-mediated Type IV hypersensitivity. The pathologic profile differs from that of acute rejection. The arterial endothelium is primarily involved with extensive proliferation that may gradually occlude the vessel lumen, leading to ischemia, fibrosis, a thickened intima, and atherosclerotic changes. Chronic rejection is mainly due to a progressive obliteration of graft vasculature and resembles a slow, vasculitic process.

In Type IV hypersensitivity, CD8 cytotoxic T-cells and CD4 helper T cells recognize either intracellular or extracellular synthesized antigen when it is complexed, respectively, with either Class I or Class II MHC molecules. Macrophages function as antigen-presenting cells and release IL-1, which promotes proliferation of helper T-cells. Helper T-cells release interferon gamma and IL-2, which together regulate delayed hyperactivity reactions mediated by macrophage activation and immunity mediated by T cells. In the case of organ transplant, the cytotoxic T-cells destroy the graft cells on contact.

Since JAK kinases play a critical role in the activation of T-cells, the compounds described herein can be used to treat and/or prevent many aspects of transplant rejection, and are particularly useful in the treatment and/or prevention of rejection reactions that are mediated, at least in part, by T-cells, such as HVGR or GVHR. The compounds can also be used to treat and/or prevent chronic rejection in transplant recipients and, in particular, in renal transplant recipients. The compound can also be administered to a tissue or an organ prior to transplanting the tissue or organ in the transplant recipient.

In another embodiment, this invention provides a method of treating a T-cell mediated autoimmune disease, comprising administering to a patient suffering from such an autoimmune disease an amount of a compound effective to treat the autoimmune disease wherein the compound is selected from the compounds of the invention. In certain embodiments of the methods the autoimmune disease is multiple sclerosis (MS), psoriasis, or Sjogran's syndrome. Such autoimmune disease include, but are not limited to, those autoimmune diseases that are frequently designated as single organ or single cell-type autoimmune disorders and those autoimmune disease that are frequently designated as involving systemic autoimmune disorder. Non-limiting examples of diseases frequently designated as single organ or single cell-type autoimmune disorders include: Hashimoto's thyroiditis, autoimmune hemolytic anemia, autoimmune atrophic gastritis of pernicious anemia, autoimmune encephalomyelitis, autoimmune orchitis, Goodpasture's disease, autoimmune thrombocytopenia, sympathetic ophthalmia, myasthenia gravis, Graves' disease, primary biliary cirrhosis, chronic aggressive hepatitis, ulcerative colitis and membranous glomerulopathy. Non-limiting examples of diseases often designated as involving systemic autoimmune disorder include: systemic lupus erythematosis, rheumatoid arthritis, Sjogren's syndrome, Reiter's syndrome, polymyositis-dermatomyositis, systemic sclerosis, polyarteritis nodosa, multiple sclerosis and bullous pemphigoid. Additional autoimmune diseases, which can be .beta.-cell (humoral) based or T-cell based, include Cogan's syndrome, ankylosing spondylitis, Wegener's granulomatosis, autoimmune alopecia, Type I or juvenile onset diabetes, and thyroiditis.

The types of autoimmune diseases that may be treated or prevented with such prodrugs generally include those disorders involving tissue injury that occurs as a result of a humoral and/or cell-mediated response to immunogens or antigens of endogenous and/or exogenous origin. Such diseases are frequently referred to as diseases involving the nonanaphylactic (i.e., Type II, Type III and/or Type IV) hypersensitivity reactions.

Type I hypersensitivity reactions generally result from the release of pharmacologically active substances, such as histamine, from mast and/or basophil cells following contact with a specific exogenous antigen. As mentioned above, such Type I reactions play a role in numerous diseases, including allergic asthma, allergic rhinitis, etc.

Type II hypersensitivity reactions (also referred to as cytotoxic, cytolytic complement-dependent or cell-stimulating hypersensitivity reactions) result when immunoglobulins react with antigenic components of cells or tissue, or with an antigen or hapten that has become intimately coupled to cells or tissue. Diseases that are commonly associated with Type II hypersensitivity reactions include, but are not limited, to autoimmune hemolytic anemia, erythroblastosis fetalis and Goodpasture's disease.

Type III hypersensitivity reactions, (also referred to as toxic complex, soluble complex, or immune complex hypersensitivity reactions) result from the deposition of soluble circulating antigen-immunoglobulin complexes in vessels or in tissues, with accompanying acute inflammatory reactions at the site of immune complex deposition. Non-limiting examples of prototypical Type III reaction diseases include the Arthus reaction, rheumatoid arthritis, serum sickness, systemic lupus erythematosis, certain types of glomerulonephritis, multiple sclerosis and bullous pemphingoid.

Type IV hypersensitivity reactions (frequently called cellular, cell-mediated, delayed, or tuberculin-type hypersensitivity reactions) are caused by sensitized T-lymphocytes which result from contact with a specific antigen. Non-limiting examples of diseases cited as involving Type IV reactions are contact dermatitis and allograft rejection.

Autoimmune diseases associated with any of the above nonanaphylactic hypersensitivity reactions may be treated or prevented with the prodrugs according to structural formulae (I) and (Ia). In particular, the methods may be used to treat or prevent those autoimmune diseases frequently characterized as single organ or single cell-type autoimmune disorders including, but not limited to: Hashimoto's thyroiditis, autoimmune hemolytic anemia, autoimmune atrophic gastritis of pernicious anemia, autoimmune encephalomyelitis, autoimmune orchitis, Goodpasture's disease, autoimmune thrombocytopenia, sympathetic ophthalmia, myasthenia gravis, Graves' disease, primary biliary cirrhosis, chronic aggressive hepatitis, ulcerative colitis and membranous glomerulopathy, as well as those autoimmune diseases frequently characterized as involving systemic autoimmune disorder, which include but are not limited to: systemic lupus erythematosis (SLE), rheumatoid arthritis, Sjogren's syndrome, Reiter's syndrome, polymyositis-dermatomyositis, systemic sclerosis, polyarteritis nodosa, multiple sclerosis and bullous pemphigoid.

It will be appreciated by skilled artisans that many of the above-listed autoimmune diseases are associated with severe symptoms, the amelioration of which provides significant therapeutic benefit even in instances where the underlying autoimmune disease may not be ameliorated.

Therapy using the compounds described herein can be applied alone, or it can be applied in combination with or adjunctive to other common immunosuppressive therapies, such as, for example, the following: mercaptopurine; corticosteroids such as prednisone; methylprednisolone and prednisolone; alkylating agents such as cyclophosphamide; calcineurin inhibitors such as cyclosporine, sirolimus, and tacrolimus; inhibitors of inosine monophosphate dehydrogenase (IMPDH) such as mycophenolate, mycophenolate mofetil, and azathioprine; and agents designed to suppress cellular immunity while leaving the recipient's humoral immunologic response intact, including various antibodies (for example, antilymphocyte globulin (ALG), antithymocyte globulin (ATG), monoclonal anti-T-cell antibodies (OKT3)) and irradiation. These various agents can be used in accordance with their standard or common dosages, as specified in the prescribing information accompanying commercially available forms of the drugs (see also: the prescribing information in the 2006 Edition of The Physician's Desk Reference), the disclosures of which are incorporated herein by reference. Azathioprine is currently available from Salix Pharmaceuticals, Inc., under the brand name AZASAN; mercaptopurine is currently available from Gate Pharmaceuticals, Inc., under the brand name PURINETHOL; prednisone and prednisolone are currently available from Roxane Laboratories, Inc.; Methyl prednisolone is currently available from Pfizer; sirolimus (rapamycin) is currently available from Wyeth-Ayerst under the brand name RAPAMUNE; tacrolimus is currently available from Fujisawa under the brand name PROGRAF; cyclosporine is current available from Novartis under the brand dame SANDIMMUNE and from Abbott under the brand name GENGRAF; IMPDH inhibitors such as mycophenolate mofetil and mycophenolic acid are currently available from Roche under the brand name CELLCEPT and from Novartis under the brand name MYFORTIC; azathioprine is currently available from Glaxo Smith Kline under the brand name IMURAN; and antibodies are currently available from Ortho Biotech under the brand name ORTHOCLONE, from Novartis under the brand name SIMULECT (basiliximab), and from Roche under the brand name ZENAPAX (daclizumab).

In another embodiment, the compounds could be administered either in combination or adjunctively with an inhibitor of a syk kinase. syk kinase is a tyrosine kinase known to play a critical role in Fcγ receptor signaling, as well as in other signaling cascades, such as those involving B-cell receptor signaling (Turner et al., (2000), Immunology Today 21:148-154) and integrins beta (1), beta (2), and beta (3) in neutrophils (Mocsai et al., (2002), Immunity 16:547-558). For example, syk kinase plays a pivotal role in high affinity IgE receptor signaling in mast cells that leads to activation and subsequent release of multiple chemical mediators that trigger allergic attacks. However, unlike the JAK kinases, which help regulate the pathways involved in delayed or cell-mediated Type IV hypersensitivity reactions, syk kinase helps regulate the pathways involved in immediate IgE-mediated, Type I hypersensitivity reactions. Certain compounds that affect the syk pathway may or may not also affect the JAK pathways.

Suitable syk inhibitory compounds are described, for example, in Ser. No. 10/355,543 filed Jan. 31, 2003 (publication no. 2004/0029902); WO 03/063794; Ser. No. 10/631,029 filed Jul. 29, 2003; WO 2004/014382; Ser. No. 10/903,263 filed Jul. 30, 2004; PCT/US2004/24716 filed Jul. 30, 2004 (WO005/016893); Ser. No. 10/903,870 filed Jul. 30, 2004; PCT/US2004/24920 filed Jul. 30, 2004; Ser. No. 60/630,808 filed Nov. 24, 2004; Ser. No. 60/645,424 filed Jan. 19, 2005; and Ser. No. 60/654,620, filed Feb. 18, 2005, the disclosures of which are incorporated herein by reference. The described herein and syk inhibitory compounds could be used alone or in combination with one or more conventional transplant rejection treatments, as described above.

In a specific embodiment, the compounds can be used to treat or prevent these diseases in patients that are either initially non-responsive (resistant) to or that become non-responsive to treatment with a syk inhibitory compound or one of the other current treatments for the particular disease. The compounds could also be used in combination with syk inhibitory compounds in patients that are syk-compound resistant or non-responsive. Suitable syk-inhibitory compounds with which the compounds can be administered are provided infra.

In another embodiment, this invention provides a method of treating a T-cell mediated autoimmune disease, comprising administering to a patient suffering from such an autoimmune disease an amount of a compound effective to treat the autoimmune disease wherein the compound is selected from the compounds of the invention, as described herein, and the compound is administered in combination with or adjunctively to a compound that inhibits syk kinase with an $IC_{50}$ in the range of at least 10 μM.

In another embodiment, this invention provides a method of treating or preventing allograft transplant rejection in a transplant recipient, comprising administering to the transplant recipient an amount of a compound effective to treat or prevent the rejection wherein the compound is selected from the compounds of the invention, as described herein. In a further embodiment, the compound is administered to a tissue or an organ prior to transplanting the tissue or organ in the transplant recipient.

In another embodiment, this invention provides a method of treating or preventing allograft transplant rejection in a transplant recipient, in which the rejection is acute rejection, comprising administering to the transplant recipient an amount of a compound effective to treat or prevent the rejection, wherein the compound is selected from the compounds of the invention.

In another embodiment, this invention provides a method of treating or preventing allograft transplant rejection in a transplant recipient, in which the rejection is chronic rejection, comprising administering to the transplant recipient an amount of a compound effective to treat or prevent the rejection, wherein the compound is selected from the compounds of the invention.

In another embodiment, this invention provides a method of treating or preventing allograft transplant rejection in a transplant recipient, in which the rejection is mediated by HVGR or GVHR, comprising administering to the transplant recipient an amount of a compound effective to treat or prevent the rejection, wherein the compound is selected from the compounds of this invention, as described herein.

In another embodiment, this invention provides a method of treating or preventing allograft transplant rejection in a transplant recipient, in which the allograft transplant is selected from a kidney, a heart, a liver, and a lung, comprising administering to the transplant recipient an amount of a compound effective to treat or prevent the rejection, wherein the compound is selected from the compounds of this invention, as described herein.

In another embodiment, this invention provides a method of treating or preventing allograft transplant rejection in a transplant recipient, in which the allograft transplant is selected from a kidney, a heart, a liver, and a lung, comprising administering to the transplant recipient an amount of a compound effective to treat or prevent the rejection wherein the compound is selected from the compounds of the invention, as described herein, in which the compound is administered in combination with or adjunctively to another immunosuppressant.

In another embodiment, this invention provides a method of treating or preventing allograft transplant rejection in a transplant recipient, in which the allograft transplant is selected from a kidney, a heart, a liver, and a lung, comprising administering to the transplant recipient an amount of a compound effective to treat or prevent the rejection, wherein the compound is selected from the compounds of the invention, as described herein, in which the compound is administered in combination with or adjunctively to another immunosuppressant, in which the immunosuppressant is selected from cyclosporine, tacrolimus, sirolimus, an inhibitor of IMPDH, mycophenolate, mycophanolate mofetil, an anti-T-Cell antibody, and OKT3.

The compounds described herein are cytokine moderators of IL-4 signaling. As a consequence, the compounds could slow the response of Type I hypersensitivity reactions. Thus, in a specific embodiment, the compounds could be used to treat such reactions and, therefore, the diseases associated with, mediated by, or caused by such hypersensitivity reactions (for example, allergies), prophylactically. For example, an allergy sufferer could take one or more of the JAK selective compounds described herein prior to expected exposure to allergens to delay the onset or progress of, or eliminate altogether, an allergic response.

When used to treat or prevent such diseases, the compounds can be administered singly, as mixtures of one or more compounds, or in mixture or combination with other agents useful for treating such diseases and/or the symptoms associated with such diseases. The compounds may also be administered in mixture or in combination with agents useful to treat other disorders or maladies, such as steroids, membrane stabilizers, 5-lipoxygenase (5LO) inhibitors, leukotriene synthesis and receptor inhibitors, inhibitors of IgE isotype switching or IgE synthesis, IgG isotype switching or IgG synthesis, beta.-agonists, tryptase inhibitors, aspirin, cyclooxygenase (COX) inhibitors, methotrexate, anti-TNF drugs, anti CD20 antibody, PD4 inhibitors, p38 inhibitors, PDE4 inhibitors, and antihistamines, to name a few. The compounds can be administered per se in the form of prodrugs or as pharmaceutical compositions, comprising an active compound or prodrug.

In another embodiment, this invention provides a method of treating or preventing a Type IV hypersensitivity reaction, comprising administering to a subject an amount of a compound effective to treat or prevent the hypersensitivity reaction, wherein the compound is selected from the compounds of this invention, as described herein.

In another embodiment, this invention provides a method of treating or preventing a Type IV hypersensitivity reaction, which is practical prophylactically, comprising administering to a subject an amount of a compound effective to treat or prevent the hypersensitivity reaction, wherein the compound is selected from the compounds of this invention, as described herein, and is administered prior to exposure to an allergen.

In another embodiment, this invention provides a method of inhibiting a signal transduction cascade in which JAK3 kinase plays a role, comprising contacting a cell expressing a receptor involved in such a signaling cascade with a compound wherein the compound is selected from the compounds of this invention, as described herein.

In another embodiment, this invention provides a method of treating or preventing a JAK kinase-mediated disease, comprising administering to a subject an amount of compound effective to treat or prevent the JAK kinase-mediated disease, wherein the compound is selected from the compounds of this invention, as described herein.

In another embodiment, this invention provides a method of treating or preventing a JAK kinase-mediated disease, in which the JAK-mediated disease is HVGR or GVHR, comprising administering to a subject an amount of compound effective to treat or prevent the JAK kinase-mediated disease, wherein the compound is selected from the compounds of the invention, as described herein.

In another embodiment, this invention provides a method of treating or preventing a JAK kinase-mediated disease, in which the JAK-mediated disease is acute allograft rejection, comprising administering to a subject an amount of compound effective to treat or prevent the JAK kinase-mediated disease, wherein the compound is selected from the compounds of the invention, as described herein.

In another embodiment, this invention provides a method of treating or preventing a syk and/or JAK kinase-mediated disease, in which the JAK-mediated disease is chronic allograft rejection, comprising administering to a subject an amount of compound effective to treat or prevent the JAK kinase-mediated disease, wherein the compound is selected from the compounds of the invention, as described herein.

Active compounds of the invention typically inhibit the syk and/or JAK/Stat pathway. The activity of a specified compound as an inhibitor of a syk and/or JAK kinase can be assessed in vitro or in vivo. In some embodiments, the activity of a specified compound can be tested in a cellular assay.

"Cell proliferative disorder" refers to a disorder characterized by abnormal proliferation of cells. A proliferative disorder does not imply any limitation with respect to the rate of cell growth, but merely indicates loss of normal controls that affect growth and cell division. Thus, in some embodiments, cells of a proliferative disorder can have the same cell division rates as normal cells but do not respond to signals that limit such growth. Within the ambit of "cell proliferative disorder" is neoplasm or tumor, which is an abnormal growth of tissue. Cancer refers to any of various malignant neoplasms characterized by the proliferation of cells that have the capability to invade surrounding tissue and/or metastasize to new colonization sites.

Generally, cell proliferative disorders treatable with the compounds disclosed herein relate to any disorder characterized by aberrant cell proliferation. These include various tumors and cancers, benign or malignant, metastatic or non-metastatic. Specific properties of cancers, such as tissue invasiveness or metastasis, can be targeted using the methods described herein. Cell proliferative disorders include a variety of cancers, including, among others, ovarian cancer, renal cancer, gastrointestinal cancer, kidney cancer, bladder cancer, pancreatic cancer, lung squamous carcinoma, and adenocarcinoma.

In some embodiments, the cell proliferative disorder treated is a hematopoietic neoplasm, which is aberrant growth of cells of the hematopoietic system. Hematopoietic malignancies can have its origins in pluripotent stem cells, multipotent progenitor cells, oligopotent committed progenitor cells, precursor cells, and terminally differentiated cells involved in hematopoiesis. Some hematological malignancies are believed to arise from hematopoietic stem cells, which have the ability for self renewal. For instance, cells capable of developing specific subtypes of acute myeloid leukemia (AML) (Cynthia K. Hahn, Kenneth N. Ross, Rose M. Kakoza, Steven Karr, Jinyan Du, Shao-E Ong, Todd R. Golub, Kimberly Stegmaier, Syk is a new target for AML differentiation, Blood, 2007, 110, Abstract 209) upon transplantation display the cell surface markers of hematopoietic stem cells, implicating hematopoietic stem cells as the source of leukemic cells. Blast cells that do not have a cell marker characteristic of hematopoietic stem cells appear to be incapable of establishing tumors upon transplantation (Blaire et al., 1997, Blood 89:3104-3112). The stem cell origin of certain hematological malignancies also finds support in the observation that specific chromosomal abnormalities associated with particular types of leukemia can be found in normal cells of hematopoietic lineage as well as leukemic blast cells. For instance, the reciprocal translocation t(9q34;22q11) associated with approximately 95% of chronic myelogenous leukemia appears to be present in cells of the myeloid, erythroid, and lymphoid lineage, suggesting that the chromosomal aberration originates in hematopoietic stem cells. A subgroup of cells in certain types of CML displays the cell marker phenotype of hematopoietic stem cells.

Although hematopoietic neoplasms often originate from stem cells, committed progenitor cells or more terminally differentiated cells of a developmental lineage can also be the source of some leukemias. For example, forced expression of the fusion protein Bcr/Abl (associated with chronic myelogenous leukemia) in common myeloid progenitor or granulocyte/macrophage progenitor cells produces a leukemic-like condition. Moreover, some chromosomal aberrations associated with subtypes of leukemia are not found in the cell population with a marker phenotype of hematopoietic stem cells, but are found in a cell population displaying markers of a more differentiated state of the hematopoietic pathway (Turhan et al., 1995, Blood 85:2154-2161). Thus, while committed progenitor cells and other differentiated cells may have only a limited potential for cell division, leukemic cells may have acquired the ability to grow unregulated, in some instances mimicking the self-renewal characteristics of hematopoietic stem cells (Passegue et al., Proc. Natl. Acad. Sci. USA, 2003, 100:11842-9).

In some embodiments, the hematopoietic neoplasm treated is a lymphoid neoplasm, where the abnormal cells are derived from and/or display the characteristic phenotype of cells of the lymphoid lineage. Lymphoid neoplasms can be subdivided into B-cell neoplasms, T and NK-cell neoplasms, and Hodgkin's lymphoma. B-cell neoplasms can be further subdivided into precursor B-cell neoplasm and mature/peripheral B-cell neoplasm. Exemplary B-cell neoplasms are precursor B-lymphoblastic leukemia/lymphoma (precursor B-cell acute lymphoblastic leukemia) while exemplary mature/peripheral B-cell neoplasms are B-cell chronic lymphocytic leukemia/small lymphocytic lymphoma, B-cell prolymphocytic leukemia, lymphoplasmacytic lymphoma, splenic marginal zone B-cell lymphoma, hairy cell leukemia, plasma cell myeloma/plasmacytoma, extranodal marginal zone B-cell lymphoma of MALT type, nodal marginal zone B-cell lymphoma, follicular lymphoma, mantle-cell lymphoma, diffuse large B-cell lymphoma, mediastinal large B-cell lymphoma, primary effusion lymphoma, and Burkitt's lymphoma/Burkitt cell leukemia. T-cell and Nk-cell neoplasms are further subdivided into precursor T-cell neoplasm and mature (peripheral) T-cell neoplasms. Exemplary precursor T-cell neoplasm is precursor T-lymphoblastic lymphoma/leukemia (precursor T-cell acute lymphoblastic leukemia) while exemplary mature (peripheral) T-cell neoplasms are T-cell prolymphocytic leukemia T-cell granular lymphocytic leukemia, aggressive NK-cell leukemia, adult T-cell lymphoma/leukemia (HTLV-1), extranodal NK/T-cell lymphoma, nasal type, enteropathy-type T-cell lymphoma, hepatosplenic gamma-delta T-cell lymphoma, subcutaneous panniculitis-like T-cell lymphoma, Mycosis fungoides/Sezary syndrome, Anaplastic large-cell lymphoma, T/null cell, primary cutaneous type, Peripheral T-cell lymphoma, not otherwise characterized, Angioimmunoblastic T-cell lymphoma, Anaplastic large-cell lymphoma, T/null cell, primary systemic type. The third member of lymphoid neoplasms is Hodgkin's lymphoma, also referred to as Hodgkin's disease. Exemplary diagnosis of this class that can be treated with the compounds include, among others, nodular lymphocyte-predominant Hodgkin's lymphoma, and various classical forms of Hodgkin's disease, exemplary members of which are Nodular sclerosis Hodgkin's lymphoma (grades 1 and 2), Lymphocyte-rich classical Hodgkin's lymphoma, Mixed cellularity Hodgkin's lymphoma, and Lymphocyte depletion Hodgkin's lymphoma. In various embodiments, any of the lymphoid neoplasms that are associated with aberrant JAK activity can be treated with the syk and/or JAK inhibitory compounds.

In some embodiments, the hematopoietic neoplasm treated is a myeloid neoplasm. This group comprises a large class of cell proliferative disorders involving or displaying the characteristic phenotype of the cells of the myeloid lineage. Myeloid neoplasms can be subdivided into myeloproliferative diseases, myelodysplastic/myeloproliferative diseases, myelodysplastic syndromes, and acute myeloid leukemias. Exemplary myeloproliferative diseases are chronic myelogenous leukemia (e.g., Philadelphia chromosome positive (t(9;22)(qq34;q11)), chronic neutrophilic leukemia, chronic eosinophilic leukemia/hypereosinophilic syndrome, chronic idiopathic myelofibrosis, polycythemia vera, and essential thrombocythemia. Exemplary myelodysplastic/myeloproliferative diseases are chronic myelomonocytic leukemia, atypical chronic myelogenous leukemia, and juvenile myelomonocytic leukemia. Exemplary myelodysplastic syndromes are refractory anemia, with ringed sideroblasts and without ringed sideroblasts, refractory cytopenia (myelodysplastic syndrome) with multilineage dysplasia, refractory anemia (myelodysplastic syndrome) with excess blasts, 5q-syndrome, and myelodysplastic syndrome. In various embodiments, any of the myeloid neoplasms that are associated with aberrant syk and/or JAK activity can be treated with the syk and/or JAK inhibitory compounds.

In some embodiments, the compounds can be used to treat Acute myeloid leukemias (AML), which represent a large class of myeloid neoplasms having its own subdivision of disorders. These subdivisions include, among others, AMLs with recurrent cytogenetic translocations, AML with multilineage dysplasia, and other AML not otherwise categorized. Exemplary AMLs with recurrent cytogenetic translocations include, among others, AML with t(8;21)(q22;q22), AML1 (CBF-alpha)/ETO, Acute promyelocytic leukemia (AML with t(15;17)(q22;q11-12) and variants, PML/RAR-alpha), AML with abnormal bone marrow eosinophils (inv(16) (p13q22) or t(16;16)(p13;q11), CBFb/MYH11X), and AML with 11q23 (MLL) abnormalities. Exemplary AML with multilineage dysplasia are those that are associated with or without prior myelodysplastic syndrome. Other acute myeloid leukemias not classified within any definable group include, AML minimally differentiated, AML without maturation, AML with maturation, Acute myelomonocytic leukemia, Acute monocytic leukemia, Acute erythroid leukemia, Acute megakaryocytic leukemia, Acute basophilic leukemia, and Acute panmyelosis with myelofibrosis.

"Treating" within the context of the invention means an alleviation of symptoms associated with a disorder or disease, or halt of further progression or worsening of those symptoms, or prevention or prophylaxis of the disease or disorder.

The term "mammal" includes organisms which express syk and/or JAK. Examples of mammals include mice, rats, cows, sheep, pigs, goats, horses, bears, monkeys, dogs, cats and, preferably, humans. Transgenic organisms which express syk and/or JAK are also included in this definition.

The inventive methods comprise administering an effective amount of a compound or composition described herein to a mammal or non-human animal. As used herein, "effective amount" of a compound or composition of the invention includes those amounts that antagonize or inhibit syk and/or JAK An amount which antagonizes or inhibits syk and/or JAK is detectable, for example, by any assay capable of determining syk and/or JAK activity, including the one described below as an illustrative testing method. Effective amounts may also include those amounts which alleviate symptoms of a syk and/or JAK associated disorder treatable by inhibiting syk and/or JAK. Accordingly, "antagonists of syk" or "antagonists of JAK" include compounds which interact with the syk or JAK, respectively, and modulate, e.g., inhibit or decrease, the ability of a second compound, e.g., another syk or JAK ligand, to interact with the syk or JAK, respectively. The syk or JAK binding compounds are preferably antagonists of syk or JAK, respectively. The language "syk binding compound" and "JAK-binding compound" (e.g., exhibits binding affinity to the receptor) includes those compounds which interact with syk or JAK resulting in modulation of the activity of syk or JAK, respectively. syk and/or JAK binding compounds may be identified using an in vitro (e.g., cell and non-cell based) or in vivo method. A description of in vitro methods are provided below.

The amount of compound present in the methods and compositions described herein should be sufficient to cause a detectable decrease in the severity of the disorder, as measured by any of the assays described in the examples. The amount of syk and/or JAK modulator needed will depend on the effectiveness of the modulator for the given cell type and the length of time required to treat the disorder.

In certain embodiments, the compositions of this invention may further comprise another therapeutic agent. When a second agent is used, the second agent may be administered either as a separate dosage form or as part of a single dosage form with the compounds or compositions of this invention. While one or more of the inventive compounds can be used in an application of monotherapy to treat a disorder, disease or symptom, they also may be used in combination therapy, in which the use of an inventive compound or composition (therapeutic agent) is combined with the use of one or more other therapeutic agents for treating the same and/or other types of disorders, symptoms and diseases. Combination therapy includes administration of the two or more therapeutic agents concurrently or sequentially. The agents may be administered in any order. Alternatively, the multiple therapeutic agents can be combined into a single composition that can be administered to the patient. For instance, a single pharmaceutical composition could comprise the compound or pharmaceutically acceptable salt, ester or prodrug thereof according to the formula I, another therapeutic agent (e.g., methotrexate) or a pharmaceutically acceptable salt, ester or prodrug thereof, and a pharmaceutically acceptable excipient or carrier.

The invention comprises a compound having the formula I, a method for making an inventive compound, a method for making a pharmaceutical composition from at least one inventive compound and at least one pharmaceutically acceptable carrier or excipient, and a method of using one or more inventive compounds to treat a variety of disorders, symptoms and diseases (e.g., inflammatory, autoimmune, neurological, neurodegenerative, oncology and cardiovascular), such as RA, osteoarthritis, irritable bowel disease IBD, asthma, chronic obstructive pulmonary disease COPD and MS. The inventive compounds and their pharmaceutically acceptable salts and/or neutral compositions may be formulated together with a pharmaceutically acceptable excipient or carrier and the resulting composition may be administered in vivo to mammals, such as men, women and animals, to treat a variety of disorders, symptoms and diseases. Furthermore, the inventive compounds can be used to prepare a medicament that is useful for treating a variety of disorders, symptoms and diseases.

All of the compounds of the present invention are either potent inhibitors of syk and/or JAK kinases, exhibiting $IC_{50}$s in the respective assay in the range of less than 5 μM, with most being in the nanomolar, and several in the sub-nanomolar, range. In some embodiments, the compounds of the present invention may be "dual" syk/JAK inhibitors in that they inhibit both syk and JAK kinase to some degree. In other embodiments, the compounds of the present invention may selectively inhibit syk kinase, but not appreciably inhibit one or more JAK kinases. In other embodiments, the compounds of the present invention may selectively inhibit JAK kinase, but not appreciably inhibit one or more syk kinases.

f. Kits

Still another aspect of this invention is to provide a kit comprising separate containers in a single package, wherein the inventive pharmaceutical compounds, compositions and/or salts thereof are used in combination with pharmaceutically acceptable carriers to treat states, disorders, symptoms and diseases where syk and/or JAK plays a role.

EXAMPLES

The following examples are offered to illustrate, but not to limit, the claimed invention.

The starting materials and reagents used in preparing these compounds generally are either available from commercial suppliers, such as Aldrich Chemical Co., or are prepared by methods known to those skilled in the art following procedures set forth in references such as *Fieser and Fieser's Reagents for Organic Synthesis*; Wiley & Sons: New York, 1967-2004, Volumes 1-22; *Rodd's Chemistry of Carbon Compounds*, Elsevier Science Publishers, 1989, Volumes 1-5 and Supplementals; and Organic Reactions, Wiley & Sons: New York, 2005, Volumes 1-65.

The starting materials and the intermediates of the synthetic reaction schemes can be isolated and purified if desired using conventional techniques, including but not limited to, filtration, distillation, crystallization, chromatography, and the like. Such materials can be characterized using conventional means, including physical constants and spectral data.

Unless specified to the contrary, the reactions described herein preferably are conducted under an inert atmosphere at atmospheric pressure at a reaction temperature range of from about −78° C. to about 150° C., more preferably from about 0° C. to about 125° C., and most preferably and conveniently at about room (or ambient) temperature, e.g., about 20° C. to about 75° C.

Referring to the examples that follow, compounds of the present invention were synthesized using the methods described herein, or other methods, which are well known in the art.

The compounds and/or intermediates may be characterized by high performance liquid chromatography (HPLC) using a Waters Alliance chromatography system with a 2695 Separation Module (Milford, Mass.). The analytical columns may be C-18 SpeedROD RP-18E Columns from Merck KGaA (Darmstadt, Germany). Alternately, characterization may be performed using a Waters Unity (UPLC) system with Waters Acquity UPLC BEH C-18 2.1 mm×15 mm columns. A gradient elution may be used, typically starting with 5% acetonitrile/95% water and progressing to 95% acetonitrile over a period of 5 minutes for the Alliance system and 1 minute for the Acquity system. All solvents may contain 0.1% trifluoroacetic acid (TFA). Compounds may be detected by ultraviolet light (UV) absorption at either 220 nm or 254 nm. HPLC solvents may be from EMD Chemicals, Inc. (Gibbstown, N.J.). In some instances, purity may be assessed by thin layer chromatography (TLC) using glass backed silica gel plates, such as, for example, EMD Silica Gel 60 2.5 cm×7.5 cm plates. TLC results may be readily detected visually under ultraviolet light, or by employing well known iodine vapor and other various staining techniques.

Mass spectrometric analysis may be performed on one of two Agilent 1100 series LCMS instruments with acetonitrile/water as the mobile phase. One system may use TFA as the modifier and measure in positive ion mode [reported as MH+, (M+1) or (M+H)+] and the other may use either formic acid or ammonium acetate and measure in both positive [reported as $MH^+$, (M+1) or $(M+H)^+$] and negative [reported as M−, (M−1) or (M−H)−] ion modes.

Nuclear magnetic resonance (NMR) analysis may be performed on some of the compounds with a Varian 400 MHz NMR (Palo Alto, Calif.). The spectral reference may be either TMS or the known chemical shift of the solvent.

The purity of some of the invention compounds may be assessed by elemental analysis (Robertson Microlit, Madison, N.J.).

Melting points may be determined on a Laboratory Devices Mel-Temp apparatus (Holliston, Mass.).

Preparative separations may be carried out as needed, using either an Sq16x or an Sg100c chromatography system and prepackaged silica gel columns all purchased from Teledyne Isco, (Lincoln, Nebr.). Alternately, compounds and intermediates may be purified by flash column chromatography using silica gel (230-400 mesh) packing material, or by HPLC using a C-18 reversed phase column. Typical solvents employed for the Isco systems and flash column chromatography may be dichloromethane, methanol, ethyl acetate, hexane, acetone, aqueous hydroxyamine and triethyl amine. Typical solvents employed for the reverse phase HPLC may be varying concentrations of acetonitrile and water with 0.1% trifluoroacetic acid.

General Methods

The following synthetic reaction schemes are merely illustrative of some methods by which the compounds of the present invention can be synthesized, and various modifications to these synthetic reaction schemes can be made and will be suggested to one skilled in the art having referred to the disclosure contained in this application.

Example 1. 2-(4-(4-acetylpiperazin-1-yl)phenylamino)-4-(cyclobutylamino)pyrimidine-5-carboxamide 1

Scheme 1:

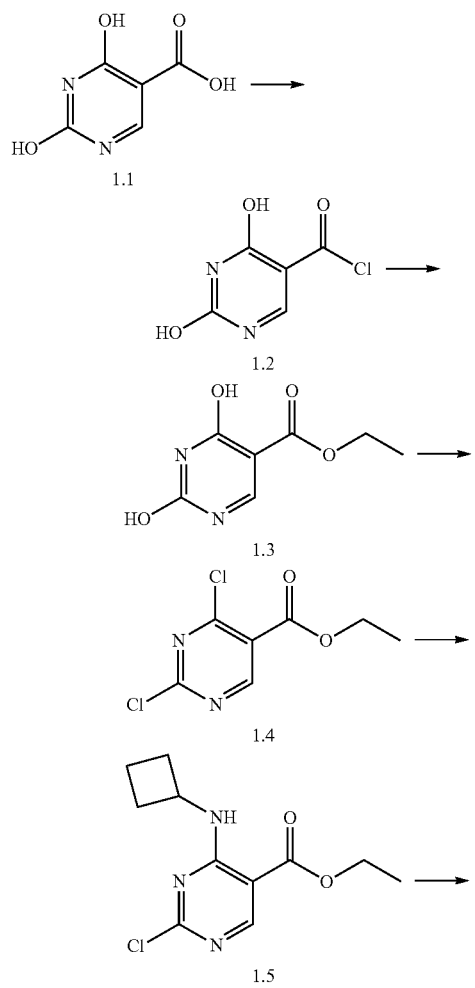

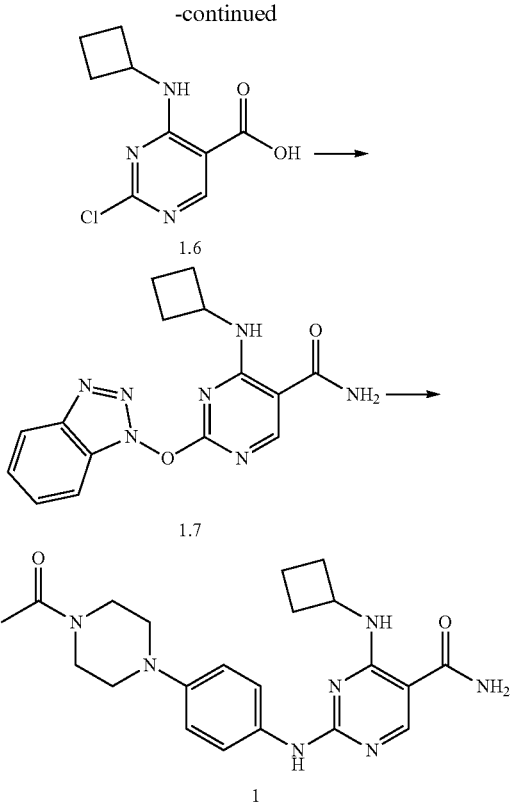

Step 1: To a stirring solution of carboxylic acid 1.1 (85 g, 540 mmol) in thionyl chloride (425 mL) was added pyridine (8.5 mL, 0.11 mmol), slowly. The reaction was stirred at 75° C. overnight at which time it was concentrated and dried under vacuum to a light yellow powder which was used immediately for the next step.

Step 2: The yellow solid from the previous step was slowly diluted with 750 mL of ethanol and refluxed overnight. The next day the reaction was determined to be complete by HPLC and then cooled in an ice bath and the solid filtered and washed with diethyl ether affording the desired ethyl ester (1.3) as an off-white powder (91 g, 87% for two steps). MS found for $C_7H_8N_2O_4$ as $(M+H)^+$ 185.0.

Step 3: Ester 1.3 (22 g, 120 mmol) was dissolved in phosphorous oxychloride (60 mL, 600 mmol) and the mixture treated with N,N-diethylaniline (27 mL, 167 mmol) and the mixture heated to 105° C. until the reaction was determined to be complete by HPLC. It was then cooled to rt and slowly added to 1 L of crushed ice resulting in the formation of a beige precipitate which was collected by filtration and dried under vacuum affording the desired dichloride (1.4) as a light yellow powder (22.5 g, 85%). $^1$H NMR (DMSO-$d_6$, 400 MHz): δ 9.13 (s, 1H), 4.37 (q, 2H), 1.32 (t, 3H).

Step 4: Dichloropyrimidine 1.4 (5.9 g, 27 mmol) was dissolved in acetonitrile (50 mL) and treated sequentially with diisopropylamine (5.2 mL, 30 mmol) followed by cyclobutyl amine (1.9 g, 27 mmol) and stirred at rt until all starting material had been consumed. The reaction mixture was then diluted with water to a total volume of 150 mL and the precipitate collected by filtration affording the desired product as a light yellow solid (6.02 g, 87%). $^1$H NMR (DMSO-$d_6$, 400 MHz): δ 8.60 (S, 1H), 8.48 (d, 1H), 4.52 (m, 1H), 4.29 (q, 2H), 2.30 (m, 2H), 2.04 (m, 2H), 1.73 (m, 2H), 1.30 (t, 3H).

Step 5: Ethyl ester 1.5 (6.02 g, 24 mmol) was diluted with 1,4-dioxane (26 mL) followed by aqueous lithium hydroxide (1.0 M, 26 mL, 26 mmol) and stirred at rt until all starting material had been converted to the carboxylic acid. The reaction was then diluted with water to a total volume of 100 mL and acidified to pH=2 with 6 M HCl. The resulting suspension was then filtered and dried by aspiration giving 3.51 g of the carboxylic acid (64%). $^1$H NMR (DMSO-$d_6$, 400 MHz): δ 8.64 (d, 1H), 8.74 (s, 1H), 4.50 (m, 1H), 2.31 (m, 2H), 2.03 (m, 2H), 1.72 (m, 2H).

Step 6: Carboxylic acid 1.6 (3.15 g, 15 mmol) was dissolved in N,N-dimethylformamide (70 mL) and treated with HOBt (3.13 g, 23 mmol) and EDC (4.4 g, 23 mmol). After stirring ca. 25 min ammonia (0.5 M in 1,4-dioxane, 72 mL, 36 mmol) was added and the reaction stirred overnight. The following morning the reaction was diluted with water to a total volume of 500 mL and the desired product collected by filtration affording 3.62 g (74%) of a light-beige solid. $^1$H NMR (DMSO-$d_6$, 400 MHz): δ 9.30 (d, 1H), 8.54 (s, 1H), 8.15 (d, 1H), 8.09 (s, 1H), 7.74 (d, 1H), 7.64 (m, 2H), 7.51 (t, 1H), 3.77 (m, 1H), 1.79 (m, 2H), 1.74 (m, 2H), 1.53 (m, 1H), 1.41 (m, 1H).

Step 7: Benzotriazolyl ether 1.7 (50 mg, 0.17 mmol), 1-(4-(4-aminophenyl)piperazin-1-yl)ethanone (prepared from 1-acetylpiperazine and 4-fluoronitrobenze in two steps) (45 mg, 0.20 mmol) and p-toluenesulfonic acid (30 mg, 0.17 mmol) were diluted with 1,4-dioxane (5 mL) and stirred at 120° C. until all starting material had been consumed. The reaction was cooled to rt, diluted with water and directly purified by preparative HPLC affording the desired product, 1, after lyophilization. MS found for $C_{21}H_{27}N_7O_2$ as $(M+H)^+$ 410.2.

The following compound was prepared using a procedure similar to that described in Example 1 with reagent A in place of cyclobutylamine in Step 4.

TABLE 6

| Ex No | Structure | Reagent A | MW | MS | Name |
|---|---|---|---|---|---|
| 2 | [structure] | meta-anisidine | 461.526 | 462.3 | 2-(4-(4-acetylpiperazin-1-yl)phenylamino)-4-(3-methoxyphenylamino)pyrimidine-5-carboxamide |
| 3 | [structure] | cyclopropylamine | 395.467 | 396 | 2-(4-(4-acetylpiperazin-1-yl)phenylamino)-4-(cyclopropylamino)pyrimidine-5-carboxamide |
| 4 | [structure] | cyclopentylamine | 423.521 | 424 | 2-(4-(4-acetylpiperazin-1-yl)phenylamino)-4-(cyclopentylamino)pyrimidine-5-carboxamide |
| 5 | [structure] | t-butylamine | 411.51 | 412.3 | 2-(4-(4-acetylpiperazin-1-yl)phenylamino)-4-(tert-butylamino)pyrimidine-5-carboxamide |

TABLE 6-continued

| Ex No | Structure | Reagent A | MW | MS | Name |
|---|---|---|---|---|---|
| 6 | 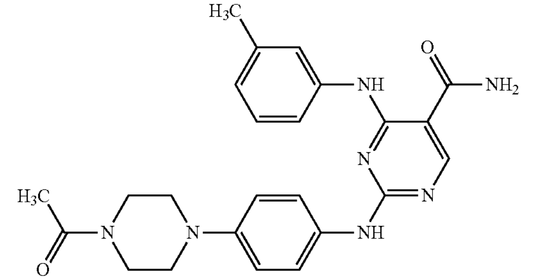 [SMILES: CC(=O)N1CCN(c2ccc(Nc3ncc(C(N)=O)c(Nc4cccc(C)c4)n3)cc2)CC1] | 3-toluidine | 445.527 | 446.1 | 2-(4-(4-acetylpiperazin-1-yl)phenylamino)-4-(m-tolylamino)pyrimidine-5-carboxamide |
| 7 | 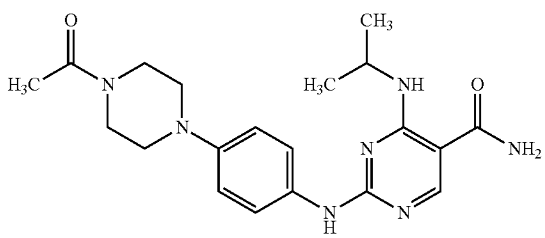 [SMILES: CC(=O)N1CCN(c2ccc(Nc3ncc(C(N)=O)c(NC(C)C)n3)cc2)CC1] | isopropyl-amine | 397.483 | 398.3 | 2-(4-(4-acetylpiperazin-1-yl)phenylamino)-4-(isopropylamino)pyrimidine-5-carboxamide |
| 8 | 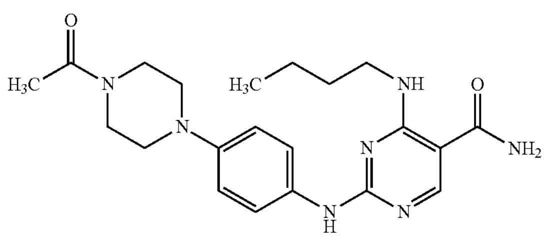 [SMILES: CCCCNc1nc(Nc2ccc(N3CCN(C(C)=O)CC3)cc2)ncc1C(N)=O] | n-butylamine | 411.51 | 412 | 2-(4-(4-acetylpiperazin-1-yl)phenylamino)-4-(butylamino)pyrimidine-5-carboxamide |
| 9 | 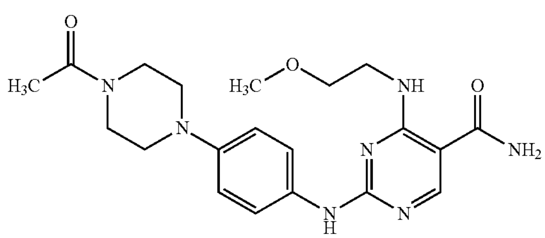 [SMILES: COCCNc1nc(Nc2ccc(N3CCN(C(C)=O)CC3)cc2)ncc1C(N)=O] | 2-methoxy-ethylamine | 413.482 | 413 | 2-(4-(4-acetylpiperazin-1-yl)phenylamino)-4-(2-methoxyethylamino)pyrimidine-5-carboxamide |
| 10 | 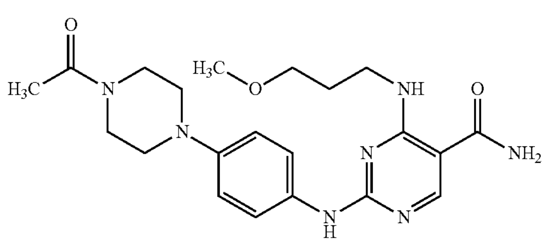 [SMILES: COCCCNc1nc(Nc2ccc(N3CCN(C(C)=O)CC3)cc2)ncc1C(N)=O] | 3-methoxy-propylamine | 427.509 | 428 | 2-(4-(4-acetylpiperazin-1-yl)phenylamino)-4-(3-methoxypropylamino)pyrimidine-5-carboxamide |
| 11 | 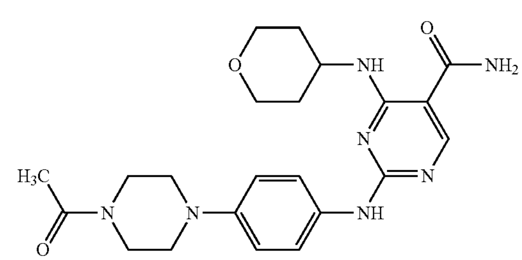 [SMILES: CC(=O)N1CCN(c2ccc(Nc3ncc(C(N)=O)c(NC4CCOCC4)n3)cc2)CC1] | tetrahydro-2H-pyran-4-amine | 439.52 | 440 | 2-(4-(4-acetylpiperazin-1-yl)phenylamino)-4-(tetrahydro-2H-pyran-4-ylamino)pyrimidine-5-carboxamide |

TABLE 6-continued

| Ex No | Structure | Reagent A | MW | MS | Name |
|---|---|---|---|---|---|
| 12 | 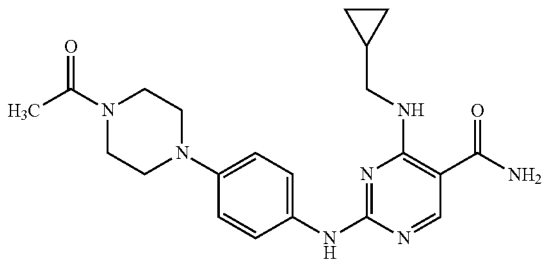 [SMILES: CC(=O)N1CCN(c2ccc(Nc3ncc(C(N)=O)c(NCC4CC4)n3)cc2)CC1] | cyclopropyl-methylamine | 409.494 | 410.2 | 2-(4-(4-acetylpiperazin-1-yl)phenylamino)-4-(cyclopropylmethyl-amino)pyrimidine-5-carboxamide |
| 13 | 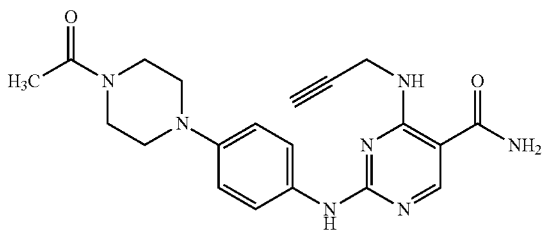 [SMILES: C#CCNc1nc(Nc2ccc(N3CCN(C(C)=O)CC3)cc2)ncc1C(N)=O] | propargylamine | 393.451 | 394.2 | 2-(4-(4-acetylpiperazin-1-yl)phenylamino)-4-(prop-2-ynylamino)pyrimidine-5-carboxamide |
| 14 | 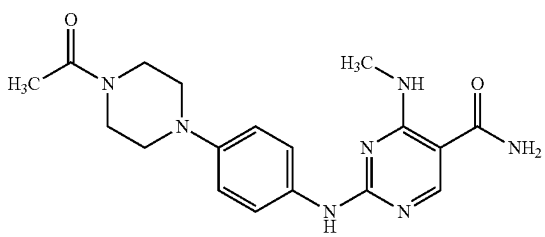 [SMILES: CNc1nc(Nc2ccc(N3CCN(C(C)=O)CC3)cc2)ncc1C(N)=O] | methylamine | 369.429 | 370.2 | 2-(4-(4-acetylpiperazin-1-yl)phenylamino)-4-(methylamino)pyrimidine-5-carboxamide |
| 15 | 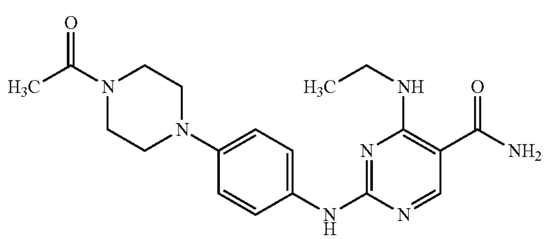 [SMILES: CCNc1nc(Nc2ccc(N3CCN(C(C)=O)CC3)cc2)ncc1C(N)=O] | ethylamine | 383.456 | 384.2 | 2-(4-(4-acetylpiperazin-1-yl)phenylamino)-4-(ethylamino)pyrimidine-5-carboxamide |
| 16 | 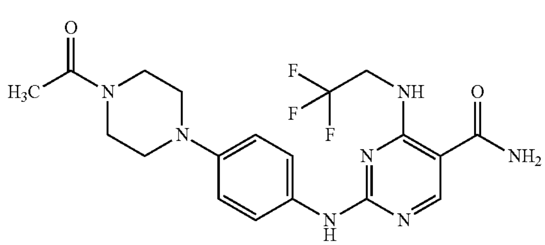 [SMILES: CC(=O)N1CCN(c2ccc(Nc3ncc(C(N)=O)c(NCC(F)(F)F)n3)cc2)CC1] | 2,2,2-trifluoro ethylamine | 437.426 | 438.2 | 2-(4-(4-acetylpiperazin-1-yl)phenylamino)-4-(2,2,2-trifluoroethylamino)pyrimidine-5-carboxamide |

TABLE 6-continued

| Ex No | Structure | Reagent A | MW | MS | Name |
|---|---|---|---|---|---|
| 17 | 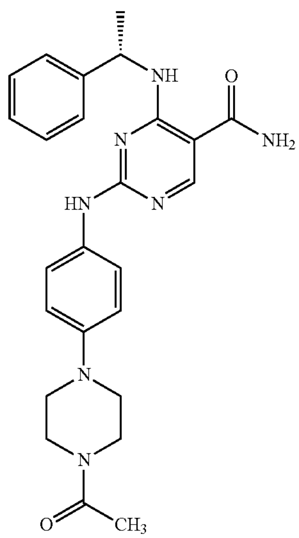 [SMILES: CC(=O)N1CCN(c2ccc(Nc3ncc(C(N)=O)c(N[C@@H](C)c4ccccc4)n3)cc2)CC1] | (S)-alpha methyl benzylamine | 459.554 | 460 | (S)-2-(4-(4-acetylpiperazin-1-yl)phenylamino)-4-(1-phenylethylamino)pyrimidine-5-carboxamide |
| 18 | 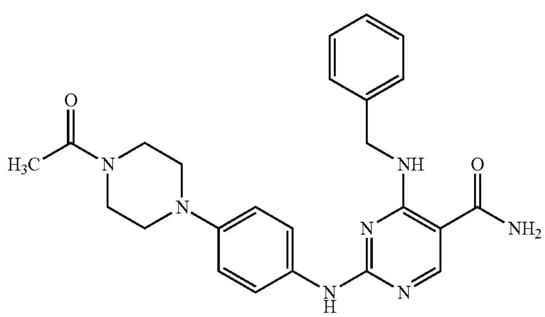 [SMILES: CC(=O)N1CCN(c2ccc(Nc3ncc(C(N)=O)c(NCc4ccccc4)n3)cc2)CC1] | benzylamine | 445.527 | 446 | 2-(4-(4-acetylpiperazin-1-yl)phenylamino)-4-(benzylamino)pyrimidine-5-carboxamide |
| 19 | 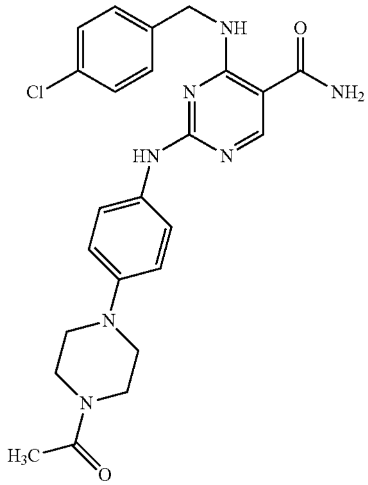 [SMILES: CC(=O)N1CCN(c2ccc(Nc3ncc(C(N)=O)c(NCc4ccc(Cl)cc4)n3)cc2)CC1] | 4-chlorobenzyl-amine | 479.972 | 480 | 2-(4-(4-acetylpiperazin-1-yl)phenylamino)-4-(4-chlorobenzylamino)pyrimidine-5-carboxamide |

TABLE 6-continued

| Ex No | Structure | Reagent A | MW | MS | Name |
|---|---|---|---|---|---|
| 20 | 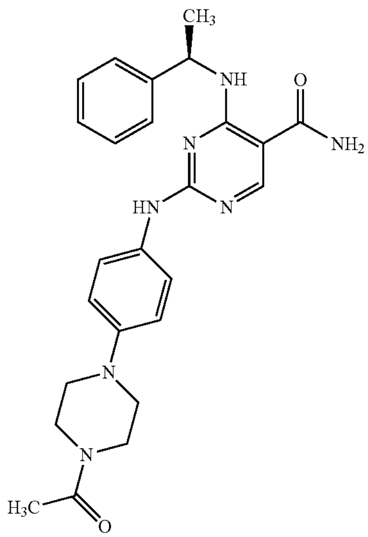 [SMILES: CC(=O)N1CCN(c2ccc(Nc3ncc(C(N)=O)c(N[C@H](C)c4ccccc4)n3)cc2)CC1] | (R)-alpha methyl benzylamine | 459.554 | 460 | (R)-2-(4-(4-acetylpiperazin-1-yl)phenylamino)-4-(1-phenylethylamino)pyrimidine-5-carboxamide |
| 21 | 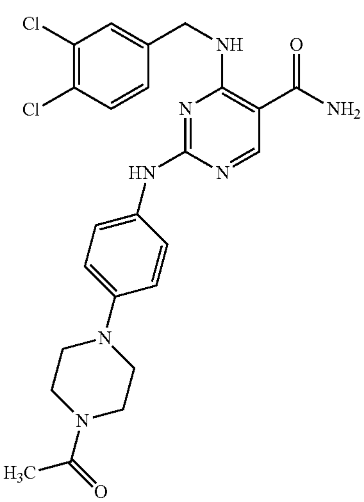 [SMILES: CC(=O)N1CCN(c2ccc(Nc3ncc(C(N)=O)c(NCc4ccc(Cl)c(Cl)c4)n3)cc2)CC1] | 3,4-dichloro benzylamine | 514.417 | 514 | 2-(4-(4-acetylpiperazin-1-yl)phenylamino)-4-(3,4-dichlorobenzylamino)pyrimidine-5-carboxamide |
| 22 | 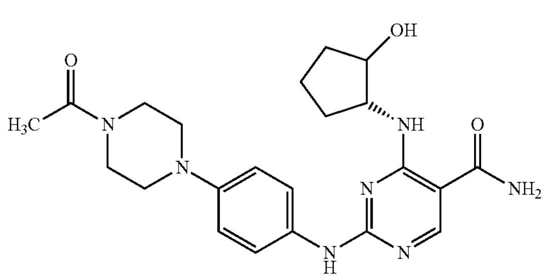 | racemic trans-2-hydroxy cyclopropyl-amine | 439.52 | 440.5 | 2-(4-(4-acetylpiperazin-1-yl)phenylamino)-4-((1R)-2-hydroxycyclopentylamino)pyrimidine-5-carboxamide |

Example 32. 2,4-bis(4-(4-acetylpiperazin-1-yl)phenylamino)pyrimidine-5-carboxamide

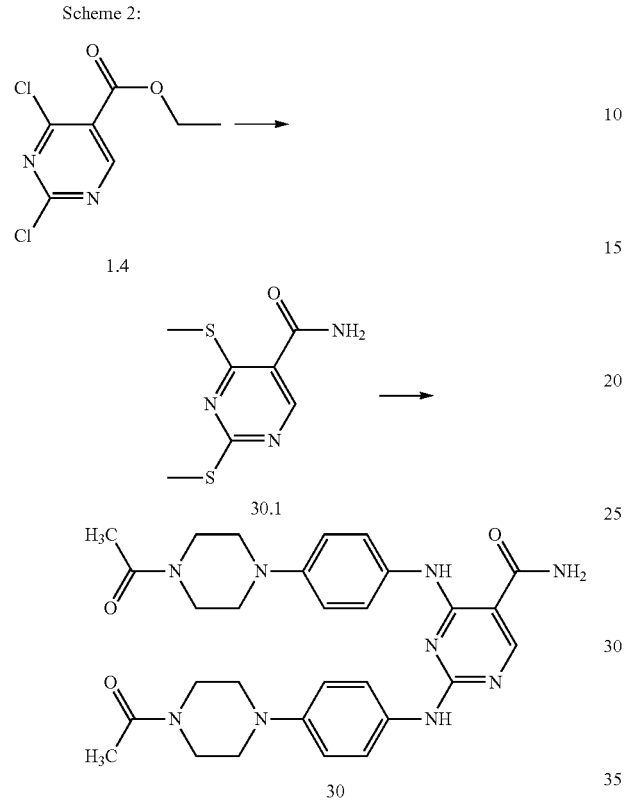

Step 1: Compound 1.4 (Example 1, 1.05 g, 4.8 mmol) was dissolved in 40 mL acetonitrile. To it was added sodium thiomethoxide (0.74 g, 10.5 mmol). It was stirred for overnight, diluted with ethyl acetate, washed with brine three times, dried and concentrated in vacuo. It was then placed in 20 mL dioxane and 10 mL water. To it was added LiOH hydrate 500 mg. The mixture was stirred for 4 hours. To the mixture was added 1N HCl till the pH reaching 3. It was concentrated, extracted with ethyl acetate three times. The organic phases were combined, dried and concentrated in vacuo to afford a white solid. This solid was then dissolved in 30 mL dry DMF. To it were added EDC hydrochloride (1.10 g, 5.7 mmol) and HOBt (0.77 g, 5.7 mmol). The mixture was stirred for 30 min, and to it was added ammonia (commercial 0.5N solution in dioxane, 29 mL, 14.5 mmol). The mixture was stirred for overnight, concentrated in vacuo, diluted with ethyl acetate, washed with brine three times, dried and concentrated in vacuo to give crude compound 30.1. MS found for $C_7H_9N_3OS_2$ as $(M+H)^+$ 216.1.

Step 2: Crude compound 30.1 (42 mg, 0.20 mmol) was dissolved in 4 mL NMP. To it was added MCPBA (133 mg, 0.50 mmol). It was stirred at RT for 1 hour. To it were then added 1-(4-(4-aminophenyl)piperazin-1-yl)ethanone (175 mg, 0.80 mmol) and DIEA (140 μL, 0.80 mmol). The mixture was then stirred in 120° C. bath for 90 min. The mixture was then subjected to reverse phase preparative HPLC to isolate the title compound. MS found for $C_{29}H_{35}N_9O_3$ as $(M+H)^+$ 558.2.

Example 33. 4-(1H-indazol-6-ylamino)-2-(4-(4-acetylpiperazin-1-yl)phenylamino)pyrimidine-5-carboxamide

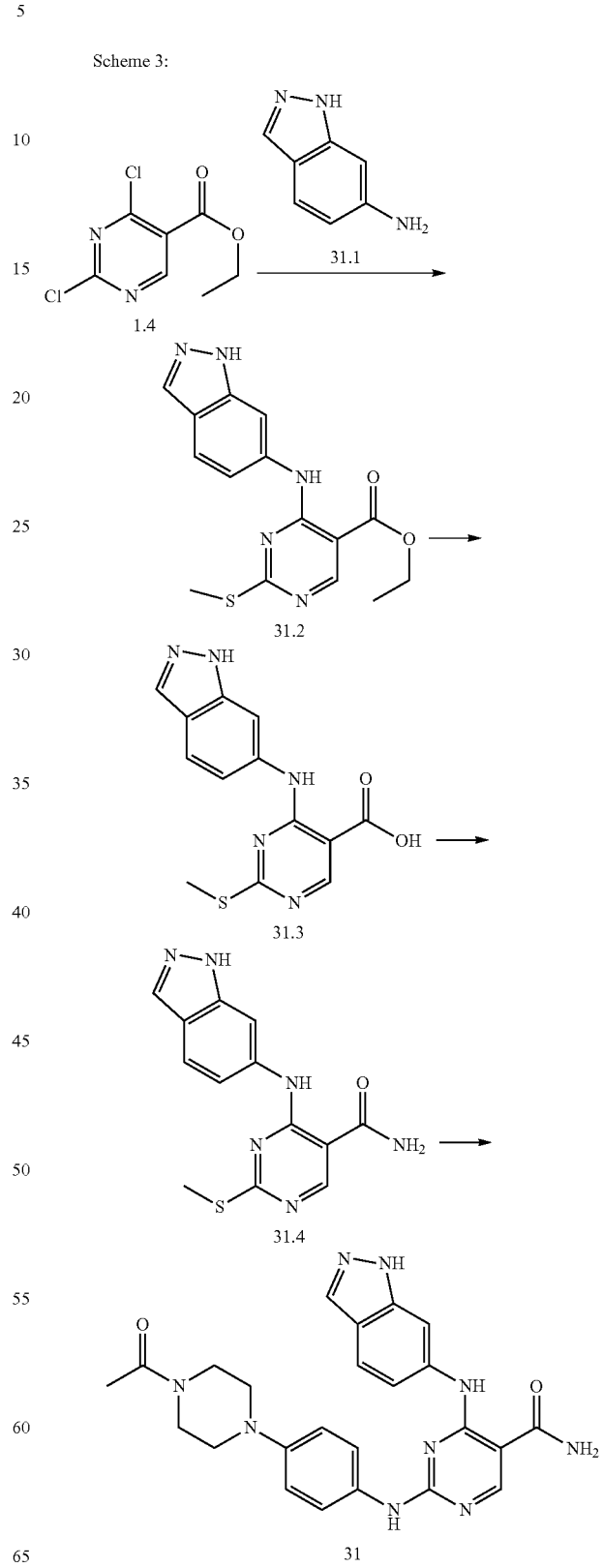

Step 3: Dichloropyrimidine 1.4 (see Example 1; 1.04 g, 4.7 mmol) was dissolved in NMP (30 mL) and stirred in ice bath. To it were added 6-aminoindazole 31.1 (690 mg, 5.2 mmol) and then dropwise ethyldiisopropylamine (DIEA, 1.64 mL, 9.4 mmol). The mixture was stirred for 40 minutes, and to it was added sodium thiomethoxide (660 mg, 9.4 mmol). The mixture was stirred for overnight, diluted with ethyl acetate, washed with brine three times, and concentrated in vacuo to give crude compound 31.2 as a light brown solid in quantitative yield. MS found for $C_{15}H_{15}N_5O_2S$ as $(M+H)^+$ 330.1.

Step 4: Ethyl ester 31.2 (4.7 mmol) was dissolved in 60 mL THF. To it were added lithium hydroxide hydrate (236 mg, 5.6 mmol) and 20 mL water. The mixture was stirred for overnight and to it was carefully added 1N HCl solution till pH reaching 2. The mixture was concentrated in vacuo to remove THF. White solid crashed out and was isolated using a Büchner funnel. It was washed with water and dried in vacuum oven to give compound 31.3 (1.14 g, 81%) as a white solid. MS found for $C_{13}H_{11}N_5O_2S$ as $(M+H)^+$ 302.1.

Step 5: Carboxylic acid 31.3 (1.14 g, 3.8 mmol) was dissolved in 30 mL DMF. To it were added EDC hydrochloride (1.09 g, 5.7 mmol) and HOBt hydrate (770 mg, 5.7 mmol). The mixture was stirred at RT for 1 hour. To it was then added ammonia (commercial 0.5N solution in dioxane, 22 mL, 11.4 mmol). The mixture was stirred for 2 hours. It was then concentrated in vacuo and taken into water and ethyl acetate. The organic phase was separated and washed with brine four times. The organic phase was then dried over $MgSO_4$ and concentrated in vacuo to afford compound 31.4 as a light yellow solid (820 mg, 72%). MS found for $C_{13}H_{12}N_6OS$ as $(M+H)^+$ 301.1.

Step 6: Compound 31.4 (36 mg, 0.12 mmol) was dissolved in 3 mL NMP. To it was added MCPBA (65% pure, 48 mg, 0.18 mmol). It was stirred at RT for 30 minutes. To it then were added 1-(4-(4-aminophenyl)piperazin-1-yl)ethanone (53 mg, 0.24 mmol) and pTSA (21 mg, 0.12 mmol). The mixture was stirred for 90 minutes at 120° C. bath. This mixture was then subjected to preparative HPLC to isolate the title compound 31. MS found for $C_{24}H_{25}N_9O_2$ as $(M+H)^+$ 472.2.

Example 34. 2-(4-(4-acetylpiperazin-1-yl)-3-chlorophenylamino)-4-(cyclopropylamino)pyrimidine-5-carboxamide

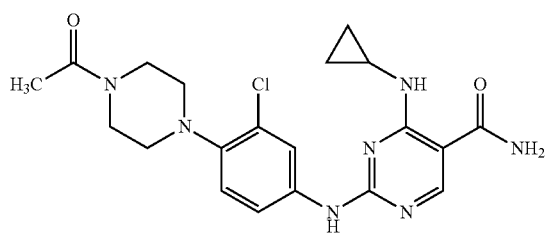

The above compound was prepared using a procedure similar to that described in Example 1 with cyclopropylamine in place of cyclobutylamine in Step 4. Synthesis of the chloropiperazinylaniline was accomplished by chlorination of the nitropiperazinyl intermediate, synthesized in a manner similar to that described in Example 36, with NCS, followed by reduction using sulfided platinum. MS found for $C_{20}H_{24}N_7O_2Cl$ as $(M+H)^+$ 430.0. UV: λ=290

Example 35. 2-(4-(4-acetylpiperazin-1-yl)-3-chlorophenylamino)-4-(cyclobutylamino)pyrimidine-5-carboxamide

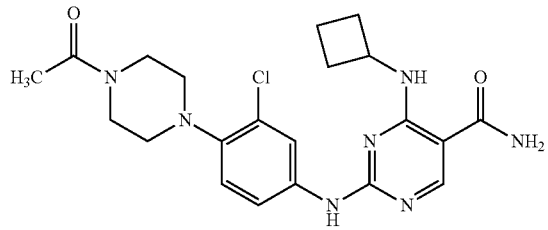 [SMILES: CC(=O)N1CCN(c2ccc(Nc3ncc(C(N)=O)c(NC4CCC4)n3)cc2Cl)CC1]

The above compound was prepared using a procedure similar to that described in Example 32. MS found for $C_{21}H_{26}N_7O_2Cl$ as $(M+H)^+$ 444.0. UV: λ=211, 290

Example 36. 4-(cyclopropylamino)-2-(4-(4-propionylpiperazin-1-yl)phenylamino)pyrimidine-5-carboxamide

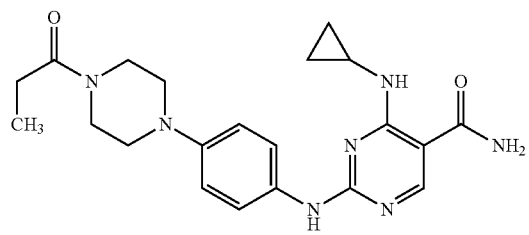 [SMILES: CCC(=O)N1CCN(c2ccc(Nc3ncc(C(N)=O)c(NC4CC4)n3)cc2)CC1]

The above compound was prepared using a procedure similar to that described in Example 1 with cyclopropylamine in place of cyclobutylamine. The piperazinylaniline was synthesized from Boc piperazine and 4-fluoronitrobenzene, followed by deprotection using HCl in dioxane and acylation using propionyl chloride, and finally hydrogenation using Pd/C. MS found for $C_{21}H_{27}N_7O_2$ as $(M+H)^+$ 410.3. $^1$H NMR (CD$_3$OD, 400 MHz): δ 8.22 (s, 1H), 7.49 (broad s, 2H), 7.06 (d, 2H), 3.73 (m, 4H), 3.22 (m, 4H), 2.47 q, 2H), 3.03 (m, 1H), 1.12 (t, 3H), 0.90 (m, 2H), 0.70 (m, 2H).

Example 37. 2-(4-(4-(cyclopropanecarbonyl)piperazin-1-yl)phenylamino)-4-(cyclopropylamino)pyrimidine-5-carboxamide

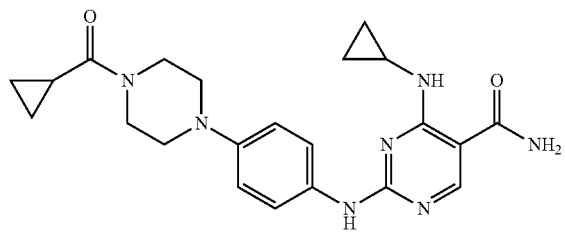 [SMILES: NC(=O)c1cnc(Nc2ccc(N3CCN(C(=O)C4CC4)CC3)cc2)nc1NC1CC1]

The above compound was prepared using a procedure similar to that described in Example 36 with cyclopropylcarbonyl chloride in place of propionyl chloride. MS found for $C_{22}H_{27}N_7O_2$ as $(M+H)^+$ 422.4. $^1$H NMR (CD$_3$OD, 400

MHz): δ 8.22 (s, 1H), 7.45 (broad s, 2H), 7.08 (d, 2H), 3.93 (m, 4H), 3.73 (m, 4H), 3.02 (m, 1H), 2.01 (m, 1H), 0.88 (m, 6H), 0.69 (m, 2H). UV: λ=203, 273.

Example 38. 4-(cyclopropylamino)-2-(4-(4-(2-methoxyacetyl)piperazin-1-yl)phenylamino)pyrimidine-5-carboxamide

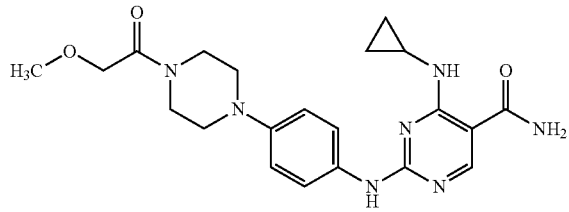 [SMILES: COCC(=O)N1CCN(c2ccc(Nc3ncc(C(N)=O)c(NC4CC4)n3)cc2)CC1]

The above compound was prepared using a procedure similar to that described in Example 36 with methoxyacetyl chloride in place of propionyl chloride. MS found for $C_{21}H_{27}N_7O_3$ as $(M+H)^+$ 426.2. $^1$H NMR (CD3OD, 400 MHz): δ 8.38 (s, 1H), 7.55 (broad s, 2H), 7.08 (d, 2H), 4.21 (s, 2H), 3.74 (m, 4H), 3.64 (m, 4H), 3.40 (s, 3H), 3.06 (m, 1H), 0.94 (m, 2H), 0.71 (m, 2H).

Example 39. 2-(4-(4-acetyl-2-oxopiperazin-1-yl) phenylamino)-4-(cyclopropylamino)pyrimidine-5-carboxamide

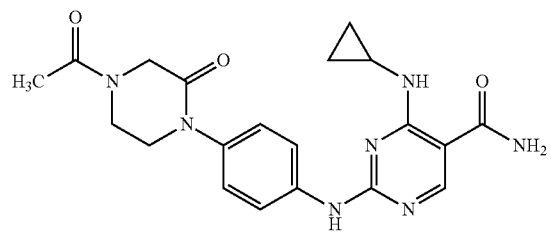 [SMILES: CC(=O)N1CCN(c2ccc(Nc3ncc(C(N)=O)c(NC4CC4)n3)cc2)C(=O)C1]

The above compound was prepared using a procedure similar to that described in Example 1 with cyclopropylamine in place of cyclobutylamine in Step 4. The oxopiperazinyl aniline was synthesized from 4-nitroiodobenzene and 4-Boc-2-oxopiperidine using copper iodide/dimethylethylenediamine catalyzed conditions. The Boc group was then removed using HCl in dioxane, the resulting amine was acylated using acetyl chloride, and finally the nitro group was reduced using hydrogen and Pd/C. MS found for $C_{20}H_{23}N_7O_3$ as $(M+H)^+$ 410.2. UV: λ=275.

Example 40. 2-(4-(4-acetylpiperazin-1-yl)-3-fluorophenylamino)-4-(cyclopropylamino)pyrimidine-5-carboxamide

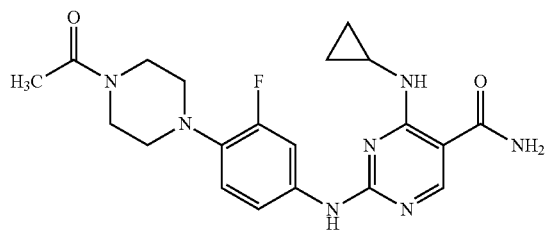 [SMILES: CC(=O)N1CCN(c2ccc(Nc3ncc(C(N)=O)c(NC4CC4)n3)cc2F)CC1]

The above compound was prepared using a procedure similar to that described in Example 1 with cyclopropylamine in place of cyclobutylamine in Step 4. The aniline was synthesized from the corresponding carboxyl azide by heating in water/DMF. The azide was ultimately synthesized from 3,4-difluorobenzoic acid. MS found for $C_{20}H_{24}N_7O_2F$ as $(M+H)^+$ 414.2. UV: λ=293.

Example 41. 2-(4-(4-acetylpiperazin-1-yl)phenylamino)-4-((1s,4s)-4-aminocyclohexylamino)pyrimidine-5-carboxamide

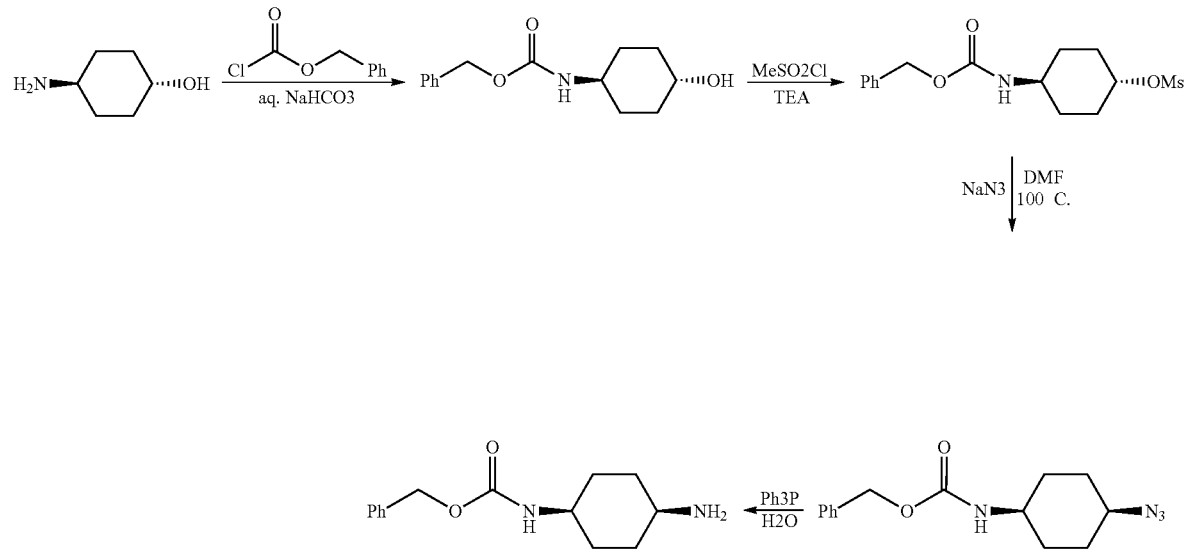

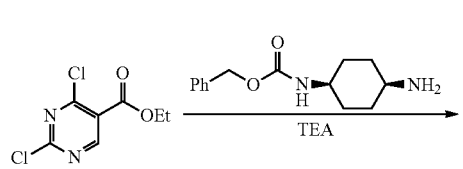
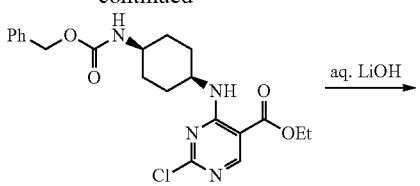
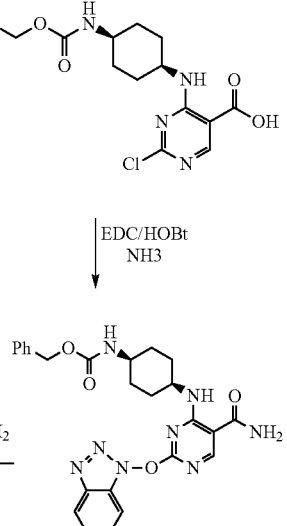
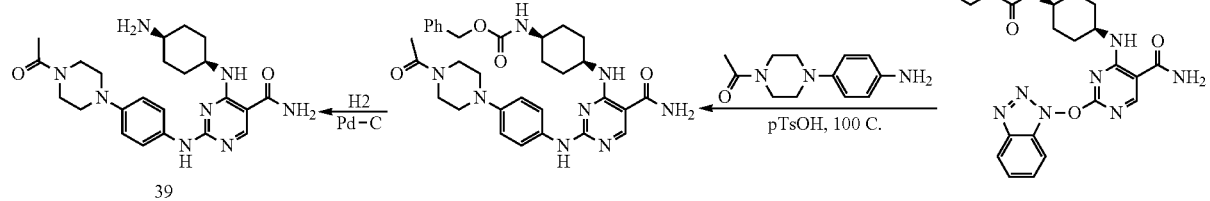

To a mixture of trans-4-aminocyclohexanol (2.07 g, 13.6 mmol) and NaHCO$_3$ (3.50 g, 41.7 mmol) in H$_2$O (20 mL) at room temperature, a solution of benzyl chloroformate (1.92 mL, 13.6 mmol) in dioxane (15 mL) was added. The mixture was stirred at room temperature for 20 h. The white precipitate was collected as benzyl (1R,4R)-4-hydroxycyclohexylcarbamate (3.37 g).

To a suspension of benzyl (1R,4R)-4-hydroxycyclohexylcarbamate (1.14 g, 4.58 mmol) and triethylamine (1.30 mL, 9.34 mmol) in CH$_2$Cl$_2$ (15 mL) at room temperature, methanesulfonyl chloride (0.425 mL, 5.49 mmol) was added. The mixture was stirred at room temperature for 20 h. More methanesulfonyl chloride (0.425 mL, 5.49 mmol) and triethylamine (1.00 mL) were added. Stirring was continued for 48 h. The reaction solution was washed with 5% NaHCO$_3$, then with 1 N HCl. The organic phase was separated, dried over Na2SO4, concentrated in vacuo to give (1R,4R)-4-(benzyloxycarbonyl)cyclohexyl methanesulfonate as a solid (1.13 g).

A mixture of (1R,4R)-4-(benzyloxycarbonyl)cyclohexyl methanesulfonate (1.13 g, 3.46 mmol) and NaN$_3$ (0.674 g, 10.4 mmol) in DMF (10 mL) was stirred at 100 C for 20 h. Water and EtOAc were added. The organic phase was separated, washed with water, dried over Na2SO4, concentrated in vacuo to give benzyl (1s,4s)-4-azidocyclohexylcarbamate (0.819 g).

To a solution of benzyl (1s,4s)-4-azidocyclohexylcarbamate (0.410 g, 1.50 mmol) in THF (8 mL) and H$_2$O (0.100 mL, 5.56 mmol) at room temperature, Ph$_3$P (0.590 g, 2.25 mmol) was added. The solution was stirred at 70 C for 20 h. EtOAc and 1N HCl were added. The aqueous phase was separated, washed with EtOAc. It was then basified with 5N NaOH to pH 12. The free amine product was extracted with EtOAc. The EtOAc solution was dried over Na2SO4, and concentrated in vacuo to give benzyl (1s,4s)-4-aminocyclohexylcarbamate (0.270 g).

A mixture of ethyl 2,4-dichloropyrimidine-5-carboxylate (0.241 g, 1.09 mmol), benzyl (1s,4s)-4-aminocyclohexylcarbamate (0.270 g, 1.09 mmol) and triethylamine (0.300 mL, 2.16 mmol) in CH$_3$CN (10 mL) was stirred at room temperature for 20 h. Water and EtOAc were added. The organic phase was separated, washed with 1N HCl, then with 5% NaHCO3, dried over Na2SO4, concentrated in vacuo to give ethyl 4-((1s,4s)-4-(benzyloxycarbonyl)cyclohexylamino)-2-chloropyrimidine-5-carboxylate (0.458 g).

To a solution of ethyl 4-((1s,4s)-4-(benzyloxycarbonyl) cyclohexylamino)-2-chloropyrimidine-5-carboxylate (0.458 g, 1.06 mmol) in THF (5 mL), aq. 1N LiOH (1.16 mL, 1.16 mmol) was added. After being stirred for 3 h, water (10 mL) was added. The solution was acidified with 1N HCl (2 mL) to pH 1-2. The product was extracted with EtOAc. The EtOAc solution was washed with brine, dried over Na$_2$SO$_4$, concentrated in vacuo to give 4-((1s,4s)-4-(benzyloxycarbonyl)cyclohexylamino)-2-chloropyrimidine-5-carboxylic acid as a solid (0.409 g).

To a solution of 4-((1s,4s)-4-(benzyloxycarbonyl)cyclohexylamino)-2-chloropyrimidine-5-carboxylic acid (0.409 g, 1.01 mmol) and HOBt (0.232 g, 1.52 mmol) in DMF (5 mL), EDC (0.291 g, 1.52 mmol) was added. After being stirred for 2 h, NH3 (0.5 M in dioxane, 6.0 mL, 3.00 mmol) was added. The mixture was stirred for 20 h. Water and EtOAc were added. The organic phase was separated, washed with 1N HCl, then with 5% NaHCO$_3$, dried over Na$_2$SO$_4$, concentrated in vacuo to give benzyl (1s,4s)-4-(2-(1H-benzo[d][1,2,3]triazol-1-yloxy)-5-carbamoylpyrimidin-4-ylamino)cyclohexylcarbamate as a solid (0.440 g).

A mixture of benzyl (1s,4s)-4-(2-(1H-benzo[d][1,2,3]triazol-1-yloxy)-5-carbamoylpyrimidin-4-ylamino)cyclohexylcarbamate (0.220 g, 0.438 mmol), 1-(4-(4-aminophenyl)piperazin-1-yl)ethanone (0.192 g, 0.877 mmol) and pTsOH monohydrate (0.083 g, 0.437 mmol) in dioxane (4 mL) was stirred at 100 C for 3 h. The mixture was then purified by HPLC to give benzyl (1s,4s)-4-(2-(4-(4-acetylpiperazin-1-yl)phenylamino)-5-carbamoylpyrimidin-4-ylamino)cyclohexylcarbamate (0.123 g).

A mixture of benzyl (1s,4s)-4-(2-(4-(4-acetylpiperazin-1-yl)phenylamino)-5-carbamoylpyrimidin-4-ylamino)cyclohexylcarbamate (0.123 g, 0.21 mmol) and Pd—C (10%, 40 mg) in MeOH (5 mL, containing three drops of 6N HCl), was hydrogenated under balloon H$_2$ for 4 h. The mixture was filtered through celite, and the filtrate was concentrated in vacuo to give the titled compound as a solid. MS 453.45 (M+H).

Example 42. 2-(4-(4-acetylpiperazin-1-yl)phenylamino)-4-(piperidin-4-ylmethylamino)pyrimidine-5-carboxamide

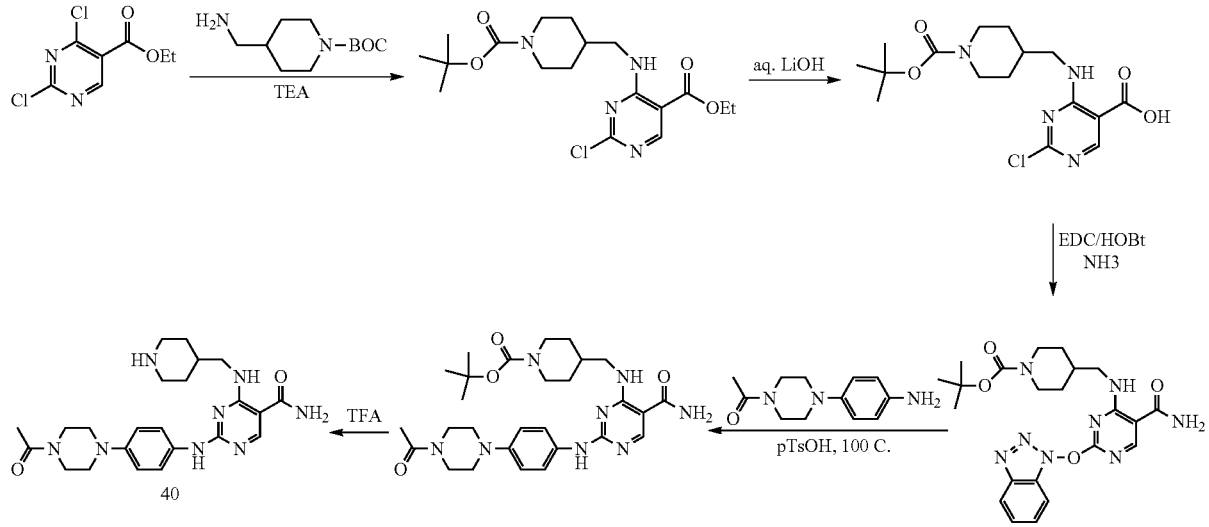

A mixture of ethyl 2,4-dichloropyrimidine-5-carboxylate (0.221 g, 1.00 mmol), 1-Boc-4-aminomethylpiperidine hydrochloride (0.251 g, 1.00 mmol) and triethylamine (0.556 mL, 4.00 mmol) in $CH_3CN$ (10 mL) was stirred at room temperature for 20 h. Water and EtOAc were added. The organic phase was separated, washed with 1N HCl, then with 5% $NaHCO_3$, dried over $Na_2SO_4$, concentrated in vacuo to give ethyl 4-((1-(tert-butoxycarbonyl)piperidin-4-yl)methylamino)-2-chloropyrimidine-5-carboxylate (0.390 g).

To a solution of ethyl 4-((1-(tert-butoxycarbonyl)piperidin-4-yl)methylamino)-2-chloropyrimidine-5-carboxylate (0.390 g, 0.979 mmol) in THF (5 mL), aq. 1N LiOH (1.10 mL, 1.10 mmol) was added. After being stirred for 20 h, water (10 mL) was added. The solution was acidified with 1N HCl (2 mL) to pH 1-2. The product was extracted with EtOAc. The EtOAc solution was washed with brine, dried over $Na_2SO_4$, concentrated in vacuo to give 4-((1-(tert-butoxycarbonyl)piperidin-4-yl)methylamino)-2-chloropyrimidine-5-carboxylic acid as a solid (0.353 g).

To a solution of 4-((1-(tert-butoxycarbonyl)piperidin-4-yl)methylamino)-2-chloropyrimidine-5-carboxylic acid (0.353 g, 0.953 mmol) and HOBt (0.219 g, 1.43 mmol) in DMF (5 mL), EDC (0.274 g, 1.43 mmol) was added. After being stirred for 1 h, $NH_3$ (0.5 M in dioxane, 5.5 mL, 2.75 mmol) was added. The mixture was stirred for 20 h. Water and EtOAc were added. The organic phase was separated, washed with 1N HCl, then with 5% $NaHCO_3$, dried over $Na_2SO_4$, concentrated in vacuo to give tert-butyl 4-((2-(1H-benzo[d][1,2,3]triazol-1-yloxy)-5-carbamoylpyrimidin-4-ylamino)methyl)piperidine-1-carboxylate as a solid (0.410 g).

A mixture of tert-butyl 4-((2-(1H-benzo[d][1,2,3]triazol-1-yloxy)-5-carbamoylpyrimidin-4-ylamino)methyl)piperidine-1-carboxylate (0.205 g, 0.438 mmol), 1-(4-(4-aminophenyl)piperazin-1-yl)ethanone (0.192 g, 0.877 mmol) and pTsOH monohydrate (0.166 g, 0.874 mmol) in dioxane (4 mL) was stirred at 100 C for 3 h. The mixture was then purified by HPLC to give tert-butyl 4-((2-(4-(4-acetylpiperazin-1-yl)phenylamino)-5-carbamoylpyrimidin-4-ylamino)methyl)piperidine-1-carboxylate (0.105 g).

A solution of tert-butyl 4-((2-(4-(4-acetylpiperazin-1-yl)phenylamino)-5-carbamoylpyrimidin-4-ylamino)methyl)piperidine-1-carboxylate (0.105 g, 0.190 mmol) in TFA (2 mL) was stirred at room temperature for 4 h. TFA was removed in vacuo. The residue was purified by HPLC to give the titled compound (90 mg). MS 453.41 (M+H).

Example 43. 2-(4-(4-acetylpiperazin-1-yl)phenylamino)-4-((1-acetylpiperidin-4-yl)methylamino)pyrimidine-5-carboxamide

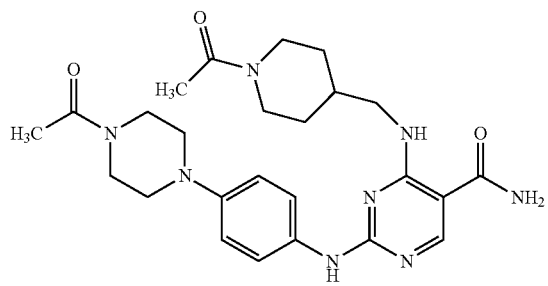 [SMILES: CC(=O)N1CCC(CNc2nc(Nc3ccc(N4CCN(C(C)=O)CC4)cc3)ncc2C(N)=O)CC1]

To a solution of 2-(4-(4-acetylpiperazin-1-yl)phenylamino)-4-(piperidin-4-ylmethylamino)pyrimidine-5-carboxamide (22 mg, 0.049 mmol) and triethylamine (0.040 mL, 0.29 mmol) in acetonitrile (2 mL) at room temperature, acetic anhydride (0.020 mL, 0.21 mmol) was added. The solution was stirred at room temperature for 1 h. The mixture was then purified by HPLC to give the titled compound (8 mg). MS 495.41 (M+H).

Example 44. 2-(4-(4-acetylpiperazin-1-yl)phenylamino)-4-((1-(methylsulfonyl)piperidin-4-yl)methylamino)pyrimidine-5-carboxamide

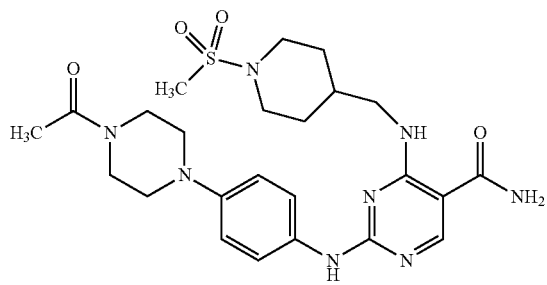 [SMILES: CC(=O)N1CCN(c2ccc(Nc3ncc(C(N)=O)c(NCC4CCN(S(C)(=O)=O)CC4)n3)cc2)CC1]

To a solution of 2-(4-(4-acetylpiperazin-1-yl)phenylamino)-4-(piperidin-4-ylmethylamino)pyrimidine-5-carboxamide (22 mg, 0.049 mmol) and triethylamine (0.040 mL, 0.29 mmol) in acetonitrile (2 mL) at room temperature, methanesulfonyl chloride (0.020 mL, 0.26 mmol) was added. The solution was stirred at room temperature for 1 h. The mixture was then purified by HPLC to give the titled compound (14 mg). MS 531.36 (M+H).

Example 45. 2-(4-(4-acetylpiperazin-1-yl)phenylamino)-4-((1-methylpiperidin-4-yl)methylamino)pyrimidine-5-carboxamide

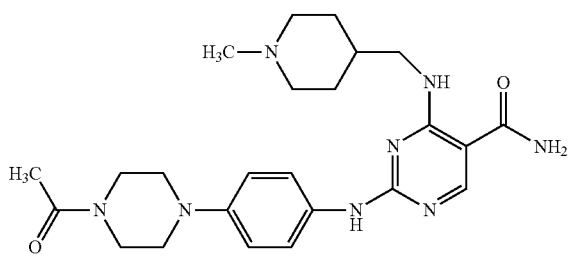 [SMILES: CC(=O)N1CCN(c2ccc(Nc3ncc(C(N)=O)c(NCC4CCN(C)CC4)n3)cc2)CC1]

To a solution of 2-(4-(4-acetylpiperazin-1-yl)phenylamino)-4-(piperidin-4-ylmethylamino)pyrimidine-5-carboxamide (25 mg, 0.055 mmol) and 37% aq. CH2O (0.020 mL, 0.27 mmol) in MeOH (1 mL) and CH3CO2H (0.1 mL) at room temperature, NaBH3CN (23 mg, 0.36 mmol) was added. The solution was stirred for 20 h. The mixture was then purified by HPLC to give the titled compound (20 mg). MS 467.46 (M+H).

Example 46. 2-(4-(4-acetylpiperazin-1-yl)phenylamino)-4-((1-carbamoylpiperidin-4-yl)methylamino)pyrimidine-5-carboxamide

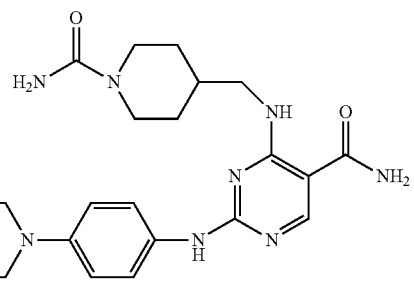

A mixture of 2-(4-(4-acetylpiperazin-1-yl)phenylamino)-4-(piperidin-4-ylmethylamino)pyrimidine-5-carboxamide (25 mg, 0.055 mmol) and KOCN (20 mg, 0.25 mmol) in acetic acid (2 mL) was stirred at 100 C for 4 h. The mixture was then purified by HPLC to give the titled compound (8 mg). MS 496.45 (M+H).

Example 47. benzyl 3-((2-(4-(4-acetylpiperazin-1-yl)phenylamino)-5-carbamoylpyrimidin-4-ylamino)methyl)piperidine-1-carboxylate

Example 48. 2-(4-(4-acetylpiperazin-1-yl)phenylamino)-4-(piperidin-3-ylmethylamino)pyrimidine-5-carboxamide Scheme 6:

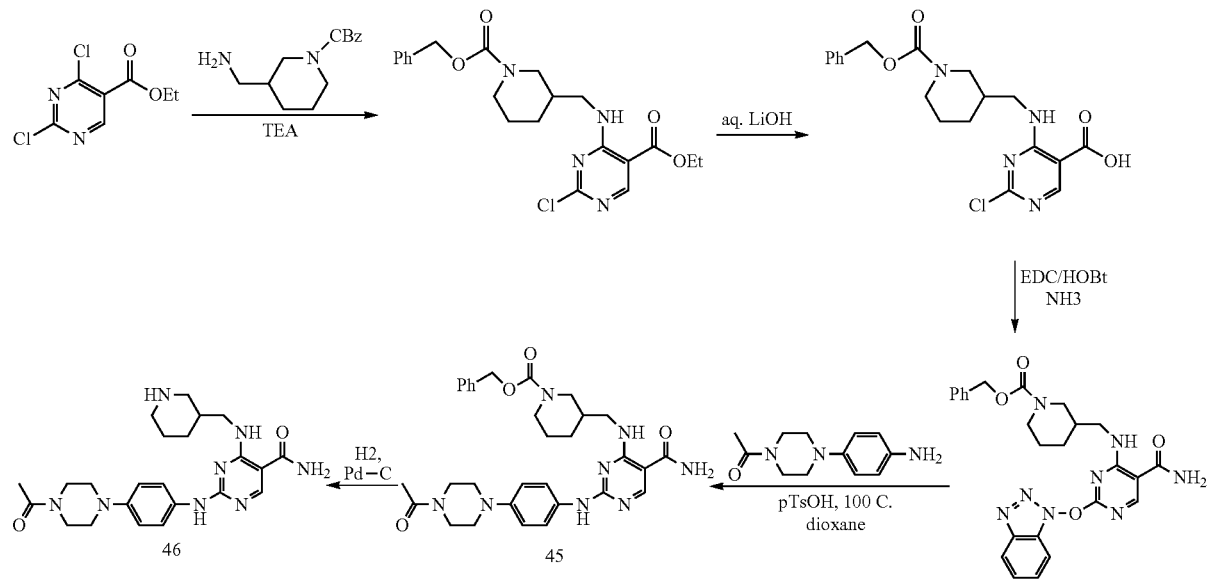

A mixture of ethyl 2,4-dichloropyrimidine-5-carboxylate (0.221 g, 1.00 mmol), 3-aminomethyl-1-N-CBz-piperidine (0.248 g, 1.00 mmol) and triethylamine (0.300 mL, 2.15 mmol) in CH3CN (10 mL) was stirred at room temperature for 20 h. Water and EtOAc were added. The organic phase was separated, washed with 1N HCl, then with 5% NaHCO3, dried over Na$_2$SO$_4$, concentrated in vacuo to give ethyl 4-((1-(benzyloxycarbonyl)piperidin-3-yl)methyl-amino)-2-chloropyrimidine-5-carboxylate (0.382 g).

To a solution of ethyl 4-((1-(benzyloxycarbonyl)piperi-din-3-yl)methylamino)-2-chloropyrimidine-5-carboxylate (0.382 g, 0.88 mmol) in THF (5 mL), aq. 1N LiOH (1.00 mL, 1.00 mmol) was added. After being stirred for 20 h, water (10 mL) was added. The solution was acidified with 1N HCl (2 mL) to pH 1-2. The product was extracted with EtOAc. The EtOAc solution was washed with brine, dried over Na2SO4, concentrated in vacuo to give 4-((1-(benzy-loxycarbonyl)piperidin-3-yl)methylamino)-2-chloropyrimi-dine-5-carboxylic acid (0.350 g).

To a solution of 4-((1-(benzyloxycarbonyl)piperidin-3-yl) methylamino)-2-chloropyrimidine-5-carboxylic acid (0.350 g, 0.87 mmol) and HOBt (0.200 g, 1.31 mmol) in DMF (5 mL), EDC (0.250 g, 1.30 mmol) was added. After being stirred for 1 h, NH3 (0.5 M in dioxane, 6.0 mL, 3.0 mmol) was added. The mixture was stirred for 20 h. Water and EtOAc were added. The organic phase was separated, washed with 1N HCl, then with 5% NaHCO3, dried over Na2SO4, concentrated in vacuo to give benzyl 3-((2-(1H-benzo[d][1,2,3]triazol-1-yloxy)-5-carbamoylpyrimidin-4-ylamino)methyl)piperidine-1-carboxylate (0.404 g).

A mixture of benzyl 3-((2-(1H-benzo[d][1,2,3]triazol-1-yloxy)-5-carbamoylpyrimidin-4-ylamino)methyl)piperi-dine-1-carboxylate (0.404 g, 0.805 mmol), 1-(4-(4-amino-phenyl)piperazin-1-yl)ethanone (0.220 g, 1.00 mmol) and pTsOH monohydrate (0.167 g, 0.879 mmol) in dioxane (8 mL) was stirred at 100 C for 3 h. The mixture was then purified by HPLC to give benzyl 3-((2-(4-(4-acetylpiper-azin-1-yl)phenylamino)-5-carbamoylpyrimidin-4-ylamino) methyl)piperidine-1-carboxylate 45 (0.270 g).

A mixture of benzyl 3-((2-(4-(4-acetylpiperazin-1-yl)phe-nylamino)-5-carbamoylpyrimidin-4-ylamino)methyl)piperi-dine-1-carboxylate (90 mg, 0.15 mmol) and Pd—C (10%, 30 mg) in MeOH (10 mL, containing 4 drops of 6N HCl) was hydrogenated under balloon H$_2$ for 4 h. The mixture was filtered through celite. The filtrate was concentrated in vacuo to give the titled compound 46 (56 mg). MS 453.45 (M+H).

Example 49. 2-(4-(4-acetylpiperazin-1-yl)phe-nylamino)-4-((1-carbamo

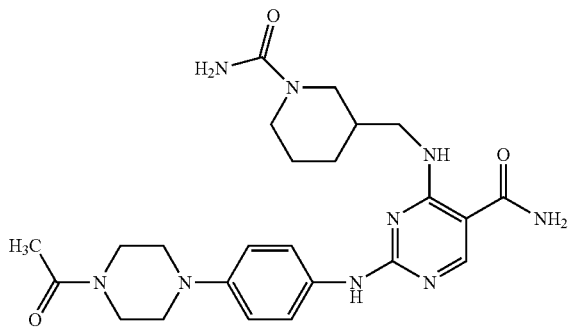 [SMILES: CC(=O)N1CCN(c2ccc(Nc3ncc(C(N)=O)c(NCC4CCCN(C(N)=O)C4)n3)cc2)CC1]

To a suspension of 2-(4-(4-acetylpiperazin-1-yl)phe-nylamino)-4-(piperidin-3-ylmethylamino)pyrimidine-5-car-boxamide (24 mg, 0.053 mmol) in CH3CN (1 mL), a solution of KOCN (27 mg, 0.33 mmol) in H2O (1 mL) was added. The suspension became clear. After being stirred at 70 C for 2 h, the mixture was purified by HPLC to give the titled compound (14 mg). MS 497 (M+H).

Example 50. 2-(4-(4-acetylpiperazin-1-yl)phe-nylamino)-4-(5-hydroxypentylamino)pyrimidine-5-carboxamide

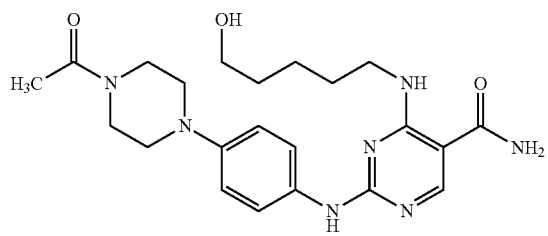 [SMILES: CC(=O)N1CCN(c2ccc(Nc3ncc(C(N)=O)c(NCCCCCO)n3)cc2)CC1]

The above compound was prepared using a procedure similar to that described in Example 1 using 5-aminopen-tanol in place of cyclobutyl amine. MS found for C$_{22}$H$_{31}$N$_7$O$_3$ as (M+H)$^+$ 442.0.

Example 51. (S)-2-(4-(4-acetylpiperazin-1-yl)phe-nylamino)-4-(1-hydroxypropan-2-ylamino)pyrimi-dine-5-carboxamide Scheme 7:

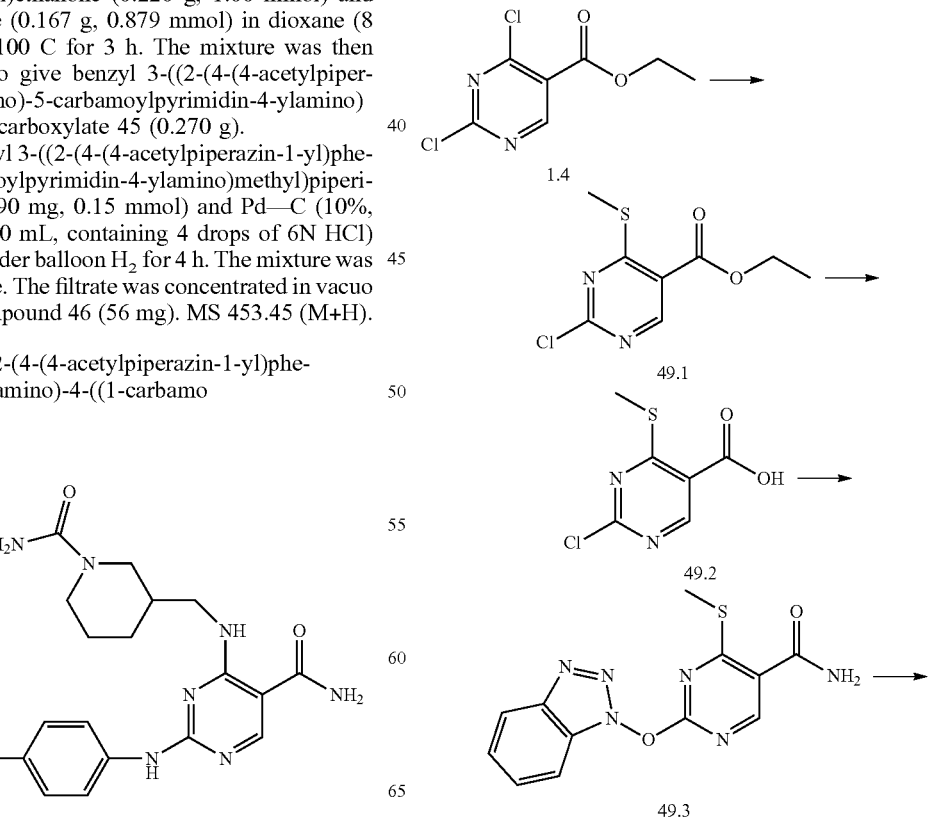

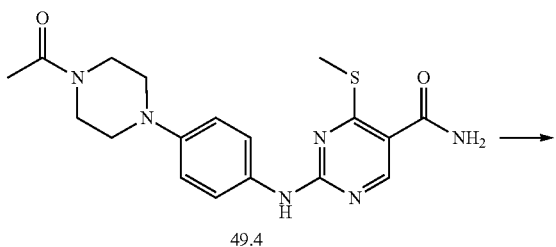

49.4

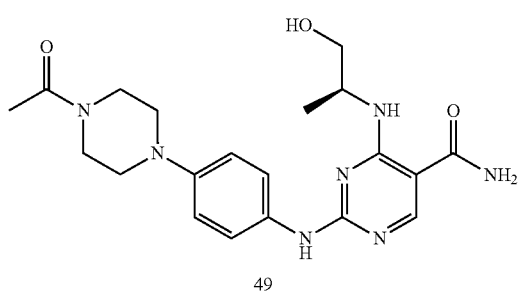

49

Step 1: Conversion of dichloropyrimide 1.4 to thiomethyl 49.1 was accomplished using a procedure similar to that described in Synthesis and evaluation of 2-{[2-(4-hydroxyphenyl)-ethyl]amino}pyrimidine-5-carboxamide derivatives as novel STAT6 inhibitors. Nagashima, Shinya; Yokota, Masaki; Nakai, Ei-ichi; Kuromitsu, Sadao; Ohga, Keiko; Takeuchi, Makoto; Tsukamoto, Shin-ichi; Ohta, Mitsuaki. Institute for Drug Discovery Research, Astellas Pharm Inc., Yodogawa-ku, Osaka, Japan. Bioorganic & Medicinal Chemistry (2007), 15(2), 1044-1055.

Steps 2-4 were accomplished using procedures similar to those described in Example 1.

Step 5: The above compound was prepared using a procedure similar to that described in Example 25, Step 2. MS found for $C_{20}H_{27}N_7O_3$ as $(M+H)^+$ 414.4.

Example 53 2-(4-(4-acetylpiperazin-1-yl)phenylamino)-4-(cyanomethylamino)pyrimidine-5-carboxamide

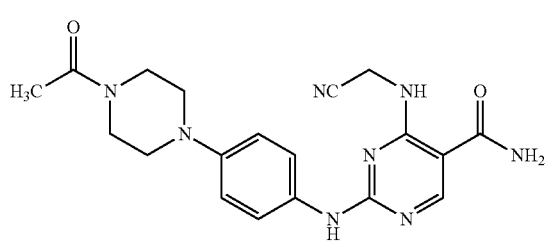 [SMILES: CC(=O)N1CCN(c2ccc(Nc3ncc(C(N)=O)c(NCC#N)n3)cc2)CC1]

The above compound was prepared using a procedure similar to that described in Example 51. MS found for $C_{19}H_{22}N_8O_2$ as $(M+H)^+$ 395.2. UV: λ=203, 273.

Example 54 (R)-2-(4-(4-acetylpiperazin-1-yl)phenylamino)-4-(1-hydroxypropan-2-ylamino)pyrimidine-5-carboxamide

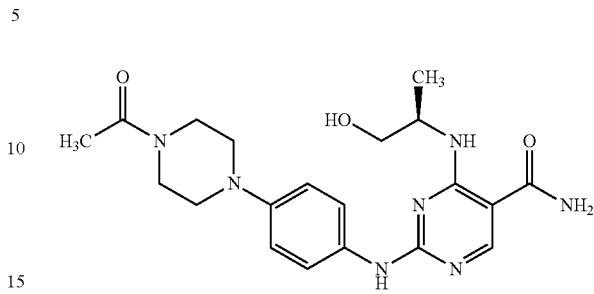

The above compound was prepared using a procedure similar to that described in Example 51. MS found for $C_{20}H_{27}N_7O_3$ as $(M+H)^+$ 414.3. UV: λ=201, 274

Example 55 2-(4-(4-acetyl-2-carbamoylpiperazin-1-yl)phenylamino)-4-(cyclopropylamino)pyrimidine-5-carboxamide

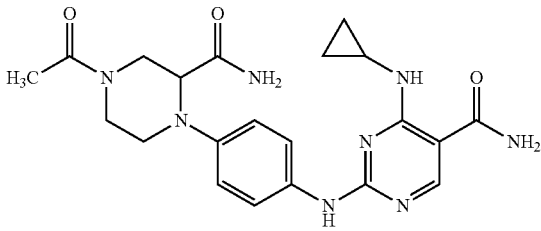 [SMILES: CC(=O)N1CCN(c2ccc(Nc3ncc(C(N)=O)c(NC4CC4)n3)cc2)C(C(N)=O)C1]

The above compound was prepared using a procedure similar to that described in Example 1, using cyclopropylamine in place of cyclobutylamine and Boc protected piperazine carboxylic acid in place of acetylpiperazine. MS found for $C_{21}H_{26}N_8O_3$ as $(M+H)^+$ 439.4.

Example 56. (R)-2-(4-(4-acetyl-3-methylpiperazin-1-yl)phenylamino)-4-(cyclopropylamino)pyrimidine-5-carboxamide

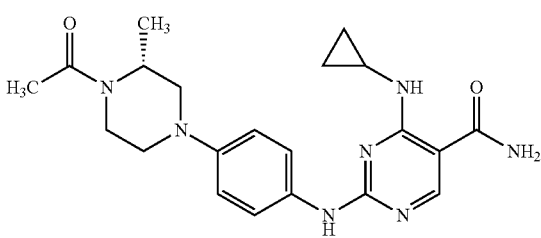 [SMILES: CC(=O)N1CCN(c2ccc(Nc3ncc(C(N)=O)c(NC4CC4)n3)cc2)C[C@H]1C]

The above compound was prepared using a procedure similar to that described in Example 1 with cyclopropylamine in place of cyclobutylamine. MS found for $C_{21}H_{27}N_7O_2$ as $(M+H)^+$ 410.4.

Example 57. 2-(4-(4-acetylpiperazin-1-yl)phenylamino)-4-(2-amino-2-oxoethylamino)pyrimidine-5-carboxamide

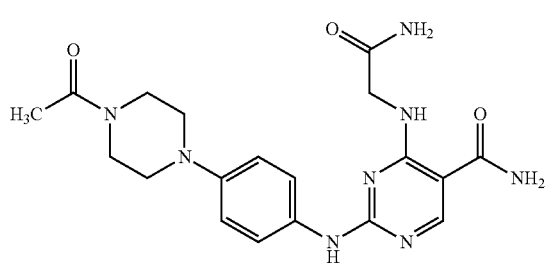 [SMILES: CC(=O)N1CCN(c2ccc(Nc3ncc(C(N)=O)c(NCC(N)=O)n3)cc2)CC1]

The above compound was prepared using a procedure similar to that described in Example 51. MS found for $C_{19}H_{24}N_8O_3$ as $(M+H)^+$ 413.4.

Example 58. 2-(4-(4-acetylpiperazin-1-yl)phenylamino)-4-(3-amino-3-oxopropylamino)pyrimidine-5-carboxamide

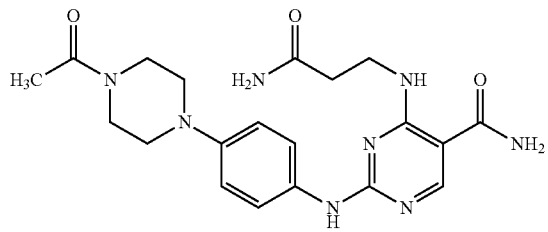 [SMILES: CC(=O)N1CCN(c2ccc(Nc3ncc(C(N)=O)c(NCCC(N)=O)n3)cc2)CC1]

The above compound was prepared using a procedure similar to that described in Example 51. MS found for $C_{20}H_{26}N_8O_3$ as $(M+H)^+$ 427.4. UV: λ=200, 270.

Example 59 2-(4-(4-acetylpiperazin-1-yl)phenylamino)-4-(4-amino-4-oxobutylamino)pyrimidine-5-carboxamide

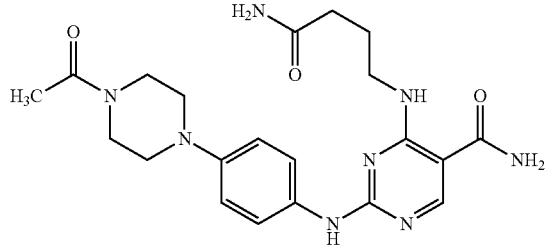 [SMILES: CC(=O)N1CCN(c2ccc(Nc3ncc(C(N)=O)c(NCCCC(N)=O)n3)cc2)CC1]

The above compound was prepared using a procedure similar to that described in Example 51. MS found for $C_{21}H_{28}N_8O_3$ as $(M+H)^+$ 441.3.

Example 60. 2-(4-(4-acetylpiperazin-1-yl)phenylamino)-4-(2-cyanoethylamino)pyrimidine-5-carboxamide

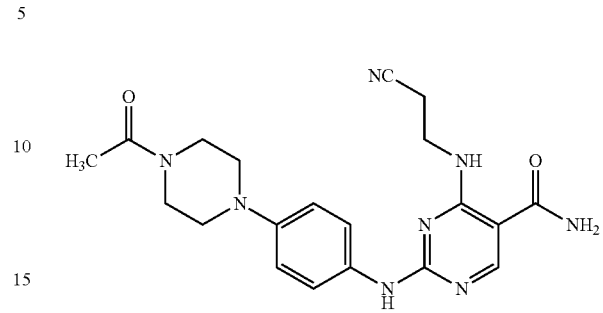

The above compound was prepared using a procedure similar to that described in Example 51. MS found for $C_{20}H_{24}N_8O_2$ as $(M+H)^+$ 409.3. UV: λ=202, 251.

Example 61. 2-(4-(4-acetylpiperazin-1-yl)phenylamino)-4-(1-carbamoylcyclopropylamino)pyrimidine-5-carboxamide

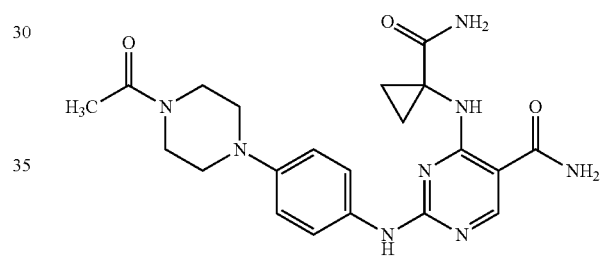

The above compound was prepared using a procedure similar to that described in Example 1. MS found for $C_{21}H_{26}N_8O_3$ as $(M+H)^+$ 439.3.

Example 62. 2-(4-(4-acetylpiperazin-1-yl)phenylamino)-4-(2-morpholinoethylamino)pyrimidine-5-carboxamide

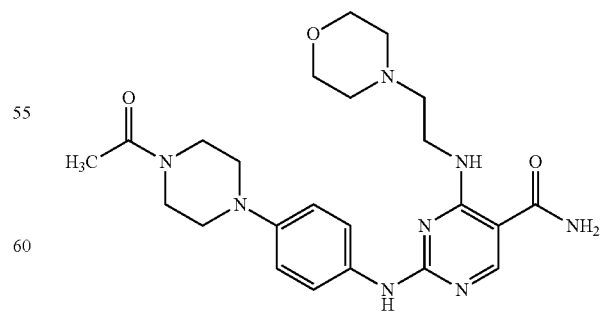

The above compound was prepared using a procedure similar to that described in Example 51. MS found for $C_{23}H_{32}N_8O_3$ as $(M+H)^+$ 469.4.

Example 63. 2-(4-(4-acetylpiperazin-1-yl)phenylamino)-4-((1R,2R)-2-carbamoylcyclopentylamino)pyrimidine-5-carboxamide

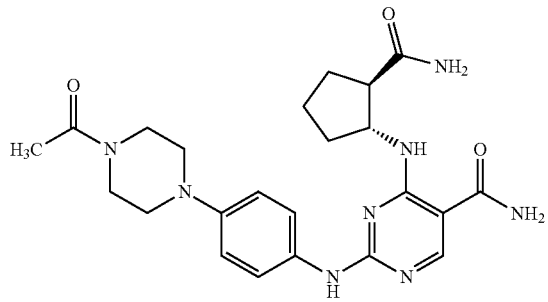 [SMILES: CC(=O)N1CCN(c2ccc(Nc3ncc(C(N)=O)c(N[C@@H]4CCC[C@H]4C(N)=O)n3)cc2)CC1]

The above compound was prepared using a procedure similar to that described in Example 51 using an amine prepared using the procedure from An Efficient Route to Either Enantiomer of trans-2-Aminocyclopentanecarboxylic Acid. LePlae, P. R.; Umezawa, N.; Lee, H.-S.; Gellman, S. H. J. Org. Chem.; (Note); 2001; 66(16); 5629-5632. MS found for $C_{23}H_{30}N_8O_3$ as $(M+H)^+$ 467.4. UV: $\lambda$=202, 258.

Example 64. 2-(4-(4-acetylpiperazin-1-yl)phenylamino)-4-(-2-trans-phenylcyclopropylamino)pyrimidine-5-carboxamide

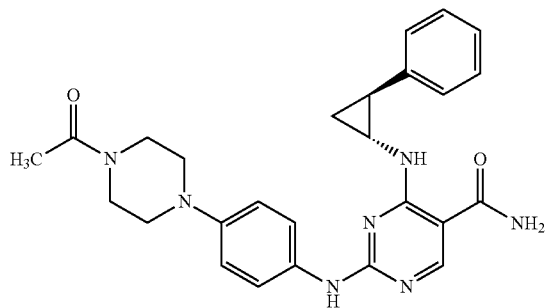 [SMILES: CC(=O)N1CCN(c2ccc(Nc3ncc(C(N)=O)c(N[C@@H]4C[C@H]4c4ccccc4)n3)cc2)CC1]

The above compound was prepared using a procedure similar to that described in Example 51. MS found for $C_{26}H_{29}N_7O_2$ as $(M+H)^+$ 472.3.

Example 65. 2-(4-(4-acetylpiperazin-1-yl)phenylamino)-4-(3-hydroxypropylamino)pyrimidine-5-carboxamide

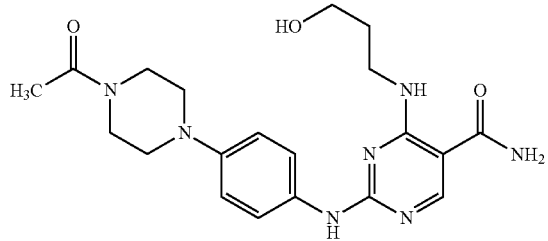 [SMILES: CC(=O)N1CCN(c2ccc(Nc3ncc(C(N)=O)c(NCCCO)n3)cc2)CC1]

The above compound was prepared using a procedure similar to that described in Example 51. MS found for $C_{20}H_{27}N_7O_3$ as $(M+H)^+$ 414.3.

Example 66. 2-(4-(4-acetylpiperazin-1-yl)phenylamino)-4-(4-hydroxybutylamino)pyrimidine-5-carboxamide

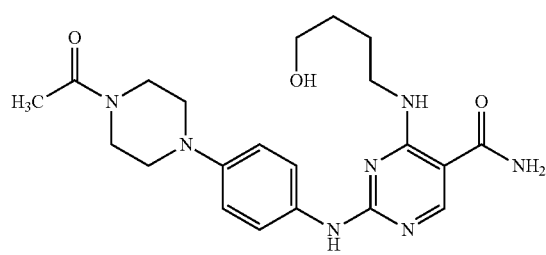 [SMILES: CC(=O)N1CCN(c2ccc(Nc3ncc(C(N)=O)c(NCCCCO)n3)cc2)CC1]

The above compound was prepared using a procedure similar to that described in Example 51. MS found for $C_{21}H_{29}N_7O_3$ as $(M+H)^+$ 428.4.

Example 67. 2-(4-(4-acetyl-2-(methylcarbamoyl)piperazin-1-yl)phenylamino)-4-(cyclopropylamino)pyrimidine-5-carboxamide

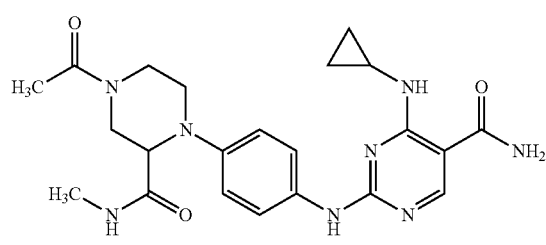 [SMILES: CNC(=O)C1CN(C(C)=O)CCN1c1ccc(Nc2ncc(C(N)=O)c(NC3CC3)n2)cc1]

The above compound was prepared using a procedure similar to that described in Example 1 using cyclopropylamine in place of cyclobutylamine and Boc protected piperazine carboxylic acid in place of acetylpiperazine. MS found for $C_{22}H_{28}N_8O_3$ as $(M+H)^+$ 453.3.

Example 69. (R)-2-(4-(4-acetylpiperazin-1-yl)phenylamino)-4-(2,3-dihydroxypropylamino)pyrimidine-5-carboxamide

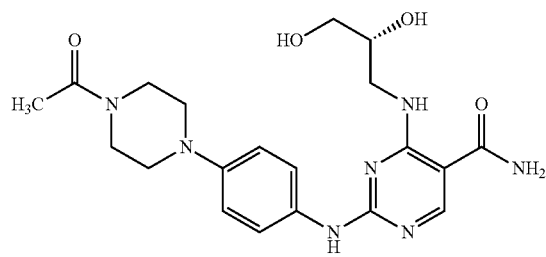 [SMILES: CC(=O)N1CCN(c2ccc(Nc3ncc(C(N)=O)c(NC[C@@H](O)CO)n3)cc2)CC1]

The above compound was prepared using a procedure similar to that described in Example 51. MS found for $C_{20}H_{27}N_7O_4$ as $(M+H)^+$ 430.3.

Example 70. 2-(4-(4-acetylpiperazin-1-yl)phenylamino)-4-((1R,3R)-3-carbamoylcyclopentylamino)pyrimidine-5-carboxamide

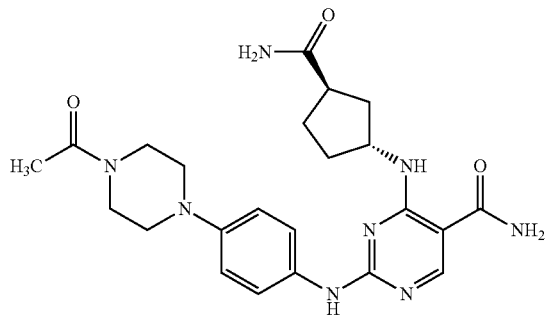 [SMILES: CC(=O)N1CCN(c2ccc(Nc3ncc(C(N)=O)c(N[C@@H]4CC[C@@H](C(N)=O)C4)n3)cc2)CC1]

The above compound was prepared using a procedure similar to that described in Example Example 51 using an amine derived Boc protected (1,R,3R)-3-aminocyclopentane carboxylic acid. MS found for $C_{23}H_{30}N_8O_3$ as $(M+H)^+$ 467.4.

Example 71. methyl 4-(4-(5-carbamoyl-4-(cyclopropylamino)pyrimidin-2-ylamino)phenyl)piperazine-1-carboxylate

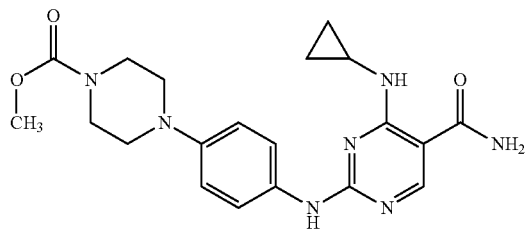 [SMILES: COC(=O)N1CCN(c2ccc(Nc3ncc(C(N)=O)c(NC4CC4)n3)cc2)CC1]

The above compound was prepared using a procedure similar to that described in Example 1 using cyclopropylamine in place of cyclobutylamine and a suitable aniline. MS found for $C_{20}H_{25}N_7O_3$ as $(M+H)^+$ 412.3.

Example 72 2-(4-(4-acetylpiperazin-1-yl)phenylamino)-4-(2-oxo-1,2,3,4-tetrahydroquinolin-6-ylamino)pyrimidine-5-carboxamide

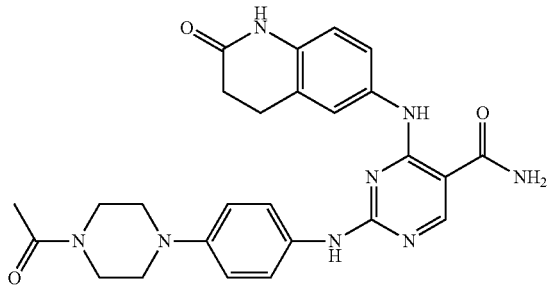 [SMILES: CC(=O)N1CCN(c2ccc(Nc3ncc(C(N)=O)c(Nc4ccc5c(c4)CCC(=O)N5)n3)cc2)CC1]

The titled compound was synthesized analogously by using 6-amino-3,4-dihydroquinolin-2(1H)-one. MS 501.3 (M+H); UV: λ=207.8, 293.8.

Example 73. 4-((1s,4s)-4-aminocyclohexylamino)-2-(4-(piperazin-1-yl)phenylamino)pyrimidine-5-carboxamide Scheme 8:

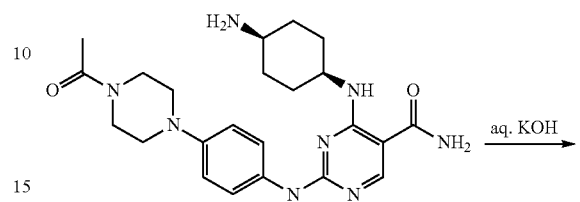

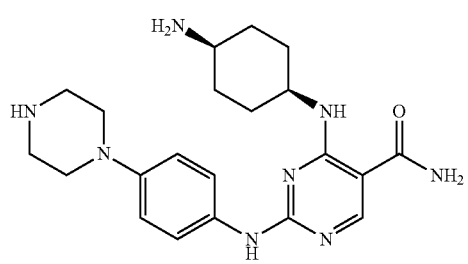

To a solution of 2-(4-(4-acetylpiperazin-1-yl)phenylamino)-4-((1s,4s)-4-aminocyclohexylamino)pyrimidine-5-carboxamide (52 mg, 0.12 mmol) in EtOH (3 mL), aq. 3M KOH (1.0 mL, 3.0 mmol) was added. The mixture was stirred at 85 C for 4 h., then at 70 C for 20 h. It was concentrated in vacuo. The residue was acidified with acetic acid (2 mL) before it was purified by HPLC to give the titled compound (25 mg). MS 411.43 (M+H); UV: λ=228.5, 285.3.

Example 74. (R)-2-(4-(4-acetyl-2-methylpiperazin-1-yl)phenylamino)-4-(cyclopropylamino)pyrimidine-5-carboxamide

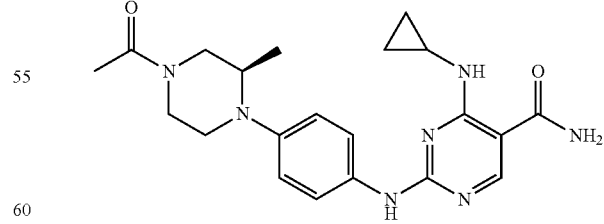

The above compound was prepared using a procedure similar to that described in Scheme 1 using cyclopropylamine in place of cyclobutylamine. MS found for $C_{21}H_{27}N_7O_2$ as $(M+H)^+$ 410.4. UV: λ=209, 265.

Example 75. (R)-2-(4-(4-acetyl-2-methylpiperazin-1-yl)phenylamino)-4-(2,2,2-trifluoroethylamino)pyrimidine-5-carboxamide

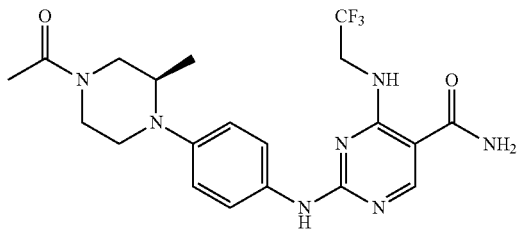 [SMILES: CC(=O)N1CCN(c2ccc(Nc3ncc(C(N)=O)c(NCC(F)(F)F)n3)cc2)[C@H](C)C1]

The above compound was prepared using a procedure similar to that described in Scheme 1 using trifluoroethylamine in place of cyclobutylamine. MS found for $C_{20}H_{24}F_3N_7O_2$ as $(M+H)^+$ 452.4. UV: $\lambda$=216, 276.

Example 76. (S)-2-(4-(4-acetyl-2-methylpiperazin-1-yl)phenylamino)-4-(2,2,2-trifluoroethylamino)pyrimidine-5-carboxamide

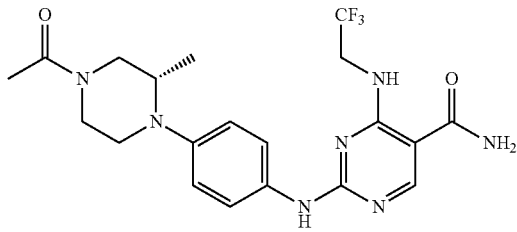 [SMILES: CC(=O)N1CCN(c2ccc(Nc3ncc(C(N)=O)c(NCC(F)(F)F)n3)cc2)[C@@H](C)C1]

The above compound was prepared using a procedure similar to that described in Scheme 1 using trifluoroethylamine in place of cyclobutylamine. MS found for $C_{20}H_{24}F_3N_7O_2$ as $(M+H)^+$ 452.4. UV: $\lambda$=201, 274.

Example 77. 2-(4-(4-carbamoylpiperazin-1-yl)phenylamino)-4-(cyclobutylamino)pyrimidine-5-carboxamide

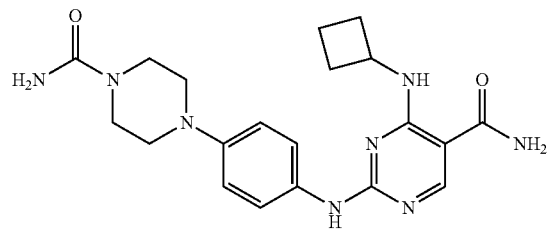 [SMILES: NC(=O)c1cnc(Nc2ccc(N3CCN(C(N)=O)CC3)cc2)nc1NC1CCC1]

The above compound was prepared using a procedure similar to that described in Example 1. MS found for $C_{20}H_{26}N_8O_2$ as $(M+H)^+$ 411.2. UV: $\lambda$=204, 262.

Example 78. 4-(cyclobutylamino)-2-(4-(4-(dimethylcarbamoyl)piperazin-1-yl)phenylamino)pyrimidine-5-carboxamide

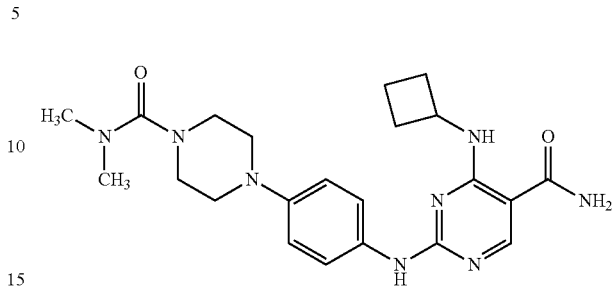

The above compound was prepared using a procedure similar to that described in Example 1. MS found for $C_{22}H_{30}N_8O_2$ as $(M+H)^+$ 439.3. UV: $\lambda$=206, 263.

Example 79. 2-(6-(4-acetylpiperazin-1-yl)pyridin-3-ylamino)-4-(2,2,2-trifluoroethylamino)pyrimidine-5-carboxamide

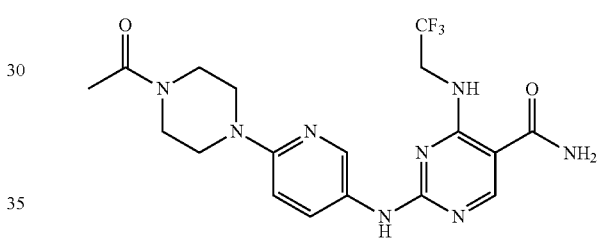

The above compound was prepared using a procedure similar to that described in Scheme 1 using trifluoroethylamine in place of cyclobutylamine. MS found for $C_{18}H_{21}F_3N_8O_2$ as $(M+H)^+$ 439.4. $^1$H NMR (CD$_3$OD, 400 MHz): δ 8.52 (s, 1H), 8.49 (s, 1H), 7.98 (dd, 1H), 7.23 (d, 1H), 4.52 (q, 2H), 3.74 (m, 6H), 3.64 (m, 2H), 2.15 (s, 3H).

Example 80. 2-(4-(4-acetylpiperazin-1-yl)-2-methylphenylamino)-4-(2,2,2-trifluoroethylamino)pyrimidine-5-carboxamide

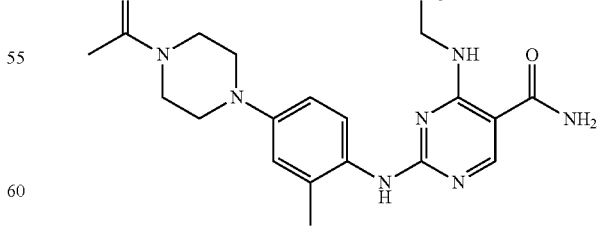

The above compound was prepared using a procedure similar to that described in Scheme 1 using trifluoroethylamine in place of cyclobutylamine. MS found for $C_{20}H_{24}F_3N_7O_2$ as $(M+H)^+$ 452.4. UV: $\lambda$=204, 227.

Example 81. (S)-2-(4-(4-(2-methoxyacetyl)-2-methylpiperazin-1-yl)phenylamino)-4-(2,2,2-trifluoroethylamino)pyrimidine-5-carboxamide

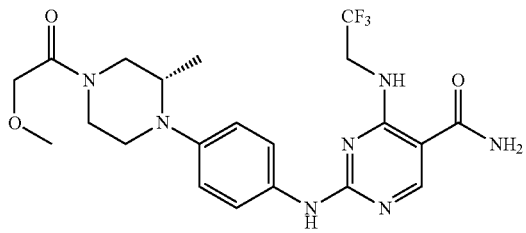 [SMILES: COCC(=O)N1CCN(c2ccc(Nc3ncc(C(N)=O)c(NCC(F)(F)F)n3)cc2)[C@@H](C)C1]

The above compound was prepared using a procedure similar to that described in Scheme 1 using trifluoroethylamine in place of cyclobutylamine. MS found for $C_{21}H_{26}F_3N_7O_3$ as $(M+H)^+$ 482.5. UV: $\lambda$=202, 274.

Example 82. (S)-methyl 4-(4-(5-carbamoyl-4-(2,2,2-trifluoroethylamino)pyrimidin-2-ylamino)phenyl)-3-methylpiperazine-1-carboxylate

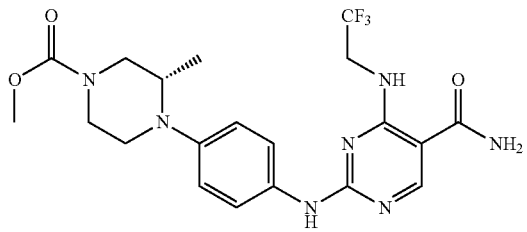 [SMILES: COC(=O)N1CCN(c2ccc(Nc3ncc(C(N)=O)c(NCC(F)(F)F)n3)cc2)[C@@H](C)C1]

The above compound was prepared using a procedure similar to that described in Scheme 1 using trifluoroethylamine in place of cyclobutylamine. MS found for $C_{20}H_{24}F_3N_7O_3$ as $(M+H)^+$ 468.5. UV: $\lambda$=202, 274.

Example 83. 2-(4-(4-acetylpiperazin-1-yl)phenylamino)-4-(1-methyl-1H-indazol-4-ylamino)pyrimidine-5-carboxamide

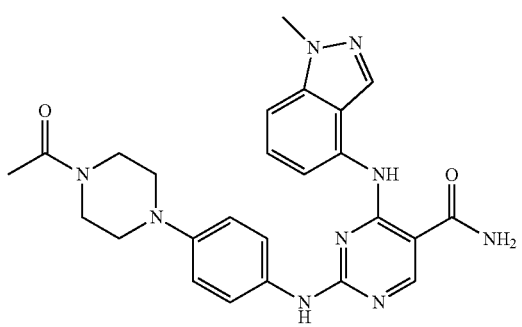 [SMILES: CC(=O)N1CCN(c2ccc(Nc3ncc(C(N)=O)c(Nc4cccc5c4cnn5C)n3)cc2)CC1]

The above compound was prepared using a procedure similar to that described in Example 48. MS found for $C_{25}H_{27}N_9O_2$ as $(M+H)^+$ 486.4. UV: $\lambda$=205.8, 299.4.

Example 84. 2-(4-(4-acetylpiperazin-1-yl)phenylamino)-4-(benzo[c]thiadiazol-4-ylamino) pyrimidine-5-carboxamide

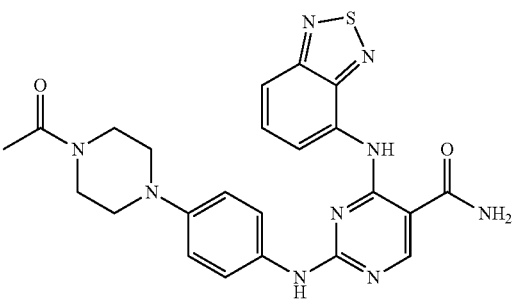 [SMILES: CC(=O)N1CCN(c2ccc(Nc3ncc(C(N)=O)c(Nc4cccc5nsnc45)n3)cc2)CC1]

The above compound was prepared using using a procedure similar to that described in Example 48. MS found for C23H23N9O2S as $(M+H)^+$ 490.4. UV: $\lambda$=236.2, 283.4, 305.6.

Example 85 4-(benzo[c]thiadiazol-4-ylamino)-2-(4-(4-propionylpiperazin-1-yl)phenylamino)-pyrimidine-5-carboxamide

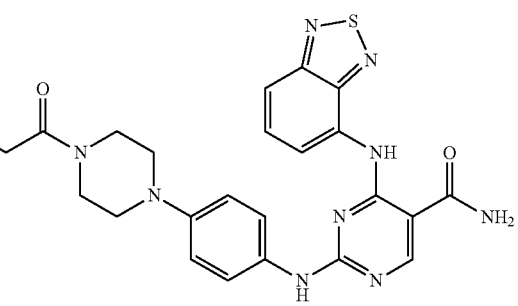

The above compound was prepared using using a procedure similar to that described in Example 48. MS found for C24H25N9O2S as $(M+H)^+$ −504.4. UV: $\lambda$=202.8, 236.2, 301.9, 314.9.

Example 86. 4-(1-methyl-1H-indol-4-ylamino)-2-(4-(4-propionylpiperazin-1yl)phenylamino)pyrimidine-5-carboxamide

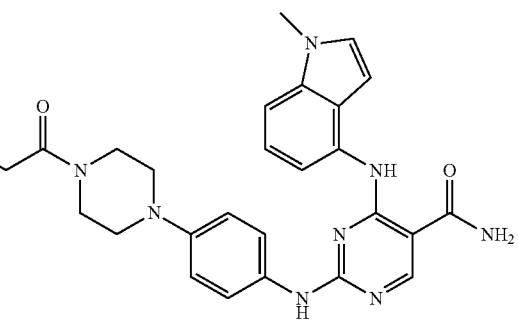

The title compound was prepared using the same synthetic scheme demonstrated in Example 33. MS found for $C_{27}H_{30}N_8O_2$ as (M+H)$^+$ 499.4. UV: λ=219.2.

Example 87. 4-(1,2-dimethyl-1H-indol-4-ylamino)-2-(4-(4-propionylpiperazin-1yl)phenylamino)pyrimidine-5-carboxamide

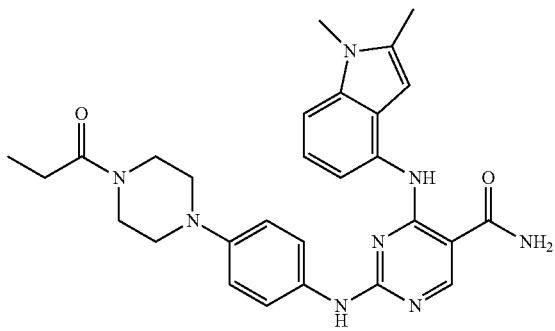 [SMILES: CCC(=O)N1CCN(c2ccc(Nc3ncc(C(N)=O)c(Nc4cccc5c4cc(C)n5C)n3)cc2)CC1]

The title compound was prepared using the same synthetic scheme demonstrated in Example 32. MS found for $C_{28}H_{32}N_8O_2$ as (M+H)$^+$ 513.4. UV: λ=208.6.

Example 88. 4-(1-methyl-1H-indol-4-ylamino)-2-(4-(4-propionylpiperazin-1yl)phenylamino)pyrimidine-5-carboxamide

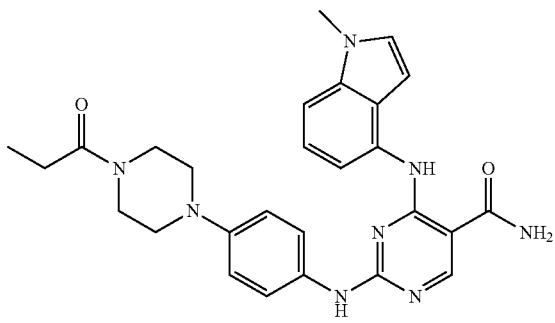 [SMILES: CCC(=O)N1CCN(c2ccc(Nc3ncc(C(N)=O)c(Nc4cccc5c4ccn5C)n3)cc2)CC1]

The title compound was prepared using the same synthetic scheme demonstrated in Example 33. MS found for $C_{27}H_{30}N_8O_2$ as (M+H)$^+$ 499.4. UV: λ=219.2.

Example 89. 4-(1,2-dimethyl-1H-indol-4-ylamino)-2-(4-(4-propionylpiperazin-1yl)phenylamino)pyrimidine-5-carboxamide

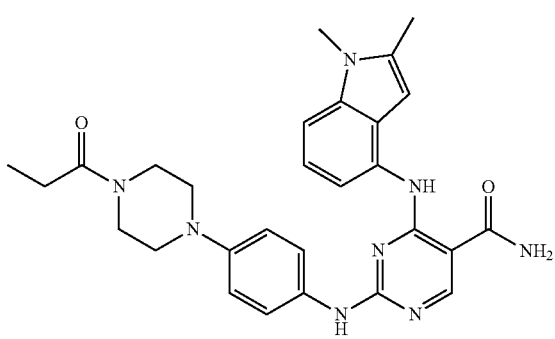 [SMILES: CCC(=O)N1CCN(c2ccc(Nc3ncc(C(N)=O)c(Nc4cccc5c4cc(C)n5C)n3)cc2)CC1]

The title compound was prepared using the same synthetic scheme demonstrated in Example 33. MS found for $C_{28}H_{32}N_8O_2$ as (M+H)$^+$ 513.4. UV: λ=208.6.

Example 92. 4-(cyclobutylamino)-2-(2-oxoindolin-5-ylamino)pyrimidine-5-carboxamide

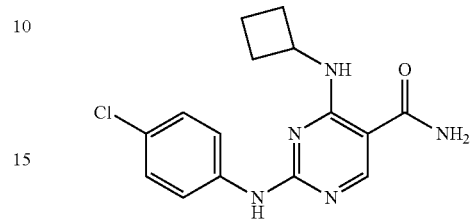

MS found for $C_{15}H_{16}N_5OCl$ as (M+H)$^+$ 318.0, 320.0. $^1$H NMR (DMSO-d$_6$, 400 MHz): δ 8.32 (s, 1H), 7.56 (d, 2H), 7.41 (d, 2H), 4.51 (m, 1H), 2.43 (m, 2H), 2.08 (m, 2H), 1.88 (m, 2H). UV: λ=205, 264.

Example 93. 2-(6-(4-acetylpiperazin-1-yl)pyridin-3-ylamino)-4-(cyclopropylamino)pyrimidine-5-carboxamide

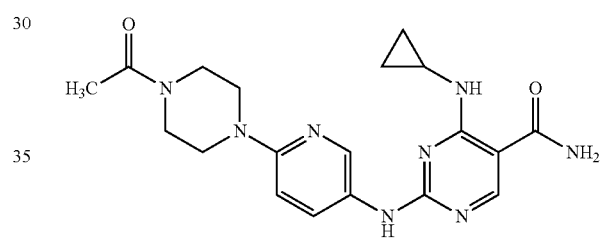

The above compound was prepared using an intermediate synthesized as described in Scheme 1 with cyclopropylamine in place of cyclobutylamine, and 1-(4-(5-aminopyridin-2-yl)piperazin-1-yl)ethanone (prepared from 1-acetylpiperazine and 2-chloro-5-nitropyridine in two steps). MS found for $C_{19}H_{24}N_8O_2$ as (M+H)$^+$ 397.0. $^1$H NMR (CD$_3$OD, 400 MHz): δ 8.62 (s, 1H), 8.41 (s, 1H), 8.08 (broad s, 1H), 7.17 (d, 1H) 3.64-3.78 (m, 8H), 2.98 (m, 1H), 2.15 (s, 3H), 0.96 (m, 2H), 0.70 (m, 2H).

Example 94 (R)-2-(4-(2-methyl-4-(methylsulfonyl)piperazin-1-yl)phenylamino)-4-(2,2,2-trifluoroethylamino)pyrimidine-5-carboxamide

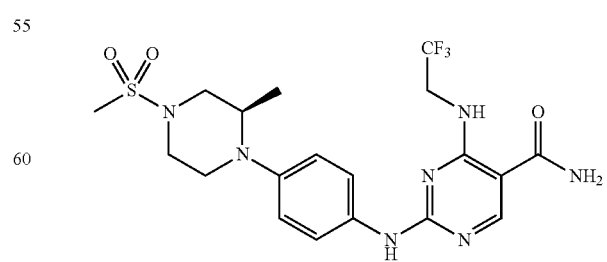

The above compound was prepared using a procedure similar to that described in Scheme 1 using trifluoroethylamine in place of cyclobutylamine. MS found for $C_{19}H_{24}F_3N_7O_3S$ as (M+H)⁺ 488.4.

Example 95. (S)-2-(4-(2-methyl-4-(methylsulfonyl)piperazin-1-yl)phenylamino)-4-(2,2,2-trifluoroethylamino)pyrimidine-5-carboxamide

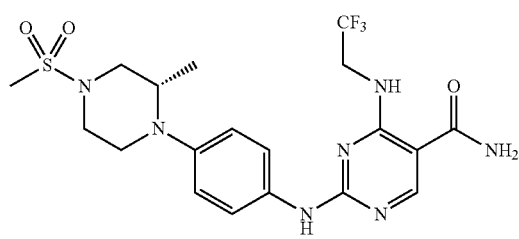 [SMILES: C[C@H]1CN(S(C)(=O)=O)CCN1c1ccc(Nc2ncc(C(N)=O)c(NCC(F)(F)F)n2)cc1]

The above compound was prepared using a procedure similar to that described in Scheme 1 using trifluoroethylamine in place of cyclobutylamine. MS found for $C_{19}H_{24}F_3N_7O_3S$ as (M+H)⁺ 488.3. UV: λ=201, 275.

Example 96. 4-(cyclopropylamino)-2-(4-(1-(methylsulfonyl)-1,2,3,6-tetrahydropyridin-4-yl)phenylamino)pyrimidine-5-carboxamide

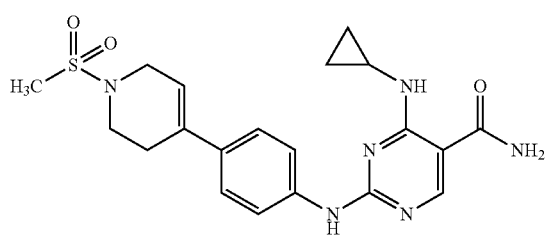 [SMILES: CS(=O)(=O)N1CC=C(c2ccc(Nc3ncc(C(N)=O)c(NC4CC4)n3)cc2)CC1]

The above compound was prepared using a procedure similar to that described in Scheme 1 using cyclopropylamine in place of cyclobutylamine. MS found for $C_{20}H_{24}N_6O_3S$ as (M+H)⁺ 429.3.

Example 97. 4-(cyclopropylamino)-2-(4-(1-(methylsulfonyl)piperidin-4-yl)phenylamino)pyrimidine-5-carboxamide

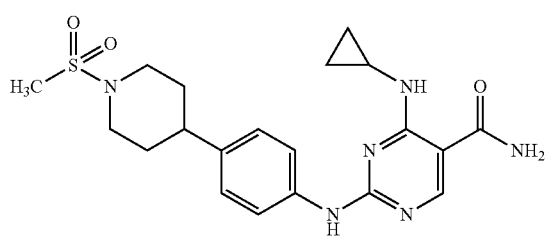 [SMILES: CS(=O)(=O)N1CCC(c2ccc(Nc3ncc(C(N)=O)c(NC4CC4)n3)cc2)CC1]

The above compound was prepared using a procedure similar to that described in Scheme 1 using cyclopropylamine in place of cyclobutylamine. MS found for $C_{20}H_{26}N_6O_3$ as (M+H)⁺ 431.3.

Example 98. 4-(cyclopropylamino)-2-(4-(4-(N-methylmethylsulfonamido)piperidin-1-yl)phenylamino)pyrimidine-5-carboxamide

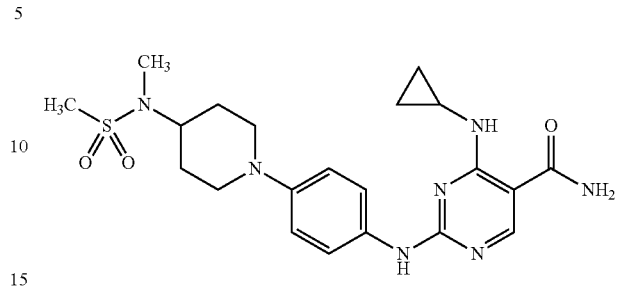

The above compound was prepared using a procedure similar to that described in Scheme 1, using cyclopropylamine in place of cyclobutylamine and an aniline derived from tert-butyl piperidin-4-ylcarbamate and 4-fluoronitrobenzene. MS found for $C_{21}H_{29}N_7O_3S$ as (M+H)⁺ 460.2. UV: λ=202, 272.

Example 99. 4-(cyclopropylamino)-2-(4-(4-(methylsulfonyl)piperazin-1-yl)phenylamino)pyrimidine-5-carboxamide

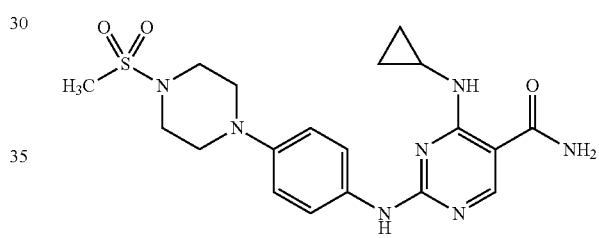

The above compound was prepared using a procedure similar to that described in Scheme 1, using cyclopropylamine in place of cyclobutylamine. MS found for $C_{19}H_{25}N_7O_3S$ as (M+H)+432.0.

Example 100a. 4-(cyclopropylamino)-2-(4-(4-(ethylsulfonyl)piperazin-1-yl)phenylamino)pyrimidine-5-carboxamide

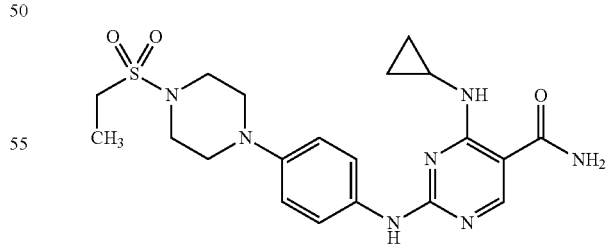

The above compound was prepared using a procedure similar to that described in Scheme 1, using cyclopropylamine in place of cyclobutylamine. MS found for $C_{20}H_{27}N_7O_3S$ as (M+H)⁺ 446.2. ¹H NMR (CD₃OD, 400 MHz): δ 8.37 (s, 1H), 7.59 (broad s, 2H), 7.09 (d, 2H), 3.45 (m, 4H), 3.50 (m, 4H), 3.12 (q, 2H), 3.07 (m, 1H), 1.35 (t, 3H), 0.93 (m, 2H), 0.73 (m, 2H). UV: λ=275.

Example 100b. 4-(cyclobutylamino)-2-(4-(4-(methylsulfonyl)piperazin-1-yl)phenylamino)pyrimidine-5-carboxamide

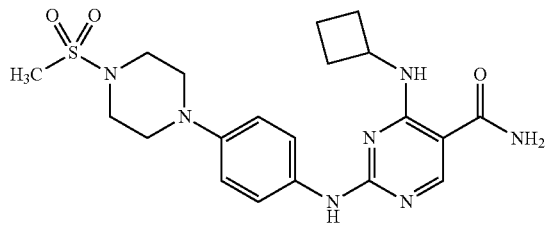 [SMILES: CS(=O)(=O)N1CCN(c2ccc(Nc3ncc(C(N)=O)c(NC4CCC4)n3)cc2)CC1]

The above compound was prepared using a procedure similar to that described in Example 1. MS found for $C_{20}H_{27}N_7O_3S$ as $(M+H)^+$ 446.0.

Example 100c. 2-(2-methyl-4-(4-(methylsulfonyl)piperazin-1-yl)phenylamino)-4-(2,2,2-trifluoroethylamino)pyrimidine-5-carboxamide

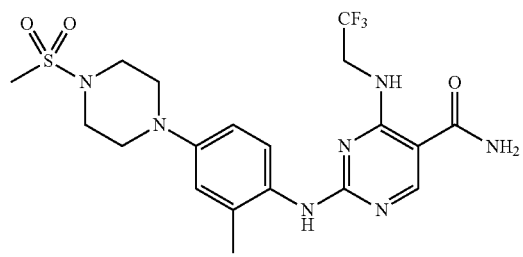 [SMILES: Cc1cc(N2CCN(S(C)(=O)=O)CC2)ccc1Nc1ncc(C(N)=O)c(NCC(F)(F)F)n1]

The above compound was prepared using a procedure similar to that described in Scheme 1 using trifluoroethylamine in place of cyclobutylamine and an aniline derived from 4-fluoro-2-methylnitrobenzene. MS found for $C_{19}H_{24}F_3N_7O_3S$ as $(M+H)^+$ 488.4. UV: λ=227.

Example 101a. (S)-2-(4-(4-(ethylsulfonyl)-2-methylpiperazin-1-yl)phenylamino)-4-(2,2,2-trifluoroethylamino)pyrimidine-5-carboxamide

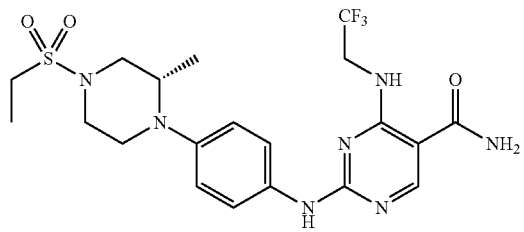 [SMILES: CCS(=O)(=O)N1CCN(c2ccc(Nc3ncc(C(N)=O)c(NCC(F)(F)F)n3)cc2)[C@@H](C)C1]

The above compound was prepared using a procedure similar to that described in Scheme 1 using trifluoroethylamine in place of cyclobutylamine. MS found for $C_{20}H_{26}F_3N_7O_3S$ as $(M+H)^+$ 502.4. UV: λ=203, 274.

Example 102. (S)-2-(4-(4-(cyclopropylsulfonyl)-2-methylpiperazin-1-yl)phenylamino)-4-(2,2,2-trifluoroethylamino)pyrimidine-5-carboxamide

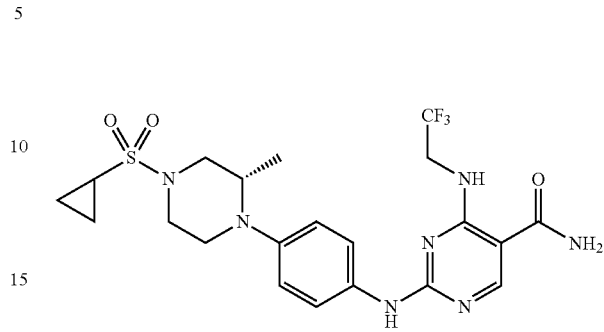

The above compound was prepared using a procedure similar to that described in Scheme 1 using trifluoroethylamine in place of cyclobutylamine. MS found for $C_{21}H_{26}F_3N_7O_3S$ as $(M+H)^+$ 514.5. UV: λ=202, 274.

Example 103. 4-(cyclobutylamino)-2-(4-sulfamoylphenylamino)pyrimidine-5-carboxamide

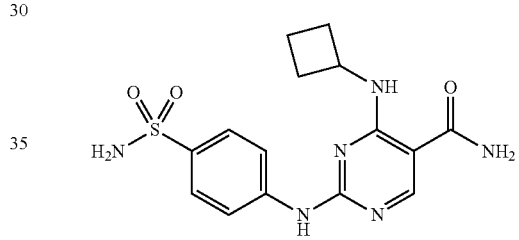

The above compound was prepared using 4-aminobenzenesulfonamide using a procedure similar to that described in Scheme 1. MS found for $C_{15}H_{18}N_6O_3S$ as $(M+H)^+$ 363.0.

Example 104. methyl 4-(5-carbamoyl-4-(cyclobutylamino)pyrimidin-2-ylamino)phenyl(methyl)carbamate

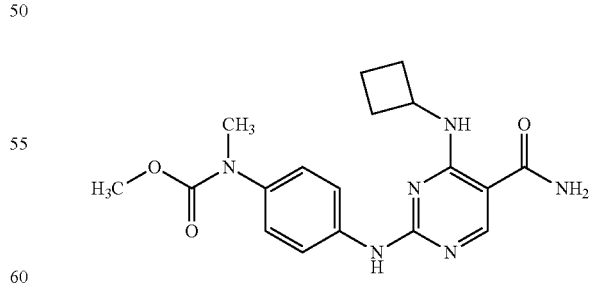

The above compound was prepared using methyl 4-aminophenyl(methyl)carbamate (synthesized from N-methyl 4-nitroaniline in two steps) using a procedure similar to that described in Scheme 1. MS found for $C_{18}H_{22}N_6O_3$ as $(M+H)^+$ 371.0. UV: λ=203, 263.

Example 105. isopropyl 4-(5-carbamoyl-4-(cyclobutylamino)pyrimidin-2-ylamino)phenyl(methyl)carbamate

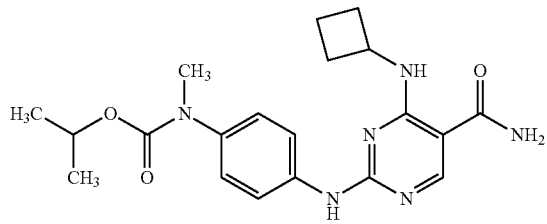 [SMILES: CC(C)OC(=O)N(C)c1ccc(Nc2ncc(C(N)=O)c(NC3CCC3)n2)cc1]

The above compound was prepared using isopropyl 4-aminophenyl(methyl)carbamate (synthesized from N-methyl 4-nitroaniline in two steps) using a procedure similar to that described in Scheme 1. MS found for $C_{20}H_{26}N_6O_3$ as $(M+H)^+$ 399.0. UV: $\lambda=277$.

Example 106. 4-(cyclobutylamino)-2-(4-(N,N-dimethylsulfamoyl)phenylamino)pyrimidine-5-carboxamide

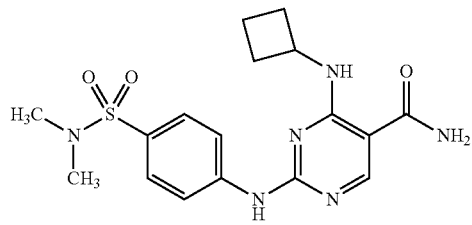 [SMILES: CN(C)S(=O)(=O)c1ccc(Nc2ncc(C(N)=O)c(NC3CCC3)n2)cc1]

The above compound was prepared using 4-amino-N,N-dimethylbenzenesulfonamide (prepared from 4-nitrobenzenesulfonic chloride and dimethyl amine followed by reduction) using a procedure similar to that described in Scheme 1. MS found for $C_{17}H_{22}N_6O_3S$ as $(M+H)^+$ 391.0. UV: $\lambda=213, 288$.

Example 107. methyl 4-(5-carbamoyl-4-(cyclopropylamino)pyrimidin-2-ylamino)phenyl(methyl)carbamate

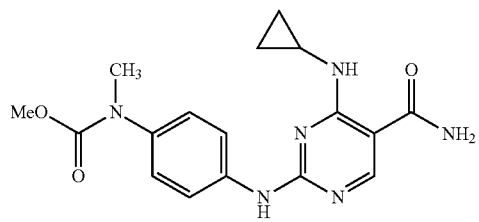 [SMILES: COC(=O)N(C)c1ccc(Nc2ncc(C(N)=O)c(NC3CC3)n2)cc1]

The above compound was prepared using an intermediate synthesized as described in Scheme 1 with cyclopropylamine in place of cyclobutylamine, and methyl 4-aminophenyl(methyl)carbamate (synthesized from N-methyl 4-nitroaniline in two steps) using a procedure similar to that described in Scheme 1. MS found for $C_{17}H_{20}N_6O_3$ as $(M+H)^+$ 357.0. UV: $\lambda=204, 273$.

Example 108. isopropyl 4-(5-carbamoyl-4-(cyclopropylamino)pyrimidin-2-ylamino)phenyl(methyl)carbamate

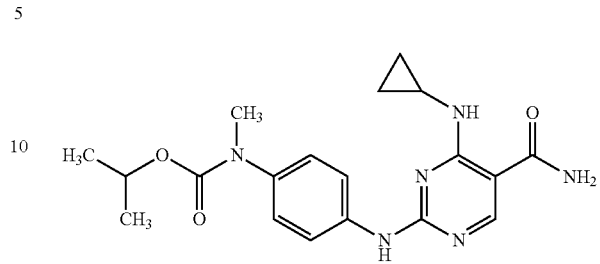

The above compound was prepared using an intermediate synthesized as described in Scheme 1 with cyclopropylamine in place of cyclobutylamine in Step 4, and isopropyl 4-aminophenyl(methyl)carbamate (synthesized from N-methyl 4-nitroaniline in two steps). MS found for $C_{19}H_{24}N_6O_3$ as $(M+H)^+$ 385.0. UV: $\lambda=201, 276$.

Example 109. 4-(cyclopropylamino)-2-(4-sulfamoylphenylamino)pyrimidine-5-carboxamide

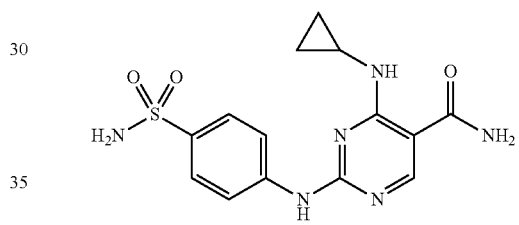

The above compound was prepared using an intermediate synthesized as described in Scheme 1 with cyclopropylamine in place of cyclobutylamine, and 4-aminobenzenesulfonamide. MS found for $C_{14}H_{16}N_6O_3S$ as $(M+H)^+$ 349.0. $^1$H NMR (DMSO-$d_6$, 400 MHz): δ 8.38 (s, 1H), 7.93 (d, 2H), 7.73 (d, 2H), 4.76 (m, 1H), 2.47 (m, 2H), 2.08 (m, 2H), 1.87 (m, 2H). UV: $\lambda=285$.

Example 110. 4-(cyclopropylamino)-2-(4-(1-methylureido)phenylamino)pyrimidine-5-carboxamide

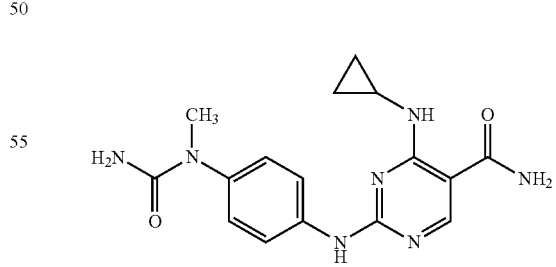

The above compound was prepared using a procedure similar to that described in Scheme 1, using cyclopropylamine in place of cyclobutylamine and an aniline prepared from protected N'Boc-N-methylphenylene diamine in two steps. MS found for $C_{16}H_{19}N_7O_2$ as $(M+H)^+$ 342.0. UV: $\lambda=205, 272$.

Example 111. 4-(cyclopropylamino)-2-(4-(methyl-sulfinyl)phenylamino)pyrimidine-5-carboxamide

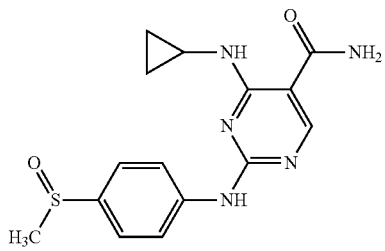 [SMILES: CS(=O)c1ccc(Nc2ncc(C(N)=O)c(NC3CC3)n2)cc1]

The above compound was prepared using a procedure similar to that described in Scheme 1, using cyclopropylamine in place of cyclobutylamine, and using 4-thiomethylaniline followed by oxidation using mCPBA. MS found for $C_{15}H_{17}N_5O_2S$ as $(M+H)^+$ 332.1.

Example 112 2-(4-(4-acetylpiperazine-1-carbonyl)phenylamino)-4-(cyclopropylamino)pyrimidine-5-carboxamide

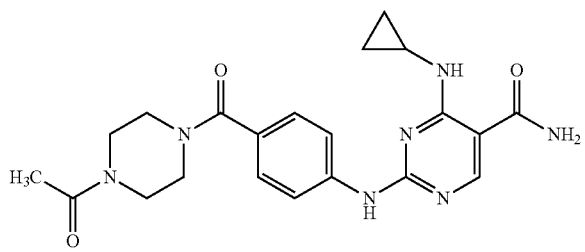 [SMILES: CC(=O)N1CCN(C(=O)c2ccc(Nc3ncc(C(N)=O)c(NC4CC4)n3)cc2)CC1]

The above compound was prepared using a procedure similar to that described in Scheme 1, using cyclopropylamine in place of cyclobutylamine and an aniline prepared from 4-nitrobenzoyl chloride and N-acetylpiperazine in two steps. MS found for $C_{21}H_{25}N_7O_3$ as $(M+H)^+$ 424.1.

Example 113. 2-(4-(1-acetylpiperidin-4-yl)phenylamino)-4-(cyclopropylamino)pyrimidine-5-carboxamide

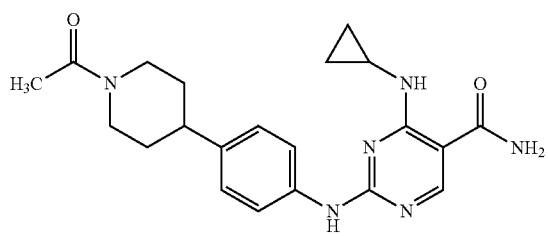 [SMILES: CC(=O)N1CCC(c2ccc(Nc3ncc(C(N)=O)c(NC4CC4)n3)cc2)CC1]

The above compound was prepared using a procedure similar to that described in Scheme 1 using cyclopropylamine in place of cyclobutylamine. MS found for $C_{21}H_{26}N_6O_2$ as $(M+H)^+$ 395.3.

Example 114. (cyclopropylamino)-2-(4-(4-(pyrrolidine-1-carbonyl)piperidin-1-yl)phenylamino)pyrimidine-5-carboxamide

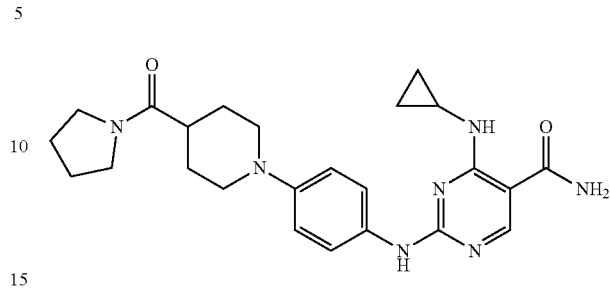

The above compound was prepared using a procedure similar to that described in Scheme 1 using cyclopropylamine in place of cyclobutylamine and an aniline derived from 4-fluoronitrobenzene and ethyl isonipecotate. MS found for $C_{24}H_{31}N_7O_2$ as $(M+H)^+$ 450.3. UV: $\lambda=271$.

Example 115. 4-(cyclopropylamino)-2-(4-(4-(piperidine-1-carbonyl)piperidin-1-yl)phenylamino)pyrimidine-5-carboxamide

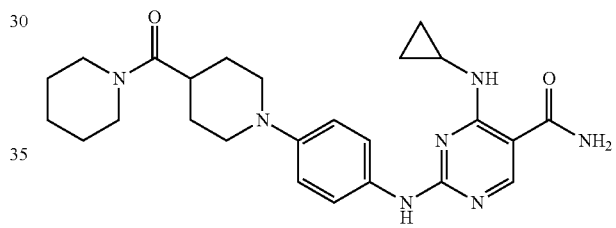

The above compound was prepared using a procedure similar to that described in Scheme 1 using cyclopropylamine in place of cyclobutylamine and an aniline derived from 4-fluoronitrobenzene and ethyl isonipecotate. MS found for $C_{25}H_{33}N_7O_2$ as $(M+H)^+$ 464.3. UV: $\lambda=201,271$.

Example 116. 4-(cyclopropylamino)-2-(4-(4-(morpholine-4-carbonyl)piperidin-1-yl)phenylamino)pyrimidine-5-carboxamide

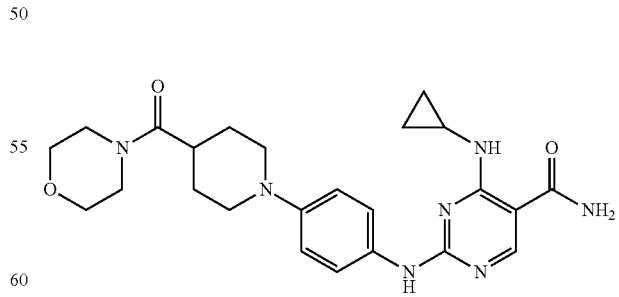

The above compound was prepared using a procedure similar to that described in Scheme 1 using cyclopropylamine in place of cyclobutylamine and an aniline derived from 4-fluoronitrobenzene and ethyl isonipecotate. MS found for $C_{24}H_{31}N_7O_3$ as $(M+H)^+$ 466.3. UV: $\lambda=201, 230, 285$.

Example 117. 4-(cyclopropylamino)-2-(4-(4-(cyclopropylsulfonyl)piperazin-1-yl)phenylamino)pyrimidine-5-carboxamide

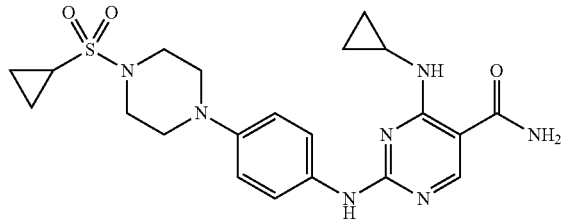 [SMILES: NC(=O)c1cnc(Nc2ccc(N3CCN(S(=O)(=O)C4CC4)CC3)cc2)nc1NC1CC1]

The above compound was prepared using a procedure similar to that described in Scheme 1. MS found for $C_{21}H_{27}N_7O_3S$ as $(M+H)^+$ 458.2. UV: $\lambda$=201, 231, 282.

Example 118. 2-(4-(4-acetyl-1,4-diazepan-1-yl)phenylamino)-4-(cyclopropylamino)pyrimidine-5-carboxamide

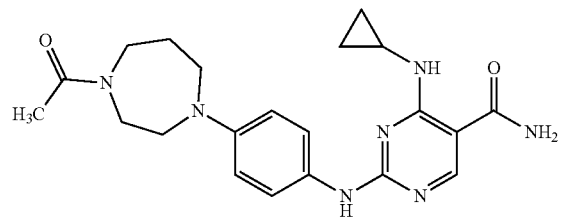 [SMILES: CC(=O)N1CCCN(c2ccc(Nc3ncc(C(N)=O)c(NC4CC4)n3)cc2)CC1]

The above compound was prepared using a procedure similar to that described in Scheme 1. MS found for $C_{21}H_{27}N_7O_2$ as $(M+H)^+$ 410.2. UV: $\lambda$=234, 258.

Example 119. 2-(4-(4-acetamidopiperidin-1-yl)phenylamino)-4-(cyclopropylamino)pyrimidine-5-carboxamide

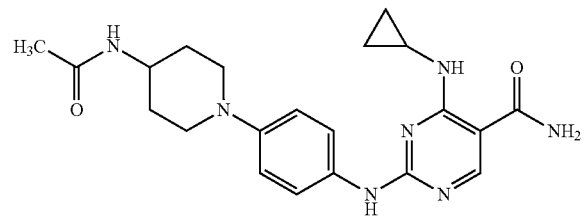 [SMILES: CC(=O)NC1CCN(c2ccc(Nc3ncc(C(N)=O)c(NC4CC4)n3)cc2)CC1]

The above compound was prepared using a procedure similar to that described in Scheme 1 using an aniline derived from 4-Boc aminopiperidine and 4-fluoronitrobenzene which was converted to the acetyl after Boc deprotection, then the nitro group was reduced to the aniline using hydrogenation. MS found for $C_{21}H_{27}N_7O_2$ as $(M+H)^+$ 410.2.

Example 120. 4-(cyclopropylamino)-2-(4-(2-oxopyridin-1(2H)-yl)phenylamino)pyrimidine-5-carboxamide

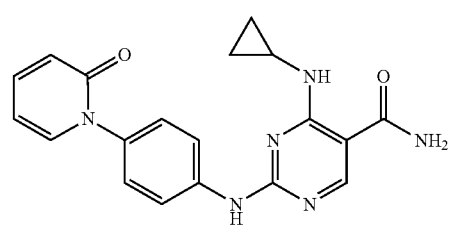 [SMILES: NC(=O)c1cnc(Nc2ccc(-n3ccccc3=O)cc2)nc1NC1CC1]

The above compound was prepared using a procedure similar to that described in Scheme 1 using an aniline derived from 4-iodoaniline and 2-hydroxypyridine which were coupled using CuI and a suitable ligand. MS found for $C_{21}H_{27}N_7O_2$ as $(M+H)^+$ 363.2. UV: $\lambda$=201, 274.

Example 121. 4-(cyclopropylamino)-2-(4-dioxothiomorpholinophenylamino)pyrimidine-5-carboxamide

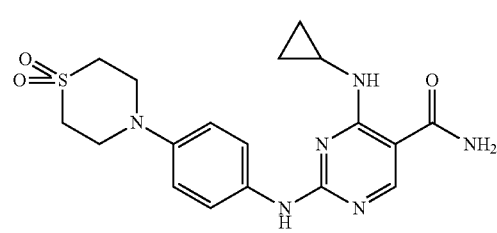 [SMILES: NC(=O)c1cnc(Nc2ccc(N3CCS(=O)(=O)CC3)cc2)nc1NC1CC1]

The above compound was prepared using a procedure similar to that described in Scheme 1. MS found for $C_{18}H_{22}N_6O_2S$ as $(M+H)^+$ 403.2.

Example 122. 4-(cyclopropylamino)-2-(4-(4-(2-methoxyethyl)piperazin-1-yl)phenylamino)pyrimidine-5-carboxamide

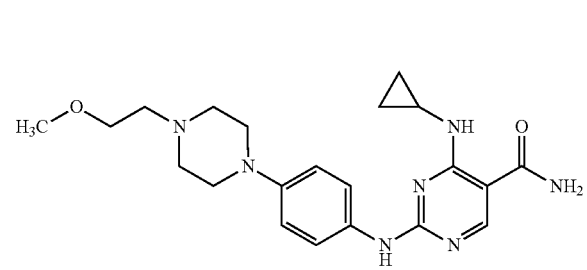 [SMILES: COCCN1CCN(c2ccc(Nc3ncc(C(N)=O)c(NC4CC4)n3)cc2)CC1]

The above compound was prepared using a procedure similar to that described in Scheme 1 using cyclopropylamine in place of cyclobutylamine and an aniline derived from 4-fluoronitrobenzene and 1-methoxyethylpiperazine in two steps. MS found for $C_{21}H_{29}N_7O_2$ as $(M+H)^+$ 412.0.

Example 123. 4-(cyclopropylamino)-2-(4-(4-(1-methylcyclopropyl)piperazin-1-yl)phenylamino)pyrimidine-5-carboxamide

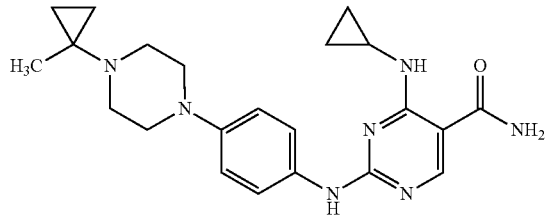 [SMILES: CC1(N2CCN(c3ccc(Nc4ncc(C(N)=O)c(NC5CC5)n4)cc3)CC2)CC1]

The above compound was prepared using a procedure similar to that described in Scheme 1 using cyclopropylamine in place of cyclobutylamine. MS found for $C_{22}H_{29}N_7O$ as $(M+H)^+$ 408.3.

Example 124. 4-(cyclopropylamino)-2-(4-(4-(N-methylacetamido)piperidin-1-yl)phenylamino)pyrimidine-5-carboxamide

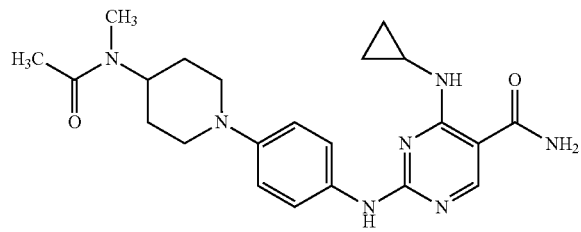 [SMILES: CC(=O)N(C)C1CCN(c2ccc(Nc3ncc(C(N)=O)c(NC4CC4)n3)cc2)CC1]

The above compound was prepared using a procedure similar to that described in Scheme 1 using cyclopropylamine in place of cyclobutylamine and an aniline described previously with the methylation of the N-acetyl group (CH₃I, Cs₂CO₃, DMF) being performed before the nitro reduction step. MS found for $C_{22}H_{29}N_7O_2$ as $(M+H)^+$ 424.2.

Example 125. 2-(4-(N-cyclobutylsulfamoyl)phenylamino)-4-(cyclopropylamino)pyrimidine-5-carboxamide

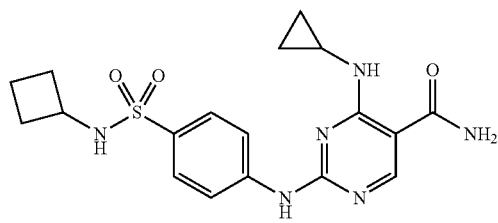 [SMILES: NC(=O)c1cnc(Nc2ccc(S(=O)(=O)NC3CCC3)cc2)nc1NC1CC1]

The above compound was prepared using a procedure similar to that described in Scheme 1 with cyclopropylamine in place of cyclobutylamine and an aniline derived from 4-nitrobenzenesulfonyl chloride and cyclobutylamine. MS found for $C_{18}H_{22}N_6O_3S$ as $(M+H)^+$ 403.0.

Example 126. 4-(cyclopropylamino)-2-(4-(N-cyclopropylsulfamoyl)phenylamino)pyrimidine-5-carboxamide

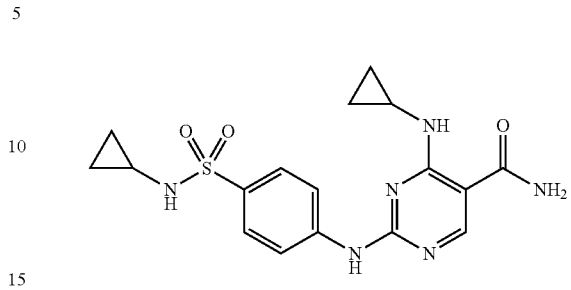

The above compound was prepared using a procedure similar to that described in Scheme 1 with cyclopropylamine in place of cyclobutylamine and an aniline similar to that described previously. MS found for $C_{17}H_{20}N_6O_3S$ as $(M+H)^+$ 389.0.

Example 127. 4-(cyclopropylamino)-2-(4-(N-(2-methoxyethyl)sulfamoyl)phenylamino)pyrimidine-5-carboxamide

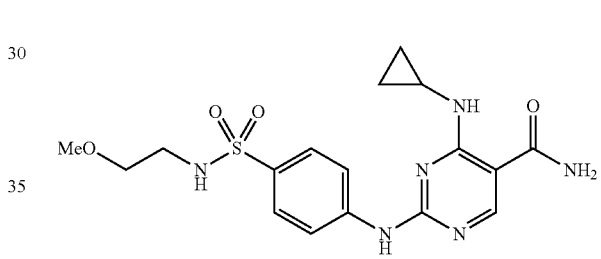

The above compound was prepared using a procedure similar to that described in Scheme 1 with cyclopropylamine in place of cyclobutylamine and an aniline similar to that described previously. MS found for $C_{17}H_{22}N_6O_4S$ as $(M+H)^+$ 407.0.

Example 128. 4-(cyclopropylamino)-2-(4-(N-(2-hydroxyethyl)sulfamoyl)phenylamino)pyrimidine-5-carboxamide

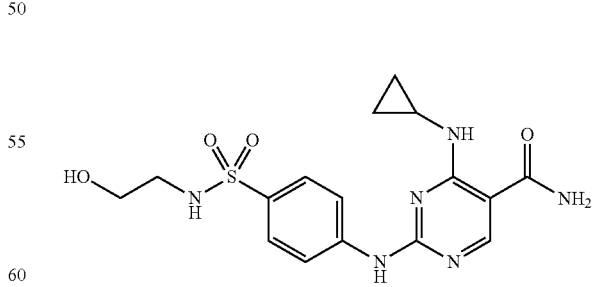

The above compound was prepared using a procedure similar to that described in Scheme 1 with cyclopropylamine in place of cyclobutylamine and an aniline similar to that described previously. MS found for $C_{16}H_{20}N_6O_4S$ as $(M+H)^+$ 393.0.

Example 129. 4-(cyclobutylamino)-2-(4-(methylsulfonyl)phenylamino)pyrimidine-5-carboxamide

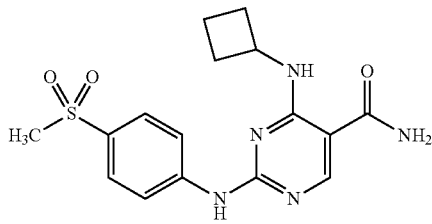 [SMILES: CS(=O)(=O)c1ccc(Nc2ncc(C(N)=O)c(NC3CCC3)n2)cc1]

The above compound was prepared using a procedure similar to that described in Scheme 1 with cyclopropylamine in place of cycobutylamine. MS found for $C_{16}H_{19}N_5O_3S$ as $(M+H)^+$ 362.1. UV: $\lambda=292$.

Example 130. 4-(cyclobutylamino)-2-(4-(piperazin-1-yl)phenylamino)pyrimidine-5-carboxamide

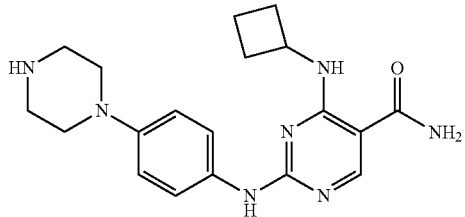 [SMILES: NC(=O)c1cnc(Nc2ccc(N3CCNCC3)cc2)nc1NC1CCC1]

The above compound was prepared using a procedure similar to that described in Scheme 1. MS found for $C_{19}H_{25}N_7O$ as $(M+H)^+$ 368.3. UV: $\lambda=203, 229, 256, 288$.

Example 131. 4-(cyclopropylamino)-2-(4-(4-(pyridin-2-yl)piperazin-1-yl)phenylamino)pyrimidine-5-carboxamide

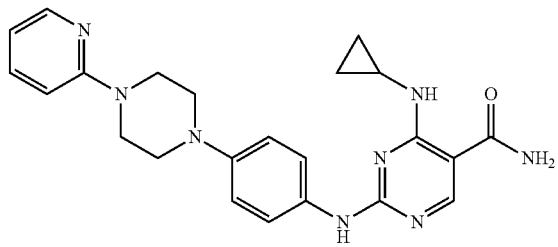 [SMILES: NC(=O)c1cnc(Nc2ccc(N3CCN(c4ccccn4)CC3)cc2)nc1NC1CC1]

The above compound was prepared using a procedure similar to that described in Scheme 1 with cyclopropylamine in place of cyclobutylamine. MS found for $C_{23}H_{26}N_8O$ as $(M+H)^+$ 431.4.

Example 132. 4-(cyclobutylamino)-2-(4-(methylsulfonyl)phenylamino)pyrimidine-5-carboxamide

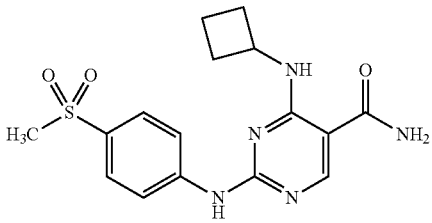 [SMILES: CS(=O)(=O)c1ccc(Nc2ncc(C(N)=O)c(NC3CCC3)n2)cc1]

The above compound was prepared using a procedure similar to that described in Example 1. MS found for $C_{16}H_{19}N_5O_3S$ as $(M+H)^+$ 362.1.

Example 133. 4-(cyclobutylamino)-2-(4-(piperazin-1-yl)phenylamino)pyrimidine-5-carboxamide

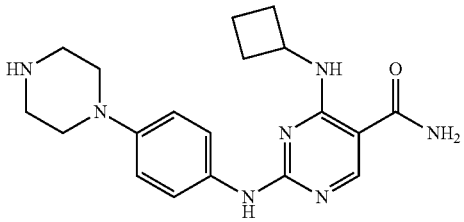 [SMILES: NC(=O)c1cnc(Nc2ccc(N3CCNCC3)cc2)nc1NC1CCC1]

The above compound was prepared using a procedure similar to that described in Example 1. MS found for $C_{19}H_{25}N_7O$ as $(M+H)^+$ 368.3.

Example 134. 4-(cyclopropylamino)-2-(4-(4-(pyridin-2-yl)piperazin-1-yl)phenylamino)pyrimidine-5-carboxamide

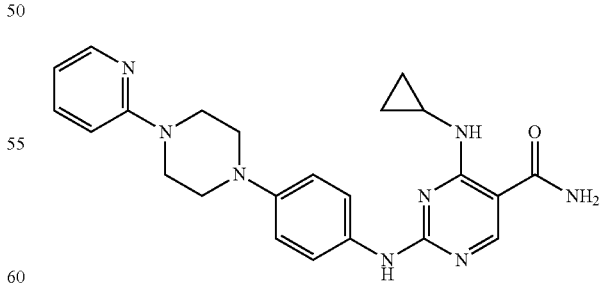

The above compound was prepared using a procedure similar to that described in Scheme 1 with cyclopropylamine in place of cyclobutylamine. MS found for $C_{23}H_{26}N_8O$ as $(M+H)^+$ 431.4.

Example 135. 2-(4-(4-(aminomethyl)piperidin-1-yl) phenylamino)-4-(cyclopropylamino)pyrimidine-5-carboxamide

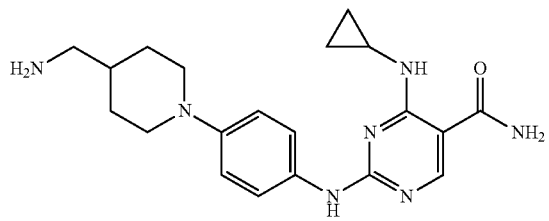 [SMILES: NCC1CCN(c2ccc(Nc3ncc(C(N)=O)c(NC4CC4)n3)cc2)CC1]

The above compound was prepared using a procedure similar to that described in Scheme 1 with cyclopropylamine in place of cyclobutylamine. MS found for $C_{20}H_{27}N_7O$ as $(M+H)^+$ 382.5.

Example 136. 4-(cyclopropylamino)-2-(4-(N-pyrimidin-2-ylsulfamoyl)phenylamino)pyrimidine-5-carboxamide

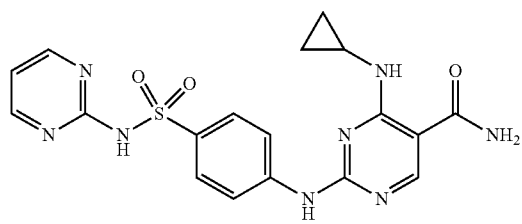 [SMILES: NC(=O)c1cnc(Nc2ccc(S(=O)(=O)Nc3ncccn3)cc2)nc1NC1CC1]

The above compound was prepared using a procedure similar to that described in Scheme 1 with cyclopropylamine in place of cyclobutylamine. MS found for $C_{18}H_{18}N_8O_3S$ as $(M+H)^+$ 427.0.

Example 137. 4-(cyclopropylamino)-2-(4-(N-thiazol-2-ylsulfamoyl)phenylamino)pyrimidine-5-carboxamide

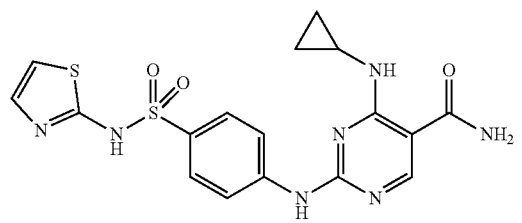 [SMILES: NC(=O)c1cnc(Nc2ccc(S(=O)(=O)Nc3nccs3)cc2)nc1NC1CC1]

The above compound was prepared using a procedure similar to that described in Scheme 1 with cyclopropylamine in place of cyclobutylamine. MS found for $C_{17}H_{17}N_7O_3S_2$ as $(M+H)^+$ 432.0.

Example 138. 4-(cyclopropylamino)-2-(4-(N-(5-methylisoxazol-3-yl)sulfamoyl)phenylamino)pyrimidine-5-carboxamide

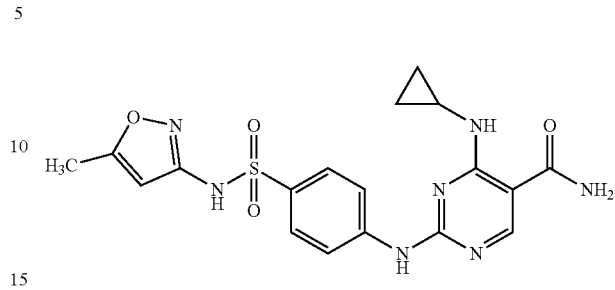

The above compound was prepared using a procedure similar to that described in Scheme 1 with cyclopropylamine in place of cyclobutylamine. MS found for $C_{18}H_{19}N_7O_4S$ as $(M+H)^+$ 430.0.

Example 139. 4-(cyclopropylamino)-2-(4-(N-(2,6-dimethylpyrimidin-4-yl)sulfamoyl)phenylamino) pyrimidine-5-carboxamide

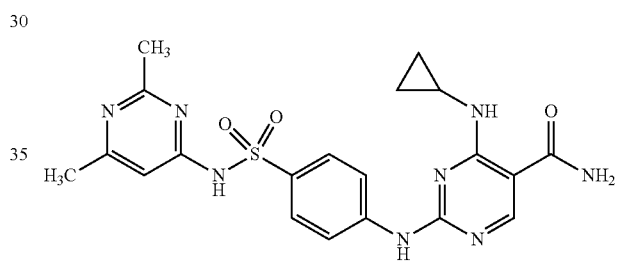

The above compound was prepared using a procedure similar to that described in Scheme 1 with cyclopropylamine in place of cyclobutylamine. MS found for $C_{20}H_{22}N_8O_3S$ as $(M+H)+455.0$.

Example 140. 4-(cyclobutylamino)-2-(4-(1-methylureido)phenylamino)pyrimidine-5-carboxamide

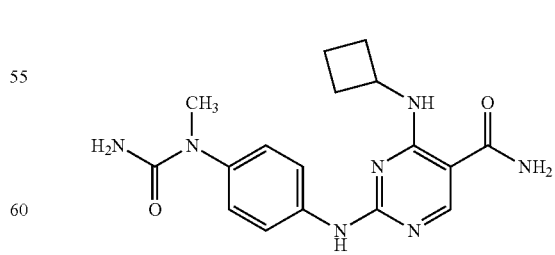

The above compound was prepared using a procedure similar to that described in Scheme 1. MS found for $C_{17}H_{21}N_7O_2$ as $(M+H)^+$ 356.3. UV: $\lambda$=202, 263.

Example 141. 4-(cyclobutylamino)-2-(4-(trifluoromethoxy)phenylamino)pyrimidine-5-carboxamide

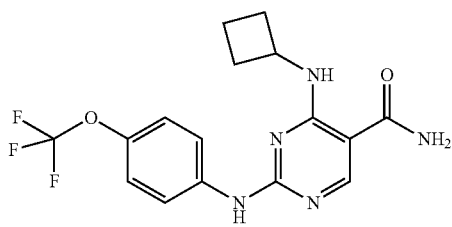 [SMILES: NC(=O)c1cnc(Nc2ccc(OC(F)(F)F)cc2)nc1NC1CCC1]

The above compound was prepared using a procedure similar to that described in Scheme 1. MS found for $C_{16}H_{16}N_5O_2F_3$ as $(M+H)^+$ 368.0.

Example 143. 2-(4-(2-morpholino-2-oxoethoxy)phenylamino)-4-(m-tolylamino)pyrimidine-5-carboxamide

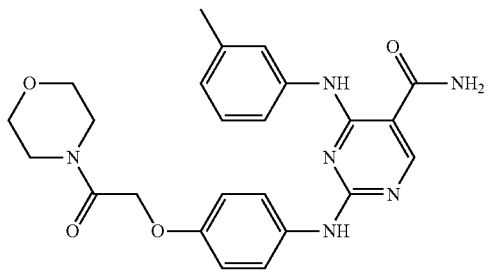 [SMILES: Cc1cccc(Nc2nc(Nc3ccc(OCC(=O)N4CCOCC4)cc3)ncc2C(N)=O)c1]

The above compound was prepared using a procedure similar to that described in Scheme 1, with meta-toluidine in place of cyclobutylamine. MS found for $C_{24}H_{26}N_6O_4$ as $(M+H)^+$ 463.3. UV: $\lambda=282$.

Example 145. 2-(4-(2-morpholinoethoxy)phenylamino)-4-(m-tolylamino)pyrimidine-5-carboxamide

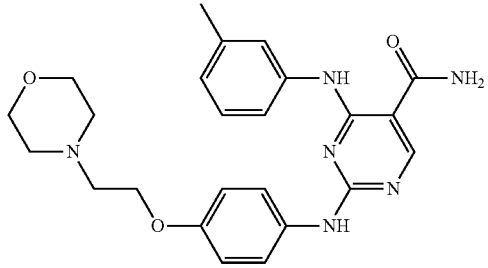 [SMILES: Cc1cccc(Nc2nc(Nc3ccc(OCCN4CCOCC4)cc3)ncc2C(N)=O)c1]

The above compound was prepared using a procedure similar to that described in Scheme 1, with meta-toluidine in place of cyclobutylamine. MS found for $C_{24}H_{28}N_6O_3$ as $(M+H)^+$ 449.3. UV: $\lambda=281$.

Example 147. 4-(cyclopropylamino)-2-(4-(isoxazol-3-yl)phenylamino)pyrimidine-5-carboxamide

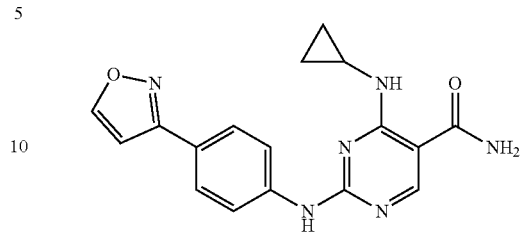

The above compound was prepared using using a procedure similar to that described in Scheme 1 with cyclopropylamine in place of cyclobutylamine. MS found for $C_{17}H_{16}N_6O_2$ as $(M+H)^+$ 337.3. UV: $\lambda=298.5$.

Example 148. (S)-2-(4-(1-amino-3-methyl-1-oxobutan-2-ylamino)phenylamino)-4-(2,2,2-trifluoroethylamino)pyrimidine-5-carboxamide

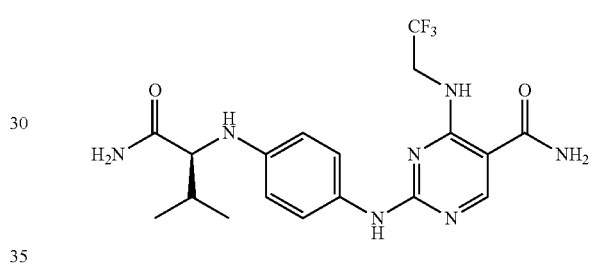

The above compound was prepared using a procedure similar to that described in Scheme 1 using trufluoroethylamine in place of cyclobutylamine and an aniline derived from (S)-valine and 4-fluoronitrobenzene. MS found for $C_{18}H_{22}F_3N_7O_2$ as $(M+H)^+$ 426.4. UV: $\lambda=225, 294$. $^1$H NMR (CD$_3$OD, 400 MHz): δ 8.32 (s, 1H), 7.19 (broad s, 2H), 6.76 (d, 2H), 4.35 (broad s, 2H), 3.58 (d, 1H), 2.11 (m, 1H), 1.10 (dd, 6H).

Example 149. (S)-2-(4-(1-amino-4-methyl-1-oxopentan-2-ylamino)phenylamino)-4-(2,2,2-triloroetylamino)pyrimidine-5-carboxamide

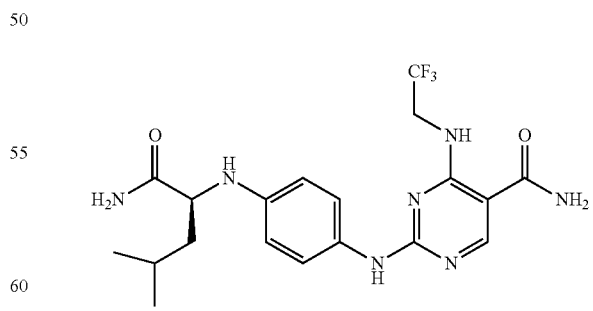

The above compound was prepared using a procedure similar to that described in Scheme 1 using trifluoroethylamine in place of cyclobutylamine and an aniline similar to that described previously. MS found for $C_{19}H_{24}F_3N_7O_2$ as $(M+H)^+$ 440.4. UV: $\lambda=226, 303$.

Example 151. 4-(1-methyl-1H-indol-4-ylamino)-2-(4-(2-(pyrrolidin-1-yl)ethoxy)phenylamino)pyrimidine-5-carboxamide

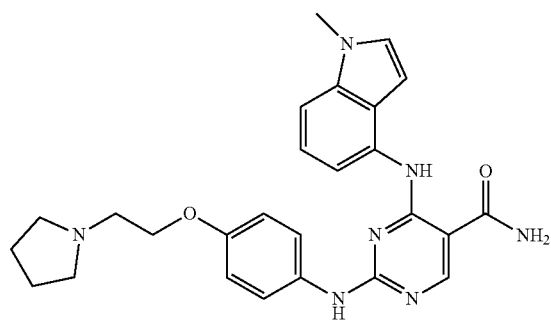 [SMILES: Cn1ccc2c(Nc3nc(Nc4ccc(OCCN5CCCC5)cc4)ncc3C(N)=O)cccc21]

Scheme 9:

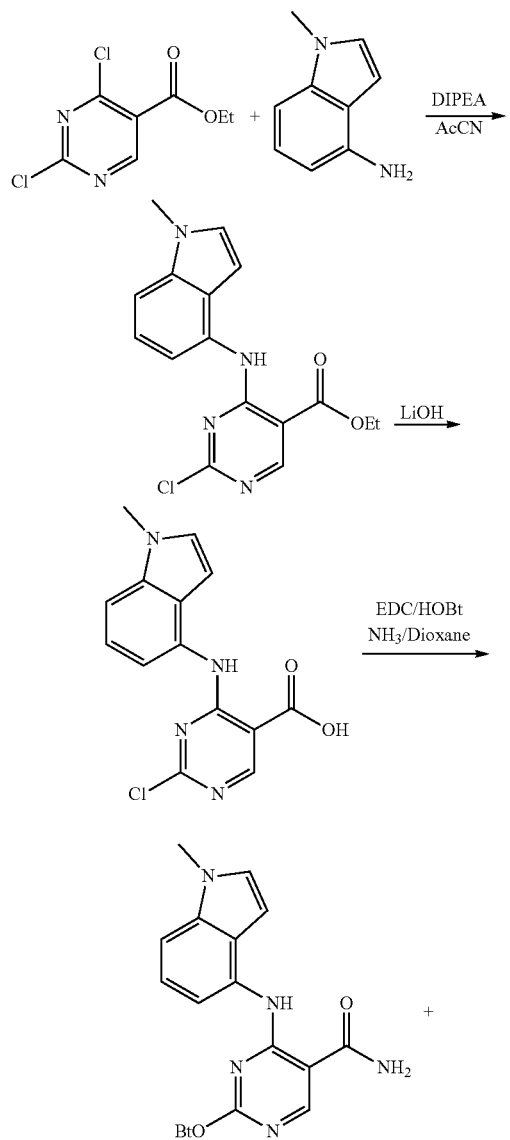

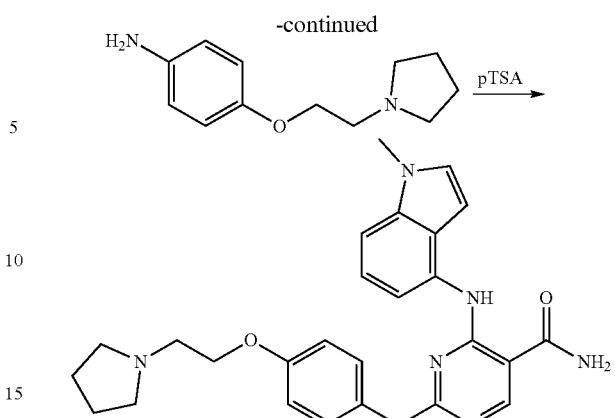

Step 1: To a solution of ethyl 2,4-dichloropyrimidine-5-carboxylate (328 mg, 1.48 mmol) and 1-methyl-1H-indol-4-amine (260 mg, 1.78 mmol) in CH3CN (6 mL) at room temperature, DIEA (0.4 mL, 2.22 mmol) was added. The mixture was stirred at room temperature for 24 h. Water (15 mL) was added to induce precipitation. The precipitate was collected, dried on vacuum to give ethyl 2-chloro-4-(1-methyl-1H-indol-4-ylamino) pyrimidine-5-carboxylate as a solid.

Step 2: To a solution of ethyl 2-chloro-4-(1-methyl-1H-indol-4-ylamino) pyrimidine-5-carboxylate (crude from step 1) in THF (4 mL), aq. 1N LiOH (2.25 mL, 2.25 mmol) was added. The mixture was stirred at room temperature overnight. Upon acidification of the mixture with 1N HCl, white solids precipitated out, which were collected, and dried on vacuum to give 2-chloro-4-(1-methyl-1H-indol-4-ylamino) pyrimidine-5-carboxylic acid (325 mg). MS 303.3, 305.3 (M+H, Cl pattern)

Step 3: To a solution of 2-chloro-4-(1-methyl-1H-indol-4-ylamino)pyrimidine-5-carboxylic acid (325 mg, 1.08 mmol) and HOBt (198 mg, 1.29 mmol) in DMF (4 mL), EDC (248 mg, 1.29 mmol) was added. The mixture was stirred at room temperature for 1.5 h. Ammonia (0.5 M in dioxane, 8.00 mL, 4.00 mmol) was added. It was stirred at room temperature overnight. Water and EtOAc were added. The organic phase was separated, washed with 1 N HCl, then with 5% NaHCO3, dried over Na2SO4, concentrated in vacuo to give 2-(1H-benzo[d][1,2,3]triazol-1-yloxy)-4-(1-methyl-1H-indol-4-ylamino)pyrimidine-5-carboxamide (378 mg). MS 401.4 (M+H)

Step 4: To a solution of 2-(1H-benzo[d][1,2,3]triazol-1-yloxy)-4-(1-methyl-1H-indol-4-ylamino)pyrimidine-5-carboxamide (62 mg, 0.15 mmol) in NMP (1 ml) was added 4-(2-(pyrrolidin-1-yl)ethoxy)aniline (31 mg, 0.15 mmol) and p-toluenesulfonic acid hydrate (28 mg, 0.15 mmol). It was heated at 100° C. for 4 h, and was purified by preparative HPLC to give 4-(1-methyl-1H-indol-4-ylamino)-2-(4-(2-(pyrrolidin-1-yl)ethoxy)phenylamino)pyrimidine-5-carboxamide (32 mg). MS found for C26H29N7O2 as (M+H)+ 472.4. UV: λ=216.9, 257.0.

Example 152. 4-(1H-indol-4-ylamino)-2-(4-(2-(pyrrolidin-1-yl)ethoxy)phenylamino)pyrimidine-5-carboxamide

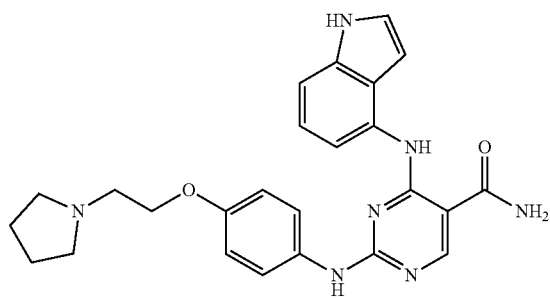 [SMILES: NC(=O)c1cnc(Nc2ccc(OCCN3CCCC3)cc2)nc1Nc1cccc2[nH]ccc12]

The above compound was prepared using a procedure similar to that described in Example 151. MS found for C25H27N7O2 as (M+H)+ 458.4. UV: λ=214.5, 249.9, 280.7.

Example 153. 4-(2-methyl-2H-indazol-7-ylamino)-2-(4-(2-(pyrrolidin-1-yl)ethoxy)phenylamino)pyrimidine-5-carboxamide

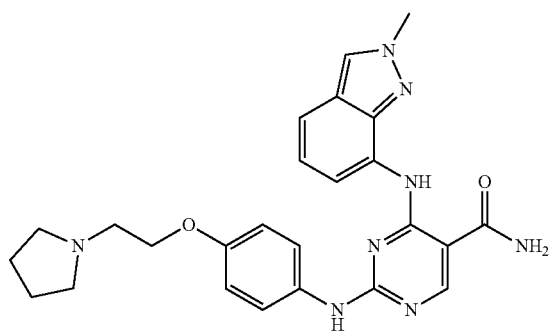 [SMILES: Cn1cc2cccc(Nc3nc(Nc4ccc(OCCN5CCCC5)cc4)ncc3C(N)=O)c2n1]

The above compound was prepared using using a procedure similar to that described in Example 151. MS found for C25H28N8O2 as (M+H)+ 473.4. UV: λ=211.0, 275.9.

Example 154. 4-(1-methyl-1H-indazol-7-ylamino)-2-(4-(2-(pyrrolidin-1-yl)ethoxy) phenylamino)pyrimidine-5-carboxamide

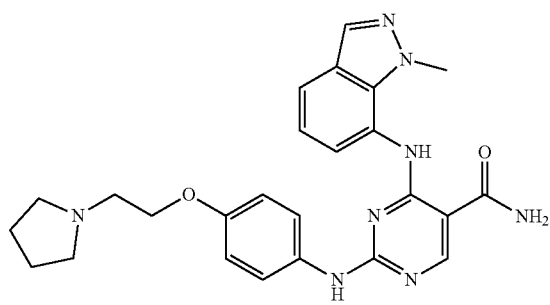 [SMILES: Cn1ncc2cccc(Nc3nc(Nc4ccc(OCCN5CCCC5)cc4)ncc3C(N)=O)c21]

The above compound was prepared using a procedure similar to that described in Example 151. MS found for C25H28N8O2 as (M+H)+ 473.4. UV: λ=208.6, 286.6.

Example 155. 2-(4-(1H-imidazol-1-ylphenylamino)-4-(cyclopropylamino)pyrimidine-5-carboxamide

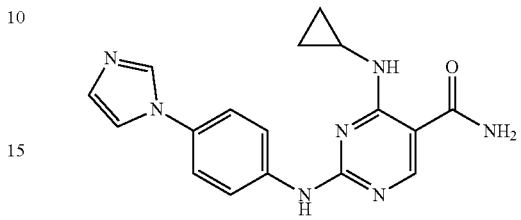

The above compound was prepared using using a procedure similar to that described above. MS found for C17H17N7O as (M+H)+ 336.3. UV: λ=245.2, 321.1.

Example 156. 2-(4-(2-(pyrrolidin-1-yl)ethoxy)phenylamino)-4-(m-tolylamino)pyrimidine-5-carboxamide

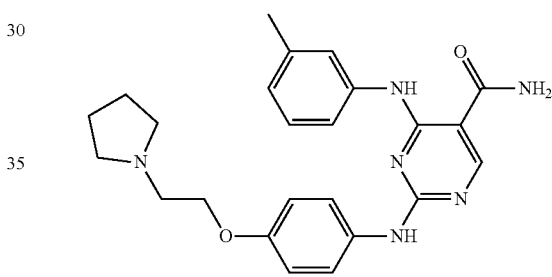

The above compound was prepared using a procedure similar to that described in Scheme 1 using meta-anisidine in place of cyclobutylamine. MS found for C24H28N6O2 as (M+H)+ 433.3. UV: λ=283.

Example 157. 4-(3,5-dimethylphenylamino)-2-(4-(2-(pyrrolidin-1-yl)ethoxy)phenylamino)pyrimidine-5-carboxamide

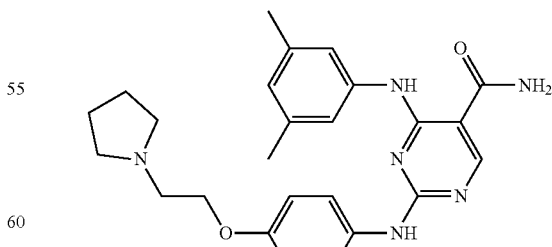

The above compound was prepared using a procedure similar to that described in Scheme 1 using 3,5-dimethylaniline in place of cyclobutylamine. MS found for C25H30N6O2 as (M+H)+ 447.3. UV: λ=283.

Example 158. 4-(3-methoxyphenylamino)-2-(4-(2-(pyrrolidin-1-yl)ethoxy)phenylamino)pyrimidine-5-carboxamide

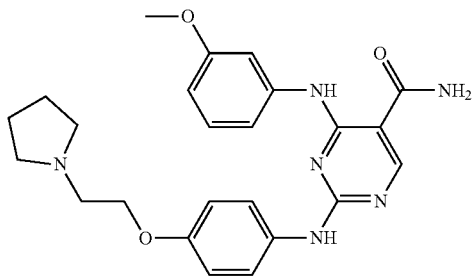 [SMILES: COc1cccc(Nc2nc(Nc3ccc(OCCN4CCCC4)cc3)ncc2C(N)=O)c1]

The above compound was prepared using a procedure similar to that described in Scheme 1 with meta-anisidine in place of cyclobutylamine. MS found for $C_{24}H_{28}N_6O_3$ as $(M+H)^+$ 449.3. UV: $\lambda=282$.

Example 161. 2-(4-(2-hydroxyethylcarbamoyl)phenylamino)-4-(2,2,2-trifluoroethylamino)pyrimidine-5-carboxamide

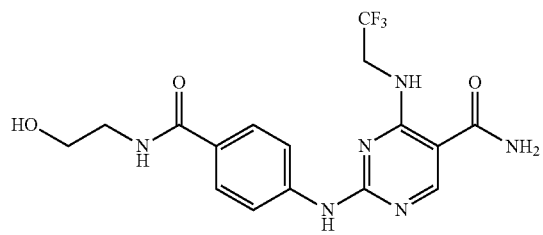 [SMILES: NC(=O)c1cnc(Nc2ccc(C(=O)NCCO)cc2)nc1NCC(F)(F)F]

The above compound was prepared using a procedure similar to that described Scheme 1 using trifluoroethylamine in place of cyclobutylamine. MS found for $C_{16}H_{17}F_3N_6O_3$ as $(M+H)^+$ 399.3.

Example 162. 4-(4-(2-morpholinoethoxy)phenylamino)-2-(4-(2-(pyrrolidin-1-yl)ethoxy)phenylamino)pyrimidine-5-carboxamide

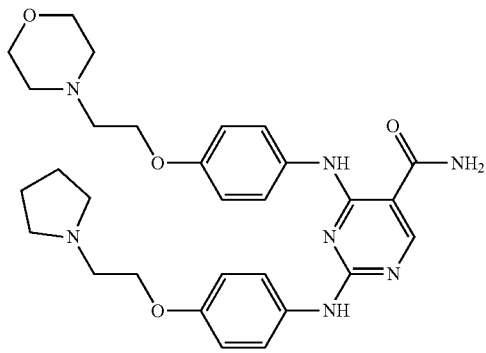 [SMILES: NC(=O)c1cnc(Nc2ccc(OCCN3CCCC3)cc2)nc1Nc1ccc(OCCN2CCOCC2)cc1]

The above compound was prepared using a procedure similar to that described in Scheme 2. MS found for $C_{29}H_{37}N_7O_4$ as $(M+H)^+$ 548.3. UV: $\lambda=283$.

Example 163. 2-(4-(2-(piperidin-1-yl)ethoxy)phenylamino)-4-(m-tolylamino)pyrimidine-5-carboxamide

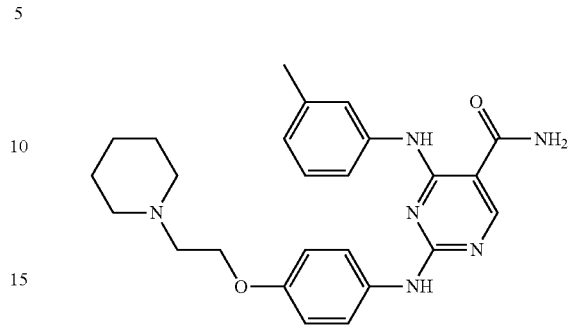

The above compound was prepared using a procedure similar to that described in Scheme 1 using meta-toluidine in place of cyclobutylamine. MS found for $C_{25}H_{30}N_6O_2$ as $(M+H)^+$ 447.3.

Example 165. 2-(4-(2-methoxyethoxy)phenylamino)-4-(m-tolylamino)pyrimidine-5-carboxamide

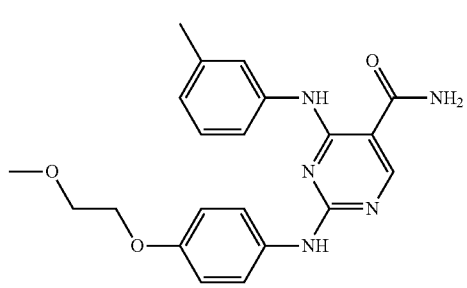 [SMILES: COCCOc1ccc(Nc2ncc(C(N)=O)c(Nc3cccc(C)c3)n2)cc1]

MS found for $C_{21}H_{23}N_5O_3$ as $(M+H)^+$ 394.3. UV: $\lambda=285$.

Example 166. 2-(4-(3-hydroxypropylcarbamoyl)phenylamino)-4-(2,2,2-trifluoroethylamino)pyrimidine-5-carboxamide

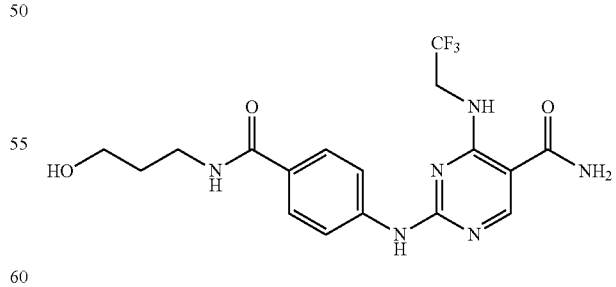

The above compound was prepared using a procedure similar to that described in Scheme 1 using trifluoroethylamine in place of cyclobutylamine. MS found for $C_{17}H_{19}F_3N_6O_3$ as $(M+H)^+$ 413.4. $^1$H NMR (CD$_3$OD, 400 MHz): $\delta$ 8.59 (s, 1H), 7.88 (d, 2H), 7.77 (d, 2H), 4.42 (q, 2H), 3.64 (t, 2H), 3.49 (t, 2H), 1.83 (m, 2H).

Example 167. 2-(4-(5,6-dihydro-4H-1,3-oxazin-2-yl)phenylamino)-4-(2,2,2-trifluoroethylamino)pyrimidine-5-carboxamide

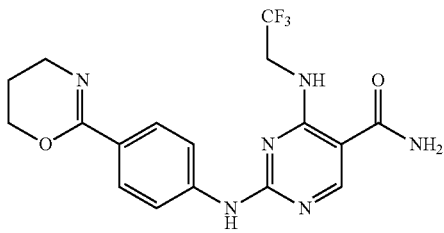 [SMILES: NC(=O)c1cnc(Nc2ccc(C3=NCCCO3)cc2)nc1NCC(F)(F)F]

The above compound was prepared by treating Example 166 with diethylaminosulfurtrifluoride and DIPEA in dichloromethane. MS found for $C_{17}H_{17}F_3N_6O_2$ as $(M+H)^+$ 395.2. UV: λ=221, 310. $^1$H NMR (CD$_3$OD, 400 MHz): δ 8.60 (s, 1H), 7.97 (dd, 2H), 7.93 (dd, 2H), 4.33 (q, 2H), 3.73 (t, 2H), 253 (m, 2H), 1.21 (t, 2H).

Example 168. 4-(cyclobutylamino)-2-(p-tolylamino)pyrimidine-5-carboxamide

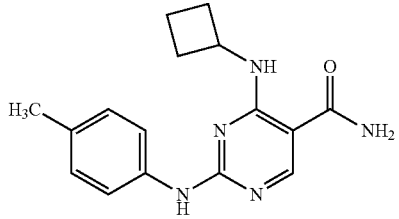 [SMILES: Cc1ccc(Nc2ncc(C(N)=O)c(NC3CCC3)n2)cc1]

The above compound was prepared using para-toluidine and a procedure similar to that described in Scheme 1. MS found for $C_{16}H_{19}N_5O$ as (M+H) 298.0.

Example 169. 2-(4-carbamoylphenylamino)-4-(cyclobutylamino)pyrimidine-5-carboxamide

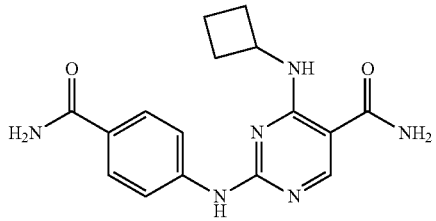 [SMILES: NC(=O)c1ccc(Nc2ncc(C(N)=O)c(NC3CCC3)n2)cc1]

The above compound was prepared using 4-aminobenzamide using a procedure similar to that described in Scheme 1. MS found for $C_{16}H_{18}N_6O_2$ as $(M+H)^+$ 327.0.

Example 170. 4-(cyclobutylamino)-2-(4-(N-methyl-cyclopropanecarboxamido)phenylamino)pyrimidine-5-carboxamide

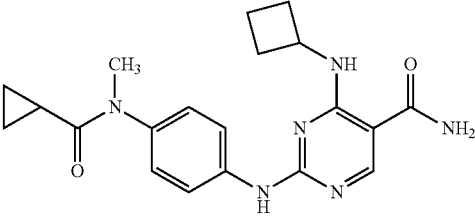 [SMILES: CN(C(=O)C1CC1)c1ccc(Nc2ncc(C(N)=O)c(NC3CCC3)n2)cc1]

The above compound was prepared using N-(4-aminophenyl)-N-methylcyclopropanecarboxamide (synthesized from N-methyl 4-nitroaniline in two steps) using a procedure similar to that described in Scheme 1. MS found for $C_{20}H_{24}N_6O_2$ as $(M+H)^+$ 381.0.

Example 171. 2-(3-chloro-4-(N-methylacetamido)phenylamino)-4-(cyclobutylamino)pyrimidine-5-carboxamide

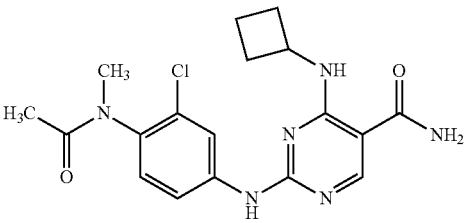 [SMILES: CC(=O)N(C)c1ccc(Nc2ncc(C(N)=O)c(NC3CCC3)n2)cc1Cl]

The above compound was prepared using N-(4-amino-2-chlorophenyl)-N-methylacetamide (prepared from 2-chloro-4-nitroaniline in three steps) using a procedure similar to that described in Scheme 1. MS found for $C_{17}H_{19}ClN_6O_2$ as $(M+H)^+$ 375.0, 377.0.

Example 172. 2-(3-chloro-4-(N-methylacetamido)phenylamino)-4-(cyclopropylamino)pyrimidine-5-carboxamide

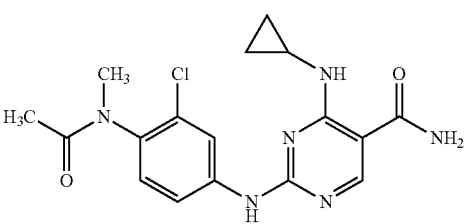 [SMILES: CC(=O)N(C)c1ccc(Nc2ncc(C(N)=O)c(NC3CC3)n2)cc1Cl]

The above compound was prepared using an intermediate synthesized as described in Scheme 1 with cyclopropylamine in place of cyclobutylamine in Step 4, and N-(4-amino-2-chlorophenyl)-N-methylacetamide (prepared from 2-chloro-4-nitroaniline in three steps) using a procedure similar to that described in Scheme 1. MS found for $C_{17}H_{19}ClN_6O_2$ as $(M+H)^+$ 375.0, 377.0. $^1$H NMR (CD$_3$OD, 400 MHz): δ 8.43 (d, 1H), 8.20 (s, 1H), 7.61 (dd, 1H), 7.43 (d, 1H), 3.18 (s, 3H), 2.98 (m, 1H), 1.82 (s, 3H), 1.01 (m, 2H), 0.73 (m, 2H).

Example 173. 4-(cyclopropylamino)-2-(4-(N-methylcyclopropanecarboxamido)phenylamino)pyrimidine-5-carboxamide

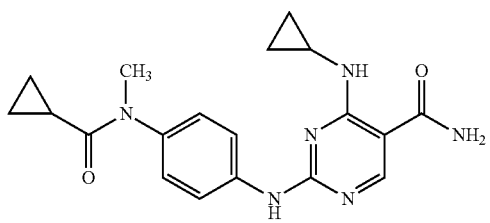 [SMILES: CN(C(=O)C1CC1)c1ccc(Nc2ncc(C(N)=O)c(NC3CC3)n2)cc1]

The above compound was prepared using an intermediate synthesized as described in Example 139 with cyclopropylamine in place of cyclobutylamine in Step 4, and N-(4-aminophenyl)-N-methylcyclopropanecarboxamide (synthesized from N-methyl 4-nitroaniline in two steps) using a procedure similar to that described in Scheme 1. MS found for $C_{19}H_{22}N_6O_2$ as $(M+H)^+$ 367.1.

Example 174. 4-(cyclopropylamino)-2-(4-(4-(2-hydroxyethyl)piperazin-1-yl)phenylamino)pyrimidine-5-carboxamide

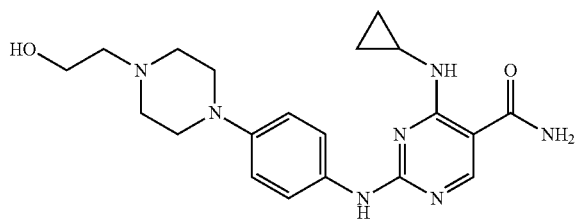 [SMILES: NC(=O)c1cnc(Nc2ccc(N3CCN(CCO)CC3)cc2)nc1NC1CC1]

The above compound was prepared using a procedure similar to that described in Scheme 1 with cyclopropylamine in place of cyclobutylamine. MS found for $C_{20}H_{27}N_7O_2$ as $(M+H)+398.3$.

Example 175. 4-(cyclopropylamino)-2-(4-(4-(methylcarbamoyl)piperidin-1-yl)phenylamino)pyrimidine-5-carboxamide

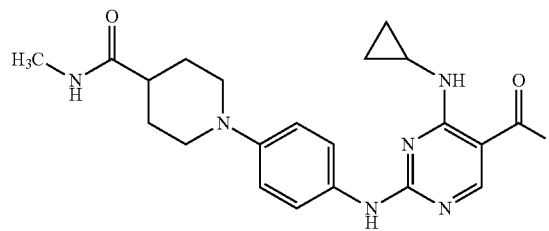

The above compound was prepared using a procedure similar to that described in Scheme 1 using cyclopropylamine in place of cyclobutylamine and an aniline derived from 4-fluoronitrobenzene and ethyl isonipecotate. MS found for $C_{21}H_{27}N_7O_2$ as $(M+H)^+$ 410.0.

Example 176. 4-(cyclopropylamino)-2-(4-(4-(dimethylcarbamoyl)piperidin-1-yl)phenylamino)pyrimidine-5-carboxamide

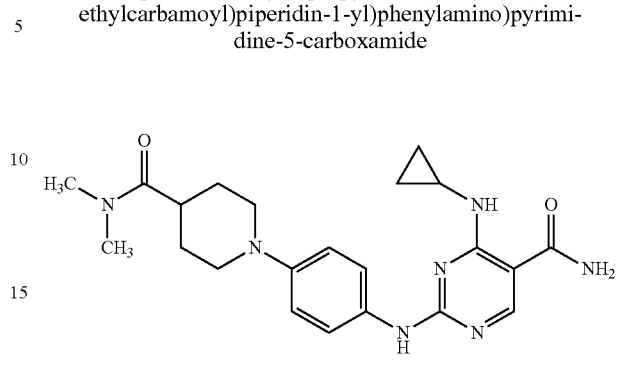

The above compound was prepared using a procedure similar to that described in Scheme 1 using cyclopropylamine in place of cyclobutylamine and an aniline derived from 4-fluoronitrobenzene and ethyl isonipecotate. MS found for $C_{22}H_{29}N_7O_2$ as $(M+H)^+$ 424.0.

Example 177. 4-(cyclopropylamino)-2-(4-(4-(dimethylcarbamoyl)piperazin-1-yl)phenylamino)pyrimidine-5-carboxamide

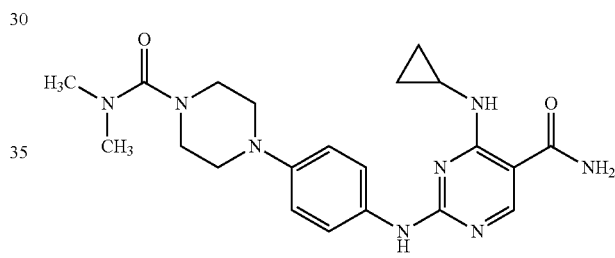

The above compound was prepared by treating 4-(4-nitrophenyl)piperazine-1-carboxamide with sodium hydride and methyl iodide, then reducing the nitro using hydrogenation. The aniline was then coupled using a procedure similar to that described in Scheme 1 with cyclopropylamine in place of cyclobutylamine. MS found for $C_{21}H_{28}N_8O_2$ as $(M+H)^+$ 425.2.

Example 178. 2-(3-chloro-4-morpholinophenylamino)-4-(cyclopropylamino)pyrimidine-5-carboxamide

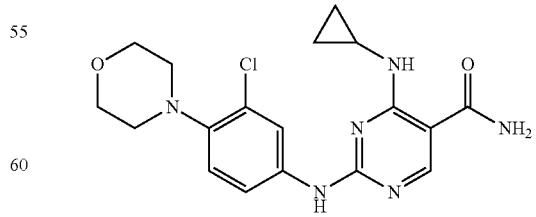

The above compound was prepared using a procedure similar to that described in Scheme 1 with cyclopropylamine in place of cyclobutylamine. MS found for $C_{18}H_{21}N_6O_2Cl$ as $(M+H)^+$ 389.0, 391.0.

Example 179 4-(cyclopropylamino)-2-(4-(3,3-difluoropyrrolidin-1-yl)phenylamino)pyrimidine-5-carboxamide

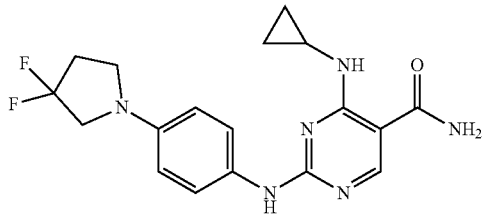 [SMILES: NC(=O)c1cnc(Nc2ccc(N3CCC(F)(F)C3)cc2)nc1NC1CC1]

The above compound was prepared using a procedure similar to that described in Scheme 1 with cyclopropylamine in place of cyclobutylamine and an aniline derived from 3,3-difluoropyrrolidine and 4-fluoronitrobenzene in two steps. MS found for $C_{18}H_{20}N_6OF_2$ as (M+H)$^+$ 375.0.

Example 180. 4-(cyclopropylamino)-2-(4-(methylcarbamoyl)phenylamino)pyrimidine-5-carboxamide

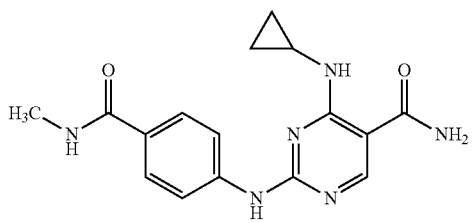 [SMILES: CNC(=O)c1ccc(Nc2ncc(C(N)=O)c(NC3CC3)n2)cc1]

The above compound was prepared using a procedure similar to that described in Scheme 1 with cyclopropylamine in place of cyclobutylamine and an aniline derived from 4-nitrobenzoylchloride and methylamine. MS found for $C_{16}H_{18}N_6O_2$ as (M+H)$^+$ 327.0.

Example 181. 4-(cyclopropylamino)-2-(4-(dimethylcarbamoyl)phenylamino)pyrimidine-5-carboxamide

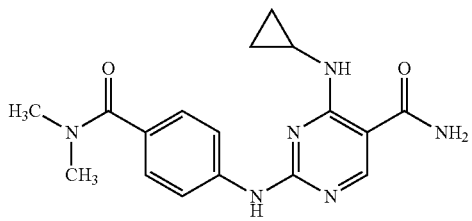 [SMILES: CN(C)C(=O)c1ccc(Nc2ncc(C(N)=O)c(NC3CC3)n2)cc1]

The above compound was prepared using a procedure similar to that described in Scheme 1 with cyclopropylamine in place of cyclobutylamine and an aniline derived from 4-nitrobenzoylchloride and dimethylamine. MS found for $C_{17}H_{20}N_6O_2$ as (M+H)$^+$ 341.0.

Example 182. 4-(cyclopropylamino)-2-(4-(4-(methylsulfonyl)piperazine-1-carbonyl)phenylamino)pyrimidine-5-carboxamide

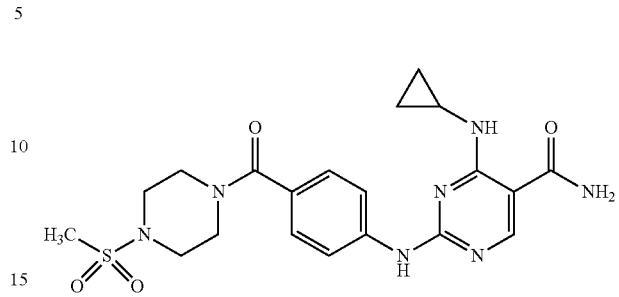

The above compound was prepared using a procedure similar to that described in Scheme 1 with cyclopropylamine in place of cyclobutylamine and an aniline derived from 4-nitrobenzoylchloride. MS found for $C_{20}H_{25}N_7O_4S$ as (M+H)$^+$ 460.1.

Example 183. 4-(cyclopropylamino)-2-(4-(thiazol-4-yl)phenylamino)pyrimidine-5-carboxamide

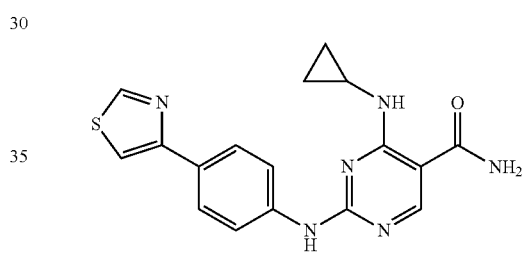

The above compound was prepared using a procedure similar to that described in Scheme 1 with cyclopropylamine in place of cyclobutylamine. MS found for $C_{17}H_{16}N_6OS$ as (M+H)$^+$ 353.2.

Example 184. 2-(4-(1H-pyrazol-1-yl)phenylamino)-4-(cyclopropylamino)pyrimidine-5-carboxamide

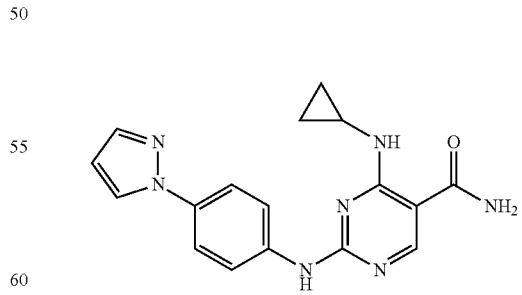

The above compound was prepared using a procedure similar to that described in Scheme 1 with cyclopropylamine in place of cyclobutylamine. MS found for $C_{17}H_{17}N_7O$ as (M+H)$^+$ 336.3.

Example 185. 2-(4-(1H-tetrazol-1-yl)phenylamino)-4-(cyclopropylamino)pyrimidine-5-carboxamide

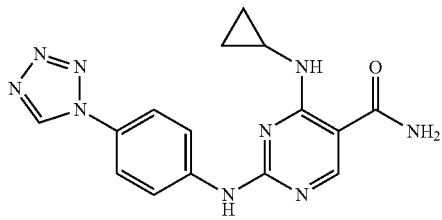 [SMILES: NC(=O)c1cnc(Nc2ccc(-n3cnnn3)cc2)nc1NC1CC1]

The above compound was prepared using a procedure similar to that described in Scheme 1 with cyclopropylamine in place of cyclobutylamine. MS found for $C_{15}H_{15}N_9O$ as $(M+H)^+$ 338.2.

Example 186. 4-(cyclopropylamino)-2-(4-(thiophen-2-yl)phenylamino)pyrimidine-5-carboxamide

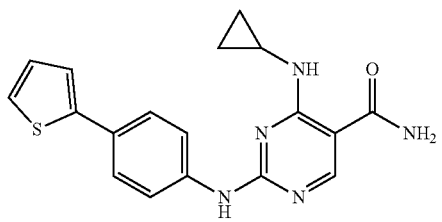 [SMILES: NC(=O)c1cnc(Nc2ccc(-c3cccs3)cc2)nc1NC1CC1]

The above compound was prepared using a procedure similar to that described in Scheme 1 with cyclopropylamine in place of cyclobutylamine. MS found for $C_{18}H_{17}N_5OS$ as $(M+H)^+$ 352.2.

Example 187. 4-(cyclopropylamino)-2-(4-formamido-3-hydroxyphenylamino)pyrimidine-5-carboxamide

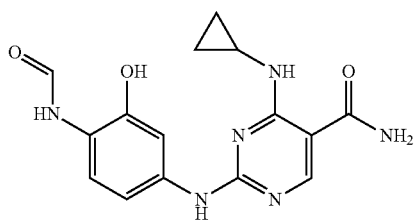 [SMILES: NC(=O)c1cnc(Nc2ccc(NC=O)c(O)c2)nc1NC1CC1]

The above compound was prepared using a procedure similar to that described in Scheme 1 with cyclopropylamine in place of cyclobutylamine using 6-aminobenzoxazole which subsequently hydrolyzed during purification affording the titled compound. MS found for $C_{15}H_{16}N_6O_3$ as $(M+H)^+$ 329.2.

Example 188. 4-(cyclopropylamino)-2-(4-(pyridin-2-yl)phenylamino)pyrimidine-5-carboxamide

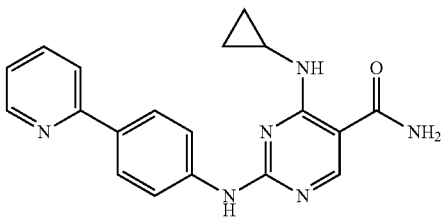 [SMILES: NC(=O)c1cnc(Nc2ccc(-c3ccccn3)cc2)nc1NC1CC1]

The above compound was prepared using a procedure similar to that described in Scheme 1 with cyclopropylamine in place of cyclobutylamine. MS found for $C_{19}H_{18}N_6O$ as $(M+H)^+$ 347.3.

Example 189. 2-(4-(1-acetyl-1,2,3,6-tetrahydropyridin-4-yl)phenylamino)-4-(cyclopropylamino)pyrimidine-5-carboxamide

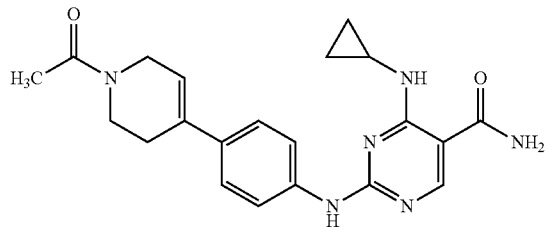 [SMILES: CC(=O)N1CC=C(c2ccc(Nc3ncc(C(N)=O)c(NC4CC4)n3)cc2)CC1]

The above compound was prepared using a procedure similar to that described in Scheme 1 with cyclopropylamine in place of cyclobutylamine. MS found for $C_{21}H_{24}N_6O_2$ as $(M+H)^+$ 393.3.

Example 190. (R)-4-(cyclopropylamino)-2-(4-(2-(methoxymethyl)pyrrolidin-1-yl)phenylamino)pyrimidine-5-carboxamide

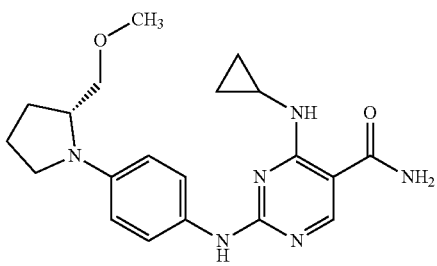 [SMILES: COC[C@H]1CCCN1c1ccc(Nc2ncc(C(N)=O)c(NC3CC3)n2)cc1]

The above compound was prepared using a procedure similar to that described in Scheme 1 with cyclopropylamine in place of cyclobutylamine and using an aniline prepared in two steps from 4-fluoronitrobenzene and (R)-2-methoxymethylpyrrolidine. MS found for $C_{20}H_{26}N_6O_2$ as $(M+H)^+$ 383.3.

Example 191. (S)-4-(cyclopropylamino)-2-(4-(2-(methoxymethyl)pyrrolidin-1-yl)phenylamino)pyrimidine-5-carboxamide

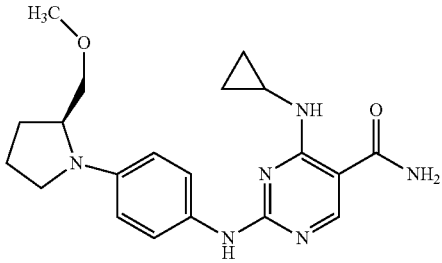 [SMILES: COC[C@@H]1CCCN1c1ccc(Nc2ncc(C(N)=O)c(NC3CC3)n2)cc1]

The above compound was prepared using a procedure similar to that described in Example 190 using (S)-2-methoxymethylpyrrolidine in place of the (R)-isomer. MS found for $C_{20}H_{26}N_6O_2$ as $(M+H)^+$ 383.3. $^1$H NMR (CD$_3$OD, 400 MHz): δ 8.21 (s, 1H), 7.38 (broad s, 2H), 6.78 (d, 2H), 3.89 (m, 1H), 3.49 (m, 2H), 3.33 (s, 3H), 3.18 (m, 2H), 3.03 (m, 1H), 2.03 (m, 4H), 0.93 (m, 2H), 0.72 (m, 2H).

Example 192. 4-(cyclopropylamino)-2-(4-(pyridin-3-yl)phenylamino)pyrimidine-5-carboxamide

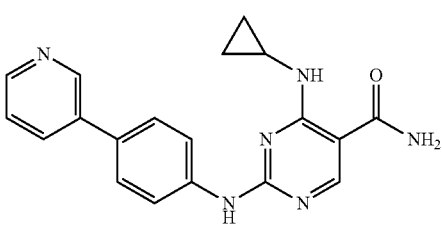 [SMILES: NC(=O)c1cnc(Nc2ccc(-c3cccnc3)cc2)nc1NC1CC1]

The above compound was prepared using a procedure similar to that described in Scheme 1 with cyclopropylamine in place of cyclobutylamine. MS found for $C_{19}H_{18}N_6O$ as $(M+H)^+$ 347.3.

Example 193. 4-(cyclopropylamino)-2-(4-(ethylsulfonyl)phenylamino)pyrimidine-5-carboxamide

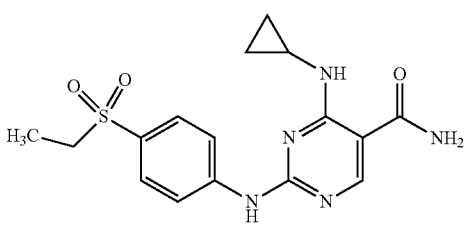 [SMILES: CCS(=O)(=O)c1ccc(Nc2ncc(C(N)=O)c(NC3CC3)n2)cc1]

The above compound was prepared using a procedure similar to that described in Scheme 1 with cyclopropylamine in place of cyclobutylamine. MS found for $C_{16}H_{19}N_5O_3S$ as $(M+H)^+$ 362.1.

Example 194. 2-(1H-indol-6-ylamino)-4-(cyclopropylamino)pyrimidine-5-carboxamide

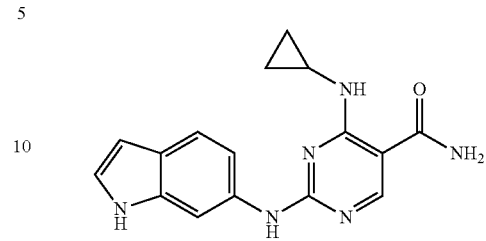

The above compound was prepared using a procedure similar to that described in Scheme 1 with cyclopropylamine in place of cyclobutylamine. MS found for $C_{16}H_{16}N_6O$ as $(M+H)^+$ 309.2.

Example 195. 1-(4-(5-carbamoyl-4-(cyclopropylamino)pyrimidin-2-ylamino)phenyl)piperidine-4-carboxylic acid

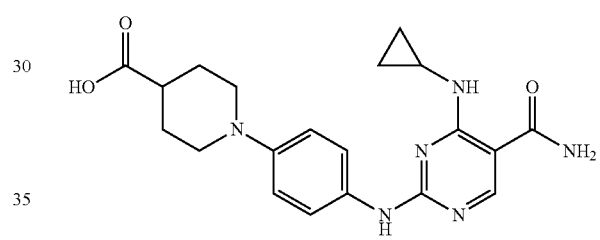

The above compound was prepared using a procedure similar to that described in Scheme 1 with cyclopropylamine in place of cyclobutylamine and an aniline derived from ethyl isonipecotate and 4-fluoronitrobenzene. MS found for $C_{20}H_{24}N_6O_3$ as $(M+H)^+$ 397.2.

Example 196 4-(cyclopropylamino)-2-(4-(4-(methylsulfonyl)-1,4-diazepan-1-yl)phenylamino)pyrimidine-5-carboxamide

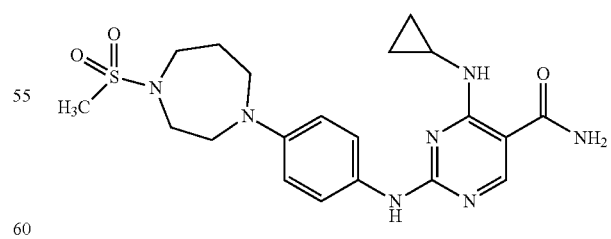

The above compound was prepared using a procedure similar to that described in Scheme 1 with cyclopropylamine in place of cyclobutylamine and an aniline derived from Boc protected homopiperazine and 4-fluoronitrobenzene. MS found for $C_{20}H_{27}N_7O_3S$ as $(M+H)^+$ 446.2.

Example 197. 4-(cyclopropylamino)-2-(4-(3,5-dimethyl-1H-pyrazol-1-yl)phenylamino)pyrimidine-5-carboxamide

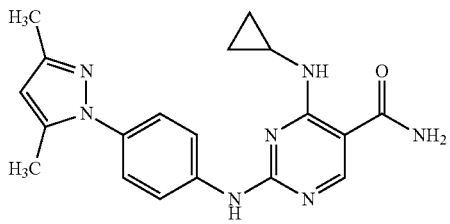 [SMILES: Cc1cc(C)n(-c2ccc(Nc3ncc(C(N)=O)c(NC4CC4)n3)cc2)n1]

The above compound was prepared using a procedure similar to that described in Scheme 1 with cyclopropylamine in place of cyclobutylamine. MS found for $C_{19}H_{21}N_7O$ as $(M+H)^+$ 364.2.

Example 198. (S)-2-(4-(2-carbamoylpyrrolidin-1-yl)phenylamino)-4-(cyclopropylamino)pyrimidine-5-carboxamide

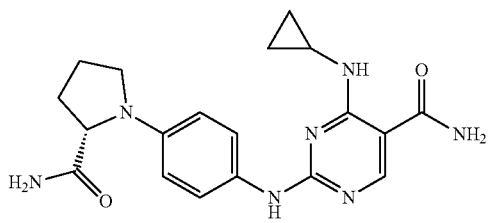 [SMILES: NC(=O)c1cnc(Nc2ccc(N3CCC[C@H]3C(N)=O)cc2)nc1NC1CC1]

The above compound was prepared using a procedure similar to that described in Scheme 1 with cyclopropylamine in place of cyclobutylamine and an aniline derived from (S)-prolinamide and 4-fluoronitrobenzene. MS found for $C_{19}H_{23}N_7O_2$ as $(M+H)^+$ 382.0.

Example 199. 4-(cyclopropylamino)-2-(4-(cyclopropylcarbamoyl)phenylamino)pyrimidine-5-carboxamide

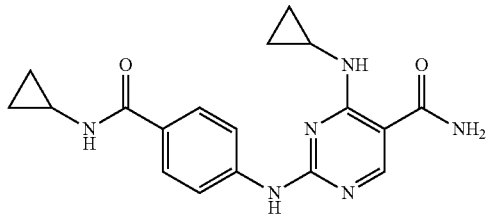 [SMILES: NC(=O)c1cnc(Nc2ccc(C(=O)NC3CC3)cc2)nc1NC1CC1]

The above compound was prepared using a procedure similar to that described in Scheme 1 with cyclopropylamine in place of cyclobutylamine, using an aniline derived from 4-nitrobenzoyl chloride in two steps. MS found for $C_{18}H_{20}N_6O_2$ as $(M+H)^+$ 353.0.

Example 200. 2-(4-(cyclobutylcarbamoyl)phenylamino)-4-(cyclopropylamino)pyrimidine-5-carboxamide

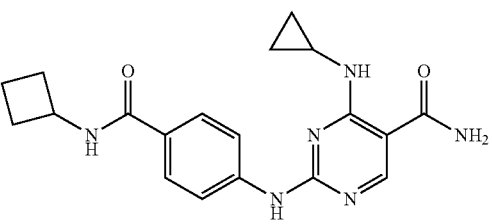 [SMILES: NC(=O)c1cnc(Nc2ccc(C(=O)NC3CCC3)cc2)nc1NC1CC1]

The above compound was prepared using a procedure similar to that described in Example 199. MS found for $C_{19}H_{22}N_6O_2$ as $(M+H)^+$ 367.3.

Example 201. (S)-4-(cyclopropylamino)-2-(4-(2-(methylcarbamoyl)pyrrolidin-1-yl)phenylamino)pyrimidine-5-carboxamide

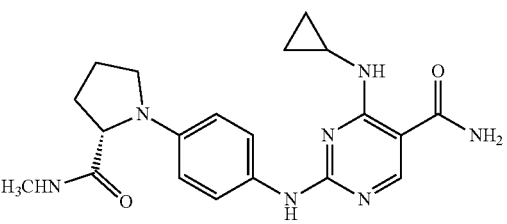

The above compound was prepared using a procedure similar to that described in Scheme 1, with cyclopropylamine in place of cyclobutylamine and an aniline derived from (S)-proline and 4-fluoronitrobenzene. MS found for $C_{20}H_{25}N_7O_2$ as $(M+H)^+$ 396.0.

Example 202. (S)-4-(cyclopropylamino)-2-(4-(2-(dimethylcarbamoyl)pyrrolidin-1-yl)phenylamino)pyrimidine-5-carboxamide

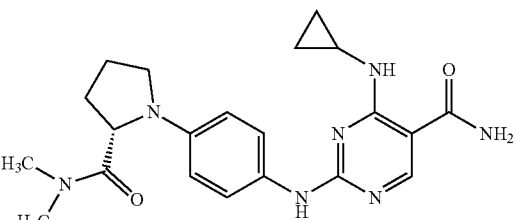

The above compound was prepared using a procedure similar to that described in Example 201. MS found for $C_{21}H_{27}N_7O_2$ as $(M+H)^+$ 410.0.

Example 203. 4-(cyclopropylamino)-2-(4-(2-hydroxyethylcarbamoyl)phenylamino)pyrimidine-5-carboxamide

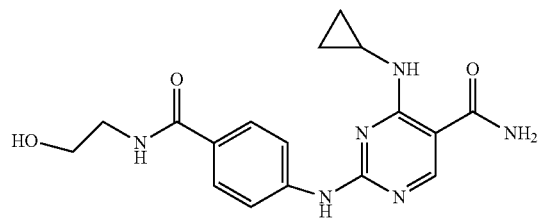 [SMILES: NC(=O)c1cnc(Nc2ccc(C(=O)NCCO)cc2)nc1NC1CC1]

The above compound was prepared using a procedure similar to that described in Scheme 1 using cyclopropylamine in place of cyclobutylamine and an aniline derived from 4-nitrobenzoyl chloride and ethanolamine. MS found for $C_{17}H_{20}N_6O_3$ as $(M+H)^+$ 357.0.

Example 204. 4-(cyclopropylamino)-2-(4-(3-hydroxypropylcarbamoyl)phenylamino)pyrimidine-5-carboxamide

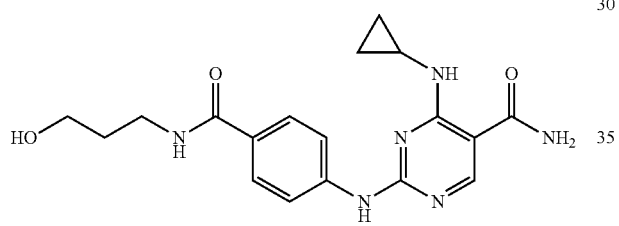

The above compound was prepared using a procedure similar to that described in Scheme 1 using cyclopropylamine in place of cyclobutylamine and an aniline derived from 4-nitrobenzoyl chloride and propanolamine. MS found for $C_{18}H_{22}N_6O_3$ as $(M+H)^+$ 371.0.

Example 205. (R)-4-(cyclopropylamino)-2-(4-(3-(methylcarbamoyl)piperidin-1-yl)phenylamino)pyrimidine-5-carboxamide

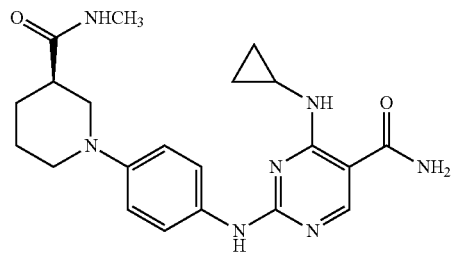 [SMILES: CNC(=O)[C@@H]1CCCN(c2ccc(Nc3ncc(C(N)=O)c(NC4CC4)n3)cc2)C1]

The above compound was prepared using a procedure similar to that described in Example 201. MS found for $C_{21}H_{27}N_7O_2$ as $(M+H)^+$ 410.0.

Example 206. (R)-4-(cyclopropylamino)-2-(4-(3-(dimethylcarbamoyl)piperidin-1-yl)phenylamino)pyrimidine-5-carboxamide

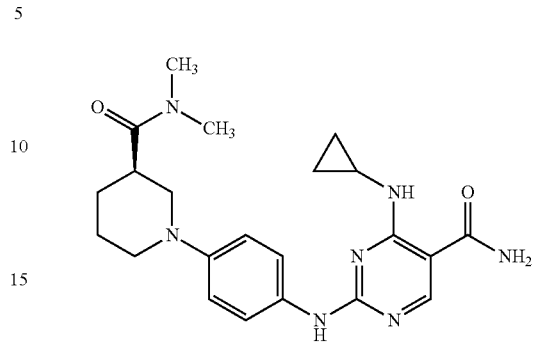

The above compound was prepared using a procedure similar to that described in Example 201. MS found for $C_{22}H_{29}N_7O_2$ as $(M+H)^+$ 424.0.

Example 207. (S)-4-(cyclopropylamino)-2-(4-(3-(methylcarbamoyl)piperidin-1-yl)phenylamino)pyrimidine-5-carboxamide

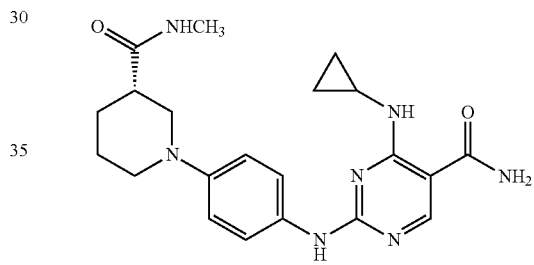

The above compound was prepared using a procedure similar to that described in Example 201. MS found for $C_{21}H_{27}N_7O_2$ as $(M+H)^+$ 410.2.

Example 208. (S)-4-(cyclopropylamino)-2-(4-(3-(dimethylcarbamoyl)piperidin-1-yl)phenylamino)pyrimidine-5-carboxamide

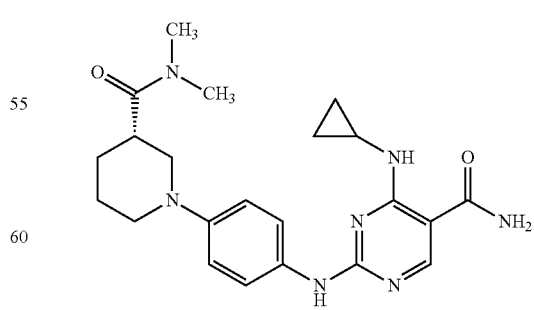

The above compound was prepared using a procedure similar to that described in Example 201. MS found for $C_{22}H_{29}N_7O_2$ as $(M+H)^+$ 424.2.

Example 209. (S)-4-(cyclopropylamino)-2-(4-(2-(methylcarbamoyl)piperidin-1-yl)phenylamino)pyrimidine-5-carboxamide

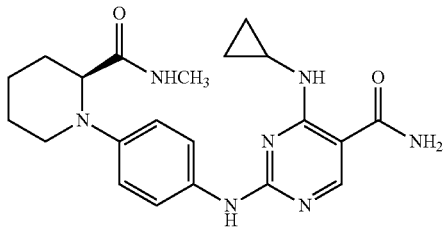 [SMILES: CNC(=O)[C@@H]1CCCCN1c1ccc(Nc2ncc(C(N)=O)c(NC3CC3)n2)cc1]

The above compound was prepared using a procedure similar to that described in Example 201. MS found for $C_{21}H_{27}N_7O_2$ as $(M+H)^+$ 410.2.

Example 210. (S)-4-(cyclopropylamino)-2-(4-(2-(dimethylcarbamoyl)piperidin-1-yl)phenylamino)pyrimidine-5-carboxamide

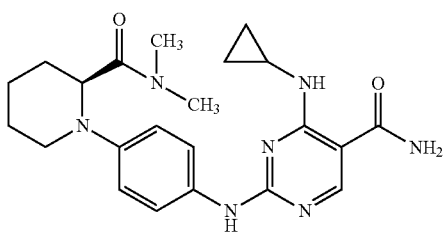 [SMILES: CN(C)C(=O)[C@@H]1CCCCN1c1ccc(Nc2ncc(C(N)=O)c(NC3CC3)n2)cc1]

The above compound was prepared using a procedure similar to that described in Example 201. MS found for $C_{22}H_{29}N_7O_2$ as $(M+H)^+$ 424.2.

Example 211. 4-(cyclopropylamino)-2-(quinoxalin-6-ylamino)pyrimidine-5-carboxamide

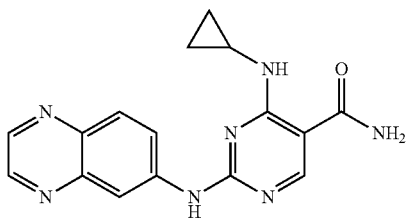

The above compound was prepared using a procedure similar to that described in Scheme 1 using cyclopropylamine in place of cyclobutylamine. MS found for $C_{16}H_{15}N_7O$ as $(M+H)^+$ 322.1.

Example 212. (S)-2-(4-(2-carbamoylazetidin-1-yl)phenylamino)-4-(cyclopropylamino)pyrimidine-5-carboxamide

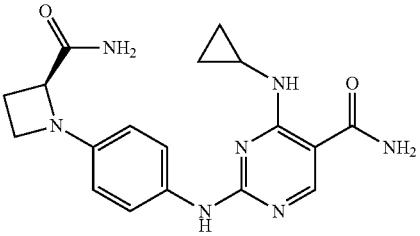 [SMILES: NC(=O)c1cnc(Nc2ccc(N3CC[C@H]3C(N)=O)cc2)nc1NC1CC1]

The above compound was prepared using a procedure similar to that described in Example 201. MS found for $C_{18}H_{21}N_7O_2$ as $(M+H)^+$ 368.1.

Example 213. 4-(cyclopropylamino)-2-(4-(4-hydroxypiperidin-1-ylsulfonyl)phenylamino)pyrimidine-5-carboxamide

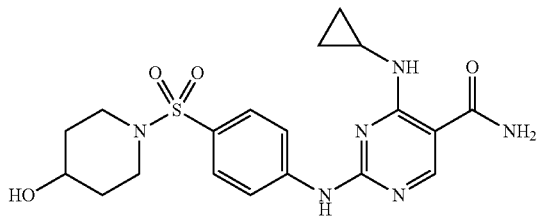 [SMILES: NC(=O)c1cnc(Nc2ccc(S(=O)(=O)N3CCC(O)CC3)cc2)nc1NC1CC1]

The above compound was prepared using a procedure similar to that described in Scheme 1, using cyclopropylamine in place of cyclobutylamine and an aniline prepared from 4-nitrobenzenesulfonyl chloride and 4-hydroxypoperidine. MS found for $C_{19}H_{24}N_6O_4S$ as $(M+H)^+$ 433.0.

Example 214. 2-(4-(cyclopropyl(methyl)carbamoyl)phenylamino)-4-(cyclopropylamino)pyrimidine-5-carboxamide

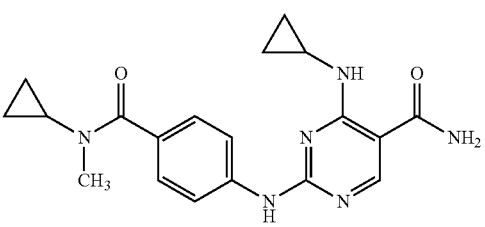 [SMILES: CN(C(=O)c1ccc(Nc2ncc(C(N)=O)c(NC3CC3)n2)cc1)C1CC1]

The above compound was prepared using a procedure similar to that described in Scheme 1 using cyclopropylamine in place of cyclobutylamine. MS found for $C_{19}H_{22}N_6O_2$ as $(M+H)^+$ 367.0.

Example 215. 2-(4-(cyclobutyl(methyl)carbamoyl) phenylamino)-4-(cyclopropylamino)pyrimidine-5-carboxamide

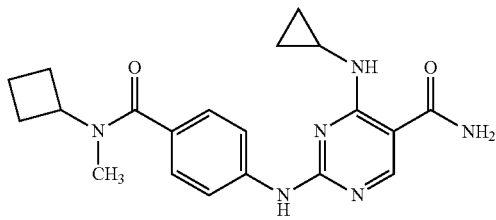 [SMILES: CN(C(=O)c1ccc(Nc2ncc(C(N)=O)c(NC3CC3)n2)cc1)C1CCC1]

The above compound was prepared using a procedure similar to that described in Scheme 1 using cyclopropylamine in place of cyclobutylamine. MS found for $C_{20}H_{24}N_6O_2$ as $(M+H)^+$ 381.0.

Example 216. 2-(4-(2-aminopyridin-4-yl)phenylamino)-4-(cyclopropylamino)pyrimidine-5-carboxamide

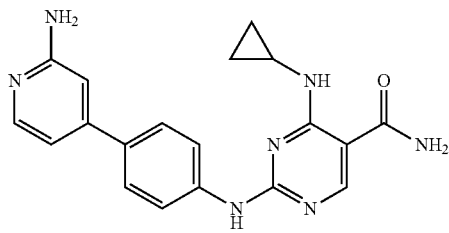 [SMILES: NC(=O)c1cnc(Nc2ccc(-c3ccnc(N)c3)cc2)nc1NC1CC1]

The above compound was prepared using a procedure similar to that described in Scheme 1 using cyclopropylamine in place of cyclobutylamine. MS found for $C_{19}H_{19}N_7O$ as $(M+H)^+$ 362.4.

Example 217. (R)-4-(cyclopropylamino)-2-(4-(2-(methylcarbamoyl)pyrrolidin-1-yl)phenylamino) pyrimidine-5-carboxamide

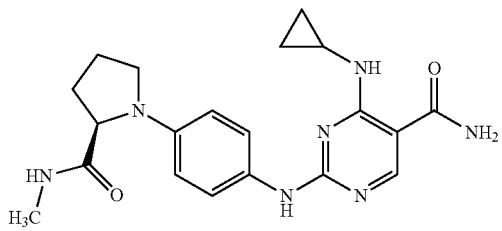 [SMILES: CNC(=O)[C@H]1CCCN1c1ccc(Nc2ncc(C(N)=O)c(NC3CC3)n2)cc1]

The above compound was prepared using a procedure similar to that described in Example 201. MS found for $C_{20}H_{25}N_7O_2$ as $(M+H)^+$ 396.0.

Example 218. (R)-4-(cyclopropylamino)-2-(4-(2-(dimethylcarbamoyl)pyrrolidin-1-yl)phenylamino) pyrimidine-5-carboxamide

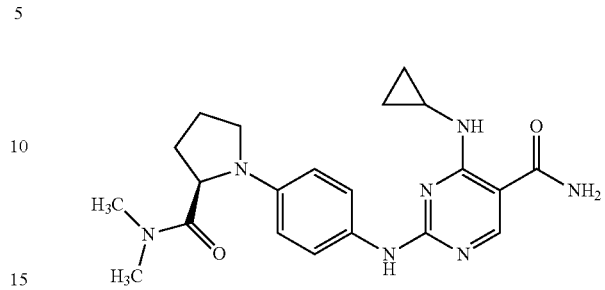

The above compound was prepared using a procedure similar to that described in Example 201. MS found for $C_{21}H_{27}N_7O_2$ as $(M+H)^+$ 410.0.

Example 219. 4-(cyclopropylamino)-2-(4-(3-(methylcarbamoyl)pyrrolidin-1-yl)phenylamino)pyrimidine-5-carboxamide

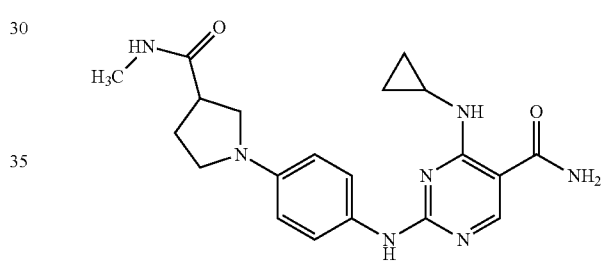

The above compound was prepared using a procedure similar to that described in Example 201. MS found for $C_{20}H_{25}N_7O_2$ as $(M+H)^+$ 396.5.

Example 220. 2-(4-((2S,4S)-2-carbamoyl-4-hydroxypyrrolidin-1-yl)phenylamino)-4-(cyclopropylamino)pyrimidine-5-carboxamide

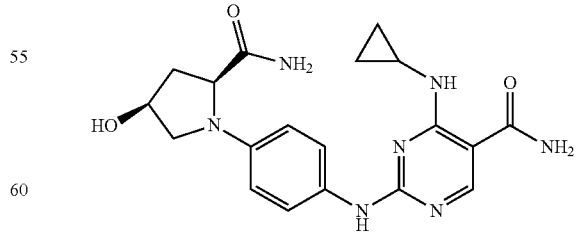

The above compound was prepared using a procedure similar to that described in Example 201. MS found for $C_{19}H_{23}N_7O_3$ as $(M+H)^+$ 398.5.

Example 221. 4-(cyclopropylamino)-2-(4-((2S,4S)-4-hydroxy-2-(methylcarbamoyl)pyrrolidin-1-yl)phenylamino)pyrimidine-5-carboxamide

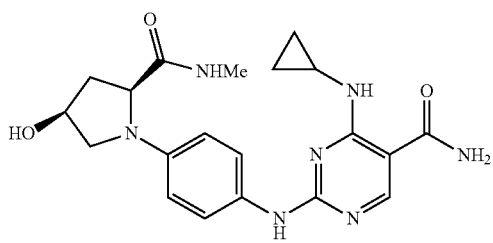 [SMILES: CNC(=O)[C@@H]1C[C@H](O)CN1c1ccc(Nc2ncc(C(N)=O)c(NC3CC3)n2)cc1]

The above compound was prepared using a procedure similar to that described in Example 201. MS found for $C_{20}H_{25}N_7O_3$ as $(M+H)^+$ 412.5.

Example 222. 4-(cyclobutylamino)-2-(4-(dimethylamino)phenylamino)pyrimidine-5-carboxamide

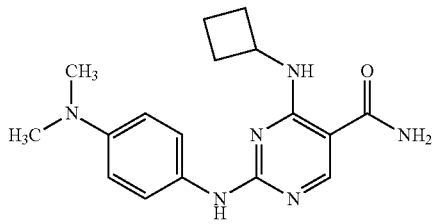 [SMILES: CN(C)c1ccc(Nc2ncc(C(N)=O)c(NC3CCC3)n2)cc1]

The above compound was prepared using N,N-dimethylbenzene-1,4-diamine using a procedure similar to that described in Scheme 1. MS found for $C_{17}H_{22}N_6O$ as $(M+H)^+$ 327.0.

Example 223. 2-(4-acetamidophenylamino)-4-(cyclobutylamino)pyrimidine-5-carboxamide

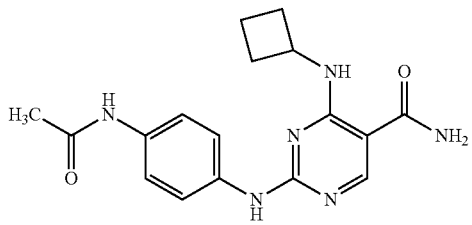 [SMILES: CC(=O)Nc1ccc(Nc2ncc(C(N)=O)c(NC3CCC3)n2)cc1]

The above compound was prepared using N-(4-aminophenyl)acetamide using a procedure similar to that described in Scheme 1. MS found for $C_{17}H_{20}N_6O_2$ as $(M+H)^+$ 341.0.

Example 224. 2-(1H-indazol-5-ylamino)-4-(cyclobutylamino)pyrimidine-5-carboxamide 16

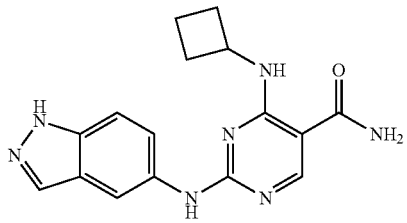 [SMILES: NC(=O)c1cnc(Nc2ccc3[nH]ncc3c2)nc1NC1CCC1]

The above compound was prepared using 1H-indazol-5-amine using a procedure similar to that described in Scheme 1. MS found for $C_{16}H_{17}N_7O$ as $(M+H)^+$ 324.0.

Example 225. 2-(1H-indazol-6-ylamino)-4-(cyclobutylamino)pyrimidine-5-carboxamide

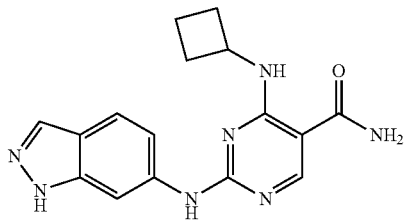 [SMILES: NC(=O)c1cnc(Nc2ccc3cn[nH]c3c2)nc1NC1CCC1]

The above compound was prepared using 1H-indazol-6-amine using a procedure similar to that described in Scheme 1. MS found for $C_{16}H_{17}N_7O$ as $(M+H)^+$ 324.0. $^1$H NMR (CD$_3$OD, 400 MHz): δ 8.44 (s, 1H), 8.13 (s, 1H), 7.99 (s, 1H), 7.88 (d, 1H), 7.27 (m, 2H), 4.63 (m, 1H), 2.48 (m, 2H), 2.13 (m, 2H), 1.92 (m, 2H)

Example 226. 4-(cyclobutylamino)-2-(4-methoxyphenylamino)pyrimidine-5-carboxamide

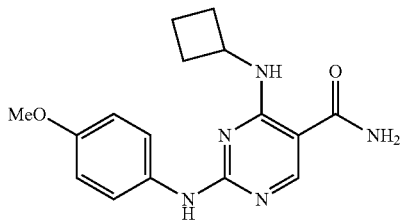 [SMILES: COc1ccc(Nc2ncc(C(N)=O)c(NC3CCC3)n2)cc1]

The above compound was prepared using p-anisidine using a procedure similar to that described in Scheme 1. MS found for $C_{16}H_{19}N_5O_2$ as $(M+H)^+$ 314.0.

Example 227. 4-(cyclobutylamino)-2-(4-(diethylamino)phenylamino)pyrimidine-5-carboxamide

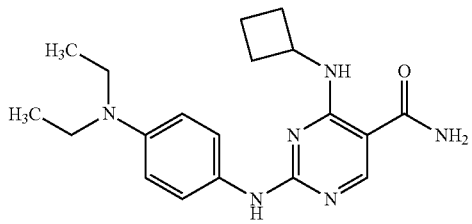 [SMILES: CCN(CC)c1ccc(Nc2ncc(C(N)=O)c(NC3CCC3)n2)cc1]

The above compound was prepared using N,N-diethyl phenylenediamine using a procedure similar to that described in Scheme 1. MS found for $C_{19}H_{26}N_6O$ as $(M+H)^+$ 355.2.

Example 228. 4-(cyclobutylamino)-2-(phenylamino)pyrimidine-5-carboxamide

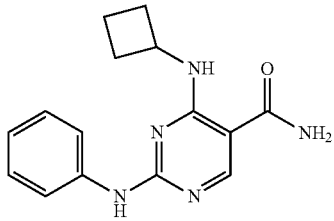 [SMILES: NC(=O)c1cnc(Nc2ccccc2)nc1NC1CCC1]

The above compound was prepared using aniline using a procedure similar to that described in Scheme 1. MS found for $C_{15}H_{17}N_5O$ as $(M+H)^+$ 284.0.

Example 229. 4-(cyclobutylamino)-2-(4-(N-methylpropionamido)phenylamino)pyrimidine-5-carboxamide

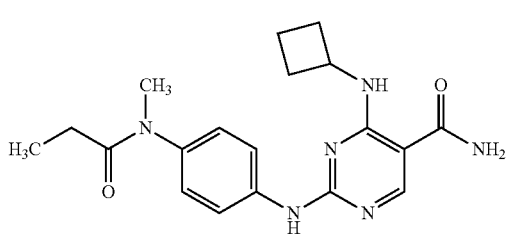 [SMILES: CCC(=O)N(C)c1ccc(Nc2ncc(C(N)=O)c(NC3CCC3)n2)cc1]

The above compound was prepared using N-(4-aminophenyl)-N-methylpropionamide (synthesized from N-methyl 4-nitroaniline in two steps) using a procedure similar to that described in Scheme 1. MS found for $C_{19}H_{24}N_6O_2$ as $(M+H)^+$ 369.0.

Example 230. 4-(cyclopropylamino)-2-(4-(N-methylpropionamido)phenylamino)pyrimidine-5-carboxamide

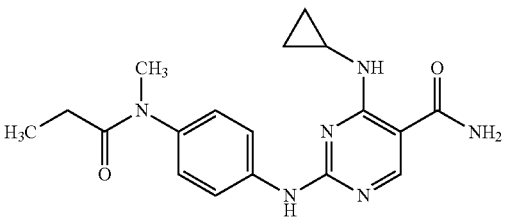 [SMILES: CCC(=O)N(C)c1ccc(Nc2ncc(C(N)=O)c(NC3CC3)n2)cc1]

The above compound was prepared using an intermediate synthesized as described in Scheme 1 with cyclopropylamine in place of cyclobutylamine and N-(4-aminophenyl)-N-methylpropionamide (synthesized from N-methyl 4-nitroaniline in two steps). MS found for $C_{18}H_{22}N_6O_2$ as $(M+H)^+$ 355.0.

Example 231. 4-(cyclopropylamino)-2-(4-(N-methylacetamido)phenylamino)pyrimidine-5-carboxamide

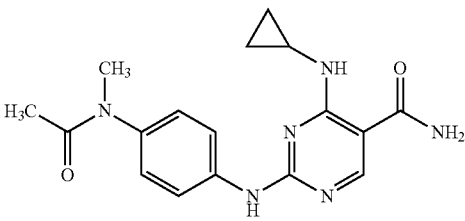 [SMILES: CC(=O)N(C)c1ccc(Nc2ncc(C(N)=O)c(NC3CC3)n2)cc1]

The above compound was prepared using an intermediate synthesized as described in Scheme 1 with cyclopropylamine in place of cyclobutylamine and N-(4-aminophenyl)-N-methylacetamide (which was prepared from N-methyl 4-nitroaniline in two steps) MS found for $C_{17}H_{20}N_6O_2$ as $(M+H)^+$ 341.0.

Example 232. isopropyl 4-(5-carbamoyl-4-(cyclopropylamino)pyrimidin-2-ylamino)phenyl(methyl)carbamate

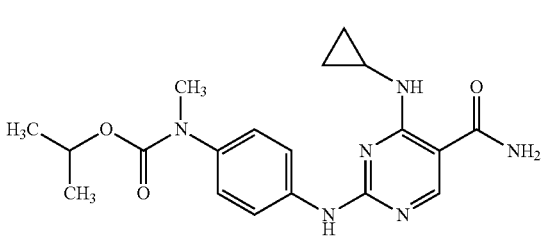 [SMILES: CC(C)OC(=O)N(C)c1ccc(Nc2ncc(C(N)=O)c(NC3CC3)n2)cc1]

The above compound was prepared using an intermediate synthesized as described in Scheme 1 with cyclopropylamine in place of cyclobutylamine and isopropyl 4-aminophenyl(methyl)carbamate (synthesized from N-methyl 4-nitroaniline in two steps). MS found for $C_{19}H_{24}N_6O_3$ as $(M+H)^+$ 385.0.

Example 233. 4-(cyclopropylamino)-2-(2,3-dihydrobenzo[b][1,4]dioxin-6-ylamino)pyrimidine-5-carboxamide

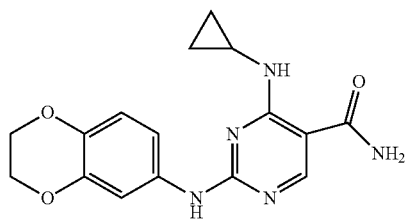 [SMILES: NC(=O)c1cnc(Nc2ccc3c(c2)OCCO3)nc1NC1CC1]

The above compound was prepared using a procedure similar to that described in Scheme 1 with cyclopropylamine in place of cyclobutylamine. MS found for $C_{16}H_{17}N_5O_3$ as $(M+H)^+$ 328.2.

Example 234. 4-(cyclopropylamino)-2-(4-morpholinophenylamino)pyrimidine-5-carboxamide

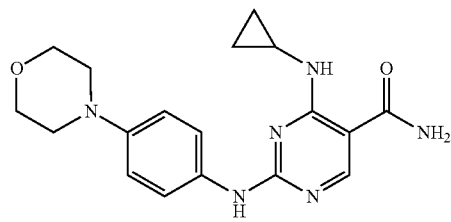 [SMILES: NC(=O)c1cnc(Nc2ccc(N3CCOCC3)cc2)nc1NC1CC1]

The above compound was prepared using a procedure similar to that described in Scheme 1 with cyclopropylamine in place of cyclobutylamine. MS found for $C_{18}H_{22}N_6O_2$ as $(M+H)^+$ 355.0. $^1$H NMR (DMSO-$d_6$, 400 MHz): δ 8.24 (s, 1H), 7.50 (broad s, 2H), 7.06 (d, 2H), 3.84 (m, 4H), 3.21 (m, 4H), 0.92 (m, 2H), 0.71 (m, 2H).

Example 235. 4-(cyclopropylamino)-2-(4-(piperidin-1-yl)phenylamino)pyrimidine-5-carboxamide

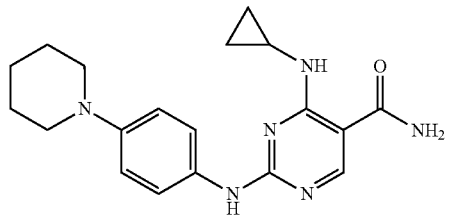 [SMILES: NC(=O)c1cnc(Nc2ccc(N3CCCCC3)cc2)nc1NC1CC1]

The above compound was prepared using a procedure similar to that described in Scheme 1 with cyclopropylamine in place of cyclobutylamine. MS found for $C_{19}H_{24}N_{x6}O$ as $(M+H)^+$ 353.2.

Example 236. 4-(cyclopropylamino)-2-(4-(4-hydroxypiperidin-1-yl)phenylamino)pyrimidine-5-carboxamide

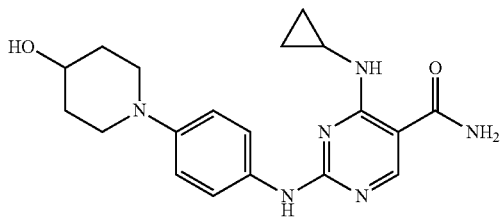 [SMILES: NC(=O)c1cnc(Nc2ccc(N3CCC(O)CC3)cc2)nc1NC1CC1]

The above compound was prepared using a procedure similar to that described in Scheme 1 with cyclopropylamine in place of cyclobutylamine and an aniline derived from 4-fluoronitrobenzene and 4-hydroxypiperidine. MS found for $C_{19}H_{24}N_6O_2$ as $(M+H)^+$ 369.0.

Example 237. 4-(cyclopropylamino)-2-(4-(4-fluoropiperidin-1-yl)phenylamino)pyrimidine-5-carboxamide

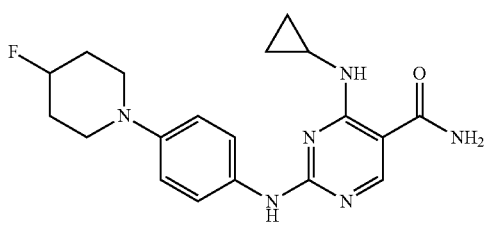 [SMILES: NC(=O)c1cnc(Nc2ccc(N3CCC(F)CC3)cc2)nc1NC1CC1]

The above compound was prepared using a procedure similar to that described in Scheme 1 with cyclopropylamine in place of cyclobutylamine and an aniline derived from 4-fluoronitrobenzene and 4-fluoropiperidine. MS found for $C_{19}H_{23}N_6OF$ as $(M+H)^+$ 371.0.

Example 238. 4-(cyclopropylamino)-2-(4-(4-methylpiperazin-1-yl)phenylamino)pyrimidine-5-carboxamide

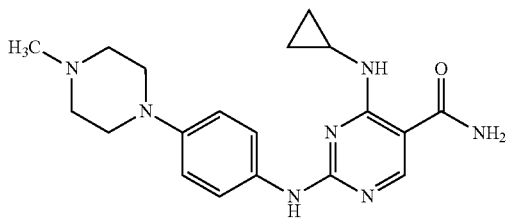 [SMILES: CN1CCN(c2ccc(Nc3ncc(C(N)=O)c(NC4CC4)n3)cc2)CC1]

The above compound was prepared using a procedure similar to that described in Scheme 1 with cyclopropylamine in place of cyclobutylamine and an aniline derived from 4-fluoronitrobenzene and 1-methylpiperazine. MS found for $C_{19}H_{25}N_7O$ as $(M+H)^+$ 368.3.

Example 239. 4-(cyclopropylamino)-2-(4-(3,3-difluoropiperidin-1-yl)phenylamino)pyrimidine-5-carboxamide

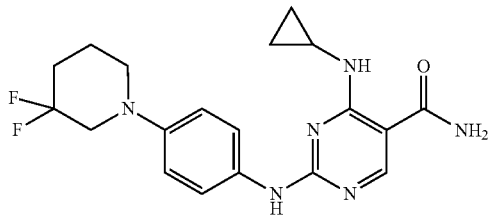 [SMILES: NC(=O)c1cnc(Nc2ccc(N3CCCC(F)(F)C3)cc2)nc1NC1CC1]

The above compound was prepared using a procedure similar to that described in Scheme 1 with cyclopropylamine in place of cyclobutylamine and an aniline derived from 4-fluoronitrobenzene and 3,3-difluoropiperidine. MS found for $C_{19}H_{22}N_6OF_2$ as $(M+H)^+$ 389.0.

Example 240. 2-(4-(4-carbamoylpiperidin-1-yl)phenylamino)-4-(cyclopropylamino)pyrimidine-5-carboxamide

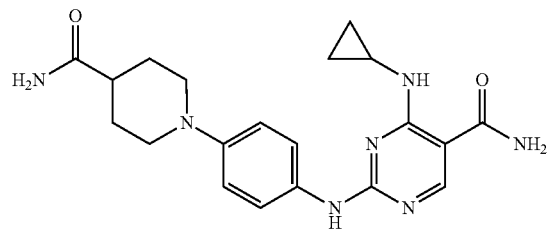

The above compound was prepared using a procedure similar to that described in Scheme 1 with cyclopropylamine in place of cyclobutylamine and an aniline prepared from 4-fluoronitrobenzene and isonipecotamide followed by reduction using hydrogen and Pd/C in methanol. MS found for $C_{20}H_{25}N_7O_2$ as $(M+H)^+$ 396.2.

Example 241. 2-(4-(4-carbamoylpiperazin-1-yl)phenylamino)-4-(cyclopropylamino)pyrimidine-5-carboxamide

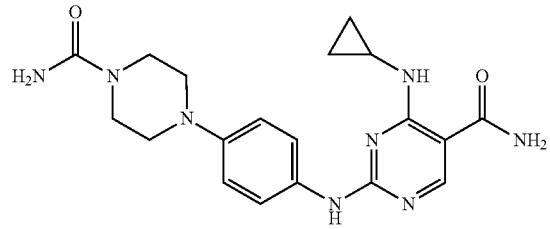

The above compound was prepared using a procedure similar to that described in Scheme 1 using an aniline prepared from 4-piperazinylnitrobenzene in two steps. MS found for $C_{19}H_{24}N_8O_2$ as $(M+H)^+$ 397.2.

Example 242. 4-(cyclopropylamino)-2-(4-(4,4-difluoropiperidin-1-yl)phenylamino)pyrimidine-5-carboxamide

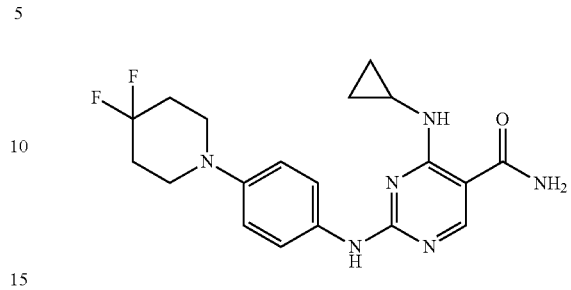

The above compound was prepared using a procedure similar to that described in Scheme 1 with cyclopropylamine in place of cyclobutylamine and an aniline derived from 4-fluoronitrobenzene and 4,4-difluoropiperidine. MS found for $C_{19}H_{22}N_6OF_2$ as $(M+H)^+$ 389.0.

Example 244. 4-(cyclopropylamino)-2-(4-(methylsulfonyl)phenylamino)pyrimidine-5-carboxamide

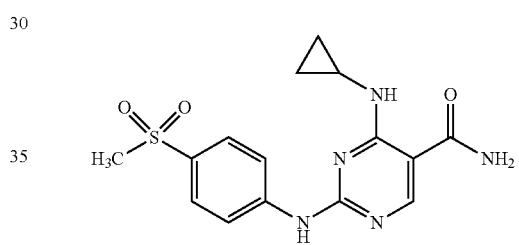

The above compound was prepared using a procedure similar to that described in Scheme 1 using cyclopropylamine in place of cyclobutylamine. MS found for $C_{15}H_{17}N_5O_3S$ as $(M+H)^+$ 348.1.

Example 245. 4-(cyclopropylamino)-2-(4-(methylthio)phenylamino)pyrimidine-5-carboxamide

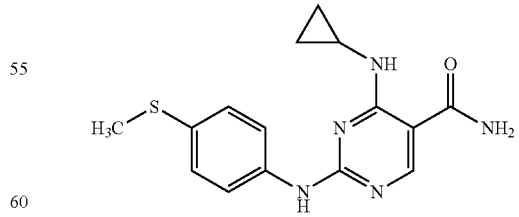

The above compound was prepared using a procedure similar to that described in Scheme 1 using cyclopropylamine in place of cyclobutylamine. MS found for $C_{15}H_{17}N_5OS$ as $(M+H)^+$ 316.1.

Example 246. 4-(cyclopropylamino)-2-(4-((4-(methylsulfonyl)piperazin-1-yl)methyl)phenylamino)pyrimidine-5-carboxamide

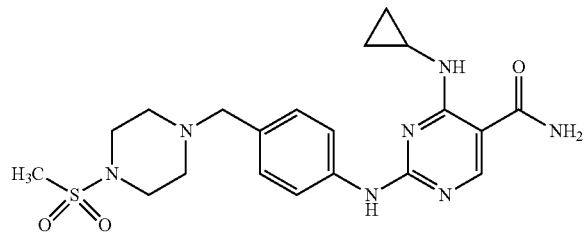 [SMILES: CS(=O)(=O)N1CCN(Cc2ccc(Nc3ncc(C(N)=O)c(NC4CC4)n3)cc2)CC1]

The above compound was prepared using a procedure similar to that described in Scheme 1 using cyclopropylamine in place of cyclobutylamine. MS found for $C_{20}H_{27}N_7O_3S$ as $(M+H)^+$ 446.3.

Example 247. 4-(cyclopropylamino)-2-(4-(piperazin-1-yl)phenylamino)pyrimidine-5-carboxamide

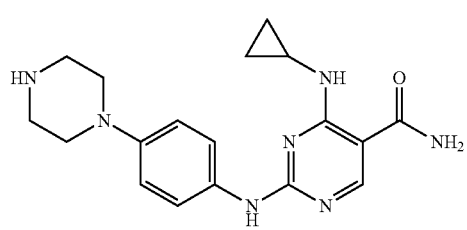 [SMILES: NC(=O)c1cnc(Nc2ccc(N3CCNCC3)cc2)nc1NC1CC1]

The above compound was prepared using a procedure similar to that described in Scheme 1 using cyclopropylamine in place of cyclobutylamine. MS found for $C_{18}H_{23}N_7O$ as $(M+H)^+$ 354.2.

Example 248. 2-(4-(1H-1,2,4-triazol-1-yl)phenylamino)-4-(cyclopropylamino)pyrimidine-5-carboxamide

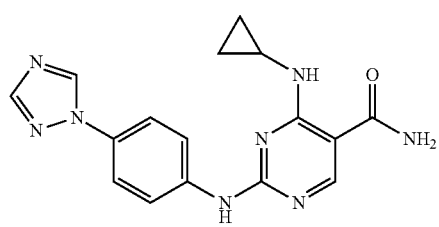

The above compound was prepared using a procedure similar to that described in Scheme 1 using cyclopropylamine in place of cyclobutylamine. MS found for $C_{16}H_{16}N_8O$ as $(M+H)^+$ 352.2.

Example 249. 2-(1H-indol-5-ylamino)-4-(cyclopropylamino)pyrimidine-5-carboxamide

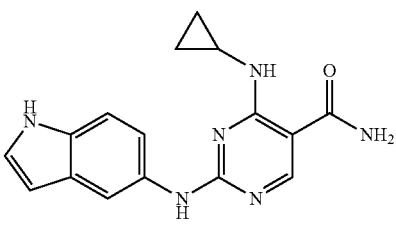 [SMILES: NC(=O)c1cnc(Nc2ccc3[nH]ccc3c2)nc1NC1CC1]

The above compound was prepared using a procedure similar to that described in Scheme 1 using cyclopropylamine in place of cyclobutylamine. MS found for $C_{16}H_{16}N_6O$ as $(M+H)^+$ 309.2.

Example 250. 2-(1H-indazol-5-ylamino)-4-(cyclopropylamino)pyrimidine-5-carboxamide

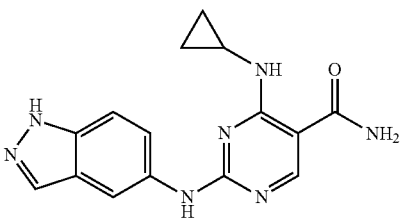 [SMILES: NC(=O)c1cnc(Nc2ccc3[nH]ncc3c2)nc1NC1CC1]

The above compound was prepared using a procedure similar to that described in Scheme 1 using cyclopropylamine in place of cyclobutylamine. MS found for $C_{15}H_{15}N_7O$ as $(M+H)^+$ 310.2.

Example 251. 4-(cyclopropylamino)-2-(4-(oxazol-5-yl)phenylamino)pyrimidine-5-carboxamide

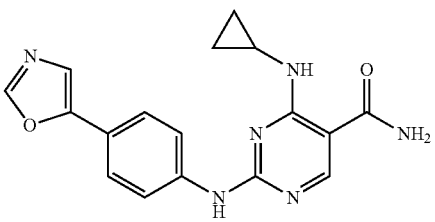 [SMILES: NC(=O)c1cnc(Nc2ccc(-c3cnco3)cc2)nc1NC1CC1]

The above compound was prepared using a procedure similar to that described in Scheme 1 using cyclopropylamine in place of cyclobutylamine. MS found for $C_{17}H_{16}N_6O_2$ as $(M+H)^+$ 337.1.

Example 252. 2-(1H-indazol-6-ylamino)-4-(cyclopropylamino)pyrimidine-5-carboxamide

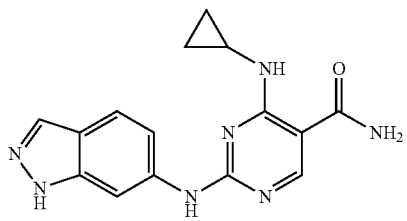 [SMILES: NC(=O)c1cnc(Nc2ccc3cn[nH]c3c2)nc1NC1CC1]

The above compound was prepared using a procedure similar to that described in Scheme 1 using cyclopropylamine in place of cyclobutylamine. MS found for $C_{15}H_{15}N_7O$ as $(M+H)^+$ 310.2.

Example 253. 4-(cyclopropylamino)-2-(quinolin-6-ylamino)pyrimidine-5-carboxamide

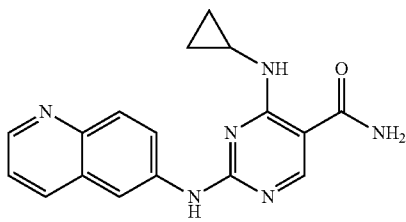 [SMILES: NC(=O)c1cnc(Nc2ccc3ncccc3c2)nc1NC1CC1]

The above compound was prepared using a procedure similar to that described in Scheme 1 using cyclopropylamine in place of cyclobutylamine. MS found for $C_{17}H_{16}N_6O$ as $(M+H)^+$ 321.2.

Example 254. (R)-2-(4-(3-carbamoylpiperidin-1-yl)phenylamino)-4-(cyclopropylamino)pyrimidine-5-carboxamide

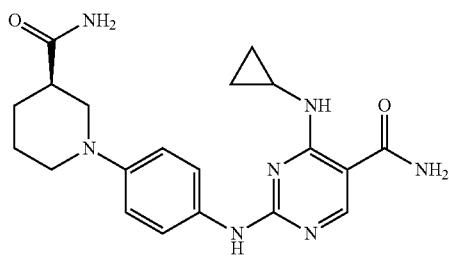 [SMILES: NC(=O)c1cnc(Nc2ccc(N3CCC[C@@H](C(N)=O)C3)cc2)nc1NC1CC1]

The above compound was prepared using a procedure similar to that described in Example 201. MS found for $C_{20}H_{25}N_7O_2$ as $(M+H)^+$ 396.0.

Example 255. (S)-2-(4-(3-carbamoylpiperidin-1-yl)phenylamino)-4-(cyclopropylamino)pyrimidine-5-carboxamide

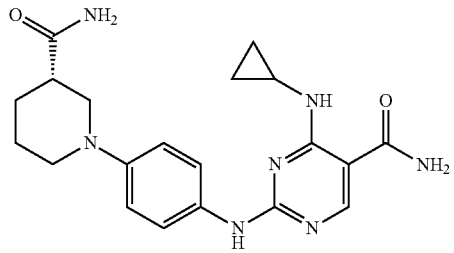 [SMILES: NC(=O)c1cnc(Nc2ccc(N3CCC[C@H](C(N)=O)C3)cc2)nc1NC1CC1]

The above compound was prepared using a procedure similar to that described in Example 201. MS found for $C_{20}H_{25}N_7O_2$ as $(M+H)^+$ 396.2.

Example 256. 4-(cyclobutylamino)-2-(2,3-dihydrobenzo[b][1,4]dioxin-6-ylamino)pyrimidine-5-carboxamide

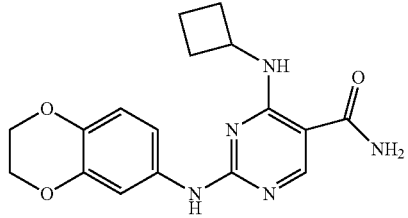 [SMILES: NC(=O)c1cnc(Nc2ccc3c(c2)OCCO3)nc1NC1CCC1]

The above compound was prepared using a procedure similar to that described in Scheme 1 using cyclopropylamine in place of cyclobutylamine. MS found for $C_{17}H_{19}N_5O_3$ as $(M+H)^+$ 342.2.

Example 257. 4-(cyclobutylamino)-2-(4-(piperidin-1-yl)phenylamino)pyrimidine-5-carboxamide

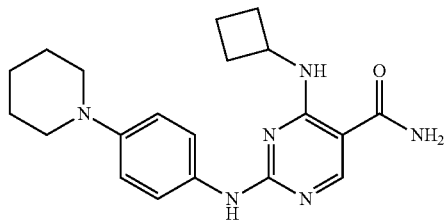 [SMILES: NC(=O)c1cnc(Nc2ccc(N3CCCCC3)cc2)nc1NC1CCC1]

The above compound was prepared using a procedure similar to that described in Scheme 1 using cyclopropylamine in place of cyclobutylamine and an aniline derived from piperidine and 4-fluoronitrobenzene. MS found for $C_{20}H_{26}N_6O$ as $(M+H)^+$ 367.3.

Example 258. 4-(cyclobutylamino)-2-(4-(4-hydroxypiperidin-1-yl)phenylamino)pyrimidine-5-carboxamide

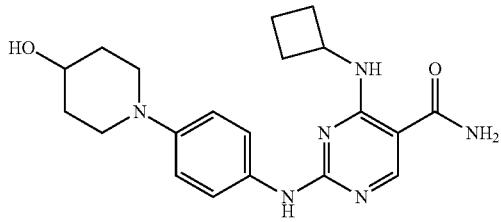 [SMILES: NC(=O)c1cnc(Nc2ccc(N3CCC(O)CC3)cc2)nc1NC1CCC1]

The above compound was prepared using a procedure similar to that described in Scheme 1 using cyclopropylamine in place of cyclobutylamine and an aniline derived from 4-hydroxypiperidine and 4-fluoronitrobenzene. MS found for $C_{20}H_{26}N_6O_2$ as $(M+H)^+$ 383.3.

Example 259. 4-(cyclobutylamino)-2-(4-(4-fluoropiperidin-1-yl)phenylamino)pyrimidine-5-carboxamide

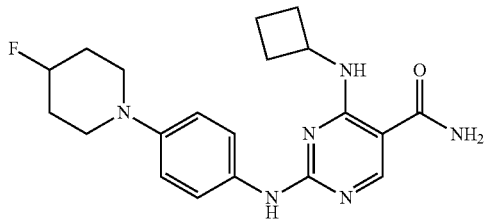 [SMILES: NC(=O)c1cnc(Nc2ccc(N3CCC(F)CC3)cc2)nc1NC1CCC1]

The above compound was prepared using a procedure similar to that described in Scheme 1 using cyclopropylamine in place of cyclobutylamine and an aniline derived from 4-fluoropiperidine and 4-fluoronitrobenzene. MS found for $C_{20}H_{25}N_6OF$ as $(M+H)^+$ 385.0.

Example 260. 4-(cyclobutylamino)-2-(4-morpholinophenylamino)pyrimidine-5-carboxamide

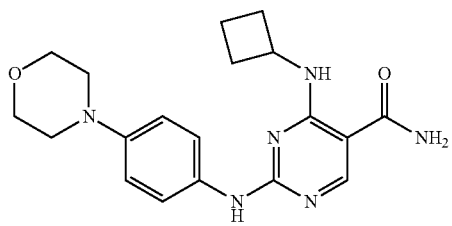 [SMILES: NC(=O)c1cnc(Nc2ccc(N3CCOCC3)cc2)nc1NC1CCC1]

The above compound was prepared using a procedure similar to that described in Scheme 1 using cyclopropylamine in place of cyclobutylamine and an aniline derived from 4-morpholine and 4-fluoronitrobenzene. MS found for $C_{19}H_{24}N_6O_2$ as $(M+H)^+$ 369.0.

Example 261. 4-(cyclobutylamino)-2-(4-(4-methylpiperazin-1-yl)phenylamino)pyrimidine-5-carboxamide

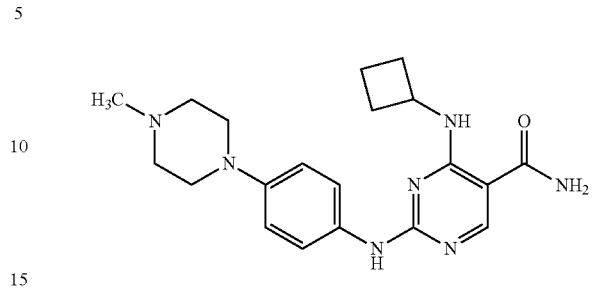

The above compound was prepared using a procedure similar to that described in in Scheme 1 using cyclopropylamine in place of cyclobutylamine and an aniline derived from 1-methylpiperazine and 4-fluoronitrobenzene. MS found for $C_{20}H_{27}N_7O$ as $(M+H)^+$ 382.3.

Example 262. 4-(cyclobutylamino)-2-(4-(3,3-difluoropiperidin-1-yl)phenylamino)pyrimidine-5-carboxamide

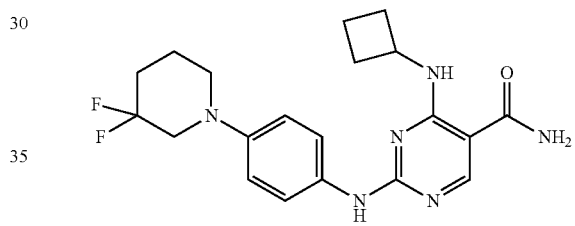

The above compound was prepared using a procedure similar to that described in Scheme 1 using cyclopropylamine in place of cyclobutylamine and an aniline derived from 3,3-difluoropiperidine and 4-fluoronitrobenzene. MS found for $C_{20}H_{24}N_6OF_2$ as $(M+H)^+$ 403.0.

Example 263. 4-(cyclobutylamino)-2-(4-(4,4-difluoropiperidin-1-yl)phenylamino)pyrimidine-5-carboxamide

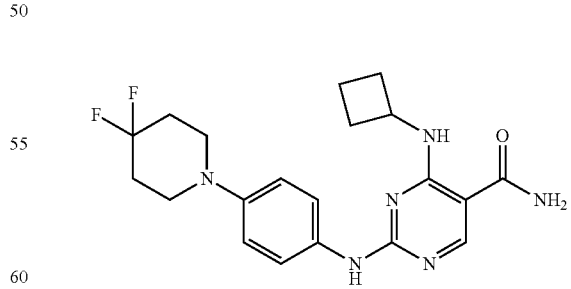

The above compound was prepared using a procedure similar to that described in Scheme 1 using cyclopropylamine in place of cyclobutylamine and an aniline derived from 4,4-difluoropiperidine and 4-fluoronitrobenzene. MS found for $C_{20}H_{24}N_6OF_2$ as $(M+H)^+$ 403.0.

Example 264. (R)-2-(4-(2-carbamoylpyrrolidin-1-yl)phenylamino)-4-(cyclopropylamino)pyrimidine-5-carboxamide

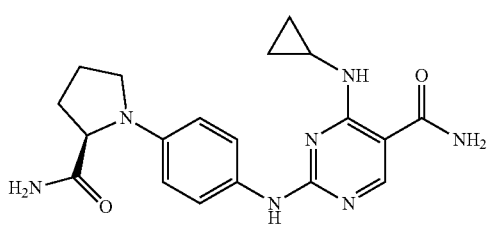 [SMILES: NC(=O)c1cnc(Nc2ccc(N3CCC[C@@H]3C(N)=O)cc2)nc1NC1CC1]

The above compound was prepared using a procedure similar to that described in Example 201. MS found for $C_{19}H_{23}N_7O_2$ as $(M+H)^+$ 382.0.

Example 265. 2-(4-((2S,4R)-2-carbamoyl-4-hydroxypyrrolidin-1-yl)phenylamino)-4-(cyclopropylamino)pyrimidine-5-carboxamide

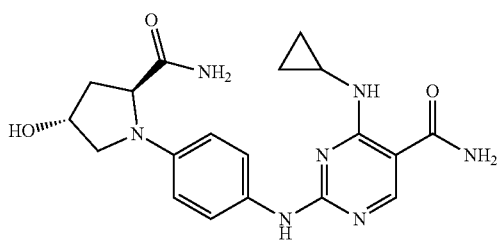 [SMILES: NC(=O)c1cnc(Nc2ccc(N3C[C@H](O)C[C@H]3C(N)=O)cc2)nc1NC1CC1]

The above compound was prepared using a procedure similar to that described in Example 201.

Example 266. 4-(cyclopropylamino)-2-(4-((2S,4R)-4-hydroxy-2-(methylcarbamoyl)pyrrolidin-1-yl)phenylamino)pyrimidine-5-carboxamide

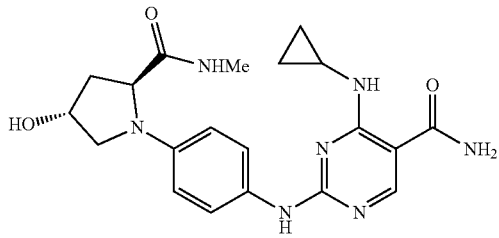 [SMILES: CNC(=O)[C@@H]1C[C@@H](O)CN1c1ccc(Nc2ncc(C(N)=O)c(NC3CC3)n2)cc1]

The above compound was prepared using a procedure similar to that described in Example 201. MS found for $C_{20}H_{25}N_7O_3$ as $(M+H)^+$ 412.5.

Example 267. 4-(cyclopropylamino)-2-(4-((2S,4R)-2-(dimethylcarbamoyl)-4-hydroxypyrrolidin-1-yl)phenylamino)pyrimidine-5-carboxamide

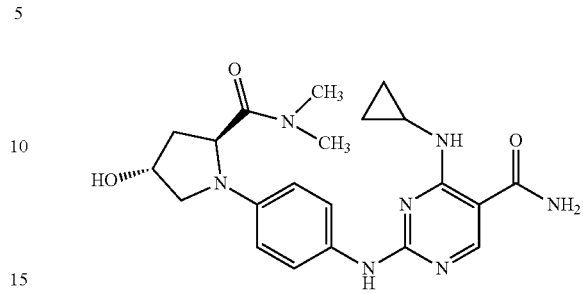

The above compound was prepared using a procedure similar to that described in Example 201. MS found for $C_{21}H_{27}N_7O_3$ as $(M+H)^+$ 426.5.

Example 268. 4-(cyclobutylamino)-2-(4-(4-(methylcarbamoyl)piperidin-1-yl)phenylamino)pyrimidine-5-carboxamide

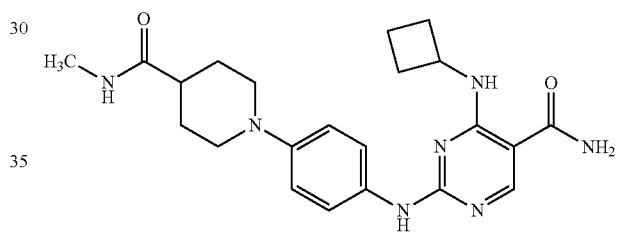

The above compound was prepared using a procedure similar to that described in in Scheme 1 using an aniline derived from ethyl isonipecotate and 4-fluoronitrobenzene. MS found for $C_{22}H_{29}N_7O_2$ as $(M+H)^+$ 424.0.

Example 269. 4-(cyclobutylamino)-2-(4-(4-(dimethylcarbamoyl)piperidin-1-yl)phenylamino)pyrimidine-5-carboxamide

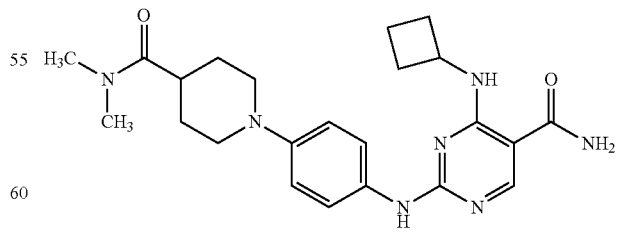

The above compound was prepared using a procedure similar to that described in Scheme 1 in Scheme 1 using an aniline derived from ethyl isonipecotate and 4-fluoronitrobenzene. MS found for $C_{23}H_{31}N_7O_2$ as $(M+H)^+$ 438.3.

Example 270. 4-(cyclobutylamino)-2-(4-(4-(2-hydroxyethyl)piperazin-1-yl)phenylamino)pyrimidine-5-carboxamide

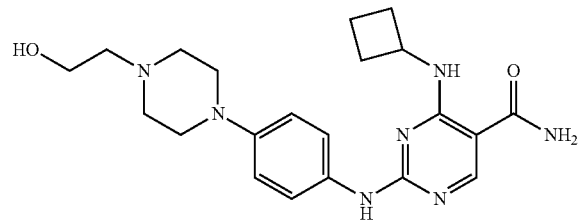 [SMILES: NC(=O)c1cnc(Nc2ccc(N3CCN(CCO)CC3)cc2)nc1NC1CCC1]

The above compound was prepared using a procedure similar to that described in in Scheme 1 using an aniline derived from 1-hydroxyethylpiperazine and 4-fluoronitrobenzene. MS found for $C_{21}H_{29}N_7O_2$ as $(M+H)^+$ 412.3.

Example 271. 2-(3-chloro-4-morpholinophenylamino)-4-(cyclobutylamino)pyrimidine-5-carboxamide

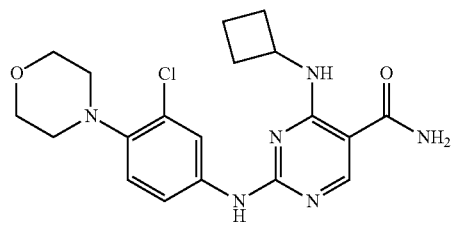

The above compound was prepared using a procedure similar to that described in Scheme 1. MS found for $C_{19}H_{23}N_{x6}O_2Cl$ as $(M+H)^+$ 403.0, 405.0.

Example 272. 4-(cyclobutylamino)-2-(4-(3,3-difluoropyrrolidin-1-yl)phenylamino)pyrimidine-5-carboxamide

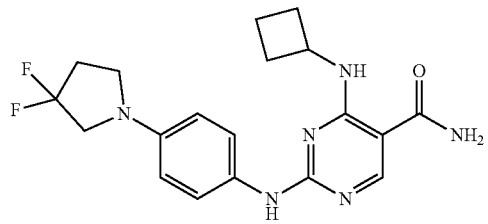 [SMILES: NC(=O)c1cnc(Nc2ccc(N3CCC(F)(F)C3)cc2)nc1NC1CCC1]

The above compound was prepared using a procedure similar to that described in Scheme 1 using an aniline derived from 3,3-difluoropyrrolidine and 4-fluoronitrobenzene. MS found for $C_{19}H_{22}N_6OF_2$ as $(M+H)^+$ 389.0.

Example 273. 4-(cyclobutylamino)-2-(4-(methylcarbamoyl)phenylamino)pyrimidine-5-carboxamide

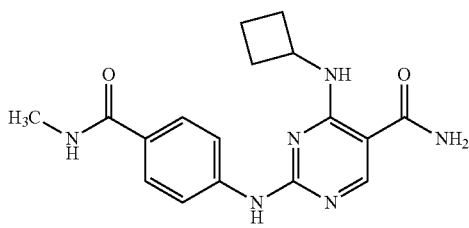 [SMILES: CNC(=O)c1ccc(Nc2ncc(C(N)=O)c(NC3CCC3)n2)cc1]

The above compound was prepared using a procedure similar to that described in Scheme 1. MS found for $C_{17}H_{20}N_6O_2$ as $(M+H)^+$ 341.0.

Example 274. 4-(cyclobutylamino)-2-(4-(dimethylcarbamoyl)phenylamino)pyrimidine-5-carboxamide

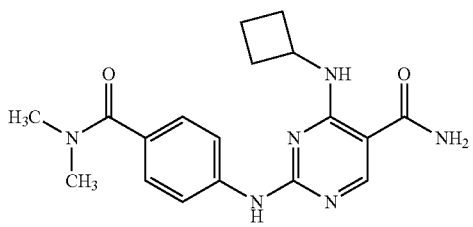 [SMILES: CN(C)C(=O)c1ccc(Nc2ncc(C(N)=O)c(NC3CCC3)n2)cc1]

The above compound was prepared using a procedure similar to that described in Scheme 1. MS found for $C_{18}H_{22}N_6O_2$ as $(M+H)^+$ 355.2.

Example 275. (S)-4-(methylamino)-2-(4-(2-(methylcarbamoyl)piperidin-1-yl)phenylamino)pyrimidine-5-carboxamide

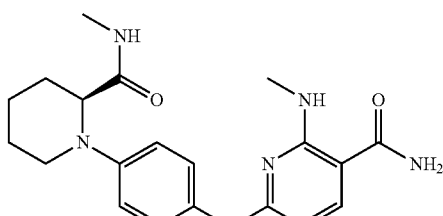

The above compound was prepared using a procedure similar to that described in Example 201 using methylamine in place of cyclobutylamine in the synthesis of the starting material described in Scheme 1. MS found for $C_{19}H_{25}N_7O_2$ as $(M+H)^+$ 384.3. UV: $\lambda$=208, 276.

Example 276. (S)-4-(ethylamino)-2-(4-(2-(methyl-carbamoyl)piperidin-1-yl)phenylamino)pyrimidine-5-carboxamide

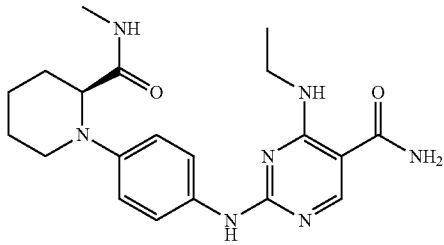 [SMILES: CCNc1nc(Nc2ccc(N3CCCC[C@H]3C(=O)NC)cc2)ncc1C(N)=O]

The above compound was prepared using a procedure similar to that described in Example 201 using ethylamine in place of cyclobutylamine in the synthesis of the starting material described in Scheme 1. MS found for $C_{20}H_{27}N_7O_2$ as $(M+H)^+$ 398.3. UV: $\lambda$=203, 272.

Example 277. (S)-2-(4-(2-(methylcarbamoyl)piperidin-1-yl)phenylamino)-4-(prop-2-ynylamino)pyrimidine-5-carboxamide

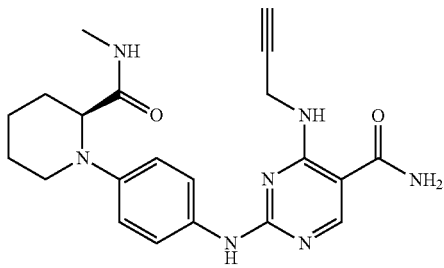 [SMILES: C#CCNc1nc(Nc2ccc(N3CCCC[C@H]3C(=O)NC)cc2)ncc1C(N)=O]

The above compound was prepared using a procedure similar to that described in Example 201 using propargylamine in place of cyclobutylamine in the synthesis of the starting material described in Scheme 1 with propargylamine in place of methylamine. MS found for $C_{21}H_{25}N_7O_2$ as $(M+H)^+$ 408.3. UV: $\lambda$=207, 273.

Example 278. (S)-4-(cyclopropylmethylamino)-2-(4-(2-(methylcarbamoyl)piperidin-1-yl)phenylamino)pyrimidine-5-carboxamide

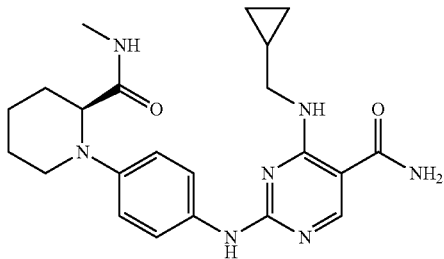 [SMILES: CNC(=O)[C@@H]1CCCCN1c1ccc(Nc2ncc(C(N)=O)c(NCC3CC3)n2)cc1]

The above compound was prepared using a procedure similar to that described in Example 201 using cyclopropylmethylamine in place of cyclobutylamine in the synthesis of the starting material described in Scheme 1. MS found for $C_{22}H_{29}N_7O_2$ as $(M+H)^+$ 424.4. UV: $\lambda$=204, 260.

Example 279. (R)-2-(4-(3-carbamoylpiperidin-1-yl)phenylamino)-4-(2,2,2-trifluoroethylamino)pyrimidine-5-carboxamide

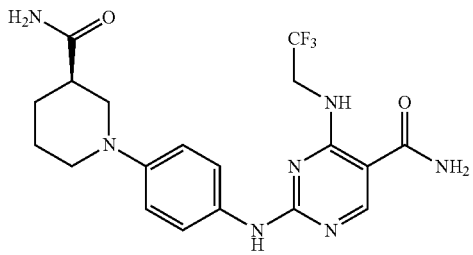 [SMILES: NC(=O)c1cnc(Nc2ccc(N3CCC[C@@H](C(N)=O)C3)cc2)nc1NCC(F)(F)F]

The above compound was prepared using a procedure similar to that described in Example 201 using trifluoroethylamine in place of cyclobutylamine in the synthesis of the starting material described in Scheme 1. MS found for $C_{19}H_{22}F_3N_7O_2$ as $(M+H)^+$ 438.3.

Example 280. (R)-2-(4-(3-(methylcarbamoyl)piperidin-1-yl)phenylamino)-4-(2,2,2-trifluoroethylamino)pyrimidine-5-carboxamide

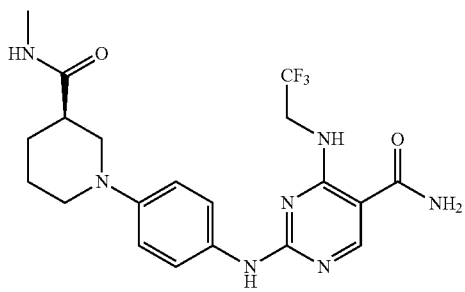 [SMILES: CNC(=O)[C@@H]1CCCN(c2ccc(Nc3ncc(C(N)=O)c(NCC(F)(F)F)n3)cc2)C1]

The above compound was prepared using a procedure similar to that described in Example 201 using trifluoroethylamine in place of cyclobutylamine in the synthesis of the starting material described in Scheme 1. MS found for $C_{20}H_{24}F_3N_7O_2$ as $(M+H)^+$ 452.3.

Example 281. (S)-2-(4-(2-carbamoylpiperidin-1-yl)phenylamino)-4-(2,2,2-trifluoroethylamino)pyrimidine-5-carboxamide

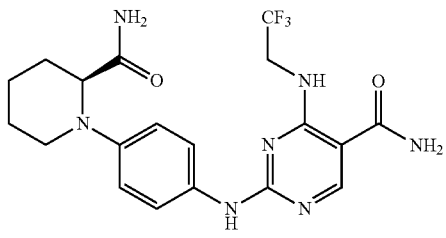 [SMILES: NC(=O)c1cnc(Nc2ccc(N3CCCC[C@H]3C(N)=O)cc2)nc1NCC(F)(F)F]

The above compound was prepared using a procedure similar to that described in Example 201 using trifluoroethylamine in place of cyclobutylamine in the synthesis of the starting material described in Scheme 1. MS found for $C_{19}H_{22}F_3N_7O_2$ as (M+H)+ 438.3.

Example 282. (S)-2-(4-(2-(dimethylcarbamoyl)piperidin-1-yl)phenylamino)-4-(2,2,2-trifluoroethylamino)pyrimidine-5-carboxamide

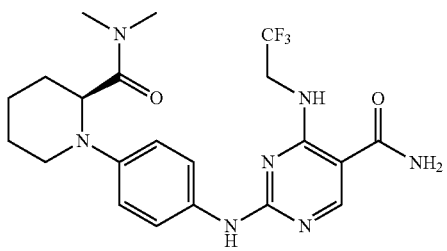 [SMILES: CN(C)C(=O)[C@@H]1CCCCN1c1ccc(Nc2ncc(C(N)=O)c(NCC(F)(F)F)n2)cc1]

The above compound was prepared using a procedure similar to that described in Example 201 using trifluoroethylamine in place of cyclobutylamine in the synthesis of the starting material described in Scheme 1. MS found for C21H26F3N7O2 as (M+H)+ 466.4.

Example 283. 2-(4-methoxyphenylamino)-4-(2,2,2-trifluoroethylamino)pyrimidine-5-carboxamide

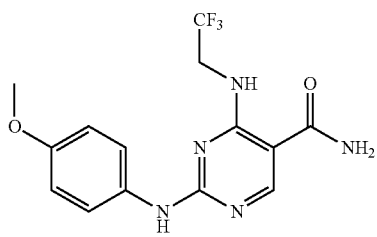 [SMILES: COc1ccc(Nc2ncc(C(N)=O)c(NCC(F)(F)F)n2)cc1]

The above compound was prepared using a procedure similar to that described in Scheme 1, using trifluoroethylamine in place of cyclobutylamine and by using para-anisidine in the last step. MS found for C14H14F3N5O2 as (M+H)+ 342.2. UV: λ=217.

Example 284. 2-(4-carbamoylphenylamino)-4-(2,2,2-trifluoroethylamino)pyrimidine-5-carboxamide

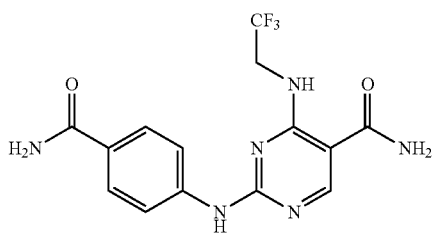 [SMILES: NC(=O)c1ccc(Nc2ncc(C(N)=O)c(NCC(F)(F)F)n2)cc1]

The above compound was prepared using a procedure similar to that described in Scheme 1 using trifluoroethylamine in place of cyclobutylamine and by using 4-aminobenzamide in the last step. MS found for $C_{14}H_{13}F_3N_6O_2$ as (M+H)+ 355.2. UV: λ=200, 290.

Example 285. (S)-4-(tert-butylamino)-2-(4-(2-(methylcarbamoyl)piperidin-1-yl)phenylamino)pyrimidine-5-carboxamide

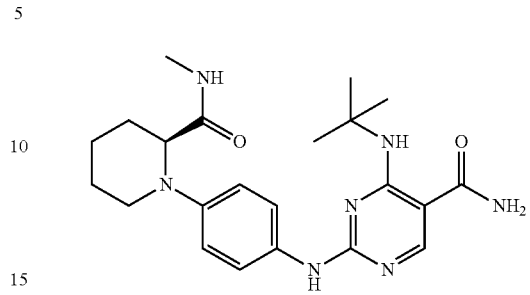

The above compound was prepared using a procedure similar to that described in Example 201 using tert-butylamine in place of cyclobutylamine in the synthesis of the starting material described in Scheme 1. MS found for $C_{22}H_{31}N_7O_2$ as (M+H)+ 426.3.

Example 286. (S)-4-(2-methoxyethylamino)-2-(4-(2-(methylcarbamoyl)piperidin-1-yl)phenylamino)pyrimidine-5-carboxamide

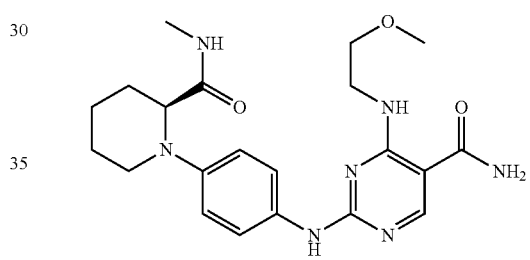

The above compound was prepared using a procedure similar to that described in Example 201 using 2-methoxyethylamine in place of cyclobutylamine in the synthesis of the starting material described in Scheme 1. MS found for $C_{21}H_{29}N_7O_3$ as (M+H)+ 428.3. UV: λ=202, 268.

Example 287. (S)-4-(cyclopentylamino)-2-(4-(2-(methylcarbamoyl)piperidin-1-yl)phenylamino)pyrimidine-5-carboxamide

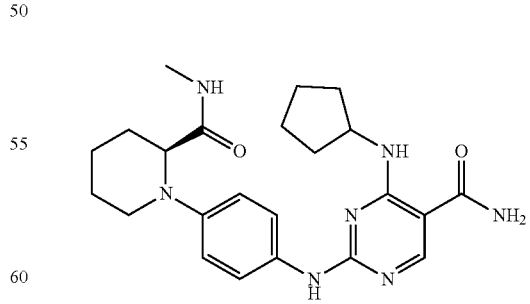

The above compound was prepared using a procedure similar to that described in Example 201 using cyclopentylamine in place of cyclobutylamine in the synthesis of the starting material described in Scheme 1. MS found for $C_{23}H_{31}N_7O_2$ as (M+H)+ 438.3. UV: λ=203, 262.

Example 288: 4-(cyclopropylamino)-2-(4-ethoxy-phenylamino)pyrimidine-5-carboxamide

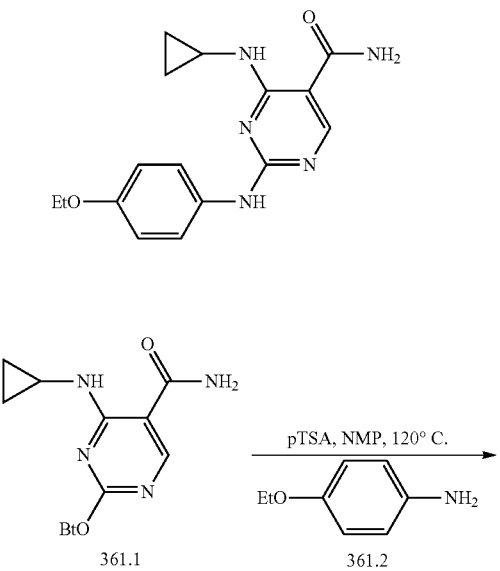

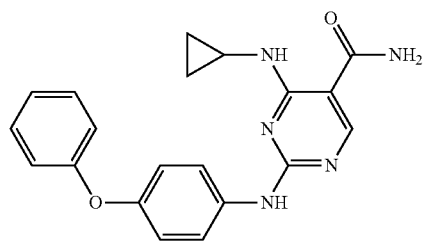 [SMILES: NC(=O)c1cnc(Nc2ccc(Oc3ccccc3)cc2)nc1NC1CC1]

Intermediate 361.1 stirred with 4-ethoxyaniline 361.2 [CAS 156-43-4] and pTSA in NMP. Reaction heated at 120° C. for 2 h in a sealed tube. The reaction cooled, turned slightly acidic with aqueous TFA, and purified by reverse phase preparative HPLC to afford the title compound. MS found for $C_{16}H_{19}N_5O_2$ as (M+H)$^+$ 314.3. λ=275 nm.

Example 289: 4-(cyclopropylamino)-2-(4-phenoxy-phenylamino)pyrimidine-5-carboxamide Intermediate 361.1 stirred with 4-phenoxyaniline [CAS 139-59-3] and pTSA in NMP as described in example 288. Reverse phase preparative HPLC afforded the title compound. MS found for $C_{20}H_{19}N_5O_2$ as (M+H)$^+$ 362.2. UV λ=277 nm.

Example 290: 4-(cyclopropylamino)-2-(4-(trifluoromethoxy)phenylamino)pyrimidine-5-carboxamide

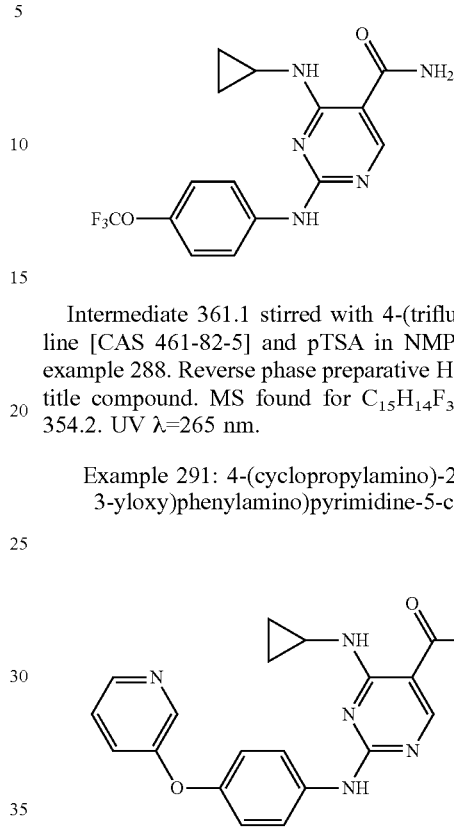

Intermediate 361.1 stirred with 4-(trifluoromethoxy)aniline [CAS 461-82-5] and pTSA in NMP as described in example 288. Reverse phase preparative HPLC afforded the title compound. MS found for $C_{15}H_{14}F_3N_5O_2$ as (M+H) 354.2. UV λ=265 nm.

Example 291: 4-(cyclopropylamino)-2-(4-(pyridin-3-yloxy)phenylamino)pyrimidine-5-carboxamide

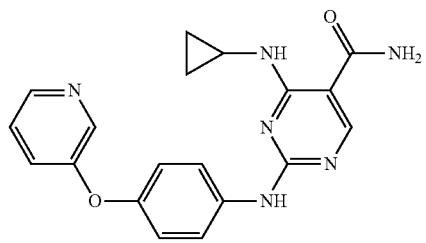 [SMILES: NC(=O)c1cnc(Nc2ccc(Oc3cccnc3)cc2)nc1NC1CC1]

Intermediate 361.1 stirred with 4-(3-Pyridyloxy)aniline [CAS 80650-45-9] and pTSA in NMP as described in example 288. Reverse phase preparative HPLC afforded the title compound. MS found for $C_{19}H_{18}N_6O_2$ as (M+H)$^+$ 363.3. UV λ=205, 267 nm.

Example 292: 2-(4-(2-cyanoethylsulfonyl)phenylamino)-4-(cyclopropylamino)pyrimidine-5-carboxamide

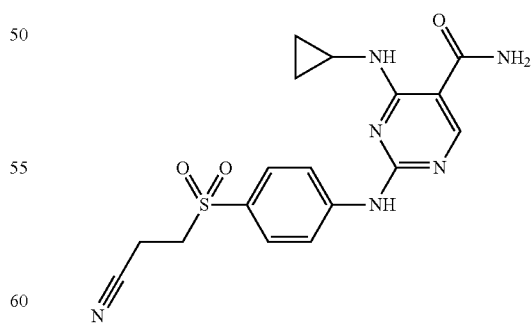

Intermediate 361.1 stirred with 3-(4-aminophenyl)sulfonyl propanenitrile [CAS 84362-27-6] and pTSA in NMP as described in example 288. Reverse phase preparative HPLC afforded the title compound. MS found for $C_{17}H_{18}N_6O_3S$ as (M+H)$^+$ 387.2. UV λ=290 nm.

Example 293: 4-(cyclopropylamino)-2-(4-isobutoxyphenylamino)pyrimidine-5-carboxamide

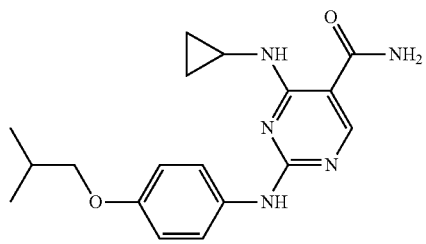 [SMILES: CC(C)COc1ccc(Nc2ncc(C(N)=O)c(NC3CC3)n2)cc1]

Intermediate 361.1 stirred with 4-(2-methylpropoxy)aniline hydrochloride [CAS 1050161-26-6] and pTSA in NMP as described in example 288. Reverse phase preparative HPLC afforded the title compound. MS found for $C_{18}H_{23}N_5O_2$ as $(M+H)^+$ 342.4. UV $\lambda$=280 nm.

Example 294: 4-(cyclopropylamino)-2-(4-(thiazol-4-ylmethylsulfonyl)phenylamino)pyrimidine-5-carboxamide

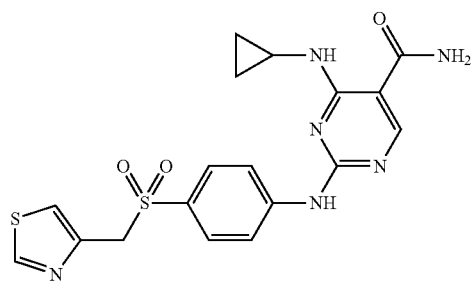 [SMILES: NC(=O)c1cnc(Nc2ccc(S(=O)(=O)Cc3cscn3)cc2)nc1NC1CC1]

Intermediate 361.1 stirred with 4-(thiazol-4-ylmethylsulfonyl)aniline and pTSA in NMP as described in example 288. Reverse phase preparative HPLC afforded the title compound. MS found for $C_{18}H_{18}N_6O_3S_2$ as $(M+H)^+$ 431.2. UV $\lambda$=291 nm.

Example 295. (S)-4-(benzylamino)-2-(4-(2-(methylcarbamoyl)piperidin-1-yl)phenylamino)pyrimidine-5-carboxamide

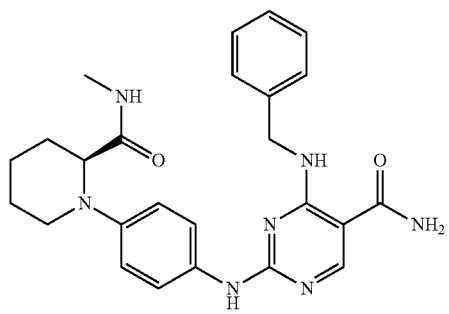 [SMILES: CNC(=O)[C@@H]1CCCCN1c1ccc(Nc2ncc(C(N)=O)c(NCc3ccccc3)n2)cc1]

The above compound was prepared using a procedure similar to that described in Example 201 using benzylamine in place of cyclobutylamine in the synthesis of the starting material described in Scheme 1. MS found for $C_{25}H_{29}N_7O_2$ as $(M+H)^+$ 460.3. UV: $\lambda$=208, 261.

Example 296. (S)-4-(isopropylamino)-2-(4-(2-(methylcarbamoyl)piperidin-1-yl)phenylamino)pyrimidine-5-carboxamide

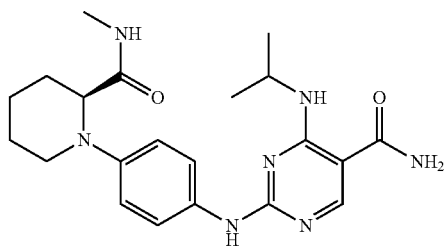 [SMILES: CNC(=O)[C@@H]1CCCCN1c1ccc(Nc2ncc(C(N)=O)c(NC(C)C)n2)cc1]

The above compound was prepared using a procedure similar to that described in Example 201 using isopropylamine in place of cyclobutylamine in the synthesis of the starting material described in Scheme 1. MS found for $C_{21}H_{29}N_7O_2$ as $(M+H)^+$ 412.4. UV: $\lambda$=202, 271.

Example 297. (S)-2-(4-(2-(methylcarbamoyl)piperidin-1-yl)phenylamino)-4-(2,3,6-trifluorobenzylamino)pyrimidine-5-carboxamide

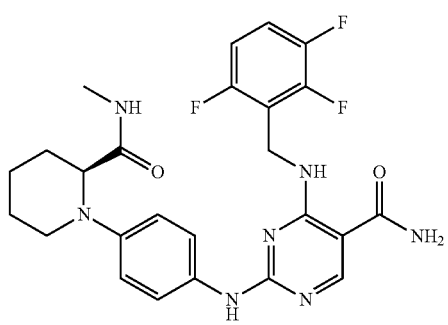 [SMILES: CNC(=O)[C@@H]1CCCCN1c1ccc(Nc2ncc(C(N)=O)c(NCc3c(F)ccc(F)c3F)n2)cc1]

The above compound was prepared using a procedure similar to that described in Example 201 using 2,3,6-trifluorobenzylamine in place of cyclobutylamine in the synthesis of the starting material described in Scheme 1. MS found for $C_{25}H_{26}F_3N_7O_2$ as $(M+H)^+$ 514.4.

Example 298. (S)-4-(2-methoxyethylamino)-2-(4-(2-(methylcarbamoyl)piperidin-1-yl)phenylamino)pyrimidine-5-carboxamide

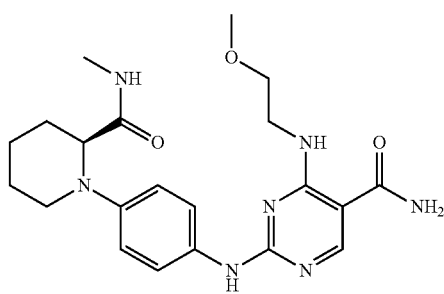 [SMILES: CNC(=O)[C@@H]1CCCCN1c1ccc(Nc2ncc(C(N)=O)c(NCCOC)n2)cc1]

The above compound was prepared using a procedure similar to that described in Example 201 using 2-methoxy-ethylamine in place of cyclobutylamine in the synthesis of the starting material described in Scheme 1. MS found for $C_{22}H_{31}N_7O_3$ as $(M+H)^+$ 442.4. UV: λ=203, 273.

Example 299. 4-(1-methyl-1H-indazol-4-ylamino)-2-(4-(2-(pyrrolidin-1-yl)ethoxy)phenylamino) pyrimidine-5-carboxamide

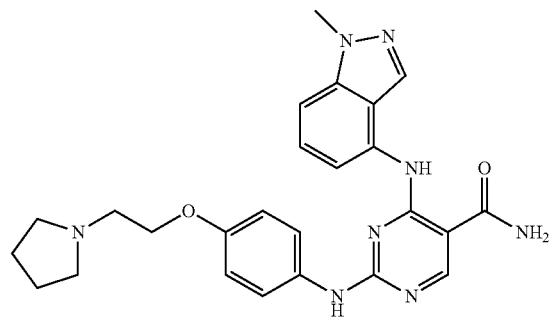 [SMILES: Cn1ncc2c(Nc3nc(Nc4ccc(OCCN5CCCC5)cc4)ncc3C(N)=O)cccc21]

The above compound was prepared using a procedure similar to that described in Example 151. MS found for $C_{25}H_{28}N_8O_2$ as $(M+H)^+$ 473.4. UV: λ=212.2, 285.4.

Example 300. 4-(1,2-dimethyl-1H-indol-4-ylamino)-2-(4-(2-(pyrrolidin-1-yl)ethoxy)phenylamino) pyrimidine-5-carboxamide

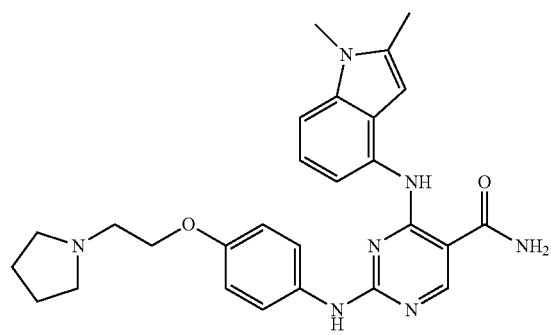 [SMILES: Cc1cc2c(Nc3nc(Nc4ccc(OCCN5CCCC5)cc4)ncc3C(N)=O)cccc2n1C]

The above compound was prepared using a procedure similar to that described in Example 48. MS found for $C_{27}H_{31}N_7O_2$ as $(M+H)^+$ 486.5. UV: λ=218.6, 258.9.

Example 301. 4-(4-chloronaphthalen-1-ylamino)-2-(4-(2-(pyrrolidin-1-yl)ethoxy)phenylamino) pyrimidine-5-carboxamide

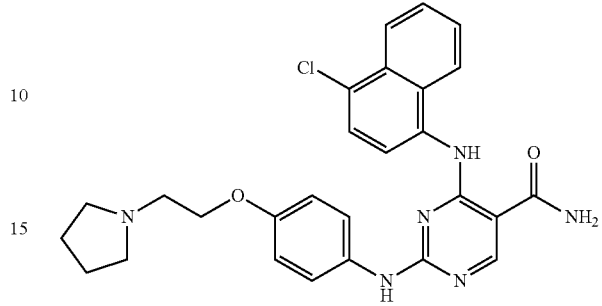

The above compound was prepared using using a procedure similar to that described in Example 48. MS found for C27H27ClN6O2 as $(M+H)^+$ 503.4, 505.4 (Cl pattern). UV: λ=222.8, 284.2.

Example 302. 4-(3-methylcinnolin-5-ylamino)-2-(4-(2-(pyrrolidin-1-yl)ethoxy)phenylamino) pyrimidine-5-carboxamide

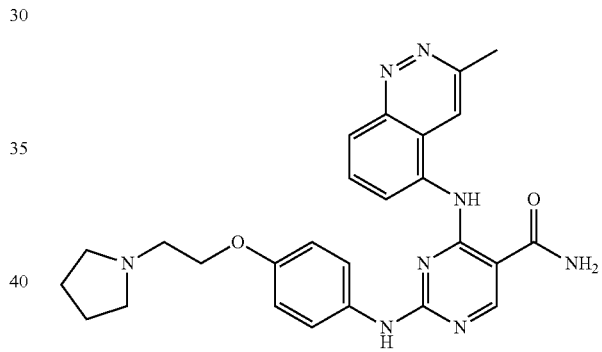

The above compound was prepared using a procedure similar to that described in Example 48. MS found for C26H28N8O2 as $(M+H)^+$ 485.4. UV: λ=276.1.

Example 303. 4-(benzo[d]thiazol-7-ylamino)-2-(4-(2-(pyrrolidin-1-yl)ethoxy)phenylamino) pyrimidine-5-carboxamide

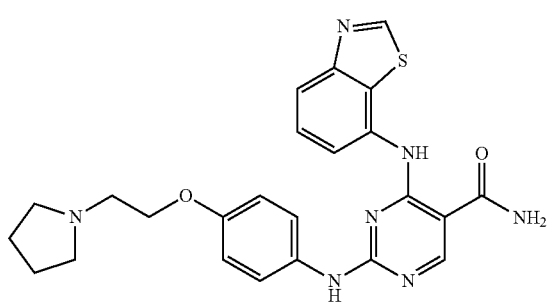 [SMILES: NC(=O)c1cnc(Nc2ccc(OCCN3CCCC3)cc2)nc1Nc1cccc2ncsc12]

The above compound was prepared using a procedure similar to that described in Example 48. MS found for C24H25N7O2S as (M+H)+ 476.4. UV: λ=216.9, 281.9.

Example 304. 4-(naphthalen-1-ylamino)-2-(4-(2-(pyrrolidin-1-yl)ethoxy)phenylamino) pyrimidine-5-carboxamide

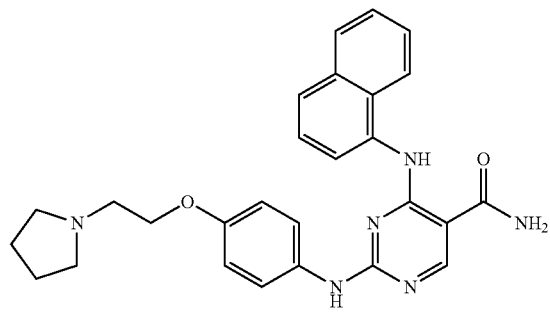 [SMILES: NC(=O)c1cnc(Nc2ccc(OCCN3CCCC3)cc2)nc1Nc1cccc2ccccc12]

The above compound was prepared using a procedure similar to that described in Example 48. MS found for C27H28N6O2 as (M+H)+ 469.4. UV: λ=219.2, 280.7.

Example 305. 4-(4-(methylsulfonyl)phenylamino)-2-(4-(2-(pyrrolidin-1-yl)ethoxy)phenylamino)pyrimidine-5-carboxamide

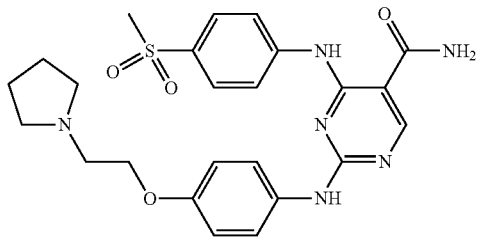 [SMILES: CS(=O)(=O)c1ccc(Nc2nc(Nc3ccc(OCCN4CCCC4)cc3)ncc2C(N)=O)cc1]

The above compound was prepared using a procedure similar to that described in Example 48. MS found for C24H28N6O4S as (M+H)+ 497.4. UV: λ=292.

Example 306: 2-(4-(2-(pyrrolidin-1-yl)ethoxy)phenylamino)-4-(2,2,2-trifluoroethylamino)pyrimidine-5-carboxamide

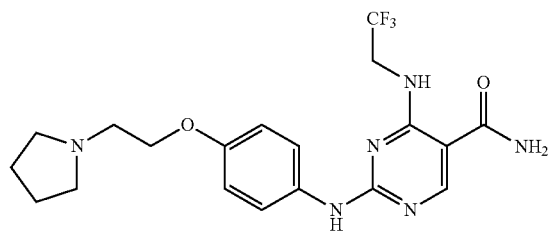 [SMILES: NC(=O)c1cnc(Nc2ccc(OCCN3CCCC3)cc2)nc1NCC(F)(F)F]

This compound was synthesized utilizing the chemistry described in Scheme 1 with trifluoroethylamine in place of cyclobutylamine. MS found for C19H23F3N6O2 as (M+H)+ 425.3. UV λ=215, 245, 275 nm.

Example 307: 4-(benzylamino)-2-(4-(2-(pyrrolidin-1-yl)ethoxy)phenylamino)pyrimidine-5-carboxamide

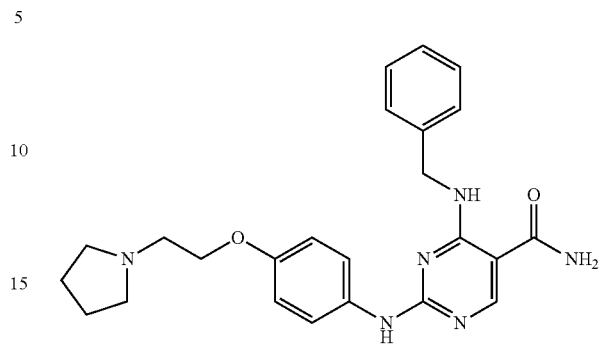

This compound was synthesized utilizing the chemistry described in Scheme 1 with benzylamine in place of cyclobutylamine. MS found for C24H28N6O2 as (M+H)+ 433.4. UV λ=251 nm.

Example 309. 4-(cyclobutylamino)-2-(2-oxoindolin-5-ylamino)pyrimidine-5-carboxamide

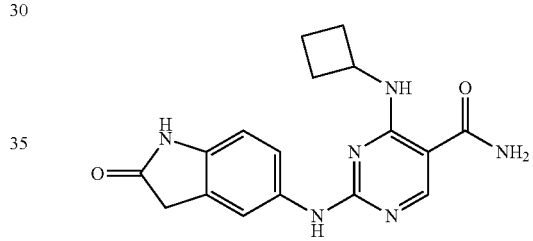

The above compound was prepared using 5-aminoindolin-2-one and a the procedure described in Scheme 1. MS found for C17H18N6O2 as (M+H)+ 339.0.

Example 310. 4-(cyclobutylamino)-2-(4-methyl-3-oxo-3,4-dihydro-2H-benzo[b][1,4]oxazin-7-ylamino)pyrimidine-5-carboxamide

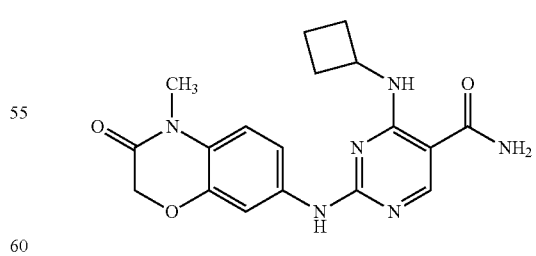

The above compound was prepared using N7-amino-4-methyl-2H-benzo[b][1,4]oxazin-3(4H)-one (synthesized from 2-amino-5-nitrophenol and ethyl bromoacetate in three steps) using a procedure similar to that described in Scheme 1. MS found for C18H20N6O3 as (M+H)+ 369.0.

Example 311. 4-(cyclobutylamino)-2-(2-oxo-1,2,3,4-tetrahydroquinolin-6-ylamino)pyrimidine-5-carboxamide

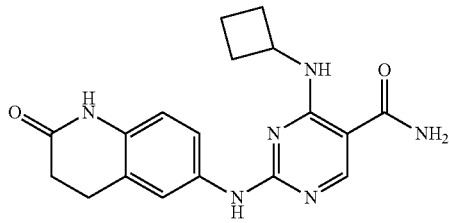 [SMILES: NC(=O)c1cnc(Nc2ccc3c(c2)CCC(=O)N3)nc1NC1CCC1]

The above compound was prepared using 6-amino-3,4-dihydroquinolin-2(1H)-one (prepared by nitration of 3,4-dihydroquinolin-2(1H)-one followed by reduction with iron powder) using a procedure similar to that described in Scheme 1. MS found for $C_{18}H_{20}N_6O_2$ as (M+H)$^+$ 353.0

Example 312. 4-(cyclobutylamino)-2-(2,2,4-trimethyl-3-oxo-3,4-dihydro-2H-benzo[b][1,4]oxazin-7-ylamino)pyrimidine-5-carboxamide

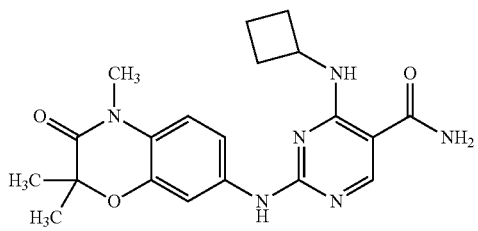 [SMILES: CN1C(=O)C(C)(C)Oc2cc(Nc3ncc(C(N)=O)c(NC4CCC4)n3)ccc21]

The above compound was prepared using $N_7$-amino-4-methyl-2H-benzo[b][1,4]oxazin-3(4H)-one (synthesized from 2-amino-5-nitrophenol and ethyl 2-bromo-2-methylpropanoate in three steps) using a procedure similar to that described in Scheme 1. MS found for $C_{20}H_{24}N_6O_3$ as (M+H)$^+$ 397.0.

Example 313. 4-(cyclobutylamino)-2-(1-methyl-2-oxo-1,2,3,4-tetrahydroquinolin-6-ylamino)pyrimidine-5-carboxamide

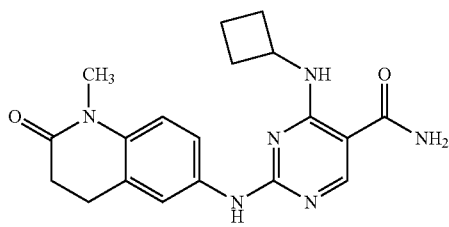 [SMILES: CN1C(=O)CCc2cc(Nc3ncc(C(N)=O)c(NC4CCC4)n3)ccc21]

The above compound was prepared using 6-amino-1-methyl-3,4-dihydroquinolin-2(1H)-one (prepared by nitration of 3,4-dihydroquinolin-2(1H)-one followed by methylation and subsequent reduction with iron powder) using a procedure similar to that described in Scheme 1. MS found for $C_{19}H_{22}N_6O_2$ as (M+H)$^+$ 367.0.

Example 314. 4-(cyclobutylamino)-2-(4-methyl-3-oxo-3,4-dihydro-2H-benzo[b][1,4]oxazin-6-ylamino)pyrimidine-5-carboxamide

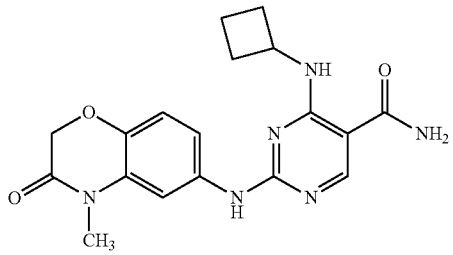 [SMILES: CN1C(=O)COc2ccc(Nc3ncc(C(N)=O)c(NC4CCC4)n3)cc21]

The above compound was prepared using 6-amino-4-methyl-2H-benzo[b][1,4]oxazin-3(4H)-one (synthesized from 2-amino-4-nitrophenol and ethyl bromoacetate in three steps) using a procedure similar to that described in Scheme 1. MS found for $C_{18}H_{20}N_6O_3$ as (M+H)$^+$ 369.0.

Example 315. 4-(cyclobutylamino)-2-(3-oxo-3,4-dihydro-2H-benzo[b][1,4]oxazin-6-ylamino)pyrimidine-5-carboxamide

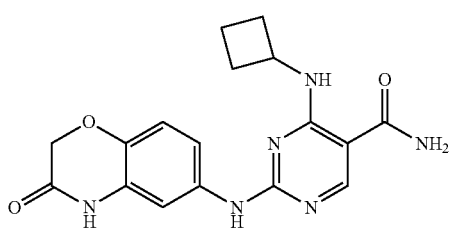 [SMILES: NC(=O)c1cnc(Nc2ccc3c(c2)NC(=O)CO3)nc1NC1CCC1]

The above compound was prepared using 6-amino-2H-benzo[b][1,4]oxazin-3(4H)-one (synthesized from 2-amino-4-nitrophenol and ethyl bromoacetate in two steps) using a procedure similar to that described in Scheme 1. MS found for $C_{17}H_{18}N_6O_3$ as (M+H)$^+$ 355.0.

Example 316. 2-(1H-benzo[d][1,2,3]triazol-6-ylamino)-4-(cyclobutylamino)pyrimidine-5-carboxamide

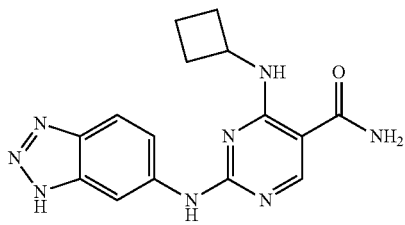

The above compound was prepared using 1H-benzo[d][1,2,3]triazol-6-amine using a procedure similar to that described in Scheme 1. MS found for $C_{15}H_{16}N_8O$ as (M+H)$^+$ 325.0.

Example 317. 4-(cyclobutylamino)-2-(2-oxo-2,3-dihydrobenzofuran-5-ylamino)pyrimidine-5-carboxamide

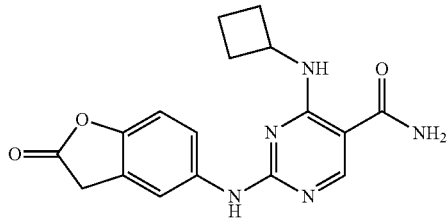 [SMILES: NC(=O)c1cnc(Nc2ccc3c(c2)CC(=O)O3)nc1NC1CCC1]

The above compound was prepared using 5-aminobenzofuran-2(3H)-one using a procedure similar to that described in Scheme 1. MS found for $C_{17}H_{17}N_5O_3$ as $(M+H)^+$ 340.0. $^1$H NMR (DMSO-$d_6$, 400 MHz): δ 8.41 (s, 1H), 8.05 (s, 1H) 7.88 (d, 1H) 7.78 (d, 1H), 4.59 (m, 1H), 2.47 (m, 2H), 2.09 (m, 2H), 1.90 (m, 2H).

Example 318. 4-(cyclopropylamino)-2-(2,2-difluorobenzo[d][1,3]dioxol-5-ylamino)pyrimidine-5-carboxamide

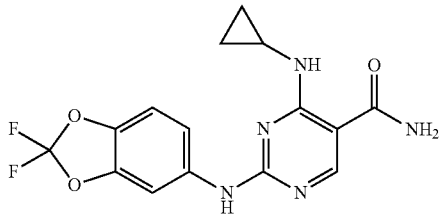 [SMILES: NC(=O)c1cnc(Nc2ccc3c(c2)OC(F)(F)O3)nc1NC1CC1]

The above compound was prepared using a procedure similar to that described in Scheme 1 using cyclopropylamine in place of cyclobutylamine. MS found for $C_{15}H_{13}N_5O_3F_2$ as $(M+H)^+$ 350.1.

Example 319. 4-(cyclopropylamino)-2-(2-methylbenzo[d]thiazol-5-ylamino)pyrimidine-5-carboxamide

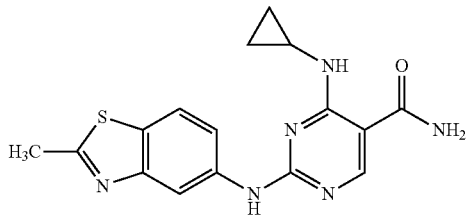 [SMILES: Cc1nc2cc(Nc3ncc(C(N)=O)c(NC4CC4)n3)ccc2s1]

The above compound was prepared using a procedure similar to that described in Scheme 1 using cyclopropylamine in place of cyclobutylamine. MS found for $C_{16}H_{16}N_6OS$ as $(M+H)^+$ 341.0.

Example 320. 2-(benzo[d]thiazol-5-ylamino)-4-(cyclopropylamino)pyrimidine-5-carboxamide

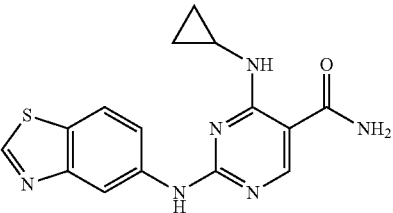 [SMILES: NC(=O)c1cnc(Nc2ccc3scnc3c2)nc1NC1CC1]

The above compound was prepared using a procedure similar to that described in Scheme 1 using cyclopropylamine in place of cyclobutylamine. MS found for $C_{15}H_{14}N_6OS$ as $(M+H)^+$ 327.1.

Example 321. 4-(cyclopropylamino)-2-(imidazo[1,2-a]pyridin-6-ylamino)pyrimidine-5-carboxamide

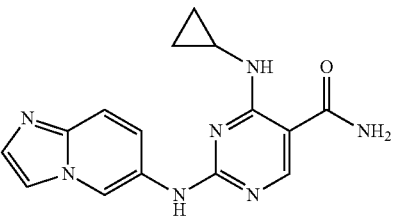 [SMILES: NC(=O)c1cnc(Nc2ccc3nccn3c2)nc1NC1CC1]

The above compound was prepared using a procedure similar to that described in Scheme 1 using cyclopropylamine in place of cyclobutylamine. MS found for $C_{15}H_{15}N_7O$ as $(M+H)^+$ 310.2.

Example 322. 2-(1H-benzo[d]imidazol-6-ylamino)-4-(cyclopropylamino)pyrimidine-5-carboxamide

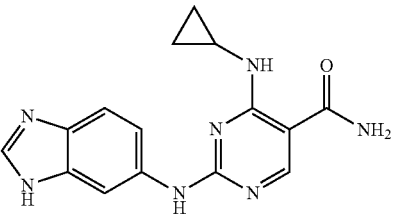

The above compound was prepared using a procedure similar to that described in Scheme 1 using cyclopropylamine in place of cyclobutylamine. MS found for $C_{15}H_{15}N_7O$ as $(M+H)^+$ 310.1.

Example 323. 2-(1H-benzo[d][1,2,3]triazol-6-ylamino)-4-(cyclopropylamino)pyrimidine-5-carboxamide

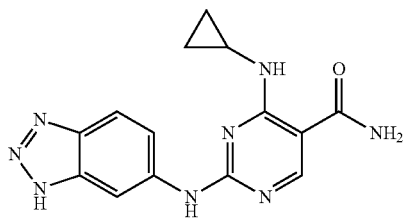 [SMILES: NC(=O)c1cnc(Nc2ccc3nn[nH]c3c2)nc1NC1CC1]

The above compound was prepared using a procedure similar to that described in Scheme 1 using cyclopropylamine in place of cyclobutylamine. MS found for $C_{14}H_{14}N_8O$ as $(M+H)^+$ 311.2. $^1$H NMR (CD$_3$OD, 400 MHz): δ 8.63 (s, 1H), 8.42 (s, 1H), 7.92 (d, 1H), 7.58 (d, 1H), 3.04 (m, 1H), 1.03 (m, 2H), 0.87 (m, 2H).

Example 324. 4-(cyclopropylamino)-2-(3-methyl-1H-indazol-6-ylamino)pyrimidine-5-carboxamide

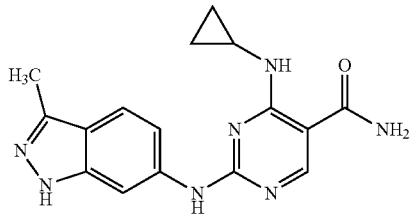 [SMILES: Cc1n[nH]c2cc(Nc3ncc(C(N)=O)c(NC4CC4)n3)ccc12]

The above compound was prepared using a procedure similar to that described in Scheme 1 using cyclopropylamine in place of cyclobutylamine. MS found for $C_{16}H_{17}N_7O_1$ as $(M+H)^+$ 324.

Example 325. 2-(benzo[c][1,2,5]thiadiazol-5-ylamino)-4-(cyclopropylamino)pyrimidine-5-carboxamide

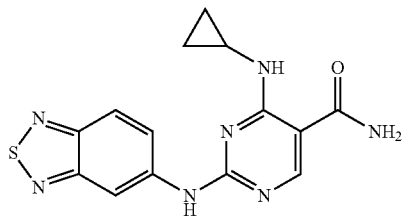 [SMILES: NC(=O)c1cnc(Nc2ccc3nsnc3c2)nc1NC1CC1]

The above compound was prepared using a procedure similar to that described in Scheme 1 using cyclopropylamine in place of cyclobutylamine. MS found for $C_{14}H_{13}N_7OS$ as $(M+H)^+$ 328.2.

Example 326. 2-(7-chloro-1H-indazol-6-ylamino)-4-(cyclopropylamino)pyrimidine-5-carboxamide

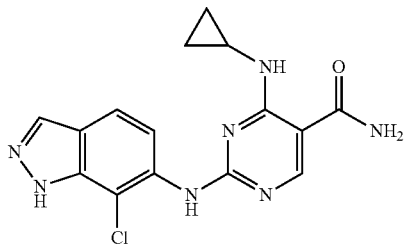 [SMILES: NC(=O)c1cnc(Nc2ccc3cn[nH]c3c2Cl)nc1NC1CC1]

The above compound was prepared using a procedure similar to that described in Scheme 1 using cyclopropylamine in place of cyclobutylamine, after chlorinating the 6-aminoindazole ring using N-chlorosuccinimide. MS found for $C_{15}H_{17}N_7OCl$ as $(M+H)^+$ 344.2, 346.2.

Example 327. 2-(3-chloro-1H-indazol-5-ylamino)-4-(cyclopropylamino)pyrimidine-5-carboxamide

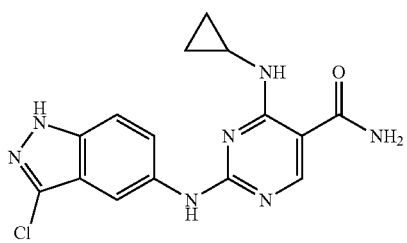 [SMILES: NC(=O)c1cnc(Nc2ccc3[nH]nc(Cl)c3c2)nc1NC1CC1]

The above compound was prepared using a procedure similar to that described in Example 326. MS found for $C_{15}H_{17}N_7OCl$ as $(M+H)^+$ 344.2, 346.2. $^1$H NMR (CD$_3$OD, 400 MHz): δ 8.24 (s, 1H), 8.18 (s, 1H), 7.59 (m, 2H), 2.97 (m, 1H), 0.80 (m, 2H), 0.64 (m, 2H).

Example 328. 2-(1-(2-amino-2-oxoethyl)-1H-indazol-6-ylamino)-4-(cyclopropylamino)pyrimidine-5-carboxamide

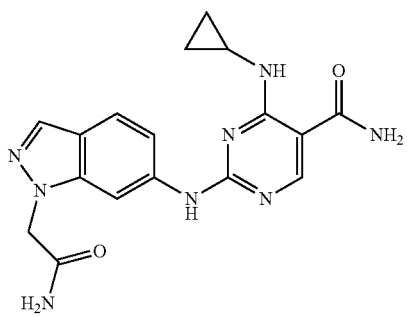 [SMILES: NC(=O)Cn1ncc2ccc(Nc3ncc(C(N)=O)c(NC4CC4)n3)cc21]

The above compound was prepared using a procedure similar to that described in Scheme 1 using cyclopropylamine in place of cyclobutylamine, using an intermediate derived from 6-nitroindazole and ethyl bromoacetate. MS found for $C_{17}H_{18}N_8O_2$ as $(M+H)^+$ 367.2.

Example 329. 4-(cyclobutylamino)-2-(2,2-difluorobenzo[d][1,3]dioxol-5-ylamino)pyrimidine-5-carboxamide

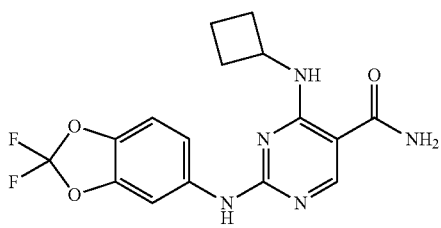 [SMILES: NC(=O)c1cnc(Nc2ccc3c(c2)OC(F)(F)O3)nc1NC1CCC1]

The above compound was prepared using a procedure similar to that described in Scheme 1. MS found for $C_{16}H_{15}N_5O_3F_2$ as $(M+H)^+$ 364.1.

Example 330. 4-(cyclobutylamino)-2-(imidazo[1,2-a]pyridin-6-ylamino)pyrimidine-5-carboxamide

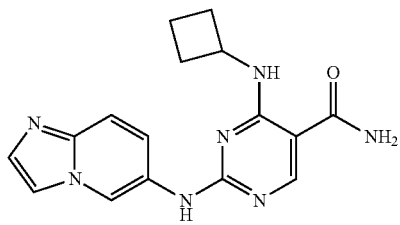 [SMILES: NC(=O)c1cnc(Nc2ccc3nccn3c2)nc1NC1CCC1]

The above compound was prepared using a procedure similar to that described in Scheme 1. MS found for $C_{16}H_{17}N_7O$ as $(M+H)^+$ 324.2.

Example 331. 4-(cyclobutylamino)-2-(3-methyl-1H-indazol-6-ylamino)pyrimidine-5-carboxamide

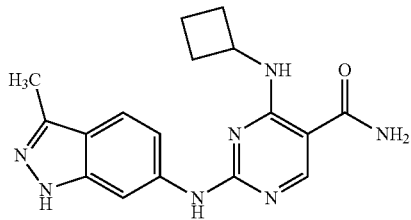 [SMILES: Cc1n[nH]c2cc(Nc3ncc(C(N)=O)c(NC4CCC4)n3)ccc12]

The above compound was prepared using a procedure similar to that described in Scheme 1. MS found for $C_{17}H_{19}N_7O$ as $(M+H)^+$ 338.0.

Example 332

This example illustrates methods for evaluating the compounds of the invention, along with results obtained for such assays. The in vitro and in vivo human syk activities of the inventive compounds can be determined by various procedures known in the art, such as a test for their ability to inhibit the activity of human plasma syk. The potent affinities for human syk inhibition exhibited by the inventive compounds can be measured by an IC50 value (in nM). The $IC_{50}$ value is the concentration (in nM) of the compound required to provide 50% inhibition of human syk proteolytic activity. The smaller the $IC_{50}$ value, the more active (potent) is a compound for inhibiting syk activity.

An in vitro assay for detecting and measuring inhibition activity against syk is as follows:
Inhibition of Syk Tyrosine Phosphorylation Activity Potency of candidate molecules for inhibiting syk tyrosine phosphorylation activity is assessed by measuring the ability of a test compound to inhibit syk-mediated tyrosine phosphorylation of a syk-specific substrate.

SYK tyrosine phosphorylation activity is measured using the LANCE™ Technology developed by Perkin Elmer Life and Analytical Sciences (Boston, Mass.). LANCE™ refers to homogeneous time resolved fluorometry applications using techniques such as time-resolved fluorescence resonance energy transfer assay (TR-FRET) (see generally for procedures in Perkin Elmer Application Note—How to Optimize a Tyrosine Kinase Assay Using Time Resolved Fluorescence-Based LANCE Detection, wwww.perkinelmer.com/lifesciences). The assay principle involves detection of a phosphorylated substrate using energy transfer from a phosphospecific europium-labeled antibody to streptavidin-allophycocyanin as an acceptor.

To test the ability of candidate molecules to inhibit SYK tyrosine phosphorylation activity, molecules are reconstituted in 30% DMSO and serially diluted 1:3 with the final dilution containing DMSO in the absence of the candidate molecule. The final DMSO concentration in the assay is 3%. Kinase assays are performed as a two part reaction. The first reaction is a kinase reaction and which comprises of a candidate molecule, full length active recombinant SYK enzyme (Millipore, Calif.) and biotin-labeled SYK-specific substrate biotin-DEEDYESP-OH. The second reaction involves termination of the kinase reaction and the simultaneous addition of the detection reagents—europium-labeled anti-phosphotyrosine reagent (Eu-W1024-PY100, Perkin Elmer, Boston, Mass.) and Streptavidin-Allophycocyanin detection reagent (SA-APC, Prozyme, Calif.). The kinase reaction is performed in a black U-bottom 96-well microtitre plate. The final reaction volume is 50 µL and contains a final concentration of 1 nM active SYK enzyme, 550 nM SYK-substrate, and 100 µM ATP diluted in a buffer containing 50 mM Tris pH 7.5, 5 mM $MgCl_2$, and 1 mM DTT. The reaction is allowed to proceed for 1 hour at room temperature. The quench buffer contains 100 mM Tris pH 7.5, 300 mM $NaCl_2$, 20 mM EDTA, 0.02% Brij35, and 0.5% BSA. The detection reagents are added to the reaction mixture at the following dilutions—1:500 for Eu-W1024-PY100 and 1:250 for SA-APC. The kinase reaction is terminated by the addition of 50 µL quench buffer containing the detection reagents. The detection is allowed to proceed for 1 hr at room temperature. Detection of the phosphorlated substrate in the absence and presence of inhibitors is measured in the TR-FRET instrument, Analyst HT (Molecular Probes, Sunnyvale, Calif.) and the condition for measurements are set up using CriterionHost Release 2.0 (Molecular Probes, Sunnyvale, Calif.). The settings used are a follows: excitation 360 nm, emission 665-7.5 nm, beam splitter 350 nm 50/50, flash 100 pulses, delay 60 us, integration 400 us, z-height 2 mm. Inhibition of SYK-tyrosine kinase activity is calculated as the maximum response observed in the presence of inhibitor, compared to that in the absence of inhibitor. $IC_{50}$s were derived by non-linear regression analysis.

Intracellular phospho-flow cytometry was used to test compound inhibition of Syk activity in intact non-Hodgkin's lymphoma cell lines Ramos and SUDHL-6. $10 \times 10^6$ cells in log phase growth were aliquoted; Syk kinase is activated by incubating cells for 10 minutes with 3 µg/ml antibody specific to the B cell receptor. Directly following, cells are fixed in 1% paraformaldehyde for 5 minutes at room temperature, washed in phosphate buffered saline, and then permeablized by incubation for 2 hours in ice cold methanol. Cells are again washed in phosphate buffered saline, then incubated for 30 minutes with antibody specific for phosphorylated Erk (Y204) and BLNK (Y84), which are indicators of Syk kinase activity, and phosphorylated Syk (Y352), a measure of Src family kinase activity. All antibodies used are purchased from BD Pharmingen (San Jose, Calif.). After incubation with antibodies, cells are again washed and subjected to flow cytometry. Representative data detailing inhibition of B cell receptor signaling by compounds are shown in Table 1 as $IC_{50}$ ranges.

The anti-proliferative effects of compounds on non-Hodgkin's lymphoma B cell lines SUDHL-4, SUDHL-6, and Toledo was also assessed. SUDHL-4 and SUDHL-6 require B cell receptor signaling for growth and survival, while the Toledo cell line (serving here as a negative control) does not. Cells were aliquoted into each well of a 96-well plate and incubated with increasing concentrations of compound for 72 hours, after which cell survival and proliferation was determined using the MTT assay (Chemicon International, Inc., Temecula, Calif.) following protocols supplied by the manufacturer. Data are detailed in Table 2 as $IC_{50}$ values plus or minus standard deviations from 5 or 6 independent experiments.

Induction of apoptosis in non-Hodgkin's lymphoma B cell lines SUDHL-4, SUDHL-6, and Toledo was assessed by measuring the apoptotis marker Caspase 3. Cells were incubated with 1, 3, or 10 µM compound for 24, 48, and 72 hours. At the conclusion of each time point, cells were processed for flow cytometry analysis using the Monoclonal Rabbit Anti-Active Caspase-3 Antibody Kit and related protocols (BD Pharmingen). Data from two independent experiments are presented in Tables 3A and 3B, representing the percent of total cells undergoing apoptosis following incubation with compounds under the indicated conditions.

Syk activity is not only required for B cell signaling, proliferation, and survival, as shown, but is also critical for cellular activation upon cross-linking of the B cell receptor. B cell activation leads to increased cell surface expression of several proteins involved in cell signaling, antigen presentation, and adhesion. Among these, CD80, CD86, and CD69 are commonly measured to determine B cell activation status. Therefore, primary mouse B cells isolated from spleen were aliquoted and incubated with increasing concentrations of compound (0.05 to 2 µM) in the presence of goat anti-mouse IgD (eBiosciences, Inc., San Diego, Calif.) for 20 hours to cross-link the B cell receptor. Following, cells were washed and incubated for 30 minutes on ice with antibodies specific for the CD80, CD86, and CD69 B cell activation markers. B cells were identified from the pooled population by staining with the B cell marker CD45RO. All antibodies were purchased from BD Pharmingen. Table 4 depicts the $IC_{50}$ range in which these compounds inhibited B cell receptor induced activation of mouse primary B cells.

In the table below, activity in the Syk and/or Jak assays is provided as follows: +++++=$IC_{50}$<0.0010 µM; ++++= 0.0010 µM<$IC_{50}$<0.010 µM, +++=0.010 µM<$IC_{50}$<0.10 µM, ++=0.10 µM<$IC_{50}$<1 µM, +=$IC_{50}$>1 µM.

TABLE 7

| Example | UV | MW | MH+ | Syk IC50 |
|---|---|---|---|---|
| 1 |  | 409.49 | 410.0 | +++ |
|  |  |  | 410.2 |  |
| 2 |  | 461.53 | 462.3 | ++ |
| 3 |  | 395.47 | 396.0 | +++ |
|  |  |  | 396.3 |  |
|  |  |  | 396.4 |  |
|  |  |  | ES (+) MS M + H = 396 |  |
| 4 |  | 423.52 | 424 | ++ |
| 5 |  | 411.51 | 412.3 | ++ |
| 6 |  | 445.53 | 446.1 | ++ |
| 7 |  | 397.48 | 398.3 | ++ |
| 8 |  | 411.51 | 412 | ++ |
| 9 |  | 413.48 | 413 | ++ |
| 10 |  | 427.51 | 428 | ++ |
| 12 |  | 409.49 | 410.2 | ++ |
| 13 |  | 393.45 | 394.2 | ++ |
| 14 |  | 369.43 | 370.2 | ++ |
| 15 |  | 383.46 | 384.2 | ++ |
|  |  |  | Turb Spray MS[M + 1] = 384 |  |
|  |  |  | Turbo Spray MS [M + 1] = 384 |  |
| 16 |  | 437.43 | 438.2 | ++ |
| 17 |  | 459.55 | M + 1 = 460 | ++ |
| 18 |  | 445.53 | 446 | ++ |
| 32 |  | 557.66 | 558.2 | ++ |
| 33 |  | 471.53 | 472.2 | ++ |
| 34 |  | 429.91 | 430.0, 432.0 | +++ |
| 35 |  | 443.94 | 444.0, 446.0 | +++ |
| 36 | 256, 249.5 | 409.49 | 410.3 | +++ |
|  |  |  | 420.2 |  |
|  |  |  | 420.4 |  |
|  |  |  | ES(+) MS [M + 1] = 410 |  |
|  |  |  | Turbo Spray MS [M + 1] = 410 |  |
| 37 |  | 421.51 | 422.4 | +++ |
| 38 |  | 425.49 | 426.2 | +++ |
|  |  |  | ES(+) MS [M + 1] = 426 |  |
|  |  |  | Turbo Spray MS [M + 1] = 426 |  |
| 39 |  | 409.45 | 410.2 | ++ |
| 40 |  | 413.46 | 414.2 | +++ |
| 41 |  | 452.56 | 453.45 | ++++ |
| 42 |  | 452.56 | 453.41 | +++ |
| 45 |  | 466.59 | 467.46 | ++ |
| 46 |  | 495.59 | 496.45 | ++ |
| 48 |  | 452.56 | 453.45 | +++ |
| 49 |  | 495.59 | 497 | ++ |
| 50 |  | 441.54 | ES(+) MS [M + 1] = 442 | ++ |
| 51 |  | 413.48 | 414.4 | ++ |
| 52 |  | 413.48 | 414.4 | ++ |
| 53 |  | 394.44 | 395.2 | ++ |
| 54 |  | 413.48 | 414.3 | ++ |
| 55 |  | 438.49 | 439.4 | +++ |
| 56 |  | 409.49 | 410.4 | +++ |
| 58 |  | 426.48 | 427.4 | ++ |
| 59 |  | 440.51 | 441.3 | ++ |
| 60 |  | 408.47 | 409.3 | ++ |
| 63 |  | 466.55 | 467.4 | ++ |
| 64 |  | 471.57 | 472.3 | ++ |
| 65 |  | 413.48 | 414.3 | ++ |
| 66 |  | 427.51 | 428.4 | ++ |
| 67 |  | 452.52 | 453.3 | +++ |
| 69 |  | 429.48 | 430.3 | ++ |
| 70 |  | 466.55 | 467.4 | +++ |
| 71 |  | 425.49 | 426.3 | +++ |
| 72 | 207.8, 293.8 | 500.56 | 501.3 | ++ |
| 73 | 228.5, 285.3 | 410.53 | 411.43 | +++ |
| 77 |  | 410.48 | 342 | +++ |
| 78 |  | 438.54 | 439.3 | ++ |
| 86 | 219.2 | 498.59 | 499.4 | ++ |
| 87 | 208.6 | 512.62 | 513.4 | ++ |
| 92 |  | 317.78 | 318.0, 320.0 | ++ |
| 93 |  | 396.46 | 397 | ++ |
| 96 |  | 428.52 | 429.3 (M + 1) | +++ |
| 97 |  | 430.53 | 431.3 (M + 1) | +++ |

TABLE 7-continued

| Example | UV | MW | MH+ | Syk IC50 |
|---|---|---|---|---|
| 98 | | 459.57 | 460.2 | +++ |
| 99 | | 431.52 | 432.0 | +++ |
| | | | 432.2 | |
| | | | ES (+) MS | |
| | | | [M + 1] = 432 | |
| | | | ES(+) MS [M + H] = 432 | |
| | | | Turb Spray MS | |
| | | | [M + 1] = 432 | |
| | | | Turbo Spray MS | |
| | | | [M + 1] = 432 | |
| 100 | | 445.55 | 426 (M + H) | +++ |
| | | | 446 | |
| | | | 446.2 | |
| | | | 446.2 (M + H) | |
| | | | 446.4 | |
| | | | ES(+) MS [M + 1] = 446 | |
| | | | Turbo Spray MS | |
| | | | [M + 1] = 446 | |
| 101 | 203.6, 230.8, 258.0 | 445.55 | 446.0 | +++ |
| | | | ES (+) MS | |
| | | | [M + 1] = 446 | |
| 103 | | 362.41 | 363 | +++ |
| 104 | | 370.41 | 371 | +++ |
| 105 | | 398.47 | 399 | ++ |
| 106 | | 390.47 | 391 | +++ |
| 107 | | 356.39 | 355 | +++ |
| 108 | 201.4, 275.8 | 384.44 | 385.0 | ++ |
| | | | ES (+) MS | |
| | | | [M + 1] = 385 | |
| 109 | | 348.39 | 349.0 | +++ |
| | | | 349.1 | |
| 110 | | 341.38 | 342 | ++ |
| 111 | | 331.4 | 332.1 | ++ |
| 112 | | 423.48 | 424.1 (M + 1) | ++ |
| 113 | | 394.48 | 395.3 (M + 1) | +++ |
| 114 | | 449.56 | 450.3 | ++ |
| 115 | | 463.59 | 464.3 | ++ |
| 116 | | 465.56 | 466.3 | ++ |
| 117 | | 457.56 | 458.2 | +++ |
| 118 | | 409.49 | 410.2 | +++ |
| 119 | | 409.49 | 410.2 | ++ |
| 120 | | 362.39 | 363.2 | ++ |
| 121 | | 402.48 | 403.2 | +++ |
| 122 | | 411.51 | M + 1 = 412 | ++ |
| 123 | | 407.52 | 408.3 (M + 1) | +++ |
| 124 | | 423.52 | 424.2 | +++ |
| 125 | | 402.48 | M + 1 = 403 | +++ |
| 127 | | 406.47 | M + 1 = 407 | +++ |
| 128 | | 392.44 | M + 1 = 393 | +++ |
| 129 | | 361.42 | 362.1 | ++ |
| 130 | | 367.46 | 368.3 | +++ |
| 131 | | 430.52 | MS: 431.42 (M + H) | ++ |
| 135 | | 381.48 | 382.5 (M + 1) | +++ |
| 136 | | 426.46 | M + 1 = 427 | ++ |
| 137 | | 431.5 | M + 1 = 432 | +++ |
| 138 | | 429.46 | M + 1 = 430 | +++ |
| 139 | | 454.51 | M + 1 = 455 | +++ |
| 140 | | 355.4 | 356.3 | ++ |
| 141 | | 367.33 | 368 | ++ |
| 168 | | 297.36 | 298 | ++ |
| 169 | | 326.36 | 327 | ++ |
| 170 | | 380.45 | 381 | +++ |
| 171 | 207.3, 266.2 | 388.86 | 389.0, 391.0 | ++ |
| | | | ES (+) MS M + H = 389, | |
| | | | Chlorine patteren | |
| 172 | | 374.83 | 375.0, 377.0 | ++ |
| 173 | | 366.43 | 367.1 | ++ |
| 174 | | 397.48 | 398.3 | +++ |
| | | | ES (+/−) MS | |
| | | | M + H = 398 | |
| | | | Turbo Spray MS | |
| | | | [M + 1] = 398 | |
| 175 | | 409.49 | 410 | +++ |
| 176 | 206.1, 268.7 | 423.52 | 424 (M + H) | +++ |
| | | | 424 (M + H) | |
| | | | 424.0 | |
| | | | 424.4 | |
| | | | ES(+) MS [M + 1] = 424 | |
| 177 | | 424.51 | 425.2 | ++ |
| 178 | | 388.86 | 389.0, 391.0 | ++ |
| 179 | | 374.4 | 375 | ++ |
| 180 | | 326.36 | 8 | ++ |
| 181 | | 340.39 | 341 | ++ |
| 182 | | 459.53 | 460.1 (M + 1) | ++ |
| 183 | | 352.42 | MS: 353.2 (M + H) | ++ |
| 184 | | 335.37 | MS: 336.3 (M + H) | ++ |
| 185 | | 337.35 | MS: 338.2 | ++ |
| 186 | | 351.43 | MS: 352.2 (M + H) | ++ |
| 187 | | 328.33 | 329.2 | +++ |
| 188 | | 346.39 | MS: 347.3 (M + H) | ++ |
| 189 | | 392.46 | 393.3 (M + 1) | +++ |
| 191 | | 382.47 | 383.3 | ++ |
| 192 | | 346.39 | MS: 347.3 (M + H) | +++ |
| 193 | | 361.42 | 362.1 (M + 1) | +++ |
| 194 | | 308.35 | 309.2 | +++ |
| 195 | | 396.45 | 397.2 | +++ |
| 196 | | 445.55 | 446.2 | +++ |
| 197 | | 363.43 | MS: 364.2 (M + H) | ++ |
| 198 | 232.0, 305.0 | 381.44 | ES(+) MS [M + 1] = 382 | +++ |
| 199 | | 352.4 | M + 1 = 353 | +++ |
| 200 | | 366.43 | M + ! = 367 | +++ |
| 201 | 252.0, 299.5, 313.6 | 395.47 | ES(+) MS [M + 1] = 396 | +++ |
| 202 | 232.0, 252.1 | 409.49 | ES(+) MS [M + 1 ] = 410 | ++ |
| 203 | | 356.39 | M + ! = 357 | +++ |
| 204 | | 370.41 | M + 1 = 371 | +++ |
| 205 | | 409.49 | M + 1 = 410 | +++ |
| 206 | | 423.52 | M + 1 = 424 | +++ |
| 207 | | 409.49 | 410.2 | +++ |
| 208 | | 423.52 | 424.2 | +++ |
| 209 | | 409.49 | 410.2 | ++ |
| | | | ES(+)MS [M + 1] = 410 | |
| 210 | | 423.52 | 424.2 | ++ |
| 211 | | 321.34 | 322.1 | ++ |
| 212 | | 367.41 | 368.1 | +++ |
| 212 | | 411.47 | 412.5 | ++ |
| 213 | | 432.5 | m + 1 = 433 | +++ |
| 214 | | 366.43 | 367.1 | ++ |
| 215 | | 380.45 | M + 1 = 381 | ++ |
| 216 | | 361.41 | 362.4 (M + 1) | +++ |
| 218 | 205.3, 232.1, 252.3 | 409.49 | ES(+) MS [M + 1] = 410 | ++ |
| 219 | | 395.47 | 396.5 | ++ |
| 220 | | 397.44 | 398.5 | ++ |
| 222 | | 326.4 | 327 | +++ |
| 223 | | 340.39 | 341 | ++ |
| 225 | | 323.36 | 324 | +++ |
| 226 | | 313.36 | 314 | +++ |
| 227 | | 354.46 | 355.2 | ++ |
| 228 | | 283.34 | 284 | ++ |
| 229 | | 368.44 | 369 | +++ |
| 230 | | 354.41 | 355 | ++ |
| 231 | | 340.39 | 341 | +++ |
| 233 | | 327.34 | 328.2, 329.1 | ++ |
| 234 | 205.0, 254.4 | 354.41 | 355.0 | +++ |
| | | | ES (+) MS M + H = 355 | |
| | | | Turbo Spray MS | |
| | | | [M + 1] = 355 | |
| 235 | 230.8, 280.5 | 352.44 | 353.2 | +++ |
| | | | ES (+) MS | |
| | | | [M + 1] = 353 | |
| 236 | 201.4, 271.0 | 368.44 | 369.0 | +++ |
| | | | ES(+) MS [M + 1] = 369 | |
| 237 | | 370.43 | 371 | +++ |
| 238 | 201.4, 227.3 | 367.46 | 368.3 | +++ |
| | | | ES(+) MS [M + H] = 368 | |
| | | | Turbo Spray MS | |
| | | | [M + 1] = 368 | |
| 239 | | 388.42 | 389 | +++ |
| 240 | | 395.47 | 396.2 | +++ |
| 241 | | 396.46 | 397.2 | +++ |
| 242 | | 388.42 | 389 | +++ |

TABLE 7-continued

| Example | UV | MW | MH+ | Syk IC50 |
|---|---|---|---|---|
| 244 | | 347.4 | 348 (M + H) 348.1 348.3 349 (M + H) ES(+) MS [M + 1] = 348 Turbo Spray MS [M + 1] = 348 | +++ |
| 245 | | 315.4 | 316.1 | ++ |
| 246 | | 445.55 | 446.3 (M + 1) | ++ |
| 247 | | 353.43 | 354.2 | +++ |
| 248 | | 336.36 | MS: 337.3 (M + H) | ++ |
| 249 | | 308.35 | 309.2 | +++ |
| 250 | | 309.33 | 310.2 | +++ |
| 251 | | 336.36 | MS: 337.1 (M + H) | ++ |
| 252 | | 309.33 | 310.2 ES(+) MS [M + 1] = 310 ES(+) MS [M + H] = 310 Turbo Spray MS [M + 1] = 310 | +++ |
| 253 | | 320.36 | 321.2 | +++ |
| 254 | | 395.47 | M + 1 = 396 | +++ |
| 256 | | 341.37 | 342.2, 343.2 | ++ |
| 257 | | 366.47 | 367.3 | ++ |
| 258 | | 382.47 | 383.3 | +++ |
| 259 | | 384.46 | 385 | +++ |
| 260 | | 368.44 | 369 | +++ |
| 261 | 201.5, 228.5 | 381.48 | 382.3 ES (+) MS M + H = 382 | ++ |
| 262 | | 402.45 | 403 | ++ |
| 263 | | 402.45 | 403 | +++ |
| 264 | 200.8, 231.8, 304.8 | 381.44 | ES(+) MS [M + 1] = 382 | +++ |
| 265 | | 397.44 | 398.4 | ++ |
| 266 | | 411.47 | 412.5 | ++ |
| 267 | | 425.49 | 426.5 | ++ |
| 268 | | 423.52 | 424 | +++a |
| 269 | 210.8, 253.2 | 437.55 | 438.3 ES (+) MS M + H = 438 | ++ |
| 270 | | 411.51 | 412.3 | +++ |
| 271 | | 402.89 | 403.0, 405.0 | +++ |
| 272 | | 388.42 | 389 | ++ |
| 273 | | 340.39 | 341 | ++ |
| 274 | | 354.41 | 355.2 | ++ |
| 288 | 275 | 313.36 | MW = 313.35; M + 1 = 314.2 | ++ |
| 289 | 277 | 361.41 | MW = 361.4; M + 1 = 362.2 | ++ |
| 290 | 265 | 353.3 | MW = 353.3; M + 1 = 354.1 | ++ |
| 291 | 205, 267 | 362.39 | MW = 362.4; M + 1 = 363.2 | ++ |
| 292 | 290 | 386.43 | MW = 386.4; M + 1 = 387.2 | ++ |
| 309 | | 338.37 | 339.0 (M + 1) | +++ |
| 314 | | 368.4 | 369 | ++ |
| 320 | | 326.38 | 327.1 | ++ |
| 322 | | 309.33 | 310.1 | +++ |
| 323 | | 310.32 | 311.2 | +++ |
| 324 | 218.6 247.8 | 323.36 | ES(+) MS [M + 1] = 324 | +++ |
| 325 | | 327.37 | 328.2 | ++ |
| 326 | | 343.78 | 344.2, 346.2 | ++ |
| 328 | | 366.39 | 367.2 | ++ |
| 330 | | 324.35 | 325 | +++ |
| 331 | 214.9 252.1, 298.2 | 337.39 | ES(+) MS [M + 1] = 338 | +++ |

Inhibition of GPVI-Mediated Platelet Function In Vitro

The ability for candidate molecules to inhibit syk-mediated platelet functions are tested by measuring the inhibition the GPVI-specific agonist Convulxin-induced human platelet calcium-mobilization or aggregation. Calcium-mobilization is assessed in human washed platelets in a 96-well microtiter format. Aggregation is assessed in a 96-well microtiter assay (see generally the procedures in Jantzen, H. M. et al. (1999) *Thromb. Hemost.* 81:111-117) or standard cuvette light transmittance aggregometry using human platelet-rich plasma (PRP).

Inhibition of Convulxin-Mediated Platelet Calcium-Mobilization In Vitro

Inhibition of Convulxin-induced calcium-mobilization was determined in human washed platelets using the FLIRP Calcium 3 Assay Kit (Molecular Devices, Sunnyvale, Calif.). For preparation of washed platelets, human venous blood is collected from healthy, drug-free volunteers into ACD (85 mM sodium citrate, 111 mM glucose, 71.4 mM citric acid) containing $PGI_2$ (1.25 ml ACD containing 0.2 µM $PGI_2$ final; $PGI_2$ was from Sigma, St. Louis, Mo.). Platelet-rich plasma (PRP) is prepared by centrifugation at 160×g for 20 minutes at room temperature. Washed platelets are prepared by centrifuging PRP for 10 minutes at 730 g and resuspending the platelet pellet in CGS (13 mM sodium citrate, 30 mM glucose, 120 mM NaCl; 2 ml CGS/10 ml original blood volume). After incubation at 37° C. for 15 minutes, the platelets are collected by centrifugation at 730 g for 10 minutes and resuspended at a concentration of $3\times10^8$ platelets/ml in Hepes-Tyrode's buffer (10 mM Hepes, 138 mM NaCl, 5.5 mM glucose, 2.9 mM KCl, 12 mM $NaHCO_3$, pH 7.4). This platelet suspension is kept >45 minutes at room temperature before use in calcium mobilization assays.

For 96-well plate Calcium-mobilization experiments, equal volumes of $3\times10^8$ washed platelets/ml were incubated with equal volumes of Calcium-3 Assay Reagent A resuspended in 1× Hank's Balanced Salt Solution, pH 7.4, 20 mM Hepes buffer. The total reaction volume of 0.2 ml/well includes $1.5\times10^8$/ml washed platelet/Calcium-3 Assay reagent A mix, 10 µM Eptifibatide (Millennium Pharmaceuticals Inc, Cambridge, Mass.), serial dilutions (1:3) of test compounds in 0.75% DMSO. DMSO alone is added to 1 well of each 8 set to allow for a maximal calcium-mobilization reading. After 20 minutes preincubation at room temperature the 96-well microplate reader is loaded into the FlexStation (Molecular Devices, Sunnyvale, Calif.). The FlexStation experimental conditions for measuring Calcium mobilization are set up using SOFTMax Pro. The settings used are detailed below. Fluorescence parameters-assay mode: flex, excitation 485 nM, 525 nM with a cut-off of 515 nM; Parameters-PMT sensitivity-6, pipette height 230 µl, read time 2 minutes and 40 seconds, read intervals 2 seconds, temperature-23-25° C. After 18 seconds of baseline reading, calcium-mobilization is initiated by the addition of Convulxin to a final concentration of 125 ng/ml. Inhibition of calcium-mobilization was calculated as the maximum response observed in the presence of inhibitor, compared to that in the absence of inhibitor. $IC_{50}$s were derived by non-linear regression analysis.

Inhibition of Convulxin-Mediated Platelet Aggregation In Vitro

For preparation of human platelet-rich plasma for aggregation assays, human venous blood was collected from healthy, drug-free volunteers into 0.38% sodium citrate (0.013 M, pH 7.0 final). Platelet-rich plasma (PRP) is prepared by centrifugation of whole blood at 160× g for 20 minutes at room temperature. The PRP layer is removed, transferred to a new tube, and the platelet count is adjusted, if advantageous, to achieve a platelet concentration of ~$3\times10^8$ platelets/ml using platelet-poor plasma (PPP). PPP is prepared by centrifugation of the remaining blood sample (after removal of PRP) for 20 minutes at 800× g. This preparation of PRP can subsequently be used for aggregation assays in either a 96-well plate or standard cuvette aggregometry.

Inhibition of Convulxin-induced aggregation is determined in 96-well flat-bottom microtiter plates using a microtiter plate shaker and plate reader similar to the procedure described by Frantantoni et al., *Am. J. Clin. Pathol.* 94, 613 (1990). All steps are performed at room temperature. For 96-well plate aggregation using platelet-rich plasma (PRP), the total reaction volume of 0.2 ml/well includes 190 µl of PRP (~3×10$^8$ platelets/ml, see above), and µl of either serial dilution of test compounds in 30% DMSO or buffer (for control wells). After 20 minutes preincubation at room temperature 5 µl of 320 ng/ml Convulxin agonist solution is added to each well to give a final concentration of 8 ng/ml Convulxin. The plates are then agitated for 5 min on a microtiter plate shaker and the 5 minute reading is obtained in the microtitre plate reader (Softmax, Molecular Devices, Menlo Park, Calif.). Aggregation is calculated from the decrease of OD at 650 nm at t=5 minutes. IC$_{50}$s were derived by non-linear regression analysis.

Inhibition of Convulxin-induced aggregation was also determined for cuvette light transmittance aggregation assays, serial dilutions (1:2) of test compounds were prepared in 30% DMSO in a 96 well V-bottom plate (final DMSO concentration in the cuvette was 0.3%). The test compound (5 µl of serial dilutions in DMSO) was preincubated with PRP for 20 minutes prior to initiation of aggregation reactions, which is performed in a ChronoLog aggregometer by addition of agonist (125-250 ng/ml Convulxin) to 495 µL of PRP at 37° C. The aggregation reaction is recorded for 4 min, and maximum extent of aggregation is determined by the difference in extent of aggregation at baseline, compared to the maximum aggregation that occurs during the 4 minute period of the assay. Inhibition of aggregation was calculated as the maximum aggregation observed in the presence of inhibitor, compared to that in the absence of inhibitor. IC$_{50}$s were derived by non-linear regression analysis.

Examples of compounds and their syk and PRP IC$_{50}$ values are given in tables 1-5.

Calcium Flux Assay in Ramos Cells Induced by BCR Cross-Linking

Ramos cells (2G6.4C10, Burkitt's lymphoma, ATCC Item Number: CRL-1923) are sub-cultured at 5×10$^5$ cells/ml in fresh medium 3 or 4 days ahead of experiments. Cells are harvest and re-suspend in fresh medium at 8×10$^6$ cells/ml before dye-loading. An equal volume of Calcium 3 loading dye (Molecular Device) is added and mixed into cell suspension. Loading cells are dispensed in a 96 well plate and incubated 30 min. Compounds are then added in the dye-loaded cells and incubated for another 30 min. Spin cell down at 1000 rpm for 3 min before fluorescence measurement in FlexStation. BCR stimulation is carried by the addition of 5 µg/ml antibody (AffiniPure F(ab')$_2$ fragment Donkey anti-human IgM, Jackson ImmunoResearch Laboratories).

Calcium Flux Assay in Jurkat Cells Induced by TCR Cross-Linking

The protocol is very similar to B cell calcium flux as described in the previous section. The only differences are that T cells (clone E6-1, Acute T cell Leukemia, ATCC Item Number: Tib-152) and anti-human CD3 (Functional Grade Purified anti-human CD3, clone OKT3, eBioscience, No. 16-0037) replaced B cells and anti-human IgM. Cell density is kept the same but antibody is used at a concentration of 100 ng/ml.

IL-2 Secretion in Jurkat Cells Induced by TCR Cross-Linking

Jurkat cell propagation and compound incubation procedures are the same as described in Jurkat calcium flux assay in the previous section. Antibody (anti CD3, OKT3) is coated onto a fresh plate (without cells) at 100 ng/well. Cells are suspended at 8×10$^6$ cells/ml and incubated with compounds for 30 min in a separate plate. At the end of incubation, cells are transferred to the antibody-coated plate and incubated for 16 hours. 100 µl of cell medium after incubation is used for IL-2 measurement after incubation. IL-2 level is determined using an IL-2 ELISA kit (Human IL-2 ELISA kit II, BD Bioscience, No. 550611).

Example 333 Millipore Upstate KinaseProfiler™ Screening

This assay is a direct measurement of the effect of compound on the catalytic activity of JAK3. Purified human JAK3 (GenBank AF513860) sequence (residue 781-C terminus) was obtained from insect cells. The catalytic hydrolysis of ATP is measured using a radiometric filter binding method. Incubation of kinase with $^{33}$[P]ATP and substrate leads to incorporation of $^{33}$[P]into the substrate which can then be separated from the other reaction components by filtration. Assays were performed using 10 µM ATP and in the absence or presence of 1, 0.3, or 0.1 µM compound. Activity was expressed as % of inhibition of control.

TABLE 8

Inhibition (%) of catalytic activity of JAK3 by 1, 0.3 or 0.1 µM compound as determined by Millipore using their KinaseProfiler Assay.

| Compound | Concentration (µM) | | |
| --- | --- | --- | --- |
| | 1 µM | 0.3 µM | 0.1 µM |
| (structure) | 98 | 96 | 97 |

TABLE 8-continued

Inhibition (%) of catalytic activity of JAK3 by 1, 0.3 or 0.1 μM compound as determined by Millipore using their KinaseProfiler Assay.

| Compound | Concentration (μM) | | |
|---|---|---|---|
| | 1 μM | 0.3 μM | 0.1 μM |
| [structure: H3C-SO2-N(piperazine)-N-phenyl-NH-pyrimidine(NHcyclopropyl)(CONH2)] | 100 | 84 | ND |

ND: not done

Example 334 Ambit KinomeScan Screening

This assay is an ATP-site dependent competition binding assay in which human kinases of interest are fused to a proprietary tag (T7 bacteriophage). The amount of kinase bound to an immobilized, active-site directed ligand is measured in the presence and absence of the test compound. Ambit's JAK assays use kinase domains and not full-length proteins. The domain used for JAK1 binding is the pseudo kinase domain while that for JAK3 binding is the catalytic domain (Mazen W Karaman, Sanna Herrgard, Daniel K Treiber, et. al. A Quantitative analysis of kinase inhibitor selectivity. Nature Biotechnology, 2008, Volume 26, No. 1, Page 127-132).

TABLE 9a

KD values (nM) for compound binding inhibition of JAK1 and JAK3 to immobilized ligand in the Ambit KinomeScan assay.

| Compound | JAK1 | JAK3 |
|---|---|---|
| [structure: H3C-O-CH2-C(O)-N(piperazine)-N-phenyl-NH-pyrimidine(NHcyclopropyl)(CONH2)] | 6.7 | 2.9 |
| [structure: O=C(NHCH3)-piperidine-N-phenyl-NH-pyrimidine(NHcyclopropyl)(CONH2)] | 11 | 3 |

TABLE 9a-continued

KD values (nM) for compound binding inhibition of JAK1 and JAK3 to immobilized ligand in the Ambit KinomeScan assay.

| Compound | JAK1 | JAK3 |
|---|---|---|
| [structure: H3C-SO2-N(piperazine)-N-phenyl-NH-pyrimidine(NHcyclopropyl)(CONH2)] | 4.7 | 2.7 |
| [structure: O=C(NH2)-piperidine-N-phenyl-NH-pyrimidine(NHcyclopropyl)(CONH2)] | 14 | 4.1 |

TABLE 9b

Potency and Specificity of Kinase Inhibition (IC50 in nM)

| Compound | Syk | Jak 1 | Jak 2 | Jak 3 |
|---|---|---|---|---|
| EXAMPLE 99 | 15 | 6.7 | 3.2 | 0.8 |
| P420-89 | 31 | 6.2 | 2.0 | 0.6 |

TABLE 10

(Ambit Panel) inhibition of Kinases in Kd (nM)

| Compound 1 | Compound 2 | Compound 3 |
|---|---|---|
| (methoxyacetyl-piperazine-phenyl-aminopyrimidine-cyclopropylamino-carboxamide) | (methylsulfonyl-piperazine-phenyl-aminopyrimidine-cyclopropylamino-carboxamide) | (carboxamide-piperidine-phenyl-aminopyrimidine-cyclopropylamino-carboxamide) |

| Kinase | Cmpd 1 | Cmpd 2 | Cmpd 3 |
|---|---|---|---|
| JAK1 | 6.7 | 4.7 | 14 |
| JAK2 (Kin. Dom. 2) | 5.1 | 5.1 | 10 |
| JAK3 (Kin. Dom. 2) | 2.9 | 2.7 | 4.1 |
| Syk | 98 | 4.5 | 9.4 |

Example 335 JAK3/STAT6 Cellular Assay

Stimulation of Ramos B cells by interleukin 4 (IL4) leads to signaling through JAK1/JAK3 resulting in phosphorylation of STAT6 (signal transducers and activators of transcription). The effect of compounds on inhibition of JAK3 and/or JAK1 can be assessed by measuring the amount of phosphorylated STAT6. This is performed by Western blotting using a specific phospho-STAT6 antibody.

Ramos B cells were suspended in 10 mM Hepes-buffered RPMI media ($2\times10^7$ cells/ml). Cells (90 µl) were incubated with 10 µl 3.3 µg/ml interleukin 4 (R & D Systems Inc, cat #204-IL; final concentration: 0.33 µg/ml). Incubations were for 10 min at 37° C. in the absence or presence of 2 µl compound diluted in 30% DMSO. Reactions were terminated by the addition of an equal volume of 2× lysis buffer (100 mM TRIS-HCl pH 8.0, 2% Triton-X-100, 5 mM EDTA, 250 mM NaCl, 20% glycerol, 1.25 mM PMSF, 5 mM sodium orthovandate, 5 mM β-glycerophosphate, mini complete EDTA protease inhibitor cocktail (Sigma)).

Samples were incubated with 1 l of the nuclease, benzonase (Novagen, cat #71205-3) for 1 hour, room temperature and then 50 µl 5× loading buffer (330 mM TRIS pH 6.8, 9.5% SDS, 34% glycerol, 0.01% bromophenol blue, 10% beta-mercaptoethanol) was added.

Cell lysates (15 µL) were subjected to SDS-PAGE (Novex 4-12% TRIS-glycine gels, Invitrogen) under reducing conditions, followed by electroblot-transfer onto nitrocellulose membranes. Membranes were then incubated in Zymed blocking buffer (Invitrogen) for 1 hr at room temperature (RT) then overnight at 4° C. with 1:500 anti phosphotyrosine-STAT6 (Cell Signaling Technology, cat #9364) primary antibody in Zymed blocking buffer. Following 5×10 min washes with Tris-buffered saline, 0.25% NP40 (TBSN), blots were incubated for 1 hr at room temperature in the presence of 1:10,000 HRP-conjugated donkey anti-rabbit secondary antibody (Amersham Biosciences, cat #NA934V) in Zymed blocking buffer. After 4×10 min TBSN washes, blots were visualized by ECL (Pierce Western Lightening, Perkin Elmer cat #NEL101). In order to determine total β3 content, blots were stripped, washed 4× with TBSN, and re-probed with 1:2000 C3A antibody in block buffer overnight at 4° C. After 4×10 min TBSN washes, blots were incubated with 1:10,000 goat anti-mouse secondary antibody in blocking buffer, washed 4 more times with TBSN and exposed to Western Lightening reagent. Levels of stimulation over background and the extent of inhibition of compound are determined by densitometry.

Example 336 Inhibition of JAK Kinase Activity Assay for Ramos B-Cell Line Stimulated with IL-4

These examples illustrate methods for evaluating the in vitro and in vivo human JAK kinase activities of the inventive compounds can be determined by various procedures known in the art, such as a test for their ability to inhibit the activity of human plasma JAK kinase. The potent affinities for human JAK kinase inhibition exhibited by the inventive compounds can be measured by an $IC_{50}$ value (in nM). The $IC_{50}$ value is the concentration (in nM) of the compound required to provide 50% inhibition of human JAK kinase activity. The smaller the $IC_{50}$ value, the more active (potent) is a compound for inhibiting JAK kinase activity.

An in vitro assay for detecting and measuring inhibition activity against JAK kinase is as follows:

The activity of the compounds for JAK kinases is confirmed in cellular assays designed to test for JAK inhibition. Briefly, JAK inhibition is tested in human Ramos B-cells activated with cytokine Interleukin-4 (IL-4). Twenty to 24 hours post stimulation, the cells are stained for upregulation of CD23 and analyzed by FACS. Stimulation of the B-cells with IL-4 leads to the activation of the JAK/STAT pathway through phosphorylation of the JAK kinase JAK1 and JAK3, which in turn phosphorylate and activate transcription of factors STAT-5 and STAT-6. The low-affinity IgE receptor (CD23) is upregulated by activated STAT-5.

For the assay, human Ramos B-cells (ATCC, Catalog No. CRL-1596) are cultured in RPMI 1640 medium (Cellgro, Catalog No. 10-040-CM) containing 10% fetal bovine serum (JRH, Catalog No. 12106-500M) according to the propagation protocol supplied with the cells, and maintained at a density of approximately $3.5\times10^5$ cells/ml. The day before the assay, the cells are diluted to $3.5\times10^5$ cells/ml to insure they are in the logarithmic growth phase. The cells are spun down, and suspended in RPMI 1640 medium (Cellgro, MediaTech, Inc., Herndon, Va., Cat No. 10-040-CM) containing 5-10% fetal bovine serum (FBS), heat inactivated (JRH Biosciences, Inc, Lenexa, Kans., Cat No. 12106-500M) according to ATCC propagation protocol. Cells are maintained at a density of $3.5\times10^{4-5}$ cells/ml. The day before the experiment, Ramos B-cells are diluted to $3.5\times10^5$ cells/mL to ensure that they are in a logarithmic growth phase and aliquots dispensed into a 96-well tissue culture plate. Cells are incubated with test compound (dissolved in DMSO) or DMSO (control) for 1 hr at 37° C. and then stimulated with IL-4 (Pepotech, Catalog No. 200-04) for 20-24 hours (final concentration is 50 Units/ml).

Cells are spun down and suspended in RPMI with 5% serum. $5 \times 10^4$ cells are used per point in a 96-well tissue culture plate. Cells are pre-incubated with compound or DMSO (Sigma-Aldrich, St. Louis, Mo., Cat No. D2650) vehicle control for 1 hour in a 37° C. incubator. Cells are then stimulated with IL-4 (Peprotech Inc., Rocky Hill, N.J., Cat No. 200-04) for a final concentration of 50 units/mL for 20-24 hours. Cells are then spun down and stained with anti-CD23-PE (BD Pharmingen, San Diego, Calif., Cat No. 555711) and analyzed by FACS. Detection is performed using a BD LSR I System Flow Cytometer, purchased from Becton Dickinson Biosciences of San Jose, Calif.\

Proliferation is measured using CellTiter-Glo® Luminescent Cell Viability Assay (Promega), which determines the number of viable cells in culture based on quantitation of the ATP present, as an indicator of metabolically active cells. The substrate is thawed and allowed to come to room temperature. After mixing the Cell Titer-Glo reagent and diluent together, 100 µL is added to each well. The plates are mixed on an orbital shaker for two minutes to induce lysis and incubated at room temperature for an additional ten minutes to allow the signal to equilibrate. Detection is performed using a Wallac Victor2 1420 multilabel counter purchased from Perkin Elmer, Shelton, Conn.

On day two, A549 cells are pre-incubated with a 2,4-pyrimidinediamine test compound or DMSO (control) (Sigma-Aldrich, St. Louis, Mo., Catalog No. D2650) for 1 hour. The cells are then stimulated with IFNγ (75 ng/mL) (Peprotech Inc., Rocky Hill, N.J., Cat. No. 300-02) and allowed to incubate for 24 hours. The final test compound dose range is 30 µM to 14 nM in 200 µL F12K media containing 5% FBS, 0.3% DMSO.

On day three, the cell media is removed and the cells are washed with 200 µL PBS (phosphate buffered saline). Each well is trypsinized to dissociate the cells, then neutralized by addition of 200 µL complete F12K media. Cells are pelleted and stained with an APC conjugated mouse anti-human ICAM-1 (CD54) (BD Pharmingen, San Diego, Calif., Catalog #559771) antibody for 20 minutes at 4° C. Cells are washed with ice cold FACS buffer (PBS+2% FBS) and surface ICAM-1 expression is analyzed by flow cytometry. Detection is performed using a BD LSR I System Flow Cytometer, purchased from BD Biosciences of San Jose, Calif. Events are gated for live scatter and the geometric mean is calculated (Becton-Dickinson CellQuest software version 3.3, Franklin Lakes, N.J.). Geometric means are plotted against the compound concentration to generate a dose response curve.

Example 337: Inhibition of Syk-Mediated Signal Transduction Through the B Cell Receptor in Non-Hodgkin's Lymphoma Cell Lines Cells were pre-treated for 1 hour without or with compound (0.02 to 2 uM) prior to stimulation of B cell receptor singling by incubation of cells with 3 µg/ml anti-mu antibody for 10 minutes at 37° C. $Ca^{2+}$ flux was measured using the Calcium 3 loading dye and the FlexStation (Molecular Device). B cell receptor signaling was assayed by intracellular phospho-Flow Cytometry, following protocols supplied by BD Pharmingen (San Jose, Calif.). Syk activation was measured by induction of BLNK tyrosine phosphorylation at amino acid position 84 (pBLNK Y84) and induction of ERK1/2 tyrosine phosphorylation at amino acid position 204 (pERK Y204). Activation of the Src family member Lyn was measured by induction of Syk tyrosine phosphorylation at amino acid position 352 (pSyk Y352). Data are presented as µM $IC_{50}s$. Each compound effectively inhibited B cell receptor-induced $Ca^{2+}$ fluxing and activation of Syk, but not the Src family member Lyn.

Example 338: Syk Inhibition Exerts an Anti-Proliferative Effect on Non-Hodgkin's Lymphoma Cell Lines Cells were incubated with increasing concentrations of each compound, then evaluated at 72 hours for extent of proliferation using the MTT assay (company, city, state) following the manufacturer supplied protocol. Data are presented as µM IC50 values, representing the mean plus/minus standard deviation from 5 or 6 independent experiments. Each compound inhibited proliferation of SUDHL-4 and -6 cell lines, which rely on Syk for survival and growth signals, in the low µM range. Toledo cells which do not require Syk, was noticeably less sensitive to the anti-proliferative effects of Syk inhibition.

Example 339: Syk Inhibition Induces Apoptosis in Non-Hodgkin's Lymphoma Cell Lines Data represent two independent experiments to evaluate the effect of Syk and Syk/JAK inhibition on survival of diffuse large non-Hodgkin's lymphoma B cell lines. SUDHL-4 and SUDHL-6 cells lines rely on Syk-mediated B cell receptor signaling for survival, while Toledo cells do not. Cells were incubated with compounds at the indicated concentrations and times; induction of apoptosis was measured by flow cytometry using the Caspase 3 Detection Kit (Sigma-Aldrich, Saint Luis, Mo.). Data are presented as the percent of total cells positive for the apoptosis marker, caspase 3. As expected, Syk inhibition resulted in the induction of apoptosis in SUDHL-4 and -6 cell lines, but not the Toledo cell line.

Example 340: Inhibition of Mouse Primary B Cell Activation by Syk Inhibitors

Mouse primary splenocytes were pre-treated for 1 hour with increasing concentrations of each compound (0.05-2 M) prior to addition of control or goat anti-mouse IgD serum. Anti-IgD induced B cell activation was measured 16 hours later by flow cytometry, staining for the activation markers CD80/86 and CD69.

Example 341: Mouse Model of Immune-Mediated Thrombocytopenia

Immune-mediated thrombocytopenia is caused by antibodies directed against platelet surface glycoproteins, antibodies against drug-containing complexes on the platelet surface, or by antibody-coated cells or immune complexes that interact with the platelet surface. Select compounds were evaluated for their ability to inhibit platelet clearance in a mouse model of antibody-mediated thrombocytopenia. In this model, a rapid clearance of circulating platelets (approximately 50%) results from the intravenous administration of a rat anti-mouse GPIIb (clone MWReg30) antibody (BD Biosciences, Pharmingen). To evaluate capacity for inhibition of platelet clearance, compounds were suspended into 0.5% methylcellulose in water and administered via oral gavage (100 ul/mouse) at a time prior to antibody injection when the compound would achieve maximum plasma concentration (typically 1-2 hours based on separate pharmacokinetic experiments for individual compounds). At 4 and 8 hours after injection of antibody, terminal blood samples were obtained from groups of vehicle and test article treated mice (n=5-10 mice/group) via cardiac puncture. Blood was anticoagulated using trisodium citrate or EDTA. Whole blood samples were measured for platelet counts on a hematology analyzer (Hemavet, Drew Scientific). Remaining blood was processed for plasma and compound concentrations measured by mass spectrometry.

Platelet clearance was determined by measuring the difference in platelet number between the average non-antibody treatment group and animals administered the rat anti-mouse GPIIb antibody. Inhibition of platelet clearance was determined by comparing the difference between platelet clearance of vehicle and compound treated animals.

Example 342: Mouse Model of Collagen Antibody Induced Arthritis

The inhibitory activity of select compounds was investigated in a mouse model of collagen antibody induced arthritis (CAIA). Collagen induced arthritis is mediated by autoantibodies to type II collagen and complement, thus arthritis can be induced by administration of polyclonal antibodies or a mixture of monoclonal antibodies to type II collagen. The CAIA model (Chondrex, Inc., Redmond, Wash.) uses a mixture of 4 clones which recognize individual epitopes clustered within an 83 amino acid peptide fragment of type II collagen. These epitopes share common amino acid sequences with many different species of type II collagen including chicken, mouse, rat, bovine, porcine, monkey and human. The model utilizes a monoclonal antibody cocktail followed by bacterial lipopolysaccharide (LPS) to induce a severe and consistent arthritis in mice within 7 days. This model was developed based on the hypothesis that bacterial toxins absorbed through the gastrointestinal tract play a synergistic and pathologic role with autoantibodies to type II collagen in triggering arthritis in patients with Rheumatoid Arthritis.

For these experiments, the monoclonal antibody cocktail (Lot #OC-708) was injected intravenously via tail vein at a dose of 4 mg/mouse (40 mg/ml) on day 0 followed by intraperitoneal injection of LPS diluted into normal saline at a dose of 25 ug/mouse in 8 week old, female Balb/C mice (Charles River, Inc.). Dosing of test articles was started just before or after the IV injection of antibody cocktail. Compounds were suspended into 0.5% methylcellulose in water and administered via oral gavage (100 ul/mouse) daily for the duration of the 7-10 day study. Clinical inflammation scores were obtained daily. Inhibition of clinical inflammation scores was determined based on the difference between vehicle and test article treated mice at the end of the experiment. Plasma concentrations represent peak concentration at 1 hour post last dose on the day of study termination.

Example 343: Inhibition of IL-4 Induced JAK1/3 to Stat-6 Phosphorylation in Ramos B Cells Ramos B cells were pre-treated for 1 hour with increasing concentrations of compound, as indicated prior to addition of IL-4. Cells were incubated with IL-4 for 10 minutes, and then subjected to intracellular flow cytometry to measure the percent inhibition of IL-4 induced Stat-6.

Example 344: Inhibition of IL-4 Induced JAK1/3 to Stat-6 Phosphorylation in Ramos B Cells Ramos B cells were pre-treated for 1 hour with increasing concentrations of compound, as indicated prior to addition of IL-4. Cells were incubated with IL-4 for 10 minutes, and then subjected to intracellular flow cytometry to measure the percent inhibition of IL-4 induced Stat-6.

Example 345: Primary Human T-Cell Proliferation Assay Stimulated with IL-2

Primary human T-cells derived from peripheral blood and pre-activated through stimulation of the T-cell receptor and CD28 proliferate in vitro in response to the cytokine Interleukin-2 (IL-2). This proliferative response is dependent on the activation of JAK-1 and JAK-3 tyrosine kinases, which phosphorylate and activate the transcription factor Stat-5.

Human primary T cells are prepared as follows. Whole blood is obtained from a healthy volunteer, mixed 1:1 with PBS, layered on to Ficoll Hypaque (Amersham Pharmacia Biotech, Piscataway, N.J., Catalog #17-1440-03) in 2:1 blood/PBS:ficoll ratio and centrifuged for 30 min at 4° C. at 1750 rpm. The lymphocytes at the serum: ficoll interface are recovered and washed twice with 5 volumes of PBS. The cells are resuspended in Yssel's medium (Gemini Bioproducts, Woodland, Calif., Catalog #400-103) containing 40 U/mL recombinant IL2 (R and D Systems, Minneapolis, Minn., Catalog #202-IL (20 µg)) and seeded into a flask pre-coated with 1 µg/mL anti-CD3 (BD Pharmingen, San Diego, Calif., Catalog #555336) and 5 µg/mL anti-CD28 (Immunotech, Beckman Coulter of Brea Calif., Catalog #IM1376). The primary T-cells are stimulated for 3 to 4 days, then transferred to a fresh flask and maintained in RPMI with 10% FBS and 40 U/mL IL-2.

Primary T-cells are washed twice with PBS to remove the IL-2 and resuspended in Yssel's medium at 2×10$^6$ cells/mL. 50 µL of cell suspension containing 80 U/mL IL-2 is added to each well of a flat bottom 96 well black plate. For the unstimulated control, IL-2 is omitted from the last column on the plate. Compounds are serially diluted in dimethyl sulfoxide (DMSO, 99.7% pure, cell culture tested, Sigma-Aldrich, St. Louis, Mo., Catalog No. D$^{2650}$) from 5 mM in 3-fold dilutions and then diluted 1:250 in Yssel's medium. 50 µL of 2× compound is added per well in duplicate and the cells are allowed to proliferate for 72 hours at 37° C.

Proliferation is measured using CellTiter-Glo® Luminescent Cell Viability Assay (Promega), which determines the number of viable cells in culture based on quantitation of the ATP present, as an indicator of metabolically active cells. The substrate is thawed and allowed to come to room temperature. After mixing the Cell Titer-Glo reagent and diluent together, 100 µL is added to each well. The plates are mixed on an orbital shaker for two minutes to induce lysis and incubated at room temperature for an additional ten minutes to allow the signal to equilibrate. Detection is performed using a Wallac Victor2 1420 multilabel counter purchased from Perkin Elmer, Shelton, Conn.

Example 346. A549 Epithelial Line Stimulated with IFNγ

A549 lung epithelial cells up-regulate ICAM-1 (CD54) surface expression in response to a variety of different stimuli. Therefore, using ICAM-1 expression as readout, compound effects on different signaling pathways can be assessed in the same cell type. IFNγ up-regulates ICAM-1 through activation of the JAK/Stat pathway. In this example, the up-regulation of ICAM-1 by IFNγ is assessed.

The A549 lung epithelial carcinoma cell line originated from the American Type Culture Collection. Routine culturing is with $F_{12}K$ media (Mediatech Inc., Lenexa, Kans., Cat. No. 10-025-CV) with 10% fetal bovine serum, 100 I.U. penicillin and 100 ng/mL streptomycin (complete F12k media). Cells are incubated in a humidified atmosphere of 5% $CO_2$ at 37° C. Prior to use in the assay, A549 cells are washed with PBS and trypsinized (Mediatech Inc., Cat. No. 25-052-CI) to lift the cells. The trypsin cell suspension is neutralized with complete F12K media and centrifuged to pellet the cells. The cell pellet is resuspended in complete F12K media at a concentration of $2.0\times10^5$/mL. Cells are seeded at 20,000 per well, 100 µL total volume, in a flat bottom tissue culture plate and allowed to adhere overnight.

On day two, A549 cells are pre-incubated with a 2,4-pyrimidinediamine test compound or DMSO (control) (Sigma-Aldrich, St. Louis, Mo., Catalog No. D2650) for 1 hour. The cells are then stimulated with IFNγ (75 ng/mL) (Peprotech Inc., Rocky Hill, N.J., Cat. No. 300-02) and allowed to incubate for 24 hours. The final test compound dose range is 30 µM to 14 nM in 200 µL F12K media containing 5% FBS, 0.3% DMSO.

On day three, the cell media is removed and the cells are washed with 200 µL PBS (phosphate buffered saline). Each well is trypsinized to dissociate the cells, then neutralized by addition of 200 µL complete F12K media. Cells are pelleted and stained with an APC conjugated mouse anti-human ICAM-1 (CD54) (BD Pharmingen, San Diego, Calif., Catalog #559771) antibody for 20 minutes at 4° C. Cells are washed with ice cold FACS buffer (PBS+2% FBS) and surface ICAM-1 expression is analyzed by flow cytometry. Detection is performed using a BD LSR I System Flow Cytometer, purchased from BD Biosciences of San Jose, Calif. Events are gated for live scatter and the geometric mean is calculated (Becton-Dickinson CellQuest software version 3.3, Franklin Lakes, N.J.). Geometric means are plotted against the compound concentration to generate a dose response curve.

Example 347. U937 IFNγICAM1 FACS Assay

U937 human monocytic cells up-regulate ICAM-1 (CD54) surface expression in response to a variety of different stimuli. Therefore, using ICAM-1 expression as readout, compound effects on different signaling pathways can be assessed in the same cell type. IFNγ up-regulates ICAM-1 through activation of the JAK/Stat pathway. In this example, the up-regulation of ICAM-1 by IFNγ is assessed.

The U937 human monocytic cell line is obtained from ATCC of Rockville, Md., catalog number CRL-1593.2, and cultured in RPMI-1640 medium containing 10% (v/v) FCS. U937 cells are grown in 10% RPMI. The cells are then plated at a concentration of 100,000 cells per 160 µL in 96 well flat bottom plates. The test compounds are then diluted as follows: 10 mM test compound is diluted 1:5 in DMSO (3 µL 10 mM test compound in 12 µL DMSO), followed by a 1:3 serial dilution of test compound in DMSO (6 µL test compound serially diluted into 12 µL DMSO to give 3-fold dilutions). Then 4 µL of test compound is transferred to 76 µL of 10% RPMI resulting in a 10× solution (100 µM test compound, 5% DMSO). For control wells, 4 µL of DMSO is diluted into 76 µL 10% RPMI.

The assay is performed in duplicate with 8 points (8 3-fold dilution concentrations from 10 µL) and with 4 wells of DMSO only (control wells) under stimulated conditions and 4 wells of DMSO only under unstimulated conditions.

The diluted compound plate is mixed 2× using a multimek (Beckman Coulter of Brea, Calif.) and then 20 µL of the diluted compounds is transferred to the 96 well plate containing 160 µL of cells, which are then mixed again twice at low speeds. The cells and compounds are then pre-incubated for 30 minutes at 37° C. with 5% $CO_2$.

The 10× stimulation mix is made by preparing a 100 ng/mL solution of human IFNγ in 10% RPMI. The cells and compound are then stimulated with 20 µL of IFNγ stimulation mix to give a final concentration of 10 ng/mL IFNγ, 10 µM test compound, and 0.5% DMSO. The cells are kept under conditions for stimulation for 18-24 hours at 37° C. with 5% CO2.

The cells are transferred to a 96 well round bottom plate for staining and then kept on ice for the duration of the staining procedure. Cells are spun down at 1000 rpm for 5 minutes at 4° C., following which the supernatant is removed. Following removal of the supernatant, 1 µL APC conjugated mouse anti-human ICAM-1 antibody is added per 100 µL FACS buffer. The cells are then incubated on ice in the dark for 30 minutes. Following incubation, 150 µL of FACS buffer is added and the cells are centrifuged at 1000 rpm for 5 minutes at 4° C., following which the supernatant is removed. After removal of the supernatant, 200 µL of FACS buffer is added and the cells are resuspended. After suspension, the cells are centrifuged at 1000 rpm for 5 min at 4° C. Supernatant is then removed prior to resuspension of the cells in 150 µL FACS buffer.

Detection is performed using a BD LSR I System Flow Cytometer, purchased from BD Biosciences of San Jose, Calif. The live cells are gated for live scatter and the geometric mean of ICAM-APC is measured (Becton-Dickinson CellQuest software version 3.3, Franklin Lakes, N.J.). Both % live cells and ICAM-1 expression is analyzed. The assays for the test compounds is carried out in parallel with a control compound of known activity. The $EC_{50}$ for the control compound is typically 40-100 nM.

Example 348. Analysis of B Cell Signaling

The human non-Hodgkin's lymphoma B cell lines SUDHL-4 (#ACC 495), SUDHL-6 (#ACC572), and Karpas-422 (#ACC32) were obtained from DSMZ (Braunschweig, Germany); Toledo (#CRL-2631) and Ramos (#CRL-1596) were obtained from the American Type Culture Collection (ATCC; Manassas, Va.). All cells were maintained in RPMI media (Invitrogen, Carlsbad, Calif.) supplemented with 10% fetal calf serum (ATCC) and penicillin/streptomycin (Invitrogen), and maintained in a 37° C. humidified tissue culture incubator. Antibodies used in these studies include polyclonal goat F(ab)'2 anti-human IgG (H+L) and anti-human IgM (BioSource, Camarillo, Calif.); rabbit anti-human Syk, rabbit anti-human phospho-Syk (Y525/526), rabbit anti-human phospho-Syk (Y352), anti-human BLNK, anti-human phospho-BLNK (Y84) were obtained from Cell Signaling Technologies, Inc. (Danvers, Mass.). The following antibodies were obtained from Becton Dickenson (San Jose, Calif.) for phospho-flow cytometry: Alexa fluor 488-conjugated mouse anti-human phospho-STAT6 (Y641), Phycoerythrin (PE)-conjugated mouse anti-human phospho-Zap70 (Y319)/Syk(Y352), and Fluorescein isothiocyanate (FITC)-conjugated mouse anti-human phospho-ERK1/2 (T202/Y204).

Phospho-flow cytometry was performed essentially as described elsewhere (Irish, Czerwinski et al. Blood 108(9): 3135-42 (2006). 0.5×106 cells in growth media were stimulated with 1 µg/ml anti-µ or anti-γ antibody for 10 minutes. Induced signaling was terminated immediately following the indicated time by the addition of paraformaldehyde (Electron Microscopy Sciences, Hatfield, Pa.) to a final concentration of 1%. Cells were incubated with paraformaldehyde for 5 minutes at room temperature, washed once with phosphate buffered saline (PBS), then resuspended and incubated overnight at 4° C. in pre-chilled methanol (−80° C.) (company, address). Fixed and permeablized cells were subsequently washed once in PBS, a second time in PBS containing 1% bovine serum albumin (BSA) (Sigma-Aldrich, St. Louis, Mo.), and then stained with the indicated antibodies diluted 1:20 in PBS+1% BSA. After 30 minutes, cells were washed once in PBS and subjected to flow cytometry using the FACS Calibur (Becton Dickenson). For Western blot analyses, 106 cells were stimulated for 30 minutes with 2 µg/ml of the indicated BCR-specific antibodies. Signaling was terminated by resuspending the cells in lysis buffer and incubated on ice for 1 hour. Cell debris were removed by centrifugation, and the cleared protein lysates were resolved by 10% SDS-PAGE and probed with the indicated antibodies following recommendations made by the manufacturers. Where indicated, cells were pre-treated for 1 hour at 37° C. with Syk inhibitors or vehicle control (0.5% DMSO) at several concentrations prior to stimulation with anti-BCR antibody.

Example 349. Selective Inhibition of Syk Activity

Figure 8A:
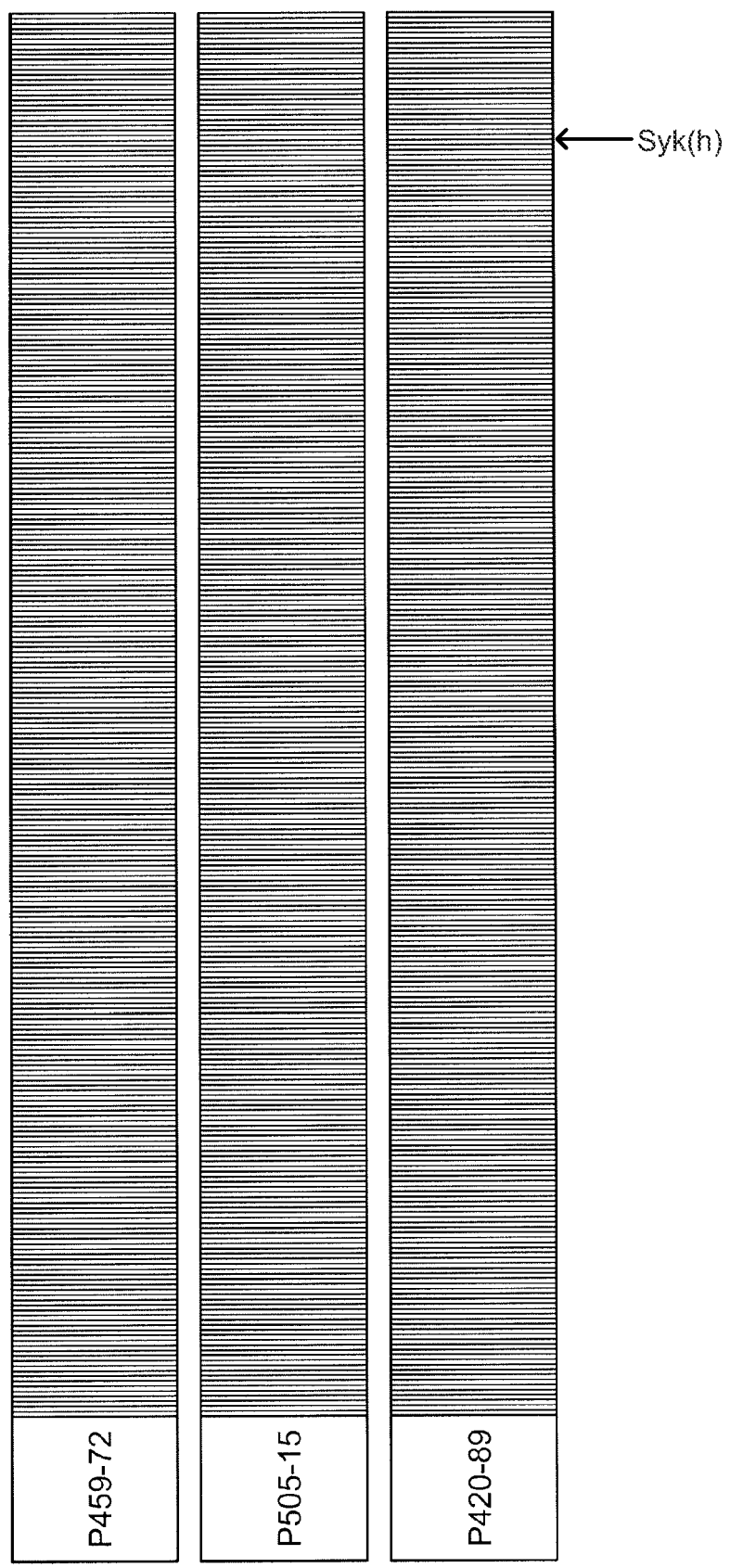
Figure 8C:
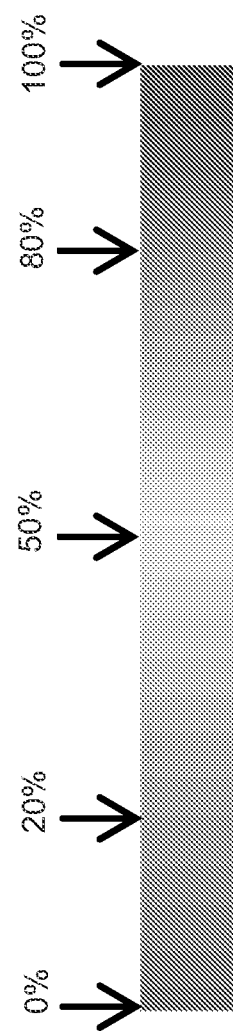

Compounds were tested for their ability to inhibit purified Syk. P459-72 and P505-15 (two compounds from a Syk-specific series as shown in Table 9b) and example 100b (from a series with dual Syk and JAK inhibitory activities) were found to suppress Syk kinase activity with IC50s of 43 nM, 6 nM, and 31 nM, respectively. The selectivity of these compounds for Syk was determined by screening each against a panel of 270 independent purified kinases at 300 nM (Millipore). The percent inhibition relative to vehicle control was calculated, and the numbers were converted into a heat-map; no inhibition is represented as green, increasing blending with red indicates increasing percent inhibition with yellow representing 50% inhibition and red representing 100% inhibition (FIG. 8). As depicted in FIG. 8A, P459-72 and P505-15 were highly Syk specific (first and second rows, respectively) whereas example 100b inhibited multiple kinases (third row). The subset of kinases that were inhibited by ≥80% by any of the three compounds are shown in FIG. 8B. Example 100b inhibited Syk and MLK-1 (first row). At 300 nM P505-15 inhibited 10 different kinases (second row). When re-tested at 50 nM (approximately 10× above its Syk IC50 value of 6 nM), however, Syk was the only kinase that remained inhibited (third row). P420-89 inhibited Syk, JAK2 and JAK3, along with several other kinases (fourth row).

Employing the Milipore panel of purified kinases P505-15 ($IC_{50}$=1 nM) inhibited 98% of purified Syk kinase activity at 50 nM. IC50 values were determined for those kinases that were inhibited by >80% at 300 nM in the Millipore kinase panel.

| Kinase | IC50 (nM) |
|---|---|
| Syk(h) | 1 |
| MLK1 | 60 |
| Fgr(h) | 81 |
| Yes(h) | 123 |
| Flt3(h) | 139 |
| PAK5 | 166 |
| Lyn(h) | 199 |
| cSRC(h) | 244 |
| Lck(h) | 300 |

By contrast, multi-kinase inhibitor P420-89 is more akin to Rigel's R788. At 300 nM, P420-89 inhibited Syk by 88%, along with >80% inhibition of 32 additional kinases. Among these were JAK 2 and 3 (93% and 85% inhibited, respectively), Flt-3 (83-92% inhibited), and cKit (95-97% inhibited), all targets for therapeutic manipulation of lymphocyte function.

Example 350. Calcium Flux Assay and Selective Inhibition of Syk in Non-Hodgkin's Lymphoma B Cell Lines Ramos cells were cultured (maintaining approximately 0.5×106 cells/ml) in growth medium 3 to 4 days ahead of experiments. Cells were harvested and re-suspended in fresh medium at 8×106 cells/ml before dye-loading. An equal volume of Calcium 3 loading dye (Molecular Device, Sunnyvale, Calif.) was added to the cell suspensions. Loaded cells were dispensed in a 96 well plate and incubated for 20 minutes. Syk inhibitors were then added to the loaded cells and incubated for another 30 minutes. B cells were stimulated with 5 µg/ml anti-µ antibody. Changes in intracellular Ca2+ concentration was measured using the FlexSTATion (Molecular Devices, Sunnyvale, Calif.).

The selectivity and potency of Syk inhibition in B cells was initially interrogated by Western blot, measuring BCR-mediated induction of pSyk Y525/526 and pBLNK Y84, both measures of Syk kinase activity, and the induction of pSyk Y352, a measure of Src kinase activity. SUDHL-6 B cells were stimulated with anti-BCR specific antibody for 30 minutes in the presence or absence of each Syk inhibitor or vehicle control. Treatment with 0.16 or 1 µM of each compound reduced BCR-induced Syk autophorphorylation (Y525/526) by roughly 40% and 60%, respectively, as estimated by densitometry (data not shown). An expanded range of concentrations was used to further evaluate the effect of these compounds on BCR induced Syk and Src kinase activity. As shown in FIG. 9, A-C, each compound inhibited Syk activity (pBLNK Y84) with IC50 values ranging from 0.16 to 1 µM, while no effect on Src activity (pSyk Y352) was observed as high as 2.5 µM.

Figure 10A:
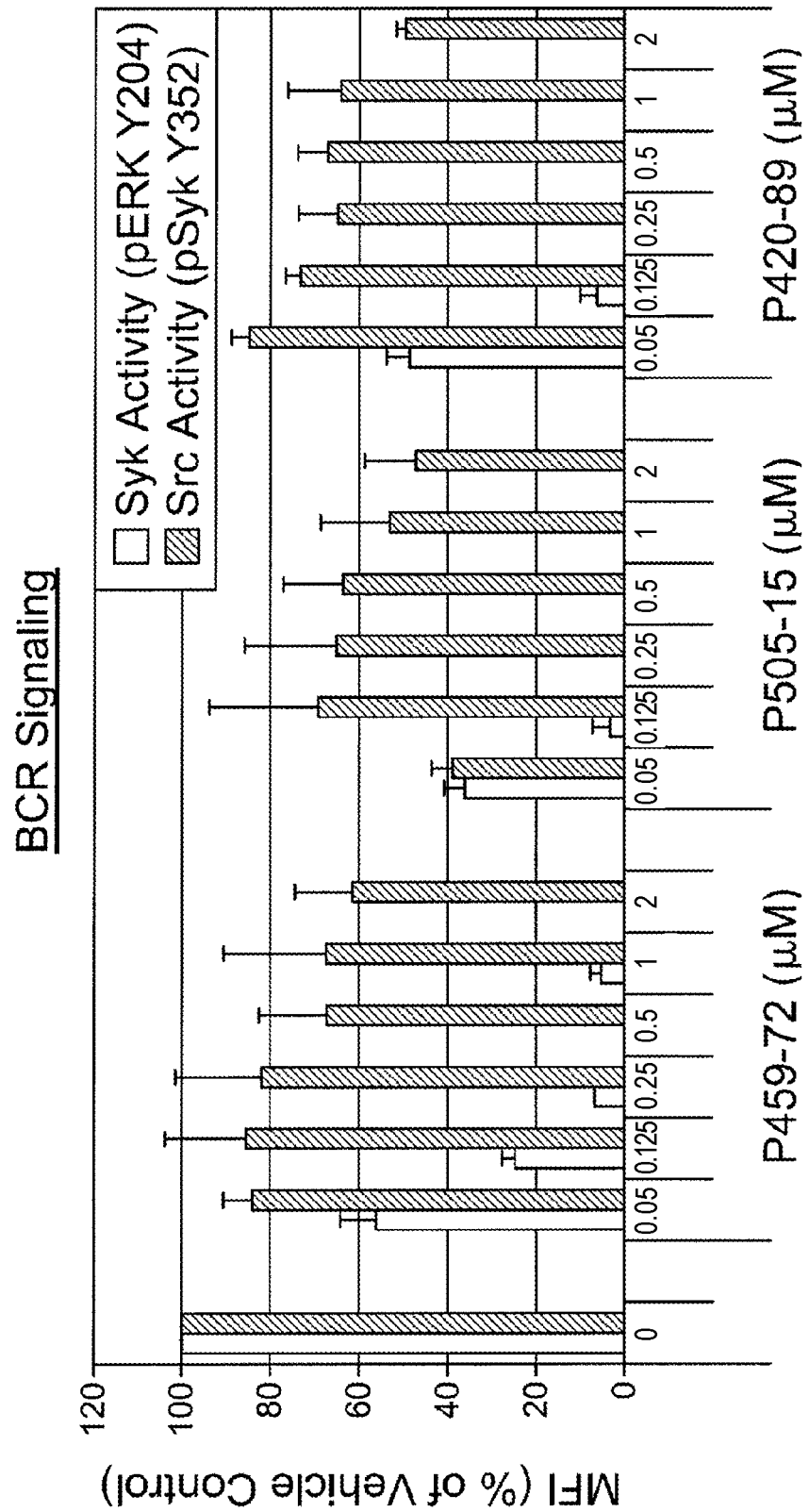
FIGS. 10A-10B provide a comparison of Syk-Specific and Dual Syk/JAK Inhibition in NHL Cell Lines. B cells were stimulated with anti-BCR (FIG. 10A), or IL-4 (FIG. 10B) for 15 min in the presence of various concentrations of each inhibitor, as indicated. Cells were then evaluated for inhibition of signaling pathways by phospho-flow cytometry.

The ability of each compound to suppress signaling events more distal to the BCR was also measured. Cells were again stimulated by anti-BCR antibody in the presence or absence of various concentrations of each Syk inhibitor. The induction of pSyk Y352 was measured as a specificity control, while that of pERK1/2 T202/Y204 was used as a measure of more distal Syk-dependent signaling (Jiang, Craxton et al. J Exp Med 188(7): 1297-306 (1998). The effect of compounds on Src and Syk activity were determined (FIG. 10A). Concentrations of less than 125 nM were sufficient to suppress BCR induced Syk signaling to ERK1/2. By contrast, much higher concentrations were required to cause a modest suppression of Src activity; an effect on Src that was not observed by Western blot (FIG. 9, A-C). None of these Syk inhibitors suppressed PMA-induced ERK1/2 tyrosine phosphorylation, demonstrating these compounds do not inhibit signaling events down-stream of PKC.

Whereas P459-72 and P505-15 specifically inhibited Syk in purified and cellular assays, example 100b additionally demonstrated activity against purified JAK kinases. These compounds were tested for inhibition of IL-4 signaling to STAT-6 via JAK1/3 in B cells, a signaling pathway that does not require Syk. The Syk specific compounds did not suppress IL4 signaling at concentrations as high as 2 µM. Conversely, example 100b did suppress IL4 signaling, with an IC50 around 125 nM (FIG. 10B).

This shows that selective inhibition of Syk suppressed BCR-induced Ca2+ flux in B cells with IC50 values around 100 nM. This suggests that by inhibiting Syk, these compounds suppress the signaling pathway, blocking the cellular response.

Figure 10B:
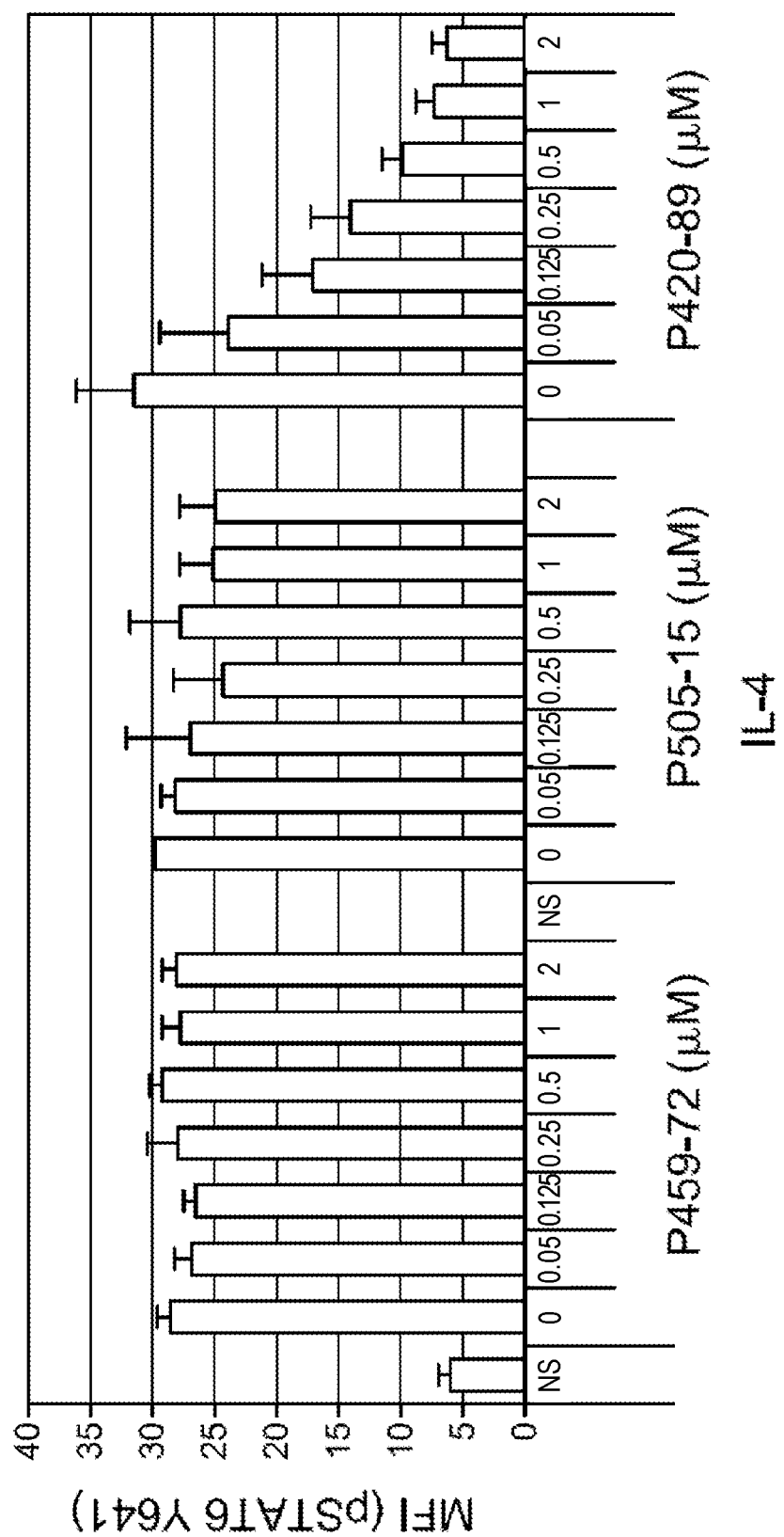
Figure 11A:
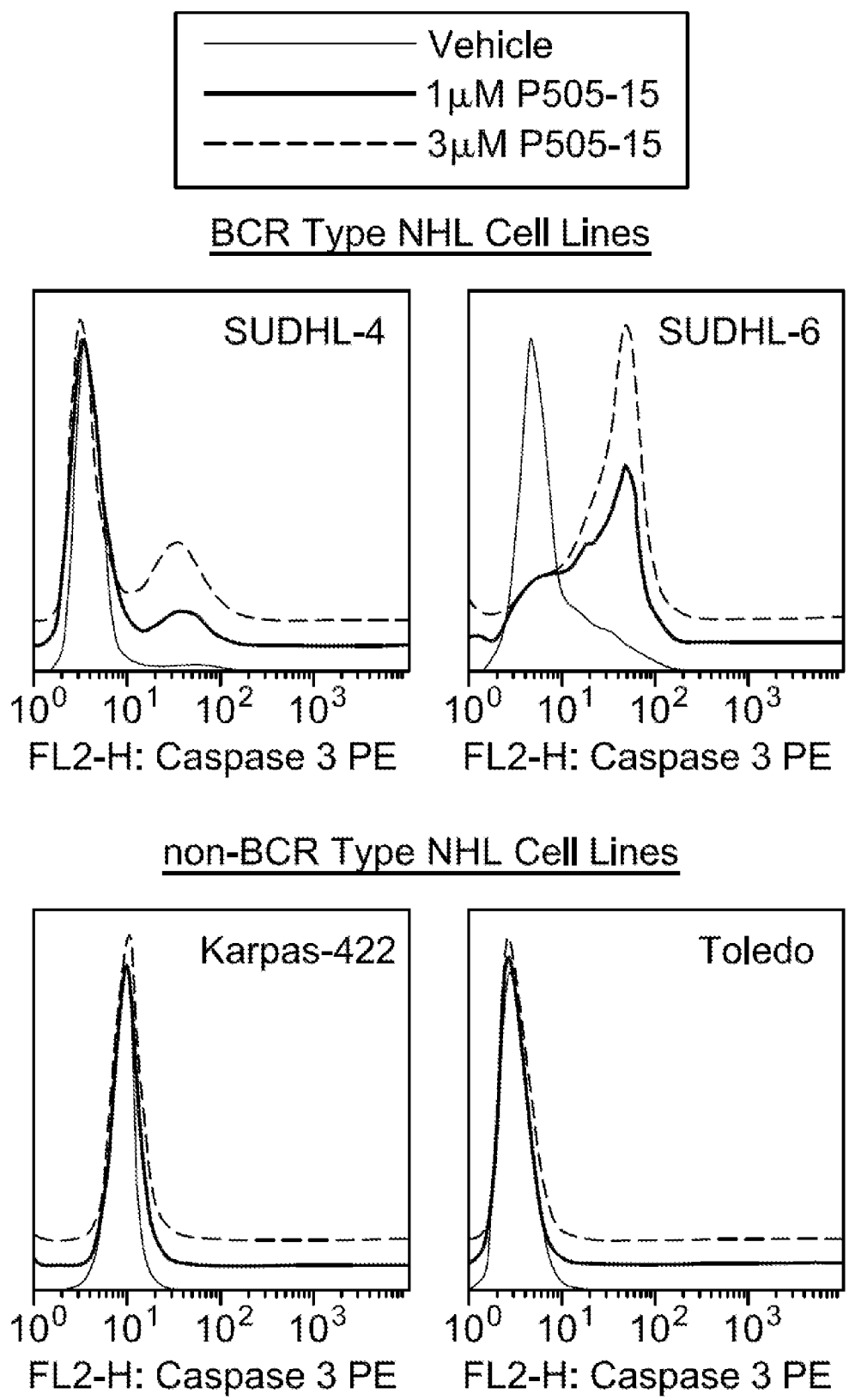
Figure 11B:
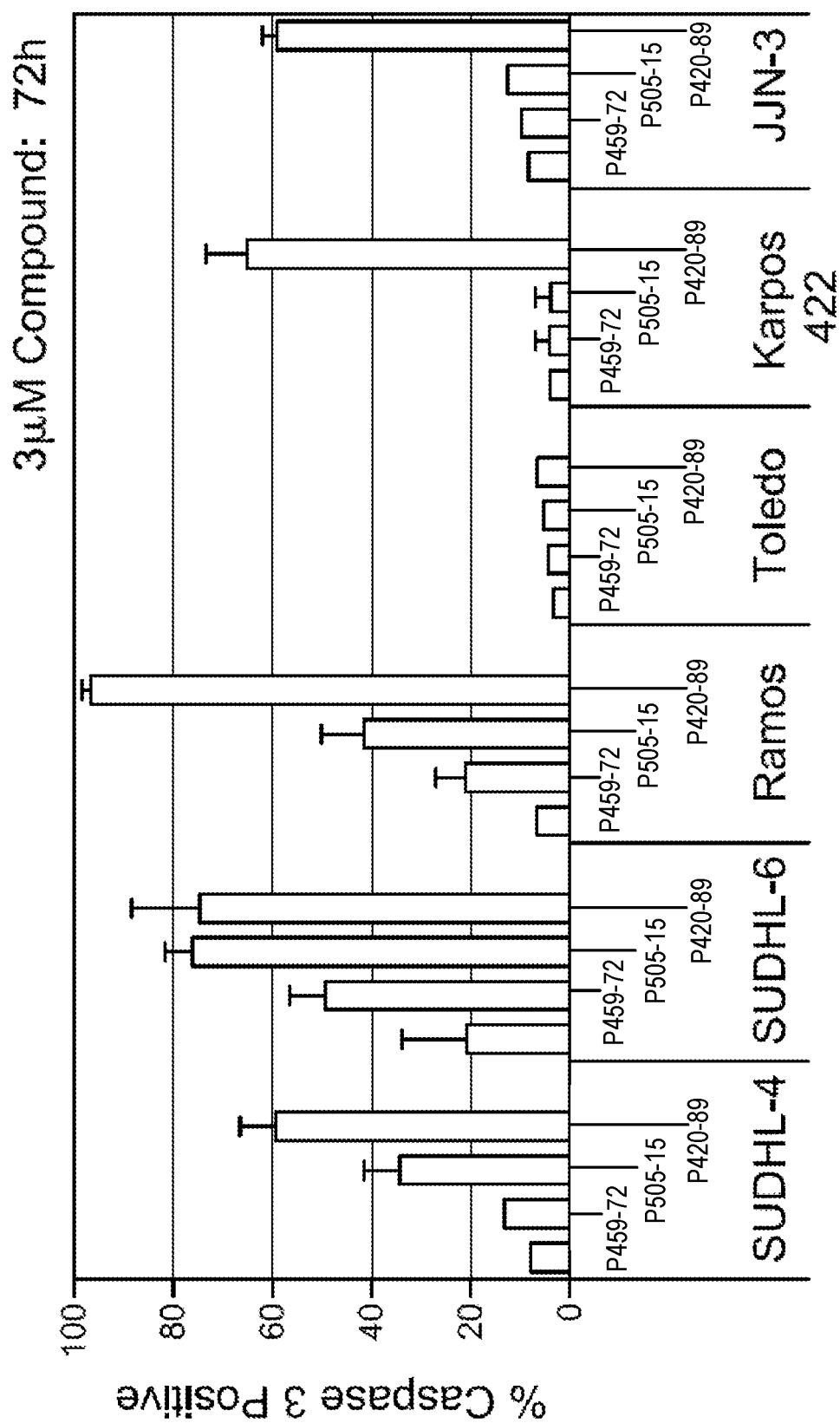

Selective inhibition of Syk is sufficient to suppress BCR signaling without affecting Src (FIG. 11) or JAK (FIG. 10B). Additionally, P505-15 and example 100b equally induced apoptosis in these cells (FIG. 11B). This data demonstrates the role of Syk signaling in the survival of NHL cell lines, and demonstrates that inhibition of kinases other than Syk is not required to achieve this effect.

Example 351. Caspase 3 and Proliferation Assays: Syk Inhibition Disrupts Proliferation and Survival of Non-Hodgkin's Lymphoma B Cell Lines Induction of apoptosis was measured using the PE-conjugated monoclonal active caspase-3 antibody apoptosis kit (Becton Dickenson) following the supplied protocol. Cells were suspended in growth media (0.5×106 cells/ml) and treated with the indicated concentrations of each Syk inhibitor or vehicle control for 24, 48, or 72 hours prior to FACS analysis. The MTT (3-(4,5-Dimethylthiazol-2-yl)-2,5-diphenyltetrazolium bromide, a tetrazole) assay (company name) was used as a measure of cell viability and growth, following protocols supplied by the manufacturer. Cells were treated with the indicated concentrations of each Syk inhibitor or vehicle control for 72 hours.

SUDHL-4 and SUDHL-6 cells were previously classified as "BCR-type" (Monti, Savage et al. Blood 105(5): 1851-61 (2005); Polo, Juszczynski et al. Proc Natl Acad Sci USA 104(9): 3207-12 (2007) and sensitive to Syk inhibition by R406 (Chen, Monti et al. 2008). The Toledo and Karpas-422 cell lines that lack BCR and BLNK expression, respectively (Gabay, Ben-Bassat et al. Eur J Haematol 63(3): 180-91 (1999); Sprangers, Feldhahn et al. Oncogene 25(36): 5056-62 (2006), having therefore adapted to survive independent of BCR signals, were insensitive to R406 (Chen, Monti et al. 2008). The proliferation of these cell lines when cultured in the presence or absence of various concentrations of each Syk inhibitor for 72 hours was tested.

Selective inhibition of Syk was sufficient to induce apoptosis in "BCR-type" NHL cell lines. Cells were incubated with 1 or 3 µM of the inhibitor for 72 h. As demonstrated in FIG. 11A, SUDHL-4 and -6 cells each underwent apoptosis, whereas the Toledo and Karpas-422 cells did not (FIG. 11A). In replicate experiments, the specific inhibition of Syk by P459-72 and P505-15 induced apoptosis only in the SUDHL and Ramos cell lines. By comparison, example 100b, which potently inhibits Syk and JAK kinases, induced apoptosis in all the "BCR-type" cell lines, as well as in Karpas-422 and JJN-3, a multiple myeloma cell line that lacks BCR, and BLNK expression (Sprangers, Feldhahn et al. Oncogene 25(36): 5056-62 (2006). The Toledo cells remained insensitive to all three compounds (FIG. 11B). In a separate experiment, the SUDHL-6 and Toledo cells were found to be equally sensitive to induction of apoptosis by 72 h treatment with 1 µM PMA. These data demonstrate the specific requirement of Syk in the survival of certain NHL cell lines.

Example 352. Xenograft Studies and Tumor and Plasma Concentration Analysis

Syk Inhibition Protects Against Tumor Formation in a Xenograft Mouse Model. Mice were received (company) and acclimated in-house at least three days prior to use. Ramos cells (3×106) were injected subcutaneously into the hind flank area of conscious mice using a 27 gauge needle in an injection volume of less than 0.5 ml. Following injection, mice were randomized into treatment groups (n=15) and dosed twice daily by oral gavage with vehicle or 10, 15, or 20 mg/kg of the inhibitor. Body weights were obtained at least once per week and caliper measurements of tumors were determined twice per week beginning when palpable tumors were formed until the end of the study. Tumor volume was assessed by caliper measurement using a formula [maximum length×width×height×π/6]. Twice daily dosing of vehicle or the inhibitor continued until the vehicle or any treatment group exhibited tumors that exceeded 1.5 grams in size. At the time of termination (5 weeks post Ramos inoculation) the mice were anesthetized with a ketamine cocktail. A blood sample was obtained for CBC and plasma concentration determination via cardiac puncture and the mice were euthanized via cervical dislocation. Tumors were then be excised and weighed. One half of the tumor was snap frozen in liquid nitrogen for determination of concentration of the inhibitor in the tumor tissue and the other half was placed in 10% buffered formalin for histological investigation.

The effect of Syk inhibition on Ramos tumor formation in a xenograft mouse model was assessed. Mice were dosed twice daily with 10, 15, or 20 mg/kg P505-15 or vehicle control beginning the day of tumor cell inoculation. Caliper measurements were initiated when tumors began to form, approximately three weeks post-tumor inoculation, and repeated every third day until termination of the study. The study was terminated when tumor weights began reaching approximately 1.5 mg, at which time tumors were excised and weighed. Tumor and plasma samples were subjected to pharmacokinetic analysis.

Each tumor sample was homogenized in 3 ml of saline per gram of tumor using the Kontes® Microtube Pellet Pestle® Rods and Motor (Kimble Chase, Vineland, N.J.). Plasma and tumor samples were analyzed for P505-15 concentration using a liquid chromatography tandem mass spectrometer (LC/MS/MS). In brief, plasma and tumor samples were processed in a 96-well Captiva™ filter plate (0.2 µm, Varian, Inc., Palo Alto, Calif.). Aliquots of plasma and homogenized tumor samples were precipitated with acetonitrile containing 200 ng/mL of:

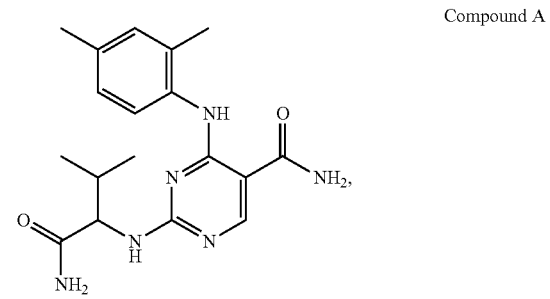 [SMILES: Cc1ccc(Nc2nc(NC(C(N)=O)C(C)C)ncc2C(N)=O)c(C)c1]

Compound A the internal standard. The mixture was vortexed and refrigerated at 4° C. for 30 minutes to allow complete protein precipitation. The mixture was filtered into a 96-well collection plate. The filtrate was injected onto a Sciex API3000 LC/MS/MS equipped with a turbo-ion spray source. P505-15 and Compound A were separated on a Phenomenex Luna 5μ HILIC column (4.6×100 mm, 5 mm; Phenomenex, Torrance, Calif.). A mobile phase gradient mixture of 10% mobile phase A (0.1% formic acid in water) and 90% mobile phase B (0.1% formic acid in 90% acetonitrile, 10% water) to 65% mobile phase B was programmed over 1.1 minutes followed by a gradient of mobile phase B from 65% to 90% over 0.01 minutes. The peak areas of the m/z 394/360 product ion of P505-15 were measured against those of the m/z 357/295 product ion of Compound A (internal standard) in positive ion mode. The analytical range was 2 to 5000 ng/ml.

Pharmacokinetic analysis revealed that at steady-state, tumor concentrations of P505-15 followed the concentration-time profiles seen with plasma in the 10, 15, and 20 mg/kg dose groups. Nonlinear increases in Cmax, AUC (0-8), and tumor Cmin were observed as the dose was increased, but a dose-proportional increase in plasma Cmin was noted. Mean Cmax and AUC (0-8) in plasma was at least 2-fold greater than that in tumor for all doses examined; however, mean nadir concentrations (Cmin) were higher in tumor than in plasma (Table 11A), indicating accumulation of P505-15 in the tumor compartment.

TABLE 11A

| Dosing regiment | Tmax (hr) | Cmin (ng/mL) | Cmax (ng/mL) | AUC (0-8) (ng*hr/mL) |
| --- | --- | --- | --- | --- |
| Determined from plasma | | | | |
| 10 mg/kg BID | 1.50 | 17.6 | 179 | 738 |
| 15 mg/kg BID | 1.50 | 26.6 | 343 | 1671 |
| 20 mg/kg BID | 4.00 | 39.5 | 570 | 3191 |
| Determined from tumor | | | | |
| 10 mg/kg BID | 8.00 | 24.5 | 55.2 | 353 |
| 15 mg/kg BID* | 4.00 | 67.8 | 163 | 475 |
| 20 mg/kg BID | 4.00 | 125 | 252 | 1453 |

TABLE 11B

| | tumor/plasma ratio | | |
| --- | --- | --- | --- |
| Dosing regimen | AUC based | Cmax based | Cmin based |
| 10 mg/kg BID | 0.478 | 0.308 | 1.39 |
| 15 mg/kg BID* | 0.284 | 0.475 | 2.55 |
| 20 mg/kg BID | 0.455 | 0.442 | 3.15 |

Note: Nadir (0), 1.5, 4, and 8 h samples were taken on the da of harvest following the AM dose. The second dose was not administered on the day of harvest; therefore, pharmacokinetic values above were determined after a single AM dose at steady-state.
*Only one tumor sample was available for the 8 h time-point and may have been an outlier (tumor concentrations at 8 h—608 ng/ml); therefore, pharmacokinetic parameters were determined between 0 to 4 h for the 15 mg/kg BID P505-15 dose group. As a result, AUC (0-8) and AUC based tumor/plasma ration for this dose group may be underestimated. The difference between plasma and tumor Cmin became more prominent as the dose was increased, as indicated by the increase in tumor/plasma ratios determined from Cmin (Table 11B). Tumor/plasma ratios determined from Cmax and AUC (0-8) were similar across the various dose groups. Tumor concentrations were sustained above 60, 170, and 640 nM over the entire dosing interval at steady-state for P505-15 at 10, 15, and 20 mg/kg, respectively.

Mice dosed with all three concentrations of P505-15 were protected from Ramos tumor growth in vivo. This was first evident from caliper measurements (data not shown), which revealed a reduced rate of tumor growth in the presence of the Syk inhibitor. Upon study completion, mice were euthanized and tumors excised and weighed. Consistent with caliper measurements, a statistically significant reduction in average tumor weight was achieved in all dosing groups, relative to vehicle control.

The Syk-specific inhibitor P505-15 was also tested for activity in a Ramos tumor mouse xenograft model. At all the concentrations tested, statistically significant reductions in tumor growth were observed in mice dosed BID with P505-15. The lowest concentration tested was 10 mg/kg, achieving tumor concentrations ranging from 64 to 140 nM over the course of the day. Suppression of tumor growth at these concentrations in vivo is consistent with concentrations of <125 nM found to suppress BCR-induced Ca2+ flux and distal BCR signaling to pERK Y204. The selective pharmacological inhibition of Syk results in effects on the proliferations and survival of NHL cell lines. These data suggest that the selective targeting of Syk may similarly have clinical benefit in a variety of B-cell proliferative disorders.

As detailed herein, Syk has been implicated experimentally in B cell development, proliferation, and survival. Moreover, Syk is implicated as an oncogene. Expression of constitutively active Syk in adoptively transferred bone marrow cells induces leukemia in mice, and over-activity of Syk is associated with a variety of lymphomas in humans Given the role of Syk in B cell biology, its selective inhibition may be sufficient to provide clinical benefit in B cell proliferative disorders, while reducing toxicities that may arise due to suppression of other off-target kinases.

The present invention provides a number of embodiments. It is apparent that the examples may be altered to provide other embodiments of this invention. Therefore, it will be appreciated that the scope of this invention is to be defined by the appended claims rather than by the specific embodiments, which have been represented by way of example.

All of the above U.S. patents, U.S. patent application publications, U.S. patent applications, foreign patents, foreign patent applications and non-patent publications referred to in this specification and/or listed in the Application Data Sheet, are incorporated herein by reference, in their entirety. From the foregoing it will be appreciated that, although specific embodiments of the invention have been described herein for purposes of illustration, various modifications may be made without deviating from the spirit and scope of the invention. Accordingly, the invention is not limited except as by the appended claims.

What is claimed is:

1. A topical pharmaceutical composition comprising a compound of Formula If

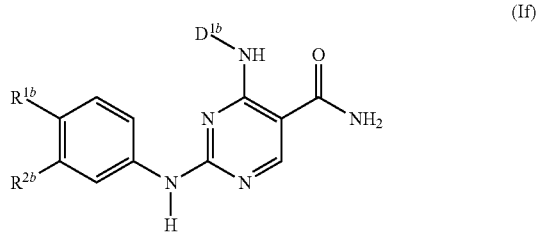

(If)

or pharmaceutically acceptable salt thereof and one or more pharmaceutically acceptable carriers,
wherein
$D^{1b}$ is $C_{3-8}$ cycloalkyl;
$R^{1b}$ is selected from the group consisting of

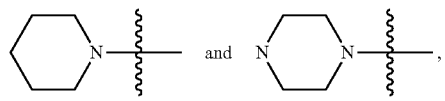 [SMILES: *N1CCCCC1 ; *N1CCNCC1]

each of which is substituted with from 1 to 2 substituents independently selected from the group consisting of hydroxyl, hydroxyC$_{1-8}$alkylene, C$_{1-8}$alkoxyC$_{1-8}$alkylene, C$_{1-8}$alkylcarbonyl, carboxy and C$_{1-8}$alkylsulfonyl;
$R^{2b}$ is H or halo; and
the wavy line in the substituents of $R^{1b}$ indicates the point of attachment to the rest of the molecule.

2. The topical pharmaceutical composition of claim 1, wherein
$R^{1b}$ is

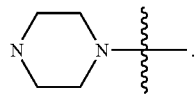

3. The topical pharmaceutical composition of claim 1, wherein $R^{1b}$ is substituted with from 1 to 2 substituents independently selected from the group consisting of C$_{1-8}$alkylcarbonyl and C$_{1-8}$alkylsulfonyl.

4. The topical pharmaceutical composition of claim 3, wherein $R^{1b}$ is substituted with a C$_{1-8}$alkylsulfonyl substituent.

5. The topical pharmaceutical composition of claim 3, wherein $R^{1b}$ is substituted with a C$_{1-8}$alkylcarbonyl substituent.

6. The topical pharmaceutical composition of claim 1, wherein $R^{2b}$ is H.

7. The topical pharmaceutical composition of claim 1, wherein said compound of Formula If has the formula

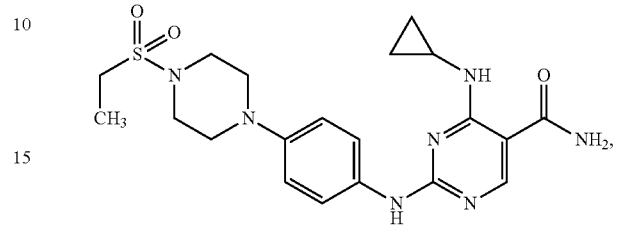

or a pharmaceutically acceptable salt thereof.

8. The topical pharmaceutical composition of claim 1, wherein said compound of Formula If has the formula

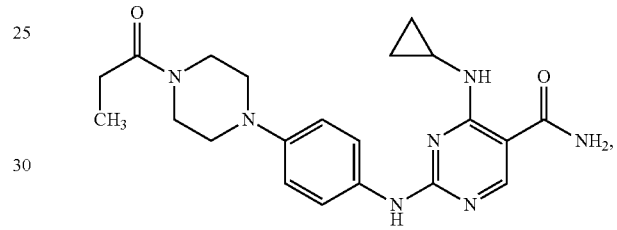

or a pharmaceutically acceptable salt thereof.

9. The topical pharmaceutical composition of claim 1, wherein said topical pharmaceutical composition is in the form of an emulsion, a lotion, a gel, a foam, a cream, a jelly, a solution, a suspension, an ointment, or a transdermal patch.

10. The topical pharmaceutical composition of claim 9, wherein said topical pharmaceutical composition is in the form of an ointment.

11. The topical pharmaceutical composition of claim 9, wherein said topical pharmaceutical composition is in the form of a lotion or a cream.

12. The topical pharmaceutical composition of claim 1, wherein said topical pharmaceutical composition is suspended or dissolved in said one or more carriers.

13. The topical pharmaceutical composition of claim 12, wherein said one or more carriers is selected from the group consisting of mineral oil, liquid petrolatum, white petrolatum, propylene glycol, polyoxyethylene, polyoxypropylene compound, emulsifying wax, sorbitan monostearate, polysorbate 60, cetyl esters, wax, cetyl alcohol, 2-octyldodecanol, benzyl alcohol and water.

* * * * *